US012600777B2

(12) United States Patent
Dranoff et al.

(10) Patent No.: US 12,600,777 B2
(45) **Date of Patent: *Apr. 14, 2026**

(54) COMBINATION THERAPIES COMPRISING ANTIBODY MOLECULES TO LAG-3

(71) Applicants: NOVARTIS AG, Basel (CH); IMMUTEP S.A.S., Orsay (FR)

(72) Inventors: Glenn Dranoff, Sudbury, MA (US); Frederic Triebel, Versailles (FR); Chrystelle Brignone, Chatenay-Malabry (FR); Walter A. Blattler, Brookline, MA (US); Jennifer Marie Mataraza, Cambridge, MA (US); Catherine Ann Sabatos-Peyton, Waban, MA (US); Hwai Wen Chang, San Marcos, CA (US); Gerhard Johann Frey, San Diego, CA (US)

(73) Assignees: Novartis AG, Basel (CH); Immutep S.A.S., Orsay (FR)

( * ) Notice: Subject to any disclaimer, the term of this patent is extended or adjusted under 35 U.S.C. 154(b) by 789 days.

This patent is subject to a terminal disclaimer.

(21) Appl. No.: 17/491,420

(22) Filed: Sep. 30, 2021

(65) Prior Publication Data

US 2022/0153835 A1 May 19, 2022

Related U.S. Application Data

(63) Continuation of application No. 15/747,227, filed as application No. PCT/US2016/044545 on Jul. 28, 2016, now abandoned.

(60) Provisional application No. 62/198,492, filed on Jul. 29, 2015.

(51) Int. Cl.
*C07K 16/28* (2006.01)

(52) U.S. Cl.
CPC ...... *C07K 16/2803* (2013.01); *C07K 2317/24* (2013.01); *C07K 2317/76* (2013.01); *C07K 2317/92* (2013.01)

(58) Field of Classification Search
CPC ............ C07K 16/2803; C07K 2317/24; C07K 2317/76; C07K 2317/92; A61P 35/00
See application file for complete search history.

(56) References Cited

U.S. PATENT DOCUMENTS

| | | | |
|---|---|---|---|
| 5,324,514 | A | 6/1994 | Sipos |
| 5,434,131 | A | 7/1995 | Linsley et al. |
| 5,629,204 | A | 5/1997 | Honjo et al. |
| 5,698,520 | A | 12/1997 | Honjo et al. |
| 5,773,578 | A | 6/1998 | Hercend et al. |
| 5,811,097 | A | 9/1998 | Allison et al. |
| 5,874,250 | A | 2/1999 | Hercend et al. |
| 5,897,862 | A | 4/1999 | Hardy et al. |
| 5,968,511 | A | 10/1999 | Akita et al. |
| 5,976,877 | A | 11/1999 | Hercend et al. |
| 6,051,227 | A | 4/2000 | Allison et al. |
| 6,084,083 | A | 7/2000 | Levinson |
| 6,143,273 | A | 11/2000 | Faure et al. |
| 6,197,524 | B1 | 3/2001 | Romagnani |
| 6,204,371 | B1 | 3/2001 | Levinson |
| 6,288,218 | B1 | 9/2001 | Levinson |
| 6,414,117 | B1 | 7/2002 | Levinson |
| 6,482,925 | B1 | 11/2002 | El Tayar et al. |
| 6,562,343 | B1 | 5/2003 | Levinson |
| 6,596,536 | B1 | 7/2003 | Hercend et al. |
| 6,632,927 | B2 | 10/2003 | Adair et al. |
| 6,632,976 | B1 | 10/2003 | Tomizuka et al. |
| RE38,313 | E | 11/2003 | Faure et al. |
| 6,803,192 | B1 | 10/2004 | Chen |
| 6,808,710 | B1 | 10/2004 | Wood et al. |
| 6,936,704 | B1 | 8/2005 | Freeman et al. |
| 7,029,674 | B2 | 4/2006 | Carreno et al. |
| 7,038,013 | B2 | 5/2006 | Freeman et al. |
| 7,041,474 | B2 | 5/2006 | Kingsbury |
| 7,101,550 | B2 | 9/2006 | Wood et al. |
| 7,105,328 | B2 | 9/2006 | Wood et al. |
| 7,122,372 | B2 | 10/2006 | Hardy et al. |
| 7,138,501 | B2 | 11/2006 | Ruben et al. |
| 7,169,791 | B2 | 1/2007 | Breitenstein et al. |
| 7,172,750 | B2 | 2/2007 | Levinson |
| 7,306,906 | B2 | 12/2007 | Maruyama et al. |
| 7,329,639 | B2 | 2/2008 | Hardy et al. |
| 7,329,737 | B2 | 2/2008 | Sexton et al. |
| 7,332,582 | B2 | 2/2008 | Hardy et al. |
| 7,414,171 | B2 | 8/2008 | Honjo et al. |
| 7,423,128 | B2 | 9/2008 | Gazit-Bornstein et al. |
| 7,449,300 | B2 | 11/2008 | Chen et al. |
| 7,470,428 | B2 | 12/2008 | Kuchroo et al. |

(Continued)

FOREIGN PATENT DOCUMENTS

| | | | |
|---|---|---|---|
| AU | 774391 | B2 | 6/2004 |
| CN | 102492038 | A | 6/2012 |

(Continued)

OTHER PUBLICATIONS

Stagg et al. (Therapeutic Advances in Medical Oncology, 5(3): 169-181, 2013).*
Verbrugge et al: "The curative outcome of radioinmunotherapy in a mouse breast cancer model relies on mTOR signaling", Radiation Research. Radiation Research Society, GB, (2014) vol. 182 No. 2 pp. 219-229.
Vietta et al. "Considering Therapeutic Antibodies" Science (2006) vol. 313, pp. 308-309.
Voskoglou-Nomikos et al. "Clinical Predictive Value of the in Vitro Cell Line, Human Xenograft, and Mouse Allograft Preclinical Cancer Models" Clinical Cancer Research (2003) vol. 9, pp. 4227-4239.

(Continued)

*Primary Examiner* — Nelson B Moseley, II
(74) *Attorney, Agent, or Firm* — K&L Gates LLP

(57) ABSTRACT

Combination therapies comprising antibody molecules that specifically bind to LAG-3 are disclosed. The combination therapies can be used to treat, prevent and/or diagnose cancerous or infectious disorders.

7 Claims, 16 Drawing Sheets

Specification includes a Sequence Listing.

(56) References Cited

U.S. PATENT DOCUMENTS 7,488,802 B2 2/2009 Collins et al.
7,521,051 B2 4/2009 Collins et al.
7,524,498 B2 4/2009 Hardy et al.
7,553,939 B2 6/2009 McIntire et al.
7,563,441 B2 7/2009 Graus et al.
7,563,869 B2 7/2009 Honjo et al.
7,595,048 B2 9/2009 Honjo et al.
7,598,257 B2 10/2009 Rodgers et al.
7,605,238 B2 10/2009 Korman et al.
7,635,757 B2 12/2009 Freeman et al.
7,695,715 B2 4/2010 Hardy et al.
7,722,868 B2 5/2010 Freeman et al.
7,767,675 B2 8/2010 Zhuo et al.
7,790,160 B2 9/2010 Von Strandmann et al.
7,794,710 B2 9/2010 Chen et al.
7,838,220 B2 11/2010 McIntire et al.
7,850,965 B2 12/2010 Jensen et al.
7,858,746 B2 12/2010 Honjo et al.
7,943,743 B2 5/2011 Korman et al.
8,008,449 B2 8/2011 Korman et al.
8,039,273 B2 10/2011 Jeffrey
8,039,479 B2 10/2011 Michellys et al.
8,088,905 B2 1/2012 Collins et al.
8,101,176 B2 1/2012 Kuchroo et al.
8,168,179 B2 5/2012 Honjo et al.
8,168,757 B2 5/2012 Finnefrock et al.
8,217,149 B2 7/2012 Irving et al.
8,287,856 B2 10/2012 Li et al.
8,329,660 B2 12/2012 Kuchroo et al.
8,354,509 B2 1/2013 Carven et al.
8,361,736 B2 1/2013 Majeti et al.
8,415,355 B2 4/2013 Brain et al.
8,460,886 B2 6/2013 Shibayama et al.
8,460,927 B2 6/2013 Chen
8,461,330 B2 6/2013 Zhuo et al.
8,501,758 B2 8/2013 Huang et al.
8,546,336 B2 10/2013 Chen et al.
8,551,481 B2 10/2013 Pardoll et al.
8,552,002 B2 10/2013 Ding et al.
8,552,154 B2 10/2013 Freeman et al.
8,552,156 B2 10/2013 Takayanagi et al.
8,568,728 B2 10/2013 Jeffrey
8,580,247 B2 11/2013 Li et al.
8,609,089 B2 12/2013 Langermann et al.
8,617,546 B2 12/2013 Kang et al.
8,647,623 B2 2/2014 Takayanagi et al.
8,685,980 B2 4/2014 Besong et al.
8,697,069 B2 4/2014 Kuchroo et al.
8,709,412 B2 4/2014 Jones et al.
8,709,416 B2 4/2014 Langermann et al.
8,709,429 B2 4/2014 Majeti et al.
8,715,619 B2 5/2014 Karsunky
8,728,474 B2 5/2014 Honjo et al.
8,735,551 B2 5/2014 Garner et al.
8,735,553 B1 5/2014 Li et al.
8,779,105 B2 7/2014 Korman et al.
8,779,108 B2 7/2014 Queva et al.
8,841,418 B2 9/2014 Karsunky et al.
8,900,587 B2 12/2014 Carven et al.
8,927,697 B2 1/2015 Davis et al.
8,952,136 B2 2/2015 Carven et al.
9,005,629 B2 4/2015 Pardoll et al.
9,045,545 B1 6/2015 Clube
9,067,999 B1 6/2015 Honjo et al.
9,073,994 B2 7/2015 Honjo et al.
9,084,776 B2 7/2015 Korman et al.
9,102,727 B2 8/2015 Freeman et al.
9,103,832 B2 8/2015 Takayanagi et al.
9,109,034 B1 8/2015 Clube
9,132,281 B2 9/2015 Zeng et al.
9,175,082 B2 11/2015 Zhou et al.
9,333,256 B2 5/2016 Kuchroo et al.
9,358,289 B2 6/2016 Korman et al.
9,387,247 B2 7/2016 Korman et al.
9,409,970 B2 8/2016 Mikesell et al.
9,457,080 B2 10/2016 Freeman et al.
9,492,539 B2 11/2016 Korman et al.
9,492,540 B2 11/2016 Korman et al.
9,505,839 B2 11/2016 Lonberg et al.
9,605,070 B2 3/2017 Sabatos-Peyton et al.
9,683,048 B2 6/2017 Freeman et al.
9,815,898 B2 11/2017 Freeman et al.
9,815,901 B2 11/2017 Brogdon et al.
9,834,605 B2 12/2017 Carven et al.
9,884,913 B2 2/2018 Sabatos-Peyton et al.
9,908,936 B2 3/2018 Triebel et al.
9,944,645 B2 4/2018 Zhuo et al.
9,988,452 B2 6/2018 Freeman et al.
10,005,832 B2 6/2018 Yoshida et al.
10,253,086 B2 4/2019 Bitter et al.
10,472,419 B2 11/2019 Sabatos-Peyton et al.
10,513,558 B2 12/2019 Tipton et al.
10,561,653 B2 2/2020 Bilic et al.
10,570,204 B2 2/2020 Johnson et al.
10,711,060 B2 7/2020 Triebel et al.
10,752,687 B2 8/2020 Freeman et al.
10,851,165 B2 12/2020 Freeman et al.
10,981,990 B2 4/2021 Sabatos-Peyton et al.
11,155,620 B2 10/2021 Sabatos-Peyton et al.
11,312,783 B2 4/2022 Prinz et al.
11,344,620 B2 5/2022 Lebwohl et al.
11,708,412 B2 7/2023 Johnson et al.
11,827,704 B2 11/2023 Freeman et al.
2002/0086014 A1 7/2002 Korman et al.
2002/0146753 A1 10/2002 Ditzel et al.
2002/0164660 A1 11/2002 Spaulding et al.
2003/0039653 A1 2/2003 Chen et al.
2003/0059937 A1 3/2003 Ruben et al.
2003/0129601 A1 7/2003 Cole
2003/0232323 A1 12/2003 Freeman et al.
2004/0072164 A1 4/2004 Maruyama et al.
2004/0073957 A1 4/2004 Tomizuka et al.
2004/0171551 A1 9/2004 Triebel
2004/0241745 A1 12/2004 Honjo et al.
2005/0009136 A1 1/2005 Nixon et al.
2005/0191721 A1 9/2005 Kuchroo et al.
2005/0226876 A1 10/2005 Graus et al.
2005/0276756 A1 12/2005 Hoo et al.
2006/0110383 A1 5/2006 Honjo et al.
2006/0177442 A1 8/2006 Von Strandmann et al.
2006/0210567 A1 9/2006 Collins et al.
2006/0240024 A1 10/2006 Pardoll et al.
2007/0004910 A1 1/2007 Sexton et al.
2007/0041982 A1 2/2007 Ponath et al.
2007/0065427 A1 3/2007 Freeman et al.
2007/0071675 A1 3/2007 Wu et al.
2007/0122378 A1 5/2007 Freeman et al.
2007/0160598 A1 7/2007 Dennis et al.
2007/0202100 A1 8/2007 Wood et al.
2008/0025979 A1 1/2008 Honjo et al.
2008/0038264 A1 2/2008 Bodary et al.
2008/0069822 A1 3/2008 Jensen et al.
2008/0167287 A1 7/2008 Zhuo et al.
2008/0311117 A1 12/2008 Collins et al.
2009/0055944 A1 2/2009 Korman et al.
2009/0076250 A1 3/2009 Honjo et al.
2009/0155275 A1 6/2009 Wu et al.
2009/0304693 A1 12/2009 Ghayur et al.
2009/0311253 A1 12/2009 Ghayur et al.
2010/0028330 A1 2/2010 Collins et al.
2010/0056576 A1 3/2010 Burger et al.
2010/0061992 A1 3/2010 Anderson et al.
2010/0074900 A1 3/2010 Ghayur et al.
2010/0076178 A1 3/2010 Ghayur et al.
2010/0105667 A1 4/2010 Furet et al.
2010/0136009 A1 6/2010 Papkoff et al.
2010/0203056 A1 8/2010 Irving et al.
2010/0233079 A1 9/2010 Jakob et al.
2010/0233183 A1 9/2010 Triebel et al.
2010/0260668 A1 10/2010 Ghayur et al.
2010/0266531 A1 10/2010 Hsieh et al.
2010/0266617 A1 10/2010 Carven et al.
2011/0008766 A1 1/2011 Ghayur et al.
2011/0044894 A1 2/2011 Karsunky

(56) References Cited

U.S. PATENT DOCUMENTS

| | | | |
|---|---|---|---|
| 2011/0044980 | A1 | 2/2011 | Ghayur et al. |
| 2011/0054151 | A1 | 3/2011 | Lazar et al. |
| 2011/0059106 | A1 | 3/2011 | Kuchroo et al. |
| 2011/0070238 | A1 | 3/2011 | Triebel et al. |
| 2011/0081341 | A1 | 4/2011 | Honjo et al. |
| 2011/0091372 | A1 | 4/2011 | Ghayur et al. |
| 2011/0091463 | A1 | 4/2011 | Ghayur et al. |
| 2011/0110852 | A1 | 5/2011 | Miller et al. |
| 2011/0123550 | A1 | 5/2011 | Shibayama et al. |
| 2011/0136781 | A1 | 6/2011 | Zhuo et al. |
| 2011/0150892 | A1 | 6/2011 | Thudium et al. |
| 2011/0171220 | A1 | 7/2011 | Davis |
| 2011/0177088 | A1 | 7/2011 | Olive et al. |
| 2011/0195068 | A1 | 8/2011 | Langermann et al. |
| 2011/0209230 | A1 | 8/2011 | Korman et al. |
| 2011/0212094 | A1 | 9/2011 | Ghayur et al. |
| 2011/0229461 | A1 | 9/2011 | Tyson |
| 2011/0236375 | A1 | 9/2011 | Lazar et al. |
| 2011/0263827 | A1 | 10/2011 | Ghayur et al. |
| 2011/0271358 | A1 | 11/2011 | Freeman et al. |
| 2011/0280800 | A1 | 11/2011 | Wu et al. |
| 2011/0280877 | A1 | 11/2011 | Tamada |
| 2011/0287009 | A1 | 11/2011 | Scheer et al. |
| 2012/0014957 | A1 | 1/2012 | Ghayur et al. |
| 2012/0034160 | A1 | 2/2012 | Ghayur et al. |
| 2012/0039870 | A9 | 2/2012 | Dolk et al. |
| 2012/0039906 | A1 | 2/2012 | Olive |
| 2012/0070450 | A1 | 3/2012 | Ishikawa et al. |
| 2012/0076805 | A1 | 3/2012 | Sharpe et al. |
| 2012/0087858 | A1 | 4/2012 | Ghayur et al. |
| 2012/0100131 | A1 | 4/2012 | Takayanagi et al. |
| 2012/0107234 | A1 | 5/2012 | Pedersen et al. |
| 2012/0114649 | A1 | 5/2012 | Langermann et al. |
| 2012/0141501 | A1 | 6/2012 | Yoshida et al. |
| 2012/0195900 | A1 | 8/2012 | Ghayur et al. |
| 2012/0201746 | A1 | 8/2012 | Liu et al. |
| 2012/0201824 | A1 | 8/2012 | Wasik |
| 2012/0258108 | A1 | 10/2012 | Ghayur et al. |
| 2012/0263722 | A1 | 10/2012 | Ghayur et al. |
| 2013/0005216 | A1 | 1/2013 | Rittberger |
| 2013/0017199 | A1 | 1/2013 | Langermann |
| 2013/0022623 | A1 | 1/2013 | Karsunky et al. |
| 2013/0039911 | A1 | 2/2013 | Bedi et al. |
| 2013/0058947 | A1 | 3/2013 | Stull et al. |
| 2013/0095098 | A1 | 4/2013 | Tyson |
| 2013/0109843 | A1 | 5/2013 | Carven et al. |
| 2013/0133091 | A1 | 5/2013 | Korman et al. |
| 2013/0156774 | A1 | 6/2013 | Kuchroo et al. |
| 2013/0183688 | A1 | 7/2013 | Kuchroo et al. |
| 2013/0202623 | A1 | 8/2013 | Chomont et al. |
| 2013/0230514 | A1 | 9/2013 | Langermann et al. |
| 2013/0324515 | A1 | 12/2013 | Zhuo et al. |
| 2014/0044728 | A1 | 2/2014 | Takayanagi et al. |
| 2014/0044738 | A1 | 2/2014 | Langermann et al. |
| 2014/0065142 | A1 | 3/2014 | Roschke et al. |
| 2014/0093511 | A1 | 4/2014 | Lonberg et al. |
| 2014/0127226 | A1 | 5/2014 | Pardoll et al. |
| 2014/0155678 | A1 | 6/2014 | Zeng et al. |
| 2014/0178370 | A1 | 6/2014 | Freeman et al. |
| 2014/0212422 | A1 | 7/2014 | Korman et al. |
| 2014/0234320 | A1 | 8/2014 | Croft et al. |
| 2014/0242094 | A1 | 8/2014 | Kuchroo et al. |
| 2014/0274788 | A1 | 9/2014 | Ishikawa et al. |
| 2014/0294852 | A1 | 10/2014 | Korman et al. |
| 2014/0314714 | A1 | 10/2014 | Honjo et al. |
| 2014/0328833 | A1 | 11/2014 | Korman et al. |
| 2014/0341902 | A1 | 11/2014 | Maecker et al. |
| 2014/0348743 | A1 | 11/2014 | Korman et al. |
| 2015/0017185 | A1 | 1/2015 | Akbar et al. |
| 2015/0023986 | A1 | 1/2015 | Jones et al. |
| 2015/0079109 | A1 | 3/2015 | Li et al. |
| 2015/0086574 | A1 | 3/2015 | Karsunky et al. |
| 2015/0093380 | A1 | 4/2015 | Honjo et al. |
| 2015/0210769 | A1 | 7/2015 | Freeman et al. |
| 2015/0218274 | A1 | 8/2015 | Sabatos-Peyton et al. |
| 2015/0232555 | A1 | 8/2015 | Carven et al. |
| 2015/0259420 | A1 | 9/2015 | Triebel et al. |
| 2015/0290316 | A1 | 10/2015 | Graziano et al. |
| 2015/0307609 | A1 | 10/2015 | Lonberg et al. |
| 2016/0002334 | A1 | 1/2016 | Kuchroo et al. |
| 2016/0016979 | A1 | 1/2016 | Anklekar et al. |
| 2016/0068601 | A1 | 3/2016 | Brogdon et al. |
| 2016/0108123 | A1 | 4/2016 | Freeman et al. |
| 2016/0159905 | A1 | 6/2016 | Abdiche et al. |
| 2016/0222121 | A1 | 8/2016 | Johnson et al. |
| 2016/0326178 | A1 | 11/2016 | Zhuo et al. |
| 2016/0362472 | A1 | 12/2016 | Bitter et al. |
| 2017/0044259 | A1 | 2/2017 | Tipton et al. |
| 2017/0088615 | A1 | 3/2017 | Korman et al. |
| 2017/0137514 | A1 | 5/2017 | Lonberg et al. |
| 2017/0190777 | A1 | 7/2017 | Sabatos-Peyton et al. |
| 2017/0198041 | A1 | 7/2017 | Sabatos-Peyton et al. |
| 2017/0209574 | A1 | 7/2017 | Cao et al. |
| 2017/0210804 | A1 | 7/2017 | Triebel et al. |
| 2017/0247456 | A1 | 8/2017 | Freeman et al. |
| 2017/0281624 | A1 | 10/2017 | Peters et al. |
| 2017/0296659 | A1 | 10/2017 | Lebwohl et al. |
| 2017/0304443 | A1 | 10/2017 | Lebwohl et al. |
| 2017/0340733 | A1 | 11/2017 | Cao |
| 2018/0066054 | A1 | 3/2018 | Thudium et al. |
| 2018/0086830 | A1 | 3/2018 | Triebel et al. |
| 2018/0155427 | A1 | 6/2018 | Freeman et al. |
| 2018/0186882 | A1 | 7/2018 | Freeman et al. |
| 2018/0207273 | A1 | 7/2018 | Dranoff et al. |
| 2018/0222982 | A1 | 8/2018 | Dranoff et al. |
| 2018/0282340 | A1 | 10/2018 | Zhuo et al. |
| 2018/0340025 | A1 | 11/2018 | Dranoff et al. |
| 2018/0371093 | A1 | 12/2018 | Bilic et al. |
| 2019/0000944 | A1 | 1/2019 | Brogdon et al. |
| 2019/0016797 | A1 | 1/2019 | Arenas-Ramirez et al. |
| 2019/0031766 | A1 | 1/2019 | Prinz et al. |
| 2019/0062365 | A1 | 2/2019 | Katibah et al. |
| 2019/0113513 | A1 | 4/2019 | Shaked |
| 2019/0151365 | A1 | 5/2019 | Anak et al. |
| 2019/0185511 | A1 | 6/2019 | Kanne et al. |
| 2019/0202917 | A1 | 7/2019 | Campbell et al. |
| 2020/0030442 | A1 | 1/2020 | Cao |
| 2020/0037760 | A1 | 2/2020 | Han |
| 2020/0172617 | A1 | 6/2020 | Stein et al. |
| 2020/0223917 | A1 | 7/2020 | Sabatos-Peyton et al. |
| 2020/0223924 | A1 | 7/2020 | Stein et al. |
| 2020/0277378 | A1 | 9/2020 | Sabatos-Peyton et al. |
| 2020/0308277 | A1 | 10/2020 | Sabatos-Peyton et al. |
| 2020/0339689 | A1 | 10/2020 | Freeman et al. |
| 2020/0369762 | A1 | 11/2020 | Bruederle et al. |
| 2020/0377600 | A1 | 12/2020 | Johnson et al. |
| 2021/0000951 | A1 | 1/2021 | Cao et al. |
| 2021/0009687 | A1 | 1/2021 | Triebel et al. |
| 2021/0284737 | A1 | 9/2021 | Freeman et al. |
| 2022/0133889 | A1 | 5/2022 | Dranoff et al. |
| 2022/0153835 | A1 | 5/2022 | Dranoff et al. |
| 2022/0185883 | A1 | 6/2022 | Sabatos-Peyton et al. |
| 2022/0306737 | A1 | 9/2022 | Eliasson et al. |
| 2023/0013364 | A1 | 1/2023 | Dranoff et al. |
| 2023/0057071 | A1 | 2/2023 | Vanasse et al. |
| 2023/0058489 | A1 | 2/2023 | Menssen et al. |
| 2023/0088070 | A1 | 3/2023 | Bruederle et al. |

FOREIGN PATENT DOCUMENTS

| | | | |
|---|---|---|---|
| CN | 103079644 | A | 5/2013 |
| CN | 103242448 | A | 8/2013 |
| EP | 0670369 | A2 | 9/1995 |
| EP | 0510079 | B1 | 5/1999 |
| EP | 1334659 | A1 | 8/2003 |
| EP | 1445264 | A1 | 8/2004 |
| EP | 1537878 | A1 | 6/2005 |
| EP | 1591527 | A1 | 11/2005 |
| EP | 0758383 | B1 | 1/2007 |
| EP | 1870399 | A1 | 12/2007 |
| EP | 2161336 | A1 | 3/2010 |
| EP | 2206517 | A1 | 7/2010 |
| EP | 2243493 | A1 | 10/2010 |
| EP | 2270051 | A2 | 1/2011 |

(56) References Cited

FOREIGN PATENT DOCUMENTS

| | | | |
|---|---|---|---|
| EP | 1576014 | B1 | 6/2011 |
| EP | 2412825 | A1 | 2/2012 |
| EP | 2099447 | B1 | 11/2012 |
| EP | 2051990 | B1 | 2/2013 |
| EP | 1897548 | B1 | 8/2013 |
| EP | 2170959 | B1 | 10/2013 |
| EP | 2344474 | B1 | 9/2015 |
| EP | 2142210 | B1 | 8/2016 |
| EP | 2474545 | B1 | 11/2016 |
| EP | 3222634 | A1 | 9/2017 |
| RU | 2494107 | C2 | 9/2013 |
| WO | 1990003394 | A2 | 4/1990 |
| WO | 9110682 | A1 | 7/1991 |
| WO | 1992013949 | A1 | 8/1992 |
| WO | 1992013950 | A2 | 8/1992 |
| WO | 9530750 | A2 | 11/1995 |
| WO | 1996027603 | A1 | 9/1996 |
| WO | 9703695 | A1 | 2/1997 |
| WO | 9713852 | A1 | 4/1997 |
| WO | 1998023741 | A1 | 6/1998 |
| WO | 9858059 | A1 | 12/1998 |
| WO | 1999004810 | A2 | 2/1999 |
| WO | 0032231 | A1 | 6/2000 |
| WO | 0058363 | A1 | 10/2000 |
| WO | 0069914 | A2 | 11/2000 |
| WO | 0071078 | A2 | 11/2000 |
| WO | 0073498 | A1 | 12/2000 |
| WO | 0114424 | A2 | 3/2001 |
| WO | 0114556 | A1 | 3/2001 |
| WO | 0114557 | A1 | 3/2001 |
| WO | 0139722 | A2 | 6/2001 |
| WO | 01077342 | A1 | 10/2001 |
| WO | 01083750 | A2 | 11/2001 |
| WO | 200194413 | A2 | 12/2001 |
| WO | 0200692 | A2 | 1/2002 |
| WO | 0200730 | A2 | 1/2002 |
| WO | 0224891 | A2 | 3/2002 |
| WO | 2002022577 | A2 | 3/2002 |
| WO | 0234205 | A2 | 5/2002 |
| WO | 0239813 | A1 | 5/2002 |
| WO | 02078731 | A1 | 10/2002 |
| WO | 02079499 | A1 | 10/2002 |
| WO | 02086083 | A2 | 10/2002 |
| WO | 03000066 | A1 | 1/2003 |
| WO | 03002722 | A2 | 1/2003 |
| WO | 03011911 | A1 | 2/2003 |
| WO | 03033644 | A2 | 4/2003 |
| WO | 03042402 | A2 | 5/2003 |
| WO | 03063792 | A2 | 8/2003 |
| WO | 03077914 | A1 | 9/2003 |
| WO | 03088808 | A2 | 10/2003 |
| WO | 03099196 | A2 | 12/2003 |
| WO | 2004004771 | A1 | 1/2004 |
| WO | 2004005281 | A1 | 1/2004 |
| WO | 2004007679 | A2 | 1/2004 |
| WO | 2004008218 | A1 | 1/2004 |
| WO | 2004039956 | A2 | 5/2004 |
| WO | 2004056875 | A1 | 7/2004 |
| WO | 2004072286 | A1 | 8/2004 |
| WO | 2004078928 | A2 | 9/2004 |
| WO | 2005027854 | A2 | 3/2005 |
| WO | 2005033144 | A2 | 4/2005 |
| WO | 2005034733 | A2 | 4/2005 |
| WO | 2005097211 | A2 | 10/2005 |
| WO | 2006004988 | A2 | 1/2006 |
| WO | 2006007850 | A1 | 1/2006 |
| WO | 2006021955 | A2 | 3/2006 |
| WO | 2006042237 | A2 | 4/2006 |
| WO | 2006121168 | A1 | 11/2006 |
| WO | 2006124269 | A2 | 11/2006 |
| WO | 2006133396 | A2 | 12/2006 |
| WO | 2007005874 | A2 | 1/2007 |
| WO | 2007011968 | A2 | 1/2007 |
| WO | 2007024705 | A2 | 3/2007 |
| WO | 2007024715 | A2 | 3/2007 |
| WO | 2007070514 | A1 | 6/2007 |
| WO | 2007082154 | A2 | 7/2007 |
| WO | 2007084786 | A1 | 7/2007 |
| WO | 2007113648 | A2 | 10/2007 |
| WO | 2007146968 | A2 | 12/2007 |
| WO | 2008007648 | A1 | 1/2008 |
| WO | 2008016893 | A1 | 2/2008 |
| WO | 2008060617 | A2 | 5/2008 |
| WO | 2008064157 | A1 | 5/2008 |
| WO | 2008071447 | A2 | 6/2008 |
| WO | 2008073160 | A2 | 6/2008 |
| WO | 2008073687 | A2 | 6/2008 |
| WO | 2008083174 | A2 | 7/2008 |
| WO | 2008085562 | A2 | 7/2008 |
| WO | 2008132601 | A1 | 11/2008 |
| WO | 2008156712 | A1 | 12/2008 |
| WO | 2009014708 | A2 | 1/2009 |
| WO | 2009024531 | A1 | 2/2009 |
| WO | 2009029342 | A2 | 3/2009 |
| WO | 2009032256 | A2 | 3/2009 |
| WO | 2009044273 | A2 | 4/2009 |
| WO | 2009091547 | A1 | 7/2009 |
| WO | 2009097394 | A2 | 8/2009 |
| WO | 2009101611 | A1 | 8/2009 |
| WO | 2009114335 | A2 | 9/2009 |
| WO | 2009120905 | A2 | 10/2009 |
| WO | 2009141386 | A1 | 11/2009 |
| WO | 2010001617 | A1 | 1/2010 |
| WO | 2010019570 | A2 | 2/2010 |
| WO | 2010019571 | A2 | 2/2010 |
| WO | 2010026124 | A1 | 3/2010 |
| WO | 2010027423 | A2 | 3/2010 |
| WO | 2010027827 | A2 | 3/2010 |
| WO | 2010027828 | A2 | 3/2010 |
| WO | 2010029082 | A1 | 3/2010 |
| WO | 2010029434 | A1 | 3/2010 |
| WO | 2010029435 | A1 | 3/2010 |
| WO | 2010036959 | A2 | 4/2010 |
| WO | 2010051502 | A2 | 5/2010 |
| WO | 2010063011 | A2 | 6/2010 |
| WO | 2010077634 | A1 | 7/2010 |
| WO | 2010084999 | A1 | 7/2010 |
| WO | 2010089411 | A2 | 8/2010 |
| WO | 2010098788 | A2 | 9/2010 |
| WO | 2010102278 | A1 | 9/2010 |
| WO | 2010110346 | A1 | 9/2010 |
| WO | 2010117057 | A1 | 10/2010 |
| WO | 2011005481 | A1 | 1/2011 |
| WO | 2011011027 | A1 | 1/2011 |
| WO | 2011025927 | A1 | 3/2011 |
| WO | 2011034605 | A2 | 3/2011 |
| WO | 2011041613 | A2 | 4/2011 |
| WO | 2011066342 | A2 | 6/2011 |
| WO | 2011066389 | A1 | 6/2011 |
| WO | 2011069104 | A2 | 6/2011 |
| WO | 2011076786 | A1 | 6/2011 |
| WO | 2011100841 | A1 | 8/2011 |
| WO | 2011110604 | A1 | 9/2011 |
| WO | 2011110621 | A1 | 9/2011 |
| WO | 2011131472 | A1 | 10/2011 |
| WO | 2011155607 | A1 | 12/2011 |
| WO | 2011159877 | A2 | 12/2011 |
| WO | 2012018538 | A2 | 2/2012 |
| WO | 2012022814 | A1 | 2/2012 |
| WO | 2012054438 | A1 | 4/2012 |
| WO | 2012064733 | A2 | 5/2012 |
| WO | 2012079000 | A1 | 6/2012 |
| WO | 2012106587 | A1 | 8/2012 |
| WO | 2012135408 | A1 | 10/2012 |
| WO | 2012145493 | A1 | 10/2012 |
| WO | 2012177624 | A2 | 12/2012 |
| WO | 2012177788 | A1 | 12/2012 |
| WO | 2013006490 | A2 | 1/2013 |
| WO | 2013006727 | A1 | 1/2013 |
| WO | 2013019906 | A1 | 2/2013 |
| WO | 2013043647 | A1 | 3/2013 |
| WO | 2013066761 | A1 | 5/2013 |
| WO | 2013079174 | A1 | 6/2013 |
| WO | 2013079945 | A1 | 6/2013 |

(56) References Cited

FOREIGN PATENT DOCUMENTS

| | | | |
|---|---|---|---|
| WO | 2013169693 | A1 | 11/2013 |
| WO | 2013173223 | A1 | 11/2013 |
| WO | 2013181452 | A1 | 12/2013 |
| WO | 2013181634 | A2 | 12/2013 |
| WO | 2013184757 | A1 | 12/2013 |
| WO | 2014008218 | A1 | 1/2014 |
| WO | 2014018632 | A1 | 1/2014 |
| WO | 2014022138 | A2 | 2/2014 |
| WO | 2014022332 | A1 | 2/2014 |
| WO | 2014022758 | A1 | 2/2014 |
| WO | 2014028502 | A1 | 2/2014 |
| WO | 2014047350 | A1 | 3/2014 |
| WO | 2014055648 | A1 | 4/2014 |
| WO | 2014055897 | A2 | 4/2014 |
| WO | 2014072493 | A1 | 5/2014 |
| WO | 2014085318 | A1 | 6/2014 |
| WO | 2014100079 | A1 | 6/2014 |
| WO | 2014140180 | A1 | 9/2014 |
| WO | 2014165082 | A2 | 10/2014 |
| WO | 2014165422 | A1 | 10/2014 |
| WO | 2014179664 | A2 | 11/2014 |
| WO | 2014189805 | A1 | 11/2014 |
| WO | 2014195852 | A1 | 12/2014 |
| WO | 2015009856 | A2 | 1/2015 |
| WO | 2015026634 | A1 | 2/2015 |
| WO | 2015026684 | A1 | 2/2015 |
| WO | 2015035606 | A1 | 3/2015 |
| WO | 2015036394 | A1 | 3/2015 |
| WO | 2015036499 | A1 | 3/2015 |
| WO | 2015036511 | A1 | 3/2015 |
| WO | 2015042246 | A1 | 3/2015 |
| WO | 2015048312 | A1 | 4/2015 |
| WO | 2015048520 | A1 | 4/2015 |
| WO | 2015061668 | A1 | 4/2015 |
| WO | 2015070060 | A1 | 5/2015 |
| WO | 2015081158 | A1 | 6/2015 |
| WO | 2015085847 | A1 | 6/2015 |
| WO | 2015088847 | A1 | 6/2015 |
| WO | 2015095423 | A2 | 6/2015 |
| WO | 2015095811 | A2 | 6/2015 |
| WO | 2015103602 | A1 | 7/2015 |
| WO | 2015109124 | A2 | 7/2015 |
| WO | 2015109391 | A1 | 7/2015 |
| WO | 2015112800 | A1 | 7/2015 |
| WO | 2015112805 | A1 | 7/2015 |
| WO | 2015112900 | A1 | 7/2015 |
| WO | 2015116539 | A1 | 8/2015 |
| WO | 2015117002 | A1 | 8/2015 |
| WO | 2015118175 | A2 | 8/2015 |
| WO | 2015119944 | A1 | 8/2015 |
| WO | 2015120198 | A1 | 8/2015 |
| WO | 2015134605 | A1 | 9/2015 |
| WO | 2015138920 | A1 | 9/2015 |
| WO | 2015176033 | A1 | 11/2015 |
| WO | 2015181342 | A1 | 12/2015 |
| WO | 2015195163 | A1 | 12/2015 |
| WO | 2015200119 | A1 | 12/2015 |
| WO | 2016000619 | A1 | 1/2016 |
| WO | 2016028672 | A1 | 2/2016 |
| WO | 2016040880 | A1 | 3/2016 |
| WO | 2016040882 | A1 | 3/2016 |
| WO | 2016040892 | A1 | 3/2016 |
| WO | 2016054555 | A2 | 4/2016 |
| WO | 2016061142 | A1 | 4/2016 |
| WO | 2016069727 | A1 | 5/2016 |
| WO | 2016079049 | A1 | 5/2016 |
| WO | 2016100882 | A1 | 6/2016 |
| WO | 2016161239 | A1 | 10/2016 |
| WO | 2016161270 | A1 | 10/2016 |
| WO | 2017017623 | A1 | 2/2017 |
| WO | 2017017624 | A1 | 2/2017 |
| WO | 2017019894 | A1 | 2/2017 |
| WO | 2017019896 | A1 | 2/2017 |
| WO | 2017019897 | A1 | 2/2017 |
| WO | 2017034916 | A1 | 3/2017 |
| WO | 2017097407 | A1 | 6/2017 |
| WO | 2017106656 | A1 | 6/2017 |
| WO | 2017189433 | A1 | 11/2017 |
| WO | 2018222718 | A1 | 12/2018 |
| WO | 2019006007 | A1 | 1/2019 |
| WO | 2019018640 | A1 | 1/2019 |
| WO | 2019018730 | A1 | 1/2019 |
| WO | 2019099838 | A1 | 5/2019 |
| WO | 2019200229 | A1 | 10/2019 |
| WO | 2020128636 | A1 | 6/2020 |
| WO | 2021053490 | A1 | 3/2021 |
| WO | 2021079188 | A1 | 4/2021 |
| WO | 2021079195 | A1 | 4/2021 |
| WO | 2021123902 | A1 | 6/2021 |
| WO | 2021144657 | A1 | 7/2021 |
| WO | 2022195551 | A1 | 9/2022 |

OTHER PUBLICATIONS

Waldmann, Thomas A.; "Effective cancer therapy through immunomodulation"; Annual Rev.; 57(1):65-81 (2006).

Wang et al. "In Vitro Characterization of the Anti-PD-1 Antibody Nivolumab, BMS-936558, and In Vivo Toxicology in Non-Human Primates" Cancer Immunology Research (2014) vol. 2, No. 9, pp. 846-856.

Wang et al., "Vista, a novel mouse Ig superfamily ligand that negatively regulates T cell responses" The Journal of Experimental Medicine (2011) vol. 208 No. 3 pp. 577-592.

Wang et al., "The Mdm2 inhibitor, NVP-CGM097, in combination with the BRAF inhibitor NVP-LGX818 elicits synergistic antitumor effects in melanoma" Cancer Research (2014) , Abstract 5466, Retrieved from the Internet: URL: http://cancerres.aacrjournals.orgjcontent/74/19 Supplement/5466 [retrieved on Apr. 14, 2016].

Wang et al: "Abstract 2929: The Mdm2 inhibitor NVP-CGM097 enhances the anti-tumor activityof NVP-LDK378 in ALK mutant neuroblastomamodels", Cancer Research (2014) Retrieved from the Internet: URL:http:jjcancerres.aacrjournals.orgjcontent/74/19 Supplement/2929 [retrieved on Apr. 14, 2016].

Weber, J.S., et al., "Safety, Efficacy, and Biomarkers of Nivolumab with Vaccine in Ipilimumab-Refractory or -Naive Melanoma," Journal of Clinical Oncology 31 (34):4311-4318, American Society of Clinical Oncology, United States (2013).

Wilson, I.A. and Stanfield, R.L., "Antibody-antigen interactions," Current Opinion in Sturctural Biology 3:113-118, Current Biology, United States (1993).

Winslow, R., "New Cancer Drugs Harness Power of Immune System", The Wall Street Journal, May 15, 2013, accessed at http://www.wsj.com/articles/SB10001424127887323398204578485401089823868, accessed on Jun. 1, 2016, 4 pages.

Wong, R.M., et al., "Programmed death-1 blockade enhances expansion and functional capacity of human melanoma antigen-specific CTLs," International Immunology 19(10):1223-1234, Oxford University Press, England (2007).

Woo et al. "Immune Inhibitory Molecules LAG-3 and PD-1 Synergistically Regulate T-cell Function to Promote Tumoral Immune Escape" Cancer Research (2011) vol. 72, No. 4, pp. 917-927.

Woods David M et al: "The antimelanoma activity of the histone deacetylase inhibitor panobinostat (LBH589) is mediated by direct tumor cytotoxicity and increased tumor immunogenicity.", Melanoma Research, vol. 23, No. 5, Oct. 2013 (Oct. 2013), pp. 341-348.

Woods David M et al: "HDAC Inhibition Upregulates PD-1 Ligands in Melanoma and Augments Immunotherapy with PD-1 Blockade," Cancer Immunology Research, vol. 3, No. 12, Dec. 2015 (Dec. 2015), pp. 1375-1385.

Woods et al: "Abstract 4090: Inhibition of class I histone deacetylases promotes robust and durable enhancement of PDL1 expression in melanoma: Rationale for combination therapy", Cancer Research (2014) Retrieved from the Internet: URL:http://cancerres.aacrjournals.orgjcontent/74/19Supplement/4090.short [retrieved on Apr. 14, 2016].

Workman et al., "LAG-3 Regulates Plasmacytoid Dendritic Cell Homeostatis" The Journal of Immunology (2009) vol. 182 pp. 1885-1891.

(56) References Cited

OTHER PUBLICATIONS

Workman, C.J. et al., "Phenotypic analysis of the murine CD4-related glycoprotein, CD223 (LAG-3).," Eur. J. Immunol., vol. 32(8): 2255-2263 (2002).
Workman, Creg J. et al., "Negative Regulation of T Cell Homeostasis by Lympohocyte Activation Gene-3 (CD223)," The Journal of Immunology, vol. 174:688-695 (2005).
Wu et al., "Endothelial cell-expressed Tim-3 facilitates metastasis of melanoma cells by activating the NF-kB pathway" Oncology Reports (2010) vol. 24 pp. 693-699.
Wu et al., "Immunotherapies: The Blockade of Inhibitory Signals," Int J Biol Sci (2012) vol. 8, No. 10, pp. 1420-1430.
Wu, K-P., et al., "Structural Basis of a Flavivirus Recognized by Its Neutralizing Antibody: Solution Structure of the Domain III of the Japanese Encephalitis Virus Envelope Protein," The Journal of Biological Chemistry 278(46):46007-46013, AmericanSociety for Biochemistry and Molecular Biology, Inc., United States (Nov. 2003).
Xu et al., "LSECtin Expressed on Melanoma Cells Promotoes Tumor Progression by Inhibiting Antitumor T-cell Responses" Cancer Research (2014) vol. 74 No. 14 pp. 3418-3428.
Yamazaki, T., et al., "Expression of programmed death 1 ligands by murine T cells and APC," The Journal of Immunology 169(10):5538-5545, The American Association of Immunologists, United States (2002).
Yan et al., "Tim-3 Expression Defines Regulatory T Cells in Human Tumors" PLoS ONE (2013) vol. 8 No. 3 e58006.
Yang et al., "Lack of TIM-3 Immunoregulation in Multiple Sclerosis" The Journal of Immunology (2008) vol. 180 No. 7 pp. 4409-4414.
Yervoy (ipilimumab) Drug Label, Initial U.S. Approval: 2011, Revised Oct. 2015.
Yi, J., et al., "Mapping the Epitope of an Inhibitory Monoclonal Antibody to the C-terminal DNA-binding Domain of HIV-1 Integrase," The Journal of Biological Chemistry 277(14):12164-12174, American Society for Biochemistry and Molecular Biology, Inc., United States (2002).
Youngnak, Pornpan, et al.; "Differential binding properties of B7-H1 and B7-DC to programmed death-1"; Biochem. Biophys. Res. Commun.; 307:672-677 (2003).
Yuan Z et al, "Blockade of inhibitors of apoptosis (IAPs) in combination with tumor-targeted delivery of tumor necrosis factor-[alpha] leads to synergistic antitumor activity" Cancer Gene Therapy (2013) vol. 20 No. 1 pp. 46-56.
Zamarin et al. "Immune checkpoint modulation: Rational design of combination strategies" Pharmacology & Therapeutics (2015) vol. 150, pp. 23-32.
Zehavi-Willner, Tova, et al.; "The mitogenic activity of staphylococcal enterotoxin B (Seb): a monovalent T cell mitogen that stimulates cytolytic T lymphocytes but cannot mediate their lytic interaction"; J. Immunol.; 137(8):2682-2687 (1986).
Zhang et al., "Tim-3 regulates pro- and anti-inflammatory cytokine expression in human CD14+ monocytes" Journal of Leukocyte Biology (2012) vol. 91 pp. 189-196.
Zhang, "P2.01—Poster Session/Treatment of Advanced Diseases—NSCLC (ID207) A Phase 3 Study of Pembrolizumab vs Platinum-Based Chemotherapy for PD-L1," (NSCLC ID 2182) Abstract from Poster Presentation from International Association for the Study of Lung Cancer, Aug. 9, 2015, retrieved from library.iaslc.org/search-speaker?search_speaker=30076.
Zhang, Xuewu, et al.; "Structural and Functional Ana ysis of the Costimulatory Receptor Programmed Death-1"; Immunity; 20:337-347 (2004).
Zhou et al., "Coexpression of Tim-3 and PD-1 identifies a CD8+ T-cell exhaustion phenotype in mice with disseminated acute myelogenous leukemia" Blood (2011) vol. 117 No. 17 pp. 4501-4510.
Zhu et al., "CSF1/CSF1R Blockade Reprograms Tumor-Infiltrating Macrophages and Improves Response to T-cell Checkpoint Immunotherapy in Pancreatic Cancer Models," Cancer Research (2014) vol. 74, No. 18, pp. 5057-5069.
Zhuang J et al: "Selective IAP inhibition results in sensitization of unstimulated but not CD40-stimulated chronic lymphocytic leukaemia cells to TRAIL-induced apoptosis" Pharmacology Research & Perspectives (2014) vol. 2 Issue 6, Article E00081, 14 pages.
Zou, W. and Chen, L., "Inhibitory B7-family Molecules in the Tumour Microenvironment," Nature Reviews Immunology 8(6):467-477, Nature Publishing Group, England (2008).
Zuberek, K., "The role of in vivo PD-1/PD-L1 interactions in syngeneic and allogeneic antitumor responses in murine tumor models," Blood 98(11):42B (2001).
Zuberek, Krystyna, et al.; "In vitro and in vivo expression regulation of PD-1 and PD-L1 in murine tumor models"; Blood; 98(11 Part 1):25a (2001).
Villalobos, "Primer organismo con ADN artificial logra reproducirse," retrieved from www.fayerwayer.com/2014/05/primer-organismo-con-adn-artificial-logra-reproducirse (2014) last accessed Oct. 18, 2019.
Vivier et al., "Immunoreceptor tyrosine-based inhibition motifs," Immunol Today (1997) vol. 18, No. 6, pp. 286-291.
Walunas et al., "CTLA-4 can function as a negative regulator of T cell activation," Immunity (1994) vol. 1, No. 5, pp. 405-413.
Wang, "Interaction of TIM4-TIM1 Modulates the Function of CD4+CD25+Treg in Food Allergic Mice," Master's Thesis submitted at Zhengzhou University (2010) 65 pages, Chinese with English Abstract.
Watanabe et al., "Current approaches for the treatment of multiple myeloma," Int J Hematol (2013) vol. 97, pp. 333-344.
Weisberg et al., "Smac mimetics: implications for enhancement of targeted therapies in leukemia: Treating leukemia with Smac mimetics," Leukemia (2010) vol. 24, No. 12, pp. 2100-2109.
Wiener et al., "TIM-3 Is Expressed in Melanoma Cells and Is Upregulated in TGF-Beta Stimulated Mast Cells" Journal of Investigative Dermatology (2007) vol. 127 pp. 906-914.
Wolchok et al., "Nivolumab plus Ipilimumab in Advanced Melanoma," N Engl J Med (2013) vol. 369, pp. 122-133.
Workman et al., "Negative Regulation of T Cell Homeostasis by Lymphocyte Activation Gene-3 (CD223)," J Immunol (2005) vol. 174, pp. 688-695.
Abbas, A.K., et al., Cellular and Molecular Immunobiology, 2nd ed., pp. 8, 47-50, W.B. Saunders Company, United States (1991).
Acquaviva et al: "FGFR3 Translocations in Bladder Cancer: Differential Sensitivity to HSP90 Inhibition Based on Drug Metabolism" Molecular Cancer Research. vol. 12. No. 7. Jul. 1, 2014 (Jul. 1, 2014). pp. 1042-1054.
Adams, G.P. and Weiner, L.M., "Monoclonal antibody therapy of cancer," Nature Biotechnology 23(9):1147-1157, Nature Publishing Group, United States (2005).
Agata, Y., et al., "Expression of the PD-1 antigen on the surface of stimulated mouse T and B lymphocytes," International Immunology 8(5):765-772, Oxford University Press, England (1996).
Agoram, "Use of pharmacokinetic/pharmacodynamic modelling for starting dose selection in first-in-human trials of high-risk biologics," Br. J. Clin. Pharm., 67(2):153-160 (2009).
Agrawal, S., et al., "Clinical pharmacokinetics (PK) of BMS-936558, a fully human anti-PD-1 monoclonal antibody," 012 ASCO Annual Meeting, Website, 1 page (2012).
Allard et al. "Targeting CD73 Enhances the Antitumor Activity of Anti-FD-1 and Anti-CTLA-4 mAbs" Clinical Cancer Research (2013) vol. 19, No. 20, pp. 5626-5635.
Allison, J.P. and Krummel, M.F., "The Yin and Yang of T Cell Costimulation," Science 270(5238):932-933, American Association for the Advancement of Science, United States (1995).
Almagro et al. "Humanization of Antibodies" Frontiers in Bioscience (2008) vol. 13, pp. 1619-1633.
Amin et al: "Nivolumab (anti-PD-1; BMS-936558, ONO-4538) in combination with sunitinib or pazopanib in patients (pts) with metastatic renal cell carcinoma (mRCC)" Journal of Clinical Oncology (2014) vol. 32, No. 15 suppl, Abstract 5010.
Anderson et al. "Lag-3, Tim-3, and TIGIT: Co-inhibitory Receptors with Specialized Functions in Immune Regulation" Immunity (2016) vol. 44, pp. 989-1004.

(56) References Cited

OTHER PUBLICATIONS

Anderson et al. "Tim-3, a negative regulator of anti-tumor immunity" Current Opinion in Immunology (2012) vol. 24, No. 2, pp. 213-216.
Andre, E., et al., "Precise Characterization of the Epitope Recognized by a Monoclonal Antibody Against *Escherichia coli* RNA Polymerase," Hybridoma 24(1):1-5, Mary Ann Liebert, Inc., United States (Feb. 2005).
Andrews et al., "LAG3 (CD223) as a Cancer Immunotherapy Target," Immunol Rev. Mar. 2017 ; 276(1): 80-96.
Angevin et al., Analysis of T-Cell Imune Response in Renal Cell Carcinoma: Polarization to Type 1-Like Differentiation Pattern, Clonal T-Cell Expansion and Tumor-Specific Cytotoxicity Int. J. Cancer (1997) vol. 72 pp. 431-440.
Ansari, M.J., et al., "The programmed death-1 (PD-1) pathway regulates autoimmune diabetes in nonobese diabetic (NOD) mice," The Journal of Experimental Medicine 198(1):63-69, The Rockefeller University Press, United States (2003).
Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).
Armand, P., et al., "289 Nivolumab in Patients with relapsed or Refractory Hodgkin Lymphoma—Preliminary Safety, Efficacy and Biomarker Results of a Phase I Study," 56th ASH Annual Meeting and Exposition, Abstracts & Program, San Francisco, CA, Dec. 6-9, 2014.
Ashworth et al. "Management of a Patient With Advanced BRAF-Mutant Melanoma" Journal of the National Comprehensive Cancer Network (2014) vol. 12, No. 3, pp. 315-319.
Aspeslagh et al. "Rationale for anti-OX40 cancer immunotherapy" European Journal of Cancer (2016) vol. 52, pp. 50-66.
Avice et al., "Lymphocyte Activation Gene-3, a MHC Class II Ligand Expressed on Activated T Cells, Stimulates TNF-a and IL-12 Production by Monocytes and Dendritic Cells" The Journal of Immunology (1999) vol. 162 pp. 2748-2753.
Baixeras et al., "Characterization of the Lymphocyte Activation Gene 3-Encoded Protein. A New Ligand for Human Leukocyte Antigen Class II Antgens," J Exp Med (1992) vol. 176, pp. 327-337.
Barber, Daniel L., et al.; "Restoring function in exhausted CD8 T cells during chronic viral infection"; Nature 439:682-687 (2006).
Batus et al. "Optimal Management of Metastatic Melanoma: Current Strategies and Future Directions" Am. J. Clin. Dermatol. (2013) vol. 14, No. 3, pp. 179-194.
Beckman et al. "Antibody Constructs in Cancer Therapy" Cancer (2007) vol. 109, No. 2, pp. 170-179.
Bellucci et al: "JAK1 and JAK2 Modulate Tumor Cell Susceptibility to Natural Killer (NK) Cells Through Regulation of PDL1 Expression", Blood (Nov. 15, 2013), Retrieved from the Internet: www.bloodjournal.orgjcontent/12 2/21/3472.full.pdf [retrieved on Apr. 14, 2016].
Bennett, F., et al., "Program death-1 engagement upon TCR activation has distinct effects on costimulation and cytokine-driven proliferation: attenuation of ICOS, IL-4, and IL-21, but not CD28, IL-7, and IL-15 responses," The Journal of Immunology170(2):711-718, The American Association of Immunologists, United States (2003).
Berg, J.M., et al., "The Immune System," in Biochemistry 5th ed., pp. 921-950, W.H. Freeman and Company, United States (2002).
Berger, R., et al., "Phase I safety and pharmacokinetic study of CT-011, a humanized antibody interacting with PD-1, in patients with advanced hematologic malignancies," Clinical Cancer Research 14(10):3044-3051, American Association for CancerResearch, United States (2008).
Berrien-Elliott et al., "Durable Adoptive Immunotherapy for Leukemia Produced by Manipulation of Multiple Regulatory Pathways of CD8+ T-Cell Tolerance," Cancer Research (2012) vol. 73, pp. 605-616.
Blackburn, Shawn D. et al., "Coregulation of CD8+ T cell exhaustion by multiple inhibitory receptors during chronic viral infection," Nature Immunology, vol. 10(1):29-37 (2009).
Blank et al "Combination of targeted therapy and immunotherapy in melanoma" Cancer Immunol Immunother (2011) vol. 60, pp. 1359-1371.
Blank, C., et al., "Interaction of PD-L1 on tumor cells with PD-1 on tumor-specific T cells as a mechanism of immune evasion: implications for tumor immunotherapy," Cancer Immunology Immunotherapy 54(4):307-314, Springer-Verlag, Germany (2005).
Blank, C., et al., "PD-L1/B7H-1 inhibits the effector phase of tumor rejection by T cell receptor (TCR) transgenic CD8+ T cells," Cancer Research 64(3):1140-1145, American Association for Cancer Research, United States (2004).
Blank, Christian, et al.; "Contribution of the PD-L1/PD-1 pathway to T-cell exhaustion: an update on implications for chronic infections and tumor evasion"; Cancer Immunol. Immunotherapy; 56(5):739-745 (2007).
Blazar, B.R., et al., "Infusion of anti-B7.1 (CD80) and anti-B7.2 (CD86) monoclenal antibodies inhibits murine graft-versus-host disease lethality in part via direct effects on CD4+ and CD8+ T cells," The Journal of Immunology 157(8):3250-3259, TheAmerican Association of Immunologists, United States (1996).
Brahmer, J.R., et al., "Safety and activity of MDX-1106 (ONO-4538) anti-PD-1 monoclonal antibody in patients with selected refractory or relapsed malignancies," Journal of Clinical Oncology 26:Abstract No. 3006, American Society of ClinicalOncology, United States (2008).
Brignone et al., "First-line chemoimmunotherapy in metastatic breast carcinoma: combination of paclitaxel and IMP321 (LAG-3lg) enhances immune responses and antitumor activity" Journal of Translational Medicine (2010) vol. 8 No. 71 pp. 1-11.
Brown et al, "Blockade of Programmed Death-1 Ligands on Dendritic Cells Enhances T Cell Activation and Cytokine Production", J. Immunol. (2003) vol. 170, pp. 1257-1266.
Brown et al., "Tolerance to Single, but Not Multiple, Amino Acid Replacements in Antibody VH CDR2: A Means of Minimizing B Cell Wastage from Somatic Hypermutation?" J Immunol (1996) vol. 156, pp. 3285-3291.
Brown, J.A., et al., "Expression and functional consequences PD-1 ligands on natural APCS and tumors," The FASEB Journal 15(4):A345 (abstract No. 275.23), Federation of American Societies for Experimental Biology, United States (2001).
Opdivo (nivolumab) Drug Label, Initial U.S. Approval: 2014, Revised May 2016.
Ozaki, S., et al., "Immunotherapy of Multiple Myeloma with a Monoclonal Antibody Directed Against a Plasma Cell-specific Antigen, HM1.24," Blood 90(8):3179-3186, American Society of Hematology, United States (1997).
Ozkaynak, E., et al., "Programmed death-1 targeting can promote allograft survival," The Journal of Immunology 169(11):6546-6553, The American Association of Immunologists, United States (2002).
Panka, et al.; "Variable region framework differences result in decreased or increased affinity of variant anti-digoxin antibodies"; Proc. Natl. Acad. Sci. USA; 85:3080-3084 (1988).
Pardoll et al. "The blockade of immune checkpoints in cancer immunotherapy" Nature Reviews Cancer (2012) vol. 12, pp. 252-264.
Patel et al., "Taming dendritic cells with TIM-3: another immunosuppressive strategy used by tumors" Immunotherapy (2012) vol. 4 No. 12 pp. 1795-1798.
Patsoukis, N., et al., "PD-1 Increases PTEN Phosphatase Activity While Decreasing PTEN Protein Stability by Inhibiting Casein Kinase 2," Molecular and Cellular Biology 33(16):3091-3098, American Society for Microbiology, United States (Aug. 2013).
Patsoukis, N., et al., "PD-1 inhibits T cell proliferation by upregulating p. 27 and p. 15 and suppressing Cdc25A," Cell Cycle 11(23):1-5, Landes Bioscience, United States (Dec. 2012).
Patsoukis, N., et al., "Selective Effects of PD-1 on Akt and Ras Pathways Regulate Molecular Components of the Cell Cycle and Inhibit T Cell Proliferation," Science Signaling 5(230): ra46, pp. 1-14, American Association for the Advancement ofScience, United States (Jun. 2012).

(56) References Cited

OTHER PUBLICATIONS

Perez-Gracia et al, "Orchestrating immune check-point blockade for cancer inmunotherapy in combinations", Current Opinion in Immunology (2014) vol. 27 pp. 89-97.
Pinzon-Ortiz et al: "S710: The combination of JAK inhibitor, ruxolitinib, pan-PIM inhibitor, LGH447, and CDK4/6 inhibitor, LEE011, in a preclinical mouse model of myeloproliferative neoplasia", Haematologica, the Hematology Journal: Official Organ of the European Hematology Association, vol. 99. No. Supp 1 (2014) p. 252.
Polyak, M.J. and Deans, J.P., "Alanine-170 and proline-172 are critical determinants for extracellular CD20 epitopes; heterogeneity in the fine specificity of CD20 monoclonal antibodies is defined by additional requirements imposed by both aminoacid sequence and quaternary structure," Blood 99(9):3256-3262, American Society of Hematology, United States (2002).
Postel-Vinay et al. "Challenges of phase 1 clinical trials evaluating immune checkpoint-targeted antibodies" Annals of Oncology (2016) vol. 27, pp. 214-224.
Prigent et al., "Lymphocyte activation gene-3 induces tumor regression and antitumor immune responses," Eur J Immunol (1999) vol. 29, pp. 3867-3876.
Prokunina, L. and Alarcon-Riquelme, M., "The genetic basis of systemic lupus erythematosus—knowledge of today and thoughts for tomorrow," Human Molecular Genetics 13(1):R143-R148, Oxford University Press, England (2004).
Quintarelli et al: "Selective strong synergism of Ruxolitinib and second generation tyrosine kinase inhibitors to overcome bone marrow stroma related drug resistance in chronic myelogenous leukemia," Leukemia Research, New York, NY, US, vol. 38, No. 2, Nov. 15, 2013 (Nov. 15, 2013), pp. 236-242.
Riley, J.L. and June, C.H., "The CD28 family: a T-cell rheostat for therapeutic control of T-cell activation," Blood 105(1):13-21, American Society of Hematology, United States (Jan. 2005).
Rudikoff, et al.; "Single Amino Acid Substitution Altering Antigen-binding Specificity"; Proc. Natl. Acad. Sci. USA; 79:1979-1983 (1982).
Salama, A.D., et al., "Critical role of the programmed death- I (PD-1) pathway in regulation of experimental autoimmune encephalomyelitis," The Journal of Experimental Medicine 198(1):71-78, The Rockefeller University Press, United States (2003).
Sanmamed et al. "Agonists of Co-stimulation in Cancer Immunotherapy Directed Against CD137, OX40, GITR, CD27, CD28, and ICOS" Seminars in Oncology (2015) vol. 42, No. 4, pp. 640-655.
Schöffski et al., "Phase I/II study of the LAG-3 inhibitor ieramilimab (LAG525) ± anti-PD-1 spartalizumab (PDR001) in patients with advanced malignancies," Journal for Immuno Therapy of Cancer (2022) vol. 10, Article e003776, 13 pages.
Scurr et al. "Highly prevalent colorectal cancer-infiltrating LAP+ Foxp3-T cells exhibit more potent immunosuppressive activity than Foxp3+ regulatory T cells" Mucosal Immunology (2013) doi:10.1038/mi.2013.62, pp. 1-12.
Search Report and Written Opinion issued in Singapore Application No. 11201605951Y, dated Oct. 16, 2017.
Shinohara, T., et al., "Structure and chromosomal localization of the human PD-1 gene (PDCD1)," Genomics 23 (3):704-706, Academic Press, United States (1994).
Soh, E.Y., et al., "Neutralizing vascular endothelial growth factor activity inhibits thyroid cancer growth in vivo," Surgery 128(6):1059-1066, Mosby, United States (2000).
Song et al: "3681 Phenotypic and Functional Effects of Novel HDAC Inhibitor LBH589 on Human Lymphocyte Populations", 51st ASH Annual Meeting and Exposition (2009) Retrieved from the Internet: URL:https:jjash.confex.comjash/2889/webprogramjPaper22684.html [retrieved on Apr. 14, 2016].
Song W et al: "HDAC inhibition by LBH589 affects the phenotype and function of human myeloid dendritic cells," Leukemia Jan 2811, vol. 25, No. 1, Jan. 2011 (Jan. 2011), pp. 161-168.
Subramanyam, Meena et al., "Soluble human lymphocyte activation gene-3 modulates allospecific T cell responses," International Immunology, vol. 10(4):679-689 (1998).
Supplementary European Search Report for European Application No. EP 14848888.5, dated May 31, 2017.
Supplementary Partial European Search Report for European Application No. EP 1484888, dated Mar. 1, 2017. 10 pages.
Tamura, H., et al., "B7-H1 costimulation preferentially enhances CD28-independent T-helper cell function," Blood 97(6):1809-1816, The American Society of Hematology, United States (2001).
Tang et al. "Immunotherapy and tumor microenvironment" Cancer Letters (2016) vol. 370, pp. 85-90.
Teeling, J.L., et al., "Characterization of new human CD20 monoclonal antibodies with potent cytolytic activity against non-Hodgkin Lymphomas," Blood 104(6):1793-1800, American Society of Hematology, United States (2004).
Thomas, M.L., "Of ITAMs and ITIMs: turning on and off the B cell antigen receptor," The Journal of Experimental Medicine 181(6):1953-1956, The Rockefeller University Press, United States (1995).
Thompson, R. Houston, et al.; "PD-1 is expressed by tumor-infiltrating immune cells and is associated with poor outcome for patients with renal cell carcinoma"; Clin. Cancer Res. 13(6):1757-1761 (2007).
Thurber et al. "Antibody tumor penetration: Transport opposed by systemic and antigen-mediated clearance" Advanced Drug Delivery Reviews (2008) vol. 60, pp. 1421-1434.
Tiwari, J. Aaps, 19(2):510-519 (2017).
Tomlinson, I.M., et al., "The repertoire of human germline VH sequences reveals about fifty groups of VH segments with different hypervariable loops," Journal of Molecular Biology 227(3):776-798, Elsevier, Netherlands (1992).
Topalian, S., "Q&A: Suzanne Topalian on Immune Therapies", Cancer Discovery 3(7):712, American Association for Cancer Research, United States, published online Jun. 27, 2013.
Topalian, S., et al., "Nivolumab (anti-PD-1; BMS-936558; ONO-4538) in patients with advanced solid tumors: Survival and long-term safety in a phase I trial," accessed at http://meetinglibrary.asco.org/content/113543-132, accessed on Jun. 1, 2016, 2pages.
Trautmann, Lydie, et al.; "Upregulation of PD-1 expression on HIV-specific CD8+ T cells leads to reversible immune dysfunction"; Nat. Med.; 12(10):1198-1202 (2006).
Triebel et al., "LAG-3, A Novel Lymphocyte Activation Gene Closely Related to CD4," J Exp Med (1990) vol. 171, pp. 1393-1405.
Triebel, Frederic et al., "LAG-3: a regulator T-cell and DC responses and its use in therapeutic vaccination," Trends in Immunology, vol. 24(12):619-622 (2003).
Tsai P.K. et al., "Origin of the Isoelectric Heterogeneity of Monoclonal Immunoglobulin h1B4," Pharmaceutical Research, vol. 10(11): 1580-1586 (1993).
Tsai, C-J., et al., "Protein Allostery, signal transmission and dynamics: a classification scheme of allosteric mechanisms," Molecular BioSystems 5(3):207-216, Royal Society of Chemistry, England (2009).
Tsushima, Fumihiko, et al.; "Predominant expression of B7-H1 and its immunoregulatory roles in oral squamous cell carcinoma"; Oral Oncology; 42:268-274 (2006).
Turnis M. et al., "Combinatorial immunotherapy: PD-1 may not be LAG-ing behind any more," Oncolmmunolgy, vol. (7), pp. 1172-1174 (2012).
UniProtKB/Swiss-Prot Database entry, PDCD1.sub.--HUMAN, accessed at http://www.uniprot.org/uniprot/Q15116.txt, accessed on Jun. 1, 2016, 5 pages.
Van Regenmortel, M.H.V., "The recognition of Proteins and Peptides by Antibodies," Journal of Immunoassay 21(2-3):85-108, Taylor & Francis, England (2000).
Vanneman et al: "Combining immunotherapy and targeted therapies in cancer treatment" Nature Reviews Cancer (2012) vol. 12 No. 4 pp. 237-251.
Borate et al., "Phase Ib Study of the Anti-TIM-3 Antibody MBG453 in Combination with Decitabine in Patients with High-Risk Myelodysplastic Syndrome (MDS) and Acute Myeloid Leukemia (AML)," Blood (2019) vol. 134, Supp. 1, Abstract 637, 5 pages.

(56) References Cited

OTHER PUBLICATIONS

Christensen et al., "c-Met as a target for human cancer and characterization of inhibitors for therapeutic intervention," Cancer Letters (2005) vol. 225, pp. 1-26.
Curigliano et al., "Abstract CT183: Phase (Ph) I/II study of MBG453 +/− spartalizumab (PDR001) in patients (pts) ith advanced malignancies," AACR Annual Meeting 2019, Cancer Research, vol. 79, Issue 13, Supplement, 2 pages.
Extended European Search Report issued in European Application No. 19199437.5, mailed Mar. 12, 2020, 8 pages.
Fessas et al., "A molecular and preclinical comparison of the PD-1-targeted T-cell checkpoint inhibitors nivolumab and pembrolizumab," Seminars in Oncology (2017) vol. 44, pp. 136-140.
Lu et al., "Everolimus enhances the cytotoxicity of bendamustine in multiple myeloma cells through a network of pro-apoptotic and cell-cycle-progression regulatory proteins," Acta Biochim Biophys Sin (2013) vol. 45, pp. 683-691.
Mach et al., "Phase (PH) II Study of MBG453 + Spartalizumab in Patients (PTS) with Non-Small Cell Lung Cancer (NSCLC) and Melanoma Pretreated with Anti-PD-1/L1 Therapy," Poster Display Session 3 from ESMO Congress, Sep. 30, 2019, 3 pages.
Miko et al., "Involvement of Galectin-9/TIM-3 Pathway in the Systemic Inflammatory Response in Early-Onset Preeclampsia," PLOS One (2013) vol. 8, No. 8, Article e71811, 9 pages.
Opdivo (nivolumab) Drug Label, Initial U.S. Approval: 2014, Revised Nov. 2016, 58 pages.
Partial European Search Report issued in European Patent Application No. 19206634.8, mailed Apr. 30, 2020.
Wang et al., "Fixed Dosing Versus Body Size-Based Dosing of Monoclonal Antibodies in Adult Clinical Trials," J Clin Pharmacol (2009) vol. 49, pp. 1012-1024.
[No Author Listed] "Crean un ADN sintético capaz de evolucionar," retrieved from www.nationalgeographic.es/ciencia/crean-un-adn-sintetico-capaz-de-evolucionar, Apr. 25, 2012, last accessed Oct. 18, 2019.
[No Author Listed] Press Release: "Bristol-Myers Squibb Announces Collaboration to Evaluate Opdivo (nivolumab) in Combination with Targeted Therapies from Novartis to Treat Non-Small Cell Lung Cancer (NSCLC)," dated Oct. 6, 2014.
Abbas et al. "Functional diversity of helper T lymphocytes" Nature (1996) vol. 383, pp. 787-793.
Anderson "TIM-3 as a therapeutic target in human inflammatory diseases" Expert Opinion on Therapeutic Targets (2007) vol. 11, issue 8, pp. 1005-1009.
Anderson et al. "Promotion of Tissue Inflammation by the Immune Receptor Tim-3 Expressed on Innate Immune Cells" Science (2007) vol. 318, pp. 1141-1143.
Anderson, "Tim-3: An Emerging Target in the Cancer Immunotherapy Landscape" Cancer Immunology Research (2014) vol. 2 No. 5 pp. 393-398.
Ascierto et al. "Future perspectives in melanoma research" meeting report from the "Melanoma Bridge", Napoli, Dec. 5-8, 2013 Journal of Translational Medicine (2014) vol. 12, No. 277, pp. 1-29.
Bigras, et al. "Spatial distribution of DNA ploidy in colorectal carcinoma" Analytic Cellular Pathology (1994) vol. 7, pp. 289-300.
Brahmer et al., "Safety and Activity of Anti-PD-L1 Antibody in Patients with Advanced Cancer," N Engl J Med (2012) vol. 366, pp. 2455-2465.
Brand et al., "Prospect for Anti-HER2 Receptor Therapy in Breast Cancer," Anticancer Research (2006) vol. 26, pp. 463-470.
Brunet et al., "A new member of the immunoglobin superfamily CTLA-4," Nature (1987) vol. 328, pp. 267-270.
Butte et al, "Interaction of human PD-L1 and B7-1", Mol Immunol (2008) vol. 45, pp. 3567-3572.
Butte et al., "Programmed Death-1 Ligand 1 Interacts Specifically with the B7-1 Costimulatory Molecule to Inhibit T Cell Responses," Immunity (2007) vol. 27, pp. 111-122.
Cao et al. "Genetic variations and haplotypes in TIM-3 gene and the risk pf gastric cancer" Cancer Immunol Immunother (2010) vol. 59 pp. 1851-1857.
Carvalho et al., "Doxorubicin: the good, the bad and the ugly effect," Current Medicinal Chemistry (2009) vol. 16, No. 25, pp. 3267-3285.
Catherine Sabatos-Peyton, MBG453: A high affinity, ligand-blocking anti-TIM-3 monoclonal Ab. American Association for Cancer Research (AACR) Annual Meeting, Apr. 17, 2016, New Orleans, Louisiana.
Ceeraz et al., "B7 family checkpoint regulators in immune regulation and disease," Trends Immunol (2013) vol. 34, No. 11, pp. 556-563.
Chesi et al., "IAP antagonists induce anti-tumor immunity in multiple myeloma," Nat Med (2016) vol. 22, No. 12, pp. 1411-1420.
ClincalTrials.gov Identifier: NCT02323126 "Study of Efficacy and Safety of Nivolumab in Combination With EGF816 and of Nivolumab in Combination With INC280 in Patients With Previously Treated Non-small Cell Lung Cancer (EGF816)," Clinicaltrials.gov, last updated Jun. 6, 2018.
ClinicalTrials.gov "History of Changes for Study NCT01454102," ClinicalTrials.Gov, latest version submitted on Nov. 3, 2017.
ClinicalTrials.gov Identifier: NCT02608268, Safety and Efficacy of MBG453 as Single Agent and in Combination With PDR001 in Patients With Advanced Malignancies, Information provided by Novartis (Novartis Pharmaceuticals), last updated Oct. 13, 2016.
ClinicalTrials.gov Identifier: NCT02817633, A Phase 1 Study of TSR-022, an Anti-TIM-3 Monoclonal Antibody, in Patients With Advanced Solid Tumors, Information provided by Tesaro, Inc., last updated Aug. 26, 2016.
Cohen et al., "Image Cytometry of Estrogen Receptors in Breast Carcinomas" Cytometry (1988) vol. 9 pp. 579-587.
Dekruyff et al., "T Cell/Transmembrane, Ig, and Mucin-3 Allelic Variants Differentially Recognize Phosphatidylserine and MEdiate Phagocytosis of Apoptotic Cells" The Journal of Immunology (2010) vol. 184 pp. 1918-1930.
Demaria et al., "Immune-mediated inhibition of Metastases after Treatment with Local Radiation and CTLA-4 Bloackade in a Mouse Model of Breast Cancer," Clinical Cancer Research (2005) vol. 11, pp. 728-734.
Dong et al., "Tumor-associated B7-H1 promotes T-cell apoptosis: A potential mechanism of immune evasion", Nat Med (2002) vol. 8 pp. 793-800.
Dorfman et al., "The phosphatidylserine receptors, T cell immunoglobulin mucin proteins 3 and 4, are markers of histiocytic sarcoma and other histiocytic and decdritic cell neoplasms" Hum Pathol (2010) vol. 41 No. 10 pp. 1486-1494.
Dougan et al., "Regulation of innate and adaptive antitumor immunity by IAP antagonists," Immunotherapy (2018) vol. 10, No. 9, pp. 787-796.
Du Manoir et al., "Ki-67 Labeling in Postmitotic Cells Defines Different Ki-67 Pathways Within the 2c Compartment" Cytometry (1991) vol. 12 pp. 455-463.
Entzminger et al., "De novo design of antibody complementarity determining regions binding a FLAG tetrapeptide," Sci Rep (2017), retrived from www.nature.com/ articles/s41598-017-10737-9.pdf?origin=ppub, last accessed Jan. 12, 2018.
Extended European Search Report issued in European Patent Application No. 18211373.8, mailed Jun. 25, 2019.
Fourcade et al., "Upregulation of Tim-3 and PD-1 expression is associated with tumor antigen-specific CD8+ T cell dysfunction in melanoma patients" The Journal of Experimental Medicine (2010) vol. 207 No. 10 pp. 2175-2186.
Freeman et al., "Cloning of B7-2: a CTLA-4 counter-receptor that costimulates human T cell proliferation," Science (1993) vol. 262, pp. 909-911.
Freeman et al., "TIM genes: a family of cell surface phosphatidylserine receptors that regulate innate and adaptive immunity" Immunol Rev (2010) vol. 235 No. 1 pp. 172-189.
Fulda, "Molecular Pathways: Targeting Inhibitor of Apoptosis Proteins in Cancer—From Molecular Mechanism to Therapeutic Application," Clin Cancer Res (2013) vol. 20, No. 2, pp. 289-295.

(56) References Cited

OTHER PUBLICATIONS

Gao et al., "TIM-3 Expression Characterizes Regulatory T Cells in Tumor Tissues and Is Associated with Lung Cancer Progression" PLoS ONE (2012) vol. 7 No. 2 e30676.
Geng et al., "Soluble Form of T Cell Ig Mucin 3 Is an Inhibitory Molecule in T Cell-Mediated Immune Response" The Journal of Immunology (2006) vol. 176 pp. 1411-1420.
Ghebeh et al., "Doxorubicin downregulates cell surface B7-H1 expression and upregulates its nuclear expression in breast cancer cells: role of B7-H1 as an anti-apoptotic molecule," Breast Cancer Research (2010) vol. 12, No. 4, Article R48, 12 pages.
Golden-Mason et al., "Negative Immune Regulator Tim-3 Is Overexpressed on T Cells in Hepatitis C Virus Infection and Its Blockade Rescues Dysfunctional CD4+ and CD8+ T Cells," J Virol (2009) vol. 83, No. 18, pp. 9122-9130.
Camisaschi et al., "Alternative Activation of Human Plasmacytoid DCs In Vitro and in Melanoma Lesions: Involvement of LAG-3" Journal of Investigative Dermatology (2014) vol. 134 pp. 1893-1902.
Camisaschi et al., "LAG-3 Expression Defines a Subset of CD4+ CD25highFoxp3+ Regulatory T Cells That Are Expanded at Tumor Sites" The Journal of Immunology (2010) vol. 184 pp. 6546-6551.
Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215, Elsevier, the Netherlands (1984).
Carreno, B,M, and Collins, M., "The B7 family of ligands and its receptors: new pathways for costimulation and inhibition of immune responses," Annual Review of Immunology 20:29-53, Annual Reviews, United States (2002).
Carreno, B.M., "BTLA: a new inhibitory receptor with a B7-like ligand," Trends in Immunology 24(10):524-527, Elsevier, England (2003).
Carter, L.L. and Carreno, B.M., et al., "Cytotoxic T-lymphocyte antigen-4 and programmed death-1 function as negative regulators of lymphocyte activation," Immunologic Research 28(1):49-59, Humana Press, United States (2003).
Carter, L.L., et al., "PD-1:PD-L inhibitory pathway affects both CD4(+) and CD8(+) T cells and is overcome by IL-2," European Journal of Immunology 32(3):634-643, Wiley-VCH Verlag GmbH, Germany (2002).
Casati et al., "Soluble Human LAG-3 Molecule Amplifies the In vitro Generation of Type 1 Tumor-Specific Immunity," Cancer Res (2006) vol. 66, No. 8, pp. 4450-4460.
Castelli et al., "Lymphocyte activation gene-3 (LAG-3, CD223) in plasmacytoid dendritic cells (pDCs): a colecular target for the restoration of active antitumor immunity" OncoImmunology (2014) vol. 3 No. 11.
Cespedes "Mouse models in ocogenesis and cancer therapy" Clin. Tranl. Oncol. (2006) vol. 8, No. 5, pp. 318-329.
Chan et al. "Therapeutic antibodies for autoimmunity and inflammation" Nature Reviews Immunology (2010) vol. 10, pp. 301-316.
Chelius, Dirk et al., "Identification and Characterization of Deamidation Sites in the Conserved Regions of Human Immunoglobulin Gamma Antibiodies," Anal. Chemn., American Chemical Society, vol. 77(18): 6004-6011 (2005).
Chen & Flies, "Molecular mechanisms of T cell co-stimulation and co-inhibition" Nat Rev Immunol (2013) vol. 13 No. 4 pp. 227-242.
Chen, L., "Co-inhibitory molecules of the B7-CD28 family in the control of T-cell immunity," Nature Reviews Immunology 4(5):336-347, Nature Publishing Group, England (2004).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Chervontseva A M et al: "Effect of cytarabine on expression of cell adhesion molecules and on endothelium-leukocyte interaction in vitro.", Terapevticheskii Arkhiv 2006, vol. 78, No. 7, 2006, pp. 67-72.
Christiansen et al: "Eradication of solid tumors using histone deacetylase inhibitors combined with irrmune-stimulating antibodies", Proceedings of the National Academy of Sciences, vol. 108 No. 10, Feb. 22, 2011 (Feb. 22, 2011), pp. 4141-4146.
Christiansson Lisa et al: "The tyrosine kinase inhibitors imatinib and dasatinib reduce myeloid suppressor cells and release effector lymphocyte responses.", Molecular Cancer Therapeutics, vol. 14, No. 5, May 2015 (May 2015), pp. 1181-1191.
ClincalTrials.gov Identifier: NCT01988896 "A Phase 1b Study of MPDL3280A (an Engineered Anti-PDL1 Antibody) in Combination With Cobimetinib in Patients With Locally Advanced or Metastatic Solid Tumors" Clinicaltrials.gov, last updated Dec. 1, 2014.
Clinicaltrials.gov (search terms "Novartis" and "LAG3", p. 1: Mar. 30, 2017).
Clinicaltrials.gov Identifier NCT01968109: A Phase 1 Dose Escalation and Cohort Expansion Study of the Safety, Tolerability, and Efficacy of Anti-LAG-3 Monoclonal Antibody (BMS-986016) Administered Alone and in Combination With Anti-PD-1 Monoclonal Antibody (Nivolumab, BMS-936558) in Advanced Solid Tumors. 2013.
Clinicaltrials.gov Identifier NCT02061761: A Phase 1 Dose Escalation and Cohort Expansion Study of the Safety, Tolerability, and Efficacy of Anti-LAG-3 (BMS-986016) in Relapsed or Refractory Chronic Lymphocytic Leukemia and Lymphomas. 2014.
ClinicalTrials.gov Identifier: NCT02040064 "Tolerability and Efficacy of Tremelimumab in Combination With Gefitinib in NSCLC Patients", ClinicalTrials.gov; last updated Jan. 17, 2014.
ClinicalTrials.gov Identifier: NCT02263508 "A Phase 1 b/3, Multicenter, Open-label Trial of Tafimogene Laherparepvec in Combination With Pembrolizumab (MK-3475) for Treatment of Unresected,Stage IIIB to IVM1c Melanoma (Masterkey-265)", ClinicalTrials.gov; last updated Jun. 22, 2015.
ClinicalTrials.gov Identifier: NCT02339571 "Randomized Phase II/III Study of Nivolumab Plus Ipilimumab Plus Sargramostim Versus Nivolumab Plus Ipilimumab in Patients With Unresectable Stage III or Stage IV Melanoma", ClinicalTrials.gov; last updated Apr. 9, 2015.
Cloeckaert, A., et al., "O-Polysaccharide epitopic heterogeneity at the surface of *Brucella* spp.studied by enzyme-linked immunosorbent assay and flow cytometry," Clinical and Diagnostic Laboratory Immunology 5(6):862-870, American Society forMicrobiology, United States (1998).
Collins et al., "The B7 family of immune-regulatory ligands" Genome Biology (2005) vol. 6 No. 223.
Cragg, M.S. et al., "Complement-mediated lysis by anti-CD20 mAb correlated with segregation into lipid rafts," Blood 101(3):1045-1052, American Society of Hematology, United States (2003).
Creelan, B.C., "Update on Immune Checkpoint Inhibitors in Lung Cancer," Journal of the Moffitt Cancer Center 21(1):80-89, H. Lee Moffitt Cancer Center and Research Institute, United States (2014).
Cruse, J.M. and Lewis, R.E., "Antigens and Immunogens," in Atlas of Immunology, 2nd ed., pp. 105-126, CRC Press, United States (Dec. 29, 2003).
Davies, D.R. and Cohen, G.H., "Interactions of protein antigens with antibodies," Proceedings of the National Academy of Sciences USA 93(1):7-12, National Academy of Sciences, United States (1996).
Davies, Julian, et al.; "Affinity improvement of single antibody VH domains: residues in all three hypervariable regions affect antigen binding"; ; 2:169-179 (1996).
Del-Rio, Maria-Luisa, et al.; "Antibody-mediated signaling through PD-1 costimulates T cells and enhances CD28-dependent proliferation"; Eur. J. Immunol.; 35(12):3545-3560 (2005).
Dennis "Off by a whisker" Nature (2006) vol. 442, pp. 739-741.
Dey et al: "Nutl in-3 inhibits the NF[kappa]B Pathway in a p53 Dependent Manner: Implications in Lung Cancer Therapy". Cell Cycle, vol. 6, No. 17, Sep. 1, 2007 (Sep. 1, 2007), pp. 2178-2185.
Dong, H. and Chen, L., "B7-H1 pathway and its role in the evasion of tumor immunity," Journal of Molecular Medicine 81(5):281-287, Springer, Germany (2003).

(56) References Cited

OTHER PUBLICATIONS

Drake et al., "Blocking the regulatory T cell molecule LAG-3 augments in vivo anti-tumor immunity in an autochthonous model of prostate cancer," J Clin Oncol (2006) vol. 24, No. 18S, Abstract 2573.
El Mir et al., "A Soluble Lymphocyte Activation Gene-3 Molecule Used as a Vaccine Adjuvant Elicits Greater Humoral and Cellular Immune Responses to Both Particulate and Soluble Antigens," J Immunol (2000) vol. 164, pp. 5583-5589.
Extended European Search Report for European Application No. EP 1484888.5, mailed May 31, 2017.
Finger, L.R., et al., "The human PD-1 gene: complete cDNA, genomic organization, and developmentally regulated expression in B cell progenitors," Gene 197(1-2):177-187, Elsevier, United States (1997).
Fishwild, D.M. et al., "High-avidity human IgG kappa monoclonal antibodies from a novel strain of minilocus transgenic mice.," Nature Biotechnol., vol. 14, pp. 845-851 (1996).
Fivash, M., et al., "BIAcore for macromolecular interaction," Current Opinion in Biotechnology 9(1):97-101, Current Biology, England (1998).
Fleischer, Bernhard, et al.; "T cell stimulation by staphylococcal enterotoxins"; J. Exp. Medicine; 167(5):1697-1707 (1988).
Franklin, M.C., et al., "Insights into ErbB signaling from the structure of the ErbB2-pertuzumab complex," Cancer Cell 5(4):317-328, Cell Press, United States (Apr. 2004).
Freeman et al., "Engagement of the PD-1 immunoinhibitory receptor by a novel B7 family member leads to negative regulation of lymphocyte activation", J Exp Med. (2000) vol. 192, No. 7, pp. 1027-1034.
Fujimori et al. "A Modeling Analysis of Monoclonal Antibody Percolation Through Tumors: A Binding-Site Barrier" J Mucl Med (1990) vol. 31, pp. 1191-1198.
Fukushima et al.,"Antibodies to T-cell Ig and mucin domain-containing proteins (Tim)-1 and -3 suppress the induction and progression of murine allergic conjunctivitis" Biochemical and Biophysical Research Communications (2006) vol. 353 No. 1 p. 211-16.
Gagliani et al., "Coexpression of CD49b and LAG-3 identifies human and mouse T regulatory type 1 cells" Nature Medicine (2013) vol. 19 No. 6 pp. 739-746.
Garrison K et al: "The small molecule TGF-[beta] signaling inhibitor SM16 synergizes with agonistic OX40 antibody to suppress established mammary tumors and reduce spontaneous metastasis" Cancer Immunology, Immunotherapy (2012) vol. 61 No. 4 pp. 511-521.
Ge, X., et al., "CD134-Allodepletion Allows Selective Elimination of Alloreactive Human T Cells without Loss of Virus-Specific and Leukemia-Specific Effectors," Biology of Blood and Marrow Transplantation 14(5):518-530, American Society for Bloodand Marrow Transplantation, United States (2008).
Nicholson et al., "An Altered Peptide Ligand Mediates Immune Deviation and Prevents Autoimmune Encephalomyelitis" Immunity (1995) vol. 3 pp. 397-405.
Nirschl et al., "Molecular Pathways: Coexpression of Immune Checkpoint Molecules: Signaling Pathways and Implications for Cancer Immunotherapy," Cancer Res (2013) vol. 19, No. 18, pp. 4917-4924.
Nishimura et al., "Developmentally regulated expression of the PD-1 protein on the surface of double-negative (CD4-CD8-) thymocytes," Int Immunol (1996) vol. 8, No. 5, pp. 773-780.
Ohigashi et al, "Clinical Significance of Programmed Death-1 Ligand-1 and Programmed Death-1 Ligand-2 Expression in Human Esophageal Cancer" Clin Cancer Research (2005) vol. 11, pp. 2947-2953.
Ohno et al., "Antigen-binding specificities of antibodies are primarily determined by seven residues of VH," PNAS (1985) vol. 82, pp. 2945-2949.
Okamoto et al., "T-Helper Type 1/T-Helper Type 2 Balance in Malignant Pleural Effusions Compared to Tuberculous Pleural Effusions" Chest (2005) vol. 128 pp. 4030-4035.
Okazaki et al, "PD-1 and PD-1 ligands: from discovery to clinical application" Intern. Immun. (2007) vol. 19, pp. 813-824.
Okudaira et al., "A modified version of galectin-9 suppresses cell growth and induces apoptosis of human T-cell leukemia virus type 1-infected T-cell lines" Int. J. Cancer (2007) vol. 120 pp. 2251-2261.
Opdivo (nivolumab) Drug Label, Initial U.S. Approval: 2014, Revised Oct. 2016.
Opposition filed by Asilfa AG in corresponding Chilean Application No. 2017-00888 on Oct. 24, 2017, assigned litigation file number by the National Institute of Industrial Property of Chile (INAPI) on Feb. 27, 2018, notified by INAPI to agent on Mar. 2, 2018.
Opposition filed by Laboratorios Legrand S.A. in corresponding Colombian Application No. NC2017/0003490 on Dec. 7, 2017, admitted Dec. 19, 2017, published Dec. 20, 2017.
Opposition filed in Colombian Application No. NC2016/0001001, filed Feb. 15, 2017.
Pal et al., "Programmed Death-1 Inhibition in Renal Cell Carcinoma: Clinical Insights and Future Directions," Clinical Adv Hem Onc (2014) vol. 12, Issue 2, pp. 90-99.
Paterson et al., "The Programmed Death-1 Ligand 1:B7-1 Pathway Restrains Diabetogenic Effector T Cells In Vivo," J Immunol (2011) vol. 187, pp. 1097-1105.
Phong et al., "Tim-3 enhances Fc[epsilon]RI-proximal signaling to modulate mast cell activation," J Experimental Medicine (2015) vol. 212, No. 13, pp. 2289-2304.
Post Grant Opposition filed in Colombian Patent Application No. NC2016/0001001, dated Jul. 31, 2018.
Powles et al., "MPDL3280A (anti-PD-L1) treatment leads to clinical activity in metastatic bladder cancer," Nature (2014) vol. 515, pp. 558-562.
Raziorrouh et al. "The Immunoregulatory Role of CD244 in Chronic Hepatitis B Infection and its Inhibitory Potential on Virus-Specific CD8+ T-cell Function" Hepatology (2010) vol. 52 pp. 1934-1947.
Richter et al., "On the role of the inhibitory receptor LAG-3 in acute and chronic LCMV infection," Int Immunol (2009) vol. 22, No. 1, pp. 13-23.
Rowe et al., "Innate IFN-gamma is essential for programmed death ligand-1-mediated T cell stimulation following Listeria monocytogenes infection," J Immunol (2012) vol. 189, No. 2, pp. 876-884.
Sabatos et al. "Interaction of Tim-3 and Tim-3 ligand regulates T helper type 1 responses and induction of peripheral tolerance" Nature Immunology (2003) vol. 4, pp. 1102-1110.
Sabatos-Peyton et al., "Blockade of Tim-3 binding to phosphatidylserine and CEACAM1 is a shared feature of anti-Tim-3 antibodies that have functional efficacy," Oncoimmunology (2018) vol. 7, No. 2, Article e1385690, 9 pages.
Sachdev et al., "Phase 1/2a study of double immune suppression blockade by combining a CSF1R inhibitor (pexidartinib/PLX3397) with an anti-PD-1 antibody (pembrolizumab) to treat advanced melanoma and other solid tumors," Gynecologic Oncology (2016) vol. 141, pp. 147-148.
Sakuishi et al., "Emerging Tim-3 functions in anti-microbial and tumor immunity" Trends Immunol (2011) vol. 32 No. 8 pp. 345-349.
Sakuishi et al., "Targeting Tim-3 and PD-1 pathways to reverse T cell exhaustion and restore anti-tumor immunity," J Experimental Medicine (2010) vol. 207, No. 10, pp. 2187-2194.
Sakuishi et al., "TIM3+FOXP3+ regulatory T cells are tissue-specific promoters of T-cell dysfunction in cancer" OncoImmunology (2013) vol. 2 No. 4 pp. e23849-1-e23849-9.
Santiago et al., "Structures of T Cell Immunoglobulin Mucin Receptors 1 and 2 Reveal Mechanisms for Regulation of Immune Responses by the TIM Receptor Family" Immunity (2007) vol. 26 pp. 299-310.
Schroll, A. et al., "Tim3 Is Upregulated and Protective in Nephrotoxic Serum Nephritis", The American Journal of Pathology, vol. 176, No. 4, pp. 1716-1742, Apr. 2010.
Search Report and Written Opinion issued in Singapore Application No. 11201605627T dated Aug. 15, 2017.

(56) References Cited

OTHER PUBLICATIONS

Search Report and Written Opinion issued in Singapore Application No. 11201702401R, completed Mar. 29, 2018.
Shakhov et al., "Smuckler/TIM4 is a distinct member of TIM family expressed by stromal cells of secondary lymphoid tissues and associated with lymphotoxin signaling" Eur. J. Immunol (2004) vol. 34 pp. 494-503.
Sher et al. "Regulation of Immunity to Parasited by T cells and T Cell-derived Cytokines" Annual Review Immunol (1992) vol. 10, pp. 385-409.
Simeone et al., "Immunomodulating antibodies in the treatment of metastatic melanoma: The experience with anti-CTLA-4, anti-CD137, and anti-PD1," Journal of Immunotoxicology (2012) vol. 9, No. 3, pp. 241-247.
Simmons et al., "Tim-3+ T-bet+ Tumor-Specific Th1 Cells Colocalize with and Inhibit Development and Growth of Murine Neoplasms" The Journal of Immunology (2005) vol. 174 pp. 1405-1415.
Soares et al. "Recombinant Himan Tumor Antigen MUC1 Expressed in Insect Cells: Structure and Immunogenicity" Protein Expression and Purification (2001) vol. 22, pp. 92-100.
Steele et al., "CXCR2 Inhibition Profoundly Suppresses Metastases and Augments Immunotherapy in Pancreatic Ductal Adenocarcinoma," Cancel Cell (2016) vol. 29, pp. 832-845.
Stewart et al., "MEDI4736: Delivering effective blockade of immunosuppression to enhance tumour rejection: Monoclonal antibody discovery and practical development," Cancer Res (2011) vol. 71, No. 8 (Supp), Abstract LB-158.
Strome et al., "A Mechanistic Perspective of Monoclonal Antibodies in Cancer Therapy Beyond Target-Related Effects," The Oncologist (2007) vol. 12, pp. 1084-1095.
Stromnes et al., "Pancreatic Cancer: Planning Ahead for Metastatic Spread," Cancel Cell (2016) vol. 29, No. 6, pp. 774-776.
Swallow et al., "B7h, a Novel Costimulatory Homolog of B7.1 and B7.2, Is Induced by TNFa," Immunity (1999) vol. 11, pp. 423-432.
Sánchez-Fueyo et al., "Tim-3 inhibits T helper type 1-mediated auto- and alloimmune responses and promotes immunological tolerance," Nat Immunol (2003) vol. 4, No. 11, pp. 1093-1101.
Takamura et al., "Premature Terminal Exhaustion of Friend Virus-Specific Effector CD8+ T Cells by Rapid Induction of Multiple Inhibitory Receptors" J Immunol (2010) vol. 184 pp. 4696-4707.
Thangamathesvaran et al., "Immune checkpoint inhibitors and radiotherapy—concept and review of current literature," Ann Transl Med (2018) vol. 6, No. 8, Article 155, 11 pages.
Thomas et al "Combined Effects of RU486 and Tamoxifen on the Growth and Cell Cycle Phases of the MCF-7 Cell Line" Journal of Clinical Endocrinology and Metabolism (1992) vol. 75, Issue 3, pp. 865-870.
Thomas et al. "Effects of Gossypol on the Cell Cycle Phases in T-47D Human Breast Cancer Cells" Anticancer Research (1991) vol. 11, No. 4, pp. 1469-1476.
Thompson et al, "Tumor B7-H1 Is Associated with Poor Prognosis in Renal Cell Carcinoma Patients with Long-term Follow-up" Cancer Res. (2006) vol. 66, pp. 3381-3385.
Topalian et al., "Safety, Activity, and Immune Correlates of Anti-PD-1 Antibody in Cancer," N Engl J Med (2012) vol. 366, No. 26, pp. 2443-2454.
Triebel, "LAG-3: a regulator of T-cell and DC responses and its use in therapeutc vaccination," Trends Immunol (2003) vol. 24, No. 12, pp. 619-622.
Tuskan et al., "Real-time PCR analysis of candidate imprinted genes on mouse chromosome 11 shows balanced expression from the maternal and paternal chromosomes and strain-specific variation in expression levels" Epigenetics (2008) vol. 3 No. 1 pp. 43-50.
Van De Weyer et al. "A highly conserved tyosine of Tim-3 is phosphorylated upon stimulation by its ligand galectin-9" Biochemical and Biophysical Research Communications (2006) vol. 351, pp. 571-576.
Henry et al., "Structure and evolution of the extended B7 family," Immunol Today (1999) vol. 20, No. 6, pp. 285-288.
Herbst et al., "A study of MPDL3280A, an engineered PD-L1 antibody in patients with locally advanced or metastatic tumors," J Clin Oncol (2013) vol. 31, No. 15 (Supp), Abstract 3000.
Highfill et al., "Disruption of CXCR2-Mediated MDSC Tumor Trafficking Enhances Anti-PD1 Efficacy," Science Translational Medicine (2014) vol. 6, Issue 237, Article 237ra67, 15 pages.
Hofstra et al., "Prevention of Th2-like cell responses by coadministration of IL-12 and IL-18 is associated with inhibition of antigen-induced airway hyperresponsiveness, eosinophilia, and serum IgE levels." Journal of Immunology (1998) vol. 161 No. 9 pp. 5054-5060.
Hong et al., "Phase I/II study of LAG525 +/− spartalizumab (PDR001) in patients (pts) with advanced malignancies," J Clin Oncol (2018) vol. 36, No. 15, Supplement 1, Abstract Only.
Huang et al., "Lymphoma endothelium preferentially expresses Tim-3 and facilitates the progression of lymphoma by mediating immune evasion" The Journal of Experimental Medicine (2010) vol. 207 No. 3 pp. 505-520.
International Search Report and Written Opinion for International Application No. PCT/US2015/055390, dated Dec. 17, 2015.
International Search Report and Written Opinion for International Application No. PCT/US2016/044549 dated Oct. 14, 2016.
International Search Report and Written Opinion issued in International Application No. PCT/US2018/039825, mailed Oct. 4, 2018.
International Search Report and Written Opinion issued in PCT/US2007/085100, mailed Apr. 28, 2008, 11 pages.
International Search Report and Written Opinion issued in PCT/US2018/061534, mailed Apr. 1, 2019, 9 pages.
Jan et al., "Prospective separation of normal and leukemic stem cells based on differential expression of TIM3, a human acute myeloid leukemia stem cell marker" PNAS (2011) vol. 108 No. 12 pp. 5009-5014.
Jin et al. "Cooperation of Tim-3 and PD-1 in CD8 T-cell exhaustion during chronic viral infection" PNAS (2010) vol. 107, Issue 33, pp. 14733-14738.
Jones et al., "Tim-3 expression defines a novel population of dysfunctional T cells with highly elevated frequencies in progressive HIV-1 infection," J Exp Med (2008) vol. 205, No. 12, pp. 2763-2779.
Kearl et al., "PD-1/PD-L1 Blockade after Transient Lymphodepletion to Treat Myeloma," Presentation from Society for Immunotherapy of Cancer Conference, Oct. 27, 2012, North Bethesda, Maryland, 19 pages.
Keytruda (pembrolizumab) Drug Label, Initial U.S. Approval: 2014, Revised Aug. 2016.
Khaitov, Immunologia, Moscow, (2011) "Geotar-Media", p. 103.
Kikushige et al. "TIM-3 as a therapeutic target for malignant stem cells in acute myelogenous leukemia" New York Academy of Sciences (2012) vol. 1266, pp. 118-123.
Klibi et al. "Blood diffusion and Th1-suppressive effects of galectin-9-containing exosomes released by Epstein-Barr virus-infected nasopharyngeal carcinoma cells" Blood (2009) vol. 113 No. 9 pp. 1957-1966.
Koga et al., "Blockade of the Interaction Between PD-1 and PD-L1 Accelerates Graft Arterial Disease in Cardiac Allografts," Arterioscler Thromb Vasc Biol (2004) vol. 24, pp. 2057-2062.
Koya et al., "BRAF Inhibitor Vemurafenib Improves the Antitumor Activity of Adoptive Cell Immunotherapy," Cancer Res (2012) vol. 72, No. 16, pp. 3928-3937.
Kuchroo et al. "The TIM Gene Family: Emerging Roles in Immunity and Disease" Nature Reviews Immunology (2003) vol. 3, pp. 454-462.
Kuchroo et al., "B7-1 and B7-2 Costimulatory Molecules Activate Differentially the Th1/Th2 Developmental Pathways: Application to Autoimmune Disease Therapy" Cell (1995) vol. 80 No. 707-18.
Kwong et al., "Molecular Analysis of Tumor-Promoting CD8+ Cells in Two-Stage Cutaneous Chemical Carcinogenesis" J Invest Dermatol (2010) vol. 130 No. 6 pp. 1726-1736.
Lack et al. "Nebulized but not parenteral IFN-gamma decreases IgE production and normalizes airways function in a murine model of allergen sensitization" Journal of Immunology (1994) vol. 152, pp. 2546-2554.

(56) References Cited

OTHER PUBLICATIONS

Lee et al. "The inhibition of the T-cell immunoglobulin and mucin domain 3 (Tim3) pathway enhances the efficacy of tumor vaccine" Biochemical and Biophysical Reseach Communications (2010) vol. 402, pp. 88-93.
Lehmann et al, "Identification of human triple-negative breast cancer subtypes and preclinical models for selection of targeted therapies", J Clin Invest. (2011) 121(7): 2750-2767.
Lenschow et al., "Expression and functional significance of an additional ligand for CTLA-2," PNAS (1993) vol. 90, pp. 11054-11058.
Lenschow et al., "Long-term survival of xenogeneic pancreatic islet grafts induced by CTLA4lg," Science (1992) vol. 257, Issue 5071, pp. 789-792.
Liblau et al. "Th1 and Th2 CD4+ T cells in the pathogenesis of organ-specific autoimune diseases" Immunology Today (1995) vol. 16, Issue 1, pp. 34-38.
Linsley et al., "CTLA-4 Is a Second Receptor for the B Cell Activation Antigen B7," J Exp Med (1991) vol. 174, pp. 561-569.
Linsley et al., "Immunosuppression in Vivo by a Soluble Form of the CTLA-4 T Cell Activation Molecule," Science (1992) vol. 257, pp. 792-795.
Liu et al., "A Novel Kinase Inhibitor, INC28060, Blocks c-MET-Dependent Signaling, Neoplastic Activities, and Cross-Talk with EGFR and HER-3," Clin Cancer Res (2011) vol. 17, No. 22, pp. 7127-7138.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) vol. 21, No. 7, pp. 1639-1651.
Loser et al., "IL-10 Controls Ultraviolet-Induced Carcinogenesis in Mice" The Journal of Immunology (2007) vol. 179 pp. 365-371.
Maier et al., "PD-1: PD-L1 Interactions Contribute to the Functional Suppression of Virus-Specific CD8+ T Lymphocytes in the Liver," J Immunol (2007) vol. 178, pp. 2714-2720.
Makishi et al. "Retracted: A modified version of galectin-9 induces cell cycle arrest and apoptosis of Burkitt and Hodgkin lymphoma cells" British Journal of Hematology (2008) vol. 142 pp. 583-594.
Manning et al, "A model of multiple myeloma: culture of 5T33 murine myeloma cells and evaluation of tumorigenicity in the C57BL/KaLwRij mouse.", Br J Cancer., 66(6): 1088-1093 (1992).
Mocellin et al., "CTLA-4 blockade and the renaissance of cancer immunotherapy," Biochim Biophys Acta (2013) vol. 1836, pp. 187-196.
Mokyr et al, "Realization of the Therapeutic Potential of CTLA-4 Blockade in Low-Dose Chemotherapy-treated Tumor-bearing Mice", Cancer Research, 58:5301-5304 (1998).
Monney et al. "Th1-specific cell surface protein Tim-3 regulates macrophage activation and severity of an autoimmune disease" Nature (2002) vol. 415, pp. 536-541.
Mosmann et al. "The expanding universe of T-cell subsets: Th1, Th2 and more" Immunology Today (1996) vol. 17, Issue 3, pp. 138-146.
Mossman et al. "Two Types of Murine Helper T Cell Clone" Journal of Immunology (1986) vol. 136, Issue 7, pp. 2348-2357).
Mou et al., "Association Between TIM-1 Gene Polymorphisms and Allergic Rhinitis in a Han Chinese Population" J Investig Allergol Clin Immunol (2010) vol. 20 No. 1 pp. 3-8.
Murrey et al., Biokhimiya cheloveka, Mir (1993) vol. 1, p. 34.
Nagahara et al., "Galectin-9 Increases Tim-3+ Dendritic Cells and CD+ T Cells and Enhances Antitumor Immunity via Galectin-9-Tim-3 Interactions" The Journal of Immunology (2008) vol. 181 pp. 7660-7669.
Najjar et al., "Myeloid-Derived Suppressor Cell Subset Accumulation in Renal Cell Carcinoma Parenchyma Is Associated with Intratumoral Expression of IL1beta, IL8, CXCL5, and Mip-1alpha," Clinical Cancer Research (2016) vol. 23, No. 9, pp. 2346-2355.
Neubert et al., "T cell-induced CSF1 promotes melanoma resistance to PD1 blockade," Science Translational Medicine (2018) vol. 10, No. 436, Article eaan3311, 14 pages.
Ngiow et al. "Prospects for TIM3-Targeted Antitumor Immunotherapy" Cancer Research (2011) vol. 71, Issue 21, pp. 6567-6571.
Ngiow et al., "Anti-TIM3 Antibody Promotes T Cell IFN-y-Mediated Antitumor Immunity and Suppresses Established Tumors" Cancer Research (2011) vol. 71 No. 10 pp. 3540-3551.
Gettinger et al. "Safety and Response 1-98 With Nivolumab (Anti-PD-1; BMS-936558, ONO-4538) Plus Erlotinib in Patients (Pts) With Epidermal Growth Factor Receptor Mutant (EGFR MT) Advanced Non-Small Cell Lung Cancer (NSCLC} Metastatic Non-Small Cell Lung Cancer" International Journal of Radiation: Oncology Biology Physics (2014) vol. 90, No. 5, pp. S34-S35.
Giraldo et al., "Orchestration and Prognostic Significance of Immune Checkpoints in the Microenvironment of Primary Metastatic Renal Cell Cancer" Clinical Cancer Research (2015) vol. 21 No. 13 pp. 3031-3040.
Goding et al. "Restoring immune function of tumor-specific CD4+ T cells during recurrence of melanoma" J. Immunol. (2013) vol. 190, No. 9, pp. 4899-4909.
Goldberg et al. "LAG-3 in Cancer Immunology" Current Topics in Microbiology and Immunology (2010) vol. 344, pp. 269-278.
Greenspan, N.S., "Epitopes, paratopes and other topes: do immunologists know what they are talking about?" Bulletin de l'Institut Pasteur 90(4):267-279, Elsevier, France (1992).
Grimwood, Pharm. Therapeutics, 122(3):281-301 (2009).
Grosso et al "LAG-3 regulates CD8+ T cell accumulation and effector function in murine selfand tumor-tolerance systems" The Journal of Clinical Investigation (2007) vol. 117, No. 11, pp. 3383-3392.
Grosso, Joseph F. et al., "LAG-3 regulates CD8+ T cell accumulation and effector function in murine self- and tumor-tolerance systems," J. Clin. Invest., vol. 117(11 ):3383-3392 (2007).
Grygielewicz Paulina et al: "Epithelial-mesenchymal transition confers resistance to selective FGFR inhibitors in SNU-16 gastric cancer cells". Gastric Cancer. Springer Japan. Tokyo. vol. 19. No. 1., Nov. 19, 2014 (Nov. 19, 2014). pp. 53-62.
Haitov, "Immunology: Structure and Functions of the Immune System," Geotar-Media Publishing Group, Moscow (2013) p. 110. Russian.
Hallett et al., "Immunosuppressive Effects of Multiple Myeloma Are Oversome by PD-L1 Blockade" Biol Blood Marrow Transplant (2011) vol. 17, No. 8, pp. 1133-1145.
Hamid et al., "Safety and Tumor Responses with Lambrolizumab (Anti-PD-1) in Melanoma" New England Journal of Medicine (2013) vol. 369 No. 2 pp. 134-144.
Hansen, J.A., et al., "Monoclonal Antibodies Identifying a Novel T-Cell Antigen and la Antigens of Human Lymphocytes," Immunogenetics 10:247-260, Springer-Verlag (1980).
Harlow, E. and Lane, D., "Using Antibodies: A Laboratory Manual," Cold Spring Harbor Laboratory Press, Cold Spring Harbor, United States various pages (1999).
Hastings et al., "TIM-3 is Expressed on Activated Human CD4+ T Cells and Regulates Th1 and Th17 Cytokines" Eur J Immunol (2009) vol. 39 No. 9 pp. 2492-2501.
He, Y-F., et al., "Blocking programmed death-1 ligand-PD-1 interactions by local gene therapy results in enhancement of antitumor effect of secondary lymphoid tissue chemokine," The Journal of Immunology 173(8):4919-4928, The American Association of Immunologists, United States (2004).
Hemon et al,. "MHC Class II Engagement by Its Ligand LAG-3 (CD223) Contributes to Melanoma Resistance to Apoptosis" J Immunol (2011) vol. 186 pp. 5173-5183.
Hirano, F., et al., "Blockade of B7-H1 and PD-1 by monoclonal antibodies potentiates cancer therapeutic immunity," Cancer Research 65(3):1089-1096, American Association for Cancer Research, United States (2005).
Hogenesch et al. "Challenges in pre-clinical testing of anti-cancer drugs in cell culture and in animal models" Journal of Controlled Release (2012) vol. 164, No. 2, pp. 183-186.
Huang et al., "Role of LAG-3 in Regulatory T Cells," Immunity (2004) vol. 21, pp. 503-513.
Huang, Z., "Structural chemistry and therapeutic intervention of protein-protein interactions in immune response, human immuno-

(56) References Cited

OTHER PUBLICATIONS deficiency virus entry, and apoptosis," Pharmacology & Therapeutics 86(3):201-215, Pergamon Press, England (2000).
International Search Report and Written Opinion for International Application No. PCT/US2015/053799 dated May 17, 2016.
International Search Report and Written Opinion for International Application No. PCT/US2015/066812 dated Mar. 23, 2016.
International Search Report and Written Opinion for International Application No. PCT/US2016/044545 dated Oct. 28, 2016.
International Search Report and Written Opinion for International Application No. PCT/US2016/044547 dated Oct. 18, 2016.
International Search Report and Written Opinion for PCT/US2014/057491 dated Jan. 7, 2015.
International Search Report and Written Opinion for PCT/US2015/012754 dated May 20, 2015.
International Search Report and Written Opinion for PCT/US2015/013913 mailed May 4, 2015.
International Search Report and Written Opinion for PCT/US2015/020474 dated Jun. 15, 2015.
International Search Report and Written Opinion for PCT/US2015/049826 dated Dec. 16, 2015.
International Search Report and Written Opinion issued in International Application No. PCT/US2016/067200, mailed Apr. 10, 2017.
Iouzalen et al., "LAP, a lymphocyte activation gene-3 (LAG-3)-associated protein that binds to a repeated EP motif in the intracellular region of LAG-3, may participate in the down-regulation of the CD3/TCR activation pathway," Eur J Immunol (2001) vol. 31, pp. 2885-2891.
Ishida et al., "Induced expression of PD-1, a novel member of the immunoglobulin gene superfamily, upon programmed cell death," The EMBO Journal (1992) vol. 11, No. 11, pp. 3887-3895.
Ishima, R. and Torchia, D.A., "Protein Dynamics from NMR," Nature Structural Biology 7(9):740-743, Nature Publishing Company, United States (2000).
Iwai et al, "Involvement of PD-L1 on tumor cells in the escape from host immune system and tumor immunotherapy by PD-L1 blockade" PNAS (2002) vol. 99, pp. 12293-12297.
Iwai et al, "PD-1 blockade inhibits hematogenous spread of poorly immunogenic tumor cells by enhanced recruitment of effector T cells", International Immunology (2005) vol. 17, No. 2, pp. 133-144.
Iwai, Y., et al., "Microanatomical localization of PD-1 in human tonsils," Immunology Letters 83(3):215-220, Elsevier, Netherlands (2002).
Iwai, Y., et al., "PD-1 inhibits antiviral immunity at the effector phase in the liver," The Journal of Experimental Medicine 198(1):39-50, The Rockefeller University Press, United States (2003).
Jason-Moller, L., et al., "Overview of Biacore Systems and Their Applications," Current Protocols in Protein Science S45:19.13.1-19.13.14, John Wiley & Sons, Inc., United States (2006).
Jiang et al, "mTOR Kinase Inhibitor AZD8855 Enhances the Inmunotherapeutic Activity of an Agonist CD40 Antibody in Cancer Treatment" Cancer Research (2011) vol. 71 No. 12, pp. 4074-4084.
Jiang X et al: "The activation of MAPK in melanoma cells resistant to BRAF inhibition promotes PD-L1 expression that is reversible by MEK and PI3K inhibition", Clinical Cancer Research, the American Association for Cancer Research, US, vol. 19, No. 3, Feb. 1, 2013 (Feb. 1, 2013). pp. 598-609.
Jing et al., "Combined immune checkpoint protein blockade and low dose whole body irradiation as immunotherapy for myeloma," Journal for Immuno Therapy of Cancer (2015) vol. 3, No. 2, 15 pages.
Johne, B., "Protocol: Epitope Mapping by Surface Plasmon Resonance in the BIAcore," Molecular Biotechnology 9(1):65-71, Humana Press, United States (1998).
Ju et al., "T cell immunoglobulin-and mucin-domain-containing molecule-3 (Tim-3) mediates natural killer cell suppression in chronic hepatitis B" Journal of Hepatology (2010) vol. 52 No. 3 pp. 322-329.
Kanai, T., et al., "Blockade of B7-H1 Suppresses the Development of Chronic Intestinal Inflammation," The Journal of Immunology 171(8):4156-4163, American Association of Immunologists, Inc., United States (2003).
Karu et al., "Recombinant Antibody Technology," ILAR Journal, vol. 37, No. 3, pp. 132-141 (1995).
Kasagi, S., et al., "Anti-programmed cell death 1 antibody reduces CD4+PD-1+ T cells and relieves the lupus-like nephritis of Nzb/W FI mice," The Journal Immunology 184(5):2337-2347, The American Association of Immunologists, United States (2010).
Kaveri, S., "Epitope and idiotope mapping using monoclonal antibodies," Medthods in Molecular Biology 51:171-181, Humana Press, United States (1995).
Kearl et al., "Programmed Death Receptor-1/Programmed Death Receptor Ligand-1 Blockage after transient Lymphodepletion to Treat Myeloma," J Immunol (2013) vol. 190, pp. 5620-5628.
Kearley et al., "Th-2 driven, allergen-induced airway inflammation is reduced after treatment with anti-Tim-3 antibody in vivo" The Journal of Experimental Medicine (2007) vol. 204 No. 6 pp. 1289-1294.
Keytruda (pembrolizumab) Drug Label, Initial U.S. Approval: 2014, Revised Oct. 2016.
Khalil et al. "The New Era of Cancer Immunotherapy: Manipulating T-Cell Activity to Overcome Malignancy" Immunotherapy of Cancer In: Advances in Cancer Research (2015) vol. 128, pp. 1-68.
Kier et al., "PD-1 and its ligands in tolerance and immunity" Annu. Rev. Immunol. (2008) vol. 26 pp. 677-704.
Kikushige et al., "TIM-3 Is a Promising Target to Selectively Kill Acute Myeloid Leukemia Stem Cells" Cell Stem Cell (2010) vol. 7 pp. 708-717.
Kim et al: "Eradication of metastatic mouse cancers resistant to irrmune checkpoint blockade by suppression of myeloid-derived cells. (Includes Supporting Information)", Proceedings of the National Academy of Sciences of the United States of America, vol. 111, No. 32, Aug. 12, 2014 (Aug. 12, 2014), pp. 11774-11777.
Kirkwood et al, "Immunotherapy of cancer in 2012" CA: A Cancer Journal for Clinicians (2012) vol. 62 No. 5 pp. 309-335.
Klein Jan M. et al: "The histone deacetylase inhibitor LBH589 (panobinostat) modulates the crosstalk of lymphocytes with Hodgkin lymphoma cell lines," PLOS ONE (2013) vol. 8, No. 11, E79502, 2813, 6 pages.
Knight et al. "Host immunity contributes to the antimelanoma activity of BRAF inhibitors" The Journal of Clinical Investigation (2013) vol. 123, No. 3, pp. 1371-1381.
Knights et al., "Inhibitor of apoptosis protein (IAP) antagonists demonstrate divergent immunomodulatory properties in human immune subsets with implications for combination therapy" Cancer Immunology and Immunotherapy (2013) vol. 62 No. 2 pp. 321-335.
Kocak, Ergun et al., "Combination Therapy with Anti-CTL Antigen-4 and Anti-4-1 BB Antibodies Enhances Cancer Immunity and Reduces Autoimmunity," Cancer Res., vol. 66(14):7276-7284 (2006).
Konishi, J., et al., "B7-H1 expression on non-small cell lung cancer cells and its relationship with tumor-infiltrating lymphocytes and their PD-1 expression," Clinical Cancer Research 10(15):5094-5100, American Association for Cancer Research, United States (2004).
Korman et al, "Checkpoint Blockade in Cancer Immunotherapy" Adv Immunol (2006) vol. 90 pp. 297-339.
Kroon D. et al., "Identification of Sites of Degradation in a Therapeutic Monoclonal Antibody by Peptide Mapping," Pharmaceutical Research, vol. 9(11 ): 1386-1393 (1992).
Ladner, R.C., "Mapping the epitopes of Antibodies," Biotechnology and Genetic Engineering Reviews 24(1):1-30, Taylor & Francis, England (2007).
Laricchia,Robbio, L., et al., "Mapping of Monoclonal Antibody-and Receptor-Binding Domains on Human Granulocyte-Macrophage Colony-Stimulation Factor (rhGM-CSF) Using a Surface Plasmon Resonance-Based Biosensor," Hybridoma 15(5):343-350, Mary AnnLiebert, Inc. United States (1996).
Latchman et al., "PD-L2 is a second ligand for PD-1 and inhibits T cell activation," Nature Immunol (2001) vol. 2, No. 3, pp. 261-268.

(56) References Cited

OTHER PUBLICATIONS

Leach, D.R., et al., "Enhancement of antitumor immunity by CTLA-4 blockade," Science 271(5256):1734-1736, American Association for the Advancement of Science, United States (1996).
Lesokhin, A.M., et al., "291 Preliminary Results of a Phase I Study of Nivolumab (BMS-936558) in Patients with Relapsed of Refractory Lymphoid Malignancies," 56th ASH Annual Meeting and Exposition, Abstracts & Program, San Francisco, CA, UnitedStates, Dec. 6-9, 2014.
Lewis, D.E., et al., "Tumor Necrosis Factor-alpha and CD80 Modulate CD28 Expression through a Similar Mechanism of T-cell Receptor-Independent of Transcription," The Journal of Biological Chemistry 279(28):29130-29138, The American Society forBiochemistry and Molecular Biology, Inc., United States (2004).
Li et al., "Contribution of PD-L1 to oncogenesis of lymphoma and its RNAi-based targeting therapy" Leukemia & Lymphoma (2012) vol. 53, No. 10, pp. 2015-2023.
Li, L., et al., "A pathway regulated by cell cycle inhibitor p27Kip1 and checkpoint inhibitor Smad3 is involved in the induction of T cell tolerance," Nature Immunology 7(11):1157-1165, Nature Publishing, United States (2006).
Li, L., et al., "CD4+CD25+ regulatory T-cell lines from human cord blood have functional and molecular properties and T-cell anergy," Blood 106(9):3068-3073, American Society of Hematology, United States (Nov. 2005).
Li, L., et al., "IL-1beta-Mediated Signals Preferentially Drive Conversion of Regulatory T Cells but Not Coventional T Cells into IL-17-Producing Cells," The Journal of Immunology 185(7):4148-4153, American Association of Immunologists, Inc., UnitedStates (2010).
Li, L., et al., "Rap1-GTP is a Negative Regulator of Th Cell Function and Promotes the Generation of CD4+CD103+ Regulatory T Cells In Vivo," The Journal of Immunology 175(5):3133-3139, American Association of Immunologists, Inc., United States (Sep. 2005).
Li, L., et al., "The cyclin dependent kinase inhibitor (R)-roscovitine prevents alloreactive T cell clonal expansion and protects against acute GvHD," Cell Cycle 8(11):1794-1802, Landes Bioscience, United States (2009).
Lin, David Yin-Wei, et al.; "The PD-1/PD-L1 complex resembles the antigen-binding Fv domains of antibodies and T cell receptors"; Proc. Natl. Acad. Sci. USA 105(8):3011-3016 (2008).
Linsley et al., "Intracellular Trafficking of CTLA-4 and Focal Localization Towards Sites of TCR Engagement" Immunity (1996) vol. 4 pp. 535-543.
Lipson et al. "Initial Experience Administering BMS-986016, a Monoclonal Antibody That Targets Lymphocyte Activation Gene (LAG)-3, Alone and in Combination With Nivolumab to Patients With Hematologic and Solid Malignancies" Presented at the Society for Immunotherapy of Cancer Annual Meeting; Nov. 9-13, 2016, National Harbor, MD.
List of anti-LAG-3 clinical trials identified in ClinicalTrials.gov as of Jan. 20, 2017.
Lonberg, N., et al., "Antigen-specific human antibodies from mice comprising four distinct genetic modifications," Nature 368(6474):856-859, Nature Publishing Group, United States (1994).
Lute, K.D., et al., "Human CTLA4 knock-in mice unravel the quantitative link between tumor immunity and autoimmunity induced by anti-CTLA-4 antibodies," Blood 106(9):3127-3133, American Society of Hematology, United States (2005).
Maon-Lemaître et al., "The negative regulatory function of the lymphocyte-activation gene-3 co-receptor (CD223) on human T cells," Immunology (2005) vol. 115, pp. 170-178.
Mahoney et al. "The Next Immune-Checkpoint Inhibitors: PD-1/PDD-L1 Blockade in Melanoma" Clinical Therapeutics (2015) vol. 37, No. 4, pp. 764-782.
Marri et al., "Human Biochemistry" Mir Publishing, Moscow (1993) vol. 1, p. 34. Russian.
Masters et al., "Abstract 5016: Antitumor activity of anti-PD-1 in combination with tyrosine kinase inhibitors in a preclinical renal cell carcinoma model" AACR Annual Meeting (2014) vol. 74, No. 5016.
May, K.F., Jr., et al., "Anti-human CTLA-4 monoclonal antibody promotes T-cell expansion and immunity it a hu-PBL-SCID model: a new method for preclinical screening of costimulatory monoclonal antibodies," Blood 105(3):1114-1120, American Society ofHematology, United States (2005).
Menzies et al., "Recent advances in melanoma systemic therapy. BRAF inhibitors, CTLA antibodies and beyond" European Journal of Cancer (2013) vol. 49 No. 15 pp. 3229-3241.
Menzies et al. "Systemic treatment for BRAF-mutant melanoma: where do we go next?" Lancet Oncology (2014) vol. 15, pp. e371-e381.
Miska et al., "Autoimmunity-mediated antitumor immunity: Tumor as an immunoprivileged self," Eur J Immunol (2012) vol. 42, pp. 2584-2596.
Mittendorf Elizabeth A et al: "PD-L1 expression in triple-negative breast cancer," Cancer Immunology Research vol. 2. No. 4. Apr. 2014 (Apr. 2014). pp. 361-370.
Moreira Da Silva, "Nivolumab Anti-PD-1 monoclonal antibody cancer immunotherapy" Drugs of the Future (2014) vol. 39 No. 1 pp. 15-24.
Naing et al. "A first-in-human phase I study of the anti-PD-1 antibody PDR001 in patients with advanced solid tumors" 2016 ASCO Annual Meeting, J Clin Oncol 34, 2016 (suppl; abstr 3060).
Nakae et al., "Mast cells enhance T cell activation: importance of mast cell costimulatory molecules and secreted TNF" The Journal of Immunology (2006) vol. 176 No. 4 pp. 2238-2248.
Nielsen, C., et al., "A putative regulatory polymorphism in PD-1 is associated with nephropathy in a population-based cohort of systemic lupus erythematosus patients," Lupus 13(7):510-516, Sage, England (2004).
Nishimura, H., et al., "Autoimmune dilated cardiomyopathy Science in PD-1 receptor-deficient mice," Science 291(5502):319-322, American Association for the Advancement of Science, United States (2001).
Nishimura, H., et al., "Development of lupus-like autoimmune diseases by disruption of the PD-1gene encoding an ITIM motif-carrying immunoreceptor," Immunity 11(2):141-151, Cell Press, United States (1999).
Nishimura, H., et al., "Immunological studies on PD-1 deficient mice: implication of PD-1 as a negative regulator for B cell responses," International Immunology 10(10):1563-1572, Oxford University Press, England (1998).
Okazaki, T., et al., "New regulatory co-receptors: inducible co-stimulator and PD-1," Current Opinion in Immunology 14(6):779-782, Elsevier, England (2002).
Okazaki, T., et al., "PD-1 immunoreceptor inhibits B cell receptor-mediated signaling by recruiting src homology 2-domain-containing tyrosine phosphatase 2 to phophotyrosine," Proceeding of the National Academy of Sciences 98(24):13866-13871,National Academy of Sciences, United States (2001).
Oki Y et al: "Immune regulatory effects of panobinostat in patients with Hodgkin lymphoma through modulation of serum cytokine levels and T-cell PD1 expression.", Blood Cancer Journal, vol. 4, E236, 2014, pp. 1-4.

* cited by examiner

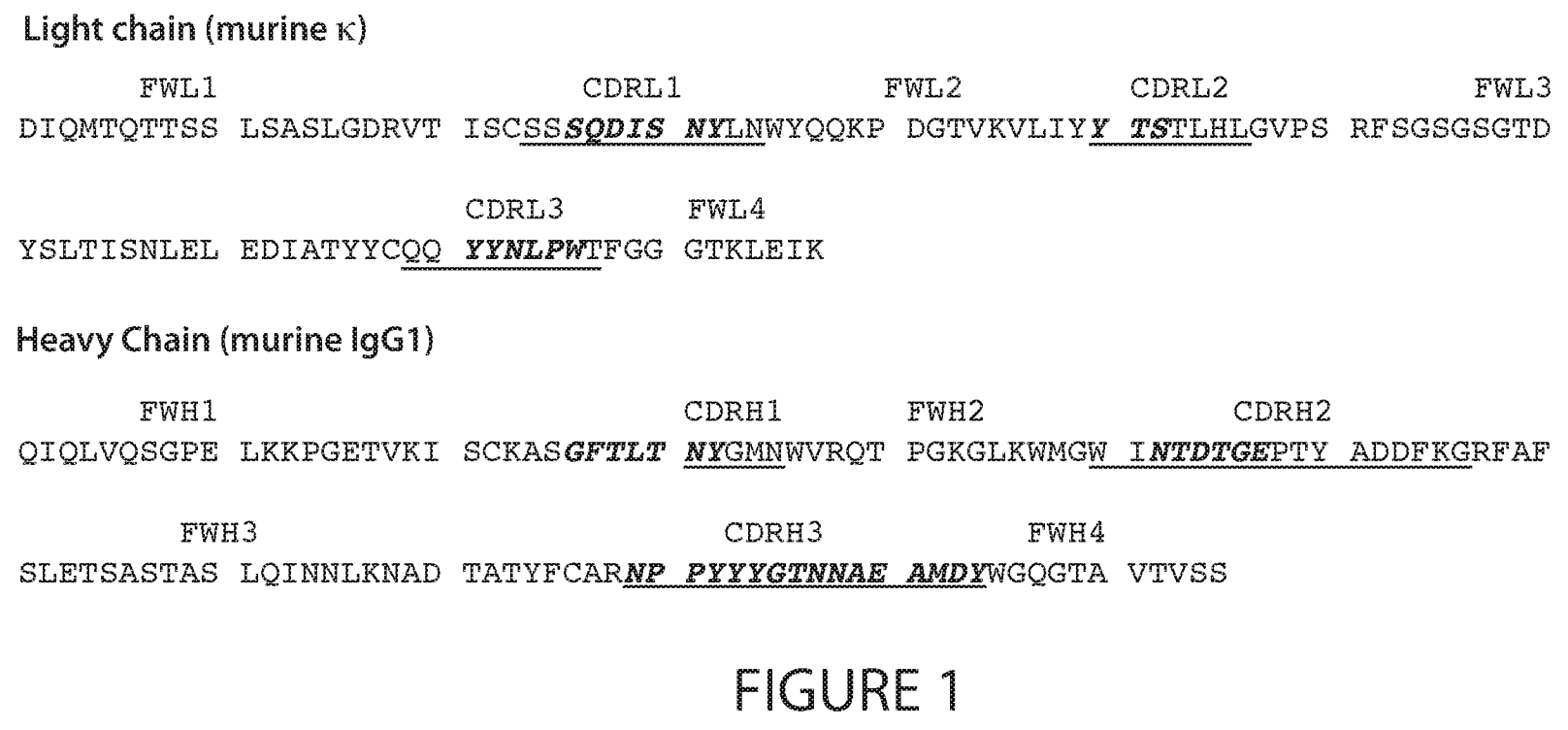

Light chain (murine κ)

```
       FWL1                       CDRL1             FWL2          CDRL2              FWL3
DIQMTQTTSS LSASLGDRVT ISCSSSQDIS NYLNWYQQKP DGTVKVLIYY TSTLHLGVPS RFSGSGSGTD

                      CDRL3       FWL4
YSLTISNLEL EDIATYYCQQ YYNLPWTFGG GTKLEIK
```

Heavy Chain (murine IgG1)

```
       FWH1                             CDRH1      FWH2              CDRH2
QIQLVQSGPE LKKPGETVKI SCKASGFTLT NYGMNWVRQT PGKGLKWMGW INTDTGEPTY ADDFKGRFAF

         FWH3                             CDRH3            FWH4
SLETSASTAS LQINNLKNAD TATYFCARNP PYYYGTNNAE AMDYWGQGTA VTVSS
```

FIGURE 1

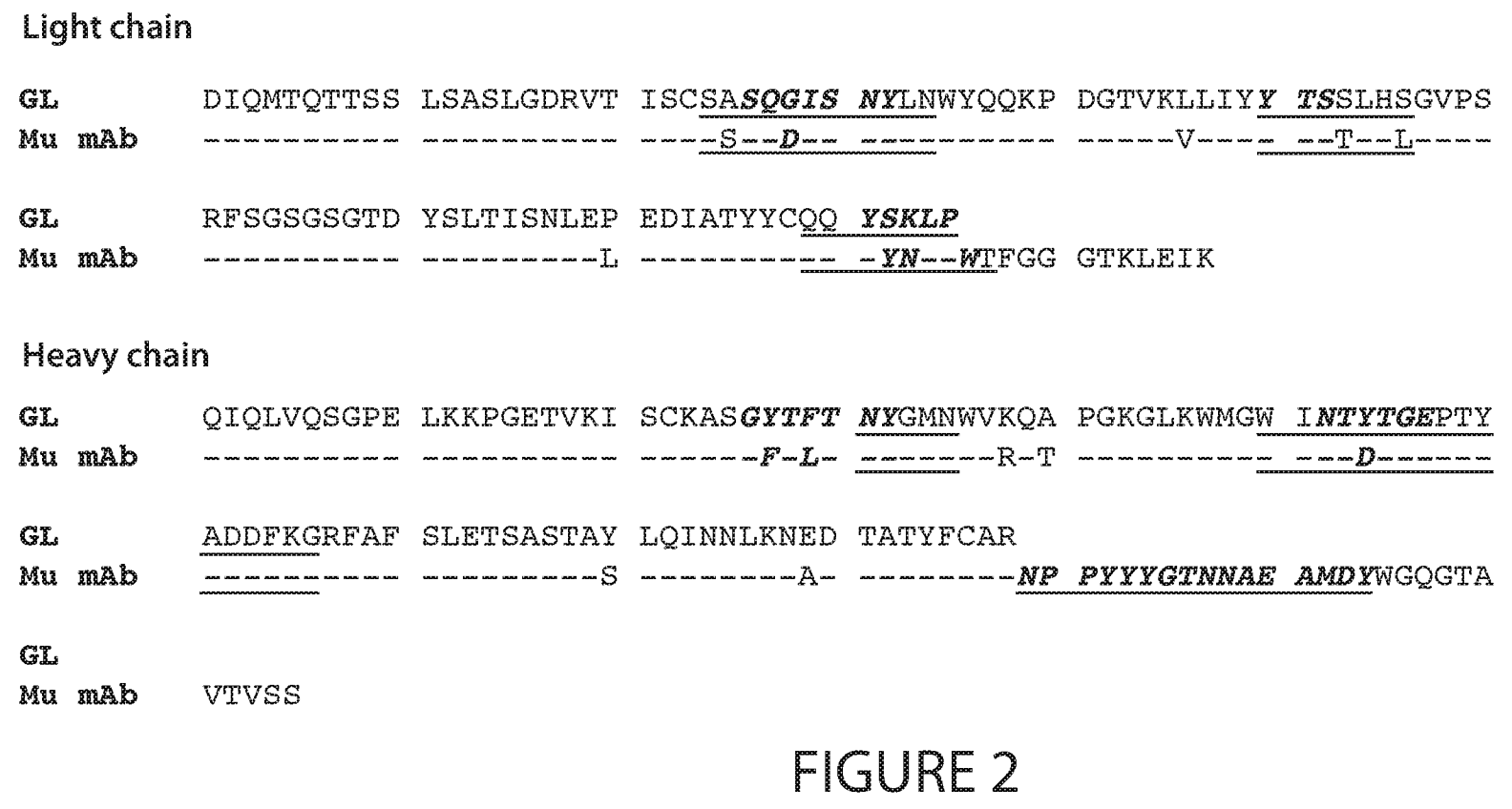

Light chain

```
GL       DIQMTQTTSS LSASLGDRVT ISCSASQGIS NYLNWYQQKP DGTVKLLIYY TSSLHSGVPS
Mu mAb   ---------- ---------- ----S--D-- ---------- -----V---- --T--L----

GL       RFSGSGSGTD YSLTISNLEP EDIATYYCQQ YSKLP
Mu mAb   ---------- ---------L ---------- -YN--WTFGG GTKLEIK
```

Heavy chain

```
GL       QIQLVQSGPE LKKPGETVKI SCKASGYTFT NYGMNWVKQA PGKGLKWMGW INTYTGEPTY
Mu mAb   ---------- ---------- ------F-L- -------R-T ---------- ----D-----

GL       ADDFKGRFAF SLETSASTAY LQINNLKNED TATYFCAR
Mu mAb   ---------- ---------S --------A- --------NP PYYYGTNNAE AMDYWGQGTA

GL
Mu mAb   VTVSS
```

FIGURE 2

| Clone No. | μg/mL | Sequence | | | | | |
|---|---|---|---|---|---|---|---|
| | | HC | | | LC | | |
| | | FW1 | FW2 | FW3 | FW1 | FW2 | FW3 |
| chimera | 31.7 | 6 unique HC | | | 12 unique LC | | |
| 1 | 35.4 | a | a | a | a | a | a |
| 2 | 25.2 | a | a | a | a | a | b |
| 3 | 3.2 | a | a | a | b | b | a |
| 4 | 26 | a | a | a | a | c | c |
| 5 | 16.9 | a | a | a | c | a | a |
| 6 | 9.1 | a | a | a | d | b | d |
| 7 | 35.8 | a | a | a | a | d | d |
| 8 | 24.7 | a | a | a | e | b | e |
| 9 | 19.9 | b | b | a | a | a | b |
| 10 | 7.7 | b | b | a | b | b | a |
| 11 | 34.9 | b | b | a | a | d | d |
| 12 | 17.9 | b | b | a | e | b | e |
| 13 | 24.9 | b | a | a | a | a | b |
| 14 | 7.5 | a | c | a | b | b | a |
| 15 | 21.9 | a | c | a | e | b | e |
| 16 | 17.7 | c | d | b | e | b | e |
| 17 | 21.2 | d | a | c | a | a | f |
| 18 | 8.1 | a | a | a | f | b | e |
| 19 | 7.5 | a | a | a | e | b | a |
| 20 | 3.2 | b | b | a | d | b | g |

FIGURE 4

| Clone No. | Conc. µg/mL | Sequence | | | | | | Ranking | | Structure |
|---|---|---|---|---|---|---|---|---|---|---|
| | | HC | | | LC | | | Binding data | Compet. data | |
| | | FW1 | FW2 | FW3 | FW1 | FW2 | FW3 | | | |
| | | 6 unique HC | | | 12 unique LC | | | | * | |
| 1 | 35.4 | a | a | a | a | a | a | 1 | 2 | D |
| 2 | 25.2 | a | a | a | a | a | b | 5 | 1 | B |
| 3 | 3.2 | a | a | a | b | b | a | 7 | 1 | E |
| 4 | 26 | a | a | a | a | c | c | 8 | 2 | E |
| 5 | 16.9 | a | a | a | c | a | a | 6 | | E |
| 6 | 9.1 | a | a | a | d | b | d | 9 | 1 | E |
| 7 | 35.8 | a | a | a | a | d | d | 8 | | C |
| 8 | 24.7 | a | a | a | e | b | e | 4 | | E |
| 9 | 19.9 | b | b | a | a | a | b | 8 | 2 | B |
| 10 | 7.7 | b | b | a | b | b | a | 9 | 2 | E |
| 11 | 34.9 | b | b | a | a | d | d | 2 | 2 | C |
| 12 | 17.9 | b | b | a | e | b | e | 3 | 2 | E |
| 13 | 24.9 | b | a | a | a | a | b | 9 | 3 | A |
| 14 | 7.5 | a | c | a | b | b | a | 9 | | F |
| 15 | 21.9 | a | c | a | e | b | e | 20 | 20 | F |
| 16 | 17.7 | c | d | b | e | b | e | 20 | 20 | D |
| 17 | 21.2 | d | a | c | a | a | f | 9 | | E |
| 18 | 8.1 | a | a | a | f | b | e | 8 | | C |
| 19 | 7.5 | a | a | a | e | b | a | 9 | | D |
| 20 | 3.2 | b | b | a | d | b | g | 9 | 3 | C |

*empty boxes means worse than 3.

FIGURE 6

```
                       10        20        30        40        50        60
               ....|....|....|....|....|....|....|....|....|....|....|....|
BAP050-chi-HC  QIQLVQSGPELKKPGETVKISCKASGFTLTNYGMNWVRQTPGKGLKWMGWINTDTGEPTY
BAP050-hum01-HC EVQLVQSGAEVKKPGATVKISCKVSGFTLTNYGMNWVRQAPGQGLEWMGWINTDTGEPTY
BAP050-hum02-HC EVQLVQSGAEVKKPGATVKISCKVSGFTLTNYGMNWVRQAPGQGLEWMGWINTDTGEPTY
BAP050-hum03-HC EVQLVQSGAEVKKPGATVKISCKVSGFTLTNYGMNWVRQAPGQGLEWMGWINTDTGEPTY
BAP050-hum04-HC EVQLVQSGAEVKKPGATVKISCKVSGFTLTNYGMNWVRQAPGQGLEWMGWINTDTGEPTY
BAP050-hum05-HC EVQLVQSGAEVKKPGATVKISCKVSGFTLTNYGMNWVRQAPGQGLEWMGWINTDTGEPTY
BAP050-hum06-HC EVQLVQSGAEVKKPGATVKISCKVSGFTLTNYGMNWVRQAPGQGLEWMGWINTDTGEPTY
BAP050-hum07-HC EVQLVQSGAEVKKPGATVKISCKVSGFTLTNYGMNWVRQAPGQGLEWMGWINTDTGEPTY
BAP050-hum08-HC EVQLVQSGAEVKKPGATVKISCKVSGFTLTNYGMNWVRQAPGQGLEWMGWINTDTGEPTY
BAP050-hum18-HC EVQLVQSGAEVKKPGATVKISCKVSGFTLTNYGMNWVRQAPGQGLEWMGWINTDTGEPTY
BAP050-hum19-HC EVQLVQSGAEVKKPGATVKISCKVSGFTLTNYGMNWVRQAPGQGLEWMGWINTDTGEPTY
BAP050-hum09-HC QVQLVQSGAEVKKPGASVKVSCKASGFTLTNYGMNWVRQARGQRLEWIGWINTDTGEPTY
BAP050-hum10-HC QVQLVQSGAEVKKPGASVKVSCKASGFTLTNYGMNWVRQARGQRLEWIGWINTDTGEPTY
BAP050-hum11-HC QVQLVQSGAEVKKPGASVKVSCKASGFTLTNYGMNWVRQARGQRLEWIGWINTDTGEPTY
BAP050-hum12-HC QVQLVQSGAEVKKPGASVKVSCKASGFTLTNYGMNWVRQARGQRLEWIGWINTDTGEPTY
BAP050-hum20-HC QVQLVQSGAEVKKPGASVKVSCKASGFTLTNYGMNWVRQARGQRLEWIGWINTDTGEPTY
BAP050-hum13-HC QVQLVQSGAEVKKPGASVKVSCKASGFTLTNYGMNWVRQAPGQGLEWMGWINTDTGEPTY
BAP050-hum14-HC EVQLVQSGAEVKKPGATVKISCKVSGFTLTNYGMNWIRQSPSRGLEWLGWINTDTGEPTY
BAP050-hum15-HC EVQLVQSGAEVKKPGATVKISCKVSGFTLTNYGMNWIRQSPSRGLEWLGWINTDTGEPTY
BAP050-hum16-HC EVQLVQSGAEVKKPGESLRISCKGSGFTLTNYGMNWVRQATGQGLEWMGWINTDTGEPTY
BAP050-hum17-HC QVQLVQSGSELKKPGASVKVSCKASGFTLTNYGMNWVRQAPGQGLEWMGWINTDTGEPTY

                       70        80        90       100       110       120
               ....|....|....|....|....|....|....|....|....|....|....|....|
BAP050-chi-HC  ADDFKGRFAFSLETSASTASLQINNLKNADTATYFCARNPPYYYGTNNAEAMDYWGQGTTVTVSS
BAP050-hum01-HC ADDFKGRFVFSLDTSVSTAYLQICSLKAEDTAVYYCARNPPYYYGTNNAEAMDYWGQGTTVTVSS
BAP050-hum02-HC ADDFKGRFVFSLDTSVSTAYLQICSLKAEDTAVYYCARNPPYYYGTNNAEAMDYWGQGTTVTVSS
BAP050-hum03-HC ADDFKGRFVFSLDTSVSTAYLQICSLKAEDTAVYYCARNPPYYYGTNNAEAMDYWGQGTTVTVSS
BAP050-hum04-HC ADDFKGRFVFSLDTSVSTAYLQICSLKAEDTAVYYCARNPPYYYGTNNAEAMDYWGQGTTVTVSS
BAP050-hum05-HC ADDFKGRFVFSLDTSVSTAYLQICSLKAEDTAVYYCARNPPYYYGTNNAEAMDYWGQGTTVTVSS
BAP050-hum06-HC ADDFKGRFVFSLDTSVSTAYLQICSLKAEDTAVYYCARNPPYYYGTNNAEAMDYWGQGTTVTVSS
BAP050-hum07-HC ADDFKGRFVFSLDTSVSTAYLQICSLKAEDTAVYYCARNPPYYYGTNNAEAMDYWGQGTTVTVSS
BAP050-hum08-HC ADDFKGRFVFSLDTSVSTAYLQICSLKAEDTAVYYCARNPPYYYGTNNAEAMDYWGQGTTVTVSS
BAP050-hum18-HC ADDFKGRFVFSLDTSVSTAYLQICSLKAEDTAVYYCARNPPYYYGTNNAEAMDYWGQGTTVTVSS
BAP050-hum19-HC ADDFKGRFVFSLDTSVSTAYLQICSLKAEDTAVYYCARNPPYYYGTNNAEAMDYWGQGTTVTVSS
BAP050-hum09-HC ADDFKGRFVFSLDTSVSTAYLQICSLKAEDTAVYYCARNPPYYYGTNNAEAMDYWGQGTTVTVSS
BAP050-hum10-HC ADDFKGRFVFSLDTSVSTAYLQICSLKAEDTAVYYCARNPPYYYGTNNAEAMDYWGQGTTVTVSS
BAP050-hum11-HC ADDFKGRFVFSLDTSVSTAYLQICSLKAEDTAVYYCARNPPYYYGTNNAEAMDYWGQGTTVTVSS
BAP050-hum12-HC ADDFKGRFVFSLDTSVSTAYLQICSLKAEDTAVYYCARNPPYYYGTNNAEAMDYWGQGTTVTVSS
BAP050-hum20-HC ADDFKGRFVFSLDTSVSTAYLQICSLKAEDTAVYYCARNPPYYYGTNNAEAMDYWGQGTTVTVSS
BAP050-hum13-HC ADDFKGRFVFSLDTSVSTAYLQICSLKAEDTAVYYCARNPPYYYGTNNAEAMDYWGQGTTVTVSS
BAP050-hum14-HC ADDFKGRFVFSLDTSVSTAYLQICSLKAEDTAVYYCARNPPYYYGTNNAEAMDYWGQGTTVTVSS
BAP050-hum15-HC ADDFKGRFVFSLDTSVSTAYLQICSLKAEDTAVYYCARNPPYYYGTNNAEAMDYWGQGTTVTVSS
BAP050-hum16-HC ADDFKGRVTISADKSISTAYLQWSSLKASDTAMYYCARNPPYYYGTNNAEAMDYWGQGTTVTVSS
BAP050-hum17-HC ADDFKGRFVFSLDTSVSTAYLQISTLKAEDTATYFCARNPPYYYGTNNAEAMDYWGQGTTVTVSS
```

FIGURE 9A

```
                         10        20        30        40        50        60
                ....|....|....|....|....|....|....|....|....|....|....|....|
BAP050-chi-HC   QIQLVQSGPELKKPGETVKISCKASGFTLTNYGMNWVRQTPGKGLKWMGWINTDTGEPTY
BAP050-hum01-HC EV......A.V....A.......V...............A..Q..E..............
BAP050-hum02-HC EV......A.V....A.......V...............A..Q..E..............
BAP050-hum03-HC EV......A.V....A.......V...............A..Q..E..............
BAP050-hum04-HC EV......A.V....A.......V...............A..Q..E..............
BAP050-hum05-HC EV......A.V....A.......V...............A..Q..E..............
BAP050-hum06-HC EV......A.V....A.......V...............A..Q..E..............
BAP050-hum07-HC EV......A.V....A.......V...............A..Q..E..............
BAP050-hum08-HC EV......A.V....A.......V...............A..Q..E..............
BAP050-hum18-HC EV......A.V....A.......V...............A..Q..E..............
BAP050-hum19-HC EV......A.V....A.......V...............A..Q..E..............
BAP050-hum09-HC .V......A.V....AS..V...................AR.QR.E.I............
BAP050-hum10-HC .V......A.V....AS..V...................AR.QR.E.I............
BAP050-hum11-HC .V......A.V....AS..V...................AR.QR.E.I............
BAP050-hum12-HC .V......A.V....AS..V...................AR.QR.E.I............
BAP050-hum20-HC .V......A.V....AS..V...................AR.QR.E.I............
BAP050-hum13-HC .V......A.V....AS..V...................A..Q..E..............
BAP050-hum14-HC EV......A.V....A.......V............I..S.SR..E.L............
BAP050-hum15-HC EV......A.V....A.......V............I..S.SR..E.L............
BAP050-hum16-HC EV......A.V.....SLR....G...............AT.Q..E..............
BAP050-hum17-HC .V......S......AS..V...................A..Q..E..............

                         70        80        90        100       110       120
                ....|....|....|....|....|....|....|....|....|....|....|....|....|
BAP050-chi-HC   ADDFKGRFAFSLETSASTASLQINNLKNADTATYFCARNPPYYYGTNNAEAMDYWGQGTTVTVSS
BAP050-hum01-HC ........V...D..V...Y...CS..AE...V.Y..............................
BAP050-hum02-HC ........V...D..V...Y...CS..AE...V.Y..............................
BAP050-hum03-HC ........V...D..V...Y...CS..AE...V.Y..............................
BAP050-hum04-HC ........V...D..V...Y...CS..AE...V.Y..............................
BAP050-hum05-HC ........V...D..V...Y...CS..AE...V.Y..............................
BAP050-hum06-HC ........V...D..V...Y...CS..AE...V.Y..............................
BAP050-hum07-HC ........V...D..V...Y...CS..AE...V.Y..............................
BAP050-hum08-HC ........V...D..V...Y...CS..AE...V.Y..............................
BAP050-hum18-HC ........V...D..V...Y...CS..AE...V.Y..............................
BAP050-hum19-HC ........V...D..V...Y...CS..AE...V.Y..............................
BAP050-hum09-HC ........V...D..V...Y...CS..AE...V.Y..............................
BAP050-hum10-HC ........V...D..V...Y...CS..AE...V.Y..............................
BAP050-hum11-HC ........V...D..V...Y...CS..AE...V.Y..............................
BAP050-hum12-HC ........V...D..V...Y...CS..AE...V.Y..............................
BAP050-hum20-HC ........V...D..V...Y...CS..AE...V.Y..............................
BAP050-hum13-HC ........V...D..V...Y...CS..AE...V.Y..............................
BAP050-hum14-HC ........V...D..V...Y...CS..AE...V.Y..............................
BAP050-hum15-HC ........V...D..V...Y...CS..AE...V.Y..............................
BAP050-hum16-HC .......VTI.ADK.I...Y..WSS..AS...M.Y..............................
BAP050-hum17-HC ........V...D..V...Y...ST..AE....................................
```

FIGURE 9B

```
                            10        20        30        40        50        60
                    ....|....|....|....|....|....|....|....|....|....|....|....|
BAP050-chi-LC       DIQMTQTTSSLSASLGDRVTISCSSSQDISNYLNWYQQKPDGTVKVLIYYTSTLHLGVPS
BAP050-hum01-LC     DIQMTQSPSSLSASVGDRVTITCSSSQDISNYLNWYQQKPGKAPKLLIYYTSTLHLGVPS
BAP050-hum02-LC     DIQMTQSPSSLSASVGDRVTITCSSSQDISNYLNWYQQKPGKAPKLLIYYTSTLHLGIPP
BAP050-hum13-LC     DIQMTQSPSSLSASVGDRVTITCSSSQDISNYLNWYQQKPGKAPKLLIYYTSTLHLGIPP
BAP050-hum09-LC     DIQMTQSPSSLSASVGDRVTITCSSSQDISNYLNWYQQKPGKAPKLLIYYTSTLHLGIPP
BAP050-hum03-LC     EIVLTQSPATLPVSLGQTASISCSSSQDISNYLNWYQQKPGQAPRLLIYYTSTLHLGVPS
BAP050-hum10-LC     EIVLTQSPATLPVSLGQTASISCSSSQDISNYLNWYQQKPGQAPRLLIYYTSTLHLGVPS
BAP050-hum14-LC     EIVLTQSPATLPVSLGQTASISCSSSQDISNYLNWYQQKPGQAPRLLIYYTSTLHLGVPS
BAP050-hum04-LC     DIQMTQSPSSLSASVGDRVTITCSSSQDISNYLNWYLQKPGQSPQLLIYYTSTLHLGIPD
BAP050-hum05-LC     EIVLTQSPATLSLSPGERATLSCSSSQDISNYLNWYQQKPGKAPKLLIYYTSTLHLGVPS
BAP050-hum06-LC     DIVMTQTPLSLPVTPGEPASISCSSSQDISNYLNWYQQKPGQAPRLLIYYTSTLHLGVPS
BAP050-hum07-LC     DIQMTQSPSSLSASVGDRVTITCSSSQDISNYLNWYLQKPGQSPQLLIYYTSTLHLGVPS
BAP050-hum11-LC     DIQMTQSPSSLSASVGDRVTITCSSSQDISNYLNWYLQKPGQSPQLLIYYTSTLHLGVPS
BAP050-hum08-LC     EIVLTQSPDFQSVTPKEKVTITCSSSQDISNYLNWYQQKPGQAPRLLIYYTSTLHLGVPS
BAP050-hum12-LC     EIVLTQSPDFQSVTPKEKVTITCSSSQDISNYLNWYQQKPGQAPRLLIYYTSTLHLGVPS
BAP050-hum15-LC     EIVLTQSPDFQSVTPKEKVTITCSSSQDISNYLNWYQQKPGQAPRLLIYYTSTLHLGVPS
BAP050-hum16-LC     EIVLTQSPDFQSVTPKEKVTITCSSSQDISNYLNWYQQKPGQAPRLLIYYTSTLHLGVPS
BAP050-hum17-LC     DIQMTQSPSSLSASVGDRVTITCSSSQDISNYLNWYQQKPGKAPKLLIYYTSTLHLGVPS
BAP050-hum18-LC     AIQLTQSPSSLSASVGDRVTITCSSSQDISNYLNWYQQKPGQAPRLLIYYTSTLHLGVPS
BAP050-hum19-LC     EIVLTQSPDFQSVTPKEKVTITCSSSQDISNYLNWYQQKPGQAPRLLIYYTSTLHLGVPS
BAP050-hum20-LC     DIVMTQTPLSLPVTPGEPASISCSSSQDISNYLNWYQQKPGQAPRLLIYYTSTLHLGIPD

                            70        80        90        100
                    ....|....|....|....|....|....|....|....|....|..
BAP050-chi-LC       RFSGSGSGTDYSLTISNLELEDIATYYCQQYYNLPWTFGQGTKVEIK
BAP050-hum01-LC     RFSGSGSGTDFTFTISSLEAEDAATYYCQQYYNLPWTFGQGTKVEIK
BAP050-hum02-LC     RFSGSGYGTDFTLTINNIESEDAAYYFCQQYYNLPWTFGQGTKVEIK
BAP050-hum13-LC     RFSGSGYGTDFTLTINNIESEDAAYYFCQQYYNLPWTFGQGTKVEIK
BAP050-hum09-LC     RFSGSGYGTDFTLTINNIESEDAAYYFCQQYYNLPWTFGQGTKVEIK
BAP050-hum03-LC     RFSGSGSGTDFTFTISSLEAEDAATYYCQQYYNLPWTFGQGTKVEIK
BAP050-hum10-LC     RFSGSGSGTDFTFTISSLEAEDAATYYCQQYYNLPWTFGQGTKVEIK
BAP050-hum14-LC     RFSGSGSGTDFTFTISSLEAEDAATYYCQQYYNLPWTFGQGTKVEIK
BAP050-hum04-LC     RFSGSGSGTDFTLTISRLEPEDFAVYYCQQYYNLPWTFGQGTKVEIK
BAP050-hum05-LC     RFSGSGSGTDFTFTISSLEAEDAATYYCQQYYNLPWTFGQGTKVEIK
BAP050-hum06-LC     RFSGSGSGTEFTLTISSLQPDDFATYYCQQYYNLPWTFGQGTKVEIK
BAP050-hum07-LC     RFSGSGSGTEFTLTISSLQPDDFATYYCQQYYNLPWTFGQGTKVEIK
BAP050-hum11-LC     RFSGSGSGTEFTLTISSLQPDDFATYYCQQYYNLPWTFGQGTKVEIK
BAP050-hum08-LC     RFSGSGSGTDFTLTISSLQPEDFATYYCQQYYNLPWTFGQGTKVEIK
BAP050-hum12-LC     RFSGSGSGTDFTLTISSLQPEDFATYYCQQYYNLPWTFGQGTKVEIK
BAP050-hum15-LC     RFSGSGSGTDFTLTISSLQPEDFATYYCQQYYNLPWTFGQGTKVEIK
BAP050-hum16-LC     RFSGSGSGTDFTLTISSLQPEDFATYYCQQYYNLPWTFGQGTKVEIK
BAP050-hum17-LC     RFSGSGSGTDFTFTISSLQPEDIATYYCQQYYNLPWTFGQGTKVEIK
BAP050-hum18-LC     RFSGSGSGTDFTLTISSLQPEDFATYYCQQYYNLPWTFGQGTKVEIK
BAP050-hum19-LC     RFSGSGSGTDFTFTISSLEAEDAATYYCQQYYNLPWTFGQGTKVEIK
BAP050-hum20-LC     RFSGSGSGTDFTLTISRLEPEDFAVYYCQQYYNLPWTFGQGTKVEIK
```

FIGURE 10A

```
                           10        20        30        40        50        60
                  ....|....|....|....|....|....|....|....|....|....|....|....|
BAP050-chi-LC     DIQMTQTTSSLSASLGDRVTISCSSSQDISNYLNWYQQKPDGTVKVLIYYTSTLHLGVPS
BAP050-hum01-LC   ......SP......V......T..................GKAP.L..............
BAP050-hum02-LC   ......SP......V......T..................GKAP.L...........I.P
BAP050-hum13-LC   ......SP......V......T..................GKAP.L...........I.P
BAP050-hum09-LC   ......SP......V......T..................GKAP.L...........I.P
BAP050-hum03-LC   E.VL..SPAT.PV...QTAS....................GQAPRL..............
BAP050-hum10-LC   E.VL..SPAT.PV...QTAS....................GQAPRL..............
BAP050-hum14-LC   E.VL..SPAT.PV...QTAS....................GQAPRL..............
BAP050-hum04-LC   ......SP......V......T..............L...GQSPQL...........I.D
BAP050-hum05-LC   E.VL..SPAT..L.P.E.A.L...................GKAP.L..............
BAP050-hum06-LC   ..V....PL..PVTP.EPAS....................GQAPRL..............
BAP050-hum07-LC   ......SP......V......T..............L...GQSPQL..............
BAP050-hum11-LC   ......SP......V......T..............L...GQSPQL..............
BAP050-hum08-LC   E.VL..SPDFQ.VTPKEK...T..................GQAPRL..............
BAP050-hum12-LC   E.VL..SPDFQ.VTPKEK...T..................GQAPRL..............
BAP050-hum15-LC   E.VL..SPDFQ.VTPKEK...T..................GQAPRL..............
BAP050-hum16-LC   E.VL..SPDFQ.VTPKEK...T..................GQAPRL..............
BAP050-hum17-LC   ......SP......V......T..................GKAP.L..............
BAP050-hum18-LC   A..L..SP......V......T..................GQAPRL..............
BAP050-hum19-LC   E.VL..SPDFQ.VTPKEK...T..................GQAPRL..............
BAP050-hum20-LC   ..V....PL..PVTP.EPAS....................GQAPRL...........I.D

                           70        80        90        100
                  ....|....|....|....|....|....|....|....|....|..
BAP050-chi-LC     RFSGSGSGTDYSLTISNLELEDIATYYCQQYYNLPWTFGQGTKVEIK
BAP050-hum01-LC   ..........FTF...S..A..A........................
BAP050-hum02-LC   ......Y...FT...N.I.S..A.Y.F....................
BAP050-hum13-LC   ......Y...FT...N.I.S..A.Y.F....................
BAP050-hum09-LC   ......Y...FT...N.I.S..A.Y.F....................
BAP050-hum03-LC   ..........FTF...S..A..A........................
BAP050-hum10-LC   ..........FTF...S..A..A........................
BAP050-hum14-LC   ..........FTF...S..A..A........................
BAP050-hum04-LC   ..........FT....R..P..F.V......................
BAP050-hum05-LC   ..........FTF...S..A..A........................
BAP050-hum06-LC   .........EFT....S.QPD.F........................
BAP050-hum07-LC   .........EFT....S.QPD.F........................
BAP050-hum11-LC   .........EFT....S.QPD.F........................
BAP050-hum08-LC   ..........FT....S.QP..F........................
BAP050-hum12-LC   ..........FT....S.QP..F........................
BAP050-hum15-LC   ..........FT....S.QP..F........................
BAP050-hum16-LC   ..........FT....S.QP..F........................
BAP050-hum17-LC   ..........FTF...S.QP...........................
BAP050-hum18-LC   ..........FT....S.QP..F........................
BAP050-hum19-LC   ..........FTF...S..A..A........................
BAP050-hum20-LC   ..........FT....R..P..F.V......................
```

FIGURE 10B

COMBINATION THERAPIES COMPRISING ANTIBODY MOLECULES TO LAG-3

CROSS REFERENCE TO RELATED APPLICATIONS

This application claims the benefit of U.S. Provisional Application No. 62/198,492, filed Jul. 29, 2015, the content of the aforementioned application is hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 25, 2016, is named C2160-7010WO_SL.txt and is 323,665 bytes in size.

BACKGROUND

Lymphocyte Activation Gene-3, or LAG-3 (also known as CD223), is a member of the immunoglobulin supergene family, and is expressed on activated T cells (Huard et al. (1994) *Immunogenetics* 39:213), NK cells (Triebel et al. (1990) *J. Exp. Med.* 171:1393-1405), regulatory T cells (Huang et al. (2004) *Immunity* 21:503-513; Camisaschi et al. (2010) *J Immunol.* 184:6545-6551; Gagliani et al. (2013) *Nat Med* 19:739-746), and plasmacytoid dendritic cells (DCs) (Workman et al. (2009) *J Immunol* 182:1885-1891). LAG-3 is a membrane protein encoded by a gene located on chromosome 12, and is structurally and genetically related to CD4.

Similar to CD4, LAG-3 can interact with MHC class II molecules on the cell surface (Baixeras et al. (1992) *J. Exp. Med.* 176:327-337; Huard et al. (1996) *Eur. J. Immunol.* 26:1180-1186). It has been suggested that the direct binding of LAG-3 to MHC class II plays a role in down-regulating antigen-dependent stimulation of $CD4^+$ T lymphocytes (Huard et al. (1994) *Eur. J. Immunol.* 24:3216-3221) and LAG-3 blockade has also been shown to reinvigorate $CD8^+$ lymphocytes in both tumor or self-antigen (Gross et al. (2007) *J Clin Invest.* 117:3383-3392) and viral models (Blackburn et al. (2009) *Nat. Immunol.* 10:29-37). Further, the intra-cytoplasmic region of LAG-3 can interact with LAP (LAG-3-associated protein), which is a signal transduction molecule involved in the downregulation of the CD3/TCR activation pathway (Iouzalen et al. (2001) *Eur. J. Immunol.* 31:2885-2891). Moreover, $CD4^+CD25^+$ regulatory T cells ($T_{reg}$) have been shown to express LAG-3 upon activation, which contributes to the suppressor activity of $T_{reg}$ cells (Huang, C. et al. (2004) *Immunity* 21:503-513). LAG-3 can also negatively regulate T cell homeostasis by $T_{reg}$ cells in both T cell-dependent and independent mechanisms (Workman, C. J. and Vignali, D. A. (2005) *J. Immunol.* 174:688-695).

Given the importance of LAG-3 in downregulating an immune response, the need exists for developing novel agents that modulate its activity to activate the immune system. Such agents can be used, e.g., for cancer immunotherapy and treatment of other conditions, such as chronic infection.

SUMMARY

Disclosed herein, at least in part, are methods and compositions comprising a combination of two, three or more therapeutic agents chosen from one, two, or all of the following categories (i)-(iii): (i) an agent that enhances antigen presentation (e.g., tumor antigen presentation); (ii) an agent that enhances an effector cell response (e.g., B cell and/or T cell activation and/or mobilization); or (iii) an agent that decreases tumor immunosuppression. In some embodiments, the combination includes an inhibitor of Lymphocyte Activation Gene-3 (LAG-3) (e.g., an anti-LAG-3 antibody molecule as described herein).

Without wishing to be bound by theory, it is believed that therapeutic approaches that enhance anti-tumor immunity work more effectively when the immune response is optimized by targeting multiple components at one or more stages of an immune response, e.g., an anti-tumor immune response. For example, approaches that enhance antigen presentation, e.g., by activation and/or maturation of dendritic cells, combined with approaches that enhance cellular and humoral immune responses (e.g., by stimulating, e.g., disinhibiting, phagocytes and/or tumor infiltrating lymphocytes (e.g., NK cells and T cells)), while blocking tumor immunosuppressive signaling (e.g., by increasing macrophage polarization, increasing $T_{reg}$ depletion and/or decreasing myeloid-derived suppressive cells (MDSCs)) can result in a more effective and/or prolonged therapeutic response. Accordingly, disclosed herein are combination therapies that optimize one, two, or all of: (i) antigen presentation, e.g., increasing antigen presentation (e.g., by enhancing one or more of dendritic cell activity or maturation, antigen uptake, or antigen processing); (ii) effector cell response, e.g., increasing effector cell response (e.g., enhancing B cell and/or T cell activation and/or mobilization, e.g., in the lymph node); or (iii) tumor immunosuppression, e.g., decreasing tumor immunosuppression (e.g., increasing T cell infiltration and tumor cell killing). The combinations described herein can provide a superior beneficial effect, e.g., in the treatment of a disorder, such as an enhanced anti-cancer effect, reduced toxicity and/or reduced side effects, compared to monotherapy administration of the therapeutic agents in the combination. For example, one or more of the therapeutic agents in the combination can be administered at a lower dosage, or for a shorter period of administration, than would be required to achieve the same therapeutic effect compared to the monotherapy administration. Thus, compositions and methods for treating cancer and other immune disorders using the aforesaid combination therapies are disclosed.

Accordingly, in one aspect, the invention features a method of treating (e.g., inhibiting, reducing, ameliorating, or preventing) a disorder, e.g., a hyperproliferative condition or disorder (e.g., a cancer) in a subject. The method includes administering to the subject a combination of two, three or more therapeutic agents chosen from one, two or all of the following categories (i)-(iii): (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby treating the disorder, e.g., the hyperproliferative condition or disorder (e.g., the cancer). In some embodiments, the combination includes a LAG-3 inhibitor (e.g., an anti-LAG-3 antibody molecule as described herein). The cancer treated can be, e.g., a cancer described herein, such as a lung cancer, a melanoma, a renal cancer, a liver cancer, a myeloma, a prostate cancer, a breast cancer, a head and neck cancer, a colorectal cancer, a pancreatic cancer, a hematological cancer, a non-Hogdkin's lymphoma, or a leukemia, or a metastatic lesion of the cancer.

In another aspect, the invention features a method of reducing an activity (e.g., growth, survival, or viability, or all), of a hyperproliferative (e.g., a cancer) cell. The method includes contacting the cell with a combination of two, three or more therapeutic agents chosen from one, two or all of the following categories (i)-(iii): (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby reducing an activity in the hyperproliferative cell. In some embodiments, the combination includes a LAG-3 inhibitor (e.g., an anti-LAG-3 antibody molecule as described herein). The method can be performed in a subject, e.g., as part of a therapeutic protocol. The cancer cell can be, e.g., a cell from a cancer described herein, such as a lung cancer, a melanoma, a renal cancer, a liver cancer, a myeloma, a prostate cancer, a breast cancer, a head and neck cancer, a colorectal cancer, a pancreatic cancer, a hematological cancer, a non-Hogdkin's lymphoma, or a leukemia, or a metastatic lesion of the cancer.

In certain embodiments of the methods disclosed herein, the method further includes determining the level of an immune cell (e.g., a T cell) infiltrate (e.g., the level of tumor infiltrating lymphocytes (TIL)) in the subject. In one embodiment, the level of the immune cell infiltrate is determined in vivo, e.g., non-invasively (e.g., by detecting an antibody to a T cell marker detectably labeled using a suitable imaging technique, e.g., positron emission tomography (PET) scan). In other embodiments, the level of the immune cell infiltrate is determined in a sample (e.g., a tumor biopsy) acquired from the subject (e.g., using immunohistochemical techniques). In embodiments, responsive to a low level of, or no detectable, tumor infiltrate in the subject, one or more agents of categories (i) or (ii), or both (i) and (ii), is/are administered. In other embodiments, responsive to a detectable level, or an elevated level, of tumor infiltrate in the subject, one or more agents of category (iii) is/are administered. The detection steps can also be used, e.g., to monitor the effectiveness of a therapeutic agent described herein. For example, the detection step can be used to monitor the effectiveness of therapeutic agents of categories (i), (ii) and/or (iii).

In another aspect, the invention features a composition (e.g., one or more compositions or dosage forms), that includes a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression. In some embodiments, the combination includes a LAG-3 inhibitor (e.g., an anti-LAG-3 antibody molecule as described herein).

In yet another aspect, the invention features a composition (e.g., one or more compositions or dosage forms as described hereom), for use in treating a disorder, e.g., a cancer. In embodiments, the composition for use includes a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression. In some embodiments, the combination used includes a LAG-3 inhibitor (e.g., an anti-LAG-3 antibody molecule as described herein). The cancer can be, e.g., a cancer described herein, such as lung a lung cancer, a melanoma, a renal cancer, a liver cancer, a myeloma, a prostate cancer, a breast cancer, a head and neck cancer, a colorectal cancer, a pancreatic cancer, a hematological cancer, a non-Hogdkin's lymphoma, or a leukemia, or a metastatic lesion of the cancer.

Formulations, e.g., dosage formulations, and kits, e.g., therapeutic kits, that include a combination of two, three or more therapeutic agents chosen from one, two or all of the following categories (i)-(iii): (i) an agent that enhances antigen (e.g., tumor antigen) presentation; (ii) an agent that enhances an effector cell response (e.g., activation and/or mobilization of B cell and/or T cell); or (iii) an agent that decreases tumor immunosuppression, thereby reducing an activity in the cell, and (optionally) instructions for use, are also disclosed. In some embodiments, the combination includes a LAG-3 inhibitor (e.g., an anti-LAG-3 antibody molecule as described herein).

The combinations of therapeutic agents disclosed herein include two or more therapeutic agents described herein. The therapeutic agents in the combination can belong to the same category, e.g., two or more therapeutic agents of category (i), or can include at least one agent of two or more categories (e.g., a therapeutic agent of category (i) combined with a therapeutic agent of category (ii)), as described below. Certain therapeutic agents can belong to two or more categories of categories (i)-(iii). For example, a therapeutic agent (e.g., a GITR agonist, an IDO antagonist, a TGF-b inhibitor, among others) can act as a therapeutic agent in multiple categories.

Additional features or embodiments of the methods, compositions, dosage formulations, and kits described herein include one or more of the following:

Combinations

In certain embodiments, the combination includes one, two, three, four or more therapeutic agents that enhance antigen (e.g., tumor antigen) presentation (referred to herein as an "antigen-presentation combination"). In certain embodiments, the antigen presentation combination includes one or more of: an agent that enhances antigen presentation (e.g., a vaccine, e.g., a cell- or antigen-based vaccine); an agent that enhances lysis of tumor cells (e.g., an oncolytic virus); an agent that stimulates (e.g., disinhibits) a phagocyte, e.g., a Type I interferon (IFN) activator (e.g., a TLR agonist, a RIG-I-like receptor agonist (RLRs)), and/or an agent that activates and/or recruits a dendritic cell or a macrophage (e.g., a macrophage I), e.g., a bi- or tri-specific cell engager.

In some embodiments, the antigen-presentation combination includes one, two, three, four, five or more therapeutic agents chosen from: (i) an agonist of Stimulator of Interferon Genes (a STING agonist), (ii) an agonist of a Toll-like receptor (TLR) (e.g., an agonist of TLR-3, -4, -5, -7, -8, or -9), (iii) a TIM-3 modulator (e.g., an anti-TIM-3 antibody molecule), (iv) a vascular endothelial growth factor receptor (VEGFR) inhibitor, (v) a c-Met inhibitor, (vi) a TGFb inhibitor (e.g., an anti-TGFb antibody), (vii) an IDO/TDO inhibitor, (viii) an A2AR antagonist, (ix) an oncolytic virus, (x) a vaccine (e.g., a scaffold vaccine), or (xi) a bi- or tri-specific cell engager. Any combination of the aforesaid agents (i)-(xi) can be used in the antigen-presentation combination. In one exemplary embodiment, the antigen-presentation combination includes a STING agonist. In another exemplary embodiment, the antigen-presentation combination includes a TLR agonist (e.g., a TLR7 agonist). In another exemplary embodiment, the antigen-presentation combination includes a STING agonist and a TLR agonist (e.g., a TLR7 agonist). In some embodiments, the antigen presentation combination is chosen from a STING agonist, a TLR agonist, an A2AR antagonist, or an oncolytic virus or a combination thereof, and optionally, one or more of (iii)-(vii) or (x)-(xi). In some embodiments, the antigen presentation combination is chosen from a STING agonist or a TLR agonist, or a combination of both, and optionally, one or more of (iii)-(xi). In another embodiment, the antigen-presentation combination includes a STING agonist, a TLR agonist (e.g., a TLR7 agonist) and a TIM-3 modulator (e.g., an anti-TIM-3 inhibitor). In another embodiment, the antigen-presentation combination includes a STING agonist, a TLR agonist (e.g., a TLR7 agonist) and a VEGFR inhibitor. In another embodiment, the antigen-presentation combination includes a STING agonist, a TLR agonist (e.g., a TLR7 agonist) and a c-MET inhibitor. In yet other embodiments, the antigen-presenting combination includes an oncolytic virus. In other embodiments, the antigen-presenting combination includes an oncolytic virus and a cytokine, e.g., an oncolytic virus expressing one or more of GM-CSF, or a CSF (e.g., CSF1, or CSF2). In some embodiments, the antigen-presenting combination includes a bi- or tri-specific cell engager, e.g., a bi- or tri-specific antibody molecule to CD47 and CD19, with or without an Fc domain. In some embodiments, the antigen-presenting combination includes a TGFb inhibitor (e.g., an anti-TGFb antibody). In other embodiments, the antigen-presenting combination includes an IDO/TDO inhibitor. In yet other embodiments, the antigen-presenting combination includes an A2AR antagonist. In yet other embodiments, the antigen-presenting combination includes a vaccine (e.g., IL-2 in combination with MUC1, or a dendritic cell based vaccine (e.g., Provenge®)). In yet other embodiments, the antigen-presenting combination includes a vaccine and a TLR agonist (e.g., a TLR agonist as described herein). In certain embodiment, the antigen-presentation combination includes a vaccine and a STING agonist. In certain embodiment, the antigen-presentation combination includes a vaccine, a STING agonist and a TLR agonist.

In certain embodiments, the combination includes one, two, three, four, five or more therapeutic agents that enhance an effector cell response (referred to herein as an "effector cell combination"). In some embodiments, the effector cell combination includes a lymphocyte activator, e.g., an NK cell activator and/or a T cell activator. In some embodiments, the effector cell combination activates (e.g., disinhibits) a tumor infiltrating lymphocyte (TIL), e.g., an NK cell or a T cell. In some embodiments, the effector cell combination includes an NK cell modulator chosen from a modulator (e.g., an antibody molecule) of an NK receptor (e.g., a modulator of one or more of NKG2A, KIR3DL, NKp46, MICA or CEACAM1); an interleukin or an interleukin variant (e.g., IL-2, IL-15, IL-21, IL-13R or IL-12 cytokine or variant thereof, or a combination thereof); a bi- or tri-specific cell engager (e.g., a bispecific antibody molecule of NKG2A and CD138, or a bispecific antibody molecule of CD3 and TCR); an NK cell therapy; or a vaccine that includes NK cells and an antigen/immune stimulant. In some embodiments, the effector cell combination includes an immunomodulator (e.g., one or more of: an activator of a costimulatory molecule or an inhibitor of an immune checkpoint molecule as described herein). In some embodiments, the effector cell combination includes a T cell modulator chosen from an inhibitor of a checkpoint inhibitor (e.g., an inhibitor of one or more of: PD-1, PD-L1, TIM-3, LAG-3, VISTA, DKG-α, B7-H3, B7-H4, TIGIT, CTLA4, BTLA, CD160, TIM1, IDO, LAIR1, IL-12, or a combination thereof, e.g., an inhibitor of LAG-3 and PD-1, or an inhibitor of LAG-3 and TIM-3). In one embodiment, the inhibitor of the checkpoint inhibitor is an antibody molecule (e.g., a mono- or bispecific antibody or fragment thereof as described herein). For example, the inhibitor of the checkpoint inhibitor is an antibody molecule against PD-1, PD-L1, TIM-3, LAG-3, VISTA, B7-H4, CTLA-4 or TIGIT, or any combination thereof (e.g. a combination as described herein). In some embodiments, the effector cell combination includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, ICOS, SLAM (e.g., SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In some embodiments, the effector cell combination includes one, two, three, four, five or more therapeutic agents chosen from: (i) a GITR modulator (e.g., a GITR agonist), (ii) a PD-1 inhibitor (e.g., an anti-PD-1 antibody molecule as described herein), (iii) a PD-L1 inhibitor, (iv) an inhibitor of IAP (Inhibitor of Apoptosis Protein), (v) an inhibitor of EGFR (Epidermal Growth Factor Receptor), (vi) an inhibitor of target of rapamycin (mTOR), (vii) IL-15 or a variant thereof, (viii) a CTLA-4 inhibitor, (ix) a bispecific T cell engager (e.g., a bispecific antibody molecule that binds to CD3 and a tumor antigen (e.g., EGFR, PSCA, PSMA, EpCAM, HER2 among others), (x) a CD40 agonist (e.g., an anti-CD40 antibody molecule), (xi) an OX40 agonist (e.g., an anti-OX40 antibody molecule), or (xii) a CD27 agonist (e.g., an anti-CD27 antibody molecule). Any combination of the aforesaid agents can be used in the effector cell combination. In one exemplary embodiment, the effector cell combination includes a GITR agonist. In another embodiment, the effector cell combination includes a PD-1 inhibitor (e.g., an anti-PD-1 antibody molecule as described herein). In another embodiment, the effector cell combination includes a PD-L1 inhibitor. In other embodiments, the effector cell combination includes a GITR agonist and a PD-1 inhibitor (e.g., an anti-PD-1 antibody molecule as described herein). In other embodiments, the effector cell combination includes a GITR agonist and a PD-L1 inhibitor. In other embodiments, the effector cell combination includes a GITR agonist, a PD-1 inhibitor (e.g., an anti-PD-1 antibody molecule as described herein), and a PD-L1 inhibitor. In other embodiments, the effector cell combination includes a PD-1 inhibitor (e.g., an anti-PD-1 antibody molecule as described herein), and a PD-L1 inhibitor. In one embodiment, the effector cell combination includes a GITR agonist and an inhibitor of IAP. In another embodiment, the effector cell combination includes a GITR agonist and an inhibitor of an EGFR inhibitor. In yet another embodiment, the effector cell combination includes a GITR agonist and an inhibitor of an mTOR inhibitor. In one embodiment, the effector cell combination includes IL-15 or a variant thereof. In one embodiment, the effector cell combination includes a CTLA-4 inhibitor. In one embodiment, the effector cell combination includes a bispecific T cell engager (e.g., a bispecific antibody molecule that binds to CD3 and a tumor antigen (e.g., EGFR, PSCA, PSMA, EpCAM, HER2 among others). In one embodiment, the effector cell combination includes a CD40 agonist (e.g., an anti-CD40 antibody molecule). In one embodiment, the effector cell combination includes an OX40 agonist (e.g., an anti-OX40 antibody molecule). In one embodiment, the effector cell combination includes a CD27 agonist (e.g., an anti-CD27 antibody molecule).

In certain embodiments, the combination includes one, two, three, four, five or more therapeutic agents that decrease tumor immunosuppression (referred to herein as an "anti-tumor immunosuppression combination"). In some embodiments, the combination modulates the activity or level of one or more of $T_{reg}$, macrophage 2 or MDSCs. In some embodiments, the combination increases one or more of M2 polarization, $T_{reg}$ depletion, or T cell recruitment. In some embodiments, the anti-tumor immunosuppression combination includes one, two, three, four, five or more therapeutic agents chosen from: (i) an immunomodulator (e.g., one or more of: an activator of a costimulatory molecule (e.g., a GITR agonist), or an inhibitor of an immune checkpoint molecule (e.g., one or more of PD-1, PD-L1, LAG-3, TIM-3 or CTLA-4), as described herein), (ii) a CSF-1/1R inhibitor (e.g., an inhibitor of macrophage colony-stimulating factor (M-CSF)), (iii) an IL-17 inhibitor, (iv) an IL-1β inhibitor, (v) a CXCR2 inhibitor, (vi) an inhibitor of a phosphoinositide 3-kinase (PI3K, e.g., PI3Kγ or PI3Kδ), (vii) a BAFF-R inhibitor, (viii) a MALT-1/BTK inhibitor, (ix) a JAK inhibitor, (x) a CRTH2 inhibitor, (xi) a VEGFR inhibitor, (xiii) an IL-15 or a variant thereof, (xiv) a CTLA-4 inhibitor, (xv) an IDO/TDO inhibitor, (xvi) an A2AR antagonist, (xvii) a TGFb inhibitor, or (xviii) a PFKFB3 inhibitor. In certain embodiments, the immunomodulator is an inhibitor of an immune checkpoint molecule (e.g., an inhibitor of PD-1, PD-L1, LAG-3, TIM-3, CEACAM (e.g., CEACAM-1, -3 and/or -5), or CTLA-4, or any combination thereof). Any combination of the aforesaid agents can be used in the tumor immunosuppression combination. In one exemplary embodiment, the anti-tumor immunosuppression combination includes one, two, three, four, five or more therapeutic agents chosen from a LAG-3 inhibitor (e.g., an anti-LAG-3 antibody molecule as described herein), a PD-1 inhibitor, a PD-L1 inhibitor, a TIM-3 modulator (e.g., an anti-TIM-3 inhibitor), a GITR agonist, a CSF-1/1R inhibitor (e.g., an M-CSF inhibitor), an IL-17 inhibitor, an IL-1β inhibitor, or a CXCR2 inhibitor. In one embodiment, the anti-tumor immunosuppression combination includes one, two, or all of a CSF-1/1R inhibitor (e.g., an M-CSF inhibitor), an IL-17 inhibitor, an IL-1β inhibitor. In one embodiment, the anti-tumor immunosuppression combination includes an IL-17 inhibitor, a CXCR2 inhibitor, a CRTH2 inhibitor, an A2AR antagonist, or a PFKFB3 inhibitor, or a combination thereof.

In some embodiments, the combination includes one or more therapeutic agents of the antigen-presentation combination. In other embodiments, the combination includes one or more therapeutic agents of the effector cell combination. In yet other embodiments, the combination includes one or more therapeutic agents of the anti-tumor immunosuppression combination. In other embodiments, the combination includes one or more therapeutic agents of the antigen-presentation combination and one or more therapeutic agents of the effector cell combination. In other embodiments, the combination includes one or more therapeutic agents of the antigen-presentation combination and one or more therapeutic agents of the anti-tumor immunosuppression combination. In other embodiments, the combination includes one or more therapeutic agents of the antigen-presentation combination, one or more therapeutic agents of the effector cell combination and one or more therapeutic agents of the anti-tumor immunosuppression combination. In other embodiments, the combination includes one or more therapeutic agents of the antigen-presentation combination, one or more therapeutic agents of the effector cell combination and one or more therapeutic agents of the anti-tumor immunosuppression combination.

In certain embodiments, the combination includes:

(i) one or more therapeutic agents of the antigen-presentation combination chosen from one, two or all of a STING agonist, a TLR agonist (e.g., a TLR7 agonist), or a TIM-3 modulator (e.g., a TIM-3 inhibitor);
(ii) one or more therapeutic agents of the effector cell combination chosen from one, two or all of a GITR modulator (e.g., a GITR agonist), a PD-1 inhibitor (e.g., an anti-PD-1 antibody molecule as described herein), or a PD-L1 inhibitor;
(iii) one or more therapeutic agents of the anti-tumor immunosuppression combination chosen from one, two or all of a CSF-1/1R inhibitor (e.g., an M-CSF inhibitor), an IL-17 inhibitor, or an IL-1β inhibitor:
(iv) a combination of (i) and (ii);
(v) a combination of (i) and (iii);
(vi) a combination of (ii) and (iii); or
(vii) a combination of (i), (ii) and (iii).

The combination can be used to treat a cancer as described herein, such as a lung cancer, a melanoma, a renal cancer, a liver cancer, a myeloma, a prostate cancer, a breast cancer, a head and neck cancer, a colorectal cancer, a pancreatic cancer, a hematological cancer, a non-Hogdkin's lymphoma, or a leukemia, or a metastatic lesion of the cancer.

In other embodiments, the combination includes a therapeutic agent from the antigen-presentation combination (e.g., one or more of a STING agonist, a TLR agonist, a vaccine or an oncolytic virus) in combination with a therapeutic agent from the effector cell and/or anti-tumor immunosuppression combination (e.g., an inhibitor of a checkpoint inhibitor, e.g., an inhibitor of PD-1, PD-L1, LAG-3, TIM-3, CEACAM (e.g., CEACAM-1, -3 and/or -5), or CTLA-4, or any combination thereof. In one embodiment, one or more of a STING agonist, a TLR agonist, a vaccine or an oncolytic virus is administered in combination with an anti-LAG-3 antibody molecule as described herein. In one embodiment, a STING agonist and/or a vaccine is administered in combination with an anti-LAG-3 antibody molecule as described herein. In one embodiment, an oncolytic virus is administered in combination with an anti-LAG-3 antibody molecule as described herein. The combination can be used to treat a cancer as described herein, such as a lung cancer, a melanoma, a renal cancer, a liver cancer, a myeloma, a prostate cancer, a breast cancer, a head and neck cancer, a colorectal cancer, a pancreatic cancer, a hematological cancer, a non-Hogdkin's lymphoma, or a leukemia, or a metastatic lesion of the cancer.

In certain embodiments, the combination includes a combination of therapeutic agents as provided in the section entitled "Exemplary Combinations of Antigen-Presentation Combinations, Effector Cell Combinations and Anti-tumor Immunosuppression Combinations" provided in the Detailed Description.

The combinations disclosed herein can be administered together in a single composition or administered separately in two or more different compositions, e.g., compositions or dosage forms as described herein. The administration of the therapeutic agents can be in any order. The first agent and the additional agents (e.g., second, third agents) can be administered via the same administration route or via different administration routes. For example, a first therapeutic agent can be administered concurrently with, prior to, or subsequent to, the additional agent. In certain embodiments, a first agent is administered locally, e.g., a therapeutic agent of any of categories (i)-(iii) can be coupled to a tumor targeting agent, e.g., a tumor-targeting antibody (e.g., to form an antibody-drug conjugate), or any other delivery agent (e.g., a formulation such as a targeted formulation) such that administration of the first agent is localized to a desired site, e.g., a tumor site (e.g., a dendritic cell-enriched site). In one embodiment, the therapeutic agent is an antigen (e.g., a vaccine, e.g., an in situ cancer vaccine), which is targeted to the tumor environment, thus resulting in activation of dendritic cells. The therapeutic agent also can be locally administered, e.g., injected, at a tumor site (e.g., intratumoral or peritumoral administration). Localized delivery or administration of the therapeutic agent can reduce one or more side effects or toxicities that would otherwise be associated with systemic administration of the therapeutic agent. In one exemplary embodiment, a therapeutic agent (e.g., STING or a TLR) can be conjugated to a tumor-binding antibody (e.g., an antibody that binds to HER2), thereby delivering the therapeutic agent to a HER-2-expressing cell.

When administered in combination, the first agent, the additional agent (e.g., second or third agent), or all, can be administered in an amount or dose that is higher, lower or the same than the amount or dosage of each agent used individually, e.g., as a monotherapy. In certain embodiments, the administered amount or dosage of the first agent, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the first agent, the additional agent (e.g., second or third agent), or all, that results in a desired effect (e.g., treatment of cancer) is lower (e.g., at least 20%, at least 30%, at least 40%, or at least 50% lower).

In one embodiment, the anti-LAG-3 antibody molecule is administered, alone or in combination (e.g., in combination with an anti-PD-1 antibody molecule), at a dose of less than, or about, 5 mg/kg; less than, or about, 4 mg/kg; less than, or about, 3 mg/kg; less than, or about, 2 mg/kg; less than, or about, 1 mg/kg, every other week. In one embodiment, the anti-LAG-3 antibody molecule is administered at a dose of 1 to 5 mg/kg every other week; 1 to 4 mg/kg every other week, 1 to 3 mg/kg every other week, or 1 to 2 mg/kg every other week. In one embodiment, the anti-PD-1 antibody molecule is administered, alone or in combination (e.g., in combination with an anti-LAG-3 antibody molecule) at a dose of 1 to 5 mg/kg every other week; 1 to 4 mg/kg every other week, 1 to 3 mg/kg every other week, or 1 to 2 mg/kg every other week.

In certain embodiments, the combinations can be in the form of an antibody molecule, e.g., a bi- or tri-specific molecule, against one or more therapeutic agents chosen from the antigen-presentation combination, the effector cell combination, or the anti-tumor immunosuppression combination, or any combination thereof. For example, a bispecific molecule against two or more checkpoint inhibitors (e.g., an anti-LAG-3 and anti-PD-1 antibody molecule). In other embodiments, the combinations can be in the form of an antibody molecule, e.g., a bi- or tri-specific molecule, against one or more therapeutic agents chosen from two or all of the antigen-presentation combination, the effector cell combination, and/or the anti-tumor immunosuppression combination. In one embodiment, the antibody molecule is a full antibody or fragment thereof (e.g., a Fab, $F(ab')_2$, Fv, or a single chain Fv fragment (scFv)). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of: Fc receptor binding, antibody glycosylation, the number of cysteine residues, effector cell function, or complement function). In certain embodiments, the antibody molecule is in the form of a bispecific or multispecific antibody molecule, e.g., a bispecific, trispecific antibody molecule as described herein.

Certain exemplary therapeutic agents and combinations thereof are provided herein below. A more detailed description of the therapeutic agents used in the combinations is provided in the Detailed Description.

Immunomodulators

In certain embodiments, the immunomodulator used in the combinations disclosed herein (e.g., in combination with a therapeutic agent chosen from an antigen-presentation combination) is an inhibitor of an immune checkpoint molecule. In one embodiment, the immunomodulator is an inhibitor of PD-1, PD-L1, PD-L2, CTLA-4, TIM-3, LAG-3, CEACAM (e.g., CEACAM-1, -3 and/or -5), VISTA, BTLA, TIGIT, LAIR1, CD160, 2B4 and/or TGF beta. In one embodiment, the inhibitor of an immune checkpoint molecule inhibits PD-1, PD-L1, LAG-3, TIM-3, CEACAM (e.g., CEACAM-1, -3 and/or -5), CTLA-4, or any combination thereof.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, that binds to the inhibitory molecule; e.g., an antibody or fragment thereof (also referred to herein as "an antibody molecule") that binds to PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4 and/or TGF beta, or a combination thereof.

In certain embodiments, the antibody molecule is in the form of a bispecific or a multispecific antibody molecule. In one embodiment, the bispecific antibody molecule has a first binding specificity for LAG-3 and a second binding specify for PD-1, TIM-3, CEACAM (e.g., CEACAM-1 and/or CEACAM-5), PD-L1 or PD-L2. In one embodiment, the bispecific antibody molecule binds to LAG-3 and PD-1. In another embodiment, the bispecific antibody molecule binds to LAG-3 and TIM-3. In another embodiment, the bispecific antibody molecule binds to LAG-3 and CEACAM (e.g., CEACAM-1, -3 and/or CEACAM-5). In another embodiment, the bispecific antibody molecule binds to LAG-3 and CEACAM-1. In still another embodiment, the bispecific antibody molecule binds to LAG-3 and CEACAM-3. In yet another embodiment, the bispecific antibody molecule binds to LAG-3 and CEACAM-5. In another embodiment, the bispecific antibody molecule binds to LAG-3 and PD-L1. In yet another embodiment, the bispecific antibody molecule binds to LAG-3 and PD-L2. Any combination of the aforesaid molecules can be made in a multispecific antibody molecule, e.g., a trispecific antibody that includes a first binding specificity to LAG-3, and a second and third binding specificity to one or more of: PD-1, TIM-3, CEACAM (e.g., CEACAM-1, -3, and/or CEACAM-5), PD-L1 or PD-L2.

In other embodiments, the immunomodulator is an inhibitor of LAG-3, e.g., human LAG-3. In one embodiment, the inhibitor of LAG-3 is an antibody molecule to LAG-3. The LAG-3 inhibitor can be administered alone, or in combination with other immunomodulators, e.g., in combination with an inhibitor of CEACAM (e.g., CEACAM-1, -3 and/or -5), TIM-3, PD-1, PD-L1 or CTLA-4. In an exemplary embodiment, the inhibitor of LAG-3, e.g., the anti-LAG-3 antibody molecule, is administered in combination with a PD-1 inhibitor, e.g., an anti-PD-1 antibody molecule. In an exemplary embodiment, the inhibitor of LAG-3, e.g., the anti-LAG-3 antibody molecule, is administered in combination with a PD-L1 inhibitor, e.g., an anti-PD-L1 antibody molecule. In another embodiment, the inhibitor of LAG-3, e.g., the anti-LAG-3 antibody molecule, is administered in combination with a TIM-3 inhibitor, e.g., an anti-TIM-3 antibody molecule. In another embodiment, the inhibitor of LAG-3, e.g., the anti-LAG-3 antibody molecule, is administered in combination with a CEACAM inhibitor (e.g., CEACAM-1, -3 and/or -5 inhibitor), e.g., an anti-CEACAM antibody molecule. In another embodiment, the inhibitor of LAG-3, e.g., the anti-LAG-3 antibody molecule, is administered in combination with a CEACAM-1 inhibitor, e.g., an anti-CEACAM-1 antibody molecule. In another embodiment, the inhibitor of LAG-3, e.g., the anti-LAG-3 antibody molecule, is administered in combination with a CEACAM-5 inhibitor, e.g., an anti-CEACAM-5 antibody molecule. In yet other embodiments, the inhibitor of LAG-3, e.g., the anti-LAG-3 antibody molecule, is administered in combination with a PD-1 inhibitor, e.g., an anti-PD-1 antibody molecule, and a TIM-3 inhibitor, e.g., an anti-TIM-3 antibody molecule. Other combinations of immunomodulators with a LAG-3 inhibitor (e.g., one or more of PD-1, PD-L1, PD-L2, CTLA-4, TIM-3, CEACAM (e.g., CEACAM-1, -3 and/or -5), VISTA, BTLA, TIGIT, LAIR1, CD160, 2B4 and/or TGF beta) are also within the present invention. Any of the antibody molecules known in the art or disclosed herein can be used in the aforesaid combinations of inhibitors of checkpoint molecule In certain embodiments, the immunomodulator is an inhibitor of PD-1, e.g., human PD-1. In another embodiment, the immunomodulator is an inhibitor of PD-L1, e.g., human PD-L1. In one embodiment, the inhibitor of PD-1 or PD-L1 is an antibody molecule to PD-1 or PD-L1. The PD-1 or PD-L1 inhibitor can be administered alone, or in combination with other immunomodulators, e.g., in combination with an inhibitor of LAG-3, TIM-3, CEACAM (e.g., CEACAM-1, -3 and/or -5) or CTLA-4. In an exemplary embodiment, the inhibitor of PD-1 or PD-L1, e.g., the anti-PD-1 or PD-L1 antibody molecule, is administered in combination with a LAG-3 inhibitor, e.g., an anti-LAG-3 antibody molecule. In another embodiment, the inhibitor of PD-1 or PD-L1, e.g., the anti-PD-1 or PD-L1 antibody molecule, is administered in combination with a TIM-3 inhibitor, e.g., an anti-TIM-3 antibody molecule. In another embodiment, the inhibitor of PD-1 or PD-L1, e.g., the anti-PD-1 or PD-L1 antibody molecule, is administered in combination with a CEACAM inhibitor (e.g., CEACAM-1, -3 and/or -5 inhibitor), e.g., an anti-CEACAM antibody molecule. In another embodiment, the inhibitor of PD-1 or PD-L1, e.g., the anti-PD-1 or PD-L1 antibody molecule, is administered in combination with a CEACAM-1 inhibitor, e.g., an anti-CEACAM-1 antibody molecule. In another embodiment, the inhibitor of PD-1 or PD-L1, e.g., the anti-PD-1 or PD-L1 antibody molecule, is administered in combination with a CEACAM-5 inhibitor, e.g., an anti-CEACAM-5 antibody molecule. In yet other embodiments, the inhibitor of PD-1 or PD-L1, e.g., the anti-PD-1 antibody molecule, is administered in combination with a LAG-3 inhibitor, e.g., an anti-LAG-3 antibody molecule, and a TIM-3 inhibitor, e.g., an anti-TIM-3 antibody molecule. Other combinations of immunomodulators with a PD-1 inhibitor (e.g., one or more of PD-L2, CTLA-4, TIM-3, LAG-3, CEACAM (e.g., CEACAM-1, -3 and/or -5), VISTA, BTLA, TIGIT, LAIR1, CD160, 2B4 and/or TGF beta) are also within the present invention. Any of the antibody molecules known in the art or disclosed herein can be used in the aforesaid combinations of inhibitors of checkpoint molecule.

In other embodiments, the immunomodulator is an inhibitor of CEACAM (e.g., CEACAM-1, -3 and/or -5), e.g., human CEACAM (e.g., CEACAM-1, -3 and/or -5). In one embodiment, the immunomodulator is an inhibitor of CEACAM-1, e.g., human CEACAM-1. In another embodiment, the immunomodulator is an inhibitor of CEACAM-3, e.g., human CEACAM-3. In another embodiment, the immunomodulator is an inhibitor of CEACAM-5, e.g., human CEACAM-5. In one embodiment, the inhibitor of CEACAM (e.g., CEACAM-1, -3 and/or -5) is an antibody molecule to CEACAM (e.g., CEACAM-1, -3 and/or -5). The CEACAM (e.g., CEACAM-1, -3 and/or -5) inhibitor can be administered alone, or in combination with other immunomodulators, e.g., in combination with an inhibitor of LAG-3, TIM-3, PD-1, PD-L1 or CTLA-4.

In other embodiments, the immunomodulator is an inhibitor of TIM-3, e.g., human TIM-3. In one embodiment, the inhibitor of TIM-3 is an antibody molecule to TIM-3. The TIM-3 inhibitor can be administered alone, or in combination with other immunomodulators, e.g., in combination with an inhibitor of CEACAM (e.g., CEACAM-1, -3 and/or -5), LAG-3, PD-1, PD-L1 or CTLA-4.

In certain embodiments, the immunomodulator used in the combinations disclosed herein (e.g., in combination with a therapeutic agent chosen from an antigen-presentation combination) is an activator or agonist of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CD28, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In other embodiments, the immunomodulator is a GITR agonist. In one embodiment, the GITR agonist is an antibody molecule to GITR. The GITR agonist can be administered alone, or in combination with other immunomodulators, e.g., in combination with an inhibitor of PD-1, PD-L1, CTLA-4, CEACAM (e.g., CEACAM-1, -3 and/or -5), TIM-3 or LAG-3. In some embodiments, the anti-GITR antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, the anti-GITR antibody molecule is administered in combination with an anti-PD-1 antibody molecule (e.g., an anti-PD-1 molecule as described herein). The GITR antibody molecule and the anti-PD-1 antibody molecule may be in the form of separate antibody composition, or as a bispecific antibody molecule. In other embodiments, a GITR agonist can be administered in combination with other costimulatory molecule, e.g., an agonist of OX40, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand.

In other embodiments, the immunomodulator is an activator of a costimulatory molecule (e.g., an OX40 agonist). In one embodiment, the OX40 agonist is an antibody molecule to OX40. The OX40 agonist can be administered alone, or in combination with other immunomodulators, e.g., in combination with an inhibitor of PD-1, PD-L1, CTLA-4, CEACAM (e.g., CEACAM-1, -3 and/or -5), TIM-3 or LAG-3. In some embodiments, the anti-OX40 antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, an OX40 antibody molecule is administered in combination with an anti-PD-1 antibody molecule (e.g., an anti-PD-1 molecule as described herein). The OX40 antibody molecule and the anti-PD-1 antibody molecule may be in the form of separate antibody composition, or as a bispecific antibody molecule. In other embodiments, the OX40 agonist can be administered in combination with other costimulatory molecule, e.g., an agonist of GITR, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand.

It is noted that only exemplary combinations of inhibitors of checkpoint inhibitors or agonists of costimulatory molecules are provided herein. Additional combinations of these agents are within the scope of the present invention.

Antibody Molecules to LAG-3

In one embodiment, the LAG-3 inhibitor is an anti-LAG-3 antibody molecule as described in U.S. Patent Application Publication No. US 2015/0259420 (U.S. Ser. No. 14/657,260), entitled "Antibody Molecules to LAG-3 and Uses Thereof," incorporated by reference in its entirety.

In one embodiment, the anti-LAG-3 antibody molecule comprises at least one antigen-binding region, e.g., a variable region or an antigen-binding fragment thereof, from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In another embodiment, the anti-LAG-3 antibody molecule comprises at least one, two, three or four variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. In one embodiment, the antibody molecule includes a substitution (e.g., a Cys to Ser substitution at position 84) in the heavy chain framework region 3 (VHFW3) (e.g., as shown in Tables 1 and 2).

In yet another embodiment, the anti-LAG-3 antibody molecule comprises at least one or two heavy chain variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule comprises at least one or two light chain variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes a heavy chain constant region for an IgG4, e.g., a human IgG4. In one embodiment, the human IgG4 includes a substitution at position 228 according to EU numbering (e.g., a Ser to Pro substitution). In still another embodiment, the anti-LAG-3 antibody molecule includes a heavy chain constant region for an IgG1, e.g., a human IgG1. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 according to EU numbering and/or a Pro to Ala substitution at position 329 according to EU numbering). In one embodiment, the human IgG1 includes a substitution at position 234 according to EU numbering, a substitution at position 235 according to EU numbering, or both (e.g., a Leu to Ala substitution at position 234 according to EU numbering and/or a Leu to Ala substitution at position 235 according to EU numbering). In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In yet another embodiment, the anti-LAG-3 antibody molecule includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In another embodiment, the anti-LAG-3 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the constant region is a mutated IgG4, e.g., a mutated human IgG4 (e.g., has a mutation at position 228 according to EU numbering (e.g., a S228P mutation). In yet another embodiment, the anti-LAG-3 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 according to EU numbering and/or a Pro to Ala substitution at position 329 according to EU numbering). In one embodiment, the human IgG1 includes a substitution at position 234 according to EU numbering, a substitution at position 235 according to EU numbering, or both (e.g., a Leu to Ala substitution at position 234 according to EU numbering and/or a Leu to Ala substitution at position 235 according to EU numbering).

In another embodiment, the anti-LAG-3 antibody molecule includes a heavy chain variable domain and a constant region, a light chain variable domain and a constant region, or both, comprising the amino acid sequence of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-LAG-3 antibody molecule, optionally, comprises a leader sequence from a heavy chain, a light chain, or both, as shown in Table 4; or a sequence substantially identical thereto.

In yet another embodiment, the anti-LAG-3 antibody molecule includes at least one, two, or three complementarity determining regions (CDRs) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs shown in Table 1.

In one embodiment, the anti-LAG-3 antibody molecule includes at least one, two or three CDRs (or collectively all of the CDRs) from a heavy chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-LAG-3 antibody molecule includes at least one, two, or three complementarity determining regions (CDRs) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs shown in Table 1.

In yet another embodiment, the anti-LAG-3 antibody molecule includes at least one, two, or three CDRs (or collectively all of the CDRs) from a light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid shown in Table 1, or encoded by a nucleotide sequence shown in Table 1. In another embodiment, the anti-LAG-3 antibody molecule includes at least one, two, three, four, five or six CDRs (or collectively all of the CDRs) from a heavy and light chain variable region comprising an amino acid shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid shown in Table 1, or encoded by a nucleotide sequence shown in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs shown in Table 1.

In another embodiment, the anti-LAG-3 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-LAG-3 antibody molecule includes all six CDRs from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions) relative to one, two, three, four, five, or six CDRs shown in Table 1. In one embodiment, the anti-LAG-3 antibody molecule may include any CDR described herein.

In one embodiment, the anti-LAG-3 antibody molecule includes at least one, two or three CDRs according to Kabat (e.g., at least one, two, or three CDRs according to the Kabat definition as set out in Table 1) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat shown in Table 1.

In one embodiment, the anti-LAG-3 antibody molecule includes at least one, two or three CDRs according to Kabat (e.g., at least one, two, or three CDRs according to the Kabat definition as set out in Table 1) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat shown in Table 1.

In yet another embodiment, the anti-LAG-3 antibody molecule includes at least one, two, three, four, five, or six CDRs according to Kabat (e.g., at least one, two, three, four, five, or six CDRs according to the Kabat definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to at least one, two, three, four, five, or six CDRs according to Kabat et al. shown in Table 1. In one embodiment, the anti-LAG-3 antibody molecule may include any CDR described herein.

In yet another embodiment, the anti-LAG-3 antibody molecule includes all six CDRs according to Kabat (e.g., all six CDRs according to the Kabat definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-LAG-3 antibody molecule may include any CDR described herein.

In another embodiment, the anti-LAG-3 antibody molecule includes at least one, two or three hypervariable loops (e.g., at least one, two, or three hypervariable loops according to the Chothia definition as set out in Table 1) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, according to Chothia (e.g., at least one, two, or three hypervariable loops according to the Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three hypervariable loops according to Chothia shown in Table 1.

In another embodiment, the anti-LAG-3 antibody molecule includes at least one, two or three hypervariable loops according to Chothia (e.g., at least one, two, or three CDRs according to the Chothia definition as set out in Table 1) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three hypervariable loops according to Chothia shown in Table 1.

In yet another embodiment, the anti-LAG-3 antibody molecule includes at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or at least the amino acids from those hypervariable loops that contact LAG-3. In one embodiment, the anti-LAG-3 antibody molecule includes at least one, two, three, four, five, or six Chothia hypervariable loops of Table 1.

In one embodiment, the anti-LAG-3 antibody molecule includes all six hypervariable loops (e.g., all six hypervariable loops according to the Chothia definition as set out in Table 1) of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, or closely related hypervariable loops, e.g., hypervariable loops which are identical or which have at least one amino acid alteration, but not more than two, three or four alterations (e.g., substitutions, deletions, or insertions, e.g., conservative substitutions) relative to all six hypervariable loops shown in Table 1. In one embodiment, the anti-LAG-3 antibody molecule may include any hypervariable loop described herein.

In still another embodiment, the anti-LAG-3 antibody molecule includes at least one, two, or three hypervariable loops that have the same canonical structures as the corresponding hypervariable loop of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-LAG-3 antibody molecule includes a combination of CDRs or hypervariable loops defined according to the Kabat et al. and Chothia et al.

In one embodiment, the anti-LAG-3 antibody molecule includes at least one, two or three CDRs or hypervariable loops from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, according to the Kabat and Chothia definition (e.g., at least one, two, or three CDRs or hypervariable loops according to the Kabat and Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

For example, the anti-LAG-3 antibody molecule can include VH CDR1 according to Kabat et al. or VH hypervariable loop 1 according to Chothia et al., or a combination thereof, e.g., as shown in Table 1. In one embodiment, the combination of Kabat and Chothia CDR of VH CDR1 comprises the amino acid sequence GFTLTNYGMN (SEQ ID NO: 286), or an amino acid sequence substantially identical thereto (e.g., having at least one amino acid alteration, but not more than two, three or four alterations (e.g., substitutions, deletions, or insertions, e.g., conservative substitutions)). The anti-LAG-3 antibody molecule can further include, e.g., VH CDRs 2-3 according to Kabat et al. and VL CDRs 1-3 according to Kabat et al., e.g., as shown in Table 1. Accordingly, in some embodiments, framework regions are defined based on a combination of CDRs defined according to Kabat et al. and hypervariable loops defined according to Chothia et al. For example, the anti-LAG-3 antibody molecule can include VH FR1 defined based on VH hypervariable loop 1 according to Chothia et al. and VH FR2 defined based on VH CDRs 1-2 according to Kabat et al., e.g., as shown in Table 1. The anti-LAG-3 antibody molecule can further include, e.g., VH FRs 3-4 defined based on VH CDRs 2-3 according to Kabat et al. and VL FRs 1~4 defined based on VL CDRs 1-3 according to Kabat et al.

The anti-LAG-3 antibody molecule can contain any combination of CDRs or hypervariable loops according to the Kabat and Chothia definitions. In one embodiment, the anti-LAG-3 antibody molecule includes at least one, two or three CDRs from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, according to the Kabat and Chothia definition (e.g., at least one, two, or three CDRs according to the Kabat and Chothia definition as set out in Table 1).

In one embodiment, the anti-LAG-3 antibody includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;

(c) a VH comprising a VHCDR1 amino acid sequence of SEQ ID NO: 286, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or (d) a VH comprising a VHCDR1 amino acid sequence of SEQ ID NO: 286; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

In the combinations therein, in another embodiment, the antibody molecule comprises (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12.

In the combination therein, in yet another embodiment, the antibody molecule includes: (i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15.

In an embodiment, e.g., an embodiment comprising a variable region, CDR (e.g., CDR or Kabat CDR), or other sequence referred to herein, e.g., in Table 1, the antibody molecule is a monospecific antibody molecule, a bispecific antibody molecule, or is an antibody molecule that comprises an antigen binding fragment of an antibody, e.g., a half antibody or antigen binding fragment of a half antibody. In certain embodiments, the antibody molecule is a bispecific antibody molecule having a first binding specificity for LAG-3 and a second binding specify for PD-1, TIM-3, CEACAM (e.g., CEACAM-1, CEACAM-3, and/or CEACAM-5), PD-L1 or PD-L2. In one embodiment, the bispecific antibody molecule binds to LAG-3 and TIM-3. In another embodiment, the bispecific antibody molecule binds to LAG-3 and PD-1. In another embodiment, the bispecific antibody molecule binds to LAG-3 and CEACAM (e.g., CEACAM-1, CEACAM-3, and/or CEACAM-5). In another embodiment, the bispecific antibody molecule binds to LAG-3 and CEACAM-1. In yet another embodiment, the bispecific antibody molecule binds to LAG-3 and CEACAM-5. In another embodiment, the bispecific antibody molecule binds to LAG-3 and PD-L1. In yet another embodiment, the bispecific antibody molecule binds to LAG-3 and PD-L2. Any combination of the aforesaid molecules can be made in a multispecific antibody molecule, e.g., a trispecific antibody that includes a first binding specificity to LAG-3, and a second and third binding specificity to one or more of: TIM-3, PD-1, CEACAM (e.g., CEACAM-1, CEACAM-3, or CEACAM-5), PD-L1 or PD-L2.

In other embodiments, the anti-LAG-3 antibody molecule is used in combination with a bispecific molecule comprising one or more of: TIM-3, PD-1, CEACAM (e.g., CEACAM-1, CEACAM-3, or CEACAM-5), PD-L1 or PD-L2. In one embodiment, the bispecific antibody molecule used in combination binds to CEACAM (e.g., CEACAM-1, CEACAM-3, and/or CEACAM-5) and PD-1.

In another embodiment, the bispecific antibody molecule used in combination binds to CEACAM (e.g., CEACAM-1, CEACAM-3, and/or CEACAM-5) and TIM-3. In another embodiment, the bispecific antibody molecule used in combination binds to PD-1 and TIM-3.

Uses of the Combination Therapies

The combinations disclosed herein can result in one or more of: an increase in antigen presentation, an increase in effector cell function (e.g., one or more of T cell proliferation, IFN-γ secretion or cytolytic function), inhibition of regulatory T cell function, an effect on the activity of multiple cell types, such as regulatory T cell, effector T cells and NK cells), an increase in tumor infiltrating lymphocytes, an increase in T-cell receptor mediated proliferation, and a decrease in immune evasion by cancerous cells. In one embodiment, the use of a LAG-3 inhibitor in the combinations inhibits, reduces or neutralizes one or more activities of LAG-3, resulting in blockade or reduction of an immune checkpoint. Thus, such combinations can be used to treat or prevent disorders where enhancing an immune response in a subject is desired.

Accordingly, in another aspect, a method of modulating an immune response in a subject is provided. The method comprises administering to the subject a combination disclosed herein (e.g., a combination comprising a therapeutically effective amount of an anti-LAG-3 antibody molecule), alone or in combination with one or more agents or procedures, such that the immune response in the subject is modulated. In one embodiment, the antibody molecule restores, enhances, stimulates or increases an immune response in the subject.

The subject can be a mammal, e.g., a primate, preferably a higher primate, e.g., a human (e.g., a patient having, or at risk of having, a disorder described herein). In one embodiment, the subject is in need of enhancing an immune response. In some embodiments, the anti-LAG-3 antibody molecule restores, enhances or stimulates an antigen-specific T cell response, e.g., interleukin-2 (IL-2) or interferon-gamma (IFN-γ) production in an antigen-specific T cell response, in the subject. In some embodiments, the immune response is an anti-tumor response. In one embodiment, the subject has, or is at risk of, having a disorder described herein, e.g., a cancer or an infectious disorder as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

In one aspect, a method of treating (e.g., one or more of reducing, inhibiting, or delaying progression) a cancer or tumor in a subject is provided. The method comprises administering to the subject an anti-LAG-3 antibody molecule described herein (e.g., a combination comprising a therapeutically effective amount of an anti-LAG-3 antibody molecule).

In certain embodiments, the cancer treated with the combination, includes but is not limited to, a solid tumor, a hematological cancer (e.g., leukemia, lymphoma, myeloma), and a metastatic lesion thereof. In one embodiment, the cancer is a solid tumor. Examples of solid tumors include malignancies, e.g., sarcomas and carcinomas (e.g., adenocarcinomas), of the various organ systems, such as those affecting lung, breast, lymphoid, gastrointestinal or colorectal, genitals and genitourinary tract (e.g., renal, urothelial, bladder cells), pharynx, CNS (e.g., brain, neural or glial cells), skin (e.g., melanoma), head and neck (e.g., head and neck squamous cell carcinoma (HNSCC)), and pancreas. For example, the cancer can be chosen from a skin cancer (e.g., a melanoma or a Merkel cell carcinoma), a colon cancer, a gastric cancer, a rectal cancer, a kidney cancer (e.g., a renal cancer (e.g., renal-cell carcinoma)), a breast cancer (e.g., a breast cancer that does not express one, two or all of estrogen receptor, progesterone receptor, or Her2/neu, e.g., a triple negative breast cancer), a liver cancer, a lung cancer (e.g., a non-small cell lung cancer (NSCLC) (e.g., a NSCLC with squamous and/or non-squamous histology) or small cell lung cancer), a prostate cancer, a cancer of head or neck (e.g., HPV+ squamous cell carcinoma), a cancer of the small intestine, a brain cancer (e.g., a glioblastoma), an endometrial cancer, or a cancer of the esophagus. Examples of hematological cancer include, but is not limited to, leukemia (e.g., a myeloid leukemia, lymphoid leukemia, or chronic lymphocytic leukemia (CLL)), lymphoma (e.g., Hogdkin lymphoma (HL), non-Hogdkin lymphoma (NHL), Diffuse large B-cell lymphoma (DLBCL), T-cell lymphoma, or mantle cell lymphoma (MCL)), and myeloma, e.g., multiple myeloma. The cancer may be at an early, intermediate, late stage or metastatic cancer.

In some embodiments, the cancer is chosen from a colorectal cancer (e.g., CRC), melanoma, e.g., advanced stage melanoma (e.g., stage II-IV melanoma) or HLA-A2 positive-melanoma; a pancreatic cancer, e.g., advanced pancreatic cancer; a breast cancer, e.g., metastatic breast carcinoma or triple negative breast cancer; a head and neck cancer (e.g., HNSCC); an esophageal cancer; a renal cell carcinoma (RCC), e.g., clear renal cell carcinoma (ccRCC) or metastatic renal cell carcinoma (MRCC); a lung cancer (e.g., NSCLC); a cervical cancer; bladder cancer; or a hematologic malignancy, e.g., a leukemia (e.g., a lymphocytic leukemia), or a lymphoma (e.g., a Hogdkin's lymphoma (HL), a non-Hogdkin's lymphoma (NHL), a diffuse large B-cell lymphoma (DLBCL), a mantle cell lymphoma (MCL), or a CLL, e.g., a relapsed or refractory chronic lymphocytic leukemia).

In some embodiments, the cancer is MSI-high (high microsatellite instability) cancer (e.g., an MSI-high endometrial cancer). In other embodiments, the cancer is an EBV+ cancer. In certain embodiments, the cancer is a FoxP3-expressing cancer (e.g., a FoxP3-expressing non-small cell lung cancer or a head and neck squamous cell carcinoma). In other embodiments, the cancer is EGFR mutated or cMET positive (e.g., an EGFR mutated or cMET positive non-small cell lung cancer). In other embodiments, the cancer has a KRAS mutation (e.g., a non-small cell lung cancer having a KRAS mutation).

In one embodiment, the cancer is an advanced or unresectable melanoma that does not respond to other therapies. In other embodiments, the cancer is a melanoma with a BRAF mutation (e.g., a BRAF V600 mutation). In yet other embodiments, the combination disclosed herein (e.g., the combination comprising the anti-LAG-3 antibody molecule) is administered alone, or in combination with one or more second agents (e.g., a BRAF inhibitor). In one embodiment, the combination disclosed herein (e.g., the combination comprising the anti-LAG-3 antibody molecule) is administered in combination with (e.g., before or after treatment or simultaneously with) an inhibitor of an immune checkpoint modulator (e.g., a PD-1 inhibitor, a PD-L1 inhibitor, a TIM-3 inhibitor, a CEACAM (e.g., CEACAM-1, -3 and/or CEACAM-5) inhibitor, or a CTLA-4 inhibitor (e.g., an anti-CTLA-4 antibody, e.g., ipilimumab)) with or without a BRAF inhibitor (e.g., vemurafenib or dabrafenib) to treat a melanoma. In one embodiment, the combination disclosed herein (e.g., the combination comprising the anti-LAG-3 antibody molecule) is administered in combination with a PD-1 or a PD-L1 inhibitor, e.g., an anti-PD-1 or an anti-PD-L1 antibody molecule, to treat a melanoma as described herein.

In one embodiment, the combination disclosed herein (e.g., the combination comprising the anti-LAG-3 antibody molecule) is administered alone, or in combination with an inhibitor of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 inhibitor (e.g., an anti-TIM-3 antibody molecule), a CEACAM (e.g., CEACAM1 and/or CEACAM5) inhibitor (e.g., an anti-CEACAM antibody molecule), or a CTLA-4 inhibitor (e.g., an anti-CTLA4 antibody) to treat a head and neck cancer (e.g., HNSCC). In one embodiment, the combination disclosed herein (e.g., the combination comprising the anti-LAG-3 antibody molecule) is administered in combination with a PD-1 or a PD-L1 inhibitor, e.g., an anti-PD-1 or anti-PD-L1 antibody molecule, to treat a head and neck cancer as described herein.

In one embodiment, the combination disclosed herein (e.g., the combination comprising the anti-LAG-3 antibody molecule) is administered alone, or in combination with an inhibitor or activator of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 modulator (e.g., a TIM-3 activator or inhibitor, e.g., an anti-TIM-3 antibody molecule), a CEACAM (e.g., CEACAM1 and/or CEACAM5) inhibitor (e.g., an anti-CEACAM antibody molecule), or a CTLA-4 inhibitor (e.g., an anti-CTLA4 antibody) to treat a lung cancer (e.g., a NSCLC). In one embodiment, the combination disclosed herein (e.g., the combination comprising the anti-LAG-3 antibody molecule) is administered in combination with a PD-1 or a PD-L1 inhibitor, e.g., an anti-PD-1 or anti-PD-L1 antibody molecule, to treat a lung cancer (e.g., a NSCLC) as described herein.

In one embodiment, the combination disclosed herein (e.g., the combination comprising the anti-LAG-3 antibody molecule) is administered alone, or in combination with an inhibitor of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 inhibitor (e.g., an anti-TIM-3 antibody molecule), a CEACAM (e.g., CEACAM1 and/or CEACAM5) inhibitor (e.g., an anti-CEACAM antibody molecule), or a CTLA-4 inhibitor (e.g., an anti-CTLA4 antibody) to treat a gastric cancer. In one embodiment, the combination disclosed herein (e.g., the combination comprising the anti-LAG-3 antibody molecule) is administered in combination with a PD-1 or a PD-L1 inhibitor, e.g., an anti-PD-1 or anti-PD-L1 antibody molecule, to treat a gastric cancer as described herein.

In one embodiment, the combination disclosed herein (e.g., the combination comprising the anti-LAG-3 antibody molecule) is administered alone, or in combination with an inhibitor of an immune checkpoint modulator (e.g., a PD-1 inhibitor (e.g., an anti-PD-1 antibody molecule), a PD-L1 inhibitor (e.g., an anti-PD-L1 antibody molecule), a TIM-3 inhibitor (e.g., an anti-TIM-3 antibody molecule), a CEACAM (e.g., CEACAM1 and/or CEACAM5) inhibitor (e.g., an anti-CEACAM antibody molecule), or a CTLA-4 inhibitor (e.g., an anti-CTLA4 antibody) to treat a lymphoma (e.g., Hogdkin's lymphoma (HL), non-Hogdkin's lymphoma (NHL), Diffuse large B-cell lymphoma (DLBCL), mantle cell lymphoma (MCL), or CLL, e.g., a relapsed or refractory chronic lymphocytic leukemia). In one embodiment, the combination disclosed herein (e.g., the combination comprising the anti-LAG-3 antibody molecule) is administered in combination with a PD-1 or a PD-L1 inhibitor, e.g., an anti-PD-1 or anti-PD-L1 antibody molecule, to treat a lymphoma as described herein.

In one aspect, a method of treating a cancer in a subject is provided. The method comprises administering to the subject a combination of two, three or more therapeutic agents chosen from two or all of the following categories (i)-(iii):

(i) an agent that enhances tumor antigen presentation chosen from a STING agonist, a TLR agonist, an A2AR antagonist, or an oncolytic virus, or a combination thereof, and, optionally, one or more of: a TIM-3 modulator, a vascular endothelial growth factor receptor (VEGFR) inhibitor, a c-Met inhibitor, a TGFb inhibitor, an IDO/TDO inhibitor, a vaccine, or a bi- or tri-specific cell engager;

(ii) (optionally) an agent that enhances an effector cell response chosen chosen from one or more of: a GITR agonist, a PD-1 inhibitor, a PD-L1 inhibitor, an inhibitor of IAP (Inhibitor of Apoptosis Protein), an inhibitor of EGFR (Epidermal Growth Factor Receptor), an inhibitor of target of rapamycin (mTOR), IL-15 or a variant thereof, a CTLA-4 inhibitor, a bispecific antibody molecule that binds to CD3 and a tumor antigen, a CD40 agonist, an OX40 agonist, or a CD27 agonist; or (iii) an agent that decreases tumor immunosuppression chosen from an anti-LAG-3 antibody molecule, and, optionally, one or more of: a GITR agonist, an inhibitor of an immune checkpoint molecule chosen from one or more of PD-L1, PD-1, TIM-3 or CTLA-4, a CSF-1/1R inhibitor, an IL-17 inhibitor, an IL-1β inhibitor, a CXCR2 inhibitor, an inhibitor of PI3γ or PI3Kδ), (vii) a BAFF-R inhibitor, a MALT-1/BTK inhibitor, a JAK inhibitor, a CRTH2 inhibitor, a VEGFR inhibitor, an IL-15 or a variant thereof, a CTLA-4 inhibitor, an IDO/TDO inhibitor, an A2AR antagonist, a TGFb inhibitor, or a PFKFB3 inhibitor, wherein the anti-LAG-3 antibody molecule, comprises:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;

(c) a VH comprising a VHCDR1 amino acid sequence of SEQ ID NO: 286, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or (d) a VH comprising a VHCDR1 amino acid sequence of SEQ ID NO: 286; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

In some embodiments, the anti-LAG-3 antibody molecule comprises:

(a) a heavy chain variable domain comprising the amino acid sequence of SEQ ID NO: 28 or SEQ ID NO: 100; and a light chain variable domain comprising the amino acid sequence of SEQ ID NO: 32;

(b) a heavy chain variable domain comprising the amino acid sequence of SEQ ID NO: 28 or SEQ ID NO: 100; and a light chain variable domain comprising the amino acid sequence of SEQ ID NO: 36;

(c) a heavy chain variable domain comprising the amino acid sequence of SEQ ID NO: 28 or SEQ ID NO: 100; and a light chain variable domain comprising the amino acid sequence of SEQ ID NO: 40;

(d) a heavy chain variable domain comprising the amino acid sequence of SEQ ID NO: 28 or SEQ ID NO: 100; and a light chain variable domain comprising the amino acid sequence of SEQ ID NO: 44;

(e) a heavy chain variable domain comprising the amino acid sequence of SEQ ID NO: 28 or SEQ ID NO: 100; and a light chain variable domain comprising the amino acid sequence of SEQ ID NO: 48;

(f) a heavy chain variable domain comprising the amino acid sequence of SEQ ID NO: 28 or SEQ ID NO: 100; and a light chain variable domain comprising the amino acid sequence of SEQ ID NO: 52;

(g) a heavy chain variable domain comprising the amino acid sequence of SEQ ID NO: 28 or SEQ ID NO: 100; and a light chain variable domain comprising the amino acid sequence of SEQ ID NO: 56;

(h) a heavy chain variable domain comprising the amino acid sequence of SEQ ID NO: 28 or SEQ ID NO: 100; and a light chain variable domain comprising the amino acid sequence of SEQ ID NO: 60;

(i) a heavy chain variable domain comprising the amino acid sequence of SEQ ID NO: 64 or SEQ ID NO: 104; and a light chain variable domain comprising the amino acid sequence of SEQ ID NO: 36;

(j) a heavy chain variable domain comprising the amino acid sequence of SEQ ID NO: 64 or SEQ ID NO: 104; and a light chain variable domain comprising the amino acid sequence of SEQ ID NO: 40;

(k) a heavy chain variable domain comprising the amino acid sequence of SEQ ID NO: 64 or SEQ ID NO: 104; and a light chain variable domain comprising the amino acid sequence of SEQ ID NO: 56;

(l) a heavy chain variable domain comprising the amino acid sequence of SEQ ID NO: 64 or SEQ ID NO: 104; and a light chain variable domain comprising the amino acid sequence of SEQ ID NO: 60.

(m) a heavy chain variable domain comprising the amino acid sequence of SEQ ID NO: 68 or SEQ ID NO: 108; and a light chain variable domain comprising the amino acid sequence of SEQ ID NO: 36;

(n) a heavy chain variable domain comprising the amino acid sequence of SEQ ID NO: 72 or SEQ ID NO: 8; and a light chain variable domain comprising the amino acid sequence of SEQ ID NO: 40;

(o) a heavy chain variable domain comprising the amino acid sequence of SEQ ID NO: 72 or SEQ ID NO: 8; and a light chain variable domain comprising the amino acid sequence of SEQ ID NO: 60.

(p) a heavy chain variable domain comprising the amino acid sequence of SEQ ID NO: 76; and a light chain variable domain comprising the amino acid sequence of SEQ ID NO: 60;

(q) a heavy chain variable domain comprising the amino acid sequence of SEQ ID NO: 80; and a light chain variable domain comprising the amino acid sequence of SEQ ID NO: 84;

(r) a heavy chain variable domain comprising the amino acid sequence of SEQ ID NO: 28 or SEQ ID NO: 100; and a light chain variable domain comprising the amino acid sequence of SEQ ID NO: 88;

(s) a heavy chain variable domain comprising the amino acid sequence of SEQ ID NO: 28 or SEQ ID NO: 100; and a light chain variable domain comprising the amino acid sequence of SEQ ID NO: 92; or (t) a heavy chain variable domain comprising the amino acid sequence of SEQ ID NO: 64 or SEQ ID NO: 104; and a light chain variable domain comprising the amino acid sequence of SEQ ID NO: 96.

In some embodiments, the cancer is chosen from a cancer described herein, e.g., a lung cancer, a melanoma, a renal cancer, a liver cancer, a myeloma, a prostate cancer, a breast cancer, a head and neck cancer, a colorectal cancer, a pancreatic cancer, a hematological cancer, a non-Hogdkin's lymphoma, or a leukemia, or a metastatic lesion of the cancer. In certain embodiments, the cancer is chosen from a melanoma, pancreatic cancer, breast cancer, a head and neck cancer, or a renal cell carcinoma.

In one embodiment, the cancer microenvironment has an elevated level of PD-L1 expression. Alternatively, or in combination, the cancer microenvironment can have increased IFNγ and/or CD8 expression.

In some embodiments, the subject has, or is identified as having, a tumor that has one or more of high PD-L1 level or expression, or as being Tumor Infiltrating Lymphocyte (TIL)+ (e.g., as having an increased number of TILs), or both. In certain embodiments, the subject has, or is identified as having, a tumor that has high PD-L1 level or expression and that is TIL+. In some embodiments, the methods described herein further include identifying a subject based on having a tumor that has one or more of high PD-L1 level or expression or as being TIL+, or both. In certain embodiments, the methods described herein further include identifying a subject based on having a tumor that has high PD-L1 level or expression and as being TIL+. In some embodiments, tumors that are TIL+ are positive for CD8 and IFNγ. In some embodiments, the subject has, or is identified as having, a high percentage of cells that are positive for one, two or more of PD-L1, CD8, and/or IFNγ. In certain embodiments, the subject has or is identified as having a high percentage of cells that are positive for all of PD-L1, CD8, and IFNγ.

In some embodiments, the methods described herein further include identifying a subject based on having a high percentage of cells that are positive for one, two or more of PD-L1, CD8, and/or IFNγ. In certain embodiments, the methods described herein further include identifying a subject based on having a high percentage of cells that are positive for all of PD-L1, CD8, and IFNγ. In some embodiments, the subject has, or is identified as having, one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; an esophageal cancer; a thyroid cancer; a melanoma, and/or a nasopharyngeal cancer (NPC). In certain embodiments, the methods described herein further describe identifying a subject based on having one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; a thyroid cancer; a melanoma, and or a nasopharyngeal cancer.

Methods and compositions disclosed herein are useful for treating metastatic lesions associated with the aforementioned cancers.

In a further aspect, the invention provides a method of treating an infectious disease in a subject, comprising administering to a subject a therapeutically effective amount of an anti-LAG-3 antibody molecule described herein, alone or in combination with one or more agents or procedures. The antibodies of the invention are preferred for use in the method although other anti-LAG-3 antibodies, or antigen-binding fragments thereof, can be used instead (or in combination with an anti-LAG-3 antibody molecule described herein).

In one embodiment, the infectious disease is hepatitis (e.g., hepatitis B infection). In certain embodiment, the anti-LAG-3 antibody molecule is administered in combination with a hepatitis B antigen or vaccine, and optionally in combination with an aluminum-containing adjuvant.

In another embodiment, the infectious disease is influenza. In certain embodiment, the anti-LAG-3 antibody molecule is administered in combination with an influenza antigen or vaccine.

Still further, the invention provides a method of enhancing an immune response to an antigen in a subject, comprising administering to the subject: (i) the antigen; and (ii) an anti-LAG-3 antibody molecule, such that an immune response to the antigen in the subject is enhanced. The antigen can be, for example, a tumor antigen, a viral antigen, a bacterial antigen or an antigen from a pathogen.

The anti-LAG-3 antibody molecule, alone or in combination, can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

Dosages and therapeutic regimens of the therapeutic agents disclosed herein can be determined by a skilled artisan. In certain embodiments, the anti-LAG-3 antibody molecule is administered by injection (e.g., subcutaneously or intravenously) at a dose of about 1 to 30 mg/kg, e.g., about 5 to 25 mg/kg, about 10 to 20 mg/kg, about 1 to 10 mg/kg, or about 1 mg/kg, 3 mg/kg, or 10 mg/kg. The dosing schedule can vary from e.g., once a week to once every 2, 3, or 4 weeks. In one embodiment, the anti-LAG-3 antibody molecule is administered at a dose from about 10 to 20 mg/kg every other week. In one embodiment, the anti-LAG-3 antibody molecule is administered (e.g., intravenously) at a dose from about 3 to 800 mg, e.g., about 3, 20, 80, 240, or 800 mg. In certain embodiments, the anti-LAG-3 antibody molecule is administered alone at a dose from about 20 to 800 mg, e.g., about 3, 20, 80, 240, or 800 mg. In other embodiments, the anti-LAG-3 antibody molecule is administered at a dose from about 3 to 240 mg, e.g., about 3, 20, 80, or 240 mg, when it is combined with a second agent or therapeutic modality, e.g., a second agent or therapeutic modality described herein. In one embodiment, the anti-LAG-3 antibody molecule is administered every 2 weeks (e.g., during weeks 1, 3, 5, 7) during each 8 week cycle, e.g., up to 96 weeks.

In one embodiment, the anti-LAG-3 antibody molecule is administered, alone or in combination (e.g., in combination with an anti-PD-1 antibody molecule), at a dose of less than, or about, 5 mg/kg; less than, or about, 4 mg/kg; less than, or about, 3 mg/kg; less than, or about, 2 mg/kg; less than, or about, 1 mg/kg, every other week. In one embodiment, the anti-LAG-3 antibody molecule is administered at a dose of 1 to 5 mg/kg every other week; 1 to 4 mg/kg every other week, 1 to 3 mg/kg every other week, or 1 to 2 mg/kg every other week. In one embodiment, the anti-PD-1 antibody molecule is administered, alone or in combination (e.g., in combination with an anti-LAG-3 antibody molecule) at a dose of 1 to 5 mg/kg every other week; 1 to 4 mg/kg every other week, 1 to 3 mg/kg every other week, or 1 to 2 mg/kg every other week.

The antibody molecules described herein are preferred for use in the methods described herein, although other anti-LAG-3 antibodies can be used instead, or in combination with an anti-LAG-3 antibody molecule of the invention.

Further Combination Therapies

The methods and compositions described herein can be used in combination with other agents or therapeutic modalities. In one embodiment, the methods described herein include administering to the subject a combination comprising an anti-LAG-3 antibody molecule as described herein, in combination with an agent or therapeutic procedure or modality, in an amount effective to treat or prevent a disorder. The anti-LAG-3 antibody molecule and the agent or therapeutic procedure or modality can be administered simultaneously or sequentially in any order. Any combination and sequence of the anti-LAG-3 antibody molecules and other therapeutic agents, procedures or modalities (e.g., as described herein) can be used. The antibody molecule and/or other therapeutic agents, procedures or modalities can be administered during periods of active disorder, or during a period of remission or less active disease. The antibody molecule can be administered before the other treatment, concurrently with the treatment, post-treatment, or during remission of the disorder.

In certain embodiments, the methods and compositions described herein are administered in combination with one or more of other antibody molecules, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) and/or radiation procedures, or a combination of any of the foregoing. The additional therapy may be in the form of adjuvant or neoadjuvant therapy. In some embodiments, the additional therapy is an enzymatic inhibitor (e.g., small molecule enzymatic inhibitor) or a metastatic inhibitor.

Exemplary cytotoxic agents that can be administered in combination with include antimicrotubule agents, topoisomerase inhibitors, anti-metabolites, mitotic inhibitors, alkylating agents, anthracyclines, *vinca* alkaloids, intercalating agents, agents capable of interfering with a signal transduction pathway, agents that promote apoptosis, proteosome inhibitors, and radiation (e.g., local or whole body irradiation (e.g., gamma irradiation). In other embodiments, the additional therapy is surgery or radiation, or a combination thereof. In other embodiments, the additional therapy is a therapy targeting one or more of PI3K/AKT/mTOR pathway, an HSP90 inhibitor, or a tubulin inhibitor. Exemplary other antibody molecules that can be administered in combination include, but are not limited to, checkpoint inhibitors (e.g., anti-PD-1, anti-PD-L1); antibodies that stimulate an immune cell (e.g., agonistic GITR or CD137 antibodies); anti-cancer antibodies (e.g., rituximab (Rituxan® or MabThera®), trastuzumab (Herceptin®), cetuximab (Erbitux®), among others.

Alternatively, or in combination with the aforesaid combinations, the methods and compositions described herein can be administered in combination with one or more of: an immunomodulator (e.g., an activator of a costimulatory molecule or an inhibitor of an immunoinhibitory molecule, e.g., an immune checkpoint molecule); a vaccine, e.g., a therapeutic cancer vaccine; or other forms of cellular immunotherapy.

Exemplary non-limiting combinations and uses of the anti-LAG-3 antibody molecules include the following.

In certain embodiments, the combination disclosed herein, e.g., a combination comprising an anti-LAG-3 antibody molecule, is administered in combination with a modulator of a costimulatory molecule (e.g., an agonist of a costimulatory molecule) or a modulator of an inhibitory molecule (e.g., an inhibitor of an immune checkpoint inhibitor).

In one embodiment, the combination disclosed herein, e.g., a combination comprising an anti-LAG-3 antibody molecule, is administered in combination with a modulator, e.g., an agonist, of a costimulatory molecule. In one embodiment, the agonist of the costimulatory molecule is chosen from an agonist (e.g., an agonistic antibody or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In one embodiment, the combination disclosed herein, e.g., a combination comprising an anti-LAG-3 antibody molecule, is administered in combination with an inhibitor of an inhibitory (or immune checkpoint) molecule chosen from PD-1, PD-L1, PD-L2, CTLA-4, TIM-3, VISTA, BTLA, TIGIT, LAIR1, CD160, 2B4, CEACAM (e.g., CEACAM-1, CEACAM-3 and/or CEACAM-5), VISTA, BTLA, TIGIT, LAIR1, CD160, 2B4 and/or TGF beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antibody fragment, that binds to the inhibitory molecule. In one embodiment, the inhibitor is a soluble ligand (e.g., a CTLA-4-Ig), or an antibody or antibody fragment that binds to PD-1, PD-L1, PD-L2 or CTLA-4.

For example, the combination disclosed herein, e.g., a combination comprising an anti-LAG-3 antibody molecule, can be administered in combination with an inhibitor of, e.g., an antibody or antibody fragment that binds to, PD-1, PD-L1, PD-L2 or CTLA-4, to treat a cancer (e.g., a cancer chosen from: a colorectal cancer (e.g., CRC); a melanoma, e.g., advanced stage melanoma (e.g., stage II-IV melanoma) or HLA-A2 positive-melanoma; a pancreatic cancer, e.g., advanced pancreatic cancer; a breast cancer, e.g., metastatic breast carcinoma or triple negative breast cancer; a head and neck cancer (e.g., HNSCC); an esophageal cancer; a renal cell carcinoma (RCC), e.g., clear renal cell carcinoma (ccRCC) or metastatic renal cell carcinoma (MRCC); a lung cancer (e.g., NSCLC); a cervical cancer; a bladder cancer; or a hematologic malignancy, e.g., a leukemia (e.g., a lymphocytic leukemia), or a lymphoma (e.g., a Hogdkin's lymphoma (HL), a non-Hogdkin's lymphoma (NHL), a diffuse large lymphoma (DLBCL), a mantle cell lymphoma (MCL), or a CLL, e.g., a relapsed or refractory chronic lymphocytic leukemia).

In one embodiment, the combination disclosed herein, e.g., a combination comprising an anti-LAG-3 antibody molecule, is administered in combination with (e.g., before, with, or after) treatment with an anti-CTLA4 antibody (e.g., ipilimumab) with or without a BRAF inhibitor (e.g., vemurafenib or dabrafenib).

In another embodiment, the combination disclosed herein, e.g., a combination comprising an anti-LAG-3 antibody molecule, is administered in combination with an anti-PD-1 antibody (e.g., Nivolumab or Pembrokizumab) or antigen-binding fragment thereof. In another embodiment, the combination disclosed herein, e.g., a combination comprising an anti-LAG-3 antibody molecule, is administered in combination with an anti-TIM-3 antibody or antigen-binding fragment thereof. In still another embodiment, the combination disclosed herein, e.g., a combination comprising an anti-LAG-3 antibody molecule, is administered in combination with an anti-PD-L1 antibody or antigen-binding fragment thereof.

In yet other embodiments, the combination disclosed herein, e.g., a combination comprising an anti-LAG-3 antibody molecule, is administered in combination with an anti-PD-1 antibody and an anti-TIM-3 antibody (or antigen-binding fragments thereof). In certain embodiments, the combination disclosed herein, e.g., a combination comprising an anti-LAG-3 antibody molecule, is administered in combination with an anti-PD-1 antibody and an anti-PD-L1 antibody (or antigen-binding fragments thereof). In certain embodiments, the combination disclosed herein, e.g., a combination comprising an anti-LAG-3 antibody molecule, is administered in combination with an anti-TIM-3 antibody and an anti-PD-L1 antibody (or antigen-binding fragments thereof).

In another embodiment, the combination disclosed herein, e.g., a combination comprising an anti-LAG-3 antibody molecule, is administered in combination with a CEACAM inhibitor (e.g., CEACAM-1 and/or CEACAM-5 inhibitor), e.g., an anti-CEACAM antibody molecule. In another embodiment, the anti-LAG-3 antibody molecule is administered in combination with a CEACAM-1 inhibitor, e.g., an anti-CEACAM-1 antibody molecule. In another embodiment, the anti-LAG-3 antibody molecule is administered in combination with a CEACAM-5 inhibitor, e.g., an anti-CEACAM-5 antibody molecule.

In yet other embodiments, the combination disclosed herein, e.g., a combination comprising an anti-LAG-3 antibody molecule, is administered in combination with an anti-CEACAM (e.g., anti-CEACAM-1 and/or anti-CEACAM-5) antibody molecule and an anti-PD-1 antibody molecule. In yet other embodiments, the combination disclosed herein, e.g., a combination comprising an anti-LAG-3 antibody molecule is administered in combination with an anti-CEACAM (e.g., anti-CEACAM-1 and/or anti-CEACAM-5) antibody molecule and an anti-TIM-3 antibody molecule. In yet other embodiments, the combination disclosed herein, e.g., a combination comprising an anti-LAG-3 antibody molecule is administered in combination with an anti-CEACAM (e.g., anti-CEACAM-1 and/or anti-CEACAM-5) antibody molecule and an anti-PD-L1 antibody molecule.

The combination of antibodies recited herein can be administered separately, e.g., as separate antibodies or antigen-binding fragments thereof, or linked, e.g., as a bispecific or trispecific antibody molecule. In one embodiment, a bispecific antibody that includes an anti-LAG-3 antibody molecule and one of: an anti-TIM-3 antibody, anti-CEACAM (e.g., anti-CEACAM-1 and/or anti-CEACAM-5) antibody, anti-PD-L1 antibody, or anti-PD-1 antibody, or an antigen-binding fragment thereof, is administered. In certain embodiments, the combination of antibodies recited herein is used to treat a cancer, e.g., a cancer as described herein (e.g., a solid tumor or a hematolgocial malignancy). In one embodiment, the anti-LAG-3 antibody molecule is administered in combination with an anti-PD-1 or anti-PD-L1 antibody to treat a solid tumor.

In other embodiments, the combination disclosed herein, e.g., a combination comprising an anti-LAG-3 antibody molecule, is administered in combination with a cytokine. The cytokine can be administered as a fusion molecule to the anti-LAG-3 antibody molecule, or as separate compositions. In one embodiment, the anti-LAG-3 antibody is administered in combination with one, two, three or more cytokines, e.g., as a fusion molecule or as separate compositions. In one embodiment, the cytokine is an interleukin (IL) chosen from one, two, three or more of IL-1, IL-2, IL-12, IL-12, IL-15 or IL-21. In one embodiment, a bispecific antibody molecule has a first binding specificity to a first target (e.g., to LAG-3), a second binding specificity to a second target (e.g., PD-1, TIM-3, or PD-L1), and is optionally linked to an interleukin (e.g., IL-12) domain e.g., full length IL-12 or a portion thereof. In certain embodiments, the combination of anti-LAG-3 antibody molecule and the cytokine described herein is used to treat a cancer, e.g., a cancer as described herein (e.g., a solid tumor).

In other embodiments, the anti-LAG-3 antibody molecule is administered in combination with a vaccine, e.g., a therapeutic cancer vaccine, or other forms of cellular immunotherapy. In one embodiment, the vaccine is peptide-based, DNA-based, RNA-based, or antigen-based, or a combination thereof. In embodiments, the vaccine comprises one or more peptides, nucleic acids (e.g., DNA or RNA), antigens, or a combination thereof. In certain embodiments, the cancer vaccine comprises an adjuvant (e.g., aluminium phosphate or aluminum hydroxide). In some embodiments, the methods described herein are administered in combination with one or more of surgical removal of a tissue, chemotherapy, or other anti-cancer therapy and the primary or sole target will be metastatic lesions, e.g., metastases in the bone marrow or lymph nodes.

In one embodiment, the cancer is a melanoma, e.g., an advanced stage melanoma (e.g., stage II-IV melanoma) or HLA-A2 positive melanoma. In certain embodiment, the anti-LAG-3 antibody molecule is administered in combination with a tumor antigenic peptide, e.g., one or more HLA-A2 peptides, and optionally in combination with an adjuvant, e.g., Montanide™. Exemplary tumor peptides that can be administered in combination with the anti-LAG-3 antibody molecule include one or more of Tyrosinase.A2, MAGE-C2.A2, NY-ESO-1b.A2, MAGE-4.A2, MAGE-3.A2, MAGE-1.A2, NA17.A2 (GnTV), and MAGE-10.A2.

In another embodiment, the cancer is a pancreatic cancer, e.g., advanced pancreatic cancer. In certain embodiment, the antibody molecule can be administered in combination with a chemotherapeutic agent, e.g., gemcitabine.

In another embodiment, the cancer is a breast cancer, e.g., metastatic breast carcinoma or triple negative breast cancer. In certain embodiment, the antibody molecule can be administered in combination with a chemotherapeutic agent, e.g., paclitaxel.

In another embodiment, the cancer is a renal cell carcinoma, e.g., clear cell carcimoma, advanced (e.g., stage IV) or metastatic renal cell carcinoma (MRCC).

In another embodiment, the cancer is a cancer of head or neck, e.g., HPV+ squamous cell carcinoma.

In another embodiment, the anti-LAG-3 antibody molecule is administered in combination with an antigen. For example, the anti-LAG-3 antibody molecule can be combined with a hepatitis B antigen (e.g., Engerix B). In other embodiments, the anti-LAG-3 antibody molecule is administered in combination with a flu antigen.

The anti-LAG-3 antibody molecule can be used alone in unconjugated form, or can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody can be coupled to a radioactive isotope such as an α-, β-, or γ-emitter, or a β- and γ-emitter.

Additional Combination Therapies

The methods and compositions described herein (e.g., LAG-3 antibodies and methods of using them) can be used in combination with other agents or therapeutic modalities, e.g., a second therapeutic agent chosen from one or more of the agents listed in Table 7.

In some embodiments, the additional therapeutic agent is chosen from one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11(3-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase, e.g., as described herein and in Table 7.

In one embodiment, the additional therapeutic agent is chosen from one or more of: Compound A8, Compound A17, Compound A23, Compound A24, Compound A27, Compound A29, Compound A33, and Compound A13.

In other embodiments, the additional therapeutic agent is chosen from one or more of: Compound A5, Compound A8, Compound A17, Compound A23, Compound A24, Compound A29, and Compound A40.

In other embodiments, the additional therapeutic agent is chosen from one or more of: Compound A9, Compound A16, Compound A17, Compound A21, Compound A22, Compound A25, Compound A28, Compound A48, and Compound 49.

In one embodiment, the cancer is chosen from a lung cancer (e.g., a non-small cell lung cancer (NSCLC) (e.g., a NSCLC with squamous and/or non-squamous histology, or a NSCLC adenocarcinoma), or disclosed in a publication listed in Table 7.

Additional Embodiments

Additional embodiments provide a method of treating a cancer, comprising: identifying in a sample (e.g., a subject's sample comprising cancer cells and optionally immune cells such as TILs) the presence of one, two or all of PD-L1, CD8, or IFN-γ, thereby providing a value for one, two or all of PD-L1, CD8, and IFN-γ. The method can further include comparing the PD-L1, CD8, and/or IFN-γ values to a reference value, e.g., a control value. If the PD-L1, CD8, and/or IFN-γ values are greater than the reference value, e.g., the control values, administering a therapeutically effective amount of a combination as described herein (e.g., a combination that includes an anti-LAG-3 antibody described herein), alone or in combination with an anti-PD-1 antibody molecule, an anti-PD-L1 antibody molecule, or both, to the subject, optionally in combination with one or more other agents, thereby treating the cancer. The cancer may be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer, or breast cancer, e.g., TN breast cancer, e.g., IM-TN breast cancer. In some embodiments, the cancer is ER+ breast cancer or pancreatic cancer.

Also provided is a method of treating a cancer, comprising: testing a sample (e.g., a subject's sample comprising cancer cells) for the presence of PD-L1, thereby identifying a PD-L1 value, comparing the PD-L1 value to a control value, and if the PD-L1 value is greater than the control value, administering a therapeutically effective amount of a combination as described herein (e.g., a combination that includes an anti-LAG-3 antibody described herein), alone or in combination with an anti-PD-1 antibody molecule, an anti-PD-L1 antibody molecule, or both, to the subject, optionally in combination with one or more other agents, thereby treating the cancer. The cancer may be, e.g., a cancer as described herein, such as cancer is non-small cell lung (NSCLC) adenocarcinoma (ACA), NSCLC squamous cell carcinoma (SCC), or hepatocellular carcinoma (HCC).

In another aspect, the invention features diagnostic or therapeutic kits that include the combination molecules described herein and instructions for use.

All publications, patent applications, patents, and other references mentioned herein are incorporated by reference in their entirety.

Other features, objects, and advantages of the invention will be apparent from the description and drawings, and from the claims.

BRIEF DESCRIPTION OF THE DRAWINGS

FIG. 1 depicts the amino acid sequences of the light (SEQ ID NO: 16) and heavy (SEQ ID NO: 6) chain variable regions of murine anti-LAG-3 mAb BAP050. The light and heavy chain CDR sequences based on Kabat numbering are underlined. The light and heavy chain CDR sequences based on Chothia numbering are shown in bold italics.

FIG. 2 depicts the amino acid sequences of the light (SEQ ID NO: 16) and heavy (SEQ ID NO: 6) chain variable regions of murine anti-LAG-3 mAb BAP050 aligned with the germline sequences (SEQ ID NOs: 290-291, respectively, in order of appearance). The upper and lower sequences are the germline (GL) and BAP050 (Mu mAb) sequences, respectively. The light and heavy chain CDR sequences based on Kabat numbering are underlined. The light and heavy chain CDR sequences based on Chothia numbering are shown in bold italics. "-" means identical amino acid residue.

FIG. 4 depicts the structural analysis of the humanized BAP049 clones (a, b, c, d, e, f, g represent various types of framework region sequences). The concentrations of the mAbs in the samples are also shown.

FIG. 6 depicts the ranking of humanized BAP050 clones based on FACS data, competition binding and structural analysis. The concentrations of the mAbs in the samples are also shown.

FIGS. 9A-9B depict the alignment of heavy chain variable domain sequences for the twenty humanized BAP050 clones and BAP050 chimera (BAP050-chi). In FIG. 9A, all of the sequences are shown (SEQ ID NOs: 20, 28, 28, 28, 28, 28, 28, 28, 28, 28, 28, 64, 64, 64, 64, 64, 68, 72, 72, 76 and 80, respectively, in order of appearance). In FIG. 9B, only amino acid sequences that are different from mouse sequence are shown (SEQ ID NOs: 20, 28, 28, 28, 28, 28, 28, 28, 28, 28, 28, 64, 64, 64, 64, 64, 68, 72, 72, 76 and 80, respectively, in order of appearance).

FIGS. 10A-10B depict the alignment of light chain variable domain sequences for the twenty humanized BAP050 clones and BAP050 chimera (BAP050-chi). In FIG. 10A, all of the sequences are shown (SEQ ID NOs: 24, 32, 36, 36, 36, 292, 292, 292, 44, 48, 52, 56, 56, 60, 60, 60, 60, 84, 88, 92 and 96, respectively, in order of appearance). In FIG. 10B, only amino acid sequences that are different from mouse sequence are shown (SEQ ID NOs: 24, 32, 36, 36, 36, 292, 292, 292, 44, 48, 52, 56, 56, 60, 60, 60, 60, 84, 88, 92 and 96, respectively, in order of appearance).

BRIEF DESCRIPTION OF THE TABLES

Table 1 is a summary of the amino acid and nucleotide sequences for the murine, chimeric and humanized anti-LAG-3 antibody molecules. The antibody molecules include murine mAb BAP050 and chimeric mAbs BAP050-chi, humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J. The amino acid and nucleotide sequences of the heavy and light chain CDRs, the amino acid and nucleotide sequences of the heavy and light chain variable regions, and the amino acid and nucleotide sequences of the heavy and light chains are shown in this Table.

Table 2 depicts the amino acid and nucleotide sequences of the heavy and light chain framework regions for humanized mAbs BAP050-hum01 to BAP049-hum20, BAP050-hum01-Ser to BAP050-hum15-Ser, BAP050-hum18-Ser to BAP050-hum20-Ser, and BAP049-Clone-F to BAP049-Clone-J.

Table 3 depicts the constant region amino acid sequences of human IgG heavy chains and human kappa light chain.

Table 4 shows the amino acid sequences of the heavy and light chain leader sequences for humanized mAbs BAP050-Clone-F to BAP050-Clone-J.

Table 5 is a summary of yield, titre, monomer content and endotoxin levels for exemplary humanized BAP050 mAbs expressed in CHO cells.

Table 6 shows the charge isoforms as detected by Novex IEF analysis for exemplary humanized BAP050 mAbs expressed in CHO cells.

Table 7 is a summary of selected therapeutic agents that can be administered in combination with the anti-LAG-3 antibody molecules and other immunomodulators (e.g., one or more of: an activator of a costimulatory molecule and/or an inhibitor of an immune checkpoint molecule) described herein. Table 7 provides from left to right the following: the Compound Designation of the second therapeutic agent, the Compound structure, and Patent publication(s) disclosing the Compound.

Table 8 provides an exemplary listing of the therapeutic agents from Antigen-Presentation Combinations (Category A), Effector Cell Combinations (Category B) and Anti-tumor Immunosuppression Combinations (Category C).

DETAILED DESCRIPTION

Figure 15:
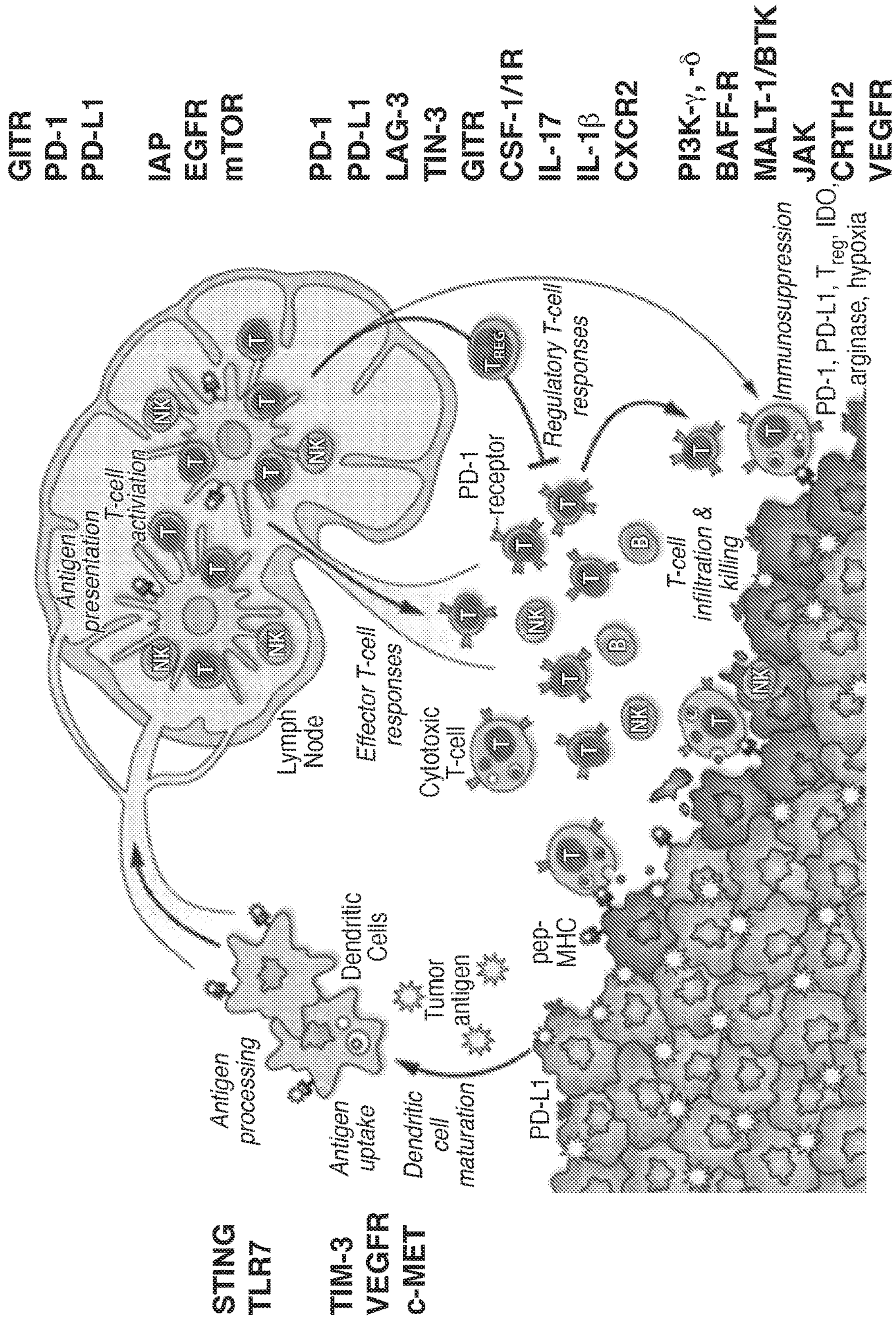
FIG. 15 is a schematic diagram that outlines the antigen processing and presentation, effector cell responses and immunosuppression pathways targeted by the combination therapies disclosed herein.

Disclosed herein, at least in part, are methods and compositions comprising a combination of two, three or more therapeutic agents chosen from one, two, or all of the following categories (i)-(iii): (i) an agent that enhances antigen presentation (e.g., tumor antigen presentation) (e.g., by enhancing one or more of dendritic cell activity or maturation, antigen uptake, or antigen processing); (ii) an agent that enhances an effector cell response (e.g., an immune effector cell response, e.g., B cell and/or T cell activation and/or mobilization, e.g., in the lymph node); or (iii) an agent that decreases tumor immunosuppression (e.g., increasing T cell infiltration and tumor cell killing). In some embodiments, the combination includes a PD-1 inhibitor (e.g., an anti-PD-1 antibody molecule as described herein). Without wishing to be bound by theory, it is believed that therapeutic approaches that enhance anti-tumor immunity work more effectively when the immune response is optimized via multiple targets at different stages of the immune response. Each of these stages in depicted in schematic form in FIG. 15. For example, approaches that result in activation of dendritic cells combined with approaches that enhance cellular and humoral immune can result in a more effective and/or prolonged therapeutic response.

Additional terms are defined below and throughout the application.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

By "a combination" or "in combination with," it is not intended to imply that the therapy or the therapeutic agents must be administered at the same time and/or formulated for delivery together, although these methods of delivery are within the scope described herein. The therapeutic agents in the combination can be administered concurrently with, prior to, or subsequent to, one or more other additional therapies or therapeutic agents. The therapeutic agents or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In embodiments, the additional therapeutic agent is administered at a therapeutic or lower-than therapeutic dose. In certain embodiments, the concentration of the second therapeutic agent that is required to achieve inhibition, e.g., growth inhibition, is lower when the second therapeutic agent is administered in combination with the first therapeutic agent, e.g., the anti-PD-1 antibody molecule, than when the second therapeutic agent is administered individually. In certain embodiments, the concentration of the first therapeutic agent that is required to achieve inhibition, e.g., growth inhibition, is lower when the first therapeutic agent is administered in combination with the second therapeutic agent than when the first therapeutic agent is administered individually. In certain embodiments, in a combination therapy, the concentration of the second therapeutic agent that is required to achieve inhibition, e.g., growth inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration of the first therapeutic agent that is required to achieve inhibition, e.g., growth inhibition, is lower than the therapeutic dose of the first therapeutic agent as a monotherapy, e.g., 10-20%, 20-30%, 30-40%, 40-50%, 50-60%, 60-70%, 70-80%, or 80-90% lower.

The term "inhibition," "inhibitor," or "antagonist" includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40% or more is included by this term. Thus, inhibition need not be 100%.

The term "activation," "activator," or "agonist" includes an increase in a certain parameter, e.g., an activity, of a given molecule, e.g., a costimulatory molecule. For example, increase of an activity, e.g., a costimulatory activity, of at least 5%, 10%, 25%, 50%, 75% or more is included by this term.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place.

The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer (e.g., triple negative breast cancer), prostate cancer, ovarian cancer, cervical cancer, skin cancer (e.g., melanoma), pancreatic cancer, colorectal cancer, renal cancer (e.g., renal cell carcinoma), liver cancer (e.g., hepatocellular carcinoma), brain cancer (e.g., glioblastoma), head and neck cancer, endometrial cancer, nasopharyngeal cancer, bladder cancer, lymphoma, leukemia, lung cancer (e.g., non-small cell lung cancer), and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to, an MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

"Immune effector cell," or "effector cell" as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector" or "effector" "function" or "response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

As used herein, the terms "treat", "treatment" and "treating" refer to the reduction or amelioration of the progression, severity and/or duration of a disorder, e.g., a proliferative disorder, or the amelioration of one or more symptoms (preferably, one or more discernible symptoms) of the disorder resulting from the administration of one or more therapies. In specific embodiments, the terms "treat," "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The compositions and methods of the present invention encompass polypeptides and nucleic acids having the sequences specified, or sequences substantially identical or similar thereto, e.g., sequences at least 70%, 75%, 80%, 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Exemplary Combinations of Antigen-Presentation Combinations, Effector Cell Combinations and Anti-tumor Immunosuppression Combinations Exemplary combinations of therapeutic agents from two or more of the antigen-presentation category (A), effector cell category (B), and anti-tumor immunosuppression category (C) are provided herein.

TABLE 8

Listing of Therapeutic Agents in Categories (A)-(C)

| | A = Antigen-Presentation | B = Effector Cell | C = Anti-tumor Immunosuppression |
|---|---|---|---|
| 1 | STING agonist | GITR agonist | PD-1 inhibitor |
| 2 | TLR agonist | PD-1 inhibitor | PD-L1 inhibitor |
| 3 | TIM-3 modulator | PD-L1 inhibitor | LAG-3 inhibitor |
| 4 | VEGFR inhibitor | IAP inhibitor | TIM-3 inhibitor |
| 5 | c-MET inhibitor | EGFR inhibitor | GITR inhibitor |
| 6 | TGFb inhibitor | mTOR inhibitor | CSF-1/1R inhibitor |
| 7 | IDO/TDO inhibitor | IL-15 agonist | IL-17 inhibitor |
| 8 | A2AR antagonist | CTLA-4 inhibitor | IL-1β inhibitor |
| 9 | Oncolytic viruses | Bispecific T-cell engagers | CXCR2 inhibitor |
| 10 | Scaffold vaccines | CD40 agonist | PI3K-γ, -δ inhibitor |
| 11 | Bispecific T-cell engagers | OX40 agonist | BAFF-R inhibitor |
| 12 | | CD27 agonist | MALT-1/BTK inhibitor |
| 13 | | | JAK inhibitor |
| 14 | | | CRTH2 inhibitor |
| 15 | | | VEGFR inhibitor |
| 16 | | | IL-15 agonist |
| 17 | | | Anti-TGFb inhibitor |
| 18 | | | IDO/TDO inhibitor |
| 19 | | | A2AR antagonist |
| 20 | | | CTLA-4 inhibitor |
| 21 | | | PFKFB3 inhibitor |

In some embodiments, the combinations of the present invention include one or more of the following:

A1B1, A1B2, A1B3, A1B4, A1B5, A1B6, A1B7, A1B8, A1B9, A1B10, A1B11, A1B12, A2B1, A2B2, A2B3, A2B4, A2B5, A2B6, A2B7, A2B8, A2B9, A2B10, A2B11, A2B12, A3B1, A3B2, A3B3, A3B4, A3B5, A3B6, A3B7, A3B8, A3B9, A3B10, A3B11, A3B12, A4B1, A4B2, A4B3, A4B4, A4B5, A4B6, A4B7, A4B8, A4B9, A4B10, A4B11, A4B12, A5B1, A5B2, A5B3, A5B4, A5B5, A5B6, A5B7, A5B8, A5B9, A5B10, A5B11, A5B12, A6B1, A6B2, A6B3, A6B4, A6B5, A6B6, A6B7, A6B8, A6B9, A6B10, A6B11, A6B12, A7B1, A7B2, A7B3, A7B4, A7B5, A7B6, A7B7, A7B8, A7B9, A7B10, A7B11, A7B12, A8B1, A8B2, A8B3, A8B4, A8B5, A8B6, A8B7, A8B8, A8B9, A8B10, A8B11, A8B12, A9B1, A9B2, A9B3, A9B4, A9B5, A9B6, A9B7, A9B8, A9B9, A9B10, A9B11, A9B12, A10B1, A10B2, A10B3, A10B4, A10B5, A10B6, A10B7, A10B8, A10B9, A10B10, A10B11, A10B12, A11B1, A11B2, A11B3, A11B4, A11B5, A11B6, A11B7, A11B8, A11B9, A11B10, A11B11, A11B12, A1C1, A1C2, A1C3, A1C4, A1C5,

A1C6, A1C7, A1C8, A1C9, A1C10, A1C11, A1C12, A1C13, A1C14, A1C15, A1C16, A1C17, A1C18, A1C19, A1C20, A1C21, A2C1, A2C2, A2C3, A2C4, A2C5, A2C6, A2C7, A2C8, A2C9, A2C10, A2C11, A2C12, A2C13, A2C14, A2C15, A2C16, A2C17, A2C18, A2C19, A2C20, A2C21, A3C1, A3C2, A3C3, A3C4, A3C5, A3C6, A3C7, A3C8, A3C9, A3C10, A3C11, A3C12, A3C13, A3C14, A3C15, A3C16, A3C17, A3C18, A3C19, A3C20, A3C21, A4C1, A4C2, A4C3, A4C4, A4C5, A4C6, A4C7, A4C8, A4C9, A4C10, A4C11, A4C12, A4C13, A4C14, A4C15, A4C16, A4C17, A4C18, A4C19, A4C20, A4C21, A5C1, A5C2, A5C3, A5C4, A5C5, A5C6, A5C7, A5C8, A5C9, A5C10, A5C11, A5C12, A5C13, A5C14, A5C15, A5C16, A5C17, A5C18, A5C19, A5C20, A5C21, A6C1, A6C2, A6C3, A6C4, A6C5, A6C6, A6C7, A6C8, A6C9, A6C10, A6C11, A6C12, A6C13, A6C14, A6C15, A6C16, A6C17, A6C18, A6C19, A6C20, A6C21, A7C1, A7C2, A7C3, A7C4, A7C5, A7C6, A7C7, A7C8, A7C9, A7C10, A7C11, A7C12, A7C13, A7C14, A7C15, A7C16, A7C17, A7C18, A7C19, A7C20, A7C21, A8C1, A8C2, A8C3, A8C4, A8C5, A8C6, A8C7, A8C8, A8C9, A8C10, A8C11, A8C12, A8C13, A8C14, A8C15, A8C16, A8C17, A8C18, A8C19, A8C20, A8C21, A9C1, A9C2, A9C3, A9C4, A9C5, A9C6, A9C7, A9C8, A9C9, A9C10, A9C11, A9C12, A9C13, A9C14, A9C15, A9C16, A9C17, A9C18, A9C19, A9C20, A9C21, A10C1, A10C2, A10C3, A10C4, A1005, A1006, A1007, A1008, A10C9, A10C10, A10C11, A10C12, A10C13, A10C14, A10C15, A10C16, A10C17, A10C18, A10C19, A10C20, A10C21, A11C1, A11C2, A11C3, A11C4, A1105, A1106, A11C7, A11C8, A11C9, A11C10, A11C11, A11C12, A11C13, A11C14, A11C15, A11C16, A11C17, A11C18, A11C19, A11C20, A11C21, B1C1, B1C2, B1C3, B1C4, B1C5, B1C6, B1C7, B1C8, B1C9, B1C10, B1C11, B1C12, B1C13, B1C14, B1C15, B1C16, B1C17, B1C18, B1C19, B1C20, B1C21, B2C1, B2C2, B2C3, B2C4, B2C5, B2C6, B2C7, B2C8, B2C9, B2C10, B2C11, B2C12, B2C13, B2C14, B2C15, B2C16, B2C17, B2C18, B2C19, B2C20, B2C21, B3C1, B3C2, B3C3, B3C4, B3C5, B3C6, B3C7, B3C8, B3C9, B3C10, B3C11, B3C12, B3C13, B3C14, B3C15, B3C16, B3C17, B3C18, B3C19, B3C20, B3C21, B4C1, B4C2, B4C3, B4C4, B4C5, B4C6, B4C7, B4C8, B4C9, B4C10, B4C11, B4C12, B4C13, B4C14, B4C15, B4C16, B4C17, B4C18, B4C19, B4C20, B4C21, B5C1, B5C2, B5C3, B5C4, B5C5, B5C6, B5C7, B5C8, B5C9, B5C10, B5C11, B5C12, B5C13, B5C14, B5C15, B5C16, B5C17, B5C18, B5C19, B5C20, B5C21, B6C1, B6C2, B6C3, B6C4, B6C5, B6C6, B6C7, B6C8, B6C9, B6C10, B6C11, B6C12, B6C13, B6C14, B6C15, B6C16, B6C17, B6C18, B6C19, B6C20, B6C21, B7C1, B7C2, B7C3, B7C4, B7C5, B7C6, B7C7, B7C8, B7C9, B7C10, B7C11, B7C12, B7C13, B7C14, B7C15, B7C16, B7C17, B7C18, B7C19, B7C20, B7C21, B8C1, B8C2, B8C3, B8C4, B8C5, B8C6, B8C7, B8C8, B8C9, B8C10, B8C11, B8C12, B8C13, B8C14, B8C15, B8C16, B8C17, B8C18, B8C19, B8C20, B8C21, B9C1, B9C2, B9C3, B9C4, B9C5, B9C6, B9C7, B9C8, B9C9, B9C10, B9C11, B9C12, B9C13, B9C14, B9C15, B9C16, B9C17, B9C18, B9C19, B9C20, B9C21, B10C1, B10C2, B10C3, B10C4, B10C5, B10C6, B10C7, B10C8, B10C9, B10C10, B10C11, B10C12, B10C13, B10C14, B10C15, B10C16, B10C17, B10C18, B10C19, B10C20, B10C21, B11C1, B11C2, B11C3, B11C4, B1105, B1106, B11C7, B11C8, B11C9, B11C10, B11C11, B11C12, B11C13, B11C14, B11C15, B11C16, B11C17, B11C18, B11C19, B11C20, B11C21, B12C1, B12C2, B12C3, B12C4, B12C5, B12C6, B12C7, B12C8, B12C9, B12C10, B12C11, B12C12, B12C13, B12C14, B12C15, B12C16, B12C17, B12C18, B12C19, B12C20, B12C21, A1B1C1, A1B1C2, A1B1C3, A1B1C4, A1B1C5, A1B1C6, A1B1C7, A1B1C8, A1B1C9, A1B1C10, A1B1C11, A1B1C12, A1B1C13, A1B1C14, A1B1C15, A1B1C16, A1B1C17, A1B1C18, A1B1C19, A1B1C20, A1B1C21, A1B2C1, A1B2C2, A1B2C3, A1B2C4, A1B2C5, A1B2C6, A1B2C7, A1B2C8, A1B2C9, A1B2C10, A1B2C11, A1B2C12, A1B2C13, A1B2C14, A1B2C15, A1B2C16, A1B2C17, A1B2C18, A1B2C19, A1B2C20, A1B2C21, A1B3C1, A1B3C2, A1B3C3, A1B3C4, A1B3C5, A1B3C6, A1B3C7, A1B3C8, A1B3C9, A1B3C10, A1B3C11, A1B3C12, A1B3C13, A1B3C14, A1B3C15, A1B3C16, A1B3C17, A1B3C18, A1B3C19, A1B3C20, A1B3C21, A1B4C1, A1B4C2, A1B4C3, A1B4C4, A1B4C5, A1B4C6, A1B4C7, A1B4C8, A1B4C9, A1B4C10, A1B4C11, A1B4C12, A1B4C13, A1B4C14, A1B4C15, A1B4C16, A1B4C17, A1B4C18, A1B4C19, A1B4C20, A1B4C21, A1B5C1, A1B5C2, A1B5C3, A1B5C4, A1B5C5, A1B5C6, A1B5C7, A1B5C8, A1B5C9, A1B5C10, A1B5C11, A1B5C12, A1B5C13, A1B5C14, A1B5C15, A1B5C16, A1B5C17, A1B5C18, A1B5C19, A1B5C20, A1B5C21, A1B6C1, A1B6C2, A1B6C3, A1B6C4, A1B6C5, A1B6C6, A1B6C7, A1B6C8, A1B6C9, A1B6C10, A1B6C11, A1B6C12, A1B6C13, A1B6C14, A1B6C15, A1B6C16, A1B6C17, A1B6C18, A1B6C19, A1B6C20, A1B6C21, A1B7C1, A1B7C2, A1B7C3, A1B7C4, A1B7C5, A1B7C6, A1B7C7, A1B7C8, A1B7C9, A1B7C10, A1B7C11, A1B7C12, A1B7C13, A1B7C14, A1B7C15, A1B7C16, A1B7C17, A1B7C18, A1B7C19, A1B7C20, A1B7C21, A1B8C1, A1B8C2, A1B8C3, A1B8C4, A1B8C5, A1B8C6, A1B8C7, A1B8C8, A1B8C9, A1B8C10, A1B8C11, A1B8C12, A1B8C13, A1B8C14, A1B8C15, A1B8C16, A1B8C17, A1B8C18, A1B8C19, A1B8C20, A1B8C21, A1B9C1, A1B9C2, A1B9C3, A1B9C4, A1B9C5, A1B9C6, A1B9C7, A1B9C8, A1B9C9, A1B9C10, A1B9C11, A1B9C12, A1B9C13, A1B9C14, A1B9C15, A1B9C16, A1B9C17, A1B9C18, A1B9C19, A1B9C20, A1B9C21, A1B10C1, A1B10C2, A1B10C3, A1B10C4, A1B10C5, A1B10C6, A1B10C7, A1B10C8, A1B10C9, A1B10C10, A1B10C11, A1B10C12, A1B10C13, A1B10C14, A1B10C15, A1B10C16, A1B10C17, A1B10C18, A1B10C19, A1B10C20, A1B10C21, A1B11C1, A1B11C2, A1B11C3, A1B11C4, A1B11C5, A1B11C6, A1B11C7, A1B11C8, A1B11C9, A1B11C10, A1B11C11, A1B11C12, A1B11C13, A1B11C14, A1B11C15, A1B11C16, A1B11C17, A1B11C18, A1B11C19, A1B11C20, A1B11C21, A1B12C1, A1B12C2, A1B12C3, A1B12C4, A1B12C5, A1B12C6, A1B12C7, A1B12C8, A1B12C9, A1B12C10, A1B12C11, A1B12C12, A1B12C13, A1B12C14, A1B12C15, A1B12C16, A1B12C17, A1B12C18, A1B12C19, A1B12C20, A1B12C21, A2B1C1, A2B1C2, A2B1C3, A2B1C4, A2B1C5, A2B1C6, A2B1C7, A2B1C8, A2B1C9, A2B1C10, A2B1C11, A2B1C12, A2B1C13,

A2B1C14, A2B1C15, A2B1C16, A2B1C17, A2B1C18, A2B1C19, A2B1C20, A2B1C21, A2B2C1, A2B2C2, A2B2C3, A2B2C4, A2B2C5, A2B2C6, A2B2C7, A2B2C8, A2B2C9, A2B2C10, A2B2C11, A2B2C12, A2B2C13, A2B2C14, A2B2C15, A2B2C16, A2B2C17, A2B2C18, A2B2C19, A2B2C20, A2B2C21, A2B3C1, A2B3C2, A2B3C3, A2B3C4, A2B3C5, A2B3C6, A2B3C7, A2B3C8, A2B3C9, A2B3C10, A2B3C11, A2B3C12, A2B3C13, A2B3C14, A2B3C15, A2B3C16, A2B3C17, A2B3C18, A2B3C19, A2B3C20, A2B3C21, A2B4C1, A2B4C2, A2B4C3, A2B4C4, A2B4C5, A2B4C6, A2B4C7, A2B4C8, A2B4C9, A2B4C10, A2B4C11, A2B4C12, A2B4C13, A2B4C14, A2B4C15, A2B4C16, A2B4C17, A2B4C18, A2B4C19, A2B4C20, A2B4C21, A2B5C1, A2B5C2, A2B5C3, A2B5C4, A2B5C5, A2B5C6, A2B5C7, A2B5C8, A2B5C9, A2B5C10, A2B5C11, A2B5C12, A2B5C13, A2B5C14, A2B5C15, A2B5C16, A2B5C17, A2B5C18, A2B5C19, A2B5C20, A2B5C21, A2B6C1, A2B6C2, A2B6C3, A2B6C4, A2B6C5, A2B6C6, A2B6C7, A2B6C8, A2B6C9, A2B6C10, A2B6C11, A2B6C12, A2B6C13, A2B6C14, A2B6C15, A2B6C16, A2B6C17, A2B6C18, A2B6C19, A2B6C20, A2B6C21, A2B7C1, A2B7C2, A2B7C3, A2B7C4, A2B7C5, A2B7C6, A2B7C7, A2B7C8, A2B7C9, A2B7C10, A2B7C11, A2B7C12, A2B7C13, A2B7C14, A2B7C15, A2B7C16, A2B7C17, A2B7C18, A2B7C19, A2B7C20, A2B7C21, A2B8C1, A2B8C2, A2B8C3, A2B8C4, A2B8C5, A2B8C6, A2B8C7, A2B8C8, A2B8C9, A2B8C10, A2B8C11, A2B8C12, A2B8C13, A2B8C14, A2B8C15, A2B8C16, A2B8C17, A2B8C18, A2B8C19, A2B8C20, A2B8C21, A2B9C1, A2B9C2, A2B9C3, A2B9C4, A2B9C5, A2B9C6, A2B9C7, A2B9C8, A2B9C9, A2B9C10, A2B9C11, A2B9C12, A2B9C13, A2B9C14, A2B9C15, A2B9C16, A2B9C17, A2B9C18, A2B9C19, A2B9C20, A2B9C21, A2B10C1, A2B10C2, A2B10C3, A2B10C4, A2B10C5, A2B10C6, A2B10C7, A2B10C8, A2B10C9, A2B10C10, A2B10C11, A2B10C12, A2B10C13, A2B10C14, A2B10C15, A2B10C16, A2B10C17, A2B10C18, A2B10C19, A2B10C20, A2B10C21, A2B11C1, A2B11C2, A2B11C3, A2B11C4, A2B11C5, A2B11C6, A2B11C7, A2B11C8, A2B11C9, A2B11C10, A2B11C11, A2B11C12, A2B11C13, A2B11C14, A2B11C15, A2B11C16, A2B11C17, A2B11C18, A2B11C19, A2B11C20, A2B11C21, A2B12C1, A2B12C2, A2B12C3, A2B12C4, A2B12C5, A2B12C6, A2B12C7, A2B12C8, A2B12C9, A2B12C10, A2B12C11, A2B12C12, A2B12C13, A2B12C14, A2B12C15, A2B12C16, A2B12C17, A2B12C18, A2B12C19, A2B12C20, A2B12C21, A3B1C1, A3B1C2, A3B1C3, A3B1C4, A3B1C5, A3B1C6, A3B1C7, A3B1C8, A3B1C9, A3B1C10, A3B1C11, A3B1C12, A3B1C13, A3B1C14, A3B1C15, A3B1C16, A3B1C17, A3B1C18, A3B1C19, A3B1C20, A3B1C21, A3B2C1, A3B2C2, A3B2C3, A3B2C4, A3B2C5, A3B2C6, A3B2C7, A3B2C8, A3B2C9, A3B2C10, A3B2C11, A3B2C12, A3B2C13, A3B2C14, A3B2C15, A3B2C16, A3B2C17, A3B2C18, A3B2C19, A3B2C20, A3B2C21, A3B3C1, A3B3C2, A3B3C3, A3B3C4, A3B3C5, A3B3C6, A3B3C7, A3B3C8, A3B3C9, A3B3C10, A3B3C11, A3B3C12, A3B3C13, A3B3C14, A3B3C15, A3B3C16, A3B3C17, A3B3C18, A3B3C19, A3B3C20, A3B3C21, A3B4C1, A3B4C2, A3B4C3, A3B4C4, A3B4C5, A3B4C6, A3B4C7, A3B4C8, A3B4C9, A3B4C10, A3B4C11, A3B4C12, A3B4C13, A3B4C14, A3B4C15, A3B4C16, A3B4C17, A3B4C18, A3B4C19, A3B4C20, A3B4C21, A3B5C1, A3B5C2, A3B5C3, A3B5C4, A3B5C5, A3B5C6, A3B5C7, A3B5C8, A3B5C9, A3B5C10, A3B5C11, A3B5C12, A3B5C13, A3B5C14, A3B5C15, A3B5C16, A3B5C17, A3B5C18, A3B5C19, A3B5C20, A3B5C21, A3B6C1, A3B6C2, A3B6C3, A3B6C4, A3B6C5, A3B6C6, A3B6C7, A3B6C8, A3B6C9, A3B6C10, A3B6C11, A3B6C12, A3B6C13, A3B6C14, A3B6C15, A3B6C16, A3B6C17, A3B6C18, A3B6C19, A3B6C20, A3B6C21, A3B7C1, A3B7C2, A3B7C3, A3B7C4, A3B7C5, A3B7C6, A3B7C7, A3B7C8, A3B7C9, A3B7C10, A3B7C11, A3B7C12, A3B7C13, A3B7C14, A3B7C15, A3B7C16, A3B7C17, A3B7C18, A3B7C19, A3B7C20, A3B7C21, A3B8C1, A3B8C2, A3B8C3, A3B8C4, A3B8C5, A3B8C6, A3B8C7, A3B8C8, A3B8C9, A3B8C10, A3B8C11, A3B8C12, A3B8C13, A3B8C14, A3B8C15, A3B8C16, A3B8C17, A3B8C18, A3B8C19, A3B8C20, A3B8C21, A3B9C1, A3B9C2, A3B9C3, A3B9C4, A3B9C5, A3B9C6, A3B9C7, A3B9C8, A3B9C9, A3B9C10, A3B9C11, A3B9C12, A3B9C13, A3B9C14, A3B9C15, A3B9C16, A3B9C17, A3B9C18, A3B9C19, A3B9C20, A3B9C21, A3B10C1, A3B10C2, A3B10C3, A3B10C4, A3B10C5, A3B10C6, A3B10C7, A3B10C8, A3B10C9, A3B10C10, A3B10C11, A3B10C12, A3B10C13, A3B10C14, A3B10C15, A3B10C16, A3B10C17, A3B10C18, A3B10C19, A3B10C20, A3B10C21, A3B11C1, A3B11C2, A3B11C3, A3B11C4, A3B11C5, A3B11C6, A3B11C7, A3B11C8, A3B11C9, A3B11C10, A3B11C11, A3B11C12, A3B11C13, A3B11C14, A3B11C15, A3B11C16, A3B11C17, A3B11C18, A3B11C19, A3B11C20, A3B11C21, A3B12C1, A3B12C2, A3B12C3, A3B12C4, A3B12C5, A3B12C6, A3B12C7, A3B12C8, A3B12C9, A3B12C10, A3B12C11, A3B12C12, A3B12C13, A3B12C14, A3B12C15, A3B12C16, A3B12C17, A3B12C18, A3B12C19, A3B12C20, A3B12C21, A4B1C1, A4B1C2, A4B1C3, A4B1C4, A4B1C5, A4B1C6, A4B1C7, A4B1C8, A4B1C9, A4B1C10, A4B1C11, A4B1C12, A4B1C13, A4B1C14, A4B1C15, A4B1C16, A4B1C17, A4B1C18, A4B1C19, A4B1C20, A4B1C21, A4B2C1, A4B2C2, A4B2C3, A4B2C4, A4B2C5, A4B2C6, A4B2C7, A4B2C8, A4B2C9, A4B2C10, A4B2C11, A4B2C12, A4B2C13, A4B2C14, A4B2C15, A4B2C16, A4B2C17, A4B2C18, A4B2C19, A4B2C20, A4B2C21, A4B3C1, A4B3C2, A4B3C3, A4B3C4, A4B3C5, A4B3C6, A4B3C7, A4B3C8, A4B3C9, A4B3C10, A4B3C11, A4B3C12, A4B3C13, A4B3C14, A4B3C15, A4B3C16, A4B3C17, A4B3C18, A4B3C19, A4B3C20, A4B3C21, A4B4C1, A4B4C2, A4B4C3, A4B4C4, A4B4C5, A4B4C6, A4B4C7, A4B4C8, A4B4C9, A4B4C10, A4B4C11, A4B4C12, A4B4C13, A4B4C14, A4B4C15, A4B4C16, A4B4C17, A4B4C18, A4B4C19, A4B4C20, A4B4C21, A4B5C1, A4B5C2, A4B5C3, A4B5C4, A4B5C5, A4B5C6, A4B5C7, A4B5C8, A4B5C9, A4B5C10, A4B5C11, A4B5C12, A4B5C13, A4B5C14, A4B5C15, A4B5C16, A4B5C17, A4B5C18, A4B5C19, A4B5C20, A4B5C21, A4B6C1, A4B6C2, A4B6C3, A4B6C4, A4B6C5, A4B6C6, A4B6C7, A4B6C8, A4B6C9, A4B6C10, A4B6C11,

A4B6C12, A4B6C13, A4B6C14, A4B6C15, A4B6C16, A4B6C17, A4B6C18, A4B6C19, A4B6C20, A4B6C21, A4B7C1, A4B7C2, A4B7C3, A4B7C4, A4B7C5, A4B7C6, A4B7C7, A4B7C8, A4B7C9, A4B7C10, A4B7C11, A4B7C12, A4B7C13, A4B7C14, A4B7C15, A4B7C16, A4B7C17, A4B7C18, A4B7C19, A4B7C20, A4B7C21, A4B8C1, A4B8C2, A4B8C3, A4B8C4, A4B8C5, A4B8C6, A4B8C7, A4B8C8, A4B8C9, A4B8C10, A4B8C11, A4B8C12, A4B8C13, A4B8C14, A4B8C15, A4B8C16, A4B8C17, A4B8C18, A4B8C19, A4B8C20, A4B8C21, A4B9C1, A4B9C2, A4B9C3, A4B9C4, A4B9C5, A4B9C6, A4B9C7, A4B9C8, A4B9C9, A4B9C10, A4B9C11, A4B9C12, A4B9C13, A4B9C14, A4B9C15, A4B9C16, A4B9C17, A4B9C18, A4B9C19, A4B9C20, A4B9C21, A4B10C1, A4B10C2, A4B10C3, A4B10C4, A4B10C5, A4B10C6, A4B10C7, A4B10C8, A4B10C9, A4B10C10, A4B10C11, A4B10C12, A4B10C13, A4B10C14, A4B10C15, A4B10C16, A4B10C17, A4B10C18, A4B10C19, A4B10C20, A4B10C21, A4B11C1, A4B11C2, A4B11C3, A4B11C4, A4B11C5, A4B11C6, A4B11C7, A4B11C8, A4B11C9, A4B11C10, A4B11C11, A4B11C12, A4B11C13, A4B11C14, A4B11C15, A4B11C16, A4B11C17, A4B11C18, A4B11C19, A4B11C20, A4B11C21, A4B12C1, A4B12C2, A4B12C3, A4B12C4, A4B12C5, A4B12C6, A4B12C7, A4B12C8, A4B12C9, A4B12C10, A4B12C11, A4B12C12, A4B12C13, A4B12C14, A4B12C15, A4B12C16, A4B12C17, A4B12C18, A4B12C19, A4B12C20, A4B12C21, A5B1C1, A5B1C2, A5B1C3, A5B1C4, A5B1C5, A5B1C6, A5B1C7, A5B1C8, A5B1C9, A5B1C10, A5B1C11, A5B1C12, A5B1C13, A5B1C14, A5B1C15, A5B1C16, A5B1C17, A5B1C18, A5B1C19, A5B1C20, A5B1C21, A5B2C1, A5B2C2, A5B2C3, A5B2C4, A5B2C5, A5B2C6, A5B2C7, A5B2C8, A5B2C9, A5B2C10, A5B2C11, A5B2C12, A5B2C13, A5B2C14, A5B2C15, A5B2C16, A5B2C17, A5B2C18, A5B2C19, A5B2C20, A5B2C21, A5B3C1, A5B3C2, A5B3C3, A5B3C4, A5B3C5, A5B3C6, A5B3C7, A5B3C8, A5B3C9, A5B3C10, A5B3C11, A5B3C12, A5B3C13, A5B3C14, A5B3C15, A5B3C16, A5B3C17, A5B3C18, A5B3C19, A5B3C20, A5B3C21, A5B4C1, A5B4C2, A5B4C3, A5B4C4, A5B4C5, A5B4C6, A5B4C7, A5B4C8, A5B4C9, A5B4C10, A5B4C11, A5B4C12, A5B4C13, A5B4C14, A5B4C15, A5B4C16, A5B4C17, A5B4C18, A5B4C19, A5B4C20, A5B4C21, A5B5C1, A5B5C2, A5B5C3, A5B5C4, A5B5C5, A5B5C6, A5B5C7, A5B5C8, A5B5C9, A5B5C10, A5B5C11, A5B5C12, A5B5C13, A5B5C14, A5B5C15, A5B5C16, A5B5C17, A5B5C18, A5B5C19, A5B5C20, A5B5C21, A5B6C1, A5B6C2, A5B6C3, A5B6C4, A5B6C5, A5B6C6, A5B6C7, A5B6C8, A5B6C9, A5B6C10, A5B6C11, A5B6C12, A5B6C13, A5B6C14, A5B6C15, A5B6C16, A5B6C17, A5B6C18, A5B6C19, A5B6C20, A5B6C21, A5B7C1, A5B7C2, A5B7C3, A5B7C4, A5B7C5, A5B7C6, A5B7C7, A5B7C8, A5B7C9, A5B7C10, A5B7C11, A5B7C12, A5B7C13, A5B7C14, A5B7C15, A5B7C16, A5B7C17, A5B7C18, A5B7C19, A5B7C20, A5B7C21, A5B8C1, A5B8C2, A5B8C3, A5B8C4, A5B8C5, A5B8C6, A5B8C7, A5B8C8, A5B8C9, A5B8C10, A5B8C11, A5B8C12, A5B8C13, A5B8C14, A5B8C15, A5B8C16, A5B8C17, A5B8C18, A5B8C19, A5B8C20, A5B8C21, A5B9C1, A5B9C2, A5B9C3, A5B9C4, A5B9C5, A5B9C6, A5B9C7, A5B9C8, A5B9C9, A5B9C10, A5B9C11, A5B9C12, A5B9C13, A5B9C14, A5B9C15, A5B9C16, A5B9C17, A5B9C18, A5B9C19, A5B9C20, A5B9C21, A5B10C1, A5B10C2, A5B10C3, A5B10C4, A5B10C5, A5B10C6, A5B10C7, A5B10C8, A5B10C9, A5B10C10, A5B10C11, A5B10C12, A5B10C13, A5B10C14, A5B10C15, A5B10C16, A5B10C17, A5B10C18, A5B10C19, A5B10C20, A5B10C21, A5B11C1, A5B11C2, A5B11C3, A5B11C4, A5B11C5, A5B11C6, A5B11C7, A5B11C8, A5B11C9, A5B11C10, A5B11C11, A5B11C12, A5B11C13, A5B11C14, A5B11C15, A5B11C16, A5B11C17, A5B11C18, A5B11C19, A5B11C20, A5B11C21, A5B12C1, A5B12C2, A5B12C3, A5B12C4, A5B12C5, A5B12C6, A5B12C7, A5B12C8, A5B12C9, A5B12C10, A5B12C11, A5B12C12, A5B12C13, A5B12C14, A5B12C15, A5B12C16, A5B12C17, A5B12C18, A5B12C19, A5B12C20, A5B12C21, A6B1C1, A6B1C2, A6B1C3, A6B1C4, A6B1C5, A6B1C6, A6B1C7, A6B1C8, A6B1C9, A6B1C10, A6B1C11, A6B1C12, A6B1C13, A6B1C14, A6B1C15, A6B1C16, A6B1C17, A6B1C18, A6B1C19, A6B1C20, A6B1C21, A6B2C1, A6B2C2, A6B2C3, A6B2C4, A6B2C5, A6B2C6, A6B2C7, A6B2C8, A6B2C9, A6B2C10, A6B2C11, A6B2C12, A6B2C13, A6B2C14, A6B2C15, A6B2C16, A6B2C17, A6B2C18, A6B2C19, A6B2C20, A6B2C21, A6B3C1, A6B3C2, A6B3C3, A6B3C4, A6B3C5, A6B3C6, A6B3C7, A6B3C8, A6B3C9, A6B3C10, A6B3C11, A6B3C12, A6B3C13, A6B3C14, A6B3C15, A6B3C16, A6B3C17, A6B3C18, A6B3C19, A6B3C20, A6B3C21, A6B4C1, A6B4C2, A6B4C3, A6B4C4, A6B4C5, A6B4C6, A6B4C7, A6B4C8, A6B4C9, A6B4C10, A6B4C11, A6B4C12, A6B4C13, A6B4C14, A6B4C15, A6B4C16, A6B4C17, A6B4C18, A6B4C19, A6B4C20, A6B4C21, A6B5C1, A6B5C2, A6B5C3, A6B5C4, A6B5C5, A6B5C6, A6B5C7, A6B5C8, A6B5C9, A6B5C10, A6B5C11, A6B5C12, A6B5C13, A6B5C14, A6B5C15, A6B5C16, A6B5C17, A6B5C18, A6B5C19, A6B5C20, A6B5C21, A6B6C1, A6B6C2, A6B6C3, A6B6C4, A6B6C5, A6B6C6, A6B6C7, A6B6C8, A6B6C9, A6B6C10, A6B6C11, A6B6C12, A6B6C13, A6B6C14, A6B6C15, A6B6C16, A6B6C17, A6B6C18, A6B6C19, A6B6C20, A6B6C21, A6B7C1, A6B7C2, A6B7C3, A6B7C4, A6B7C5, A6B7C6, A6B7C7, A6B7C8, A6B7C9, A6B7C10, A6B7C11, A6B7C12, A6B7C13, A6B7C14, A6B7C15, A6B7C16, A6B7C17, A6B7C18, A6B7C19, A6B7C20, A6B7C21, A6B8C1, A6B8C2, A6B8C3, A6B8C4, A6B8C5, A6B8C6, A6B8C7, A6B8C8, A6B8C9, A6B8C10, A6B8C11, A6B8C12, A6B8C13, A6B8C14, A6B8C15, A6B8C16, A6B8C17, A6B8C18, A6B8C19, A6B8C20, A6B8C21, A6B9C1, A6B9C2, A6B9C3, A6B9C4, A6B9C5, A6B9C6, A6B9C7, A6B9C8, A6B9C9, A6B9C10, A6B9C11, A6B9C12, A6B9C13, A6B9C14, A6B9C15, A6B9C16, A6B9C17, A6B9C18, A6B9C19, A6B9C20, A6B9C21, A6B10C1, A6B10C2, A6B10C3, A6B10C4, A6B10C5, A6B10C6, A6B10C7, A6B10C8, A6B10C9, A6B10C10, A6B10C11, A6B10C12, A6B10C13, A6B10C14, A6B10C15, A6B10C16, A6B10C17, A6B10C18, A6B10C19, A6B10C20, A6B10C21, A6B11C1, A6B11C2, A6B11C3,

A6B11C4, A6B11C5, A6B11C6, A6B11C7, A6B11C8, A6B11C9, A6B11C10, A6B11C11, A6B11C12, A6B11C13, A6B11C14, A6B11C15, A6B11C16, A6B11C17, A6B11C18, A6B11C19, A6B11C20, A6B11C21, A6B12C1, A6B12C2, A6B12C3, A6B12C4, A6B12C5, A6B12C6, A6B12C7, A6B12C8, A6B12C9, A6B12C10, A6B12C11, A6B12C12, A6B12C13, A6B12C14, A6B12C15, A6B12C16, A6B12C17, A6B12C18, A6B12C19, A6B12C20, A6B12C21, A7B1C1, A7B1C2, A7B1C3, A7B1C4, A7B1C5, A7B1C6, A7B1C7, A7B1C8, A7B1C9, A7B1C10, A7B1C11, A7B1C12, A7B1C13, A7B1C14, A7B1C15, A7B1C16, A7B1C17, A7B1C18, A7B1C19, A7B1C20, A7B1C21, A7B2C1, A7B2C2, A7B2C3, A7B2C4, A7B2C5, A7B2C6, A7B2C7, A7B2C8, A7B2C9, A7B2C10, A7B2C11, A7B2C12, A7B2C13, A7B2C14, A7B2C15, A7B2C16, A7B2C17, A7B2C18, A7B2C19, A7B2C20, A7B2C21, A7B3C1, A7B3C2, A7B3C3, A7B3C4, A7B3C5, A7B3C6, A7B3C7, A7B3C8, A7B3C9, A7B3C10, A7B3C11, A7B3C12, A7B3C13, A7B3C14, A7B3C15, A7B3C16, A7B3C17, A7B3C18, A7B3C19, A7B3C20, A7B3C21, A7B4C1, A7B4C2, A7B4C3, A7B4C4, A7B4C5, A7B4C6, A7B4C7, A7B4C8, A7B4C9, A7B4C10, A7B4C11, A7B4C12, A7B4C13, A7B4C14, A7B4C15, A7B4C16, A7B4C17, A7B4C18, A7B4C19, A7B4C20, A7B4C21, A7B5C1, A7B5C2, A7B5C3, A7B5C4, A7B5C5, A7B5C6, A7B5C7, A7B5C8, A7B5C9, A7B5C10, A7B5C11, A7B5C12, A7B5C13, A7B5C14, A7B5C15, A7B5C16, A7B5C17, A7B5C18, A7B5C19, A7B5C20, A7B5C21, A7B6C1, A7B6C2, A7B6C3, A7B6C4, A7B6C5, A7B6C6, A7B6C7, A7B6C8, A7B6C9, A7B6C10, A7B6C11, A7B6C12, A7B6C13, A7B6C14, A7B6C15, A7B6C16, A7B6C17, A7B6C18, A7B6C19, A7B6C20, A7B6C21, A7B7C1, A7B7C2, A7B7C3, A7B7C4, A7B7C5, A7B7C6, A7B7C7, A7B7C8, A7B7C9, A7B7C10, A7B7C11, A7B7C12, A7B7C13, A7B7C14, A7B7C15, A7B7C16, A7B7C17, A7B7C18, A7B7C19, A7B7C20, A7B7C21, A7B8C1, A7B8C2, A7B8C3, A7B8C4, A7B8C5, A7B8C6, A7B8C7, A7B8C8, A7B8C9, A7B8C10, A7B8C11, A7B8C12, A7B8C13, A7B8C14, A7B8C15, A7B8C16, A7B8C17, A7B8C18, A7B8C19, A7B8C20, A7B8C21, A7B9C1, A7B9C2, A7B9C3, A7B9C4, A7B9C5, A7B9C6, A7B9C7, A7B9C8, A7B9C9, A7B9C10, A7B9C11, A7B9C12, A7B9C13, A7B9C14, A7B9C15, A7B9C16, A7B9C17, A7B9C18, A7B9C19, A7B9C20, A7B9C21, A7B10C1, A7B10C2, A7B10C3, A7B10C4, A7B10C5, A7B10C6, A7B10C7, A7B10C8, A7B10C9, A7B10C10, A7B10C11, A7B10C12, A7B10C13, A7B10C14, A7B10C15, A7B10C16, A7B10C17, A7B10C18, A7B10C19, A7B10C20, A7B10C21, A7B11C1, A7B11C2, A7B11C3, A7B11C4, A7B11C5, A7B11C6, A7B11C7, A7B11C8, A7B11C9, A7B11C10, A7B11C11, A7B11C12, A7B11C13, A7B11C14, A7B11C15, A7B11C16, A7B11C17, A7B11C18, A7B11C19, A7B11C20, A7B11C21, A7B12C1, A7B12C2, A7B12C3, A7B12C4, A7B12C5, A7B12C6, A7B12C7, A7B12C8, A7B12C9, A7B12C10, A7B12C11, A7B12C12, A7B12C13, A7B12C14, A7B12C15, A7B12C16, A7B12C17, A7B12C18, A7B12C19, A7B12C20, A7B12C21, A8B1C1, A8B1C2, A8B1C3, A8B1C4, A8B1C5, A8B1C6, A8B1C7, A8B1C8, A8B1C9, A8B1C10, A8B1C11, A8B1C12, A8B1C13, A8B1C14, A8B1C15, A8B1C16, A8B1C17, A8B1C18, A8B1C19, A8B1C20, A8B1C21, A8B2C1, A8B2C2, A8B2C3, A8B2C4, A8B2C5, A8B2C6, A8B2C7, A8B2C8, A8B2C9, A8B2C10, A8B2C11, A8B2C12, A8B2C13, A8B2C14, A8B2C15, A8B2C16, A8B2C17, A8B2C18, A8B2C19, A8B2C20, A8B2C21, A8B3C1, A8B3C2, A8B3C3, A8B3C4, A8B3C5, A8B3C6, A8B3C7, A8B3C8, A8B3C9, A8B3C10, A8B3C11, A8B3C12, A8B3C13, A8B3C14, A8B3C15, A8B3C16, A8B3C17, A8B3C18, A8B3C19, A8B3C20, A8B3C21, A8B4C1, A8B4C2, A8B4C3, A8B4C4, A8B4C5, A8B4C6, A8B4C7, A8B4C8, A8B4C9, A8B4C10, A8B4C11, A8B4C12, A8B4C13, A8B4C14, A8B4C15, A8B4C16, A8B4C17, A8B4C18, A8B4C19, A8B4C20, A8B4C21, A8B5C1, A8B5C2, A8B5C3, A8B5C4, A8B5C5, A8B5C6, A8B5C7, A8B5C8, A8B5C9, A8B5C10, A8B5C11, A8B5C12, A8B5C13, A8B5C14, A8B5C15, A8B5C16, A8B5C17, A8B5C18, A8B5C19, A8B5C20, A8B5C21, A8B6C1, A8B6C2, A8B6C3, A8B6C4, A8B6C5, A8B6C6, A8B6C7, A8B6C8, A8B6C9, A8B6C10, A8B6C11, A8B6C12, A8B6C13, A8B6C14, A8B6C15, A8B6C16, A8B6C17, A8B6C18, A8B6C19, A8B6C20, A8B6C21, A8B7C1, A8B7C2, A8B7C3, A8B7C4, A8B7C5, A8B7C6, A8B7C7, A8B7C8, A8B7C9, A8B7C10, A8B7C11, A8B7C12, A8B7C13, A8B7C14, A8B7C15, A8B7C16, A8B7C17, A8B7C18, A8B7C19, A8B7C20, A8B7C21, A8B8C1, A8B8C2, A8B8C3, A8B8C4, A8B8C5, A8B8C6, A8B8C7, A8B8C8, A8B8C9, A8B8C10, A8B8C11, A8B8C12, A8B8C13, A8B8C14, A8B8C15, A8B8C16, A8B8C17, A8B8C18, A8B8C19, A8B8C20, A8B8C21, A8B9C1, A8B9C2, A8B9C3, A8B9C4, A8B9C5, A8B9C6, A8B9C7, A8B9C8, A8B9C9, A8B9C10, A8B9C11, A8B9C12, A8B9C13, A8B9C14, A8B9C15, A8B9C16, A8B9C17, A8B9C18, A8B9C19, A8B9C20, A8B9C21, A8B10C1, A8B10C2, A8B10C3, A8B10C4, A8B10C5, A8B10C6, A8B10C7, A8B10C8, A8B10C9, A8B10C10, A8B10C11, A8B10C12, A8B10C13, A8B10C14, A8B10C15, A8B10C16, A8B10C17, A8B10C18, A8B10C19, A8B10C20, A8B10C21, A8B11C1, A8B11C2, A8B11C3, A8B11C4, A8B11C5, A8B11C6, A8B11C7, A8B11C8, A8B11C9, A8B11C10, A8B11C11, A8B11C12, A8B11C13, A8B11C14, A8B11C15, A8B11C16, A8B11C17, A8B11C18, A8B11C19, A8B11C20, A8B11C21, A8B12C1, A8B12C2, A8B12C3, A8B12C4, A8B12C5, A8B12C6, A8B12C7, A8B12C8, A8B12C9, A8B12C10, A8B12C11, A8B12C12, A8B12C13, A8B12C14, A8B12C15, A8B12C16, A8B12C17, A8B12C18, A8B12C19, A8B12C20, A8B12C21, A9B1C1, A9B1C2, A9B1C3, A9B1C4, A9B1C5, A9B1C6, A9B1C7, A9B1C8, A9B1C9, A9B1C10, A9B1C11, A9B1C12, A9B1C13, A9B1C14, A9B1C15, A9B1C16, A9B1C17, A9B1C18, A9B1C19, A9B1C20, A9B1C21, A9B2C1, A9B2C2, A9B2C3, A9B2C4, A9B2C5, A9B2C6, A9B2C7, A9B2C8, A9B2C9, A9B2C10, A9B2C11, A9B2C12, A9B2C13, A9B2C14, A9B2C15, A9B2C16, A9B2C17, A9B2C18, A9B2C19, A9B2C20, A9B2C21, A9B3C1, A9B3C2, A9B3C3, A9B3C4, A9B3C5, A9B3C6, A9B3C7, A9B3C8, A9B3C9, A9B3C10, A9B3C11, A9B3C12, A9B3C13, A9B3C14, A9B3C15, A9B3C16, A9B3C17,

A9B3C18, A9B3C19, A9B3C20, A9B3C21, A9B4C1, A9B4C2, A9B4C3, A9B4C4, A9B4C5, A9B4C6, A9B4C7, A9B4C8, A9B4C9, A9B4C10, A9B4C11, A9B4C12, A9B4C13, A9B4C14, A9B4C15, A9B4C16, A9B4C17, A9B4C18, A9B4C19, A9B4C20, A9B4C21, A9B5C1, A9B5C2, A9B5C3, A9B5C4, A9B5C5, A9B5C6, A9B5C7, A9B5C8, A9B5C9, A9B5C10, A9B5C11, A9B5C12, A9B5C13, A9B5C14, A9B5C15, A9B5C16, A9B5C17, A9B5C18, A9B5C19, A9B5C20, A9B5C21, A9B6C1, A9B6C2, A9B6C3, A9B6C4, A9B6C5, A9B6C6, A9B6C7, A9B6C8, A9B6C9, A9B6C10, A9B6C11, A9B6C12, A9B6C13, A9B6C14, A9B6C15, A9B6C16, A9B6C17, A9B6C18, A9B6C19, A9B6C20, A9B6C21, A9B7C1, A9B7C2, A9B7C3, A9B7C4, A9B7C5, A9B7C6, A9B7C7, A9B7C8, A9B7C9, A9B7C10, A9B7C11, A9B7C12, A9B7C13, A9B7C14, A9B7C15, A9B7C16, A9B7C17, A9B7C18, A9B7C19, A9B7C20, A9B7C21, A9B8C1, A9B8C2, A9B8C3, A9B8C4, A9B8C5, A9B8C6, A9B8C7, A9B8C8, A9B8C9, A9B8C10, A9B8C11, A9B8C12, A9B8C13, A9B8C14, A9B8C15, A9B8C16, A9B8C17, A9B8C18, A9B8C19, A9B8C20, A9B8C21, A9B9C1, A9B9C2, A9B9C3, A9B9C4, A9B9C5, A9B9C6, A9B9C7, A9B9C8, A9B9C9, A9B9C10, A9B9C11, A9B9C12, A9B9C13, A9B9C14, A9B9C15, A9B9C16, A9B9C17, A9B9C18, A9B9C19, A9B9C20, A9B9C21, A9B10C1, A9B10C2, A9B10C3, A9B10C4, A9B10C5, A9B10C6, A9B10C7, A9B10C8, A9B10C9, A9B10C10, A9B10C11, A9B10C12, A9B10C13, A9B10C14, A9B10C15, A9B10C16, A9B10C17, A9B10C18, A9B10C19, A9B10C20, A9B10C21, A9B11C1, A9B11C2, A9B11C3, A9B11C4, A9B11C5, A9B11C6, A9B11C7, A9B11C8, A9B11C9, A9B11C10, A9B11C11, A9B11C12, A9B11C13, A9B11C14, A9B11C15, A9B11C16, A9B11C17, A9B11C18, A9B11C19, A9B11C20, A9B11C21, A9B12C1, A9B12C2, A9B12C3, A9B12C4, A9B12C5, A9B12C6, A9B12C7, A9B12C8, A9B12C9, A9B12C10, A9B12C11, A9B12C12, A9B12C13, A9B12C14, A9B12C15, A9B12C16, A9B12C17, A9B12C18, A9B12C19, A9B12C20, A9B12C21, A10B1C1, A10B1C2, A10B1C3, A10B1C4, A10B105, A10B106, A10B1C7, A10B1C8, A10B1C9, A10B1C10, A10B1C11, A10B1C12, A10B1C13, A10B1C14, A10B1C15, A10B1C16, A10B1C17, A10B1C18, A10B1C19, A10B1C20, A10B1C21, A10B2C1, A10B2C2, A10B2C3, A10B2C4, A10B2C5, A10B2C6, A10B2C7, A10B2C8, A10B2C9, A10B2C10, A10B2C11, A10B2C12, A10B2C13, A10B2C14, A10B2C15, A10B2C16, A10B2C17, A10B2C18, A10B2C19, A10B2C20, A10B2C21, A10B3C1, A10B3C2, A10B3C3, A10B3C4, A10B3C5, A10B3C6, A10B3C7, A10B3C8, A10B3C9, A10B3C10, A10B3C11, A10B3C12, A10B3C13, A10B3C14, A10B3C15, A10B3C16, A10B3C17, A10B3C18, A10B3C19, A10B3C20, A10B3C21, A10B4C1, A10B4C2, A10B4C3, A10B4C4, A10B4C5, A10B4C6, A10B4C7, A10B4C8, A10B4C9, A10B4C10, A10B4C11, A10B4C12, A10B4C13, A10B4C14, A10B4C15, A10B4C16, A10B4C17, A10B4C18, A10B4C19, A10B4C20, A10B4C21, A10B5C1, A10B5C2, A10B5C3, A10B5C4, A10B5C5, A10B5C6, A10B5C7, A10B5C8, A10B5C9, A10B5C10, A10B5C11, A10B5C12, A10B5C13, A10B5C14, A10B5C15, A10B5C16, A10B5C17, A10B5C18, A10B5C19, A10B5C20, A10B5C21, A10B6C1, A10B6C2, A10B6C3, A10B6C4, A10B6C5, A10B6C6, A10B6C7, A10B6C8, A10B6C9, A10B6C10, A10B6C11, A10B6C12, A10B6C13, A10B6C14, A10B6C15, A10B6C16, A10B6C17, A10B6C18, A10B6C19, A10B6C20, A10B6C21, A10B7C1, A10B7C2, A10B7C3, A10B7C4, A10B7C5, A10B7C6, A10B7C7, A10B7C8, A10B7C9, A10B7C10, A10B7C11, A10B7C12, A10B7C13, A10B7C14, A10B7C15, A10B7C16, A10B7C17, A10B7C18, A10B7C19, A10B7C20, A10B7C21, A10B8C1, A10B8C2, A10B8C3, A10B8C4, A10B8C5, A10B8C6, A10B8C7, A10B8C8, A10B8C9, A10B8C10, A10B8C11, A10B8C12, A10B8C13, A10B8C14, A10B8C15, A10B8C16, A10B8C17, A10B8C18, A10B8C19, A10B8C20, A10B8C21, A10B9C1, A10B9C2, A10B9C3, A10B9C4, A10B9C5, A10B9C6, A10B9C7, A10B9C8, A10B9C9, A10B9C10, A10B9C11, A10B9C12, A10B9C13, A10B9C14, A10B9C15, A10B9C16, A10B9C17, A10B9C18, A10B9C19, A10B9C20, A10B9C21, A10B10C1, A10B10C2, A10B10C3, A10B10C4, A10B10C5, A10B10C6, A10B10C7, A10B10C8, A10B10C9, A10B10C10, A10B10C11, A10B10C12, A10B10C13, A10B10C14, A10B10C15, A10B10C16, A10B10C17, A10B10C18, A10B10C19, A10B10C20, A10B10C21, A10B11C1, A10B11C2, A10B11C3, A10B11C4, A10B11C5, A10B11C6, A10B11C7, A10B11C8, A10B11C9, A10B11C10, A10B11C11, A10B11C12, A10B11C13, A10B11C14, A10B11C15, A10B11C16, A10B11C17, A10B11C18, A10B11C19, A10B11C20, A10B11C21, A10B12C1, A10B12C2, A10B12C3, A10B12C4, A10B12C5, A10B12C6, A10B12C7, A10B12C8, A10B12C9, A10B12C10, A10B12C11, A10B12C12, A10B12C13, A10B12C14, A10B12C15, A10B12C16, A10B12C17, A10B12C18, A10B12C19, A10B12C20, A10B12C21, A11B1C1, A11B1C2, A11B1C3, A11B1C4, A11B105, A11B106, A11B1C7, A11B1C8, A11B1C9, A11B1C10, A11B1C11, A11B1C12, A11B1C13, A11B1C14, A11B1C15, A11B1C16, A11B1C17, A11B1C18, A11B1C19, A11B1C20, A11B1C21, A11B2C1, A11B2C2, A11B2C3, A11B2C4, A11B2C5, A11B2C6, A11B2C7, A11B2C8, A11B2C9, A11B2C10, A11B2C11, A11B2C12, A11B2C13, A11B2C14, A11B2C15, A11B2C16, A11B2C17, A11B2C18, A11B2C19, A11B2C20, A11B2C21, A11B3C1, A11B3C2, A11B3C3, A11B3C4, A11B3C5, A11B3C6, A11B3C7, A11B3C8, A11B3C9, A11B3C10, A11B3C11, A11B3C12, A11B3C13, A11B3C14, A11B3C15, A11B3C16, A11B3C17, A11B3C18, A11B3C19, A11B3C20, A11B3C21, A11B4C1, A11B4C2, A11B4C3, A11B4C4, A11B4C5, A11B4C6, A11B4C7, A11B4C8, A11B4C9, A11B4C10, A11B4C11, A11B4C12, A11B4C13, A11B4C14, A11B4C15, A11B4C16, A11B4C17, A11B4C18, A11B4C19, A11B4C20, A11B4C21, A11B5C1, A11B5C2, A11B5C3, A11B5C4, A11B5C5, A11B5C6, A11B5C7, A11B5C8, A11B5C9, A11B5C10, A11B5C11, A11B5C12, A11B5C13, A11B5C14, A11B5C15, A11B5C16, A11B5C17, A11B5C18, A11B5C19, A11B5C20, A11B5C21, A11B6C1, A11B6C2, A11B6C3, A11B6C4, A11B6C5, A11B6C6, A11B6C7, A11B6C8, A11B6C9, A11B6C10, A11B6C11, A11B6C12,

A11B6C13, A11B6C14, A11B6C15, A11B6C16, A11B6C17, A11B6C18, A11B6C19, A11B6C20, A11B6C21, A11B7C1, A11B7C2, A11B7C3, A11B7C4, A11B7C5, A11B7C6, A11B7C7, A11B7C8, A11B7C9, A11B7C10, A11B7C11, A11B7C12, A11B7C13, A11B7C14, A11B7C15, A11B7C16, A11B7C17, A11B7C18, A11B7C19, A11B7C20, A11B7C21, A11B8C1, A11B8C2, A11B8C3, A11B8C4, A11B8C5, A11B8C6, A11B8C7, A11B8C8, A11B8C9, A11B8C10, A11B8C11, A11B8C12, A11B8C13, A11B8C14, A11B8C15, A11B8C16, A11B8C17, A11B8C18, A11B8C19, A11B8C20, A11B8C21, A11B9C1, A11B9C2, A11B9C3, A11B9C4, A11B9C5, A11B9C6, A11B9C7, A11B9C8, A11B9C9, A11B9C10, A11B9C11, A11B9C12, A11B9C13, A11B9C14, A11B9C15, A11B9C16, A11B9C17, A11B9C18, A11B9C19, A11B9C20, A11B9C21, A11B10C1, A11B10C2, A11B10C3, A11B10C4, A11B10C5, A11B10C6, A11B10C7, A11B10C8, A11B10C9, A11B10C10, A11B10C11, A11B10C12, A11B10C13, A11B10C14, A11B10C15, A11B10C16, A11B10C17, A11B10C18, A11B10C19, A11B10C20, A11B10C21, A11B11C1, A11B11C2, A11B11C3, A11B11C4, A11B11C5, A11B11C6, A11B11C7, A11B11C8, A11B11C9, A11B11C10, A11B11C11, A11B11C12, A11B11C13, A11B11C14, A11B11C15, A11B11C16, A11B11C17, A11B11C18, A11B11C19, A11B11C20, A11B11C21, A11B12C1, A11B12C2, A11B12C3, A11B12C4, A11B12C5, A11B12C6, A11B12C7, A11B12C8, A11B12C9, A11B12C10, A11B12C11, A11B12C12, A11B12C13, A11B12C14, A11B12C15, A11B12C16, A11B12C17, A11B12C18, A11B12C19, A11B12C20, or A11B12C21.

Antibody Molecules

In one embodiment, the antibody molecule binds to a mammalian, e.g., human, LAG-3. For example, the antibody molecule binds specifically to an epitope, e.g., linear or conformational epitope, (e.g., an epitope as described herein) on LAG-3. In some embodiments, the antibody molecule binds to one or more extracellular Ig-like domains of LAG-3, e.g., the first, second, third or fourth extracellular Ig-like domain of LAG-3.

As used herein, the term "antibody molecule" refers to a protein, e.g., an immunoglobin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full length antibody, or a full length immunoglobin chain. In an embodiment, an antibody molecule comprises an antigen binding or functional fragment of a full length antibody, or a full length immunoglobulin chain.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule, In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope. In an embodiment, the first epitope is located on LAG-3 and the second epitope is located on a PD-1, TIM-3, CEACAM (e.g., CEACAM-1, CEACAM-3 and/or CEACAM-5), PD-L1, or PD-L2.

In an embodiment, an antibody molecule comprises a diabody, and a single-chain molecule, as well as an antigen-binding fragment of an antibody (e.g., Fab, $F(ab')_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', $F(ab')_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibody molecules can be monoclonal or polyclonal. An antibodymolecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibodies of the present invention can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW). The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), A1-Lazikani et al., (1997) JMB 273, 927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the anti-LAG-3 antibody molecules can include any combination of one or more Kabat CDRs and/or Chothia hypervariable loops, e.g., described in Table 1. In one embodiment, the following definitions are used for the anti-LAG-3 antibody molecules described in Table 1: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the LAG-3 polypeptide, or an epitope thereof. With respect to proteins (or protein mimetics), the antigen-binding site typically includes one or more loops (of at least four amino acids or amino acid mimics) that form an interface that binds to the LAG-3 polypeptide. Typically, the antigen-binding site of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-LAG-3 antibody molecule, e.g., an anti-LAG-3 antibody molecule provided herein, to a target, e.g., human LAG-3. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-LAG-3 antibody molecule is said to compete for binding to the target with a second anti-LAG-3 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

As used herein, the term "epitope" refers to the moieties of an antigen (e.g., human LAG-3) that specifically interact with an antibody molecule. Such moieties, referred to herein as epitopic determinants, typically comprise, or are part of, elements such as amino acid side chains or sugar side chains. An epitopic determinate can be defined by methods known in the art or disclosed herein, e.g., by crystallography or by hydrogen-deuterium exchange. At least one or some of the moieties on the antibody molecule, that specifically interact with an epitopic determinant, are typically located in a CDR(s). Typically an epitope has a specific three dimensional structural characteristics. Typically an epitope has specific charge characteristics. Some epitopes are linear epitopes while others are conformational epitopes.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.,* 32:180-190 (1990)) and also because of potential allergic reactions (see, e.g., LoBuglio et al., *Hybridoma,* 5:5117-5123 (1986)).

The antibody molecule can be a polyclonal or a monoclonal antibody. In other embodiments, the antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 PNAS 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to LAG-3. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann NY Acad Sci* 880: 263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g., altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody molecule of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecules may be conjugated to another molecular entity, typically a label or a therapeutic (e.g., a cytotoxic or cytostatic) agent or moiety. Radioactive isotopes can be used in diagnostic or therapeutic applications. Radioactive isotopes that can be coupled to the anti-PSMA antibodies include, but are not limited to α-, β-, or γ-emitters, or β- and γ-emitters. Such radioactive isotopes include, but are not limited to iodine ($^{131}I$ or $^{125}I$), yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), indium ($^{111}In$), technetium ($^{99}mTc$), phosphorus ($^{32}P$), rhodium sulfur ($^{35}S$), carbon ($^{14}C$), tritium ($^{3}H$), chromium ($^{51}Cr$), chlorine ($^{36}Cl$), cobalt ($^{57}Co$ or $^{58}Co$), iron ($^{59}Fe$), selenium ($^{75}Se$), or gallium ($^{67}Ga$). Radioisotopes useful as therapeutic agents include yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), and rhodium ($^{188}Rh$). Radioisotopes useful as labels, e.g., for use in diagnostics, include iodine ($^{131}I$ or $^{125}I$), indium ($^{111}In$), technetium ($^{99}mTc$), phosphorus ($^{32}P$), carbon ($^{14}C$), and tritium ($^{3}H$), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In one aspect, the invention features a method of providing a target binding molecule that specifically binds to a LAG-3 receptor. For example, the target binding molecule is an antibody molecule. The method includes: providing a target protein that comprises at least a portion of non-human protein, the portion being homologous to (at least 70, 75, 80, 85, 87, 90, 92, 94, 95, 96, 97, 98% identical to) a corresponding portion of a human target protein, but differing by at least one amino acid (e.g., at least one, two, three, four, five, six, seven, eight, or nine amino acids); obtaining an antibody molecule that specifically binds to the antigen; and evaluating efficacy of the binding agent in modulating activity of the target protein. The method can further include administering the binding agent (e.g., antibody molecule) or a derivative (e.g., a humanized antibody molecule) to a human subject.

This invention provides an isolated nucleic acid molecule encoding the above antibody molecule, vectors and host cells thereof. The nucleic acid molecule includes but is not limited to RNA, genomic DNA and cDNA.

Multispecific Antibody Molecules

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

In other embodiments, the anti-LAG-3 antibody molecule (e.g., a monospecific, bispecific, or multispecific antibody molecule) is covalently linked, e.g., fused, to another partner e.g., a protein e.g., one, two or more cytokines, e.g., as a fusion molecule for example a fusion protein. In other embodiments, the fusion molecule comprises one or more proteins, e.g., one, two or more cytokines. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to LAG-3), a second binding specificity to a second target (e.g., PD-1, TIM-3, or PD-L1), and is optionally linked to an interleukin (e.g., IL-12) domain e.g., full length IL-12 or a portion thereof.

A "fusion protein" and a "fusion polypeptide" refer to a polypeptide having at least two portions covalently linked together, where each of the portions is a polypeptide having a different property. The property may be a biological property, such as activity in vitro or in vivo. The property can also be simple chemical or physical property, such as binding to a target molecule, catalysis of a reaction, etc. The two portions can be linked directly by a single peptide bond or through a peptide linker, but are in reading frame with each other.

This invention provides an isolated nucleic acid molecule encoding the above antibody molecules, vectors and host cells thereof. The nucleic acid molecule includes but is not limited to RNA, genomic DNA and cDNA.

Exemplary Agents used in the Combinations

Described herein are methods and compositions that include a combination of one or more of: (i) an agent that enhances antigen (e.g., tumor antigen) presentation; (ii) an agent that enhances an effector cell response (e.g., B cell and/or T cell activation and/or mobilization); or (iii) an agent that decreases tumor immunosuppression, thereby treating the disorder, e.g., the hyperproliferative condition or disorder (e.g., the cancer). In some embodiments, the combination includes a LAG-3 inhibitor (e.g., an anti-LAG-3 antibody molecule as described herein). Exemplary agents that can be used in these combinations are provided herein.

Exemplary STING Agonists

In an embodiment, the combination includes a STING agonist. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a lung cancer (e.g., a non-small cell lung cancer), a breast cancer, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

In some embodiments, the STING agonist is cyclic dinucleotide, e.g., a cyclic dinucleotide comprising purine or pyrimidine nucleobases (e.g., adenosine, guanine, uracil, thymine, or cytosine nucleobases). In some embodiments, the nucleobases of the cyclic dinucleotide comprise the same nucleobase or different nucleobases.

In some embodiments, the STING agonist comprises an adenosine or a guanosine nucleobase. In some embodiments, the STING agonist comprises one adenosine nucleobase and one guanosine nucleobase. In some embodiments, the STING agonist comprises two adenosine nucleobases or two guanosine nucleobases.

In some embodiments, the STING agonist comprises a modified cyclic dinucleotide, e.g., comprising a modified nucleobase, a modified ribose, or a modified phosphate linkage. In some embodiments, the modified cyclic dinucleotide comprises a modified phosphate linkage, e.g., a thiophosphate.

In some embodiments, the STING agonist comprises a cyclic dinucleotide (e.g., a modified cyclic dinucleotide) with 2',5' or 3',5' phosphate linkages. In some embodiments, the STING agonist comprises a cyclic dinucleotide (e.g., a modified cyclic dinucleotide) with Rp or Sp stereochemistry around the phosphate linkages.

In some embodiments, the STING agonist is Rp,Rp dithio 2',3' c-di-AMP (e.g., Rp,Rp-dithio c-[A(2',5')pA(3',5')p]), or a cyclic dinucleotide analog thereof. In some embodiments, the STING agonist is a compound depicted in U.S. Patent Publication No. US2015/0056224 (e.g., a compound in FIG. 2*c*, e.g., compound 21 or compound 22). In some embodiments, the STING agonist is c-[G(2',5')pG(3',5')p], a dithio ribose 0-substituted derivative thereof, or a compound depicted in FIG. 4 of PCT Publication Nos. WO 2014/189805 and WO 2014/189806. In some embodiments, the STING agonist is c-[A(2',5')pA(3',5')p] or a dithio ribose 0-substituted derivative thereof, or is a compound depicted in FIG. 5 of PCT Publication Nos. WO 2014/189805 and WO 2014/189806. In some embodiments, the STING agonist is c-[G(2',5')pA(3',5')p], or a dithio ribose 0-substituted derivative thereof, or is a compound depicted in FIG. 5 of PCT Publication Nos. WO 2014/189805 and WO 2014/189806. In some embodiments, the STING agonist is 2'-0-propargyl-cyclic-[A(2',5')pA(3',5')p] (2'-0-propargyl-ML-CDA) or a compound depicted in FIG. 7 of PCT Publication No. WO 2014/189806.

Other exemplary STING agonists are disclosed, e.g., in PCT Publication Nos. WO 2014/189805 and WO 2014/189806, and U.S. Publication No. 2015/0056225.

Exemplary TLR Agonists

In an embodiment, a combination described herein includes a Toll-like receptor (TLR) agonist. In some embodiments, the combination is used to treat a cancer, e.g., a cancer described herein, e.g., a solid tumor (e.g., a breast cancer, a squamous cell carcinoma, a melanoma, an ovarian cancer, a fallopian tube carcinoma, a peritoneal carcinoma, a soft tissue sarcoma, a melanoma, a breast cancer, an esophageal cancer, a head and neck cancer, an endometrial cancer, a cervical cancer, a colon cancer (e.g., a metastatic mismatch repair-proficient (MRP) colon cancer), a kidney cancer (e.g., a renal cell carcinoma), or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)).

TLRs are a family of pattern recognition receptors that were initially identified as sensors of the innate immune system that recognize microbial pathogens. In humans, the TLRs include TLR-1, TLR-2, TLR-3, TLR-4, TLR-5, TLR-6, TLR-7, TLR-8, TLR-9, and TLR-10. TLR-1, -2, -4, -5, and -6, are expressed on the surface of cells and TLR-3, -7/8, and -9 are expressed with the ER compartment. Human dendritic cell subsets can be identified on the basis of distinct TLR expression patterns. The myeloid or "conventional" subset of human dendritic cells express TLRs 1-8 and the plasmacytoid subset of dendritic cells express only TLR-7 and TLR-9. Ligand binding to TLRs invokes a cascade of intra-cellular signaling pathways that induce the production of factors involved in inflammation and immunity. Upon stimulation, the myeloid subset and the plasmacytoid subset of human dendritic cells result in antigen-specific CD4+ and CD8+ T cell priming and activation of NK cells and T-cells, respectively.

In some embodiments, the TLR agonist is chosen from one or more of a TLR-1 agonist, a TLR-2 agonist, a TLR-3 agonist, a TLR-4 agonist, a TLR-5 agonist, a TLR-6 agonist, a TLR-7 agonist, a TLR-8 agonist, a TLR-9 agonist, a TLR-10 agonist, a TLR-1/2 agonist, a TLR-2/6 agonist, or a TLR-7/8 agonist. In one embodiment, the TLR agonist is a TLR7 agonist.

In some embodiments, the TLR agonist is imiquimod or 3-(2-Methylpropyl)-3,5,8-triazatricyclo[7.4.0.02,6]trideca-1(9),2(6),4,7,10,12-hexaen-7-amine. Imiquimod or 3-(2-Methylpropyl)-3,5,8-triazatricyclo[7.4.0.02,6]trideca-1(9),2(6),4,7,10,12-hexaen-7-amine can bind to and activate TLR-7 and/or TLR-8.

In some embodiments, the TLR agonist is 852A. 852A is disclosed, e.g., in Inglefield et al. J Interferon Cytokine Res. 2008; 28(4):253-63. 852A can bind to and activate TLR-7 and/or TLR-8.

In some embodiments, the TLR agonist is Bacille Calmette-Guérin (BCG). BCG can bind to and activate TLR-9.

In some embodiments, the TLR agonist is EMD 120108. EMD 120108 is a synthetic oligonucleotide containing phosphorothioate oligodeoxynucleotide. EMD 1201081 can bind to and activate TLR-9, e.g, in monocytes/macrophages, plasmacytoid dendritic cells (DCs) and B cells, initiating immune signaling pathways, activating B cells and inducing T-helper cell cytokine production.

In some embodiments, the TLR agonist is IMO-2055. IMO-2055 is a synthetic oligonucleotide containing unmethylated CpG dinucleotides. Mimicking unmethylated CpG sequences in bacterial DNA, IMO-2055 can bind to and activate TLR-9, e.g., in monocytes/macrophages, plasmacytoid dendritic cells (DCs) and B cells, initiating immune signaling pathways and activating B cells and DCs and inducing T-helper cell cytokine production.

Other exemplary TLR agonists that can be used in the combination include, e.g., TLR-1/2 agonists (e.g., Pam3Cys), TLR-2 agonists (e.g., CFA, MALP2, Pam2Cys, FSL-1, or Hib-OMPC), TLR-3 agonists (e.g., polyribosinic:polyribocytidic acid (Poly I:C), polyadenosine-polyuridylic acid (poly AU), polyinosinic-polycytidylic acid stabilized with poly-L-lysine and carboxymethylcellulose (Hiltonol®)), TLR-4 agonists (e.g., monophosphoryl lipid A (MPL), LPS, sialyl-Tn (STn)), TLR-5 agonists (e.g., bacterial flagellin), TLR-7 agonists (e.g., imiquimod), TLR-7/8 agonists (e.g., resiquimod or loxoribine), and TLR-9 agonists (e.g., unmethylated CpG dinucleotide (CpG-ODN)).

In another embodiment, the TLR agonist is used in combination with a GITR agonist, e.g., as described in WO2004/060319, and International Publication No.: WO2014/012479.

Exemplary VEGFR Inhibitors

In one embodiment, a combination described herein includes a vascular endothelial growth factor (VEGF) receptor inhibitor (e.g., an inhibitor of one or more of VEGFR (e.g., VEGFR-1, VEGFR-2, VEGFR-3) or VEGF). In some embodiments, the combination is used to treat a cancer, e.g., a cancer described herein, e.g., a solid tumor (e.g., a melanoma, a breast cancer, a colon cancer, an esophageal cancer, a gastrointestinal stromal tumor (GIST), a kidney cancer (e.g., a renal cell cancer), a liver cancer, a non-small cell lung cancer (NSCLC), an ovarian cancer, a pancreatic cancer, a prostate cancer, or a stomach cancer), e.g., a hematologic malignancy (e.g., a lymphoma).

In some embodiments, the VEGFR inhibitor is vatalanib succinate (Compound A47) or a compound disclosed in EP 296122.

In some embodiment, the VEGFR inhibitor is an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377.

Other exemplary VEGFR pathway inhibitors that can be used in the combinations disclosed herein include, e.g., bevacizumab (AVASTIN®), axitinib (INLYTA®); brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); sorafenib (NEXAVAR®); pazopanib (VOTRIENT®); sunitinib malate (SUTENT®); cediranib (AZD2171, CAS 288383-20-1); vargatef (BIBF1120, CAS 928326-83-4); Foretinib (GSK1363089); telatinib (BAY57-9352, CAS 332012-40-5); apatinib (YN968D1, CAS 811803-05-1); imatinib (GLEEVEC®); ponatinib (AP24534, CAS 943319-70-8); tivozanib (AV951, CAS 475108-18-0); regorafenib (BAY73-4506, CAS 755037-03-7); vatalanib dihydrochloride (PTK787, CAS 212141-51-0); brivanib (BMS-540215, CAS 649735-46-6); vandetanib (CAPRELSA® or AZD6474); motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); dovitinib dilactic acid (TKI258, CAS 852433-84-2); linfanib (ABT869, CAS 796967-16-3); cabozantinib (XL184, CAS 849217-68-1); lestaurtinib (CAS 111358-88-4); N-[5-[[[5-(1,1-dimethylethyl)-2-oxazolyl]methyl]thio]-2-thiazolyl]-4-piperidinecarboxamide (BMS38703, CAS 345627-80-7); (3R,4R)-4-amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); aflibercept (EYLEA®), and endostatin (ENDOSTAR®).

Exemplary anti-VEGF antibodies that can be used in the combinations disclosed herein include, e.g., a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is Bevacizumab (BV), also known as rhuMAb VEGF or AVASTIN®. It comprises mutated human IgG1 framework regions and antigen-binding complementarity—determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies see U.S. Pat. Nos. 7,060,269, 6,582,959, 6,703,020, 6,054,297, WO98/45332, WO 96/30046, WO94/10202, EP 0666868B1, U.S. Patent Application Publication Nos. 2006/009360, 2005/0186208, 2003/0206899, 2003/0190317, 2003/0203409, and 2005/0112126; and Popkov et al, *Journal of Immunological Methods* 288: 149-164 (2004). Other antibodies include those that bind to a functional epitope on human VEGF comprising of residues F17, M18, D19, Y21, Y25, Q89, 191, K1 01, E1 03, and C104 or, alternatively, comprising residues F17, Y21, Q22, Y25, D63, 183 and Q89.

Exemplary c-MET Inhibitors

In one embodiment, a combination described herein includes an inhibitor of c-MET. In some embodiments, the combination is used to treat a cancer, e.g., a cancer described herein, e.g., a solid tumor (e.g., a non-small cell lung cancer, a pancreatic cancer, a liver cancer (e.g., a hepatocellular carcinoma, e.g., a c-MET overexpressing hepatocellular carcinoma), a thyroid cancer, a brain tumor (e.g., a glioblastoma), a kidney cancer (e.g., a renal cell carcinoma), a head and neck cancer (e.g., a head and neck squamous cell carcinoma).

In some embodiments, the c-MET inhibitor is Compound A17 or a compound described in U.S. Pat. Nos. 7,767,675 and 8,420,645). c-MET, a receptor tyrosine kinase overexpressed or mutated in many tumor cell types, plays key roles in tumor cell proliferation, survival, invasion, metastasis, and tumor angiogenesis. Inhibition of c-MET may induce cell death in tumor cells overexpressing c-MET protein or expressing constitutively activated c-MET protein.

In some embodiments, the c-MET inhibitor is JNJ-38877605. JNJ-38877605 is an orally available, small molecule inhibitor of c-Met. JNJ-38877605 selectively binds to c-MET, thereby inhibiting c-MET phosphorylation and disrupting c-Met signal transduction pathways.

In some embodiments, the c-Met inhibitor is AMG 208. AMG 208 is a selective small-molecule inhibitor of c-MET. AMG 208 inhibits the ligand-dependent and ligand-independent activation of c-MET, inhibiting its tyrosine kinase activity, which may result in cell growth inhibition in tumors that overexpress c-Met.

In some embodiments, the c-Met inhibitor is AMG 337. AMG 337 is an orally bioavailable inhibitor of c-Met. AMG 337 selectively binds to c-MET, thereby disrupting c-MET signal transduction pathways.

In some embodiments, the c-Met inhibitor is LY2801653. LY2801653 is an orally available, small molecule inhibitor of c-Met. LY2801653 selectively binds to c-MET, thereby inhibiting c-MET phosphorylation and disrupting c-Met signal transduction pathways.

In some embodiments, c-Met inhibitor is MSC2156119J. MSC2156119J is an orally bioavailable inhibitor of c-Met. MSC2156119J selectively binds to c-MET, which inhibits c-MET phosphorylation and disrupts c-Met-mediated signal transduction pathways.

In some embodiments, the c-MET inhibitor is capmatinib. Capmatinib is also known as INCB028060. Capmatinib is an orally bioavailable inhibitor of c-MET. Capmatinib selectively binds to c-Met, thereby inhibiting c-Met phosphorylation and disrupting c-Met signal transduction pathways.

In some embodiments, the c-MET inhibitor is crizotinib. Crizotinib is also known as PF-02341066. Crizotinib is an orally available aminopyridine-based inhibitor of the receptor tyrosine kinase anaplastic lymphoma kinase (ALK) and the c-Met/hepatocyte growth factor receptor (HGFR). Crizotinib, in an ATP-competitive manner, binds to and inhibits ALK kinase and ALK fusion proteins. In addition, crizotinib inhibits c-Met kinase, and disrupts the c-Met signaling pathway. Altogether, this agent inhibits tumor cell growth.

In some embodiments, the c-MET inhibitor is golvatinib. Golvatinib is an orally bioavailable dual kinase inhibitor of c-MET and VEGFR-2 with potential antineoplastic activity.

Golvatinib binds to and inhibits the activities of both c-MET and VEGFR-2, which may inhibit tumor cell growth and survival of tumor cells that overexpress these receptor tyrosine kinases.

In some embodiments, the c-MET inhibitor is tivantinib. Tivantinib is also known as ARQ 197. Tivantinib is an orally bioavailable small molecule inhibitor of c-MET. Tivantinib binds to the c-MET protein and disrupts c-Met signal transduction pathways, which may induce cell death in tumor cells overexpressing c-MET protein or expressing consitutively activated c-Met protein.

Exemplary TGFb Inhibitors

In one embodiment, a combination described herein includes a transforming growth factor beta (TGF-β) inhibitor. In some embodiments, the combination is used to treat a cancer, e.g., a cancer described herein, e.g., a solid tumor (e.g., a brain cancer (e.g., a glioma), a melanoma, a kidney cancer (e.g., a renal cell carcinoma), a pleural malignant mesothelioma (e.g., a relapsed pleural malignant mesothelioma), or a breast cancer (e.g., a metastatic breast cancer)).

In some embodiments, the TGF-β inhibitor is fresolimumab (CAS Registry Number: 948564-73-6). Fresolimumab is also known as GC1008. Fresolimumab is a human monoclonal antibody that binds to and inhibits TGF-beta isoforms 1, 2 and 3.

```
The heavy chain of fresolimumab has
the amino acid sequence of:
                                  (SEQ ID NO: 294)
QVQLVQSGAEVKKPGSSVKVSCKASGYTFSSNVIS

WVRQAPGQGLEWMGGVIPIVDIANYAQRFKGRVTI

TADESTSTTYMELSSLRSEDTAVYYCASTLGLVLD

AMDYWGQGTLVTVSSASTKGPSVFPLAPCSRSTSE

STAALGCLVKDYFPEPVTVSWNSGALTSGVHTFPA

VLQSSGLYSLSSVVTVPSSSLGTKTYTCNVDHKPS

NTKVDKRVESKYGPPCPSCPAPEFLGGPSVFLFPP

KPKDTLMISRTPEVTCVVVDVSQEDPEVQFNWYVD

GVEVHNAKTKPREEQFNSTYRVVSVLTVLHQDWLN

GKEYKCKVSNKGLPSSIEKTISKAKGQPREPQVYT

LPPSQEEMTKNQVSLTCLVKGFYPSDIAVEWESNG

QPENNYKTTPPVLDSDGSFFLYSRLTVDKSRWQEG

NVFSCSVMHEALHNHYTQKSLSLSLGK.

The light chain of fresolimumab has
the amino acid sequence of:
                                  (SEQ ID NO: 295)
ETVLTQSPGTLSLSPGERATLSCRASQSLGSSYLA

WYQQKPGQAPRLLIYGASSRAPGlPDRFSGSGSGT

DFTLTISRLEPEDFAVYYCQQYADSPITFGQGTRL

EIKRTVAAPSVFIFPPSDEQLKSGTASVVCLLNNF

YPREAKVQWKVDNALQSGNSQESVTEQDSKDSTYS

LSSTLTLSKADYEKHKVYACEVTHQGLSSPVTKSF

NRGEC.
```

Fresolimumab is disclosed, e.g., in WO 2006/086469, U.S. Pat. Nos. 8,383,780, and 8,591,901.

In some embodiments, the TGF-β inhibitor is XOMA 089. XOMA 089 is also known as XPA.42.089. XOMA 089 is a fully human monoclonal antibody that specifically binds and neutralizes TGF-beta 1 and 2 ligands.

```
The heavy chain variable region of XOMA
089 has the amino acid sequence of:
                                  (SEQ 1D NO: 296)
QVQLVQSGAEVKKPGSSVKVSCKASGGTFSSYAIS

WVRQAPGQGLEWMGGIIPIFGTANYAQKFQGRVTI

TADESTSTAYMELSSLRSEDTAVYYCARGLWEVRA

LPSVYWGQGTLVTVSS

(disclosed as SEQ ID NO: 6
in WO 2012/167143).
The light chain variable region of XOMA
089 has the amino acid sequence of:
                                  (SEQ ID NO: 297)
SYELTQPPSVSVAPGQTARITCGANDIGSKSVHWY

QQKAGQAPVLVVSEDIIRPSGIPERISGSNSGNTA

TLTISRVEAGDEADYYCQVWDRDSDQYVFGTGTKV

TVLG
(disclosed as SEQ ID NO: 8
in WO 2012/167143).
```

Exemplary IDO/TDO Inhibitors

In one embodiment, a combination described herein includes an inhibitor of indoleamine 2,3-dioxygenase (IDO) and/or tryptophan 2,3-dioxygenase (TDO). In some embodiments, the combination is used to treat a cancer, e.g., a cancer described herein, e.g., a solid tumor (e.g., melanoma, non-small cell lung cancer, colon cancer, squamous cell head and neck cancer, ovarian cancer, peritoneal cancer, fallopian tube cancer, breast cancer (e.g., metastatic or HER2-negative breast cancer)), e.g., a hematologic malignancy (e.g., a lymphoma, e.g., a non-Hodgkin's lymphoma or a Hodgkin's lymphoma (e.g., a diffuse large B-cell lymphoma (DLBCL))).

In some embodiments, the IDO/TDO inhibitor is chosen from (4E)-4-[(3-chloro-4-fluoroanilino)-nitrosomethylidene]-1,2,5-oxadiazol-3-amine (also known as INCB24360), indoximod (1-methyl-D-tryptophan), or a-cyclohexyl-5H-Imidazo[5,1-a]isoindole-5-ethanol (also known as NLG919).

In some embodiments, the IDO/TDO inhibitor is epacadostat (CAS Registry Number: 1204669-58-8). Epacadostat is also known as INCB24360 or INCB024360 (Incyte). Epacadostat is a potent and selective indoleamine 2,3-dioxygenase (IDO1) inhibitor with IC50 of 10 nM, highly selective over other related enzymes such as IDO2 or tryptophan 2,3-dioxygenase (TDO).

In some embodiments, the IDO/TDO inhibitor is indoximod (New Link Genetics). Indoximod, the D isomer of 1-methyl-tryptophan, is an orally administered small-molecule indoleamine 2,3-dioxygenase (IDO) pathway inhibitor that disrupts the mechanisms by which tumors evade immune-mediated destruction.

In some embodiments, the IDO/TDO inhibitor is NLG919 (New Link Genetics). NLG919 is a potent IDO (indoleamine-(2,3)-dioxygenase) pathway inhibitor with Ki/EC50 of 7 nM/75 nM in cell-free assays.

In some embodiments, the IDO/TDO inhibitor is F001287 (Flexus/BMS). F001287 is a small molecule inhibitor of indoleamine 2,3-dioxygenase 1 (IDO1).

Exemplary A2AR Antagonists

In one embodiment, a combination described herein includes an adenosine A2a receptor (A2aR) antagonist (e.g., an inhibitor of A2aR pathway, e.g., an adenosine inhibitor, e.g., an inhibitor of A2aR or CD-73). In some embodiments, the combination is used to treat a cancer, e.g., a cancer described herein. In certain embodiments, the cancer is a lung cancer, e.g., a non-small cell lung cancer.

In some embodiments, the A2aR antagonist is istradefylline (CAS Registry Number: 155270-99-8). Istradefylline is also known as KW-6002 or 8-[(E)-2-(3,4-dimethoxyphenyl) vinyl]-1,3-diethyl-7-methyl-3,7-dihydro-1H-purine-2,6-dione. Istradefylline is disclosed, e.g., in LeWitt et al. (2008) *Annals of Neurology* 63 (3): 295-302).

In some embodiments, the A2aR antagonist is tozadenant (Biotie). Tozadenant is also known as SYN115 or 4-hydroxy-N-(4-methoxy-7-morpholin-4-yl-1,3-benzothiazol-2-yl)-4-methylpiperidine-1-carboxamide. Tozadenant blocks the effect of endogenous adenosine at the A2a receptors, resulting in the potentiation of the effect of dopamine at the D2 receptor and inhibition of the effect of glutamate at the mGluR5 receptor. In some embodiments, the A2aR antagonist is preladenant (CAS Registry Number: 377727-87-2). Preladenant is also known as SCH 420814 or 2-(2-Furanyl)-7-[2-[4-[4-(2-methoxyethoxy)phenyl]-1-piperazinyl]ethyl] 7H-pyrazolo[4,3-e][1,2,4]triazolo[1,5-c]pyrimidine-5-amine. Preladenant was developed as a drug that acted as a potent and selective antagonist at the adenosine A2A receptor.

In some embodiments, the A2aR antagonist is vipadenan. Vipadenan is also known as BIIB014, V2006, or 3-[(4-amino-3-methylphenyl)methyl]-7-(furan-2-yl)triazolo[4,5-d]pyrimidin-5-amine. e.g., In some embodiments, the A2aR antagonist is PBF-509 (Palobiofarma). e.g., In some embodiments, the A2aR antagonist, e.g., PBF-509 is administered at a daily dose of about 80 mg, 160 mg, or 240 mg.

Other exemplary A2aR antagonists include, e.g., ATL-444, MSX-3, SCH-58261, SCH-412,348, SCH-442,416, VER-6623, VER-6947, VER-7835, CGS-15943, or ZM-241,385.

In some embodiments, the A2aR antagonist is an A2aR pathway antagonist (e.g., a CD-73 inhibitor, e.g., an anti-CD73 antibody) is MEDI9447. MEDI9447 is a monoclonal antibody specific for CD73. Targeting the extracellular production of adenosine by CD73 may reduce the immunosuppressive effects of adenosine. MEDI9447 was reported to have a range of activities, e.g., inhibition of CD73 ecto-nucleotidase activity, relief from AMP-mediated lymphocyte suppression, and inhibition of syngeneic tumor growth. MEDI9447 can drive changes in both myeloid and lymphoid infiltrating leukocyte populations within the tumor microenvironment. These changes include, e.g., increases in CD8 effector cells and activated macrophages, as well as a reduction in the proportions of myeloid-derived suppressor cells (MDSC) and regulatory T lymphocytes.

Exemplary Oncolytic Viruses

In some embodiments, a combination as described herein includes an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sindbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)). In some embodiments, the combination is used to treat a cancer, e.g., a cancer described herein. In some embodiments, the cancer is a brain cancer, e.g., a glioblastoma.

In some embodiments, the oncolytic virus is a virus, e.g., recombinant oncolytic virus, described in US2010/0178684 A1, which is incorporated herein by reference in its entirety. In some embodiments, a recombinant oncolytic virus comprises, or comprises a nucleic acid sequence (e.g., heterologous nucleic acid sequence) encoding, an inhibitor of an immune or inflammatory response, e.g., as described in US2010/0178684 A1, incorporated herein by reference in its entirety. In embodiments, the recombinant oncolytic virus, e.g., oncolytic NDV, comprises, or comprises a nucleic acid sequence encoding, a pro-apoptotic protein (e.g., apoptin), a cytokine (e.g., GM-CSF, CSF, interferon-gamma, interleukin-2 (IL-2), tumor necrosis factor-alpha), an immunoglobulin (e.g., an antibody against ED-B firbonectin), a tumor associated antigen, a bispecific adapter protein (e.g., bispecific antibody or antibody fragment directed against NDV HN protein and a T cell co-stimulatory receptor, such as CD3 or CD28; or a fusion protein between human IL-2 and single chain antibody directed against NDV HN protein). See, e.g., Zamarin et al. Future Microbiol. 7.3(2012): 347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:

- Group B Oncolytic Adenovirus (ColoAd1) (PsiOxus Therapeutics Ltd.) (see, e.g., Clinical Trial Identifier: NCT02053220);
- ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);
- VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);
- Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759);
- Celyvir, which comprises bone marrow-derived autologous mesenchymal stem cells (MSCs) infected with ICOVIR5, an oncolytic adenovirus (Hospital Infantil Universitario Niño Jesus, Madrid, Spain/Ramon Alemany) (see, e.g., Clinical Trial Identifier: NCT01844661);
- CG0070, which is a conditionally replicating oncolytic serotype 5 adenovirus (Ad5) in which human E2F-1 promoter drives expression of the essential Ela viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intra-arterial, intravenous, intramuscular, intrathecal, or intraperitoneal injection. In embodiments, an oncolytic virus described herein is administered intratumorally, transdermally, transmucosally, orally, intranasally, or via pulmonary administration.

Exemplary Vaccines, e.g., Scaffold Vaccines

In one embodiment, a combination described herein includes a vaccine, e.g., a scaffold vaccine. In some embodiments, the combination is used to treat a cancer, e.g., a cancer described herein.

Cancer vaccines are disclosed, e.g., in PCT Publication Nos. WO 2007/070660 and WO 2012/167230, EP 1960009 B1, U.S. Pat. Nos. U.S. Pat. Nos. 8,067,237 and 8,932,583, and U.S. Publication No. US 2011/0020216. The components that can be used within cancer vaccines (e.g., implantable scaffold materials) are disclosed, e.g., in PCT Publication Nos. WO 2009/102465 and WO 2013/106852. Methods that can be used for administration of cancer vaccines are disclosed, e.g., in PCT Publication Nos. WO 2013/158673, WO 2012/048165, and WO 2012/149358.

In some embodiments, the cancer vaccine includes a macroporous scaffold comprising (i) cells or a cell recruitment composition, and (ii) a deployment signal capable of inducing or promoting migration of cells, and (iii) a bioactive composition coated or seeded onto/into the scaffold, which causes cells recruited into the scaffold be modified. Migration of the modified cells can be promoted by the open, interconnected macropores and the deployment signal.

In some embodiments, the cancer vaccine induces an endogenous immune response to a cancer target via administration of a porous scaffold bearing a recruitment composition and a target antigen composition, wherein an endogenous antigen presenting cell is recruited into the scaffold to encounter antigen and where said cell resides until a deployment signal induces egress to a lymph node tissue outside the scaffold, thereby stimulating an endogenous immune response to said cancer target.

In some embodiments, the cancer vaccine is used to remove a target cell from a mammal using a scaffold composition.

In some embodiments, an in situ cancer vaccine is generated via recruitment of cancer cells to an implanted scaffold and destruction of the cells using a cytotoxic agent.

In some embodiments, a cytosine-guanosine oligonucleotide (CpG-ODN) is used as a component of a scaffold, which can effectively reprogram and deploy dendritic cells recruited to the scaffold, and generate an effective anti-tumor response.

In some embodiments, polyinosine-polycytidylic acid (poly I:C) and/or CpG ODN are used to exert a synergistic effect on tumor inhibition.

In some embodiments, porous rods comprising an immune cell recruitment compound (e.g. GM-CSF) and an immune cell activation compound (e.g. CpG ODN), and optionally comprising an antigen such as a tumor lysate, are used, e.g., to elicit an immune response to a vaccine antigen. In some embodiments, pores that facilitate recruitment or release of cells are formed in situ within hydrogels following hydrogel injection. In some embodiments, injectable shape memory porous hydrogel polymer is used for administration.

In other embodiments, the combinations disclosed herein include a cancer or tumor vaccine. Non-limiting examples of tumor vaccines that can be used include peptides of melanoma antigens, such as peptides of gp100, MAGE antigens, Trp-2, MART1 and/or tyrosinase, tumor cells transfected to express the cytokine GM-CSF, DNA-based vaccines, RNA-based vaccines, and viral transduction-based vaccines. The cancer vaccine may be prophylactic or therapeutic.

Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., *Cancer Vaccines*, Ch. 61, pp. 3023-3043 in DeVita, V. et al. (eds.), 1997, *Cancer*: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

The combinations disclosed herein, e.g., LAG-3 blockade, can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (ie. bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV), Kaposi's Herpes Sarcoma Virus (KHSV), and Epstein-Barr virus (EBV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269: 1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000)

*Nature Medicine* 6:332-336). As a method of vaccination, DC immunization may be effectively combined with other agent, e.g., PD-1 blockade, to activate more potent anti-tumor responses.

Exemplary Bispecific T-Cell Engagers

In one embodiment, a combination described herein includes a bispecific T-cell engager. In some embodiments, the combination is used to treat a cancer, e.g., a cancer described herein, e.g., a solid tumor (e.g., a gastrointestinal cancer, a melanoma, or a lung cancer) or a hematologic malignancy (e.g., a lymphoma (e.g., non-Hodgkin's lymphoma) or a leukemia (e.g., an acute lymphoblastic leukemia).

Bi-specific T-cell engagers (BITE®) are a class of artificial bispecific monoclonal antibodies that can direct a host's immune system, e.g., the T cells' cytotoxic activity, against cancer cells. Bi-specific T-cell engagers can form a link between T cells and tumor cells, which causes T cells to exert cytotoxic activity on tumor cells by producing proteins like perforin and granzymes, independently of the presence of MHC I or co-stimulatory molecules. These proteins enter tumor cells and initiate the cell's apoptosis. This action mimics physiological processes observed during T cell attacks against tumor cells.

In some embodiments, the bi-specific T-cell engager is a fusion protein comprising two single-chain variable fragments (scFvs) of different antibodies. In some embodiments, one of the scFvs binds to T cells, e.g., via the CD3 receptor, and the other to a tumor cell, e.g., via a tumor specific molecule.

In some embodiments, the bi-specific T-cell engager is a bispecific antibody molecule of NKG2A and CD138, or a bispecific antibody molecule of CD3 and TCR. In some embodiments, the bispecific T-cell engager is a bispecific antibody molecule that binds to CD3 and a tumor antigen (e.g., EGFR, PSCA, PSMA, EpCAM, HER2 among others).

In some embodiments, the bi-specific T-cell engager is blinatumomab (CAS Registry Number: 853426-35-4). Blinatumomab is also known as MT103. Blinatumomab specifically targets a CD3 site for T cells and a CD19 site for B cells.

In some embodiments, the bi-specific T-cell engager is MT110. MT110 is a single-chain antibody that targets EpCAM and CD3. MT110 is disclosed, e.g., in Amann et al. J Immunother. 2009; 32(5):452-64.

In some embodiments, the bi-specific T-cell engager targets melanoma-associated chondroitin sulfate proteoglycan (MCSP). In some embodiments, the bi-specific T-cell engager targets CD33. In some embodiments the bi-specific T-cell engager comprises trastuzumab (targeting HER2/neu), cetuximab, or panitumumab (both targeting the EGF receptor), a functional fragment thereof. In some embodiments, the bi-specific T-cell engager targets CD66e and EphA2.

Exemplary GITR Agonist

In one embodiment, a combination described herein includes a GITR agonist. In some embodiments, the combination is used to treat a cancer, e.g., a cancer described herein, e.g., a solid tumor or a hematologic malignancy. In some embodiments, the cancer is a lung cancer (e.g., a non-small cell lung cancer), a head and neck cancer, or a FoxP3-expressing cancer.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 0920505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, U.S. Pat. No. 8,709,424, PCT Publication No.: WO 2013/039954, International Publication No.: WO2013/039954, U.S. Publication No.: US2014/0072566, International Publication No.: WO2015/026684, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, U.S. Pat. No. 6,689,607, PCT Publication No.: WO2006/083289, PCT Publication No.: WO 2005/115451, U.S. Pat. No. 7,618,632, PCT Publication No.: WO 2011/051726, International Publication No.: WO2004060319, and International Publication No.: WO2014/012479.

In one embodiment, the GITR agonist is used in combination with a PD-1 inhibitor, e.g., as described in WO2015/026684.

In another embodiment, the GITR agonist is used in combination with a TLR agonist, e.g., as described in WO2004/060319, and International Publication No.: WO2014/012479.

Exemplary PD-1 Inhibitors

PD-1 is a CD28/CTLA-4 family member expressed, e.g., on activated $CD4^+$ and $CD8^+$ T cells, $T_{regs}$, and B cells. It negatively regulates effector T cell signaling and function. PD-1 is induced on tumor-infiltrating T cells, and can result in functional exhaustion or dysfunction (Keir et al. (2008) *Annu. Rev. Immunol.* 26:677-704; Pardoll et al. (2012) *Nat Rev Cancer* 12(4):252-64). PD-1 delivers a coinhibitory signal upon binding to either of its two ligands, Programmed Death-Ligand 1 (PD-L1) or Programmed Death-Ligand 2 (PD-L2). PD-L1 is expressed on a number of cell types, including T cells, natural killer (NK) cells, macrophages, dendritic cells (DCs), B cells, epithelial cells, vascular endothelial cells, as well as many types of tumors. High expression of PD-L1 on murine and human tumors has been linked to poor clinical outcomes in a variety of cancers (Keir et al. (2008) *Annu. Rev. Immunol.* 26:677-704; Pardoll et al. (2012) *Nat Rev Cancer* 12(4):252-64). PD-L2 is expressed on dendritic cells, macrophages, and some tumors. Blockade of the PD-1 pathway has been pre-clinically and clinically validated for cancer immunotherapy. Both preclinical and clinical studies have demonstrated that anti-PD-1 blockade can restore activity of effector T cells and results in robust anti-tumor response. For example, blockade of PD-1 pathway can restore exhausted/dysfunctional effector T cell function (e.g., proliferation, IFN-γ secretion, or cytolytic function) and/or inhibit $T_{reg}$ cell function (Keir et al. (2008) *Annu. Rev. Immunol.* 26:677-704; Pardoll et al. (2012) *Nat Rev Cancer* 12(4):252-64). Blockade of the PD-1 pathway can be effected with an antibody, an antigen binding fragment thereof, an immunoadhesin, a fusion protein, or oligopeptide of PD-1, PD-L1 and/or PD-L2.

As used herein, the term "Programmed Death 1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) *Genomics* 23(3):704-6; Finger L R, et al. *Gene* (1997) 197(1-2):177-87.

In one embodiment, a combination described herein includes a PD-1 inhibitor. In some embodiments, the combination is used to treat a cancer, e.g., a cancer described herein, e.g., a solid tumor or a hematologic malignancy. In some embodiments, the cancer is chosen from a thyroid cancer (e.g., an anaplastic thyroid cancer), a renal cancer (e.g., a renal cell carcinoma), a skin cancer (e.g., a melanoma), a head and neck cancer, a brain cancer (e.g., a glioblastoma), a pancreatic cancer, a nasopharyngeal cancer, a colorectal cancer, a lung cancer (e.g., a non-small cell lung cancer), a breast cancer (e.g., a triple negative breast cancer), an endometrial cancer, a liver cancer (e.g., a hepatocellular carcinoma), a bladder cancer, an ovarian cancer, an MSI-high cancer, a FoxP3-expressing cancer, or a lymphoma.

Exemplary non-limiting combinations and uses of the anti-PD-1 antibody molecules are disclosed in U.S. Patent Application Publication No. 2015/0210769 (U.S. Ser. No. 14/604,415), entitled "Antibody Molecules to PD-1 and Uses Thereof," incorporated by reference in its entirety.

In one embodiment, the anti-PD-1 antibody molecule includes at least one or two heavy chain variable domain (optionally including a constant region), at least one or two light chain variable domain (optionally including a constant region), or both, comprising the amino acid sequence of BAP049-Clone-A, BAP049-Clone-B, BAP049-Clone-C, BAP049-Clone-D, or BAP049-Clone-E; or as described in Table 1 of US 2015/0210769, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-PD-1 antibody molecule, optionally, comprises a leader sequence from a heavy chain, a light chain, or both, as shown in Table 4 of US 2015/0210769; or a sequence substantially identical thereto.

In yet another embodiment, the anti-PD-1 antibody molecule includes at least one, two, or three complementarity determining regions (CDRs) from a heavy chain variable region and/or a light chain variable region of an antibody described herein, e.g., an antibody chosen from any of BAP049-hum01, BAP049-hum02, BAP049-hum03, BAP049-hum04, BAP049-hum05, BAP049-hum06, BAP049-hum07, BAP049-hum08, BAP049-hum09, BAP049-hum10, BAP049-hum11, BAP049-hum12, BAP049-hum13, BAP049-hum14, BAP049-hum15, BAP049-hum16, BAP049-Clone-A, BAP049-Clone-B, BAP049-Clone-C, BAP049-Clone-D, or BAP049-Clone-E; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-1 antibody molecule includes at least one, two, or three CDRs (or collectively all of the CDRs) from a heavy chain variable region comprising an amino acid sequence shown in Table 1 of US 2015/0210769, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-1 antibody molecule includes at least one, two, or three CDRs (or collectively all of the CDRs) from a light chain variable region comprising an amino acid sequence shown in Table 1 of US 2015/0210769, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-1 antibody molecule includes a substitution in a light chain CDR, e.g., one or more substitutions in a CDR1, CDR2 and/or CDR3 of the light chain. In one embodiment, the anti-PD-1 antibody molecule includes a substitution in the light chain CDR3 at position 102 of the light variable region, e.g., a substitution of a cysteine to tyrosine, or a cysteine to serine residue, at position 102 of the light variable region according to Table 1 (e.g., SEQ ID NO: 16 or 24 for murine or chimeric, unmodified; or any of SEQ ID NOs: 34, 42, 46, 54, 58, 62, 66, 70, 74, or 78 for a modified sequence).

In another embodiment, the anti-PD-1 antibody molecule includes at least one, two, three, four, five or six CDRs (or collectively all of the CDRs) from a heavy and light chain variable region comprising an amino acid sequence shown in Table 1 of US 2015/0210769, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-1 antibody molecule includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 33, each disclosed in Table 1 of US 2015/0210769;

(b) a VH comprising a VHCDR1 amino acid sequence chosen from SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each disclosed in Table 1 of US 2015/0210769;

(c) a VH comprising a VHCDR1 amino acid sequence of SEQ ID NO: 224, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 33, each disclosed in Table 1 of US 2015/0210769; or (d) a VH comprising a VHCDR1 amino acid sequence of SEQ ID NO: 224; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 32, each disclosed in Table 1 of US 2015/0210769.

In the combinations herein below, in another embodiment, the anti-PD-1 antibody molecule comprises (i) a heavy chain variable region (VH) comprising a VHCDR1 amino acid sequence chosen from SEQ ID NO: 1, SEQ ID NO: 4, or SEQ ID NO: 224; a VHCDR2 amino acid sequence of SEQ ID NO: 2 or SEQ ID NO: 5; and a VHCDR3 amino acid sequence of SEQ ID NO: 3; and (ii) a light chain variable region (VL) comprising a VLCDR1 amino acid sequence of SEQ ID NO: 10 or SEQ ID NO: 13, a VLCDR2 amino acid sequence of SEQ ID NO: 11 or SEQ ID NO: 14, and a VLCDR3 amino acid sequence of SEQ ID NO: 32 or SEQ ID NO: 33, each disclosed in Table 1 of US 2015/0210769.

In other embodiments, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is Nivolumab, and having a sequence disclosed herein (or a sequence substantially identical or similar thereto, e.g., a sequence at least 85%, 90%, 95% identical or higher to the sequence specified).

The heavy and light chain amino acid sequences of Nivolumab are as follows:

```
Heavy chain
                                  (SEQ ID NO: 298)
QVQLVESGGGVVQPGRSLRLDCKASGITFSNSGMH

WVRQAPGKGLEWVAVIWYDGSKRYYADSVKGRFTI

SRDNSKNTLFLQMNSLRAEDTAVYYCATNDDYWGQ

GTLVTVSSASTKGPSVFPLAPCSRSTSESTAALGC

LVKDYFPEPVTVSWNSGALTSGVHTFPAVLQSSGL

YSLSSVVTVPSSSLGTKTYTCNVDHKPSNTKVDKR
```

-continued

```
VESKYGPPCPPCPAPEFLGGPSVFLFPPKPKDTLM

ISRTPEVTCVVVDVSQEDPEVQFNWYVDGVEVHNA

KTKPREEQFNSTYRVVSVLTVLHQDWLNGKEYKCK

VSNKGLPSSIEKTISKAKGQPREPQVYTLPPSQEE

MTKNQVSLTCLVKGFYPSDIAVEWESNGQPENNYK

TTPPVLDSDGSFFLYSRLTVDKSRWQEGNVFSCSV

MHEALHNHYTQKSLSLSLGK

Light chain
                                  (SEQ ID NO: 299)
EIVLTQSPATLSLSPGERATLSCRASQSVSSYLAW

YQQKPGQAPRLLIYDASNRATGIPARFSGSGSGTD

FTLTISSLEPEDFAVYYCQQSSNWPRTFGQGTKVE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC
```

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. The heavy and light chain amino acid sequences of Pembrolizumab are as follows:

```
Heavy chain
                                                    (SEQ ID NO: 300)
QVQLVQSGVE VKKPGASVKV SCKASGYTFT NYYMYWVRQA PGQGLEWMGG  50

INPSNGGTNF NEKFKNRVTL TTDSSTTTAY MELKSLQFDD TAVYYCARRD 100

YRFDMGFDYW GQGTTVTVSS ASTKGPSVFP LAPCSRSTSE STAALGCLVK 150

DYFPEPVTVS WNSGALTSGV HTFPAVLQSS GLYSLSSVVT VPSSSLGTKT 200

YTCNVDHKPS NTKVDKRVES KYGPPCPPCP APEFLGGPSV FLFPPKPKDT 250

LMISRTPEVT CVVVDVSQED PEVQFNWYVD GVEVHNAKTK PREEQFNSTY 300

RVVSVLTVLH QDWLNGKEYK CKVSNKGLPS SIEKTISKAK GQPREPQVYT 350

LPPSQEEMTK NQVSLTCLVK GFYPSDIAVE WESNGQPENN YKTTPPVLDS 400

DGSFFLYSRL TVDKSRWQEG NVFSCSVMHE ALHNHYTQKS LSLSLGK    447

Ligh chain
                                                    (SEQ ID NO: 301)
EIVLTQSPAT LSLSPGERAT LSCRASKGVS TSGYSYLHWY QQKPGQAPRL  50

LIYLASYLES GVPARFSGSG SGTDFTLTIS SLEPEDFAVY YCQHSRDLPL 100

TFGGGTKVEI KRTVAAPSVF IFPPSDEQLK SGTASVVCLL NNFYPREAKV 150

QWKVDNALQS GNSQESVTEQ DSKDSTYSLS STLTLSKADY EKHKVYACEV 200

THQGLSSPVT KSFNRGEC                                    218
```

In one embodiment, the inhibitor of PD-1 is Pembrolizumab disclosed in, e.g., U.S. Pat. No. 8,354,509 and WO 2009/114335, and having a sequence disclosed herein (or a sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611.

Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342), is a PD-L2 Fc fusion soluble receptor that blocks the interaction between PD-1 and B7-H1.

Exemplary PD-L1 or PD-L2 Inhibitors

In one embodiment, a combination described herein includes a PD-L1 or PD-L2 inhibitor. In some embodiments, the combination is used to treat a cancer, e.g., a cancer described herein, e.g., a solid tumor or a hematologic malignancy. In some embodiments, the cancer is a thyroid cancer (e.g., an anaplastic thyroid cancer), a lung cancer (e.g., a non-small cell lung cancer), a breast cancer (e.g., a triple negative breast cancer), an endometrial cancer, an MSI-high cancer, or a lymphoma.

Exemplary non-limiting combinations and uses of the anti-PD-L1 antibody molecules are disclosed in U.S. Patent Application Publication No. 2016/0108123 (U.S. Ser. No. 14/881,888), entitled "Antibody Molecules to PD-L1 and Uses Thereof," incorporated by reference in its entirety.

In one embodiment, the anti-PD-L1 antibody molecule includes at least one or two heavy chain variable domain (optionally including a constant region), at least one or two light chain variable domain (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-0; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-PD-L1 antibody molecule includes:

(i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 2; and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 9, a VLCDR2 amino acid sequence of SEQ ID NO: 10, and a VLCDR3 amino acid sequence of SEQ ID NO: 11, each disclosed in Table 1 of US 2016/0108123.

In another embodiment, the anti-PD-L1 antibody molecule includes:

(i) a heavy chain variable region (VH) including a VHCDR1 amino acid sequence chosen from SEQ ID NO: 1, SEQ ID NO: 4 or SEQ ID NO: 195; a VHCDR2 amino acid sequence of SEQ ID NO: 5, and a VHCDR3 amino acid sequence of SEQ ID NO: 3, each disclosed in Table 1 of US 2016/0108123; and (ii) a light chain variable region (VL) including a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Table 1 of US 2016/0108123.

In one embodiment, the anti-PD-L1 antibody molecule comprises the VHCDR1 amino acid sequence of SEQ ID NO: 1. In another embodiment, the anti-PD-L1 antibody molecule comprises the VHCDR1 amino acid sequence of SEQ ID NO: 4. In yet another embodiment, the anti-PD-L1 antibody molecule comprises the VHCDR1 amino acid sequence of SEQ ID NO: 195, each disclosed in Table 1 of US 2016/0108123.

In some embodiments, the PD-L1 inhibitor is an antibody molecule. In some embodiments, the anti-PD-L1 inhibitor is chosen from YW243.55.570, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

```
Heavy chain
(SEQ ID NO: 24 as disclosed
in WO2013/079174)
                              (SEQ ID NO: 302)
EVQLLESGGGLVQPGGSLRLSCAASGFTESSYIM

MWVRQAPGKGLEWVSSTYPSGGITFYADKGRETI

SRDNSKNTLYLQMNSLRAEDTAVYYCARIKLGTV

TTVDYWGQGTLVTVSS

Light chain
(SEQ ID NO: 25 as disclosed
in WO2013/079174)
                              (SEQ ID NO: 303)
QSALTQPASVSGSPGQSITISCTGTSSDVGGYNY

VSWYQQHPGKAPKLMIYDVSNRPSGVSNRFSGSK

SGNTASLTISGLQAEDEADYYCSSYTSSSTRVEG

TGTKVTVL
```

In one embodiment, the PD-L1 inhibitor is YW243.55.570. The YW243.55.570 antibody is an anti-PD-L1 described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743, PCT Publication No. WO 2013/019906, and U.S. Publication No.: 20120039906. For example, MDPL3280A can include a heavy chain variable region comprising the amino acid sequence of SEQ ID NO:24, as disclosed in WO 2013/019906, and a light chain variable region comprising the amino acid sequence of SEQ ID NO: 21, as disclosed in WO 2013/019906 (or a sequence substantially identical or similar thereto, e.g., a sequence at least 85%, 90%, 95% identical or higher to the sequence specified).

In one embodiment, the PD-L1 inhibitor is MEDI-4736 (also known as durvalumab). MEDI-4736 is described in WO 2011/066389 and WO 2015/036499. For example, MEDI-4736 can include a light chain variable region comprising the amino acid sequence of SEQ ID NO: 1, as disclosed in WO 2015/036499, and a heavy chain variable region comprising the amino acid sequence of SEQ ID NO:2, as disclosed in WO 2015/036499 (or a sequence substantially identical or similar thereto, e.g., a sequence at least 85%, 90%, 95% identical or higher to the sequence specified).

In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO2010/027827 and WO2011/066342).

Exemplary TIM-3 Inhibitors

In one embodiment, a combination described herein includes a TIM-3 inhibitor. In some embodiments, the combination is used to treat a cancer, e.g., a cancer described herein, e.g., a solid tumor or a hematologic malignancy. In some embodiments, the cancer is a lung cancer (e.g., a non-small cell lung cancer), a skin cancer (e.g., a melanoma), or a renal cancer (e.g., a renal cell carcinoma).

In one embodiment, the anti-TIM-3 antibody or fragment thereof is an anti-TIM3 antibody molecule as described in U.S. Patent Application Publication No. 2015/0218274 (U.S. Ser. No. 14/610,837), entitled "Antibody Molecules to TIM-3 and Uses Thereof," incorporated by reference in its entirety.

In one embodiment, the anti-TIM-3 antibody molecule includes at least one or two heavy chain variable domain (optionally including a constant region), at least one or two light chain variable domain (optionally including a constant region), or both, comprising the amino acid sequence of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences. The anti-TIM-3 antibody molecule, optionally, comprises a leader sequence from a heavy chain, a light chain, or both, as shown in US 2015/0218274; or a sequence substantially identical thereto.

In yet another embodiment, the anti-TIM-3 antibody molecule includes at least one, two, or three complementarity determining regions (CDRs) from a heavy chain variable region and/or a light chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4 of US 2015/0218274; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In yet another embodiment, the anti-TIM-3 antibody molecule includes at least one, two, or three CDRs (or collectively all of the CDRs) from a heavy chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Table 1-4.

In yet another embodiment, the anti-TIM-3 antibody molecule includes at least one, two, or three CDRs (or collectively all of the CDRs) from a light chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Tables 1-4. In certain embodiments, the anti-TIM-3 antibody molecule includes a substitution in a light chain CDR, e.g., one or more substitutions in a CDR1, CDR2 and/or CDR3 of the light chain.

In another embodiment, the anti-TIM-3 antibody molecule includes at least one, two, three, four, five or six CDRs (or collectively all of the CDRs) from a heavy and light chain variable region comprising an amino acid sequence shown in Tables 1-4 of US 2015/0218274, or encoded by a nucleotide sequence shown in Tables 1-4. In one embodiment, one or more of the CDRs (or collectively all of the CDRs) have one, two, three, four, five, six or more changes, e.g., amino acid substitutions or deletions, relative to the amino acid sequence shown in Tables 1-4, or encoded by a nucleotide sequence shown in Tables 1-4.

In one embodiment, the anti-TIM-3 antibody molecule includes:

(a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274;

(b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274;

(c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274;

(d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274;

(e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14, each disclosed in Tables 1-4 of US 2015/0218274; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8, each disclosed in Tables 1-4 of US 2015/0218274.

Exemplary anti-TIM-3 antibodies are disclosed in U.S. Pat. No. 8,552,156, WO 2011/155607, EP 2581113 and U.S. Publication No.: 2014/044728.

Exemplary CTLA-4 Inhibitors

In one embodiment, a combination described herein includes a CTLA-4 inhibitor. In some embodiments, the combination is used to treat a cancer, e.g., a cancer described herein, e.g., a solid tumor or a hematologic malignancy.

Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Other exemplary anti-CTLA-4 antibodies are disclosed, e.g., in U.S. Pat. No. 5,811,097.

Exemplary IAP Inhibitors

In one embodiment, a combination described herein includes an inhibitor of Inhibitor of Apoptosis Protein (IAP). In some embodiments, the combination is used to treat a cancer, e.g., a cancer described herein, e.g., a solid tumor (e.g., a breast cancer (e.g., a triple negative breast cancer), an ovarian cancer, a lung cancer (e.g., a non-small cell lung cancer), a colorectal cancer, or a pancreatic cancer), e.g., a hematologic malignancy (e.g., a multiple myeloma).

In some embodiments, the IAP inhibitor is (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003.

In some embodiments, the IAP inhibitor, e.g., (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003, is administered at a dose of approximately 1800 mg, e.g., once weekly.

Exemplary EGFR Inhibitors

In one embodiment, a combination described herein includes an inhibitor of Epidermal Growth Factor Receptor (EGFR). In some embodiments, the combination is used to treat a cancer, e.g., a cancer described herein, e.g., a solid tumor (e.g., a lung cancer (e.g., a non-small cell lung cancer), a pancreatic cancer, a breast cancer (e.g., a triple negative breast cancer), or a colon cancer).

In some embodiments, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757.

In some embodiments, the EGFR inhibitor, e.g., (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757, is administered at a dose of 150-250 mg, e.g., per day. In some embodiments, the EGFR inhibitor, e.g., (R,E)-N-(7-chloro-1-(1-(4-(dimethylamino) but-2-enoyl)azepan-3-yl)-1H-benzo[d]imidazol-2-yl)-2-methylisonicotinamide (Compound A40) or a compound disclosed in PCT Publication No. WO 2013/184757, is administered at a dose of about 150, 200, or 250 mg, or about 150-200 or 200-250 mg.

In some embodiments, the EGFR inhibitor is chosen from one of more of erlotinib, gefitinib, cetuximab, panitumumab, necitumumab, PF-00299804, nimotuzumab, or R05083945.

Exemplary mTOR Inhibitors

In one embodiment, a combination described herein includes an inhibitor of target of rapamycin (mTOR). In some embodiments, the combination is used to treat a cancer, e.g., a cancer described herein, e.g., a solid tumor (e.g., a prostate cancer, a breast cancer (e.g., a triple negative breast cancer), a brain cancer, a bladder cancer, a pancreatic cancer, a renal cancer, a liver cancer, a lung cancer (e.g., a small cell lung cancer or a non-small cell lung cancer), a respiratory/thoracic cancer, a sarcoma, a bone cancer, an endocrine cancer, an astrocytoma, a cervical cancer, a neurologic cancer, a colorectal cancer, a gastric cancer, or a melanoma), e.g., a hematologic malignancy (e.g., a leukemia (e.g., lymphocytic leukemia), e.g., a lymphoma, or e.g., a multiple myeloma).

In some embodiments, the mTOR inhibitor is dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806.

In some embodiments, the mTOR inhibitor is everolimus (also known as AFINITOR®; Compound A36) or a compound disclosed in PCT Publication No. WO 2014/085318.

In some embodiments, the mTOR inhibitor, e.g., everolimus (Compound A36) or a compound disclosed in PCT Publication No. WO 2014/085318, is administered at a dose of about 2.5-20 mg/day. In one embodiment, the TOR inhibitor, e.g., everolimus (Compound A36) or a compound disclosed in PCT Publication No. WO 2014/085318, is administered at a dose of about 2.5, 5, 10, or 20 mg/day, e.g., about 2.5-5, 5-10, or 10-20 mg/day.

In some embodiments, the mTOR inhibitor is chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587.

ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.04,9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (AFINITOR® or RAD001); rapamycin (AY22989, SIROLIMUS®); simapimod (CAS Registry Number: 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS Registry Number: 1013101-36-4); N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine inner salt (SEQ ID NO: 304) (SF1126, CAS Registry Number: 936487-67-1), or XL765 (SAR245409).

Other exemplary mTOR Inhibitors include, but are not limited to, temsirolimus; ridaforolimus (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.$0^{4,9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl] pyrido[2,3-d]pyrimidin-7-yl}-2-methoxyphenyl)methanol (AZD8055); 2-mmino-8-[trans-4-(2-hydroxyethoxy)cyclohexyl]-6-(6-methoxy-3-pyridinyl)-4-methyl-pyrido[2,3-d] pyrimidin-7(8H)-one (PF04691502); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 304), inner salt (SF1126); and XL765.

Exemplary IL-15 Agonists

In one embodiment, a combination described herein includes an interleukin-15 (IL-15) agonist. In some embodiments, the combination is used to treat a cancer, e.g., a cancer described herein, e.g., a solid tumor (e.g., a refractory solid tumor), (e.g., a melanoma (e.g., a metastatic or advanced melanoma), a kidney cancer (e.g., a renal cell cancer), a non-small cell lung cancer, a squamous cell head and neck cancer, or a bladder cancer (e.g., a non-muscle invasive bladder cancer)), e.g., a hematologic malignancy (e.g., a leukemia, e.g., an acute myelogenous leukemia (e.g., a refractory or relapsed acute myelogenous leukemia), e.g., a lymphoma, e.g., a non-Hodgkin lymphoma (e.g., a relapsed/refractory indolent B cell non-Hodgkin lymphoma), e.g., or a multiple myeloma (e.g., a relapsed or refractory multiple myeloma)).

IL-15, secreted by mononuclear phagocytes (and some other cell types) following viral infection, regulates T and natural killer cell activation and proliferation. This cytokine induces activation of transcription activators STAT3, STATS, and STAT6 via JAK kinase signal transduction pathways in mast cells, T cells, and dendritic epidermal T cells. IL-15 and interleukin-2 (IL-2) are structurally similar and share many biological activities; both may bind to common hematopoietin receptor subunits, negatively regulating each other's activity. CD8+ memory T cell number can be regulated by a balance between IL-15 and IL-2.

In some embodiments, the IL-15 agonist is a recombinant human IL-15 (rhIL-15), e.g., CYP0150 (Cytune). CYP0150 is a recombinant protein consisting of a human IL-15 linked to the Sushi+ domain of the human alpha chain receptor (transpresentation).

CYP0150 is disclosed, e.g., in PCT Publication No. WO 2007/046006. CYP0150 has the amino acid sequence of:

```
                                  (SEQ ID NO: 305)
MAPRRARGCRTLGLPALLLLLLLRPPATRGDYKDD
DDKIEGRITCPPPMSVEHADIWVKSYSLYSRERYI
CNSGFKRKAGTSSLTECVLNKATNVAHWTTPSLKC
IRDPALVHQRPAPPSGGSGGGGSGGGSGGGGSLQN
WVNVISDLKKIEDLIQSMHIDATLYTESDVHPSCK
VTAMKCFLLELQVISLESGDASIHDTVENLIILAN
NSLSSNGNVTESGCKECEELEEKNIKEFLQSFVHI
VQMFINTS
(disclosed as SEQ ID NO: 60
in WO 2007/046006)
or
                                  (SEQ ID NO: 306)
MDSKGSSQKAGSRLLLLLVVSNLLLCQGVVSTTRD
YKDDDDKIEGRNWVNVISDLKKIEDLIQSMHIDAT
LYTESDVHPSCKVTAMKCFLLELQVISLESGDASI
HDTVENLIILANNSLSSNGNVTESGCKECEELEEK
NIKEFLQSFVHIVQMFINTSSGGGSGGGGSGGGGS
GGGGSGGGSLQITCPPPMSVEHADIWVKSYSLYSR
ERYICNSGFKRKAGTSSLTECVLNKATNVAHWTTP
SLKCIRDPALVHQRPAPP
(disclosed as SEQ ID NO: 62 in WO
2007/046006).
```

In some embodiments, the IL-15 agonist is ALT-803 (Altor BioScience). ALT-803 is an IL-15N72D:IL-15RαSu/Fc soluble complex, produced from a high-yield recombinant mammalian cell line that co-expresses IL-15N72D and IL-15RαSu/Fc fusion protein. The IL-15 mutant (N72D) has enhanced IL-15 biological activity (Zhu et al. 2009, *J Immunol.* 183:3598). The IL-15N72D mutant and the soluble domain of IL-15Ra can form stable heterodimeric complexes in solution and this complex exhibits increased biological activity (approximately 25-fold more active) compared to the non-complexed IL-15. ALT-803 is disclosed, e.g., in PCT Publication No. WO 2012/040323 and U.S. Pat. No. 8,507,222.

In some embodiments, the IL-15 agonist is hetIL-15 (Admune). HetIL-15 is a heterodimeric human IL-15 (IL-15/sIL-15Ra). HetIL-15 is disclosed, e.g., in PCT Publication Nos. WO 2009/002562 and WO 2014/066527.

Exemplary CD40 Agonists

In one embodiment, the combination includes a CD40 agonist. In some embodiments, the combination is used to treat a cancer, e.g., a cancer described herein, e.g., a solid tumor (e.g., a lung cancer, an esophageal carcinoma, a melanoma, or a renal cell carcinoma), e.g., a hematologic malignancy (e.g., a leukemia (e.g., a chronic lymphocytic leukemia (CLL)), e.g., a lymphoma (e.g., a non-Hodgkin's lymphoma), e.g., or a multiple myeloma).

In one embodiment, the CD40 agonist is ADC-1013 (Alligator/BioInvent). ADC-1013 is a fully human IgG agonistic monoclonal antibody against human CD40. CD40, an integral membrane protein found on the surface of B lymphocytes, is a member of the tumor necrosis factor receptor superfamily and is highly expressed in a number of cancers such as B-cell malignancies. CD40 agonists, e.g., anti-CD40 antibodies, are able to substitute effectively for T cell helper activity (Ridge, J. et al. (1998) Nature 393: 474-478).

ADC-1013 is disclosed, e.g., in PCT Publication No. WO 2015/091853. ADC-1013 clones include, e.g., 1136/1137, 1132/1133, 1148/1149, 1140/1135, 1134/1135, 1107/1108, 1142/1135, 1146/1147, and 1150/1151.

```
The heavy chain variable region of 1132/1133 has
the amino acid sequence of:
EVQLLESGGGLVQPGGSLRLSCAASGFTFSSYAMSWVRQAPGKGLEWVSGI
GSYGGGTYYADSVKGRFTISRDNSKNTLYLQMNSLRAEDTAVYYCARYVNF
GMDYWGQGTLVTVSS (SEQ ID NO: 307) (disclosed as SEQ
ID NO: 65 in WO 2015/091853).

The light chain variable region of 1132/1133 has
the amino acid sequence of:
DIQMTQSPSSLSASVGDRVTITCRASQSISSYLNWYQQKPGKAPKLLIYAA
SSLQSGVPSRFSGSGSGTDFTLTISSLQPEDFATYYCQQYGRNPPTFGQGT
KLEIK (SEQ ID NO: 308) (disclosed as SEQ ID NO: 66
in WO 2015/091853).
```

The heavy chain CDR1 of 1132/1133 has the amino acid sequence of: GFTFSSYA (SEQ ID NO: 309) (disclosed as SEQ ID NO: 13 in WO 2015/091853). The heavy chain CDR2 of 1132/1133 has the amino acid sequence of: IGSYGGGT (SEQ ID NO: 310) (disclosed as SEQ ID NO: 14 in WO 2015/091853). The heavy chain CDR3 of 1132/1133 has the amino acid sequence of: ARYVNFGMDY (SEQ ID NO: 311) (disclosed as SEQ ID NO: 15 in WO 2015/091853). The light chain CDR1 of 1132/1133 has the amino acid sequence of: QSISSY (SEQ ID NO: 312) (disclosed as SEQ ID NO: 16 in WO 2015/091853). The light chain CDR2 of 1132/1133 has the amino acid sequence of: AAS (SEQ ID NO: 313) (disclosed as SEQ ID NO: 17 in WO 2015/091853). The light chain CDR3 of 1132/1133 has the amino acid sequence of: QQYGRNPPT (SEQ ID NO: 314) (disclosed as SEQ ID NO: 18 in WO 2015/091853).

```
The heavy chain variable region of 1107/1108 has
the amino acid sequence of:
EVQLLESGGGLVQPGGSLRLSCAASGFTFSSYAMSWVRQAPGKGLEWVSAI
SGSGGSTYYADSVKGRFTISRDNSKNTLYLQMNSLRAEDTAVYYCARRVWG
FDYWGQGTLVTVSS (SEQ ID NO: 315) (disclosed as SEQ
ID NO: 79 in WO 2015/091853).

The light chain variable region of 1107/1108 has
the amino acid sequence of:
DIQMTQSPSSLSASVGDRVTITCRASQSISSYLNWYQQKPGKAPKLLIYAA
SSLQSGVPSRFSGSGSGTDFTLTISSLQPEDFATYYCQQYGVYPFTFGQGT
KLEIK (SEQ ID NO: 316) (disclosed as SEQ ID NO: 80
in WO 2015/091853).
```

The heavy chain CDR1 of 1107/1108 has the amino acid sequence of: GFTFSSYA (SEQ ID NO: 309) (disclosed as SEQ ID NO: 55 in WO 2015/091853). The heavy chain CDR2 of 1107/1108 has the amino acid sequence of: ISGSGGST (SEQ ID NO: 317) (disclosed as SEQ ID NO: 56 in WO 2015/091853). The heavy chain CDR3 of 1107/1108 has the amino acid sequence of: ARRVWGFDY (SEQ ID NO: 318) (disclosed as SEQ ID NO: 57 in WO 2015/091853). The light chain CDR1 of 1107/1108 has the amino acid sequence of: QSISSY (SEQ ID NO: 312) (disclosed as SEQ ID NO: 58 in WO 2015/091853). The light chain CDR2 of 1107/1108 has the amino acid sequence of: AAS (SEQ ID NO: 313) (disclosed as SEQ ID NO: 59 in WO 2015/091853). The light chain CDR3 of 1107/1108 has the amino acid sequence of: QQYGVYPFT (SEQ ID NO: 319) (disclosed as SEQ ID NO: 60 in WO 2015/091853).

In some embodiments, the CD40 agonist is ISF35. ISF35 is a chimeric CD154. ISF is disclosed in PCT Publication Nos. WO 2003/099340 and WO 2008/070743.

In some embodiments, the CD40 agonist is dacetuzumab. Dacetuzumab is also known as SGN-40 or huS2C6. Dacetuzumab is a humanized monoclonal antibody that targets CD40. Dacetuzumab is disclosed, e.g., in Advani et al. *J Clin Oncol.* 2009; 27(26):4371-7; and Khubchandani et al. *Curr Opin Investig Drugs.* 2009; 10(6):579-87.

In some embodiments, the CD40 agonist is lucatumumab (CAS Registry Number: 903512-50-5). Lucatumumab is also known as CHIR-12.12 or HCD-122. Lucatumumab binds to and inhibits CD40, thereby inhibiting CD40 ligand-induced cell proliferation and triggering cell lysis via antibody-dependent cellular cytotoxicity (ADCC) in cells overexpressing CD40. Lucatumumab is disclosed, e.g., in Tai et al. *Cancer Res.* 2005; 65(13):5898-906.

Anti-CD40 antibodies are able to substitute effectively for T cell helper activity (Ridge, J. et al. (1998) Nature 393: 474-478) and can be used in conjunction with PD-1 antibodies (Ito, N. et al. (2000) Immunobiology 201 (5) 527-40).

Exemplary OX40 Agonists

In one embodiment, a combination described herein includes an OX40 agonist. In some embodiments, the combination is used to treat a cancer, e.g., a cancer described herein, e.g., a solid tumor (e.g., a breast cancer, a melanoma, a head and neck cancer, or a prostate cancer), e.g., a hematologic malignancy (e.g., a lymphoma (e.g., a B-cell lymphoma)).

OX40, also known as CD134, is a cell surface glycoprotein and member of the tumor necrosis factor (TNF) receptor superfamily, is expressed on T-lymphocytes and provides a co-stimulatory signal for the proliferation and survival of activated T-cells. OX40 activation can induce proliferation of effector T-lymphocytes, which promotes an immune response against the tumor cells that express tumor-associated antigens (TAAs).

In some embodiments, the OX40 agonist is chosen from mAb 106-222, humanized 106-222 (Hu106), mAb 119-122, or humanized 119-122 (Hu119).

MAb 106-222, humanized 106-222 (Hu106), mAb 119-122, and humanized 119-122 (Hu119) are disclosed, e.g., in PCT Publication No. WO 2012/027328 and U.S. Pat. No. 9,006,399. The amino acid sequence of the heavy chain variable region of mAb 106-222 is disclosed as SEQ ID NO: 4 in WO 2012/027328. The amino acid sequence of the light chain variable region of mAb 106-222 is disclosed as SEQ ID NO: 10 in WO 2012/027328. The amino acid sequence of the heavy chain variable region of humanized 106-222 (Hu106) is disclosed as SEQ ID NO: 5 in WO 2012/027328. The amino acid sequence of the light chain variable region of humanized 106-222 (Hu106) is disclosed as SEQ ID NO: 11 in WO 2012/027328. The amino acid sequence of the heavy chain variable region of mAb 119-122 is disclosed as SEQ ID NO: 16 in WO 2012/027328. The amino acid sequence of the light chain variable region of mAb 119-122 is disclosed as SEQ ID NO: 22 in WO 2012/027328. The amino acid sequence of the heavy chain variable region of humanized 119-122 (Hu119) is disclosed as SEQ ID NO: 17 in WO 2012/027328. The amino acid sequence of the light chain variable region of humanized 119-122 (Hu119) is disclosed as SEQ ID NO: 23 in WO 2012/027328.

In some embodiments, the OX40 agonist is a humanized monoclonal antibody disclosed in U.S. Pat. No. 7,959,925 and PCT Publication No. WO 2006/121810.

In some embodiments, the OX40 agonist is chosen from MEDI6469, MEDI0562, or MEDI6383. MEDI6469 is a murine monoclonal antibody against OX40. MEDI0562 is a humanized monoclonal antibody against OX40. MEDI6383 is a monoclonal antibody against OX40.

In some embodiments, the OX40 agonist, e.g., MEDI6469, is administered intravenously at a dose of approximately 0.4 mg/kg, e.g., every other day.

Other exemplary anti-OX-40 antibodies are disclosed, e.g., in Weinberg, A. et al. (2000) *Immunol* 164: 2160-2169).

Exemplary CD27 Agonists

In one embodiment, a combination described herein includes a CD27 agonist. In some embodiments, the combination is used to treat a cancer, e.g., a cancer described herein, e.g., a solid tumor (e.g., a melanoma, a renal cell carcinoma, a hormone-refractory prostate adenocarcinoma, an ovarian cancer, a breast cancer, a colorectal adenocarcinoma, or a non-small cell lung cancer), e.g., a hematologic malignancy (e.g., a lymphoma (e.g., a Hodgkin's lymphoma, a Burkett's lymphoma, a mantle cell lymphoma, a primary lymphoma of the central nervous system, or a marginal zone B-cell lymphoma), or a leukemia (e.g., a chronic lymphocytic leukemia (CLL)).

In one embodiment, the CD27 agonist is Varlilumab (CAS Registry Number: 1393344-72-3). Varlilumab is also known as CDX-1127 (Celldex) or 1F5. Varlilumab is a fully human monoclonal antibody (mAb) that targets CD27, molecule in the activation pathway of lymphocytes. CDX-1127 is an agonist anti-CD27 mAb that can activate human T cells in the context of T cell receptor stimulation and therefore mediate anti-tumor effects. CDX-1127 can also provide direct therapeutic effects against tumors with CD27 expression.

Varlilumab is disclosed, e.g., in Vitale et al., *Clin Cancer Res.* 2012; 18(14):3812-21, WO 2008/051424, and U.S. Pat. No. 8,481,029.

In one embodiment, the CD27 agonist is BION-1402 (BioNovion). BION-1402 is also known as hCD27.15. BION-1402 is an anti-human CD27 monoclonal antibody. BION-1402 can stimulate the proliferation and/or survival of CD27+ cells. BION-1402 can activate human CD27 more effectively than its ligand CD70, which results in a significantly increased effect on proliferation of CD8+ and CD4+ T-cells.

BION-1402 is disclosed, e.g., as hCD27.15 in WO 2012/004367. This antibody is produced by hybridoma hCD27.15, which was deposited with the ATCC in on Jun. 2, 2010 under number PTA-11008. The heavy chain variable region of hCD27.15 has the amino acid sequence of: EVRLQQSGADLVKPGASVKLSCASGFIIKATYMHWVRQRPEQGLEWIGRIDPANGE KY DPKFQVKAITADTSSSTAYLQLNSLTSDDTAVYYCARYAWYFDVWGAGTTVTVSSAKT TPPXVYPXXPGS (SEQ ID NO: 320) (disclosed as SEQ ID NO: 3 in WO 2012/004367). The light chain variable region of hCD27.15 has the amino acid sequence of: DIQMTQSPASLSASVGDTVTITCRASENIYSFLAWYHQKQGRSPQLLVYHAKTLAEGVP SRFSGSGSGTQFSLKINSLQAEDFGSYYCQHYYGSPLTFGAGTKLEVKRADAAPTVSIFP PSSEELSL (SEQ ID NO: 321) (disclosed as SEQ ID NO: 4 in WO 2012/004367). The heavy chain CDR1 of hCD27.15 has the amino acid sequence of: GFIIKATYMH (SEQ ID NO: 322) (disclosed as SEQ ID NO: 5 in WO 2012/004367). The heavy chain CDR2 of hCD27.15 has the amino acid sequence of: RIDPANGETKYDPKFQV (SEQ ID NO: 323) (disclosed as SEQ ID NO: 6 in WO 2012/004367). The heavy chain CDR3 of hCD27.15 has the amino acid sequence of: YAWYFDV (SEQ ID NO: 324) (disclosed as SEQ ID NO: 7 in WO 2012/004367). The light chain CDR1 of hCD27.15 has the amino acid sequence of: RASENIYSFLA (SEQ ID NO: 325) (disclosed as SEQ ID NO: 8 in WO 2012/004367). The light chain CDR2 of hCD27.15 has the amino acid sequence of: HAKTLAE (SEQ ID NO: 326) (disclosed as SEQ ID NO: 9 in WO 2012/004367). The light chain CDR3 of hCD27.15 has the amino acid sequence of: QHYYGSPLT (SEQ ID NO: 327) (disclosed as SEQ ID NO: 10 in WO 2012/004367).

Exemplary LAG-3 Inhibitors

The immune system has the capability of recognizing and eliminating tumor cells; however, tumors can use multiple strategies to evade immunity. Blockade of immune checkpoints is one of the approaches to activating or reactivating therapeutic antitumor immunity. Lymphocyte Activation Gene-3 (LAG-3) has been described as an inhibitory receptor in the immunological synapse (Chen and Flies (2013) *Nat Rev Immunol.* 13(4):227-42). Thus, blocking of LAG-3 can lead to enhancement of antitumor immunity.

Several cell types express LAG-3. For example, LAG-3 is expressed on activated $CD4^+$ and $CD8^+$ T cells, $T_{reg}$ cells, natural killer (NK) cells, and plasmacytoid dendritic cells (DCs). LAG-3 is expressed in tumor-infiltrating lymphocytes, e.g., infiltrating lymphocytes in head and neck squamous cell carcinoma (HNSCC). LAG-3 is expressed on highly suppressive induced and natural Tregs. For example, highly suppressive FoxP3+ nTregs and FoxP3-iTregs are LAG-3 positive in melanoma and colorectal cancer (Camisaschi et al. (2010) J. Immunol. 184(11):6545-6551; Scurr et al. (2014) *Mucosal. Immunol.* 7(2):428-439).

LAG-3 negatively regulates T cell signaling and functions. Ligands for LAG-3 includes, e.g., MHC Class II and L-SECtin. Anti-LSECtin has been shown to inhibit B16 melanoma cell growth (Xu et al. (2014) *Cancer Res.* 74(13): 3418-3428). Blockade of LAG-3 can restore activities of effector cells, dimish suppressor activity of $T_{regs}$, and/or enhance anti-PD-1 antitumor activity.

LAG-3 is typically though not exclusively co-expressed on $PD\text{-}1^+$ cells and single blockade can restore in vitro activities of the cells. The degree of $CD8^+$ T cell exhaustion, e.g., as shown by the percentages of dual IFN-γ/TNF-α producers, correlates with the number of inhibitory receptors expressed (Blackburn et al. (2009) Nat. Immunol. 10(1): 29-37). High PD-1/LAG-3 expression correlates with T cell infiltration in melanoma. Co-blockade of LAG-3 with anti-PD-1 or PD-L1 can result in tumor suppressive activities in preclinical models. For example, anti-LAG-3 and anti-PD-1 blockade show efficacy in Sa1N fibrosarcoma and MC38 colon carcinoma models (Woo et al. (2012) *Cancer Res.* 72(4):917-27).

LAG-3 blockade is also efficacious in a lymphocytic choriomeningitis virus (LCMV) model. For example, PD-L1 plus LAG-3 blockade during chronic LCMV infection enhances antiviral CD8+ T cell responses (Blackburn et al. (2009) Nat. Immunol. 10(1): 29-37).

The term "Lymphocyte Activation Gene-3" or "LAG-3" include all isoforms, mammalian, e.g., human LAG-3, species homologs of human LAG-3, and analogs comprising at least one common epitope with LAG-3. The amino acid and nucleotide sequences of LAG-3, e.g., human LAG-3, is known in the art, e.g., Triebel et al. (1990) J. Exp. Med. 171:1393-1405.

In certain embodiments, the combinations described herein include a LAG-3 inhibitor, e.g., an anti-LAG-3 antibody molecule (e.g., humanized antibody molecules) as described herein. In some embodiments, the combination is used to treat a cancer, e.g., a cancer described herein, e.g., a solid tumor or a hematologic malignancy. In some embodiments, the cancer is a lung cancer (e.g., a non-small cell lung cancer), a skin cancer (e.g., a melanoma), or a renal cancer (e.g., a renal cell carcinoma).

In some embodiments, the LAG-3 antibody molecule (e.g., an isolated or recombinant antibody molecule) has one or more of the following properties:

(i) binds to LAG-3, e.g., human LAG-3, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger;

(ii) binds to LAG-3, e.g., a LAG-3-CHO transfectant, with a $K_D$ of less than: 5 nM, 4 nM, 3 nM, 2 nM, 1 nM, e.g., 1 to 3 nM (e.g., about 1.92 nM or about 2.3 nM);

(iii) does not substantially bind to CD4;

(iv) inhibits binding of LAG-3 to a major histocompatibility (MHC) class II molecule, e.g., shows an $IC_{50}$ of about 1 to 20 nM, 5 to 15 nM, e.g., 5.5 nM;

(v) binds to the D1 domain of LAG-3 (e.g., human LAG-3), e.g., binds to the D1 domain, but does not bind to the extra loop region of the D1 domain;

(vi) modulates (e.g., stimulates, enhances, or restores) an immune response, e.g., an antigen-specific T cell response or anti-tumor response;

(vii) binds specifically to an epitope on LAG-3, e.g., the same or similar epitope as the epitope recognized by murine monoclonal antibody BAP050 or chimeric antibody BAP050-chi;

(viii) binds to a different epitope on LAG-3 than the one recognized by antibody BMS-986016;

(ix) shows the same or similar binding affinity or specificity, or both, as any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J.

(x) shows the same or similar binding affinity or specificity, or both, as an antibody molecule (e.g., an heavy chain variable region and light chain variable region) described in Table 1;

(xi) shows the same or similar binding affinity or specificity, or both, as an antibody molecule (e.g., an heavy chain variable region and light chain variable region) having an amino acid sequence shown in Table 1;

(xii) shows the same or similar binding affinity or specificity, or both, as an antibody molecule (e.g., an heavy chain variable region and light chain variable region) encoded by the nucleotide sequence shown in Table 1;

(xiii) inhibits, e.g., competitively inhibits, the binding of a second antibody molecule to LAG-3, wherein the second antibody molecule is an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J;

(xiv) binds the same or an overlapping epitope with a second antibody molecule to LAG-3, wherein the second antibody molecule is an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J;

(xv) competes for binding, and/or binds the same epitope, with a second antibody molecule to LAG-3, e.g., as measured by a Biacore method, a FACS method, or both, wherein the second antibody molecule is an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J;

(xvi) has one or more biological properties of an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J;

(xvii) has one or more pharmacokinetic properties of an antibody molecule described herein, e.g., an antibody molecule chosen from, e.g., any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or (xviii) inhibits one or more activities of LAG-3, e.g., results in one or more of: an increase in antigen-dependent stimulation of $CD4^+$ T lymphocytes; an increase in T cell proliferation; an increase in expression of an activation antigen, e.g., CD25; an increase in expression of a cytokine, e.g., interferon-gamma (IFN-γ), interleukin-2 (IL-2), or interleukin-4 (IL-4); an increase in expression of a chemokine, e.g., CCL3, CCL4, or CCL5; a decrease in the suppressor activity of $T_{reg}$ cells; an increase in T cell homeostasis; an increase in tumor infiltrating lymphocytes; or a decrease in immune evasion by the cancerous cells.

As used herein, "huBAP050(Ser)" refers to a humanized BAP050 antibody molecule, e.g., any of the humanized BAP050 antibody molecule described herein, e.g., as described in Table 1, that has a Cys to Ser substitution at position 84 of the heavy chain framework region 3 (VHFW3). In some embodiments, the huBAP050(Ser) antibody molecule is chosen from BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser.

In some embodiments, the anti-LAG-3 antibody molecule binds to LAG-3 with high affinity, e.g., with a dissociation equilibrium constant ($K_D$) that is about the same, or at least about 10%, 20%, 30%, 40%, 50%, 60%, 70%, 80% or 90% higher or lower than the $K_D$ of a murine or chimeric anti-LAG-3 antibody molecule, e.g., a murine or chimeric anti-LAG-3 antibody molecule described herein. In one embodiment, the anti-LAG-3 antibody molecule binds to LAG-3, e.g., a LAG-3-CHO transfectant, with a $K_D$ of less than: 5 nM, 4 nM, 3 nM, 2 nM, e.g., 1 to 3 nM (e.g., about 1.92 nM or about 2.3 nM).

In some embodiments, the expression level of the anti-LAG-3 antibody molecule is about the same, higher or lower, e.g., at least about 0.5, 1, 2, 3, 4, 5, 6, 7, 8, 9 or 10-fold higher or lower, than the expression level of a murine or chimeric antibody molecule, e.g., a murine or chimeric anti-LAG-3 antibody molecule described herein. In some embodiments, the antibody molecule is expressed in CHO cells.

In some embodiments, the anti-LAG-3 antibody molecule reduces one or more LAG-3-associated activities with an $IC_{50}$ (concentration at 50% inhibition) that is about the same, higher or lower, e.g., at least about 10%, 20%, 30%, 40%, 50%, 60%, 70%, 80% or 90% higher or lower, than the $IC_{50}$ of a murine or chimeric anti-LAG-3 antibody molecule, e.g., a murine or chimeric anti-LAG-3 antibody molecule described herein. In some embodiments, the LAG-3-associated activity is the binding of an MHC class II molecule to LAG-3. In some embodiments, the LAG-3-associated activity is the binding of L-SECtin to LAG-3. In one embodiment, the anti-LAG-3 antibody has an $IC_{50}$ of about 1 to 20 nM, 5 to 15 nM, 5.5 nM (e.g., detected by inhibition of MHC class II or L-SECtin binding).

In some embodiments, the anti-LAG-3 antibody molecule has about the same or improved stability, e.g., at least about 0.5, 1, 2, 3, 4, 5, 6, 7, 8, 9 or 10-fold more stable in vivo or in vitro, than a murine or chimeric anti-LAG-3 antibody molecule, e.g., a murine or chimeric anti-LAG-3 antibody molecule described herein.

In one embodiment, the anti-LAG-3 antibody molecule is a humanized antibody molecule and has a risk score based on T cell epitope analysis of 800 to 1200, 850 to 1150, 900 to 1100, 950 to 1050, or a risk score as described herein.

In another embodiment, the anti-LAG-3 antibody molecule comprises at least one antigen-binding region, e.g., a variable region or an antigen-binding fragment thereof, from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule comprises at least one, two, three or four variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. In one embodiment, the antibody molecule includes a substitution (e.g., a Cys to Ser substitution at position 84) in the heavy chain framework region 3 (VHFW3) (e.g., as shown in Tables 1 and 2).

In yet another embodiment, the anti-LAG-3 antibody molecule comprises at least one or two heavy chain variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule comprises at least one or two light chain variable regions from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-LAG-3 antibody molecule includes a heavy chain constant region for an IgG4, e.g., a human IgG4. In one embodiment, the human IgG4 includes a substitution at position 228 (e.g., a Ser to Pro substitution). In still another embodiment, the anti-LAG-3 antibody molecule includes a heavy chain constant region for an IgG1, e.g., a human IgG1. In one embodiment, the human IgG1 includes a substitution at position 297 (e.g., an Asn to Ala substitution). In one embodiment, the human IgG1 includes a substitution at position 265, a substitution at position 329, or both (e.g., an Asp to Ala substitution at position 265 and/or a Pro to Ala substitution at position 329). In one embodiment, the human IgG1 includes a substitution at position 234, a substitution at position 235, or both (e.g., a Leu to Ala substitution at position 234 and/or a Leu to Ala substitution at position 235). In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In yet another embodiment, the anti-LAG-3 antibody molecule includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In another embodiment, the anti-LAG-3 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the constant region is a mutated IgG4, e.g., a mutated human IgG4 (e.g., has a mutation at position 228 (e.g., a S228P mutation). In yet another embodiment, the anti-LAG-3 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 3, or a sequence substantially identical (e.g., at least 80%, 85%, 90%, 92%, 95%, 97%, 98%, 99% or higher identical) thereto. In one embodiment, the human IgG1 includes a substitution at position 297 (e.g., an Asn to Ala substitution). In one embodiment, the human IgG1 includes a substitution at position 265, a substitution at position 329, or both (e.g., an Asp to Ala substitution at position 265 and/or a Pro to Ala substitution at position 329). In one embodiment, the human IgG1 includes a substitution at position 234, a substitution at position 235, or both (e.g., a Leu to Ala substitution at position 234 and/or a Leu to Ala substitution at position 235).

In another embodiment, the anti-LAG-3 antibody molecule includes a heavy chain variable domain and a constant region, a light chain variable domain and a constant region, or both, comprising the amino acid sequence of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences. The anti-LAG-3 antibody molecule, optionally, comprises a leader sequence from a heavy chain, a light chain, or both, as shown in Table 4; or a sequence substantially identical thereto.

In yet another embodiment, the anti-LAG-3 antibody molecule includes at least one, two, or three complementarity determining regions (CDRs) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs shown in Table 1.

In one embodiment, the anti-LAG-3 antibody molecule includes at least one, two or three CDRs (or collectively all of the CDRs) from a heavy chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In yet another embodiment, the anti-LAG-3 antibody molecule includes at least one, two, or three complementarity determining regions (CDRs) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs shown in Table 1.

In yet another embodiment, the anti-LAG-3 antibody molecule includes at least one, two, or three CDRs (or collectively all of the CDRs) from a light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid shown in Table 1, or encoded by a nucleotide sequence shown in Table 1. In another embodiment, the anti-LAG-3 antibody molecule includes at least one, two, three, four, five or six CDRs (or collectively all of the CDRs) from a heavy and light chain variable region comprising an amino acid shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid shown in Table 1, or encoded by a nucleotide sequence shown in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs shown in Table 1.

In another embodiment, the anti-LAG-3 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In one embodiment, the anti-LAG-3 antibody molecule includes all six CDRs from an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1, or encoded by the nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions) relative to one, two, three, four, five, or six CDRs shown in Table 1. In one embodiment, the anti-LAG-3 antibody molecule may include any CDR described herein.

In one embodiment, the anti-LAG-3 antibody molecule includes at least one, two or three CDRs according to Kabat (e.g., at least one, two, or three CDRs according to the Kabat definition as set out in Table 1) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat shown in Table 1.

In one embodiment, the anti-LAG-3 antibody molecule includes at least one, two or three CDRs according to Kabat (e.g., at least one, two, or three CDRs according to the Kabat definition as set out in Table 1) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat shown in Table 1.

In yet another embodiment, the anti-LAG-3 antibody molecule includes at least one, two, three, four, five, or six CDRs according to Kabat (e.g., at least one, two, three, four, five, or six CDRs according to the Kabat definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to at least one, two, three, four, five, or six CDRs according to Kabat et al. shown in Table 1. In one embodiment, the anti-LAG-3 antibody molecule may include any CDR described herein.

In yet another embodiment, the anti-LAG-3 antibody molecule includes all six CDRs according to Kabat (e.g., all six CDRs according to the Kabat definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-LAG-3 antibody molecule may include any CDR described herein.

In another embodiment, the anti-LAG-3 antibody molecule includes at least one, two or three hypervariable loops (e.g., at least one, two, or three hypervariable loops according to the Chothia definition as set out in Table 1) from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, according to Chothia (e.g., at least one, two, or three hypervariable loops according to the Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three hypervariable loops according to Chothia shown in Table 1.

In another embodiment, the anti-LAG-3 antibody molecule includes at least one, two or three hypervariable loops according to Chothia (e.g., at least one, two, or three CDRs according to the Chothia definition as set out in Table 1) from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three hypervariable loops according to Chothia shown in Table 1.

In yet another embodiment, the anti-LAG-3 antibody molecule includes at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J; or as described in Table 1; or encoded by the nucleotide sequence in Table 1; or at least the amino acids from those hypervariable loops that contact LAG-3. In one embodiment, the anti-LAG-3 antibody molecule includes at least one, two, three, four, five, or six Chothia hypervariable loops of Table 1.

In one embodiment, the anti-LAG-3 antibody molecule includes all six hypervariable loops (e.g., all six hypervariable loops according to the Chothia definition as set out in Table 1) of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, or closely related hypervariable loops, e.g., hypervariable loops which are identical or which have at least one amino acid alteration, but not more than two, three or four alterations (e.g., substitutions, deletions, or insertions, e.g., conservative substitutions) relative to all six hypervariable loops shown in Table 1. In one embodiment, the anti-LAG-3 antibody molecule may include any hypervariable loop described herein.

In still another embodiment, the anti-LAG-3 antibody molecule includes at least one, two, or three hypervariable loops that have the same canonical structures as the corresponding hypervariable loop of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-LAG-3 antibody molecule includes a combination of CDRs or hypervariable loops defined according to the Kabat et al. and Chothia et al.

In one embodiment, the anti-LAG-3 antibody molecule includes at least one, two or three CDRs or hypervariable loops from a heavy chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, according to the Kabat and Chothia definition (e.g., at least one, two, or three CDRs or hypervariable loops according to the Kabat and Chothia definition as set out in Table 1); or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

For example, the anti-LAG-3 antibody molecule can include VH CDR1 according to Kabat et al. or VH hypervariable loop 1 according to Chothia et al., or a combination thereof, e.g., as shown in Table 1. In one embodiment, the combination of Kabat and Chothia CDR of VH CDR1 comprises the amino acid sequence GFTLTNYGMN (SEQ ID NO: 286), or an amino acid sequence substantially identical thereto (e.g., having at least one amino acid alteration, but not more than two, three or four alterations (e.g., substitutions, deletions, or insertions, e.g., conservative substitutions)). The anti-LAG-3 antibody molecule can further include, e.g., VH CDRs 2-3 according to Kabat et al. and VL CDRs 1-3 according to Kabat et al., e.g., as shown in Table 1. Accordingly, in some embodiments, framework regions are defined based on a combination of CDRs defined according to Kabat et al. and hypervariable loops defined according to Chothia et al. For example, the anti-LAG-3 antibody molecule can include VH FR1 defined based on VH hypervariable loop 1 according to Chothia et al. and VH FR2 defined based on VH CDRs 1-2 according to Kabat et al., e.g., as shown in Table 1. The anti-LAG-3 antibody molecule can further include, e.g., VH FRs 3-4 defined based on VH CDRs 2-3 according to Kabat et al. and VL FRs 1~4 defined based on VL CDRs 1-3 according to Kabat et al.

The anti-LAG-3 antibody molecule can contain any combination of CDRs or hypervariable loops according to the Kabat and Chothia definitions. In one embodiment, the anti-LAG-3 antibody molecule includes at least one, two or three CDRs from a light chain variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, or BAP050-hum20-Ser), BAP050-Clone-F, BAP050-Clone-G, BAP050-Clone-H, BAP050-Clone-I, or BAP050-Clone-J, according to the Kabat and Chothia definition (e.g., at least one, two, or three CDRs according to the Kabat and Chothia definition as set out in Table 1).

In an embodiment, e.g., an embodiment comprising a variable region, CDR (e.g., CDR or Kabat CDR), or other sequence referred to herein, e.g., in Table 1, the antibody molecule is a monospecific antibody molecule, a bispecifc antibody molecule, or is an antibody molecule that comprises an antigen binding fragment of an antibody, e.g., a half antibody or antigen binding fragment of a half antibody. In certain embodiments, the antibody molecule is a bispecific antibody molecule having a first binding specificity for LAG-3 and a second binding specify for PD-1, TIM-3, CEACAM (e.g., CEACAM-1 and/or CEACAM-5), PD-L1 or PD-L2.

In one embodiment, the anti-LAG-3 antibody includes:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;

(c) a VH comprising a VHCDR1 amino acid sequence of SEQ ID NO: 286, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or (d) a VH comprising a VHCDR1 amino acid sequence of SEQ ID NO: 286; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

In one embodiment, the anti-LAG-3 antibody molecule comprises a VH comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;

In one embodiment, the anti-LAG-3 antibody molecule comprises a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;

In one embodiment, the anti-LAG-3 antibody molecule comprises a VH comprising a VHCDR1 amino acid sequence of SEQ ID NO: 286, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or In one embodiment, the anti-LAG-3 antibody molecule comprises a VH comprising a VHCDR1 amino acid sequence of SEQ ID NO: 286; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

In one embodiment, the antibody molecule is a humanized antibody molecule. In another embodiment, the antibody molecule is a monospecific antibody molecule. In yet another embodiment, the antibody molecule is a bispecific antibody molecule.

In one embodiment, the anti-LAG-3 antibody includes:

(i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3; and (ii) a light chain variable region (VL) including a VLCDR1 amino acid sequence of SEQ ID NO: 10, a VLCDR2 amino acid sequence of SEQ ID NO: 11, and a VLCDR3 amino acid sequence of SEQ ID NO: 12.

In another embodiment, the anti-LAG-3 antibody molecule includes:

(i) a heavy chain variable region (VH) including a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3; and (ii) a light chain variable region (VL) including a VLCDR1 amino acid sequence of SEQ ID NO: 13, a VLCDR2 amino acid sequence of SEQ ID NO: 14, and a VLCDR3 amino acid sequence of SEQ ID NO: 15.

In one embodiment, the anti-LAG-3 antibody molecule comprises the VHCDR1 amino acid sequence of SEQ ID NO: 1. In another embodiment, the anti-LAG-3 antibody molecule comprises the VHCDR1 amino acid sequence of SEQ ID NO: 4. In yet another embodiment, the anti-LAG-3 antibody molecule comprises the VHCDR1 amino acid sequence of SEQ ID NO: 286.

In one embodiment, the light or the heavy chain variable framework (e.g., the region encompassing at least FR1, FR2, FR3, and optionally FR4) of the anti-LAG-3 antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-LAG-3 antibody molecule comprises a heavy chain variable domain having at least one, two, three, four, five, six, seven, ten, fifteen, twenty or more changes, e.g., amino acid substitutions or deletions, from an amino acid sequence of BAP050-chi-HC, e.g., the amino acid sequence of the FR region in the entire variable region, e.g., shown in Figures. 9A-9B, or SEQ ID NO: 20 or 22. In one embodiment, the anti-LAG-3 antibody molecule comprises a heavy chain variable domain having one or more of: E at position 1, V at position 2, A at position 9, V at position 11, A at position 16, S at position 17, L at position 18, R at position 19, V at position 20, V or G at position 24, I at position 37, A or S at position 40, R or T at position 41, S at position 42, Q or R at position 43, R at position 44, E at position 46, I or L at position 48, V at position 68, V or T at position 69, I at position 70, A at position 72, D at position 73, K at position 74, V or I at position 76, Y at position 80, W at position 83, C or S at position 84, S or T at position 85, A at position 88, E or S at position 89, V or M at position 93, or Y at position 95 of amino acid sequence of BAP050-chi-HC, e.g., the amino acid sequence of the FR in the entire variable region, e.g., shown in Figures. 9A-9B, or SEQ ID NO: 20 or 22. In one embodiment, the antibody molecule includes a substitution (e.g., a Cys to Ser substitution at position 84) in the heavy chain framework region 3 (VHFW3) (e.g., as shown in Table 2).

Alternatively, or in combination with the heavy chain substitutions of BAP050-chi-HC described herein, the anti-LAG-3 antibody molecule comprises a light chain variable domain having at least one, two, three, four, five, six, seven, ten, fifteen, twenty or more amino acid changes, e.g., amino acid substitutions or deletions, from an amino acid sequence of BAP050-chi-LC, e.g., the amino acid sequence shown in Figures. 10A-10B, or SEQ ID NO: 24 or 26. In one embodiment, the anti-LAG-3 antibody molecule comprises a heavy chain variable domain having one or more of: E or A at position 1, V at position 3, L at position 4, S at position 7, P at position 8, A or L or D at position 9, T or F at position 10, Q at position 11, P at position 12, V or L at position 13, T at position 14, V or P at position 15, K at position 16, Q or E at position 17, T or P or K at position 18, A at position 19, S at position 20, L at position 21, T at position 22, L at position 37, G at position 41, K or Q at position 42, A or S at position 43, P at position 44, R or Q at position 45, L at position 46, I at position 58, P or D at position 60, Y at position 67, E at position 70, F at position 71, T at position 72, F at position 73, N at position 76, S or R at position 77, I at position 78, Q at position 79, A or S or P at position 80, D at position 81, A or F at position 83, Y or V at position 85, or F at position 87 of the amino acid sequence of BAP050-chi-LC, e.g., the amino acid sequence shown in Figures. 10A-10B, or SEQ ID NO: 24 or 26.

In other embodiments, the anti-LAG-3 antibody molecule includes one, two, three, or four heavy chain framework regions (e.g., a VHFW amino acid or nucleotide sequence shown in Table 2, or encoded by the nucleotide sequence shown in Table 2), or a sequence substantially identical thereto (e.g., a sequence at least about 85%, 90%, 95%, 99% or more identical thereto, and/or having one, two, three or more substitutions, insertions or deletions, e.g., conserved substitutions). In one embodiment, the antibody molecule includes a substitution (e.g., a Cys to Ser substitution at position 84) in the heavy chain framework region 3 (VHFW3) (e.g., as shown in Table 2).

In yet other embodiments, the anti-LAG-3 antibody molecule includes one, two, three, or four light chain framework regions (e.g., a VLFW amino acid sequence shown in Table 2, or encoded by the nucleotide sequence shown in Table 2), or a sequence substantially identical thereto (e.g., a sequence at least about 85%, 90%, 95%, 99% or more identical thereto, and/or having one, two, three or more substitutions, insertions or deletions, e.g., conserved substitutions).

In other embodiments, the anti-LAG-3 antibody molecule includes one, two, three, or four heavy chain framework regions (e.g., a VHFW amino acid sequence shown in Table 2, or encoded by the nucleotide sequence shown in Table 2), or a sequence substantially identical thereto; and one, two, three, or four light chain framework regions (e.g., a VLFW amino acid sequence shown in Table 2, or encoded by the nucleotide sequence shown in Table 2), or a sequence substantially identical thereto.

In some embodiments, the anti-LAG-3 antibody molecule comprises the heavy chain framework region 1 (VHFW1) of BAP050-hum01, BAP050-hum02, BAP050-hum03, BAP050-hum04, BAP050-hum05, BAP050-hum06, BAP050-hum07, BAP050-hum08, BAP050-hum14, BAP050-hum15, BAP050-hum18, BAP050-hum19, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum14-Ser, BAP050-hum15-Ser, BAP050-hum18-Ser, BAP050-hum19-Ser, BAP050-Clone-F, or BAP050-Clone-G (e.g., SEQ ID NO: 187). In some embodiments, the antibody molecule comprises the heavy chain framework region 1 (VHFW1) of BAP050-hum09, BAP050-hum10, BAP050-hum11, BAP050-hum12, BAP050-hum13, or BAP050-hum20, BAP050-hum09-Ser, BAP050-hum10-Ser, BAP050-hum11-Ser, BAP050-hum12-Ser, BAP050-hum13-Ser, BAP050-Clone-H, BAP050-Clone-I, or BAP050-Clone J (e.g., SEQ ID NO: 190). In some embodiments, the antibody molecule comprises the heavy chain framework region 1 (VHFW1) of BAP050-hum16 (e.g., SEQ ID NO: 194). In some embodiments, the antibody molecule comprises the heavy chain framework region 1 (VHFW1) of BAP050-hum17 (e.g., SEQ ID NO: 196). In other embodiments, the antibody molecule comprises a heavy chain framework region 1 (VHFW1) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework region 2 (VHFW2) of BAP050-hum01, BAP050-hum02, BAP050-hum03, BAP050-hum04, BAP050-hum05, BAP050-hum06, BAP050-hum07, BAP050-hum08, BAP050-hum13, BAP050-hum17, BAP050-hum18, BAP050-hum19, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum13-Ser, BAP050-hum18-Ser, BAP050-hum19-Ser, BAP050-Clone-F, BAP050-Clone-G, or BAP050-Clone-J (e.g., SEQ ID NO: 198). In some embodiments, the antibody molecule comprises the heavy chain framework region 2 (VHFW2) of BAP050-hum09, BAP050-hum10, BAP050-hum11, BAP050-hum12, BAP050-hum20, BAP050-hum09-Ser, BAP050-hum10-Ser, BAP050-hum11-Ser, BAP050-hum12-Ser, BAP050-hum20-Ser, or BAP050-Clone-I (e.g., SEQ ID NO: 202). In some embodiments, the antibody molecule comprises the heavy chain framework region 2 (VHFW2) of BAP050-hum14, BAP050-hum15, BAP050-hum14-Ser, or BAP050-hum15-Ser (e.g., SEQ ID NO: 206). In some embodiments, the antibody molecule comprises the heavy chain framework region 2 (VHFW2) of BAP050-hum16 (e.g., SEQ ID NO: 208). In other embodiments, the antibody molecule comprises a heavy chain framework region 2 (VHFW2) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework region 3 (VHFW3) of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum18, BAP050-hum19, or BAP050-hum20 (e.g., SEQ ID NO: 210). In some embodiments, the antibody molecule comprises the heavy chain framework region 3 (VHFW3) of BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, BAP050-hum20-Ser, BAP050-Clone-F, BAP050-Clone-G, BAP050-Clone-H, BAP050-Clone-I, or BAP050-Clone-J (e.g., SEQ ID NO: 212). In some embodiments, the antibody molecule comprises the heavy chain framework region 3 (VHFW3) of BAP050-hum16 (e.g., SEQ ID NO: 217). In some embodiments, the antibody molecule comprises the heavy chain framework region 3 (VHFW3) of BAP050-hum17 (e.g., SEQ ID NO: 219). In other embodiments, the antibody molecule comprises a heavy chain framework region 3 (VHFW3) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework region 4 (VHFW4) of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, or BAP050-hum20, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, BAP050-hum20-Ser, BAP050-Clone-F, BAP050-Clone-G, BAP050-Clone-H, BAP050-Clone-I, or BAP050-Clone-J (e.g., SEQ ID NO: 221). In other embodiments, the antibody molecule comprises a heavy chain framework region 4 (VHFW4) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework region 1 (VLFW1) of BAP050-hum01, BAP050-hum02, BAP050-hum04, BAP050-hum07, BAP050-hum09, BAP050-hum11, BAP050-hum13, BAP050-hum17, BAP050-hum01-Ser, BAP050-hum02-Ser, BAP050-hum04-Ser, BAP050-hum07-Ser, BAP050-hum09-Ser, BAP050-hum11-Ser, BAP050-hum13-Ser, BAP050-Clone-F, BAP050-Clone-G, BAP050-Clone-H, BAP050-Clone-I, or BAP050-Clone-J (e.g., SEQ ID NO: 226). In some embodiments, the antibody molecule comprises the light chain framework region 1 (VLFW1) of BAP050-hum03, BAP050-hum10, BAP050-hum14, BAP050-hum03-Ser, BAP050-hum10-Ser, or BAP050-hum14-Ser (e.g., SEQ ID NO: 230). In some embodiments, the antibody molecule comprises the light chain framework region 1 (VLFW1) of BAP050-hum05 or BAP050-hum05-Ser (e.g., SEQ ID NO: 232). In some embodiments, the antibody molecule comprises the light chain framework region 1 (VLFW1) of BAP050-hum06, BAP050-hum20, BAP050-hum06-Ser, or BAP050-hum20-Ser (e.g., SEQ ID NO: 234). In some embodiments, the antibody molecule comprises the light chain framework region 1 (VLFW1) of BAP050-hum08, BAP050-hum12, BAP050-hum15, BAP050-hum16, BAP050-hum19, BAP050-hum08-Ser, BAP050-hum12-Ser, BAP050-hum15-Ser, or BAP050-hum19-Ser (e.g., SEQ ID NO: 236). In some embodiments, the antibody molecule comprises the light chain framework region 1 (VLFW1) of BAP050-hum18 or BAP050-hum18-Ser (e.g., SEQ ID NO: 238). In other embodiments, the antibody molecule comprises a light chain framework region 1 (VLFW1) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework region 2 (VLFW2) of BAP050-hum01, BAP050-hum02, BAP050-hum05, BAP050-hum09, BAP050-hum13, BAP050-hum17, BAP050-hum01-Ser, BAP050-hum02-Ser, BAP050-hum05-Ser, BAP050-hum09-Ser, BAP050-hum13-Ser, BAP050-hum17-Ser, BAP050-Clone-F, BAP050-Clone-G, BAP050-Clone-H, BAP050-Clone-I, or BAP050-Clone-J (e.g., SEQ ID NO: 240). In some embodiments, the antibody molecule comprises the light chain framework region 2 (VLFW2) of BAP050-hum03, BAP050-hum06, BAP050-hum08, BAP050-hum10, BAP050-hum12, BAP050-hum14, BAP050-hum15, BAP050-hum16, BAP050-hum18, BAP050-hum19, BAP050-hum20, BAP050-hum03-Ser, BAP050-hum06-Ser, BAP050-hum08-Ser, BAP050-hum10-Ser, BAP050-hum12-Ser, BAP050-hum14-Ser, BAP050-hum15-Ser, BAP050-hum18-Ser, BAP050-hum19-Ser, or BAP050-hum20-Ser (e.g., SEQ ID NO: 244). In some embodiments, the antibody molecule comprises the light chain framework region 2 (VLFW2) of BAP050-hum04 or BAP050-hum04-Ser (e.g., SEQ ID NO: 246). In some embodiments, the antibody molecule comprises the light chain framework region 2 (VLFW2) of BAP050-hum07, BAP050-hum11, BAP050-hum07-Ser, or BAP050-hum11-Ser (e.g., SEQ ID NO: 248). In other embodiments, the antibody molecule comprises a light chain framework region 2 (VLFW2) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework region 3 (VLFW3) of BAP050-hum01, BAP050-hum03, BAP050-hum05, BAP050-hum10, BAP050-hum14, BAP050-hum19, BAP050-hum01-Ser, BAP050-hum03-Ser, BAP050-hum05-Ser, BAP050-hum10-Ser, BAP050-hum14-Ser, BAP050-hum19-Ser, or BAP050-Clone-F (e.g., SEQ ID NO: 252). In some embodiments, the antibody molecule comprises the light chain framework region 3 (VLFW3) of BAP050-hum02, BAP050-hum09, BAP050-hum13, BAP050-hum02-Ser, BAP050-hum09-Ser, BAP050-hum13-Ser, BAP050-Clone-G, BAP050-Clone-H, or BAP050-Clone-J (e.g., SEQ ID NO: 255). In some embodiments, the antibody molecule comprises the light chain framework region 3 (VLFW3) of BAP050-hum04 or BAP050-hum04-Ser (e.g., SEQ ID NO: 259). In some embodiments, the antibody molecule comprises the light chain framework region 3 (VLFW3) of BAP050-hum06, BAP050-hum07, BAP050-hum11, BAP050-hum06-Ser, BAP050-hum07-Ser, BAP050-hum11-Ser, or BAP050-Clone-I (e.g., SEQ ID NO: 261). In some embodiments, the antibody molecule comprises the light chain framework region 3 (VLFW3) of BAP050-hum08, BAP050-hum12, BAP050-hum15, BAP050-hum16, BAP050-hum18, BAP050-hum08-Ser, BAP050-hum12-Ser, BAP050-hum15-Ser, or BAP050-hum18-Ser (e.g., SEQ ID NO: 265). In some embodiments, the antibody molecule comprises the light chain framework region 3 (VLFW3) of BAP050-hum17 (e.g., SEQ ID NO: 267). In some embodiments, the antibody molecule comprises the light chain framework region 3 (VLFW3) of BAP050-hum20 or BAP050-hum20-Ser (e.g., SEQ ID NO: 269). In other embodiments, the antibody molecule comprises a light chain framework region 3 (VHLW3) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework region 4 (VLFW4) of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, BAP050-hum20-Ser, BAP050-Clone-F, BAP050-Clone-G, BAP050-Clone-H, BAP050-Clone-I, or BAP050-Clone-J (e.g., SEQ ID NO: 271). In other embodiments, the antibody molecule comprises a light chain framework region 4 (VLFW4) having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum01, BAP050-hum02, BAP050-hum03, BAP050-hum04, BAP050-hum05, BAP050-hum06, BAP050-hum07, BAP050-hum08, BAP050-hum18, BAP050-hum19 (e.g., SEQ ID NO: 187 (VHFW1), SEQ ID NO: 198 (VHFW2), and SEQ ID NO: 210 (VHFW3)). In some embodiments, the antibody molecule comprises the heavy chain framework regions 1-3 of BAP050-hum09, BAP050-hum10, BAP050-hum11, BAP050-hum12, BAP050-hum20 (e.g., SEQ ID NO: 190 (VHFW1), SEQ ID NO: 202 (VHFW2), and SEQ ID NO: 210 (VHFW3)). In some embodiments, the antibody molecule comprises the heavy chain framework regions 1-3 of BAP050-hum13 (e.g., SEQ ID NO: 190 (VHFW1), SEQ ID NO: 198 (VHFW2), and SEQ ID NO: 210 (VHFW3)). In some embodiments, the antibody molecule comprises the heavy chain framework regions 1-3 of BAP050-hum14 or BAP050-hum15 (e.g., SEQ ID NO: 187 (VHFW1), SEQ ID NO: 206 (VHFW2), and SEQ ID NO: 210 (VHFW3)). In some embodiments, the antibody molecule comprises the heavy chain framework regions 1-3 of BAP050-hum16 (e.g., SEQ ID NO: 194 (VHFW1), SEQ ID NO: 208 (VHFW2), and SEQ ID NO: 217 (VHFW3)). In some embodiments, the antibody molecule comprises the heavy chain framework regions 1-3 of BAP050-hum17 (e.g., SEQ ID NO: 196 (VHFW1), SEQ ID NO: 198 (VHFW2), and SEQ ID NO: 219 (VHFW3)). In some embodiments, the antibody molecule comprises the heavy chain framework regions 1-3 of BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum18-Ser, BAP050-hum19-Ser, BAP050-Clone-F, or BAP050-Clone-G (e.g., SEQ ID NO: 187 (VHFW1), SEQ ID NO: 198 (VHFW2), and SEQ ID NO: 212 (VHFW3)). In some embodiments, the antibody molecule comprises the heavy chain framework regions 1-3 of BAP050-hum09-Ser, BAP050-hum10-Ser, BAP050-hum11-Ser, BAP050-hum12-Ser, BAP050-hum20-Ser, BAP050-Clone-H, or BAP050-Clone I (e.g., SEQ ID NO: 190 (VHFW1), SEQ ID NO: 202 (VHFW2), and SEQ ID NO: 212 (VHFW3)). In some embodiments, the antibody molecule comprises the heavy chain framework regions 1-3 of BAP050-hum13-Ser or BAP050-Clone-J (e.g., SEQ ID NO: 190 (VHFW1), SEQ ID NO: 198 (VHFW2), and SEQ ID NO: 212 (VHFW3)). In some embodiments, the antibody molecule comprises the heavy chain framework regions 1-3 of BAP050-hum14-Ser or BAP050-hum15-Ser (e.g., SEQ ID NO: 187 (VHFW1), SEQ ID NO: 206 (VHFW2), and SEQ ID NO: 212 (VHFW3)). In some embodiments, the antibody molecule further comprises the heavy chain framework region 4 of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, BAP050-hum01-Ser, BAP050-hum02-Ser, BAP050-hum05-Ser, BAP050-hum09-Ser, BAP050-hum11-Ser, BAP050-hum13-Ser, BAP050-Clone-F, BAP050-Clone-G, BAP050-Clone-H, BAP050-Clone-I, or BAP050-Clone-J (e.g., SEQ ID NO: 221). In other embodiments, the antibody molecule comprises a heavy chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the light chain framework regions 1-3 of BAP050-hum01, BAP050-hum01-Ser, or BAP050-Clone-F (e.g., SEQ ID NO: 226 (VLFW1), SEQ ID NO: 240 (VLFW2), and SEQ ID NO: 252 (VLFW3)). In some embodiments, the antibody molecule comprises the light chain framework regions 1-3 of BAP050-hum02, BAP050-hum09, BAP050-hum13, BAP050-hum02-Ser, BAP050-hum09-Ser, BAP050-hum13-Ser, BAP050-Clone-G, BAP050-Clone-H, or BAP050-Clone-J (e.g., SEQ ID NO: 226 (VLFW1), SEQ ID NO: 240 (VLFW2), and SEQ ID NO: 255 (VLFW3)). In some embodiments, the antibody molecule comprises the light chain framework regions 1-3 of BAP050-hum03, BAP050-hum10, BAP050-hum14, BAP050-hum03-Ser, BAP050-hum10-Ser, or BAP050-hum14-Ser (e.g., SEQ ID NO: 230 (VLFW1), SEQ ID NO: 244 (VLFW2), and SEQ ID NO: 252 (VLFW3)). In some embodiments, the antibody molecule comprises the light chain framework regions 1-3 of BAP050-hum04 or BAP050-hum04-Ser (e.g., SEQ ID NO: 226 (VLFW1), SEQ ID NO: 246 (VLFW2), and SEQ ID NO: 259 (VLFW3)). In some embodiments, the antibody molecule comprises the light chain framework regions 1-3 of BAP050-hum05 or BAP050-hum05-Ser (e.g., SEQ ID NO: 232 (VLFW1), SEQ ID NO: 240 (VLFW2), and SEQ ID NO: 252 (VLFW3)). In some embodiments, the antibody molecule comprises the light chain framework regions 1-3 of BAP050-hum06 or BAP050-hum06-Ser (e.g., SEQ ID NO: 234 (VLFW1), SEQ ID NO: 244 (VLFW2), and SEQ ID NO: 261 (VLFW3)). In some embodiments, the antibody molecule comprises the light chain framework regions 1-3 of BAP050-hum07, BAP050-hum11, BAP050-hum07-Ser, BAP050-hum11-Ser, or BAP050-Clone-I (e.g., SEQ ID NO: 226 (VLFW1), SEQ ID NO: 248 (VLFW2), and SEQ ID NO: 261 (VLFW3)). In some embodiments, the antibody molecule comprises the light chain framework regions 1-3 of BAP050-hum08, BAP050-hum12, BAP050-hum15, BAP050-hum16, BAP050-hum08-Ser, BAP050-hum12-Ser, or BAP050-hum15-Ser (e.g., SEQ ID NO: 236 (VLFW1), SEQ ID NO: 244 (VLFW2), and SEQ ID NO: 265 (VLFW3)). In some embodiments, the antibody molecule comprises the light chain framework regions 1-3 of BAP050-hum17 (e.g., SEQ ID NO: 226 (VLFW1), SEQ ID NO: 240 (VLFW2), and SEQ ID NO: 267 (VLFW3)). In some embodiments, the antibody molecule comprises the light chain framework regions 1-3 of BAP050-hum18 or BAP050-hum18-Ser (e.g., SEQ ID NO: 238 (VLFW1), SEQ ID NO: 244 (VLFW2), and SEQ ID NO: 265 (VLFW3)). In some embodiments, the antibody molecule comprises the light chain framework regions 1-3 of BAP050-hum19 or BAP050-hum19-Ser (e.g., SEQ ID NO: 236 (VLFW1), SEQ ID NO: 244 (VLFW2), and SEQ ID NO: 252 (VLFW3)). In some embodiments, the antibody molecule comprises the light chain framework regions 1-3 of BAP050-hum20 or BAP050-hum20-Ser (e.g., SEQ ID NO: 234 (VLFW1), SEQ ID NO: 244 (VLFW2), and SEQ ID NO: 269 (VLFW3)). In some embodiments, the antibody molecule further comprises the heavy chain framework region 4 of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, BAP050-hum01-Ser, BAP050-hum02-Ser, BAP050-hum03-Ser, BAP050-hum04-Ser, BAP050-hum05-Ser, BAP050-hum06-Ser, BAP050-hum07-Ser, BAP050-hum08-Ser, BAP050-hum09-Ser, BAP050-hum10-Ser, BAP050-hum11-Ser, BAP050-hum12-Ser, BAP050-hum13-Ser, BAP050-hum14-Ser, BAP050-hum15-Ser, BAP050-hum18-Ser, BAP050-hum19-Ser, BAP050-hum20-Ser, BAP050-Clone-F, BAP050-Clone-G, BAP050-Clone-H, BAP050-Clone-I, or BAP050-Clone-J (e.g., SEQ ID NO: 271). In other embodiments, the antibody molecule comprises a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum01 (e.g., SEQ ID NO: 187 (VHFW1), SEQ ID NO: 198 (VHFW2), and SEQ ID NO: 210 (VHFW3)), or the heavy chain framework regions 1-3 of BAP050-hum01-Ser or BAP050-Clone-F (e.g., SEQ ID NO: 187 (VHFW1), SEQ ID NO: 198 (VHFW2), and SEQ ID NO: 212 (VHFW3)); and the light chain framework regions 1-3 of BAP050-hum01, BAP050-hum01-Ser, or BAP050-Clone-F (e.g., SEQ ID NO: 226 (VLFW1), SEQ ID NO: 240 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum02 (e.g., SEQ ID NO: 187 (VHFW1), SEQ ID NO: 198 (VHFW2), and SEQ ID NO: 210 (VHFW3)), or the heavy chain framework regions 1-3 of BAP050-hum02-Ser or BAP050-Clone-G (e.g., SEQ ID NO: 187 (VHFW1), SEQ ID NO: 198 (VHFW2), and SEQ ID NO: 212 (VHFW3)); and the light chain framework regions 1-3 of BAP050-hum02, BAP050-hum02-Ser, or BAP050-Clone-G (e.g., SEQ ID NO: 226 (VLFW1), SEQ ID NO: 240 (VLFW2), and SEQ ID NO: 255 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum03 (e.g., SEQ ID NO: 187 (VHFW1), SEQ ID NO: 198 (VHFW2), and SEQ ID NO: 210 (VHFW3)), or the heavy chain framework regions 1-3 of BAP050-hum03-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum03 (e.g., SEQ ID NO: 230 (VLFW1), SEQ ID NO: 244 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum04 (e.g., SEQ ID NO: 187 (VHFW1), SEQ ID NO: 198 (VHFW2), and SEQ ID NO: 210 (VHFW3)), or the heavy chain framework regions 1-3 of BAP050-hum04-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum04 (e.g., SEQ ID NO: 226 (VLFW1), SEQ ID NO: 246 (VLFW2), and SEQ ID NO: 259 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum05 (e.g., SEQ ID NO: 187 (VHFW1), SEQ ID NO: 198 (VHFW2), and SEQ ID NO: 210 (VHFW3)) or BAP050-hum05-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum05 or BAP050-hum05-Ser (e.g., SEQ ID NO: 232 (VLFW1), SEQ ID NO: 240 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum06 (e.g., SEQ ID NO: 187 (VHFW1), SEQ ID NO: 198 (VHFW2), and SEQ ID NO: 210 (VHFW3)), or the heavy chain framework regions 1-3 of BAP050-hum06-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum06 (e.g., SEQ ID NO: 234 (VLFW1), SEQ ID NO: 244 (VLFW2), and SEQ ID NO: 261 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum07 (e.g., SEQ ID NO: 187 (VHFW1), SEQ ID NO: 198 (VHFW2), and SEQ ID NO: 210 (VHFW3)), or the heavy chain framework regions 1-3 of BAP050-hum07-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum07 (e.g., SEQ ID NO: 226 (VLFW1), SEQ ID NO: 248 (VLFW2), and SEQ ID NO: 261 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum08 (e.g., SEQ ID NO: 187 (VHFW1), SEQ ID NO: 198 (VHFW2), and SEQ ID NO: 210 (VHFW3)), or the heavy chain framework regions 1-3 of BAP050-hum08-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum08 (e.g., SEQ ID NO: 236 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum09 (e.g., SEQ ID NO: 190 (VHFW1), SEQ ID NO: 202 (VHFW2), and SEQ ID NO: 210 (VHFW3)), or BAP050-hum09-Ser or BAP050-Clone-H (e.g., SEQ ID NO: 190 (VHFW1), SEQ ID NO: 202 (VHFW2), and SEQ ID NO: 212 (VHFW3)); and the light chain framework regions 1-3 of BAP050-hum09, BAP050-hum09-Ser, or BAP050-Clone-H (e.g., SEQ ID NO: 226 (VLFW1), SEQ ID NO: 240 (VLFW2), and SEQ ID NO: 255 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum10 (e.g., SEQ ID NO: 190 (VHFW1), SEQ ID NO: 202 (VHFW2), and SEQ ID NO: 210 (VHFW3)), or the heavy chain framework regions 1-3 of BAP050-hum10-Ser (e.g., SEQ ID NO: 190 (VHFW1), SEQ ID NO: 202 (VHFW2), and SEQ ID NO: 212 (VHFW3)); and the light chain framework regions 1-3 of BAP050-hum10 (e.g., SEQ ID NO: 230 (VLFW1), SEQ ID NO: 244 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum11 (e.g., SEQ ID NO: 190 (VHFW1), SEQ ID NO: 202 (VHFW2), and SEQ ID NO: 210 (VHFW3)), or BAP050-hum11-Ser, or BAP050-Clone-I (e.g., SEQ ID NO: 190 (VHFW1), SEQ ID NO: 202 (VHFW2), and SEQ ID NO: 212 (VHFW3)); and the light chain framework regions 1-3 of BAP050-hum11, BAP050-hum11-Ser, or BAP050-Clone-I (e.g., SEQ ID NO: 226 (VLFW1), SEQ ID NO: 248 (VLFW2), and SEQ ID NO: 261 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum12 (e.g., SEQ ID NO: 190 (VHFW1), SEQ ID NO: 202 (VHFW2), and SEQ ID NO: 210 (VHFW3)) or BAP050-hum12-Ser (e.g., SEQ ID NO: 190 (VHFW1), SEQ ID NO: 202 (VHFW2), and SEQ ID NO: 212 (VHFW3)); and the light chain framework regions 1-3 of BAP050-hum12 or BAP050-hum12-Ser (e.g., SEQ ID NO: 236 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum13 (e.g., SEQ ID NO: 190 (VHFW1), SEQ ID NO: 198 (VHFW2), and SEQ ID NO: 210 (VHFW3)), or the heavy chain framework regions 1-3 of BAP050-hum13-Ser or BAP050-Clone-J (e.g., SEQ ID NO: 190 (VHFW1), SEQ ID NO: 198 (VHFW2), and SEQ ID NO: 212 (VHFW3)); and the light chain framework regions 1-3 of BAP050-hum13, BAP050-hum13-Ser, or BAP050-Clone-J (e.g., SEQ ID NO: 226 (VLFW1), SEQ ID NO: 240 (VLFW2), and SEQ ID NO: 255 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum14 (e.g., SEQ ID NO: 187 (VHFW1), SEQ ID NO: 206 (VHFW2), and SEQ ID NO: 210 (VHFW3)), or the heavy chain framework regions 1-3 of BAP050-hum14-Ser (e.g., SEQ ID NO: 187 (VHFW1), SEQ ID NO: 206 (VHFW2), and SEQ ID NO: 210 (VHFW3)); and the light chain framework regions 1-3 of BAP050-hum14 (e.g., SEQ ID NO: 230 (VLFW1), SEQ ID NO: 244 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum15 (e.g., SEQ ID NO: 187 (VHFW1), SEQ ID NO: 206 (VHFW2), and SEQ ID NO: 210 (VHFW3)), or the heavy chain framework regions 1-3 of BAP050-hum15-Ser (e.g., SEQ ID NO: 187 (VHFW1), SEQ ID NO: 206 (VHFW2), and SEQ ID NO: 210 (VHFW3)); and the light chain framework regions 1-3 of BAP050-hum15 (e.g., SEQ ID NO: 236 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum16 (e.g., SEQ ID NO: 194 (VHFW1), SEQ ID NO: 208 (VHFW2), and SEQ ID NO: 217 (VHFW3)); and the light chain framework regions 1-3 of BAP050-hum16 (e.g., SEQ ID NO: 236 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum17 (e.g., SEQ ID NO: 196 (VHFW1), SEQ ID NO: 198 (VHFW2), and SEQ ID NO: 219 (VHFW3)); and the light chain framework regions 1-3 of BAP050-hum17 (e.g., SEQ ID NO: 226 (VLFW1), SEQ ID NO: 240 (VLFW2), and SEQ ID NO: 267 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum18 (e.g., SEQ ID NO: 187 (VHFW1), SEQ ID NO: 198 (VHFW2), and SEQ ID NO: 210 (VHFW3)), or the heavy chain framework regions 1-3 of BAP050-hum18-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum18 (e.g., SEQ ID NO: 238 (VLFW1), SEQ ID NO: 244 (VLFW2), and SEQ ID NO: 265 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum19 (e.g., SEQ ID NO: 187 (VHFW1), SEQ ID NO: 198 (VHFW2), and SEQ ID NO: 210 (VHFW3)), or the heavy chain framework regions 1-3 of BAP050-hum18-Ser (e.g., SEQ ID NO: 187 (VHFW1), SEQ ID NO: 198 (VHFW2), and SEQ ID NO: 212 (VHFW3)); and the light chain framework regions 1-3 of BAP050-hum19 (e.g., SEQ ID NO: 236 (VLFW1), SEQ ID NO: 244 (VLFW2), and SEQ ID NO: 252 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises the heavy chain framework regions 1-3 of BAP050-hum20 (e.g., SEQ ID NO: 190 (VHFW1), SEQ ID NO: 202 (VHFW2), and SEQ ID NO: 210 (VHFW3)), or BAP050-hum20-Ser (e.g., SEQ ID NO: 190 (VHFW1), SEQ ID NO: 202 (VHFW2), and SEQ ID NO: 212 (VHFW3)); and the light chain framework regions 1-3 of BAP050-hum20 (e.g., SEQ ID NO: 234 (VLFW1), SEQ ID NO: 244 (VLFW2), and SEQ ID NO: 269 (VLFW3)). In other embodiments, the antibody molecule comprises a heavy chain and a light chain framework region having a sequence, or encoded by a sequence, substantially identical (e.g., a sequence at least about 85%, 90%, 95%, 99% or more identical) to any of the aforesaid sequences, and/or having one, two, three or more substitutions, insertions or deletions, e.g., conserved substitutions).

In some embodiments, the anti-LAG-3 antibody molecule comprises a heavy chain framework region having a combination of framework regions FW1, FW2 and FW3 as shown in Figures. 4 or 6. In other embodiment, antibody molecule comprises a light chain framework region having a combination of framework regions FW1, FW2 and FW3 as shown in Figures. 4 or 6. In yet other embodiments, the antibody molecule comprises a heavy chain framework region having a combination of framework regions FW1, FW2 and FW3 as shown in Figures. 4 or 6, and a light chain framework region having a combination of framework regions FW1, FW2 and FW3 as shown in Figures. 4 or 6.

In one embodiment, the heavy or light chain variable domain, or both, of the of the anti-LAG-3 antibody molecule includes an amino acid sequence, which is substantially identical to an amino acid disclosed herein, e.g., at least 70%, 75%, 80%, 85%, 90%, 92%, 95%, 97%, 98%, 99% or higher identical to a variable region of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum05-Ser, BAP050-hum09-Ser, BAP050-hum11-Ser, BAP050-hum12-Ser, BAP050-hum13-Ser), BAP050-Clone-F, BAP050-Clone-G, BAP050-Clone-H, BAP050-Clone-I, or BAP050-Clone-J; or as described in Table 1, or encoded by the nucleotide sequence in Table 1; or which differs at least 1 or 5 residues, but less than 40, 30, 20, or 10 residues, from a variable region of an antibody described herein.

In one embodiment, the heavy or light chain variable region, or both, of the of the anti-LAG-3 antibody molecule includes an amino acid sequence encoded by a nucleic acid sequence described herein or a nucleic acid that hybridizes to a nucleic acid sequence described herein (e.g., a specific nucleic acid sequence or a nucleic acid sequence that encodes an amino acid sequence described herein, e.g., as shown in Tables 1 and 2) or its complement, e.g., under low stringency, medium stringency, or high stringency, or other hybridization condition described herein.

In another embodiment, the anti-LAG-3 antibody molecule comprises at least one, two, three, or four antigen-binding regions, e.g., variable regions, having an amino acid sequence as set forth in Table 1, or a sequence substantially identical thereto (e.g., a sequence at least about 85%, 90%, 95%, 99% or more identical thereto, or which differs by no more than 1, 2, 5, 10, or 15 amino acid residues from the sequences shown in Table 1). In another embodiment, the anti-LAG-3 antibody molecule includes a VH and/or VL domain encoded by a nucleic acid having a nucleotide sequence as set forth in Table 1, or a sequence substantially identical thereto (e.g., a sequence at least about 70%, 75%, 85%, 90%, 95%, 99% or more identical thereto, or which differs by no more than 3, 6, 15, 30, or 45 nucleotides from the sequences shown in Table 1).

In yet another embodiment, the anti-LAG-3 antibody molecule comprises at least one, two, or three CDRs from a heavy chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-LAG-3 antibody molecule comprises at least one, two, or three CDRs from a light chain variable region having an amino acid sequence as set forth in Table 1, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-LAG-3 antibody molecule comprises at least one, two, three, four, five or six CDRs from heavy and light chain variable regions having an amino acid sequence as set forth in Table 1), or a sequence substantially homologous thereto (e.g., a sequence at least about 85%, 90%, 95%, 99% or more identical thereto, and/or having one, two, three or more substitutions, insertions or deletions, e.g., conserved substitutions). In one embodiment, at least one, two, three, four, five or six CDR is defined according to Kabat, e.g., as shown in Table 1. In another embodiment, at least one, two, three, four, five or six CDR is defined according to Chothia, e.g., as shown in Table 1.

In one embodiment, the anti-LAG-3 antibody molecule comprises at least one, two, or three CDRs and/or hypervariable loops from a heavy chain variable region having an amino acid sequence of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum05-Ser, BAP050-hum09-Ser, BAP050-hum11-Ser, BAP050-hum12-Ser, BAP050-hum13-Ser), BAP050-Clone-F, BAP050-Clone-G, BAP050-Clone-H, BAP050-Clone-I, or BAP050-Clone-J, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In another embodiment, the anti-LAG-3 antibody molecule comprises at least one, two, or three CDRs from a light chain variable region having an amino acid sequence of an antibody described herein, e.g., an antibody chosen from any of BAP050-hum01, BAP050-hum02, BAP050-hum03, BAP050-hum04, BAP050-hum05, BAP050-hum06, BAP050-hum07, BAP050-hum08, BAP050-hum09, BAP050-hum10, BAP050-hum11, BAP050-hum12, BAP050-hum13, BAP050-hum14, BAP050-hum15, BAP050-hum16, BAP050-hum17, BAP050-hum18, BAP050-hum19, BAP050-hum20, huBAP050(Ser) (e.g., BAP050-hum01-Ser, BAP050-hum02-Ser, BAP050-hum05-Ser, BAP050-hum09-Ser, BAP050-hum11-Ser, BAP050-hum12-Ser, BAP050-hum13-Ser), BAP050-Clone-F, BAP050-Clone-G, BAP050-Clone-H, BAP050-Clone-I, or BAP050-Clone-J, as summarized in Table 1, or a sequence substantially identical thereto (e.g., a sequence at least about 85%, 90%, 95%, 99% or more identical thereto, and/or having one, two, three or more substitutions, insertions or deletions, e.g., conserved substitutions). In one embodiment, the anti-LAG-3 antibody molecule comprises all six CDRs and/or hypervariable loops described herein, e.g., described in Table 1.

In one embodiment, the anti-LAG-3 antibody molecule has a variable region that is identical in sequence, or which differs by 1, 2, 3, or 4 amino acids from a variable region described herein (e.g., an FR region disclosed herein).

In one embodiment, the anti-LAG-3 antibody molecule is a full antibody or fragment thereof (e.g., a Fab, $F(ab')_2$, Fv, or a single chain Fv fragment (scFv)). In certain embodiments, the anti-LAG-3 antibody molecule is a monoclonal antibody or an antibody with single specificity. The anti-LAG-3 antibody molecule can also be a humanized, chimeric, camelid, shark, or in vitro-generated antibody molecules. In one embodiment, the anti-LAG-3 antibody molecule thereof is a humanized antibody molecule. The heavy and light chains of the anti-LAG-3 antibody molecule can be full-length (e.g., an antibody can include at least one, and preferably two, complete heavy chains, and at least one, and preferably two, complete light chains) or can include an antigen-binding fragment (e.g., a Fab, $F(ab')_2$, Fv, a single chain Fv fragment, a single domain antibody, a diabody (dAb), a bivalent or bispecific antibody or fragment thereof, a single domain variant thereof, or a camelid antibody).

In yet other embodiments, the anti-LAG-3 antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1, IgG2 or IgG4 (e.g., human IgG1, IgG2 or IgG4). In one embodiment, the heavy chain constant region is human IgG1 or human IgG4. In another embodiment, the anti-LAG-3 antibody molecule has a light chain constant region chosen from, e.g., the light chain constant regions of kappa or lambda, preferably kappa (e.g., human kappa). In one embodiment, the constant region is altered, e.g., mutated, to modify the properties of the anti-LAG-3 antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 212 or 214; or positions 135 (M to Y), 137 (S to T), 139 (T to E), 316 (H to K) and 317 (N to F) of SEQ ID NOs: 215, 216, 217 or 218). In another embodiment, the heavy chain constant region of an IgG4, e.g., a human IgG4, is mutated at position 228 (e.g., S to P), e.g., as shown in Table 3. In certain embodiments, the anti-LAG-3 antibody molecules comprises a human IgG4 mutated at position 228 (e.g., S to P), e.g., as shown in Table 3; and a kappa light chain constant region, e.g., as shown in Table 3. In still another embodiment, the heavy chain constant region of an IgG1, e.g., a human IgG1, is mutated at one or more of position 297 (e.g., N to A), position 265 (e.g., D to A), position 329 (e.g., P to A), position 234 (e.g., L to A), or position 235 (e.g., L to A), e.g., as shown in Table 3. In certain embodiments, the anti-LAG-3 antibody molecules comprises a human IgG1 mutated at one or more of the aforesaid positions, e.g., as shown in Table 3; and a kappa light chain constant region, e.g., as shown in Table 3.

In certain embodiments, the anti-LAG-3 antibody molecule is in the form of a bispecific or a multispecific antibody molecule. In one embodiment, the bispecific antibody molecule has a first binding specificity for LAG-3 and a second binding specify for PD-1, TIM-3, CEACAM (e.g., CEACAM-1 and/or CEACAM-5), PD-L1 or PD-L2. In one embodiment, the bispecific antibody molecule binds to LAG-3 and PD-1. In another embodiment, the bispecific antibody molecule binds to LAG-3 and TIM-3. In another embodiment, the bispecific antibody molecule binds to LAG-3 and CEACAM (e.g., CEACAM-1 and/or CEACAM-5). In another embodiment, the bispecific antibody molecule binds to LAG-3 and CEACAM-1. In yet another embodiment, the bispecific antibody molecule binds to LAG-3 and CEACAM-5. In another embodiment, the bispecific antibody molecule binds to LAG-3 and PD-L1. In yet another embodiment, the bispecific antibody molecule binds to LAG-3 and PD-L2. Any combination of the aforesaid molecules can be made in a multispecific antibody molecule, e.g., a trispecific antibody that includes a first binding specificity to LAG-3, and a second and third binding specificity to one or more of: PD-1, TIM-3, CEACAM (e.g., CEACAM-1 or CEACAM-5), PD-L1 or PD-L2.

In other embodiments, the anti-LAG-3 antibody molecule is used in combination with a bispecific molecule comprising one or more of: PD-1, TIM-3, CEACAM (e.g., CEACAM-1 or CEACAM-5), PD-L1 or PD-L2. In one embodiment, the bispecific antibody molecule used in combination binds to CEACAM (e.g., CEACAM-1 and/or CEACAM-5) and PD-1. In another embodiment, the bispecific antibody molecule used in combination binds to CEACAM (e.g., CEACAM-1 and/or CEACAM-5) and TIM-3. In another embodiment, the bispecific antibody molecule used in combination binds to PD-1 and TIM-3.

In one embodiment, the anti-LAG-3 antibody molecule is isolated or recombinant.

In one embodiment, the anti-LAG-3 antibody molecule is a humanized antibody molecule.

In one embodiment, the anti-LAG-3 antibody molecule has a risk score based on T cell epitope analysis of less than 1200, 1150, 1100, 1050, 1000, 950, 900, 850, or 800.

In one embodiment, the anti-LAG-3 antibody molecule is a humanized antibody molecule and has a risk score based on T cell epitope analysis of 800 to 1200, 850 to 1150, 900 to 1100, 950 to 1050, or a risk score as described herein.

In certain embodiments, the anti-LAG-3 antibody molecule comprises:

- (i) a heavy chain variable region (VH) comprising a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3; and
- (ii) a light chain variable region (VL) comprising a VLCDR1 amino acid sequence of SEQ ID NO: 10, a VLCDR2 amino acid sequence of SEQ ID NO: 11, and a VLCDR3 amino acid sequence of SEQ ID NO: 12.

In other embodiments, the anti-LAG-3 antibody molecule comprises:

- (i) a heavy chain variable region (VH) comprising a VHCDR1 amino acid sequence chosen from SEQ ID NO: 1, SEQ ID NO: 4 or SEQ ID NO: 286; a VHCDR2 amino acid sequence of SEQ ID NO: 5, and a VHCDR3 amino acid sequence of SEQ ID NO: 3; and
- (ii) a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15.

In embodiments of the aforesaid antibody molecules, the VHCDR1 comprises the amino acid sequence of SEQ ID NO: 1. In other embodiments, the VHCDR1 comprises the amino acid sequence of SEQ ID NO: 4. In yet other embodiments, the VHCDR1 amino acid sequence of SEQ ID NO: 286.

In embodiments, the aforesaid antibody molecules have a heavy chain variable region comprising at least one framework (FW) region comprising the amino acid sequence of any of SEQ ID NOs: 187, 190, 194, 196, 198, 202, 206, 208, 210, 212, 217, 219, or 221, or an amino acid sequence at least 90% identical thereto, or having no more than two amino acid substitutions, insertions or deletions compared to the amino acid sequence of any of SEQ ID NOs: 187, 190, 194, 196, 198, 202, 206, 208, 210, 212, 217, 219, or 221.

In other embodiments, the aforesaid antibody molecules have a heavy chain variable region comprising at least one framework region comprising the amino acid sequence of any of SEQ ID NOs: 187, 190, 194, 196, 198, 202, 206, 208, 210, 212, 217, 219, or 221.

In yet other embodiments, the aforesaid antibody molecules have a heavy chain variable region comprising at least two, three, or four framework regions comprising the amino acid sequences of any of SEQ ID NOs: 187, 190, 194, 196, 198, 202, 206, 208, 210, 212, 217, 219, or 221.

In other embodiments, the aforesaid antibody molecules comprise a VHFW1 amino acid sequence of SEQ ID NO: 187, 190, 194, or 196, a VHFW2 amino acid sequence of SEQ ID NO: 198, 202, 206, or 208, and a VHFW3 amino acid sequence of SEQ ID NO: 210, 212, 217, or 219, and, optionally, further comprising a VHFW4 amino acid sequence of SEQ ID NO: 221.

In other embodiments, the aforesaid antibody molecules have a light chain variable region comprising at least one framework region comprising the amino acid sequence of any of SEQ ID NOs: 226, 230, 232, 234, 236, 238, 240, 244, 246, 248, 252, 255, 259, 261, 265, 267, 269, or 271, or an amino acid sequence at least 90% identical thereto, or having no more than two amino acid substitutions, insertions or deletions compared to the amino acid sequence of any of 226, 230, 232, 234, 236, 238, 240, 244, 246, 248, 252, 255, 259, 261, 265, 267, 269, or 271.

In other embodiments, the aforesaid antibody molecules have a light chain variable region comprising at least one framework region comprising the amino acid sequence of any of SEQ ID NOs: 226, 230, 232, 234, 236, 238, 240, 244, 246, 248, 252, 255, 259, 261, 265, 267, 269, or 271.

In other embodiments, the aforesaid antibody molecules have a light chain variable region comprising at least two, three, or four framework regions comprising the amino acid sequences of any of SEQ ID NOs: 226, 230, 232, 234, 236, 238, 240, 244, 246, 248, 252, 255, 259, 261, 265, 267, 269, or 271.

In other embodiments, the aforesaid antibody molecules comprise a VLFW1 amino acid sequence of SEQ ID NO: 226, 230, 232, 234, 236, or 2385, a VLFW2 amino acid sequence of SEQ ID NO: 240, 244, 246, or 248, and a VLFW3 amino acid sequence of SEQ ID NO: 252, 255, 259, 261, 265, 267, or 269, and, optionally, further comprising a VLFW4 amino acid sequence of SEQ ID NO: 271.

In other embodiments, the aforesaid antibody molecules comprise a heavy chain variable domain comprising an amino acid sequence at least 85% identical to any of SEQ ID NOs: 8, 28, 64, 68, 72, 76, 80, 100, 104, or 108.

In other embodiments, the aforesaid antibody molecules comprise a heavy chain variable domain comprising the amino acid sequence of SEQ ID NO: 8, 28, 64, 68, 72, 76, 80, 100, 104, or 108.

In other embodiments, the aforesaid antibody molecules comprise a light chain variable domain comprising an amino acid sequence at least 85% identical to any of SEQ ID NOs: 32, 36, 40, 44, 48, 52, 56, 60, 84, 88, 92, or 96.

In other embodiments, the aforesaid antibody molecules comprise a light chain variable domain comprising the amino acid sequence of SEQ ID NO: 32, 36, 40, 44, 48, 52, 56, 60, 84, 88, 92, or 96.

In other embodiments, the aforesaid antibody molecules comprise a heavy chain variable domain comprising the amino acid sequence of SEQ ID NO: 8.

In other embodiments, the aforesaid antibody molecules comprise a heavy chain comprising the amino acid sequence of SEQ ID NO: 18.

In other embodiments, the aforesaid antibody molecules comprise a heavy chain variable domain comprising the amino acid sequence of SEQ ID NO: 28.

In other embodiments, the aforesaid antibody molecules comprise a heavy chain comprising the amino acid sequence of SEQ ID NO: 30.

In other embodiments, the aforesaid antibody molecules comprise a heavy chain variable domain comprising the amino acid sequence of SEQ ID NO: 64.

In other embodiments, the aforesaid antibody molecules comprise a heavy chain comprising the amino acid sequence of SEQ ID NO: 66.

In other embodiments, the aforesaid antibody molecules comprise a heavy chain variable domain comprising the amino acid sequence of SEQ ID NO: 68.

In other embodiments, the aforesaid antibody molecules comprise a heavy chain comprising the amino acid sequence of SEQ ID NO: 70.

In other embodiments, the aforesaid antibody molecules comprise a heavy chain variable domain comprising the amino acid sequence of SEQ ID NO: 72.

In other embodiments, the aforesaid antibody molecules comprise a heavy chain comprising the amino acid sequence of SEQ ID NO: 74.

In other embodiments, the aforesaid antibody molecules comprise a heavy chain variable domain comprising the amino acid sequence of SEQ ID NO: 76.

In other embodiments, the aforesaid antibody molecules comprise a heavy chain comprising the amino acid sequence of SEQ ID NO: 78.

In other embodiments, the aforesaid antibody molecules comprise a heavy chain variable domain comprising the amino acid sequence of SEQ ID NO: 80.

In other embodiments, the aforesaid antibody molecules comprise a heavy chain comprising the amino acid sequence of SEQ ID NO: 82.

In other embodiments, the aforesaid antibody molecules comprise a heavy chain variable domain comprising the amino acid sequence of SEQ ID NO: 100.

In other embodiments, the aforesaid antibody molecules comprise a heavy chain comprising the amino acid sequence of SEQ ID NO: 102 or SEQ ID NO: 113.

In other embodiments, the aforesaid antibody molecules comprise a heavy chain variable domain comprising the amino acid sequence of SEQ ID NO: 104.

In other embodiments, the aforesaid antibody molecules comprise a heavy chain comprising the amino acid sequence of SEQ ID NO: 106.

In other embodiments, the aforesaid antibody molecules comprise a heavy chain comprising the amino acid sequence of SEQ ID NO: 122.

In other embodiments, the aforesaid antibody molecules comprise a heavy chain variable domain comprising the amino acid sequence of SEQ ID NO: 108.

In other embodiments, the aforesaid antibody molecules comprise a heavy chain comprising the amino acid sequence of SEQ ID NO: 110.

In other embodiments, the aforesaid antibody molecules comprise a heavy chain comprising the amino acid sequence of SEQ ID NO: 134.

In other embodiments, the aforesaid antibody molecules comprise a light chain variable domain comprising the amino acid sequence of SEQ ID NO: 32.

In other embodiments, the aforesaid antibody molecules comprise a light chain comprising the amino acid sequence of SEQ ID NO: 34.

In other embodiments, the aforesaid antibody molecules comprise a light chain variable domain comprising the amino acid sequence of SEQ ID NO: 36.

In other embodiments, the aforesaid antibody molecules comprise a light chain comprising the amino acid sequence of SEQ ID NO: 38.

In other embodiments, the aforesaid antibody molecules comprise a light chain variable domain comprising the amino acid sequence of SEQ ID NO: 40.

In other embodiments, the aforesaid antibody molecules comprise a light chain comprising the amino acid sequence of SEQ ID NO: 42.

In other embodiments, the aforesaid antibody molecules comprise a light chain variable domain comprising the amino acid sequence of SEQ ID NO: 44.

In other embodiments, the aforesaid antibody molecules comprise a light chain comprising the amino acid sequence of SEQ ID NO: 46.

In other embodiments, the aforesaid antibody molecules comprise a light chain variable domain comprising the amino acid sequence of SEQ ID NO: 48.

In other embodiments, the aforesaid antibody molecules comprise a light chain comprising the amino acid sequence of SEQ ID NO: 50.

In other embodiments, the aforesaid antibody molecules comprise a light chain variable domain comprising the amino acid sequence of SEQ ID NO: 52.

In other embodiments, the aforesaid antibody molecules comprise a light chain comprising the amino acid sequence of SEQ ID NO: 54.

In other embodiments, the aforesaid antibody molecules comprise a light chain variable domain comprising the amino acid sequence of SEQ ID NO: 56.

In other embodiments, the aforesaid antibody molecules comprise a light chain comprising the amino acid sequence of SEQ ID NO: 58.

In other embodiments, the aforesaid antibody molecules comprise a light chain variable domain comprising the amino acid sequence of SEQ ID NO: 60.

In other embodiments, the aforesaid antibody molecules comprise a light chain comprising the amino acid sequence of SEQ ID NO: 62.

In other embodiments, the aforesaid antibody molecules comprise a light chain variable domain comprising the amino acid sequence of SEQ ID NO: 84.

In other embodiments, the aforesaid antibody molecules comprise a light chain comprising the amino acid sequence of SEQ ID NO: 86.

In other embodiments, the aforesaid antibody molecules comprise a light chain variable domain comprising the amino acid sequence of SEQ ID NO: 88.

In other embodiments, the aforesaid antibody molecules comprise a light chain comprising the amino acid sequence of SEQ ID NO: 90.

In other embodiments, the aforesaid antibody molecules comprise a light chain variable domain comprising the amino acid sequence of SEQ ID NO: 92.

In other embodiments, the aforesaid antibody molecules comprise a light chain comprising the amino acid sequence of SEQ ID NO: 94.

In other embodiments, the aforesaid antibody molecules comprise a light chain variable domain comprising the amino acid sequence of SEQ ID NO: 96.

In other embodiments, the aforesaid antibody molecules comprise a light chain comprising the amino acid sequence of SEQ ID NO: 98.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 32.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 36.

In other embodiments, the aforesaid antibody molecules comprise a heavy chain variable domain comprising the amino acid sequence of SEQ ID NO: 28 or SEQ ID NO: 100;

and a light chain variable domain comprising the amino acid sequence of SEQ ID NO: 40.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 44.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 48.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 52.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 56.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 60.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 36.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 40.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 56.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 60.

In other embodiments, the aforesaid antibody molecules comprise a heavy chain variable domain comprising the amino acid sequence of SEQ ID NO: 68 or SEQ ID NO: 108; and a light chain variable domain comprising the amino acid sequence of SEQ ID NO: 36.

In other embodiments, the aforesaid antibody molecules comprise a heavy chain variable domain comprising the amino acid sequence of SEQ ID NO: 72 or SEQ ID NO: 8; and a light chain variable domain comprising the amino acid sequence of SEQ ID NO: 40.

In other embodiments, the aforesaid antibody molecules comprise a heavy chain variable domain comprising the amino acid sequence of SEQ ID NO: 72 or SEQ ID NO: 8; and a light chain variable domain comprising the amino acid sequence of SEQ ID NO: 60.

In other embodiments, the aforesaid antibody molecules comprise a heavy chain variable domain comprising the amino acid sequence of SEQ ID NO: 76 and a light chain variable domain comprising the amino acid sequence of SEQ ID NO: 60.

In other embodiments, the aforesaid antibody molecules comprise a heavy chain variable domain comprising the amino acid sequence of SEQ ID NO: 80 and a light chain variable domain comprising the amino acid sequence of SEQ ID NO: 84.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 88.

In other embodiments, the aforesaid antibody molecules comprise a heavy chain variable domain comprising the amino acid sequence of SEQ ID NO: 28 or SEQ ID NO: 100; and a light chain variable domain comprising the amino acid sequence of SEQ ID NO: 92.

In other embodiments, the aforesaid antibody molecules comprise a heavy chain variable domain comprising the amino acid sequence of SEQ ID NO: 64 or SEQ ID NO: 104; and a light chain variable domain comprising the amino acid sequence of SEQ ID NO: 96.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 34.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 38.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 42.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 46.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 50.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 54.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 58.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 62.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 38.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 42.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 58.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 62.

In other embodiments, the aforesaid antibody molecules comprise a heavy chain comprising the amino acid sequence of SEQ ID NO: 70 or SEQ ID NO: 110; and a light chain comprising the amino acid sequence of SEQ ID NO: 38.

In other embodiments, the aforesaid antibody molecules comprise a heavy chain comprising the amino acid sequence of SEQ ID NO: 74 or SEQ ID NO: 18; and a light chain comprising the amino acid sequence of SEQ ID NO: 42.

In other embodiments, the aforesaid antibody molecules comprise a heavy chain comprising the amino acid sequence of SEQ ID NO: 74 or SEQ ID NO: 18; and a light chain comprising the amino acid sequence of SEQ ID NO: 62.

In other embodiments, the aforesaid antibody molecules comprise a heavy chain comprising the amino acid sequence of SEQ ID NO: 78 and a light chain comprising the amino acid sequence of SEQ ID NO: 62.

In other embodiments, the aforesaid antibody molecules comprise a heavy chain comprising the amino acid sequence of SEQ ID NO: 82 and a light chain comprising the amino acid sequence of SEQ ID NO: 86.

In other embodiments, the aforesaid antibody molecules comprise a heavy chain comprising the amino acid sequence of SEQ ID NO: 30 or SEQ ID NO: 102; and a light chain comprising the amino acid sequence of SEQ ID NO: 94.

In other embodiments, the aforesaid antibody molecules comprise a heavy chain comprising the amino acid sequence of SEQ ID NO: 66 or SEQ ID NO: 106; and a light chain comprising the amino acid sequence of SEQ ID NO: 98.

In other embodiments, the aforesaid antibody molecules comprise a heavy chain comprising the amino acid sequence of SEQ ID NO: 113 and a light chain comprising the amino acid sequence of SEQ ID NO: 34.

In other embodiments, the aforesaid antibody molecules comprise a heavy chain comprising the amino acid sequence of SEQ ID NO: 113 and a light chain comprising the amino acid sequence of SEQ ID NO: 38.

In other embodiments, the aforesaid antibody molecules comprise a heavy chain comprising the amino acid sequence of SEQ ID NO: 122 and a light chain comprising the amino acid sequence of SEQ ID NO: 38.

In other embodiments, the aforesaid antibody molecules comprise a heavy chain comprising the amino acid sequence of SEQ ID NO: 122 and a light chain comprising the amino acid sequence of SEQ ID NO: 58.

In other embodiments, the aforesaid antibody molecules comprise a heavy chain comprising the amino acid sequence of SEQ ID NO: 134 and a light chain comprising the amino acid sequence of SEQ ID NO: 38.

In other embodiments, the aforesaid antibody molecules are chosen from a Fab, F(ab')2, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules comprise a light chain constant region chosen from the light chain constant regions of kappa or lambda.

In other embodiments, the aforesaid antibody molecules comprise a human IgG4 heavy chain constant region with a mutation at position 228 according to EU numbering or position 108 of SEQ ID NO: 275 or 277 and a kappa light chain constant region.

In other embodiments, the aforesaid antibody molecules comprise a human IgG4 heavy chain constant region with a Serine to Proline mutation at position 228 according to EU numbering or position 108 of SEQ ID NO: 275 or 277 and a kappa light chain constant region.

In other embodiments, the aforesaid antibody molecules comprise a human IgG1 heavy chain constant region with an Asparagine to Alanine mutation at position 297 according to EU numbering or position 180 of SEQ ID NO: 279 and a kappa light chain constant region.

In other embodiments, the aforesaid antibody molecules comprise a human IgG1 heavy chain constant region with an Aspartate to Alanine mutation at position 265 according to EU numbering or position 148, and Proline to Alanine mutation at position 329 according to EU numbering or position 212 of SEQ ID NO: 280 and a kappa light chain constant region.

In other embodiments, the aforesaid antibody molecules comprise a human IgG1 heavy chain constant region with a Leucine to Alanine mutation at position 234 according to EU numbering or position 117 and Leucine to Alanine mutation at position 235 according to EU numbering or position 118 of SEQ ID NO: 281 and a kappa light chain constant region.

In other embodiments, the aforesaid antibody molecules are capable of binding to human LAG-3 with a dissociation constant ($K_D$) of less than about 0.2 nM.

In some embodiments, the aforesaid antibody molecules bind to human LAG-3 with a $K_D$ of less than about 0.2 nM, 0.15 nM, 0.1 nM, 0.05 nM, or 0.02 nM, e.g., about 0.05 nM to 0.15 nM, e.g., about 0.11 nM, e.g., as measured by a Biacore method.

In other embodiments, the aforesaid antibody molecules bind to cynomolgus LAG-3 with a $K_D$ of less than about 0.2 nM, 0.15 nM, 0.1 nM, 0.05 nM, or 0.02 nM, e.g., about 0.05 nM to 0.15 nM, e.g., as measured by a Biacore method.

In certain embodiments, the aforesaid antibody molecules bind to both human LAG-3 and cynomolgus LAG-3 with similar $K_D$, e.g., in the nM range, e.g., as measured by a Biacore method. In some embodiments, the aforesaid antibody molecules bind to a human LAG-3-Ig fusion protein with a $K_D$ of less than about 0.5 nM, 0.2 nM, 0.1 nM, 0.05 nM, 0.025 nM, or 0.01 nM, e.g., as measured by ELISA.

In some embodiments, the aforesaid antibody molecules bind to CHO cells that express human LAG-3 (e.g., human LAG-3-transfected CHO cells) with a $K_D$ of less than about 4 nM, 2.5 nM, 2 nM, 1.5 nM, 1 nM, 0.75 nM, 0.5 nM, 0.4 nM, 0.3 nM, 0.2 nM, 0.1 nM, or 0.05 nM, e.g., about 2.3, 1.92 nM or about 0.2 nM, e.g., as measured by FACS analysis.

In some embodiments, the aforesaid antibody molecules bind to human T cells with a $K_D$ of less than about 0.5 nM, 0.4 nM, 0.3 nM, 0.2 nM, 0.1 nM, or 0.05 nM, e.g., about 0.26 nM, e.g., as measured by FACS analysis.

In some embodiments, the aforesaid antibody molecules bind to cells that express LAG-3 (e.g., human LAG-3-expressing 300.19 cells) with a $K_D$ of less than about 20 nM, 15 nM, 10 nM, 5 nM, 2 nM, or 1 nM, e.g., about 13.6 nM, e.g., as measured by FACS analysis.

In some embodiments, the aforesaid antibody molecules bind to cells that express rhesus LAG-3 (e.g., cells transfected with rhesus LAG-3) with a $K_D$ of less than about 15 nM, 10 nM, 9 nM, 8 nM, 6 nM, 5 nM, 2 nM, or 1 nM, e.g., about 8.03 nM, e.g., as measured by FACS analysis.

In certain embodiments, the aforesaid antibody molecules are not cross-reactive with mouse LAG-3. In some embodiments, the aforesaid antibodies are not cross-reactive with rat LAG-3. In other embodiments, the aforesaid antibodies are cross-reactive with rhesus LAG-3. In some embodiments, the aforesaid antibodies are cross-reactive with rat LAG-3. For example, the cross-reactivity can be measured by a Biacore method or a binding assay using cells that expresses LAG-3 (e.g., human LAG-3-expressing 300.19 cells).

In other embodiments, the aforesaid antibody molecules bind an extracellular Ig-like domain of LAG-3 (e.g., human LAG-3), e.g., any of Domain 1 (D1), Domain 2 (D2), Domain 3 (D3), or Domain 4 (D4). In some embodiments, the aforesaid antibody molecules bind one or more amino acid residues in D1. In some embodiments, the aforesaid antibody molecules do not bind the extra loop of D1 or a fragment thereof (e.g., as measured by a Biacore method or a FACS method). In some embodiments, the aforesaid antibodies do not bind D2. In some embodiments, the aforesaid antibody molecules bind both D1 and D2. In some embodiments, the aforesaid antibody molecules bind one or more amino acid residues in D1 and/or D2 that bind an MHC class II molecule. In other embodiments, the aforesaid antibody molecules are capable of reducing binding of LAG-3 to a major histocompatibility (MHC) class II molecule, or a cell that expresses an MHC class II molecule. In some embodiments, the aforesaid antibody molecules reduce (e.g., block) LAG-3-Ig binding to a MHC class II molecule, e.g., on Raji cells or Daudi cells, with an $IC_{50}$ of less than about 10 nM, 8 nM, 5 nM, 4 nM, 3 nM, 2 nM, 1 nM, or 0.5 nM, e.g., between about 8 nM and about 10 nM or between about 2 nM and about 3 nM, e.g., about 5.5 nM or about 2.3 nM.

In other embodiments, the aforesaid antibody molecules are capable of enhancing an antigen-specific T cell response.

In embodiments, the antibody molecule is a monospecific antibody molecule or a bispecific antibody molecule. In embodiments, the antibody molecule has a first binding specificity for LAG-3 and a second binding specify for PD-1, TIM-3, CEACAM (e.g., CEACAM-1 and/or CEACAM-5), PD-L1 or PD-L2. In embodiments, the antibody molecule comprises an antigen binding fragment of an antibody, e.g., a half antibody or antigen binding fragment of a half antibody.

In some embodiments, the aforesaid antibody molecules increase the expression of IL-2 from cells activated by Staphylococcal enterotoxin B (SEB) (e.g., at 25 μg/mL) by at least about 2, 3, 4, 5-fold, e.g., about 2 to 3-fold, compared to the expression of IL-2 when an isotype control (e.g., IgG4) is used, e.g., as measured in a SEB T cell activation assay or a human whole blood ex vivo assay.

In some embodiments, the aforesaid antibody molecules increase the expression of IFN-γ from T cells stimulated by anti-CD3 (e.g., at 0.1 μg/mL) by at least about 0.5, 1, 2, 3, 4, 5, 6, 7, or 8-fold, e.g., about 0.9 to 5.1-fold, e.g., about 3-fold, compared to the expression of IFN-γ when an isotype control (e.g., IgG4) is used, e.g., as measured in an IFN-γ activity assay.

In some embodiments, the aforesaid antibody molecules increase the expression of IFN-γ from T cells activated by SEB (e.g., at 3 pg/mL) by at least about 2, 3, 4, 5-fold, e.g., about 1.2 to 2-fold, e.g., about 1.6-fold, compared to the expression of IFN-γ when an isotype control (e.g., IgG4) is used, e.g., as measured in an IFN-γ activity assay.

In some embodiments, the aforesaid antibody molecules do not increase the expression of IL-2 or IFN-γ without T cell receptor activation (e.g. in the absence of SEB).

In some embodiments, the aforesaid antibody molecules increase the expression of IFN-γ from T cells activated with an CMV peptide by at least about 2, 3, 4, 5-fold, e.g., about 1.1 to 1.7-fold, e.g., about 1.4-fold, compared to the expression of IFN-γ when an isotype control (e.g., IgG4) is used, e.g., as measured in an IFN-γ activity assay. In some embodiments, the aforesaid antibody molecules increase the proliferation of $CD8^+$ T cells activated with an CMV peptide by at least about 1, 2, 3, 4, 5-fold, e.g., about 1.5-fold, compared to the proliferation of $CD8^+$ T cells when an isotype control (e.g., IgG4) is used, e.g., as measured by the percentage of CD8+ T cells that passed through at least n (e.g., n=2 or 4) cell divisions.

In certain embodiments, the aforesaid antibody molecules has a Cmax between about 50 μg/mL and about 400 μg/mL, between about 100 μg/mL and about 350 μg/mL, between about 150 μg/mL and about 300 μg/mL, or between about 200 μg/mL and about 250 μg/mL, e.g., about 166 μg/mL, e.g., as measured in an animal.

In certain embodiments, the aforesaid antibody molecules has a $T_{1/2}$ between about 50 hours and about 400 hours, between about 100 hours and about 350 hours, between about 150 hours and about 300 hours, or between about 200 hours and about 250 hours, e.g., about 231.9 hours, e.g., as measured in an animal.

In some embodiments, the aforesaid antibody molecules bind to LAG-3 with a Kd slower than $5\times10^{4}$, $1\times10^{4}$, $5\times10^{-5}$, or $1\times10^{-5}$ $s^{-1}$, e.g., about $7\times10^{-5}$ $s^{-1}$, e.g., as measured by a Biacore method. In some embodiments, the aforesaid antibodies bind to LAG-3 with a Ka faster than $1\times10^{4}$, $5\times10^{4}$, $1\times10^{5}$, $5\times10^{5}$, or $1\times10^{6}$ $M^{-1}S^{-1}$, e.g., about $6.41\times10^{5}$ $M^{-1}s^{-1}$, e.g., as measured by a Biacore method.

In another aspect, the invention provides an isolated nucleic acid molecule encoding any of the aforesaid antibody molecules, vectors and host cells thereof.

In one embodiment, the isolated nucleic acid encodes the antibody heavy chain variable region or light chain variable region, or both, of any the aforesaid antibody molecules.

In one embodiment, the isolated nucleic acid encodes heavy chain CDRs 1-3, wherein said nucleic acid comprises a nucleotide sequence of SEQ ID NO: 140-144, 151-155, 162-166, 173-177, 184-186, or 287.

In another embodiment, the isolated nucleic acid encodes light chain CDRs 1-3, wherein said nucleic acid comprises a nucleotide sequence of SEQ ID NO: 145-150, 156-161, 167-172, or 178-183.

In other embodiments, the aforesaid nucleic acid further comprises a nucleotide sequence encoding a heavy chain variable domain, wherein said nucleotide sequence is at least 85% identical to any of SEQ ID NO: 9, 29, 65, 69, 73, 77, 81, 101, 105, 109, 112, 121, 124, 125, 132, or 133.

In other embodiments, the aforesaid nucleic acid further comprises a nucleotide sequence encoding a heavy chain variable domain, wherein said nucleotide sequence comprises any of SEQ ID NO: 9, 29, 65, 69, 73, 77, 81, 101, 105, 109, 112, 121, 124, 125, 132, or 133.

In other embodiments, the aforesaid nucleic acid further comprises a nucleotide sequence encoding a heavy chain, wherein said nucleotide sequence is at least 85% identical to any of SEQ ID NO: 19, 31, 67, 71, 75, 79, 83, 103, 107, 111, 114, 123, 126, 127, 135, or 136.

In other embodiments, the aforesaid nucleic acid further comprises a nucleotide sequence encoding a heavy chain, wherein said nucleotide sequence comprises any of SEQ ID NO: 19, 31, 67, 71, 75, 79, 83, 103, 107, 111, 114, 123, 126, 127, 135, or 136.

In other embodiments, the aforesaid nucleic acid further comprises a nucleotide sequence encoding a light chain variable domain, wherein said nucleotide sequence is at least 85% identical to any of SEQ ID NO: 33, 37, 41, 45, 49, 53, 57, 61, 85, 89, 93, 97, 115, 118, 128, 129, or 137.

In other embodiments, the aforesaid nucleic acid further comprises a nucleotide sequence encoding a light chain variable domain, wherein said nucleotide sequence comprises any of SEQ ID NO: 33, 37, 41, 45, 49, 53, 57, 61, 85, 89, 93, 97, 115, 118, 128, 129, or 137.

In other embodiments, the aforesaid nucleic acid further comprises a nucleotide sequence encoding a light chain, wherein said nucleotide sequence is at least 85% identical to any of SEQ ID NO: 35, 39, 43, 47, 51, 55, 59, 63, 87, 91, 95, 99, 117, 120, 130, 131, 138, or 139.

In other embodiments, the aforesaid nucleic acid further comprises a nucleotide sequence encoding a light chain, wherein said nucleotide sequence comprises any of SEQ ID NO: 35, 39, 43, 47, 51, 55, 59, 63, 87, 91, 95, 99, 117, 120, 130, 131, 138, or 139.

In certain embodiments, one or more expression vectors and host cells comprising the aforesaid nucleic acids are provided.

A method of producing an antibody molecule or fragment thereof, comprising culturing the host cell as described herein under conditions suitable for gene expression is also provided.

In one aspect, the invention features a method of providing an antibody molecule described herein. The method includes: providing a LAG-3 antigen (e.g., an antigen comprising at least a portion of a LAG-3 epitope); obtaining an antibody molecule that specifically binds to the LAG-3 polypeptide; and evaluating if the antibody molecule specifically binds to the LAG-3 polypeptide, or evaluating efficacy of the antibody molecule in modulating, e.g., inhibiting, the activity of the LAG-3. The method can further include administering the antibody molecule to a subject, e.g., a human or non-human animal.

In another aspect, the invention provides, compositions, e.g., pharmaceutical compositions, which include a pharmaceutically acceptable carrier, excipient or stabilizer, and at least one of the therapeutic agents, e.g., anti-LAG-3 antibody molecules described herein. In one embodiment, the composition, e.g., the pharmaceutical composition, includes a combination of the antibody molecule and one or more agents, e.g., a therapeutic agent or other antibody molecule, as described herein. In one embodiment, the antibody molecule is conjugated to a label or a therapeutic agent.

Additional Inhibitors of LAG-3

In one embodiment, a combination described herein includes a LAG-3 inhibitor. In some embodiments, the LAG-3 inhibitor is an anti-LAG-3 antibody molecule other than the anti-LAG-3 antibody molecule of Table 1. In certain embodiments, the LAG-3 inhibitor comprises an anti-LAG-3 antibody molecule of Table 1 and an anti-LAG-3 antibody molecule other than the antibody molecule of Table 1. In some embodiments, the combination is used to treat a cancer, e.g., a cancer described herein, e.g., a solid tumor or a hematologic malignancy.

In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218

Exemplary CSF-1/1R Binding Agents

In one embodiment, a combination described herein includes a CSF-1/1R binding agent. In some embodiments, the combination is used to treat a cancer, e.g., a cancer described herein, e.g., a solid tumor (e.g., a prostate cancer, a breast cancer, or pigmented villonodular synovitis (PVNS)). In some embodiments, the cancer is a brain cancer (e.g., a glioblastoma multiforme), a pancreatic cancer, an ovarian cancer, or a breast cancer (e.g., a triple negative breast cancer).

In some embodiments, the CSF-1/1R binding agent is an inhibitor of macrophage colony-stimulating factor (M-CSF).

In another embodiment, the CSF-1/1R binding agent is a CSF-1R tyrosine kinase inhibitor, 44(2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224.

In some embodiments, the CSF-1/1R binding agent is an M-CSF inhibitor, Compound A33, or a binding agent to CSF-1 disclosed in PCT Publication No. WO 2004/045532 or PCT Publication No. WO 2005/068503 including RX1 or 5H4 (e.g., an antibody molecule or Fab fragment against M-CSF).

In some embodiments, the CSF-1/1R binding agent, e.g., an M-CSF inhibitor, Compound A33, or a compound disclosed in PCT Publication No. WO 2004/045532 (e.g., an antibody molecule or Fab fragment against M-CSF), is administered at an average dose of about 10 mg/kg.

In some embodiments, the CSF-1/1R binding agent is a CSF1R inhibitor or 4-(24(1R, 2R)-2-hydroxycyclohexylamino)benzothiazol-6-yloxy)-N-methylpicolinamide. 4-(2-((1R, 2R)-2-hydroxycyclohexylamino)benzothiazol-6-yloxy)-N-methylpicolinamide is disclosed as example 157 at page 117 of PCT Publication No. WO 2007/121484.

In some embodiments, the CSF-1/1R binding agent is pexidartinib (CAS Registry Number 1029044-16-3). Pexidrtinib is also known as PLX3397 or 54(5-chloro-1H-pyrrolo[2,3-b]pyridin-3-yl)methyl)-N-((6-(trifluoromethyl)pyridin-3-yl)methyl)pyridin-2-amine. Pexidartinib is a small-molecule receptor tyrosine kinase (RTK) inhibitor of KIT, CSF1R and FLT3. FLT3, CSF1R and FLT3 are overexpressed or mutated in many cancer cell types and play major roles in tumor cell proliferation and metastasis. PLX3397 can bind to and inhibit phosphorylation of stem cell factor receptor (KIT), colony-stimulating factor-1 receptor (CSF1R) and FMS-like tyrosine kinase 3 (FLT3), which may result in the inhibition of tumor cell proliferation and down-modulation of macrophages, osteoclasts and mast cells involved in the osteolytic metastatic disease. In some embodiments, the CSF-1/1R binding agent, e.g., pexidartinib, is used in combination with a PD-1 inhibitor, e.g., an anti-PD-1 antibody molecule described herein.

In some embodiments, the CSF-1/1R binding agent is emactuzumab. Emactuzumab is also known as RG7155 or R05509554. Emactuzumab is a humanized IgG1 mAb targeting CSF1R. In some embodiments, the CSF-1/1R binding agent, e.g., pexidartinib, is used in combination with a PD-L1 inhibitor, e.g., an anti-PD-L1 antibody molecule described herein. In some embodiments, the CSF-1/1R binding agent is FPA008. FPA008 is a humanized mAb that inhibits CSF1R. In some embodiments, the CSF-1/1R binding agent, e.g., FPA008, is used in combination with a PD-1 inhibitor, e.g., an anti-PD-1 antibody molecule described herein.

Exemplary IL-17 Inhibitors

In one embodiment, a combination described herein includes an interleukine-17 (IL-17) inhibitor. In some embodiments, the combination is used to treat a cancer, e.g., a cancer described herein, e.g., a solid tumor, e.g., breast cancer (e.g., a triple negative breast cancer), lung cancer (e.g., a non-small cell lung cancer), or colon cancer.

In some embodiments, the IL-17 inhibitor is secukinumab (CAS Registry Numbers: 875356-43-7 (heavy chain) and 875356-44-8 (light chain)). Secukinumab is also known as AIN457 and COSENTYX®. Secukinumab is a recombinant human monoclonal IgG1/κ antibody that binds specifically to IL-17A. It is expressed in a recombinant Chinese Hamster Ovary (CHO) cell line.

Secukinumab is described, e.g., in WO 2006/013107, U.S. Pat. Nos. 7,807,155, 8,119,131, 8,617,552, and EP 1776142. The heavy chain variable region of secukinumab has the amino acid sequence of: EVQLVESGG-GLVQPGGSLRLSCAASGFTFSNYWMNWVRQAPGK-GLEWVAAINQDGSE KYYVGSVKGRFTISRDNAKNS-LYLQMNSLRVEDTAVYYCVRDYYDILTDYYIHYWYFD LWGRGTLVTVSS (SEQ ID NO: 328) (disclosed as SEQ ID NO: 8 in WO 2006/013107). The light chain variable region of secukinumab has the amino acid sequence of: EIVLTQSPGTLSLSPGERATLSCRASQSVSSSY-LAWYQQKPGQAPRLLIYGASSRATGIPD RFSGSGSGTDFTLTISRLEPED-FAVYYCQQYGSSPCTFGQGTRLEIKR (SEQ ID NO: 329) (disclosed as SEQ ID NO: 10 in WO 2006/013107). The heavy chain CDR1 of secukinumab has the amino acid sequence of NYWMN (SEQ ID NO: 330) (disclosed as SEQ ID NO: 1 in WO 2006/013107). The heavy chain CDR2 of secukinumab has the amino acid sequence of AINQDGSEKYYVGSVKG (SEQ ID NO: 331) (disclosed as SEQ ID NO: 2 in WO 2006/013107). The heavy chain CDR3 of secukinumab has the amino acid sequence of DYYDILTDYYIHYWYFDL (SEQ ID NO: 332) (disclosed as SEQ ID NO: 3 in WO 2006/013107). The light chain CDR1 of secukinumab has the amino acid sequence of RASQSVSSSYLA (SEQ ID NO: 333) (disclosed as SEQ ID NO: 4 in WO 2006/013107). The light chain CDR2 of secukinumab has the amino acid sequence of GASSRAT (SEQ ID NO: 334) (disclosed as SEQ ID NO: 5 in WO 2006/013107). The light chain CDR3 of secukinumab has the amino acid sequence of QQYGSSPCT (SEQ ID NO: 335) (disclosed as SEQ ID NO: 6 in WO 2006/013107).

In some embodiments, the IL-17 inhibitor is CJM112. CJM112 is also known as XAB4. CJM112 is a fully human monoclonal antibody that targets IL-17A.

CJM112 is disclosed, e.g., in WO 2014/122613. The heavy chain of CJM112 has the amino acid sequence of:

```
                                   (SEQ ID NO: 336)
EVQLVESGGDLVQPGGSLRLSCAASGFTFSSYWMS

WVRQAPGKGLEWVANIKQDGSEKYYVDSVKGRFTI

SRDNAKNSLYLQMNSLRAEDTAVYYCARDRGSLYY

WGQGTLVTVSSASTKGPSVFPLAPSSKSTSGGTAA

LGCLVKDYFPEPVTVSWNSGALTSGVHTFPAVLQS

SGLYSLSSVVTVPSSSLGTQTYICNVNHKPSNTKV

DKRVEPKSCDKTHTCPPCPAPELLGGPSVFLFPPK

PKDTLMISRTPEVTCVVVDVSHEDPEVKFNWYVDG

VEVHNAKTKPREEQYNSTYRVVSVLTVLHQDWLNG

KEYKCKVSNKALPAPIEKTISKAKGQPREPQVYTL

PPSREEMTKNQVSLTCLVKGFYPSDIAVEWESNGQ

PENNYKTTPPVLDSDGSFFLYSKLTVDKSRWQQGN

VFSCSVMHEALHNHYTQKSLSLSPGK
(disclosed as SEQ ID NO: 14 in
WO 2014/122613).
```

-continued

```
The light chain of CJM112 has
the amino acid sequence of:
                                   (SEQ ID NO: 337)
AIQLTQSPSSLSASVGDRVTITCRPSQGINWELAW

YQQKPGKAPKLLIYDASSLEQGVPSRFSGSGSGTD

FTLTISSLQPEDFATYYCQQFNSYPLTFGGGTKVE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC
(disclosed as SEQ ID NO: 44
in WO 2014/122613).
```

In some embodiments, the IL-17 inhibitor is ixekizumab (CAS Registry Number: 1143503-69-8). Ixekizumab is also known as LY2439821. Ixekizumab is a humanized IgG4 monoclonal antibody that targets IL-17A.

Ixekizumab is described, e.g., in WO 2007/070750, U.S. Pat. Nos. 7,838,638, and 8,110,191.

```
The heavy chain variable region of
ixekizumab has the amino acid
sequence of:
                                   (SEQ iD NO: 338)
QVQLVQSGAEVKKPGSSVKVSCKASGYSFTDYHIH

WVRQAPGQGLEWMGVINPMYGTTDYNQRFKGRVTI

TADESTSTAYMELSSLRSEDTAVYYCARYDYFTGT

GVYWGQGTLVTVSS
(disclosed as SEQ ID NO: 118
in WO 2007/070750).

The light chain variable region
of ixekizumab has the amino acid
sequence of:
                                   (SEQ ID NO: 339)
DIVMTQTPLSLSVTPGQPASISCRSSRSLVHSRGN

TYLHWYLQKPGQSPQLLIYKVSNRFIGVPDRFSGS

GSGTDFTLKISRVEAEDVGVYYCSQSTHLPFTFGQ

GTKLEIK
(disclosed as SEQ ID NO: 241
in WO 2007/070750).
```

In some embodiments, the IL-17 inhibitor is brodalumab (CAS Registry Number: 1174395-19-7). Brodalumab is also known as AMG 827 or AM-14. Brodalumab binds to the interleukin-17 receptor A (IL-17RA) and prevents IL-17 from activating the receptor.

Brodalumab is disclosed, e.g., in WO 2008/054603, U.S. Pat. Nos. 7,767,206, 7,786,284, 7,833,527, 7,939,070, 8,435,518, 8,545,842, 8,790,648, and 9,073,999. The heavy chain CDR1 of brodalumab has the amino acid sequence of RYGIS (SEQ ID NO: 340) (as disclosed as SEQ ID NO: 146 in WO 2008/054603). The heavy chain CDR2 of brodalumab has the amino acid sequence of WIS-TYSGNTNYAQKLQG (SEQ ID NO: 341) (as disclosed as SEQ ID NO: 147 in WO 2008/054603). The heavy chain CDR3 of brodalumab has the amino acid sequence of RQLYFDY (SEQ ID NO: 342) (as disclosed as SEQ ID NO: 148 in WO 2008/054603). The light chain CDR1 of brodalumab has the amino acid sequence of RASQSVSSNLA (SEQ ID NO: 343) (as disclosed as SEQ ID NO: 224 in WO 2008/054603). The heavy chain CDR2 of brodalumab has the amino acid sequence of DASTRAT (SEQ ID NO: 344) (as disclosed as SEQ ID NO: 225 in WO 2008/054603). The heavy chain CDR3 of brodalumab has the amino acid sequence of QQYDNWPLT (SEQ ID NO: 345) (as disclosed as SEQ ID NO: 226 in WO 2008/054603).

Exemplary IL-1β Inhibitors

In one embodiment, a combination described herein includes an interleukine-1 beta (IL-1β) inhibitor. In some embodiments, the combination is used to treat a cancer, e.g., a cancer described herein, e.g., a hematologic malignancy (e.g., a lymphoma (e.g., Hodgkin lymphoma), a leukemia (e.g., an acute or chronic leukemia), or a multiple myeloma).

In some embodiments, the IL-1β inhibitor is canakinumab. Canakinumab is also known as ACZ885 or ILARIS®. Canakinumab is a human monoclonal IgG1/κ antibody that neutralizes the bioactivity of human IL-1β.

Canakinumab is disclosed, e.g., in WO 2002/16436, U.S. Pat. No. 7,446,175, and EP 1313769.

```
The heavy chain variable region of
canakinumab has the amino acid
sequence of:
                              (SEQ ID NO: 346)
MEFGLSWVFLVALLRGVQCQVQLVESGGGVVQPGR

SLRLSCAASGFTFSVYGMNWVRQAPGKGLEWVAII

WYDGDNQYYADSVKGRFTISRDNSKNTLYLQMNGL

RAEDTAVYYCARDLRTGPFDYWGQGTLVTVSS
(disclosed as SEQ ID NO: 1 in
U.S. Pat. No. 7,446,175).

The light chain variable region
of canakinumab has the amino acid
sequence of:
                              (SEQ ID NO: 347)
MLPSQLIGFLLLWVPASRGEIVLTQSPDFQSVTPK

EKVTITCRASQSIGSSLHWYQQKPDQSPKLLIKYA

SQSFSGVPSRFSGSGSGTDFTLTINSLEAEDAAAY

YCHQSSSLPFTFGPGTKVDIK
(disclosed as SEQ ID NO: 2
in U.S. Pat. No. 7,446,175).
```

Exemplary CXCR2 Inhibitors

In one embodiment, a combination described herein includes an inhibitor of chemokine (C-X-C motif) receptor 2 (CXCR2) inhibitor. In some embodiments, the combination is used to treat a cancer, e.g., a cancer described herein, e.g., a solid tumor, e.g., a breast cancer, a metastatic sarcoma, a pancreatic cancer, a melanoma, a renal cell carcinoma (RCC), a non-small cell lung cancer (NSCLC), or a pediatric tumor (e.g., a rhabdomyosarcoma).

In some embodiments, the CXCR2 inhibitor is danirixin (CAS Registry Number: 954126-98-8). Danirixin is also known as GSK1325756 or 1-(4-chloro-2-hydroxy-3-piperidin-3-ylsulfonylphenyl)-3-(3-fluoro-2-methylphenyl)urea. Danirixin is disclosed, e.g., in Miller et al. *Eur J Drug Metab Pharmacokinet* (2014) 39:173-181; and Miller et al. *BMC Pharmacology and Toxicology* (2015), 16:18.

In some embodiments, the CXCR2 inhibitor is reparixin (CAS Registry Number: 266359-83-5). Reparixin is also known as repertaxin or (2R)-2-[4-(2-methylpropyl)phenyl]-N-methylsulfonylpropanamide. Reparixin is a non-competitive allosteric inhibitor of CXCR1/2. Reparixin is disclosed, e.g., in Zarbock et al. *British Journal of Pharmacology* (2008), 1-8.

In some embodiments, the CXCR2 inhibitor is navarixin. Navarixin is also known as MK-7123, SCH 527123, PS291822, or 2-hydroxy-N,N-dimethyl-3-[[2-[[(1R)-1-(5-methylfuran-2-yl)propyl]amino]-3,4-dioxocyclobuten-1-yl]amino]benzamide. Navarixin is disclosed, e.g., in Ning et al. *Mol Cancer Ther.* 2012; 11(6):1353-64.

Exemplary PI3K-γ, -δ Inhibitors

In one embodiment, a combination described herein includes an inhibitor of phosphatidylinositol-4,5-bisphosphate 3-kinase (PI3K), e.g., phosphatidylinositol-4,5-bisphosphate 3-kinase gamma and/or delta (PI3K-γ,δ). In some embodiments, the combination is used to treat a cancer, e.g., a cancer described herein, e.g., a solid tumor (e.g., a prostate cancer, a breast cancer, a brain cancer, a bladder cancer, a pancreatic cancer, a renal cancer, a solid tumor, a liver cancer, a non-small cell lung cancer, an endocrine cancer, an ovarian cancer, a melanoma, a female reproductive system cancer, a digestive/gastrointestinal cancer, a glioblastoma multiforme, a head and neck cancer, or a colon cancer), e.g., a hematologic malignancy (e.g., a leukemia (e.g., a lymphocytic leukemia, e.g., chronic lymphocytic leukemia (CLL) (e.g., relapsed CLL)), e.g., a lymphoma (e.g., non-Hodgkin lymphoma (e.g., relapsed follicular B-cell non-Hodgkin lymphoma (FL) or relapsed small lymphocytic lymphoma (SLL)), or e.g., a multiple myeloma).

In some embodiments, the PI3K inhibitor is an inhibitor of delta and gamma isoforms of PI3K. Exemplary PI3K inhibitors that can be used in combination are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments, the PI3K-γ,δ inhibitor is idelalisib (CAS Registry Number: 870281-82-6). Idelalisib is also known as ZYDELIG®, GS-1101, CAL-101, or 5-Fluoro-3-phenyl-2-[(1S)-1-(7H-purin-6-ylamino)propyl]-4(3H)-quinazolinone. Idelalisib blocks P1106, the delta isoform of PI3K. Idelalisib is disclosed, e.g., in Wu et al. *Journal of Hematology & Oncology* (2013) 6: 36.

In some embodiments, the PI3K-γ,δ inhibitor is dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806.

In some embodiments, the PI3K-γ,δ inhibitor is buparlisib (Compound A6) or a compound disclosed in PCT Publication No. WO 2007/084786.

In one embodiment, the PI3K-γ,δ inhibitor, e.g., buparlisib (Compound A6) or a compound disclosed in PCT Publication No. WO 2007/084786, is administered at a dose of about 100 mg (e.g., per day).

Other exemplary PI3K-γ,δ inhibitors that can be used in the combination include, e.g., pictilisib (GDC-0941), LY294002, pilaralisib (XL147), PI-3065, PI-103, VS-5584 (SB2343), CZC24832, duvelisib (IPI-145, INK1197), TG100-115, CAY10505, GSK1059615, PF-04691502, AS-605240, voxtalisib (SAR245409, XL765), IC-87114, omipalisib (GSK2126458, GSK458), TG100713, gedatolisib (PF-05212384, PKI-587), PKI-402, XL147 analogue, PIK-90, PIK-293, PIK-294, 3-Methyladenine (3-MA), AS-252424, AS-604850, or apitolisib (GDC-0980, RG7422).

In some embodiments, the PI3K inhibitor is Compound A8 or a compound described in PCT Publication No. WO2010/029082.

In some embodiments, the PI3K inhibitor is a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826.

Exemplary PI3K-γ, -δ inhibitors include, but are not limited to, duvelisib and idelalisib. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

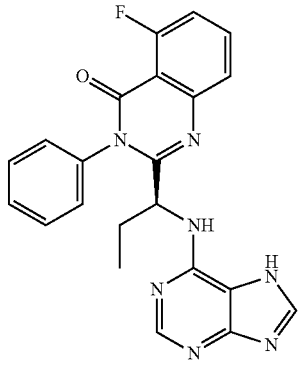 [SMILES: CC[C@H](Nc1ncnc2nc[nH]c12)c1nc2cccc(F)c2c(=O)n1-c1ccccc1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

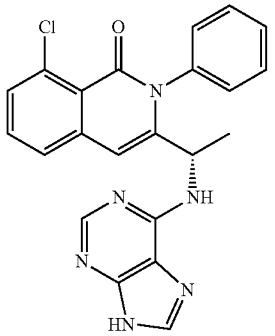 [SMILES: C[C@H](Nc1ncnc2[nH]cnc12)c1cc2cccc(Cl)c2c(=O)n1-c1ccccc1]

In one embodiment, the inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-1V-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl}propa- nenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); or N-[2-[(3,5-Dimethoxyphenyl)amino]quinoxalin-3-yl]-4-[(4-methyl-3-methoxyphenyl)carbonyl]aminophenylsulfonamide (XL765).

Exemplary BAFF-R Inhibitors

In one embodiment, a combination described herein includes a B-cell-activating factor receptor (BAFF-R) inhibitor. In some embodiments, the combination is used to treat a cancer, e.g., a cancer described herein, e.g., a hematologic malignancy, e.g., a leukemia (e.g., chronic lymphocytic leukemia (CLL), e.g., relapsed or refractory chronic lymphocytic leukemia).

In one embodiment, the BAFF-R inhibitor is VAY736. VAY736 is a fully human combinatorial antibody library (HuCAL)-derived monoclonal antibody targeting BAFF-R. BAFF-R, also known as tumor necrosis factor receptor superfamily member 13C, is overexpressed in certain tumor cell types and autoimmune diseases. VAY736 has both anti-inflammatory and antineoplastic activities. In cancer cells, BAFF-R plays a key role in B-cell proliferation and survival. VAY736 targets and binds to BAFF-R, which inhibits both BAFF/BAFF-R interaction and BAFF-R-mediated signaling. This may decrease cell growth in tumor cells expressing BAFF-R.

VAY736 is disclosed, e.g., in U.S. Pat. No. 8,106,163. The heavy chain CDR1 of VAY736 has the amino acid sequence of GDSVSSNSAAWG (SEQ ID NO: 348) (disclosed as SEQ ID NO: 3 in U.S. Pat. No. 8,106,163). The heavy chain CDR2 of VAY736 has the amino acid sequence of RIYYRSKWYNSYAVSVKS (SEQ ID NO: 349) (disclosed as SEQ ID NO: 10 in U.S. Pat. No. 8,106,163). The heavy chain CDR3 of VAY736 has the amino acid sequence of YDWVPKIGVFDS (SEQ ID NO: 350) (disclosed as SEQ ID NO: 17 in U.S. Pat. No. 8,106,163). The light chain CDR1 of VAY736 has the amino acid sequence of RASQFISSSYLS (SEQ ID NO: 351) (disclosed as SEQ ID NO: 24 in U.S. Pat. No. 8,106,163). The light chain CDR2 of VAY736 has the amino acid sequence of LLIYGSSSRAT (SEQ ID NO: 352) (disclosed as SEQ ID NO: 31 in U.S. Pat. No. 8,106,163). The light chain CDR3 of VAY736 has the amino acid sequence of QQLYSSPM (SEQ ID NO: 353) (disclosed as SEQ ID NO: 38 in U.S. Pat. No. 8,106,163). The heavy chain variable region of VAY736 has the amino acid sequence of:

(SEQ ID NO: 354)
QVQLQQSGPGLVKPSQTLSLTCAISGDSVSSNSAA

WGWIRQSPGRGLEWLGRIYYRSKWYNSYAVSVKSR

ITINPDTSKNQFSLQLNSVTPEDTAVYYCARYDWV

PKIGVFDSWGQGTLVTVSS
(disclosed as SEQ ID NO: 52
in U.S. Pat. No. 8,106,163).

The light chain variable region of
VAY736 has the amino acid
sequence of:

(SEQ ID NO: 355)
DIVLTQSPATLSLSPGERATLSCRASQFISSSYLS

WYQQKPGQAPRLLIYGSSSRATGVPARFSGSGSGT

DFTLTISSLEPEDFAVYYCQQLYSSPMTFGQGTKV

EIKRT
(disclosed as SEQ ID NO: 45
in U.S. Pat. No. 8,106,163).

-continued

The heavy chain of VAY736 has the amino acid sequence of:

(SEQ ID NO: 356)

```
QVQLQQSGPGLVKPSQTLSLTCAISGDSVSSNSAA
WGWIRQSPGRGLEWLGRIYYRSKWYNSYAVSVKSR
ITINPDTSKNQFSLQLNSVTPEDTAVYYCARYDWV
PKIGVFDSWGQGTLVTVSSASTKGPSVFPLAPSSK
STSGGTAALGCLVKDYFPEPVTVSWNSGALTSGVH
TFPAVLQSSGLYSLSSVVTVPSSSLGTQTYICNVN
HKPSNTKVDKRVEPKSCDKTHTCPPCPAPELLGGP
SVFLFPPKPKDTLMISRTPEVTCVVVDVSHEDPEV
KFNWYVDGVEVHNAKTKPREEQYNSTYRVVSVLTV
LHQDWLNGKEYKCKVSNKALPAPIEKTISKAKGQP
REPQVYTLPPSREEMTKNQVSLTCLVKGFYPSDIA
VEWESNGQPENNYKTTPPVLDSDGSFFLYSKLTVD
KSRWQQGNVFSCSVMHEALHNHYTQKSLSLSPGK
```

(disclosed as SEQ ID NO: 75 in U.S. Pat. No. 8,106,163).

The light chain variable region of VAY736 has the amino acid sequence of:

(SEQ ID NO: 357)

```
DIVLTQSPATLSLSPGERATLSCRASQFISSSYLS
WYQQKPGQAPRLLIYGSSSRATGVPARFSGSGSGT
DFTLTISSLEPEDFAVYYCQQLYSSPMTFGQGTKV
EIKRTVAAPSVFIFPPSDEQLKSGTASVVCLLNNF
YPREAKVQWKVDNALQSGNSQESVTEQDSKDSTYS
LSSTLTLSKADYEKHKVYACEVTHQGLSSPVTKSF
NRGEC
```

(disclosed as SEQ ID NO: 71 in U.S. Pat. No. 8,106,163).

Exemplary MALT-1/BTK Inhibitors

In one embodiment, a combination described herein includes an inhibitor of MALT-1 and/or BTK. In some embodiments, the combination is used to treat a cancer, e.g., a cancer described herein.

Exemplary MALT-1/BTK inhibitors include, but are not limited to, (S)-1-(6-(2H-1,2,3-triazol-2-yl)-5-(trifluoromethyl)pyridin-3-yl)-3-(2-chloro-7-(1-methoxyethyl)pyrazolo[1,5-a]pyrimidin-6-yl)urea, (S)-1-(2-chloro-7-(1-methoxyethyl)pyrazolo[1,5-a]pyrimidin-6-yl)-3-(2-(trifluoromethyl)pyridin-4-yl)urea, (S)-1-(2-chloro-7-(1-methoxyethyl)pyrazolo[1,5-a]pyrimidin-6-yl)-3-(1-methyl-2-oxo-5-(trifluoromethyl)-1,2-dihydropyridin-3-yl)urea, (R)-1-(6-(2H-1,2,3-triazol-2-yl)-5-(trifluoromethyl)pyridin-3-yl)-3-(2-chloro-7-(1-methoxy-2-methylpropyl)pyrazolo[1,5-a]pyrimidin-6-yl)urea, (R)-1-(5-chloro-6-(2H-1,2,3-triazol-2-yl)pyridin-3-yl)-3-(2-chloro-7-(1-methoxy-2-methylpropyl)pyrazolo[1,5-a]pyrimidin-6-yl)urea, (S)-1-(7-(1-methoxyethyl)-2-methylpyrazolo[1,5-a]pyrimidin-6-yl)-3-(2-(trifluoromethyl)pyridin-4-yl)urea, (S)-1-(2-fluoro-7-(1-methoxyethyl)pyrazolo[1,5-a]pyrimidin-6-yl)-3-(2-(trifluoromethyl)pyridin-4-yl)urea, (S)-1-(2-chloro-7-(1-methoxyethyl)pyrazolo[1,5-a]pyrimidin-6-yl)-3-(5-cyanopyridin-3-yl)urea, Exemplary BTK inhibitors include, but are not limited to, ibrutinib (PCI-32765); GDC-0834; RN-486; CGI-560; CGI-1764; HM-71224; CC-292; ONO-4059; CNX-774; or LFM-A13. In one embodiment, the BTK inhibitor does not reduce or inhibit the kinase activity of interleukin-2-inducible kinase (ITK), e.g., is selected from GDC-0834; RN-486; CGI-560; CGI-1764; HM-71224; CC-292; ONO-4059; CNX-774; or LFM-A13.

In one embodiment, the kinase inhibitor is a BTK inhibitor, e.g., ibrutinib (PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

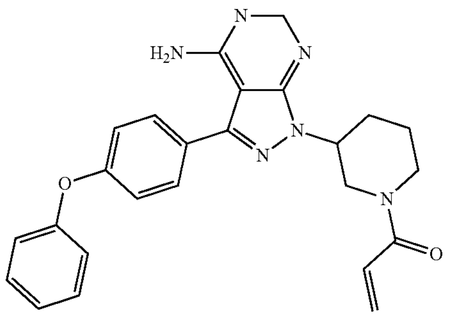 [SMILES: C=CC(=O)N1CCCC(n2nc(-c3ccc(Oc4ccccc4)cc3)c3c2=NCNC=3N)C1]

In other embodiments, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

(I)

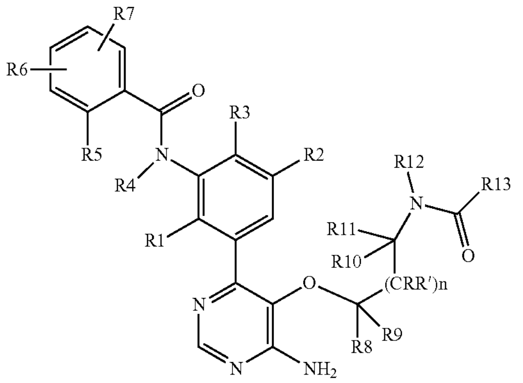

wherein,

R1 is hydrogen, C1-C6 alkyl optionally substituted by hydroxy;

R2 is hydrogen or halogen;

R3 is hydrogen or halogen;

R4 is hydrogen;

R5 is hydrogen or halogen;

or R4 and R5 are attached to each other and stand for a bond, —CH2-, —CH2-CH2-, —CH═CH—, —CH═CH—CH2-; —CH2-CH═CH—; or —CH2-CH2-CH2-;

R6 and R7 stand independently from each other for H, C1-C6 alkyl optionally substituted by hydroxyl, C3-C6 cycloalkyl optionally substituted by halogen or hydroxy, or halogen;

R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)—N-(3-(5-(2-Acrylamidopropoxy)-6-aminopyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylacrylamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-propioloylazetidin-2-yl)methoxy)pyrimidin-4-yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

Exemplary JAK Inhibitors

In one embodiment, a combination described herein includes an inhibitor of Janus kinase (JAK). In some embodiments, the combination is used to treat a cancer, e.g., a cancer described herein, e.g., a solid tumor (e.g., a colon cancer, a prostate cancer, a lung cancer, a breast cancer, or a pancreatic cancer), e.g., a hematologic malignancy (e.g., a leukemia (e.g., a myeloid leukemia or a lymphocytic leukemia), e.g., a lymphoma (e.g., a non-Hodgkin lymphoma), or e.g., a multiple myeloma.

In some embodiments, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514.

In some embodiments, the JAK inhibitor, e.g., 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, is administered at a dose of about 400-600 mg (e.g., per day), e.g., about 400, 500, or 600 mg, or about 400-500 or 500-600 mg.

In some embodiment, the JAK inhibitor is ruxolitinib phosphate (also known as JAKAFI; Compound A18) or a compound disclosed in PCT Publication No. WO 2007/070514.

In one embodiment, the JAK inhibitor, e.g., ruxolitinib phosphate (also known as JAKAFI; Compound A18) or a compound disclosed in PCT Publication No. WO 2007/070514, is administered at a dose of about 15-25 mg, e.g., twice daily. In some embodiments, the dose is about 15, 20, or 25 mg, or about 15-20 or 20-25 mg.

Exemplary CRTH2 Inhibitors

In one embodiment, a combination described herein includes an inhibitor of chemoattractant receptor homologous to the T helper 2 cell (CRTH2). In some embodiments, the combination is used to treat a cancer, e.g., a cancer described herein.

In some embodiments, the CRTH2 inhibitor is QAV680 (CAS Registry Number: 872365-16-7). QAV680 is also known as 2-[2-methyl-1-[(4-methylsulfonylphenyl)methyl]pyrrolo[2,3-b]pyridin-3-yl]acetic acid. QAV680 is disclosed, e.g., in Sandham et al. *Bioorg Med Chem.* 2013; 21(21):6582-91.

In some embodiments, the CRTH2 inhibitor is QAW039 (CAS Number: 872365-14-5).

Other CRTH2 inhibitors that can be used in the combination include, e.g., AZD1981, ARRY-502, setipiprant (ACT-453859), and ACT-129968.

Exemplary PFKFB3 Inhibitors

In one embodiment, a combination described herein includes an inhibitor of 6-phosphofructo-2-kinase/fructose-2,6-biphosphatase 3 (PFKFB3). In some embodiments, the combination is used to treat a cancer, e.g., a cancer described herein, e.g., a solid tumor (e.g., an advanced solid tumor).

In some embodiments, the PFKFB3 inhibitor is PFK-158. PFK-158 is also known as ACT-PFK-158 or (E)-1-(pyridyn-4-yl)-3-(7-(trifluoromethyl)quinolin-2-yl)-prop-2-en-1-one. PFK-158 is a derivative of 3-(3-pyridinyl)-1-[4-pyridinyl]-2-propen-1-one (3P0). PFKFB3, which catalyzes the conversion of fructose-6-phosphate to fructose-2,6-bisphosphate, is highly expressed and active in human cancer cells and plays a key role in increasing both glycolytic flux in and proliferation of cancer cells. PFKFB3 inhibitors, e.g., PFK-158, can bind to and inhibit the activity of PFKFB3, which leads to the inhibition of both the glycolytic pathway in and glucose uptake by cancer cells. This prevents the production of macromolecules and energy that causes the enhanced cellular proliferation in cancer cells as compared to that of normal, healthy cells. Depriving cancer cells of nutrients and energy leads to the inhibition of cancer cell growth.

PFK158 is disclosed, e.g., at page 5 of WO 2013/148228.

In some embodiments, the PFKFB3 inhibitor has the following structure:

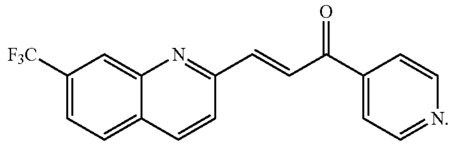 [SMILES: O=C(/C=C/c1ccc2ccc(C(F)(F)F)cc2n1)c1ccncc1]

Pharmaceutical Compositions and Kits

In another aspect, the present invention provides compositions, e.g., pharmaceutically acceptable compositions, which include combination molecules (e.g., antibody molecules) described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The combination molecules (e.g., antibody molecules) can be administered by a variety of methods known in the art, although for many therapeutic applications, the preferred route/mode of administration is intravenous injection or infusion. In one embodiment, the antibody molecule is administered by intravenous infusion at a rate of more than 20 mg/min, e.g., 20-40 mg/min, and preferably greater than or equal to 40 mg/min to reach a dose of about 35 to 440 $mg/m^2$, preferably about 70 to 310 $mg/m^2$, and more preferably, about 110 to 130 $mg/m^2$. In another embodiment, the antibody molecule is administered by intravenous infusion at a rate of less than 10 mg/min; preferably less than or equal to 5 mg/min to reach a dose of about 1 to 100 $mg/m^2$, preferably about 5 to 50 $mg/m^2$, about 7 to 25 $mg/m^2$ and more preferably, about 10 $mg/m^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody molecule can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody molecule is 0.1-30 mg/kg, more preferably 1-25 mg/kg. Dosages and therapeutic regimens of the anti-LAG-3 antibody molecule can be determined by a skilled artisan. In certain embodiments, the anti-LAG-3 antibody molecule is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-LAG-3 antibody molecule is administered at a dose from about 10 to 20 mg/kg every other week. The antibody molecule can be administered by intravenous infusion at a rate of more than 20 mg/min, e.g., 20-40 mg/min, and preferably greater than or equal to 40 mg/min to reach a dose of about 35 to 440 $mg/m^2$, preferably about 70 to 310 $mg/m^2$, and more preferably, about 110 to 130 $mg/m^2$. In embodiments, the infusion rate of about 110 to 130 $mg/m^2$ achieves a level of about 3 mg/kg. In one embodiment, the anti-LAG-3 antibody molecule is administered (e.g., intravenously) at a dose from about 3 to 800 mg, e.g., about 3, 20, 80, 240, or 800 mg. In certain embodiments, the anti-LAG-3 antibody molecule is administered alone at a dose from about 20 to 800 mg, e.g., about 3, 20, 80, 240, or 800 mg. In other embodiments, the anti-LAG-3 antibody molecule is administered at a dose from about 3 to 240 mg, e.g., about 3, 20, 80, or 240 mg, in combination with a second agent or therapeutic modality, e.g., a second agent or therapeutic modality described herein. In one embodiment, the anti-LAG-3 antibody molecule is administered every 2 weeks (e.g., during weeks 1, 3, 5, 7) during each 8 week cycle, e.g., up to 96 weeks.

The antibody molecule can be administered by intravenous infusion at a rate of more than 20 mg/min, e.g., 20-40 mg/min, and preferably greater than or equal to 40 mg/min to reach a dose of about 35 to 440 $mg/m^2$, preferably about 70 to 310 $mg/m^2$, and more preferably, about 110 to 130 $mg/m^2$. In embodiments, the infusion rate of about 110 to 130 $mg/m^2$ achieves a level of about 3 mg/kg. In other embodiments, the antibody molecule is administered by intravenous infusion at a rate of less than 10 mg/min, e.g., less than or equal to 5 mg/min to reach a dose of about 1 to 100 $mg/m^2$, e.g., about 5 to 50 $mg/m^2$, about 7 to 25 $mg/m^2$, and more preferably, about 10 $mg/m^2$. In some embodiments, the antibody is infused over a period of about 30 min.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising an antibody molecule described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

Uses of Anti-LAG-3 Antibody Molecules

The combinations, e.g., the anti-LAG-3 antibody molecules disclosed herein, have in vitro and in vivo diagnostic, as well as therapeutic and prophylactic utilities. For example, these molecules can be administered to cells in culture, in vitro or ex vivo, or to a subject, e.g., a human subject, e.g., in vivo, to enhance immunity. In one embodiment, the anti-LAG-3 antibody molecules enhance an immune response in a subject, e.g., by blockade of LAG-3 (e.g., by blockade of LAG-3 binding to an MHC molecule or other ligands).

Accordingly, in one aspect, the invention provides a method of modifying an immune response in a subject comprising administering to the subject the antibody, molecule described herein, such that the immune response in the subject is modified. In one embodiment, the immune response is enhanced, stimulated or up-regulated. In some embodiments, the anti-LAG-3 antibody molecule restores, enhances or stimulates an antigen-specific T cell response, e.g., interleukin-2 (IL-2) or interferon-gamma (IFN-γ), production in an antigen-specific T cell response, in the subject. In some embodiments, the immune response is an anti-tumor response. The methods and compositions described herein are suitable for treating human patients having a disorder that can be treated by augmenting the T-cell mediated immune response. For example, the anti-LAG-3 antibody molecules, alone or in combination, can be administered to a subject to treat, prevent, and/or diagnose a variety of disorders, such as cancers (melanoma or hepatic cancers), or an infectious disorder.

As used herein, the term "subject" is intended to include human and non-human animals. In one embodiment, the subject is a human subject, e.g., a human patient having a disorder or condition characterized by abnormal LAG-3 functioning. The term "non-human animals" of the invention includes mammals and non-mammals, such as non-human primates. In one embodiment, the subject is a human. In one embodiment, the subject is a human patient in need of enhancement of an immune response. In one embodiment, the subject has, or is at risk of, having a disorder described herein, e.g., a cancer or an infectious disorder as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection. For example, the methods and compositions described herein can enhance a number of immune activities. In one embodiment, the subject has increased number or activity of tumour-infiltrating T lymphocytes (TILs). In another embodiment, the subject has increased expression or activity of interferon-gamma (IFN-γ). In yet another embodiment, the subject has decreased PD-L1 expression or activity. Accordingly, in certain embodiments, any (e.g., one, two, three, or all) of TILs, IFN-γ, CD8, or PD-L1, can be used as biomarkers for the anti-LAG-3 immunotherapies described herein.

Therapeutic Uses

Blockade of LAG-3 by antibodies can enhance an immune response to cancerous cells in a subject. Similar to CD4, LAG-3 interacts with MHC class II molecules but, unlike CD4, LAG-3 does not interact with the human immunodeficiency virus gp120 protein (Baixeras et al. (1992) *J. Exp. Med.* 176:327-337). Studies have demonstrated direct and specific binding of LAG-3 to MHC class II on the cell surface (Huard et al. (1996) *Eur. J. Immunol.* 26:1180-1186). The LAG-3/MHC class II interaction plays a role in down-regulating antigen-dependent stimulation of $CD4^+$ and $CD8^+$ T lymphocytes. The addition of anti-LAG-3 antibodies can result in increased T cell proliferation, higher expression of activation antigens such as CD25, and higher concentrations of cytokines such as interferon-gamma and interleukin-4 (Huard et al. (1994) *Eur. J. Immunol.* 24:3216-3221). The intra-cytoplasmic region of LAG-3 can also interact with LAP, a signal transduction molecule involved in the downregulation of the CD3/TCR activation pathway (Iouzalen et al. (2001) *Eur. J. Immunol.* 31:2885-2891). Further, LAG-3 contributes to the suppressor activity of $CD4^+CD25^+$ regulatory T cells ($T_{reg}$). $T_{reg}$ cells express LAG-3 upon activation and antibodies to LAG-3 inhibit suppression by induced $T_{reg}$ cells (Huang, C. et al. (2004) *Immunity* 21:503-513). LAG-3 can also negatively regulate T cell homeostasis by regulatory T cells in both T cell-dependent and independent mechanisms (Workman, C. J. and Vignali, D. A. (2005) *J. Immunol.* 174:688-695). Thus, inhibition of LAG-3 can result in augmenting an immune response.

Accordingly, in one aspect, a method of treating (e.g., reducing or inhibiting) a cancer or tumor in a subject is provided. The method comprises administering to the subject an anti-LAG-3 antibody molecule described herein, e.g., a therapeutically effective amount of an anti-LAG-3 antibody molecule, alone or in combination, e.g., with one or more agents or procedures. In one embodiment, an anti-LAG-3 antibody molecule may be used alone to inhibit the growth of cancerous tumors. Alternatively, an anti-LAG-3 antibody may be used in combination with one or more of: a standard of care treatment (e.g., for cancers or infectious disorders), another antibody, an immunomodulator (e.g., an activator of a costimulatory molecule or an inhibitor of an inhibitory molecule); a vaccine, e.g., a therapeutic cancer vaccine; or other forms of cellular immunotherapy, as described below. In certain embodiments, the anti-LAG-3 antibody molecule is administered in combination with a modulator of a costimulatory molecule (e.g., an agonist of a costimulatory molecule) or a modulator of an inhibitory molecule (e.g., an inhibitor of an immune checkpoint inhibitor), e.g., as described herein.

In one embodiment, the methods are suitable for the treatment of cancer in vivo. To achieve antigen-specific enhancement of immunity, the anti-LAG-3 antibody molecule can be administered together with an antigen of interest. When antibodies to LAG-3 are administered in combination with one or more agents, the combination can be administered in either order or simultaneously.

In certain embodiments, a method of treating a subject, e.g., reducing or ameliorating, a hyperproliferative condition or disorder (e.g., a cancer), e.g., solid tumor, a hematological cancer, soft tissue tumor, or a metastatic lesion, in a subject is provided. The method includes administering to the subject one or more of the combinations described herein.

As used herein, the term “cancer” is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies such as those affecting the lung, esophagus, skin, head and neck region, oral cavity, anus, and cervix. Metastatic lesions of the aforementioned cancers can also be treated or prevented using the methods and compositions of the invention.

Exemplary cancers whose growth can be inhibited using the combinations disclosed herein include cancers typically responsive to immunotherapy. Non-limiting examples of preferred cancers for treatment include melanoma (e.g., an advanced stage (e.g., stage II-IV) melanoma or an HLA-A2 positive melanoma), pancreatic cancer (e.g., advanced pancreatic cancer), solid tumors, breast cancer (e.g., metastatic breast carcinoma, a breast cancer that does not express one, two or all of estrogen receptor, progesterone receptor, or Her2/neu, e.g., a triple negative breast cancer), and renal cell carcinoma (e.g., advanced (e.g., stage IV) or metastatic renal cell carcinoma (MRCC)). Additionally, refractory or recurrent malignancies can be treated using the antibody molecules described herein.

Examples of other cancers that can be treated include, e.g., a solid tumor, e.g., prostate cancer (e.g., hormone refractory prostate adenocarcinoma), colon cancer, lung cancer (e.g., non-small cell lung cancer), bone cancer, skin cancer, cancer of the head or neck (e.g., HPV+ squamous cell carcinoma), cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Merkel cell cancer, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, Kaposi’s sarcoma, epidermoid cancer, or squamous cell cancer or a hematological malignancy, e.g., Hodgkin lymphoma, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia (e.g., relapsed or refractory chronic lymphocytic leukemia), solid tumors of childhood, lymphocytic lymphoma, multiple myeloma, myelodisplastic syndromes, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi’s sarcoma, epidermoid cancer, squamous cell cancer, T-cell lymphoma, environmentally induced cancers including those induced by asbestos (e.g., mesothelioma), and combinations of said cancers. Treatment of metastatic cancers, e.g., metastatic cancers that express MHC class II molecules or LAG-3, can be effected using the antibody molecules described herein.

While not wishing to be bound by theory, in some embodiments, a patient is more likely to respond to treatment with anti-LAG-3, alone or in combination with anti-PD-1 or PD-L1 antibody molecules (optionally in combination with one or more agents as described herein) if the patient has a cancer that highly expresses PD-L1, and/or the cancer is infiltrated by anti-tumor immune cells, e.g., TILs. The anti-tumor immunce cells may be positive for CD8, PD-L1, and/or IFN-γ; thus levels of CD8, PD-L1, and/or IFN-γ can serve as a readout for levels of TILs in the microenvironment. In certain embodiments, the cancer microenvironment is referred to as triple-positive for PD-L1/CD8/IFN-γ.

Accordingly, in certain aspects, this application provides methods of determining whether a tumor sample is positive for one or more of PD-L1, CD8, and IFN-γ, and if the tumor sample is positive for one or more, e.g., two, or all three, of the markers, then administering to the patient a therapeutically effective amount of an anti-PD-1 antibody molecule, optionally in combination with one or more other immunnomodulators or anti-cancer agents.

In the following indications, a large fraction of patients are triple-positive for PD-L1/CD8/IFN-γ: lung cancer (squamous); lung cancer (adenocarcinoma); head and neck cancer; stomach cancer; NSCLC; HNSCC; gastric cancers (e.g., MSIhi and/or EBV+); CRC (e.g., MSIhi); nasopharyngeal cancer (NPC); cervical cancer (e.g., squamous); thyroid cancer e.g., papillary thyroid; melanoma; TN breast cancer; and DLBCL (Diffuse Large B-Cell Lymphoma). In breast cancer generally and in colon cancer generally, a moderate fraction of patients is triple-positive for PD-L1/CD8/IFN-γ. In the following indications, a small fraction of patients are triple-positive for PD-L1/CD8/IFN-γ: ER+ breast cancer, and pancreatic cancer. These findings are discussed further in Example 4. Regardless of whether a large or small fraction of patients is triple-positive for these markers, screening the patients for these markers allows one to identify a fraction of patients that has an especially high likelihood of responding favorably to therapy with a LAG-3 antibody, alone or in combination with a PD-1 antibody (e.g., a blocking PD-1 antibody), optionally in combination with one or more other immunomodulators (e.g., an anti-TIM-3 antibody molecule or an anti-PD-L1 antibody molecule) and/or anti-cancer agents, e.g., those listed in Table 7 and disclosed in the publications listed in Table 7.

In some embodiments, the cancer sample is classified as triple-positive for PDL1/CD8/IFN-γ. This measurement can roughly be broken down into two thresholds: whether an individual cell is classified as positive, and whether the sample as a whole is classified as positive. First, one can measure, within an individual cell, the level of PD-L1, CD8, and/or IFN-γ. In some embodiments, a cell that is positive for one or more of these markers is a cell that has a higher level of the marker compared to a control cell or a reference value. For example, in some embodiments, a high level of PD-L1 in a given cell is a level higher than the level of PD-L1 in a corresponding non-cancerous tissue in the patient. As another example, in some embodiments, a high level of CD8 or IFN-γ in a given cell is a level of that protein typically seen in a TIL. Second, one can also measure the percentage of cells in the sample that are positive for PD-L1, CD8, and/or IFN-γ. (It is not necessary for a single cell to express all three markers.) In some embodiments, a triple positive sample is one that has a high percentage of cells, e.g., higher than a reference value or higher than a control sample, that are positive for these markers.

In other embodiments, one can measure the levels of PD-L1, CD8, and/or IFN-γ overall in the sample. In this case, a high level of CD8 or IFN-γ in the sample can be the level of that protein typically seen in a tumor infiltrated with TIL. Similarly, a high level of PD-L1 can be the level of that protein typically seen in a tumor sample, e.g., a tumor microenvironment.

The identification of subsets of patients that are triple-positive for PD-L1/CD8/IFN-γ, as shown in Example 4 herein, reveals certain sub-populations of patients that are likely to be especially responsive to PD-1 antibody therapy. For instance, many IM-TN (immunomodulatory, triple negative) breast cancer patients are triple-positive for PDL1/CD8/IFN-γ. IM-TN breast cancer is described in, e.g., Brian D. Lehmann et al., "Identification of human triple-negative breast cancer subtypes and preclinical models for selection of targeted therapies", J Clin Invest. Jul. 1, 2011; 121(7): 2750-2767. Triple-negative breast cancers are those that do not express estrogen receptor (ER), progesterone receptor (PR) and Her2/neu. These cancers are difficult to treat because they are typically not responsive to agents that target ER, PR, and Her2/neu. Triple-negative breast cancers can be further subdivided into different classes, one of which is immunomodulatory. As described in Lehmann et al., IM-TN breast cancer is enriched for factors involved in immune cell processes, for example, one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing. Accordingly, in some embodiments, the cancer treated is a cancer that is, or is determined to be, positive for one or more marker of IM-TN breast cancer, e.g., a factor that promotes one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing.

As another example, it is shown herein that a subset of colon cancer patients having high MSI (microsatellite instability) is also triple-positive for PD-L1/CD8/IFN-γ. Accordingly, in some embodiments, a LAG-3 antibody, e.g., a LAG-3 antibody as described herein, alone or in combination with a PD-1 antibody, (optionally in combination with one or more immunomodulators such as a TIM-3 antibody or a PD-L1 antibody, and one or more anti-cancer agents, e.g., an anti-cancer agent described in Table 7 or in a publication in Table 7) is administered to a patient who has, or who is identified as having, colon cancer with high MSI, thereby treating the cancer. In some embodiments, a cell with high MSI is a cell having MSI at a level higher than a reference value or a control cell, e.g., a non-cancerous cell of the same tissue type as the cancer.

As another example, it is shown herein that a subset of gastric cancer patients having high MSI, and/or which is EBV+, is also triple-positive for PD-L1/CD8/IFN-γ. Accordingly, in some embodiments, a LAG-3 antibody, e.g., a LAG-3 antibody as described herein, alone or in combination with a PD-1 antibody, (optionally in combination with one or more immunomodulators such as a TIM-3 antibody or a PD-L1 antibody, and one or more anti-cancer agents, e.g., an anti-cancer agent described in Table 7 or in a publication in Table 7) is administered to a patient who has, or who is identified as having, gastric cancer with high MSI and/or EBV+, thereby treating the cancer. In some embodiments, a cell with high MSI is a cell having MSI at a level higher than a reference value or a control cell, e.g., a non-cancerous cell of the same tissue type as the cancer.

Additionally disclosed herein are methods of assaying a cancer for PD-L1, and then treating the cancer with a LAG-3 antibody, alone or in combination with a PD-1 antibody. As described in Example 5 herein, a cancer sample can be assayed for PD-L1 protein levels or mRNA levels. A sample having levels of PD-L1 (protein or mRNA) higher than a reference value or a control cell (e.g., a non-cancerous cell) can be classified as PD-L1 positive. Accordingly, in some embodiments, a LAG-3 antibody, e.g., a LAG-3 antibody as described herein, alone or in combination with a PD-1 antibody, (optionally in combination with one or more anti-cancer agents) is administered to a patient who has, or who is identified as having, a cancer that is PD-L1 positive. The cancer may be, e.g., non-small cell lung (NSCLC) adenocarcinoma (ACA), NSCLC squamous cell carcinoma (SCC), or hepatocellular carcinoma (HCC).

In some embodiments, the methods herein involve using a LAG-3 antibody, e.g., a LAG-3 antibody as described herein, e.g., in combination with a PD-1 antibody, for treating a cancer that is (or is identified as being) positive for PD-L1. In some embodiments, the cancer is colorectal cancer (e.g., MSI-high), gastric cancer (e.g., MSI-high and/or EBV+), NPC, cervical cancer, breast cancer (e.g., TN breast cancer), and ovarian cancer. In some embodiments, the cancer is NSCLC, melanoma, or HNSCC. In some embodiments, the LAG-3 antibody is administered at a dose of, e.g., 1, 3, 10, or 20 mg/kg.

Based on, e.g, Example 4 herein, it was found that certain gastric cancers that are triple-positive for PDL1/CD8/IFN-γ are also positive for PIK3CA. Accordingly, in some embodiments, a cancer can be treated with a LAG-3 antibody, alone or in combination with an anti-PD1 antibody molecule (optionally in combination with one or more immunomodulators, e.g., an anti-TIM-3 antibody molecule or an anti-PD-L1 antibody molecule) and an agent that inhibits PIK3CA. Exemplary agents in this category are described in Stein RC (September 2001). "Prospects for phosphoinositide 3-kinase inhibition as a cancer treatment". Endocrine-related Cancer 8 (3): 237-48 and Marone R, Cmiljanovic V, Giese B, Wymann M P (January 2008). "Targeting phosphoinositide 3-kinase: moving towards therapy". Biochimica et Biophysica Acta 1784 (1): 159-85.

Based on, e.g, Example 4 herein, CRC, e.g., a patient that has (or is identified as having) MSI-high CRC may be treated with a LAG-3 antibody, alone or in combination with a PD-1 antibody, optionally in combination with a therapeutic that targets one or both of RNF43 and BRAF. For instance, these cancers may be treated with a LAG-3 antibody and a PD-1 antibody, optionally in combination with one or more therapeutics that target one or more of RNF43 and BRAF. In embodiments, the one or more therapeutics include an anti-cancer agent described in Table 7 or a publication listed in Table 7. PD-1 inhibitors, e.g., antibodies, are described herein. RNF43 can be inhibited, e.g., with an antibody, small molecule (e.g., 2-(2',3-dimethyl-[2,4'-bipyridin]-5-yl)-N-(5-(pyrazin-2-yl)pyridin-2-yl)acetamide (Compound A28)), siRNA, or a Rspo ligand or derivative thereof. BRAF inhibitors (e.g., vemurafenib or dabrafenib) are described herein.

Based on, e.g, Example 4 herein, a patient that has (or is identified as having) a squamous cell lung cancer may be treated with a LAG-3 antibody molecule in combination with a therapeutic that targets PD-1, e.g., a PD-1 antibody molecule, and optionally with one or more anti-cancer agents, e.g., an anti-cancer agent described in Table 7 or in a publication in Table 7, or a therapeutic that targets TIM-3, e.g., a TIM-3 antibody.

Based on, e.g, Example 4 herein, a patient that has (or is identified as having) a thyroid cancer may be treated with a LAG-3 antibody molecule, alone or in combination with a PD-1 antibody molecule, optionally in combination with a therapeutic that targets BRAF, and optionally in combination with one or more immunomodulators, e.g., an anti-TIM-3 antibody molecule, and an anti-PD-L1 antibody molecule. BRAF inhibitors (e.g., vemurafenib or dabrafenib) are described herein, e.g., in Table 7 and the publications listed in Table 7.

In some embodiments, the therapies here can be used to treat a patient that has (or is identified as having) a cancer associated with an infection, e.g., a viral or bacterial infection. Exemplary cancers include cervical cancer, anal cancer, HPV-associated head and neck squamous cell cancer, HPV-associated esophageal papillomas, HHV6-associated lymphomas, EBV-associated lymphomas (including Burkitt lymphoma), Gastric MALT lymphoma, other infection-associated MALT lymphomas, HCC, Kaposi's sarcoma. In other embodiments, the cancer is a hematological cancer including but is not limited to a leukemia or a lymphoma. For example, the anti-LAG-3 antibody molecule can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-LAG-3 antibody molecule is administered after treatment with an anti-CTLA4 antibody (e.g., ipilimumab) with or without a BRAF inhibitor (e.g., vemurafenib or dabrafenib).

Methods and compositions disclosed herein are useful for treating metastatic lesions associated with the aforementioned cancers.

Exemplary non-limiting combinations and uses of the anti-LAG-3 antibody molecules are disclosed in US 2015/0259420 (U.S. Ser. No. 14/657,260), entitled "Antibody Molecules to LAG-3 and Uses Thereof," incorporated by reference in its entirety.

In certain embodiments, the combination includes an anti-LAG-3 antibody molecule in combination with a modulator of a costimulatory molecule or an inhibitory molecule, e.g., a co-inhibitory ligand or receptor.

In one embodiment, the anti-LAG-3 antibody molecule is administered in combination with a modulator, e.g., agonist, of a costimulatory molecule. In one embodiment, the agonist of the costimulatory molecule is chosen from an agonist (e.g., an agonistic antibody or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In another embodiment, the anti-LAG-3 antibody molecule is used in combination with a costimulatory molecule, e.g., an agonist associated with a positive signal that includes a costimulatory domain of CD28, CD27, ICOS and GITR.

In one embodiment, the anti-LAG-3 antibody molecule is administered in combination with an inhibitor of an inhibitory molecule (e.g., an inhibitor of an immune checkpoint molecule). It will be understood by those of ordinary skill in the art, that the term "immune checkpoints" means a group of molecules on the cell surface of CD4 and CD8 T cells. These molecules can effectively serve as "brakes" to down-modulate or inhibit an anti-tumor immune response. Immune checkpoint molecules include, but are not limited to, Programmed Death 1 (PD-1), Cytotoxic T-Lymphocyte Antigen 4 (CTLA-4), B7H1, B7H4, OX-40, CD137, CD40, and TIM-3, which directly inhibit immune cells, immunotherapeutic agents which can act as immune checkpoint inhibitors useful in the methods of the present invention, include, but are not limited to, inhibitors of PD-1, PD-L1, PD-L2, CTLA-4, TIM-3, VISTA, BTLA, TIGIT, LAIR1, CD160, 2B4, CEACAM (e.g., CEACAM-1 and/or CEACAM-5), and/or TGF beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antibody fragment, that binds to the inhibitory molecule. Exemplary TIM-3 antibody molecules include, but are not limited to, MBG220, MBG227, and MBG219.Exemplary TIGIT inhibitors include, but are not limited to, 10A7 and 1F4 (Roche).

Further examples of modulators include but are not limited to B7-H5, ENTPD1, ENTPD2, SIGGIR, B7-1, B7-2, VSIG4, TIM-1, CD200, RANKL, and P2X7.

In one embodiment, the inhibitor is a soluble ligand (e.g., a CTLA-4-Ig or a TIM-3-Ig), or an antibody or antibody fragment that binds to PD-L1, PD-L2 or CTLA4. For example, the anti-LAG-3 antibody molecule can be administered in combination with an anti-CTLA-4 antibody, e.g., ipilimumab. Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9). In one embodiment, the anti-LAG-3 antibody molecule is administered after treatment, e.g., after treatment of a melanoma, with an anti-CTLA4 antibody (e.g., ipilimumab) with or without a BRAF inhibitor (e.g., vemurafenib or dabrafenib). In one embodiment, the anti-CTLA-4 antibody, e.g., ipilimumab, is administered at a dose of about 3 mg/kg. The anti-LAG-3 antibody molecule can be administered in combination at a dose from about 20 to 800 mg, e.g., about 20, 80, 240, or 800 mg. In one embodiment, the anti-LAG-3 antibody molecule is administered every 2 weeks (e.g., during weeks 1, 3, 5, 7) during each 8 week cycle, e.g., up to 96 weeks.

In another embodiment, the anti-LAG-3 antibody molecule is administered in combination with an anti-PD-1 antibody molecule. Exemplary doses that can be use include a dose of anti-PD-1 antibody molecule of about 1 to 10 mg/kg, e.g., 3 mg/kg. The anti-LAG-3 antibody molecule can be administered in combination at a dose from about 20 to 800 mg, e.g., about 20, 80, 240, or 800 mg. In one embodiment, the anti-LAG-3 antibody molecule is administered every 2 weeks (e.g., during weeks 1, 3, 5, 7) during each 8 week cycle, e.g., up to 96 weeks.

Immune inhibitory molecules, e.g., PD-1 and LAG-3, can regulate, e.g., synergistically, T-cell function to promote tumoral immune escape. In another embodiment, the anti-LAG-3 antibody molecule is administered in combination with an anti-TIM-3 antibody molecule. In still another embodiment, the anti-LAG-3 antibody molecule is administered in combination with an anti-PD-L1 antibody molecule. In yet other embodiments, the anti-LAG-3 antibody molecule is administered in combination with an anti-PD-1 antibody and an anti-TIM-3 antibody. In certain embodiments, the anti-LAG-3 antibody molecule is administered in combination with an anti-PD-1 antibody and an anti-PD-L1 antibody. In certain embodiments, the anti-LAG-3 antibody molecule is administered in combination with an anti-TIM-3 antibody and an anti-PD-L1 antibody. The combination of antibodies recited herein can be administered separately, e.g., as separate antibodies, or linked, e.g., as a bispecific or trispecific antibody molecule. In another embodiment, the anti-LAG-3 antibody molecule is administered in combination with a CEACAM inhibitor (e.g., CEACAM-1 and/or CEACAM-5 inhibitor), e.g., an anti-CEACAM antibody molecule. In another embodiment, the anti-LAG-3 antibody molecule, is administered in combination with a CEACAM-1 inhibitor, e.g., an anti-CEACAM-1 antibody molecule. In another embodiment, the anti-LAG-3 antibody molecule is administered in combination with a CEACAM-5 inhibitor, e.g., an anti-CEACAM-5 antibody molecule. In one embodiment, a bispecific antibody that includes an anti-LAG-3 antibody molecule and an anti-PD-1 or anti-LAG-3 antibody is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the synergistic effect of anti-LAG-3 and anti-PD-1 are described, e.g., in Woo et al. (2012) *Cancer Res.* 72(4):917-27).

In one embodiment, the inhibitor of CEACAM (e.g., CEACAM-1 and/or CEACAM-5) is an anti-CEACAM antibody molecule. Without wishing to be bound by theory, CEACAM-1 has been described as a ligand and partner of TIM-3 (see e.g., WO 2014/022332). Synergistic in vivo effect of the combination of anti-TIM-3 and anti-CEACAM-1 antibodies have been detected in xenograft cancer models (see e.g., WO 2014/022332). Tumors are believed to use CEACAM-1 or CEACAM-5 to inhibit the immune system, as described in, e.g., Markel et al. *J Immunol.* 2002 Mar. 15; 168(6):2803-10; Markel et al. *J Immunol.* 2006 Nov. 1; 177(9):6062-71; Markel et al. *Immunology.* 2009 February; 126(2):186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529. Thus, CEACAM inhibitors can be used with the other immunomodulators described herein (e.g., anti-LAG-3, anti-PD-1, or anti-TIM-3 inhibitors) to enhance an immune response against a cancer, e.g., melanoma, lung cancer (e.g., NSCLC), bladder, colon or ovarian cancer, or other cancers as described herein. In one embodiment, the inhibitor of CEACAM is an anti-CEACAM-1 antibody as described in WO 2010/125571, WO 2013/82366 and WO 2014/022332, e.g., a monoclonal antibody 34B1, 26H7, and 5F4 or a recombinant form thereof, as described in, e.g., US 2004/0047858, U.S. Pat. No. 7,132,255 and WO 99/52552. In other embodiments, the anti-CEACAM antibody is an anti-CEACAM-1 and/or anti-CEACAM-5 antibody molecule as described in, e.g., WO 2010/125571, WO 2013/054331 and US 2014/0271618.

In some embodiments, the LAG-3 and PD-1 immune inhibitory molecules (e.g., antibody molecules) are administered in combination with each other, e.g., to treat cancer. In some embodiments, the patient is a patient who progressed (e.g., experienced tumor growth) during therapy with a PD-1 inhibitor (e.g., an antibody molecule as described herein) and/or a PD-L1 inhibitor (e.g., antibody molecule). In some embodiments, therapy with the PD-1 antibody molecule and/or PDL1 antibody molecule is continued, and a LAG-3 immune inhibitory molecule (e.g., antibody) is added to the therapy. In other embodiments, the anti-LAG-3 antibody molecule is administered in combination with a cytokine, e.g., interleukin-21, interleukin-2, or interleukin 15. In certain embodiments, the combination of anti-LAG-3 antibody molecule and cytokine described herein is used to treat a cancer, e.g., a cancer as described herein (e.g., a solid tumor or melanoma).

Exemplary immunomodulators that can be used in combination with the anti-LAG-3 antibody molecules include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

Another example of such a combination is an anti-LAG-3 antibody in combination with decarbazine for the treatment of melanoma. Another example of such a combination is an anti-LAG-3 antibody molecule in combination with interleukin-2 (IL-2) for the treatment of melanoma. In one embodiment the anti-LAG-3 antibody molecule can be combined with IL-21. Without being bound by theory, the combined use of LAG-3 blockade and chemotherapy is that cell death, is believed to be facilitated by cell death, that is a consequence of the cytotoxic action of most chemotherapeutic compounds, which can result in increased levels of tumor antigen in the antigen presentation pathway. Other combination therapies that may result in synergy with LAG-3 blockade through cell death are radiation, surgery, and hormone deprivation. Each of these protocols creates a source of tumor antigen in the host. Angiogenesis inhibitors may also be combined with LAG-3 blockade. Inhibition of angiogenesis leads to tumor cell death which may feed tumor antigen into host antigen presentation pathways.

Combinations that include LAG-3 blocking antibodies can also be used in combination with bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of LAG-3 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies to each of these entities may be used in combination with anti-LAG-3 to counteract the effects of the immunosuppressive agent and favor tumor immune responses by the host.

Other antibodies which may be used to activate host immune responsiveness can be used in the combinations herein further in combination with an anti-LAG-3 antibody molecule, e.g., an anti-LAG-3 antibody molecule as described herein. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with LAG-3 antibodies (Ito, N. et al. (2000) Immunobiology 201 (5) 527-40). Activating antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Additional exemplary standard of care treatments are described in the section entitled "Combination Therapies" in US 2015/0259420 (U.S. Ser. No. 14/657,260), entitled "Antibody Molecules to LAG-3 and Uses Thereof," incorporated by reference in its entirety, and below.

In all of the methods described herein, LAG-3 blockade can be combined with other forms of immunotherapy such as cytokine treatment (e.g., interferons, GM-CSF, G-CSF, IL-2, IL-21), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123).

Methods of administering combination molecules (e.g., the anti-LAG-3 antibody molecules) are known in the art and are described below. Suitable dosages of the molecules used will depend on the age and weight of the subject and the particular drug used. Dosages and therapeutic regimens of the anti-LAG-3 antibody molecule can be determined by a skilled artisan. In certain embodiments, the anti-LAG-3 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg, or about 10 mg/kg, about 20 mg/kg, about 30 mg/kg, or about 40 mg/kg. In some embodiments, the anti-LAG-3 antibody molecule is administered at a dose of about 1-3 mg/kg, or about 3-10 mg/kg. In some embodiments, the anti-LAG-3 antibody molecule is administered at a dose of about 0.5-2, 2-4, 2-5, 5-15, or 5-20 mg/kg. The dosing schedule can vary from e.g., once a week to once every 2, 3, or 4 weeks. In one embodiment, the anti-LAG-3 antibody molecule is administered at a dose from about 10 to 20 mg/kg every other week.

The antibody molecule can be used in unconjugated forms or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecule can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Additional Combination Therapy

The combinations disclosed herein, e.g., the combination comprising LAG-3 blocking agents, may also be combined with a standard cancer treatment, e.g., chemotherapeutic regimens. In these instances, it may be possible to reduce the dose of chemotherapeutic reagent administered (Mokyr, M. et al. (1998) Cancer Research 58: 5301-5304). In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include antimicrotubule agents, topoisomerase inhibitors, anti-metabolites, mitotic inhibitors, alkylating agents, anthracyclines, *vinca* alkaloids, intercalating agents, agents capable of interfering with a signal transduction pathway, agents that promote apoptosis, proteosome inhibitors, and radiation (e.g., local or whole body irradiation).

Alternatively, or in combination with the aforesaid combinations, the methods and compositions described herein can be administered in combination with one or more of: an immunomodulator (e.g., an activator of a costimulatory molecule or an inhibitor of an inhibitory molecule); a vaccine, e.g., a therapeutic cancer vaccine; or other forms of cellular immunotherapy.

Exemplary combinations, e.g., combinations comprising anti-LAG-3 antibody molecules and standard of care for cancer, are disclosed in US 2015/0259420 (U.S. Ser. No. 14/657,260), entitled "Antibody Molecules to LAG-3 and Uses Thereof," incorporated by reference in its entiret, including, but not limited to, alkylating agents, anthracyclines, *vinca* alkaloids, proteosome inhibitors, and tyrosine kinase inhibitors (e.g., a receptor tyrosine kinase (RTK) inhibitor).

Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor, and a RET inhibitor. Selected tyrosine kinase inhibitors are chosen from sunitinib, erlotinib, gefitinib, or sorafenib.

In certain embodiments, combinations include Vascular Endothelial Growth Factor (VEGF) receptor inhibitors, e.g., a VEGFR inhibitor as described herein.

In some embodiments, the combination includes a PI3K inhibitor, e.g., a PI3K inhibitor as described herein.

In some embodiments, the combination includes an mTOR inhibitor, e.g., an mTOR inhibitor as described herein.

In some embodiments, the combination includes, e.g., GSK2118436, RG7204, PLX4032, GDC-0879, PLX4720, and sorafenib tosylate (Bay 43-9006). In some embodiments, the combination includes a RAF inhibitor, e.g., debrafinib or N-{3-[5-(2-aminopyrimidin-4-yl)-2-tert-butyl-1,3-thiazol-4-yl]-2-fluorophenyl}-2,6-difluorobenzene-sulfonamide.

In some embodiments, the combination includes a MEK inhibitor. In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage. Any MEK inhibitor can be used in combination including, but not limited to, ARRY-142886, G02442104 (also known as GSK1120212), RDEA436, RDEA119/BAY 869766, AS703026, G00039805 (also known as AZD6244 orselumetinib), BIX 02188, BIX 02189, CI-1040 (PD-184352), PD0325901, PD98059, U0126, GDC-0973 (Methanone, [3,4-difluoro-2-[(2-fluoro-4-iodophenyl)amino]phenyl][3-hydroxy-3-(25)-2-piperidinyl-1-azetidinyl]-), G-38963, G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983, the contents of which are incorporated herein by reference. In some embodiments, the MEK inhibitor is trametinib or N-(3-{3-Cyclopropyl-5-[(2-fluoro-4-iodophenyl)amino]-6,8-dimethyl-2,4,7-trioxo-3,4,6,7-tetrahydro-pyrido[4,3-d]pyrimidin-1(2H)-yl}phenyl)acetamide.

In some embodiments, the combination includes a JAK2 inhibitor, e.g., CEP-701, INCB18424, CP-690550 (tasocitinib).

In some embodiments, the combination includes paclitaxel or a paclitaxel agent, e.g., TAXOL®, protein-bound paclitaxel (e.g., ABRAXANE®).

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy.

The combinations disclosed herein can be administered in combination with one or more of the existing modalities for treating cancers, including, but not limited to: surgery; radiation therapy (e.g., external-beam therapy which involves three dimensional, conformal radiation therapy where the field of radiation is designed, local radiation (e.g., radition directed to a preselected target or organ), or focused radiation). Focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray), e.g., as described in WO 2012/177624.

In certain embodiments, the combination includes an antibody against a Killer-cell Immunoglobulin-like Receptor (also referred to herein as an "anti-KIR antibody"), a pan-KIR antibody, an anti-NKG2D antibody, and an anti-MICA antibody. In certain embodiments, the combination of anti-LAG-3 antibody molecule, anti-PD-1 antibody molecule and anti-KIR antibody, pan-KIR antibody, anti-MICA antibody, or anti-NKG2D antibody described herein is used to treat a cancer, e.g., a cancer as described herein (e.g., a solid tumor, e.g., an advanced solid tumor).

In one embodiment, the combination includes a cellular immunotherapy (e.g., Provenge (e.g., Sipuleucel)), and optionally in combination with cyclophosphamide. In certain embodiments, the combination of anti-LAG-3 antibody molecule, anti-PD-1 antibody molecule, Provenge and/or cyclophosphamide is used to treat a cancer, e.g., a cancer as described herein (e.g., a prostate cancer, e.g., an advanced prostate cancer).

In another embodiment, the combination includes a vaccine, e.g., a dendritic cell renal carcinoma (DC-RCC) vaccine. In certain embodiments, the combination of anti-LAG-3 antibody molecule, anti-PD-1 antibody molecule and/or the DC-RCC vaccine is used to treat a cancer, e.g., a cancer as described herein (e.g., a renal carcinoma, e.g., metastatic renal cell carcinoma (RCC)).

In one embodiment, the anti-LAG-3 antibody molecule, alone or in combination with another immunomodulator (e.g., an anti-PD-1, anti-PD-L1 or anti-TIM-3 antibody molecule), is used in combination with chemotherapy to treat a lung cancer, e.g., non-small cell lung cancer. In one embodiment, the anti-LAG-3 antibody molecule is used with platinum doublet therapy to treat lung cancer.

In yet another embodiment, the anti-LAG-3 antibody molecule, alone or in combination with another immunomodulator (e.g., an anti-PD-1, anti-PD-L1 or anti-TIM-3 antibody molecule), is used to treat a renal cancer, e.g., renal cell carcinoma (RCC) or metastatic RCC. The anti-LAG-3 antibody molecule can be administered in combination with one or more of: an immune-based strategy (e.g., interleukin-2 or interferon-α), a targeted agent (e.g., a VEGF inhibitor such as a monoclonal antibody to VEGF); a VEGF tyrosine kinase inhibitor such as sunitinib, sorafenib, axitinib and pazopanib; an RNAi inhibitor), or an inhibitor of a downstream mediator of VEGF signaling, e.g., an inhibitor of the mammalian target of rapamycin (mTOR), e.g., everolimus and temsirolimus.

An example of suitable therapeutics for use in combination with the anti-LAG-3 antibody molecule described herein, alone or in combination with another immunomodulator (e.g., an anti-PD-1, anti-PD-L1 or anti-TIM-3 antibody molecule), described herein for treatment of pancreatic cancer includes, but is not limited to, a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., R05126766); Notch signaling inhibitor (e.g., MK0752); monoclonal antibody-antibody fusion protein (e.g., L19IL2); curcumin; HSP90 inhibitor (e.g., tanespimycin, STA-9090); rIL-2, denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., R04929097); ribonucleotide reductase inhibitor (e.g., 3-AP); immunotoxin (e.g., HuC242-DM4); PARP inhibitor (e.g., KU-0059436, veliparib); CTLA-4 inhibitor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the anti-PD-1 antibody molecules described herein.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of small cell lung cancer includes, but is not limited to, a chemotherapeutic agent, e.g., etoposide, carboplatin, cisplatin, oxaliplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of non-small cell lung cancer includes, but is not limited to, a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, R05083945), MET inhibitor (e.g., PF-02341066, ARQ 197), PI3K kinase inhibitor (e.g., XL147, GDC-0941), Raf/MEK dual kinase inhibitor (e.g., R05126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide (SEQ ID NO: 293)-TNF alpha conjugate, dichloroacetate (DCA), HGF inhibitor (e.g., SCH 900105), SAR240550, PPAR-gamma agonist (e.g., CS-7017), gamma-secretase inhibitor (e.g., R04929097), epigenetic therapy (e.g., 5-azacitidine), nitroglycerin, MEK inhibitor (e.g., AZD6244), cyclin-dependent kinase inhibitor (e.g., UCN-01), cholesterol-Fusl, antitubulin agent (e.g., E7389), farnesyl-OH-transferase inhibitor (e.g., lonafarnib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of ovarian cancer includes, but is not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO4929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

In one exemplary embodiment, the anti-LAG-3 antibody molecule, alone or in combination with another immunomodulator (e.g., an anti-PD-1, anti-PD-L1 or anti-TIM-3 antibody molecule), is used to treat a myeloma, alone or in combination with one or more of: chemotherapy or other anti-cancer agents (e.g., thalidomide analogs, e.g., lenalidomide), HSCT (Cook, R. (2008) *J Manag Care Pharm.* 14(7 Suppl):19-25), an anti-TIM3 antibody (Hallett, W H D et al. (2011) *J of American Society for Blood and Marrow Transplantation* 17(8):1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) *Cancer J.* 15(6):502-10).

In yet another embodiment, the anti-LAG-3 antibody molecule, alone or in combination with another immunomodulator (e.g., an anti-PD-1, anti-PD-L1 or anti-TIM-3 antibody molecule), is used to treat a renal cancer, e.g., renal cell carcinoma (RCC) or metastatic RCC. The anti-PD-1 antibody molecule can be administered in combination with one or more of: an immune-based strategy (e.g., interleukin-2 or interferon-α), a targeted agent (e.g., a VEGF inhibitor such as a monoclonal antibody to VEGF, e.g., bevacizumab (Rini, B. I. et al. (2010) J. *Clin. Oncol.* 28(13):2137-2143)); a VEGF tyrosine kinase inhibitor such as sunitinib, sorafenib, axitinib and pazopanib (reviewed in Pal. S. K. et al. (2014) *Clin. Advances in Hematology & Oncology* 12(2):90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) *N. Engl. J. Med.* 356(22):2271-2281, Motzer, R. J. et al. (2008) *Lancet* 372: 449-456).

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of chronic myelogenous leukemia (AML) according to the invention includes, but is not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), ON 01910.Na, dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Thl-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), Hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., R05045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of chronic lymphocytic leukemia (CLL) includes, but is not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, R05072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Thl-like T cells/microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., R05045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG186, radiation therapy, bone marrow transplantation, stem cell transplantation, and a combination thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of acute lymphocytic leukemia (ALL) includes, but is not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., R05045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of acute myeloid leukemia (AML) includes, but is not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT388IL3 fusion protein, HDAC inhibitor (e.g., vorinostat, LBH589), plerixafor, mTOR inhibitor (e.g., everolimus), SRC inhibitor (e.g., dasatinib), HSP90 inhbitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., R05045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of multiple myeloma (MM) includes, but is not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), radiation therapy, bone marrow transplantation, stem cell transplantation, and a combination thereof.

An example of suitable therapeutics for use in combination with the anti-LAG-3 antibody molecule, alone or in combination with another immunomodulator (e.g., an anti-PD-1, anti-PD-L1 or anti-TIM-3 antibody molecule), for treatment of prostate cancer includes, but is not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of HNSCC includes, but is not limited to, one or both of Compound A8 as described herein (or a compound described in PCT Publication No. WO2010/029082) and cetuximab (e.g., Erbitux, marketed by BMS). In some embodiments, the therapeutic (e.g., the Compound A8 or compound related to A8) is a PI3K modulator, e.g., a PI3K inhibitor. In some embodiments, the therapeutic (e.g., cetuximab) modulates, e.g., inhibits, EGFR. In some embodiments, the cancer has, or is identified as having, elevated levels or activity of PI3K or EGFR compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of gastric cancer, e.g., MSI-high and/or EBV+ gastric cancer, includes, but is not limited to, Compound A8 as described herein (or a compound described in PCT Publication No. WO2010/029082). In some embodiments, the therapeutic (e.g., the Compound A8 or compound related to A8) is a PI3K modulator, e.g., a PI3K inhibitor. In some embodiments, the cancer has, or is identified as having, elevated levels or activity of PI3K compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of gastric cancer, e.g., MSI-high and/or RNF43-inactivated gastric cancer, includes, but is not limited to, Compound A28 as described herein (or a compound described in PCT Publication No. WO2010/101849). In some embodiments, the therapeutic (e.g., the Compound A28 or compound related to A28) is a modulator, e.g., inhibitor, of porcupine. In some embodiments, the cancer has, or is identified as having, elevated levels or activity of porcupine compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of GI stromal tumor (GIST), includes, but is not limited to, Compound A16 as described herein (or a compound described in PCT Publication No. WO1999/003854). In some embodiments, the therapeutic (e.g., the Compound A16 or compound related to A16) is a modulator, e.g., inhibitor, of a tyrosine kinase. In some embodiments, the cancer has, or is determined to have, elevated levels or activity of a tyrosine kinase compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of NSCLC, e.g., squamous or adenocarcinoma, includes, but is not limited to, one or both of Compound A17 as described herein (or a compound described in U.S. Pat. Nos. 7,767,675 and 8,420,645) and Compound A23 as described herein (or a compound described in PCT Publication No. WO2003/077914). In some embodiments, the compound (e.g., the Compound A17 or compound related to A17) modulates, e.g., inhibits, c-MET. In some embodiments, the compound (e.g., the Compound A23 or compound related to A23) modulates, e.g., inhibits, Alk. In some embodiments, the cancer has, or is determined to have, elevated levels or activity of one or both of c-MET or Alk compared to a control cell or reference value. In some embodiments, the cancer has, or is identified as having, a mutation in EGFR.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of melanoma (e.g., NRAS melanoma) includes, but is not limited to, one or both of Compound A24 as described herein (or a compound described in U.S. Pat. Nos. 8,415,355 and 8,685,980) and Compound A34 as described herein (or a compound described in PCT Publication No. WO2003/077914). In some embodiments, the compound (e.g., the Compound A24 or compound related to A24) modulates, e.g., inhibits, one or more of JAK and CDK4/6. In some embodiments, the compound (e.g., the Compound A34 or compound related to A34) modulates, e.g., inhibits, MEK. In some embodiments, the cancer has, or is identified as having, elevated levels or activity of one or more of JAK, CDK4/6, and MEK compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of melanoma (e.g., NRAS melanoma) includes, but is not limited to, one or both of Compound A29 as described herein (or a compound described in PCT Publication No. WO2011/025927) and Compound A34 as described herein (or a compound described in PCT Publication No. WO2003/077914). In some embodiments, the compound (e.g., the Compound A29 or compound related to A29) modulates, e.g., inhibits, BRAF. In some embodiments, the compound (e.g., the Compound A34 or compound related to A34) modulates, e.g., inhibits, MEK. In some embodiments, the cancer has, or is identified as having, elevated levels or activity of one or both of BRAF and MEK compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of squamous NSCLC includes, but is not limited to, Compound A5 as described herein (or a compound described in U.S. Pat. No. 8,552,002). In some embodiments, the compound (e.g., the Compound A5 or compound related to A5) modulates, e.g., inhibits, FGFR. In some embodiments, the cancer has, or is identified as having, elevated levels or activity of FGFR compared to a control cell or reference value.

An example of suitable therapeutics for use in combination with the anti-LAG-3 antibody molecules, alone or in combination with another immunomodulator (e.g., an anti-PD-1, anti-PD-L1 or anti-TIM-3 antibody molecule), for treatment of colorectal cancer includes, but is not limited to, one or both of Compound A29 as described herein (or a compound PCT Publication No. WO2011/025927) and cetuximab (e.g., Erbitux, marketed by BMS). In some embodiments, the therapeutic (e.g., the Compound A29 or compound related to A29) modulates, e.g., inhibits, BRAF. In some embodiments, the therapeutic (e.g., cetuximab) modulates, e.g., inhibits EGFR. In some embodiments, the cancer has, or is identified as having, elevated levels or activity of BRAF or EGFR compared to a control cell or reference value.

This disclosure also provides a method of treating cancer with Compound A8, cetuximab, and a LAG-3 antibody molecule (optionally in combination with a PD-1 antibody molecule or TIM-3 antibody molecule). In some embodiments, the patient is first treated with Compound A8 and cetuximab. This treatment continues for an amount of time, e.g., a predetermined amount of time, e.g., about 1, 2, 4, 6, 8, 10, or 12 months. Next, the LAG-3 antibody molecule (optionally in combination with a PD-1 antibody molecule or TIM-3 antibody molecule) is administered. The LAG-3 antibody can optionally be administered in combination with cetuximab.

In some embodiments, the patient is first treated with all three of Compound A8, cetuximab, and a LAG-3 antibody molecule (optionally in combination with a PD-1 antibody molecule or TIM-3 antibody molecule). This treatment continues for an amount of time, e.g., a predetermined amount of time, e.g., about 6, 8, 10, or 12 months. Next, the Compound A8 and/or cetuximab can be tapered off, so that the maintenance phase involves treatment with the LAG-3 antibody molecule (e.g., as a monotherapy, or in combination with a PD-1 antibody molecule or TIM-3 antibody molecule) but not Compound A8 or cetuximab.

In other embodiments, the three compounds (Compound A8, cetuximab, and a LAG-3 antibody molecule, optionally in combination with a PD-1 antibody molecule or TIM-3 antibody molecule) are given sequentially at the outset of the treatment. For instance, Compound A8 and cetuximab can be given first, as described above. Next, the LAG-3 antibody molecule (optionally in combination with a PD-1 antibody molecule or TIM-3 antibody molecule) is added to the regimen. Next, the Compound A8 and/or cetuximab can be tapered off as described above.

Exemplary doses for the three (or more) agent regimens are as follows. The LAG-3 antibody molecule can be administered, e.g., at a dose of about 1 to 40 mg/kg, e.g., 1 to 30 mg/kg, e.g., about 5 to 25 mg/kg, about 10 to 20 mg/kg, about 1 to 5 mg/kg, or about 3 mg/kg. In some embodiments, the Compound A8 is administered at a dose of approximately 200-300, 300-400, or 200-400 mg. In some embodiments, the cetuximab is administered at a 400 mg/m2 initial dose as a 120-minute intravenous infusion followed by 250 mg/m2 weekly infused over 60 minutes. In embodiments, one or more of the Compound A8, cetuximab, and LAG-3 antibody molecule is administered at a dose that is lower than the dose at which that agent is typically administered as a monotherapy, e.g., about 0-10%, 10-20%, 20-30%, 30-40%, 40-50%, 50-60%, 60-70%, 70-80%, or 80-90% lower than the dose at which that agent is typically administered as a monotherapy. In embodiments, the one or more of the Compound A8, cetuximab, and LAG-3 antibody molecule is administered at a dose that is lower than the dose of that agent recited in this paragraph, e.g., about 0-10%, 10-20%, 20-30%, 30-40%, 40-50%, 50-60%, 60-70%, 70-80%, or 80-90% lower than the dose of that agent recited in this paragraph. In certain embodiments, the concentration of the Compound A8 that is required to achieve inhibition, e.g., growth inhibition, is lower when the Compound A8 is administered in combination with one or both of the cetuximab and LAG-3 antibody molecule than when the Compound A8 is administered individually. In certain embodiments, the concentration of the cetuximab that is required to achieve inhibition, e.g., growth inhibition, is lower when the cetuximab is administered in combination with one or both of the Compound A8 and LAG-3 antibody molecule than when the cetuximab is administered individually. In certain embodiments, the concentration of the LAG-3 antibody molecule that is required to achieve inhibition, e.g., growth inhibition, is lower when the LAG-3 antibody molecule is administered in combination with one or both of the cetuximab and Compound A8 than when the LAG-3 antibody molecule is administered individually.

Additionally disclosed herein is a method of treating cancer with the anti-LAG-3 antibody molecules, alone or in combination with another immunomodulator (e.g., an anti-PD-1, anti-PD-L1 or anti-TIM-3 antibody molecule), and a targeted anti-cancer agent, e.g., an agent that targets one or more proteins. In some embodiments, the anti-LAG-3 antibody molecule (and optionally other immunomodulator(s)) are administered first, and the targeted anti-cancer agent is administered second. The length of time between administration of the anti-LAG-3 antibody molecule and the targeted anti-cancer agent can be, e.g., 10, 20, or 30 minutes, 1, 2, 4, 6, or 12 hours, or 1, 2, 3, 4, 5, 6, or 7 days, or any span of time within this range. In certain embodiments, the anti-LAG-3 antibody molecule is administered repeatedly over a period of time (e.g., 1, 2, 3, 4, 5, or 6 days, or 1, 2, 4, 8, 12, 16, or 20 weeks, or any span of time within this range) before the targeted anti-cancer agent is administered. In other embodiments, the anti-LAG-3 antibody molecule and the targeted anti-cancer agent are administered at substantially the same time.

Infectious Diseases

Other methods of the invention are used to treat patients that have been exposed to particular toxins or pathogens. Accordingly, another aspect of the invention provides a method of treating an infectious disease in a subject comprising administering to the subject a combination as disclosed herein, e.g, a combination including an anti-LAG-3 antibody molecule, such that the subject is treated for the infectious disease.

In the treatment of infection (e.g., acute and/or chronic), administration of the anti-LAG-3 antibody molecules (alone or in combination with an anti-PD-1, anti-PD-L1 or anti-TIM-3 antibody molecule) can be combined with conventional treatments in addition to or in lieu of stimulating natural host immune defenses to infection. Natural host immune defenses to infection include, but are not limited to inflammation, fever, antibody-mediated host defense, T-lymphocyte-mediated host defenses, including lymphokine secretion and cytotoxic T-cells (especially during viral infection), complement mediated lysis and opsonization (facilitated phagocytosis), and phagocytosis. The ability of the anti-LAG-3 antibody molecules to reactivate dysfunctional T-cells would be useful to treat chronic infections, in particular those in which cell-mediated immunity is important for complete recovery.

Similar to its application to tumors as discussed above, antibody mediated LAG-3 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to Hepatitis (A, B, and C), Influenza, HIV, Herpes, Giardia, Malaria, *Leishmania, Staphylococcus aureus, Pseudomonas Aeruginosa*. LAG-3 blockade is particularly useful against established infections by agents such as HIV that present altered antigens over the course of the infections. These novel epitopes are recognized as foreign at the time of anti-human LAG-3 administration, thus provoking a strong T cell response that is not dampened by negative signals through LAG-3.

Additional Combination Therapies

Combinations disclosed herein, e.g., combination of anti-LAG-3 antibody molecules with one or more second therapeutics are provided herein. Many of the combinations in this section are useful in treating cancer, but other indications are also described. This section focuses on combinations of anti-LAG-3 antibody molecules, optionally in combination with one or more immunomodulators (e.g., an anti-PD-1 antibody molecule, an anti-TIM-3 antibody molecule, or an anti-PD-L1 antibody molecule), with one or more of the agents described in Table 7. In the combinations herein below, in one embodiment, the anti-LAG-3 antibody molecule comprises (i) a heavy chain variable region (VH) comprising a VHCDR1 amino acid sequence chosen from SEQ ID NO: 1, SEQ ID NO: 4 or SEQ ID NO: 286; a VHCDR2 amino acid sequence of SEQ ID NO: 2; and a VHCDR3 amino acid sequence of SEQ ID NO: 3; and (ii) a light chain variable region (VL) comprising a VLCDR amino acid sequence of SEQ ID NO: 10, a VLCDR2 amino acid sequence of SEQ ID NO: 11, and a VLCDR3 amino acid sequence of SEQ ID NO: 12.

In one embodiment, the combination, e.g., a combination comprising an anti-LAG-3 antibody molecule as described herein, is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, an anti-LAG-3 antibody molecule is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis.

In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the combination, e.g., a combination comprising an anti-LAG-3 antibody molecule as described herein, is used in combination with a BCR-ABL inhibitor, TASIGNA (Compound A2, or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, an anti-LAG-3 antibody molecule is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension.

In one embodiment, the BCR-ABL inhibitor or TASIGNA is administered at a dose of about 300 mg (e.g., twice daily, e.g., for newly diagnosed Ph+ CML-CP), or about 400 mg, e.g., twice daily, e.g., for resistant or intolerant Ph+ CML-CP and CML-AP). BCR-ABL inhibitor or a Compound A2 is administered at a dose of about 300-400 mg.

In another embodiment, the combination, e.g., a combination comprising an anti-LAG-3 antibody molecule as described herein, is used in combination with an HSP90 inhibitor, such as 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl) isoxazole-3-carboxamide (Compound A3), or a compound disclosed in PCT Publication No. WO 2010/060937 or WO 2004/072051. In one embodiment, an anti-LAG-3 antibody molecule is used in combination with 5-(2,4-dihydroxy-5-isopropylphenyl)-N-ethyl-4-(4-(morpholinomethyl)phenyl) isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the combination, e.g., a combination comprising an anti-LAG-3 antibody molecule as described herein, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, an anti-LAG-3 antibody molecule is used in combination with Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the combination, e.g., a combination comprising an anti-LAG-3 antibody molecule as described herein, is used in combination with an FGFR inhibitor, 3-(2,6-dichloro-3,5-dimethoxyphenyl)-1-(6-((4-(4-ethylpiperazin-1-yl)phenyl) amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, an anti-LAG-3 antibody molecule is used in combination with Compound A5, or a compound as described in U.S. Pat. No. 8,552,002, to treat a disorder such as a digestive/gastrointestinal cancer, a hematological cancer, or a solid tumor.

In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurea (Compound A5) is administered at a dose of about 100-125 mg (e.g., per day), e.g., about 100 mg or about 125 mg.

In another embodiment, the combination, e.g., a combination comprising an anti-LAG-3 antibody molecule as described herein, is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, an anti-LAG-3 antibody molecule is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer.

In one embodiment, the PI3K inhibitor or Buparlisib (Compound A6) is administered at a dose of about 100 mg (e.g., per day).

In another embodiment, the combination, e.g., a combination comprising an anti-LAG-3 antibody molecule as described herein, is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386 to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in a PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7). In one embodiment, an anti-LAG-3 antibody molecule is used in combination with 8-(2,6-difluoro-3,5-dimethoxyphenyl)-N-(4-((dimethylamino)methyl)-1H-imidazol-2-yl)quinoxaline-5-carboxamide (Compound A7), or a compound disclosed in PCT Publication No. WO 2009/141386, to treat a disorder such as a cancer characterized by angiogenesis.

In one embodiment, the FGFR inhibitor or 8-(2,6-difluoro-3,5-dimethoxyphenyl)-N-(4-((dimethylamino) methyl)-1H-imidazol-2-yl)quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment, the combination, e.g., a combination comprising an anti-LAG-3 antibody molecule as described herein, is used in combination with a PI3K inhibitor, (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082 to treat a disorder, e.g., a disorder described herein. In one embodiment, the PI3K inhibitor is (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, an anti-LAG-3 antibody molecule is used in combination with (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer.

In one embodiment, the PI3K inhibitor or (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the combination, e.g., a combination comprising an anti-LAG-3 antibody molecule as described herein, is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, an anti-LAG-3 antibody molecule is used in combination with a compound disclosed in PCT Publication No. WO 2010/149755, to treat prostate cancer.

In another embodiment, the combination, e.g., a combination comprising an anti-LAG-3 antibody molecule as described herein, is used in combination with an HDM2 inhibitor, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786 to treat a disorder, e.g., a disorder described herein). In one embodiment, the HDM2 inhibitor is (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, an anti-LAG-3 antibody molecule is used in combination with (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10), or a compound disclosed in PCT Publication No. WO 2011/076786, to treat a disorder such as a solid tumor.

In one embodiment, the HDM2 inhibitor or (S)-1-(4-chlorophenyl)-7-isopropoxy-6-methoxy-2-(4-(methyl(((1r,4S)-4-(4-methyl-3-oxopiperazin-1-yl)cyclohexyl)methyl) amino)phenyl)-1,2-dihydroisoquinolin-3(4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the combination, e.g., a combination comprising an anti-LAG-3 antibody molecule as described herein, is used in combination with an iron chelating agent, Deferasirox (also known as EXJADE; Compound A11), or a compound disclosed in PCT Publication No. WO 1997/049395 to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, an anti-LAG-3 antibody molecule is used in combination with Deferasirox (Compound A11), or a compound disclosed in PCT Publication No. WO 1997/049395, to treat iron overload, hemochromatosis, or myelodysplasia.

In another embodiment, the combination, e.g., a combination comprising an anti-LAG-3 antibody molecule as described herein, is used in combination with an aromatase inhibitor, Letrozole (also known as FEMARA; Compound A12), or a compound disclosed in U.S. Pat. No. 4,978,672 to treat a disorder, e.g., a disorder described herein. In one embodiment, the aromatase inhibitor is Letrozole (Compound A12) or a compound disclosed in U.S. Pat. No. 4,978,672. In one embodiment, an LAG-3 antibody molecule is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the combination, e.g., a combination comprising an anti-LAG-3 antibody molecule as described herein, is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826 to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, an anti-LAG-3 antibody molecule is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the combination, e.g., a combination comprising an anti-LAG-3 antibody molecule as described herein, is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105 to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, an anti-LAG-3 antibody molecule is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, the combination, e.g., a combination comprising an anti-LAG-3 antibody molecule as described herein, is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224 to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, a LAG-3 antibody molecule is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In another embodiment, the combination, e.g., a combination comprising an anti-LAG-3 antibody molecule as described herein, is used in combination with an apoptosis inducer and/or an angiogenesis inhibitor, such as Imatinib mesylate (also known as GLEEVEC; Compound A16) or a compound disclosed in PCT Publication No. WO1999/003854 to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, an anti-LAG-3 antibody molecule is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis.

In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the combination, e.g., a combination comprising an anti-LAG-3 antibody molecule as described herein, is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, an LAG-3 antibody molecule is used in combination with 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia.

In one embodiment, the JAK inhibitor or a 2-fluoro-N-methyl-4-(7-(quinolin-6-ylmethyl)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the combination, e.g., a combination comprising an anti-LAG-3 antibody molecule as described herein, is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, an anti-LAG-3 antibody molecule is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia.

In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the combination, e.g., a combination comprising an anti-LAG-3 antibody molecule as described herein, is used in combination with a deacetylase (DAC) inhibitor, Panobinostat (Compound A19), or a compound disclosed in PCT Publication No. WO 2014/072493 to treat a disorder, e.g., a disorder described herein. In one embodiment, the DAC inhibitor is Panobinostat (Compound A19) or a compound disclosed in PCT Publication No. WO 2014/072493. In one embodiment, an anti-LAG-3 antibody molecule is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer.

In one embodiment, the DAC inhibitor or Panobinostat (Compound A19) is administered at a dose of about 20 mg (e.g., per day).

In another embodiment, the combination, e.g., a combination comprising an anti-LAG-3 antibody molecule as described herein, is used in combination with an inhibitor of one or more of cytochrome P450 (e.g., 11B2), aldosterone or angiogenesis, Osilodrostat (Compound A20), or a compound disclosed in PCT Publication No. WO2007/024945 to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, an anti-LAG-3 antibody molecule is used in combination with Osilodrostat (Compound A20), or a compound disclosed in PCT Publication No. WO2007/024945, to treat a disorder such as Cushing's syndrome, hypertension, or heart failure therapy.

In another embodiment, the combination, e.g., a combination comprising an anti-LAG-3 antibody molecule as described herein, is used in combination with a IAP inhibitor, (S)-N-((S)-1-cyclohexyl-2-((S)-2-(4-(4-fluorobenzoyl) thiazol-2-yl)pyrrolidin-1-yl)-2-oxoethyl)-2-(methylamino) propanamide (Compound A21) or a compound disclosed in U.S. Pat. No. 8,552,003 to treat a disorder, e.g., a disorder described herein. In one embodiment, the IAP inhibitor is (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003.

In one embodiment, an anti-LAG-3 antibody molecule is used in combination with (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder.

In one embodiment, the IAP inhibitor or (S)-N-((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg, e.g., once weekly.

In another embodiment, the combination, e.g., a combination comprising an anti-LAG-3 antibody molecule as described herein, is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, an anti-LAG-3 antibody molecule is used in combination with Sonidegib phosphate (Compound A22), (R)-2-(5-(4-(6-benzyl-4,5-dimethylpyridazin-3-yl)-2-methylpiperazin-1-yl) pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation.

In certain embodiments, Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the combination, e.g., a combination comprising an anti-LAG-3 antibody molecule as described herein, is used in combination with an Alk inhibitor, ceritinib (also known as ZY KADIA; Compound A23) or a compound disclosed in PCT Publication No. WO 2007/131201 to treat a disorder, e.g., a disorder described herein. In one embodiment, the Alk inhibitor is ceritinib (Compound A23) or a compound disclosed in PCT Publication No. WO 2007/131201. In one embodiment, an anti-LAG-3 antibody molecule is used in combination with ceridinib Cornpound A23), or a compound disclosed in PCT Publication No. WO 2007/131201, to treat a disorder such as non-small cell lung cancer or solid tumors.

In one embodiment, the Alk inhibitor or ceritinib (Compound A23) is administered at a dose of approximately 750 mg, e.g., once daily.

In another embodiment, the combination, e.g., a combination comprising an anti-LAG-3 antibody molecule as described herein, is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or 8,685,980 to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. No. 8,415,355 or 8,685,980. In one embodiment, an anti-LAG-3 antibody molecule is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or 8,685,980, to treat a disorder such as a lymphoma, a neurologic cancer, a melanoma, a breast cancer, or a solid tumor.

In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the combination, e.g., a combination comprising an anti-LAG-3 antibody molecule as described herein, is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, an anti-LAG-3 antibody molecule is used in combination with human monoclonal antibody molecule (Compound A26) described in U.S. Pat. No. 7,867,493 to treat a disorder such as, a cancer, a prostate cancer, or a breast cancer.

In another embodiment, the combination, e.g., a combination comprising an anti-LAG-3 antibody molecule as described herein, is used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124 to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, an anti-LAG-3 antibody molecule is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the combination, e.g., a combination comprising an anti-LAG-3 antibody molecule as described herein, is used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849 to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, an anti-LAG-3 antibody molecule is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer).

In certain embodiments, 2-(2',3-dimethyl-[2,4'-bipyridin]-5-yl)-N-(5-(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg, 5 mg, 10 mg, 20 mg, 30 mg, or 40 mg. The dosing schedule can vary from e.g., every other day to daily, twice or three times a day.

In another embodiment, the combination, e.g., a combination comprising an anti-LAG-3 antibody molecule as described herein, is used in combination with a BRAF inhibitor, Encorafenib (Compound A29), or a compound disclosed in PCT Publication No. WO 2011/025927 to treat a disorder, e.g., a disorder described herein. In one embodiment, the BRAF inhibitor is Encorafenib (Compound A29) or a compound disclosed in PCT Publication No. WO 2011/025927. In one embodiment, an anti-LAG-3 antibody molecule is used in combination with Encorafenib (Compound A29), or a compound disclosed in PCT Publication No. WO 2011/025927, to treat a disorder such as a non-small cell lung cancer, a melanoma, or a colorectal cancer.

In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the combination, e.g., a combination comprising an anti-LAG-3 antibody molecule as described herein, is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409 to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, an anti-LAG-3 antibody molecule is used in combination with 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the combination, e.g., a combination comprising an anti-LAG-3 antibody molecule as described herein, is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, an anti-LAG-3 antibody molecule is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer.

In some embodiments, Compound A31 is a human monoclonal antibody molecule.

In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the combination, e.g., a combination comprising an anti-LAG-3 antibody molecule as described herein, is used in combination an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, an anti-LAG-3 antibody molecule is used in combination with Compound A32, or a compound as described in Table 7, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer.

In some embodiments, Compound A32 is an antibody molecule drug conjugate against an FGFR2 and/or FGFR4, e.g., mAb 12425.

In another embodiment, the combination, e.g., a combination comprising an anti-LAG-3 antibody molecule as described herein, is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, an anti-LAG-3 antibody molecule is used in combination with Compound A33, or a compound as described in PCT Publication No. WO 2004/045532, to treat a disorder such as a cancer, a prostate cancer, a breast cancer, or pigmented villonodular synovitis (PVNS).

In embodiments, Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

In another embodiment, the combination, e.g., a combination comprising an anti-LAG-3 antibody molecule as described herein, is used in combination with a MEK inhibitor, Binimetinib (Compound A34), or a compound disclosed in PCT Publication No. WO 2003/077914 to treat a disorder, e.g., a disorder described herein. In one embodiment, the MEK inhibitor is Binimetinib (Compound A34), or a compound disclosed in PCT Publication No. WO 2003/077914. In one embodiment, an anti-LAG-3 antibody molecule is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer.

In one embodiment, the MEK inhibitor or Binimetinib (Compound A34) is administered at a dose of about 45 mg, e.g., twice daily.

In another embodiment, the combination, e.g., a combination comprising an anti-LAG-3 antibody molecule as described herein, is used in combination an inhibitor of one or more of c-KIT, histamine release, Flt3 (e.g., FLK2/STK1) or PKC, Midostaurin (Compound A35) or a compound disclosed in PCT Publication No. WO 2003/037347 to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, an anti-LAG-3 antibody molecule is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related mascular degeration, a diabetic complication, or a dermatologic disorder.

In another embodiment, the combination, e.g., a combination comprising an anti-LAG-3 antibody molecule as described herein, is used in combination with a TOR inhibitor (e.g., mTOR inhibitor), Everolimus (also known as AFINITOR; Compound A36) or a Compound disclosed in PCT Publication No. WO 2014/085318 to treat a disorder, e.g., a disorder described herein). In one embodiment, the TOR inhibitor is Everolimus (Compound A36) or a Compound disclosed in PCT Publication No. WO 2014/085318. In one embodiment, an anti-LAG-3 antibody molecule is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer (e.g., an atypical pulmonary carcinoid tumor), a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer.

In one embodiment, the TOR inhibitor or Everolimusis (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the combination, e.g., a combination comprising an anti-LAG-3 antibody molecule as described herein, is used in combination an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377 to treat a disorder, e.g., a disorder described herein. In one embodiment, the inhibitor of one or more of VEGFR-2, PDGFR-beta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, an anti-LAG-3 antibody molecule is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the combination, e.g., a combination comprising an anti-LAG-3 antibody molecule as described herein, is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761 to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, an anti-LAG-3 antibody molecule is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a nurologic cancer, a skin cancer (e.g., a melanoma), a pancreatic cancer, a liver cancer, Cushing's syndrome, a gastrointestinal disorder, acromegaly, a liver and biliary tract disorder, or liver cirrhosis.

In another embodiment, the combination, e.g., a combination comprising an anti-LAG-3 antibody molecule as described herein, is used in combination a signal transduction modulator and/or angiogenesis inhibitor, Dovitinib (Compound A39) or a compound disclosed in PCT Publication No. WO 2009/115562 to treat a disorder, e.g., a disorder described herein. In one embodiment, the signal transduction modulator and/or angiogenesis inhibitor is Dovitinib (Compound A39) or a compound disclosed in PCT Publication No. WO 2009/115562. In one embodiment, an anti-LAG-3 antibody molecule is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the combination, e.g., a combination comprising an anti-LAG-3 antibody molecule as described herein, is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757 to treat a disorder, e.g., a disorder described herein. In one embodiment, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, an anti-LAG-3 antibody molecule is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor.

In one embodiment, the EGFR inhibitor or (R,E)-N-(7-chloro-1-(1-(4-(dimethylamino)but-2-enoyl)azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In another embodiment, the combination, e.g., a combination comprising an anti-LAG-3 antibody molecule as described herein, is used in combination an ALK inhibitor, N6-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687 to treat a disorder, e.g., a disorder described herein. In one embodiment, the ALK inhibitor is N6-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, an anti-LAG-3 antibody molecule is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the combination, e.g., a combination comprising an anti-LAG-3 antibody molecule as described herein, is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-N2-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-N4-(5-methyl-1H-pyrazol-3-yl)pyrimidine-2,4-diamine (Compound A45) or a compound disclosed in PCT Publication No. WO 2010/002655 to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-N2-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655. In one embodiment, an anti-LAG-3 antibody molecule is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the combination, e.g., a combination comprising an anti-LAG-3 antibody molecule as described herein, is used in combination a P-Glycoprotein 1 inhibitor, Valspodar (also known as AMDRAY; Compound A46) or a compound disclosed in EP 296122 to treat a disorder, e.g., a disorder described herein. In one embodiment, the P-Glycoprotein 1 inhibitor is Valspodar (Compound A46) or a compound disclosed in EP 296122. In one embodiment, an anti-LAG-3 antibody molecule is used in combination with Valspodar (Compound A46), or a compound disclosed in EP 296122, to treat a disorder such as a cancer or a drug-resistant tumor.

In another embodiment, the combination, e.g., a combination comprising an anti-LAG-3 antibody molecule as described herein, is used in combination one or more of a VEGFR inhibitor, Vatalanib succinate (Compound A47) or a compound disclosed in EP 296122 to treat a disorder, e.g., a disorder described herein. In one embodiment, the VEGFR inhibitor is Vatalanib succinate (Compound A47) or a compound disclosed in EP 296122. In one embodiment, an anti-LAG-3 antibody molecule is used in combination with Vatalanib succinate (Compound A47), or a compound disclosed in EP 296122, to treat cancer.

In another embodiment, the combination, e.g., a combination comprising an anti-LAG-3 antibody molecule as described herein, is used in combination with an IDH inhibitor or a compound disclosed in WO2014/141104 to treat a disorder, e.g., a disorder described herein. In one embodiment, the IDH inhibitor is a compound disclosed in PCT Publication No. WO2014/141104. In one embodiment, an anti-LAG-3 antibody molecule is used in combination with a compound disclosed in WO2014/141104 to treat a disorder such as a cancer.

In another embodiment, the combination, e.g., a combination comprising an anti-LAG-3 antibody molecule as described herein, is used in combination with a BCL-ABL inhibitor or a compound disclosed in PCT Publication No. WO2013/171639, WO2013/171640, WO2013/171641, or WO2013/171642 to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, an anti-LAG-3 antibody molecule is used in combination with a compound disclosed in PCT Publication No. WO2013/171639, WO2013/171640, WO2013/171641, or WO2013/171642 to treat a disorder such as a cancer.

In another embodiment, the combination, e.g., a combination comprising an anti-LAG-3 antibody molecule as described herein, is used in combination with a c-RAF inhibitor or a compound disclosed in PCT Publication No. WO2014/151616 to treat a disorder, e.g., a disorder described herein. In one embodiment, the c-RAF inhibitor is Compound A50 or a compound disclosed in PCT Publication No. WO2014/151616. In one embodiment, an anti-LAG-3 antibody molecule is used in combination with a compound disclosed in PCT Publication No. WO2014/151616 to treat a disorder such as a cancer.

In another embodiment, the combination, e.g., a combination comprising an anti-LAG-3 antibody molecule as described herein, is used in combination with an ERK1/2 ATP competitive inhibitor or a compound disclosed in PCT Publication No. WO2015/066188 to treat a disorder, e.g., a disorder described herein. In one embodiment, the ERK1/2 ATP competitive inhibitor is a compound disclosed in PCT Publication No. WO2015/066188. In one embodiment, an anti-LAG-3 antibody molecule is used in combination with Compound A51 or a compound disclosed in PCT Publication No. WO2015/066188 to treat a disorder such as a cancer.

In another embodiment, the combination, e.g., a combination comprising an anti-LAG-3 antibody molecule as described herein, is used in combination with a tyrosine kinase inhibitor, (Compound A52) or a compound disclosed in PCT Publication No. WO2005/073224 to treat a disorder, e.g., a disorder described herein. In one embodiment, the tyrosine kinase inhibitor is 4-((2-(((1R,2R)-2-hydroxycyclohexyl)amino)benzo[d]thiazol-6-yl)oxy)-N-methylpicolinamide (Compound A52) or a compound disclosed in PCT Publication No. WO2005/073224. In one embodiment, an anti-LAG-3 antibody molecule is used in combination with 4-((2-(((1R,2R)-2-hydroxycyclohexyl)amino)benzo[d]thiazol-6-yl)oxy)-N-methylpicolinamide (Compound A52), or a compound disclosed in PCT Publication No. WO2005/073224, to treat a disorder such as a cancer.

In some embodiments, the combination, e.g., a combination comprising an anti-LAG-3 antibody molecule as described herein, is administered in combination with one or more agents selected from, Compound A8, Compound A17, Compound A23, Compound A24, Compound A27, Compound A29, and Compound A33.

In some embodiments, the combination, e.g., a combination comprising an anti-LAG-3 antibody molecule as described herein, is administered in combination with an anti-cancer agent having a known activity in an immune cell assay, e.g., in one or more of a huMLR assay, a T cell proliferation assay, and a B-cell proliferation assay. Exemplary assays are described below. Based on the assay, an IC50 for can be calculated for each test agent. In embodiments, the anti-cancer agent has an IC50 of, e.g., 0-1 μM, 1-4 μM, or greater than 4 μM, e.g., 4-10 μM or 4-20 μM. In embodiments, the second therapeutic agent is chosen from one or more of: Compound A9, Compound A16, Compound A17, Compound A21, Compound A22, Compound A25, Compound A28, Compound A48, and Compound 49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg.

In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In some embodiments, the Compound A10 (or compound related to Compound A10) is administered at a dose of approximately 400 to 700 mg, e.g., administered three times weekly, 2 weeks on and one week off. In some embodiments, the BCR-ABL inhibitor is administered at a dose of approximately 20 mg bid-80 mg bid.

Exemplary huMLR assay and B or T cell proliferation assays are provided below.

Human Mixed Lymphocyte Reaction

The Mixed Lymphocyte Reaction (MLR) is a functional assay which measures the proliferative response of lymphocytes from one individual (the responder) to lymphocytes from another individual (the stimulator). To perform an allogeneic MLR, peripheral blood mononuclear cells (PBMC) from three donors were isolated from buffy-coats of unknown HLA type (Kantonspital Blutspendezentrum from Bern and Aarau, Switzerland). The cells were prepared at $2\times10^5$ in 0.2 mL of culture medium containing RPMI 1640 GlutaMAX™ with 10% fetal calf serum (FCS), 100U penicillin/100 μg streptomycin, 50 μM 2-Mercaptoethanol. Individual 2-way reactions were set up by mixing PBMC from two different donors at a 1:1 ratio and co-cultures were done in triplicates in flat-bottomed 96-well tissue culture plates for 6 days at 37° C., 5% CO2, in presence or not of an 8-point concentration range of test compounds. Cells were pulsed with 3H-TdR (1 Ci/0.2 mL) for the last 16 h of culture and incorporated radioactivity was used as a measure of cell proliferation. The concentration that inhibited 50% of the maximal huMLR response (IC50) was calculated for each compound. Cyclosporine was used as a positive control of huMLR inhibition.

Human B Cell Proliferation Assay

PBMC were freshly isolated by Ficoll-Paque density gradient from human blood and subjected to negative B-cell isolation. B cells were resuspended in culture medium (RPMI 1640, HEPES, 10% FCS, 50 g/mL gentamicine, 50 μM 2-Mercaptoethanol, lx ITS (Insulin, Transferrin and Sodium Selenite), lx Non-Essential Amino-Acids) at a concentration of 9.104 per well in a flat-bottom 96-well culture plate. B cell stimulation was performed by human anti-IgM antibody molecule (30 ug/mL) and IL-4 (75 ng/mL) or by CD40 ligand (3 ug/mL) and IL-4 (75 ng/mL) in presence or not of a 7-point concentration range of test compounds. After 72 h of culture at 37° C., 10% CO2, cells were pulsed with 3H-TdR (1 μCi/well) for the last 6 h of culture.

B cells were then harvested and the incorporation of thymidine was measured using a scintillation counter. Of each duplicate treatment, the mean was calculated and these data were plotted in XLfit 4 to determine the respective IC50 values.

Human T Cell Proliferation Assay

PBMC were freshly isolated by Ficoll-Paque density gradient from human blood and subjected to negative isolation of T cells. T cells were prepared in culture medium (RPMI 1640, HEPES, 10% FCS, 50 g/mL gentamicine, 50 μM 2-Mercaptoethanol, lx ITS (Insulin, Transferrin and Sodium Selenite), lx Non-Essential Amino-Acids) at a concentration of 8.104 per well in a flat-bottom 96-well culture plate. T cell stimulation was performed by human anti-CD3 antibody molecule (10 ug/mL) or by human anti-CD3 antibody molecule (5 g/mL) and anti-CD28 antibody molecule (1 g/mL) in presence or not of a 7-point concentration range of test compounds. After 72 h of culture at 37° C., 10% $CO_2$, cells were pulsed with 3H-TdR (1 Ci/well) for the last 6 h of culture. Cell proliferation was measured by the incorporation of thymidine allowing IC50 determination for each tested compound.

Nucleic Acids

The invention also features nucleic acids comprising nucleotide sequences that encode heavy and light chain variable regions and CDRs of the anti-LAG-3 antibody molecules, as described herein. For example, the invention features a first and second nucleic acid encoding heavy and light chain variable regions, respectively, of an anti-LAG-3 antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells, MDCKJJ cells and Per C6 cell line (e.g., PER C6 cells from Crucell). Suitable insect cells include, but are not limited to, Sf9 cells.

In some embodiments, the host cell is an eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

TABLE 1

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 6 | VH | QIQLVQSGPELKKPGETVKISCKASGFTLTNYGMN<br>WVRQTPGKGLKWMGWINTDTGEPTYADDFKGRFAF<br>SLETSASTASLQINNLKNADTATYFCARNPPYYYG<br>TNNAEAMDYWGQGTAVTVSS |
| SEQ ID NO: 7 | DNA VH | CAGATCCAGTTGGTGCAGTCTGGACCTGAGCTGAA<br>GAAGCCTGGAGAGACAGTCAAGATCTCCTGCAAGG<br>CTTCTGGATTTACCCTCACAAACTATGGAATGAAC<br>TGGGTGAGGCAGACTCCAGGAAAGGGTTTAAAGTG<br>GATGGGCTGGATAAACACCGACACTGGAGAGCCAA<br>CATATGCTGATGACTTCAAGGGACGGTTTGCCTTC<br>TCTTTGGAGACCTCTGCCAGCACTGCCTCTTTGCA<br>GATCAACAACCTCAAAAATGCGGACACGGCTACAT<br>ATTTCTGTGCAAGAAACCCCCCTTATTACTACGGT<br>ACTAATAACGCGGAGGCTATGGACTACTGGGGTCA<br>AGGAACCGCAGTCACCGTCTCCTCA |
| BAP050 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 16 | VL | DIQMTQTTSSLSASLGDRVTISCSSSQDISNYLNW YQQKPDGTVKVLIYYTSTLHLGVPSRFSGSGSGTD YSLTISNLELEDIATYYCQQYYNLPWTFGGGTKLE IK |
| SEQ ID NO: 17 | DNA VL | GATATCCAGATGACACAGACTACATCCTCCCTGTC TGCCTCTCTGGGAGACAGAGTCACCATCAGTTGCA GTTCAAGTCAGGACATCAGCAATTATTTAAACTGG TATCAGCAGAAACCAGATGGAACTGTTAAAGTCCT GATCTATTACACATCAACCTTACACTTAGGAGTCC CATCAAGGTTCAGTGGCAGTGGGTCTGGGACAGAT TATTCTCTCACCATCAGCAACCTGGAACTCGAAGA TATTGCCACATACTATTGTCAGCAGTATTATAACC TTCCGTGGACGTTCGGTGGAGGCACCAAGTTGGAA ATCAAA |
| BAP050-chi HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 20 | VH | QIQLVQSGPELKKPGETVKISCKASGFTLTNYGMN WVRQTPGKGLKWMGWINTDTGEPTYADDFKGRFAF SLETSASTASLQINNLKNADTATYFCARNPPYYYG TNNAEAMDYWGQGTTVTVSS |
| SEQ ID NO: 21 | DNA VH | CAGATCCAGTTGGTGCAGTCTGGACCTGAGCTGAA GAAGCCTGGAGAGACAGTCAAGATCTCCTGCAAGG CTTCTGGATTTACCCTCACAAACTATGGAATGAAC TGGGTGAGGCAGACTCCAGGAAAGGGTTTAAAGTG GATGGGCTGGATAAACACCGACACTGGAGAGCCAA CATATGCTGATGACTTCAAGGGACGGTTTGCCTTC TCTTTGGAGACCTCTGCCAGCACTGCCTCTTTGCA GATCAACAACCTCAAAAATGCGGACACGGCTACAT ATTTCTGTGCAAGAAACCCCCCTTATTACTACGGT ACTAATAACGCGGAGGCTATGGACTACTGGGGCCA GGGCACCACCGTGACCGTGTCCTCC |
| SEQ ID NO: 22 | HC | QIQLVQSGPELKKPGETVKISCKASGFTLTNYGMN WVRQTPGKGLKWMGWINTDTGEPTYADDFKGRFAF SLETSASTASLQINNLKNADTATYFCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 23 | DNA HC | CAGATCCAGTTGGTGCAGTCTGGACCTGAGCTGAA GAAGCCTGGAGAGACAGTCAAGATCTCCTGCAAGG CTTCTGGATTTACCCTCACAAACTATGGAATGAAC TGGGTGAGGCAGACTCCAGGAAAGGGTTTAAAGTG GATGGGCTGGATAAACACCGACACTGGAGAGCCAA CATATGCTGATGACTTCAAGGGACGGTTTGCCTTC TCTTTGGAGACCTCTGCCAGCACTGCCTCTTTGCA GATCAACAACCTCAAAAATGCGGACACGGCTACAT ATTTCTGTGCAAGAAACCCCCCTTATTACTACGGT ACTAATAACGCGGAGGCTATGGACTACTGGGGCCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-huml5-Ser. BAP050-huml8-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-chi LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 24 | VL | DIQMTQTTSSLSASLGDRVTISCSSSQDISNYLNW YQQKPDGTVKVLIYYTSTLHLGVPSRFSGSGSGTD YSLTISNLELEDIATYYCQQYYNLPWTFGQGTKVE IK |
| SEQ ID NO: 25 | DNA VL | GATATCCAGATGACACAGACTACATCCTCCCTGTC TGCCTCTCTGGGAGACAGAGTCACCATCAGTTGCA GTTCAAGTCAGGACATCAGCAATTATTTAAACTGG TATCAGCAGAAACCAGATGGAACTGTTAAAGTCCT GATCTATTACACATCAACCTTACACTTAGGAGTCC CATCAAGGTTCAGTGGCAGTGGGTCTGGGACAGAT TATTCTCTCACCATCAGCAACCTGGAACTCGAAGA TATTGCCACATACTATTGTCAGCAGTATTATAACC TTCCGTGGACGTTCGGCCAAGGGACCAAGGTGGAA ATCAAA |
| SEQ ID NO: 26 | LC | DIQMTQTTSSLSASLGDRVTISCSSSQDISNYLNW YQQKPDGTVKVLIYYTSTLHLGVPSRFSGSGSGTD YSLTISNLELEDIATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 27 | DNA LC | GATATCCAGATGACACAGACTACATCCTCCCTGTC TGCCTCTCTGGGAGACAGAGTCACCATCAGTTGCA GTTCAAGTCAGGACATCAGCAATTATTTAAACTGG TATCAGCAGAAACCAGATGGAACTGTTAAAGTCCT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTATTACACATCAACCTTACACTTAGGAGTCC<br>CATCAAGGTTCAGTGGCAGTGGGTCTGGGACAGAT<br>TATTCTCTCACCATCAGCAACCTGGAACTCGAAGA<br>TATTGCCACATACTATTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum01 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 29 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 30 | HC | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 31 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum01 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 32 | VL | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IK |
| SEQ ID NO: 33 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 34 | LC | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 35 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum02 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum02 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW<br>YQQKPGKAPKLLIYYTSTLHLGIPPRFSGSGYGTD<br>FTLTINNIESEDAAYYFCQQYYNLPWTFGQGTKVE<br>IK |
| SEQ ID NO: 37 | DNA VL | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TATCAGCAGAAACCAGGGAAAGCTCCTAAGCTCCT<br>GATCTATTACACATCAACCTTACACTTAGGGATCC<br>CACCTCGATTCAGTGGCAGCGGGTATGGAACAGAT<br>TTTACCCTCACAATTAATAACATAGAATCTGAGGA<br>TGCTGCATATTACTTCTGTCAGCAGTATTATAACC<br>TTCCGTGGACGTTCGGCCAAGGGACCAAGGTGGAA<br>ATCAAA |
| SEQ ID NO: 38 | LC | DIQMTQSPSSLSASVGDRVTITCSSSQDISNYLNW<br>YQQKPGKAPKLLIYYTSTLHLGIPPRFSGSGYGTD<br>FTLTINNIESEDAAYYFCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 39 | DNA LC | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TATCAGCAGAAACCAGGGAAAGCTCCTAAGCTCCT<br>GATCTATTACACATCAACCTTACACTTAGGGATCC<br>CACCTCGATTCAGTGGCAGCGGGTATGGAACAGAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum03 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum03 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TGCTGCAACATATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum04 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 29 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 30 | HC | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ D NO: 31 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum04 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 44 | VL | DIQMTQSPSSLSASVGDRVTITCSSSQDISNYLNW<br>YLQKPGQSPQLLIYYTSTLHLGIPDRFSGSGSGTD<br>FTLTISRLEPEDFAVYYCQQYYNLPWTFGQGTKVE<br>IK |
| SEQ ID NO: 45 | DNA VL | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TACCTGCAGAAGCCAGGGCAGTCTCCACAGCTCCT<br>GATCTATTACACATCAACCTTACACTTAGGGATCC<br>CAGACAGGTTCAGTGGCAGTGGGTCTGGGACAGAC<br>TTCACTCTCACCATCAGCAGACTGGAGCCTGAAGA<br>TTTTGCAGTGTATTACTGTCAGCAGTATTATAACC<br>TTCCGTGGACGTTCGGCCAAGGGACCAAGGTGGAA<br>ATCAAA |
| SEQ ID NO: 46 | LC | DIQMTQSPSSLSASVGDRVTITCSSSQDISNYLNW<br>YLQKPGQSPQLLIYYTSTLHLGIPDRFSGSGSGTD<br>FTLTISRLEPEDFAVYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 47 | DNA LC | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TACCTGCAGAAGCCAGGGCAGTCTCCACAGCTCCT<br>GATCTATTACACATCAACCTTACACTTAGGGATCC<br>CAGACAGGTTCAGTGGCAGTGGGTCTGGGACAGAC<br>TTCACTCTCACCATCAGCAGACTGGAGCCTGAAGA<br>TTTTGCAGTGTATTACTGTCAGCAGTATTATAACC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum05 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum05 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 48 | VL | EIVLTQSPATLSLSPGERATLSCSSSQDISNYLNW YQQKPGKAPKLLIYYTSTLHLGVPSRFSGSGSGTD FTFTISSLEAEDAATYYCQQYYNLPWTFGQGTKVE IK |
| SEQ ID NO: 49 | DNA VL | GAAATTGTGTTGACACAGTCTCCAGCCACCCTGTC TTTGTCTCCAGGGGAAAGAGCCACCCTCTCCTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 50 | LC | EIVLTQSPATLSLSPGERATLSCSSSQDISNYLNW YQQKPGKAPKLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 51 | DNA LC | GAAATTGTGTTGACACAGTCTCCAGCCACCCTGTC TTTGTCTCCAGGGGAAAGAGCCACCCTCTCCTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum06 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 29 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 30 | HC | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 31 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-huml5-Ser. BAP050-huml8-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum06 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 52 | VL | DIVMTQTPLSLPVTPGEPASISCSSSQDISNYLNW<br>YQQKPGQAPRLLIYYTSTLHLGVPSRFSGSGSGTE<br>FTLTISSLQPDDFATYYCQQYYNLPWTFGQGTKVE<br>IK |
| SEQ ID NO: 53 | DNA VL | GATATTGTGATGACCCAGACTCCACTCTCCCTGCC<br>CGTCACCCCTGGAGAGCCGGCCTCCATCTCCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAA<br>TTCACTCTCACCATCAGCAGCCTGCAGCCTGATGA<br>TTTTGCAACTTATTACTGTCAGCAGTATTATAACC<br>TTCCGTGGACGTTCGGCCAAGGGACCAAGGTGGAA<br>ATCAAA |
| SEQ ID NO: 54 | LC | DIVMTQTPLSLPVTPGEPASISCSSSQDISNYLNW<br>YQQKPGQAPRLLIYYTSTLHLGVPSRFSGSGSGTE<br>FTLTISSLQPDDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 55 | DNA LC | GATATTGTGATGACCCAGACTCCACTCTCCCTGCC<br>CGTCACCCCTGGAGAGCCGGCCTCCATCTCCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAA<br>TTCACTCTCACCATCAGCAGCCTGCAGCCTGATGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum07 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum07 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 56 | VL | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IK |
| SEQ ID NO: 57 | DNA VL | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAA |
| SEQ ID NO: 58 | LC | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 59 | DNA LC | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum08 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 29 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 30 | HC | EVQLVQSGAEVKKPGATVKISCKVSGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 31 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum08 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum09 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 64 | VH | QVQLVQSGAEVKKPGASVKVSCKASGFTLTNYGMN<br>WVRQARGQRLEWIGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 65 | DNA VH | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 66 | HC | QVQLVQSGAEVKKPGASVKVSCKASGFTLTNYGMN<br>WVRQARGQRLEWIGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 67 | DNA HC | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum09 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum10 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 64 | VH | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSS |
| SEQ ID NO: 65 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 66 | HC | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 67 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum10 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA |

TABLE 1-continued

| Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown. | | |
|---|---|---|
| | | CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum11 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 64 | VH | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSS |
| SEQ ID NO: 65 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 66 | HC | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 67 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum11 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 56 | VL | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IK |
| SEQ ID NO: 57 | DNA VL | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAA |
| SEQ ID NO: 58 | LC | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 59 | DNA LC | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum12 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 64 | VH | QVQLVQSGAEVKKPGASVKVSCKASGFTLTNYGMN<br>WVRQARGQRLEWIGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 65 | DNA VH | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 66 | HC | QVQLVQSGAEVKKPGASVKVSCKASGFTLTNYGMN<br>WVRQARGQRLEWIGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 67 | DNA HC | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum12 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IK |
| SEQ ID NO: 61 | DNA VL | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAA |
| SEQ ID NO: 62 | LC | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 63 | DNA LC | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GAAACACAAAGTCTACGCCTGCGAAGTCACCCATC AGGGCCTGAGCTCGCCCGTCACAAAGAGCTTCAAC AGGGGAGAGTGT |
| BAP050-hum13 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 68 | VH | QVQLVQSGAEVKKPGASVKVSCKASGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSS |
| SEQ ID NO: 69 | DNA VH | CAGGTTCAGCTGGTGCAGTCCGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 70 | HC | QVQLVQSGAEVKKPGASVKVSCKASGFTLTNYGMN WVRQAPGQGLEWMGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 71 | DNA HC | CAGGTTCAGCTGGTGCAGTCCGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum13 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum14 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 72 | VH | EVQLVQSGAEVKKPGATVKISCKVSGFTLTNYGMN<br>WIRQSPSRGLEWLGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 73 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGATCAGGCAGTCCCCATCGAGAGGCCTTGAGTG<br>GCTGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 74 | HC | EVQLVQSGAEVKKPGATVKISCKVSGFTLTNYGMN<br>WIRQSPSRGLEWLGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 75 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGATCAGGCAGTCCCCATCGAGAGGCCTTGAGTG<br>GCTGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum14 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 40 | VL | EIVLTQSPATLPVTLGQPASISCSSSQDISNYLNW<br>YQQKPGQAPRLLIYYTSTLHLGVPSRFSGSGSGTD<br>FTFTISSLEAEDAATYYCQQYYNLPWTFGQGTKVE<br>IK |
| SEQ ID NO: 41 | DNA VL | GAAATTGTGTTGACACAGTCTCCAGCCACCCTGCC<br>CGTCACCCTTGGACAGCCGGCCTCCATCTCCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAA |
| SEQ ID NO: 42 | LC | EIVLTQSPATLPVTLGQPASISCSSSQDISNYLNW<br>YQQKPGQAPRLLIYYTSTLHLGVPSRFSGSGSGTD<br>FTFTISSLEAEDAATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 43 | DNA LC | GAAATTGTGTTGACACAGTCTCCAGCCACCCTGCC<br>CGTCACCCTTGGACAGCCGGCCTCCATCTCCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC<br>AGCAGCACCCTGACGCTGAGCAAAGCAGACTACGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GAAACACAAAGTCTACGCCTGCGAAGTCACCCATC AGGGCCTGAGCTCGCCCGTCACAAAGAGCTTCAAC AGGGGAGAGTGT |
| BAP050-hum15 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 72 | VH | EVQLVQSGAEVKKPGATVKISCKVSGFTLTNYGMN WIRQSPSRGLEWLGWINTDTGEPTYADDFKGRFVF SLDTSVSTAYLQICSLKAEDTAVYYCARNPPYYYG TNNAEAMDYWGQGTTVTVSS |
| SEQ ID NO: 73 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 74 | HC | EVQLVQSGAEVKKPGATVKISCKVSGFTLTNYGMN WIRQSPSRGLEWLGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 75 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum15 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum16 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 76 | VH | EVQLVQSGAEVKKPGESLRISCKGSGFTLTNYGMN<br>WVRQATGQGLEWMGWINTDTGEPTYADDFKGRVTI<br>SADKSISTAYLQWSSLKASDTAMYYCARNPPYYYG<br>TNNAEAMDYWGQGTTVTVSS |
| SEQ ID NO: 77 | DNA VH | GAAGTGCAGCTGGTGCAGTCTGGAGCAGAGGTGAA<br>AAAGCCCGGGGAGTCTCTGAGGATCTCCTGTAAGG<br>GTTCTGGATTTACCCTCACAAACTATGGAATGAAC<br>TGGGTGCGACAGGCCACTGGACAAGGGCTTGAGTG<br>GATGGGTTGGATAAACACCGACACTGGAGAGCCAA<br>CATATGCTGATGACTTCAAGGGAAGAGTCACCATC<br>TCAGCCGACAAGTCCATCAGCACCGCCTACCTGCA<br>GTGGAGCAGCCTGAAGGCCTCGGACACCGCCATGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 78 | HC | EVQLVQSGAEVKKPGESLRISCKGSGFTLTNYGMN<br>WVRQATGQGLEWMGWINTDTGEPTYADDFKGRVTI<br>SADKSISTAYLQWSSLKASDTAMYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 79 | DNA HC | GAAGTGCAGCTGGTGCAGTCTGGAGCAGAGGTGAA<br>AAAGCCCGGGGAGTCTCTGAGGATCTCCTGTAAGG<br>GTTCTGGATTTACCCTCACAAACTATGGAATGAAC<br>TGGGTGCGACAGGCCACTGGACAAGGGCTTGAGTG<br>GATGGGTTGGATAAACACCGACACTGGAGAGCCAA<br>CATATGCTGATGACTTCAAGGGAAGAGTCACCATC<br>TCAGCCGACAAGTCCATCAGCACCGCCTACCTGCA<br>GTGGAGCAGCCTGAAGGCCTCGGACACCGCCATGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum16 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IK |
| SEQ ID NO: 61 | DNA VL | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAA |
| SEQ ID NO: 62 | LC | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 63 | DNA LC | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum17 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 80 | VH | QVQLVQSGSELKKPGASVKVSCKASGFTLTNYGMN<br>WVRQAPGQGLEWMGWINTDTGEPTYADDFKGRFVF<br>SLDTSVSTAYLQISTLKAEDTATYFCARNPPYYYG<br>TNNAEAMDYWGQGTTVTVSS |
| SEQ ID NO: 81 | DNA VH | CAGGTGCAGCTGGTGCAATCTGGGTCTGAGTTGAA<br>GAAGCCTGGGGCCTCAGTGAAGGTTTCCTGCAAGG<br>CTTCTGGATTCACCCTGACTAACTATGGCATGAAT<br>TGGGTGCGACAGGCCCCTGGACAAGGGCTTGAGTG<br>GATGGGATGGATCAACACCGACACTGGGGAGCCAA<br>CGTATGCCGATGACTTCAAGGGACGGTTTGTCTTC<br>TCCTTGGACACCTCTGTCAGCACGGCATATCTGCA<br>GATCAGCACGCTAAAGGCTGAGGACACTGCTACAT<br>ATTTCTGTGCAAGAAACCCCCCTTATTACTACGGT<br>ACTAATAACGCGGAGGCTATGGACTACTGGGGCCA<br>GGGCACCACCGTGACCGTGTCCTCC |
| SEQ ID NO: 82 | HC | QVQLVQSGSELKKPGASVKVSCKASGFTLTNYGMN<br>WVRQAPGQGLEWMGWINTDTGEPTYADDFKGRFVF<br>SLDTSVSTAYLQISTLKAEDTATYFCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 83 | DNA HC | CAGGTGCAGCTGGTGCAATCTGGGTCTGAGTTGAA<br>GAAGCCTGGGGCCTCAGTGAAGGTTTCCTGCAAGG<br>CTTCTGGATTCACCCTGACTAACTATGGCATGAAT<br>TGGGTGCGACAGGCCCCTGGACAAGGGCTTGAGTG<br>GATGGGATGGATCAACACCGACACTGGGGAGCCAA<br>CGTATGCCGATGACTTCAAGGGACGGTTTGTCTTC<br>TCCTTGGACACCTCTGTCAGCACGGCATATCTGCA<br>GATCAGCACGCTAAAGGCTGAGGACACTGCTACAT<br>ATTTCTGTGCAAGAAACCCCCCTTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GACCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum17 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 84 | VL | DIQMTQSPSSLSASVGDRVTITCSSSQDISNYLNW<br>YQQKPGKAPKLLIYYTSTLHLGVPSRFSGSGSGTD<br>FTFTISSLQPEDIATYYCQQYYNLPWTFGQGTKVE<br>IK |
| SEQ ID NO: 85 | DNA VL | GACATCCAGATGACCCAGTCTCCATCCTCCCTGTC<br>TGCATCTGTAGGAGACAGAGTCACCATCACTTGCT<br>CCTCTAGTCAGGACATTAGCAACTATTTAAATTGG<br>TATCAGCAGAAACCAGGGAAAGCCCCTAAGCTCCT<br>GATCTACTATACATCCACTTTGCACCTGGGGGTCC<br>CATCAAGGTTCAGTGGAAGTGGATCTGGGACAGAT<br>TTTACTTTCACCATCAGCAGCCTGCAGCCTGAAGA<br>TATTGCAACATATTACTGTCAACAGTATTATAATC<br>TCCCTTGGACGTTCGGCCAAGGGACCAAGGTGGAA<br>ATCAAA |
| SEQ ID NO: 86 | LC | DIQMTQSPSSLSASVGDRVTITCSSSQDISNYLNW<br>YQQKPGKAPKLLIYYTSTLHLGVPSRFSGSGSGTD<br>FTFTISSLQPEDIATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 87 | DNA LC | GACATCCAGATGACCCAGTCTCCATCCTCCCTGTC<br>TGCATCTGTAGGAGACAGAGTCACCATCACTTGCT<br>CCTCTAGTCAGGACATTAGCAACTATTTAAATTGG<br>TATCAGCAGAAACCAGGGAAAGCCCCTAAGCTCCT<br>GATCTACTATACATCCACTTTGCACCTGGGGGTCC<br>CATCAAGGTTCAGTGGAAGTGGATCTGGGACAGAT<br>TTTACTTTCACCATCAGCAGCCTGCAGCCTGAAGA<br>TATTGCAACATATTACTGTCAACAGTATTATAATC<br>TCCCTTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum18 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSS |
| SEQ ID NO: 29 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 30 | HC | EVQLVQSGAEVKKPGATVKISCKVSGFTLTNYGMN<br>WVRQAPGQGLEWMGWINTDTGEPTYADDFKGRFVF<br>SLDTSVSTAYLQICSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 31 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCTGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum18 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 88 | VL | AIQLTQSPSSLSASVGDRVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 89 | DNA VL | GCCATCCAGTTGACCCAGTCTCCATCCTCCCTGTC TGCATCTGTAGGAGACAGAGTCACCATCACTTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 90 | LC | AIQLTQSPSSLSASVGDRVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 91 | DNA LC | GCCATCCAGTTGACCCAGTCTCCATCCTCCCTGTC TGCATCTGTAGGAGACAGAGTCACCATCACTTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT |
| BAP050-hum19 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 28 | VH | EVQLVQSGAEVKKPGATVKISCKVSGFTLTNYGMNWVRQAPGQGLEWMGWINTDTGEPTYADDFKGRFVFSLDTSVSTAYLQICSLKAEDTAVYYCARNPPYYYGTNNAEAMDYWGQGTTVTVSS |
| SEQ ID NO: 29 | DNA VH | GAGGTCCAGCTGGTACAGTCTGGGGCTGAGGTGAAGAAGCCTGGGGCTACAGTGAAAATCTCCTGCAAGGTTTCTGGATTTACCCTCACAAACTATGGAATGAACTGGGTGCGACAGGCCCCTGGACAAGGGCTTGAGTGGATGGGTTGGATAAACACCGACACTGGAGAGCCAACATATGCTGATGACTTCAAGGGAAGATTTGTCTTCTCCTTGGACACCTCTGTCAGCACGGCATATCTGCAGATCTGCAGCCTAAAGGCTGAGGACACTGCCGTGTATTACTGTGCAAGAAACCCTCCCTATTACTACGGTACTAATAACGCGGAGGCTATGGACTACTGGGGCCAGGGCACCACCGTGACCGTGTCCTCC |
| SEQ ID NO: 30 | HC | EVQLVQSGAEVKKPGATVKISCKVSGFTLTNYGMNWVRQAPGQGLEWMGWINTDTGEPTYADDFKGRFVFSLDTSVSTAYLQICSLKAEDTAVYYCARNPPYYYGTNNAEAMDYWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| SEQ ID NO: 31 | DNA HC | GAGGTCCAGCTGGTACAGTCTGGGGCTGAGGTGAAGAAGCCTGGGGCTACAGTGAAAATCTCCTGCAAGGTTTCTGGATTTACCCTCACAAACTATGGAATGAACTGGGTGCGACAGGCCCCTGGACAAGGGCTTGAGTGGATGGGTTGGATAAACACCGACACTGGAGAGCCAACATATGCTGATGACTTCAAGGGAAGATTTGTCTTCTCCTTGGACACCTCTGTCAGCACGGCATATCTGCAGATCTGCAGCCTAAAGGCTGAGGACACTGCCGTGTATTACTGTGCAAGAAACCCTCCCTATTACTACGGTACTAATAACGCGGAGGCTATGGACTACTGGGGCCAGGGCACCACCGTGACCGTGTCCTCCGCTTCCACCAAGGGCCCATCCGTCTTCCCCCTGGCGCCCTGCTCCAGGAGCACCTCCGAGAGCACAGCCGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACGAAGACCTACACCTGCAACGTAGATCACAAGCCCAGCAACACCAAGGTGGACAAGAGAGTTGAGTCCAAATATGGTCCCCCATGCCCACCGTGCCCAGCACCTGAGTTCCTGGGGGGACCATCAGTCTTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum19 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 92 | VL | EIVLTQSPDFQSVTPKEKVTITCSSSQDISNYLNW<br>YQQKPGQAPRLLIYYTSTLHLGVPSRFSGSGSGTD<br>FTFTISSLEAEDAATYYCQQYYNLPWTFGQGTKVE<br>IK |
| SEQ ID NO: 93 | DNA VL | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAA |
| SEQ ID NO: 94 | LC | EIVLTQSPDFQSVTPKEKVTITCSSSQDISNYLNW<br>YQQKPGQAPRLLIYYTSTLHLGVPSRFSGSGSGTD<br>FTFTISSLEAEDAATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 95 | DNA LC | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum20 HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 64 | VH | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSS |
| SEQ ID NO: 65 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 66 | HC | QVQLVQSGAEVKKPGASVKVSCKASGFTLTNYGMN WVRQARGQRLEWIGWINTDTGEPTYADDFKGRFVF SLDTSVSTAYLQICSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 67 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCTGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum20 LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 96 | VL | DIVMTQTPLSLPVTPGEPASISCSSSQDISNYLNW YQQKPGQAPRLLIYYTSTLHLGIPDRFSGSGSGTD FTLTISRLEPEDFAVYYCQQYYNLPWTFGQGTKVE IK |
| SEQ ID NO: 97 | DNA VL | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAA |
| SEQ ID NO: 98 | LC | DIVMTQTPLSLPVTPGEPASISCSSSQDISNYLNW YQQKPGQAPRLLIYYTSTLHLGIPDRFSGSGSGTD FTLTISRLEPEDFAVYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 99 | DNA LC | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum01-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 101 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 102 | HC | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 103 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum01-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 32 | VL | DIQMTQSPSSLSASVGDRVTITCSSSQDISNYLNW<br>YQQKPGKAPKLLIYYTSTLHLGVPSRFSGSGSGTD<br>FTFTISSLEAEDAATYYCQQYYNLPWTFGQGTKVE<br>IK |
| SEQ ID NO: 33 | DNA VL | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TATCAGCAGAAACCAGGGAAAGCTCCTAAGCTCCT<br>GATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAA |
| SEQ ID NO: 34 | LC | DIQMTQSPSSLSASVGDRVTITCSSSQDISNYLNW<br>YQQKPGKAPKLLIYYTSTLHLGVPSRFSGSGSGTD<br>FTFTISSLEAEDAATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 35 | DNA LC | GACATCCAGATGACCCAGTCTCCATCCTCCCTGTC<br>TGCATCTGTAGGAGACAGAGTCACCATCACTTGCA<br>GTTCAAGTCAGGACATCAGCAATTATTTAAACTGG<br>TATCAGCAGAAACCAGGGAAAGCTCCTAAGCTCCT<br>GATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA |

TABLE 1-continued

| Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown. | | |
|---|---|---|
| | | CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum02-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum02-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| GSEQ ID NO: 39 | DNA LC | ACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum03-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 101 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 102 | HC | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 103 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum03-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GAAACACAAAGTCTACGCCTGCGAAGTCACCCATC AGGGCCTGAGCTCGCCCGTCACAAAGAGCTTCAAC AGGGGAGAGTGT |
| BAP050-hum04-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum04-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 44 | VL | DIQMTQSPSSLSASVGDRVTITCSSSQDISNYLNW YLQKPGQSPQLLIYYTSTLHLGIPDRFSGSGSGTD FTLTISRLEPEDFAVYYCQQYYNLPWTFGQGTKVE IK |
| SEQ ID NO: 45 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAA |
| SEQ ID NO: 46 | LC | DIQMTQSPSSLSASVGDRVTITCSSSQDISNYLNW YLQKPGQSPQLLIYYTSTLHLGIPDRFSGSGSGTD FTLTISRLEPEDFAVYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 47 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum05-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GCCCAGCACCTGAGTTCCTGGGGGGACCATCAGTC<br>TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum05-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 48 | VL | EIVLTQSPATLSLSPGERATLSCSSSQDISNYLNW<br>YQQKPGKAPKLLIYYTSTLHLGVPSRFSGSGSGTD<br>FTFTISSLEAEDAATYYCQQYYNLPWTFGQGTKVE<br>IK |
| SEQ ID NO: 49 | DNA VL | GAAATTGTGTTGACACAGTCTCCAGCCACCCTGTC<br>TTTGTCTCCAGGGGAAAGAGCCACCCTCTCCTGCA<br>GTTCAAGTCAGGACATCAGCAATTATTTAAACTGG<br>TATCAGCAGAAACCAGGGAAAGCTCCTAAGCTCCT<br>GATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAA |
| SEQ ID NO: 50 | LC | EIVLTQSPATLSLSPGERATLSCSSSQDISNYLNW<br>YQQKPGKAPKLLIYYTSTLHLGVPSRFSGSGSGTD<br>FTFTISSLEAEDAATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 51 | DNA LC | GAAATTGTGTTGACACAGTCTCCAGCCACCCTGTC<br>TTTGTCTCCAGGGGAAAGAGCCACCCTCTCCTGCA<br>GTTCAAGTCAGGACATCAGCAATTATTTAAACTGG<br>TATCAGCAGAAACCAGGGAAAGCTCCTAAGCTCCT<br>GATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA |

TABLE 1-continued

| Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown. | | |
|---|---|---|
| | | CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum06-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum06-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 52 | VL | DIVMTQTPLSLPVTPGEPASISCSSSQDISNYLNW YQQKPGQAPRLLIYYTSTLHLGVPSRFSGSGSGTE FTLTISSLQPDDFATYYCQQYYNLPWTFGQGTKVE IK |
| SEQ ID NO: 53 | DNA VL | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAA |
| SEQ ID NO: 54 | LC | DIVMTQTPLSLPVTPGEPASISCSSSQDISNYLNW YQQKPGQAPRLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 55 | DNA LC | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum07-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 101 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 102 | HC | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 103 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum07-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | IQQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 56 | VL | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IK |
| SEQ ID NO: 57 | DNA VL | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAA |
| SEQ ID NO: 58 | LC | DIQMTQSPSSLSASVGDRVTITCSSSQDISNYLNW YLQKPGQSPQLLIYYTSTLHLGVPSRFSGSGSGTE FTLTISSLQPDDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 59 | DNA LC | GACATCCAGATGACCCAGTCTCCATCCTCCCTGTC TGCATCTGTAGGAGACAGAGTCACTATCACTTGCA GTTCAAGTCAGGACATCAGCAATTATTTAAACTGG TACCTGCAGAAGCCAGGGCAGTCTCCACAGCTCCT GATCTATTACACATCAACCTTACACTTAGGGGTCC CATCAAGGTTCAGCGGCAGTGGATCTGGGACAGAA TTCACTCTCACCATCAGCAGCCTGCAGCCTGATGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CAGAGCAGGACAGCAAGGACAGCACCTACAGCCTC<br>AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum08-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 101 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 102 | HC | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 103 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum08-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum09-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 104 | VH | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 105 | DNA VH | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 106 | HC | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 107 | DNA HC | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum09-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum10-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 104 | VH | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 105 | DNA VH | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 106 | HC | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 107 | DNA HC | CAGGTTCAGCTGGTGCAGTCTGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCTCGTGGACAACGCCTTGAGTG<br>GATAGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum10-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12(Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA |

TABLE 1-continued

| Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown. | | |
|---|---|---|
| | | CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum11-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 104 | VH | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSS |
| SEQ ID NO: 105 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 106 | HC | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 107 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum11-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 56 | VL | DIQMTQSPSSLSASVGDRVTITCSSSQDISNYLNW<br>YLQKPGQSPQLLIYYTSTLHLGVPSRFSGSGSGTE<br>FTLTISSLQPDDFATYYCQQYYNLPWTFGQGTKVE<br>IK |
| SEQ ID NO: 57 | DNA VL | GACATCCAGATGACCCAGTCTCCATCCTCCCTGTC<br>TGCATCTGTAGGAGACAGAGTCACTATCACTTGCA<br>GTTCAAGTCAGGACATCAGCAATTATTTAAACTGG<br>TACCTGCAGAAGCCAGGGCAGTCTCCACAGCTCCT<br>GATCTATTACACATCAACCTTACACTTAGGGGTCC<br>CATCAAGGTTCAGCGGCAGTGGATCTGGGACAGAA<br>TTCACTCTCACCATCAGCAGCCTGCAGCCTGATGA<br>TTTTGCAACTTATTACTGTCAGCAGTATTATAACC<br>TTCCGTGGACGTTCGGCCAAGGGACCAAGGTGGAA<br>ATCAAA |
| SEQ ID NO: 58 | LC | DIQMTQSPSSLSASVGDRVTITCSSSQDISNYLNW<br>YLQKPGQSPQLLIYYTSTLHLGVPSRFSGSGSGTE<br>FTLTISSLQPDDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 59 | DNA LC | GACATCCAGATGACCCAGTCTCCATCCTCCCTGTC<br>TGCATCTGTAGGAGACAGAGTCACTATCACTTGCA<br>GTTCAAGTCAGGACATCAGCAATTATTTAAACTGG<br>TACCTGCAGAAGCCAGGGCAGTCTCCACAGCTCCT<br>GATCTATTACACATCAACCTTACACTTAGGGGTCC<br>CATCAAGGTTCAGCGGCAGTGGATCTGGGACAGAA<br>TTCACTCTCACCATCAGCAGCCTGCAGCCTGATGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum12-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 104 | VH | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSS |
| SEQ ID NO: 106 | HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 105 | DNA VH | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 107 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCAAAACCCAAGGACACTCTCAT<br>GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum12-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IK |
| SEQ ID NO: 61 | DNA VL | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAA |
| SEQ ID NO: 62 | LC | EIVLTQSPDFQSVTPKEKVTITCSSSQDISNYLNW<br>YQQKPGQAPRLLIYYTSTLHLGVPSRFSGSGSGTD<br>FTLTISSLQPEDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 63 | DNA LC | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CATCAAGGTTCAGCGGCAGTGGATCTGGGACAGAT<br>TTCACTCTCACCATCAGCAGCCTGCAGCCTGAAGA<br>TTTTGCAACTTATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA<br>CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum13-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 108 | VH | QVQLVQSGAEVKKPGASVKVSCKASGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 109 | DNA VH | CAGGTTCAGCTGGTGCAGTCCGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 110 | HC | QVQLVQSGAEVKKPGASVKVSCKASGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 111 | DNA HC | CAGGTTCAGCTGGTGCAGTCCGGAGCTGAGGTGAA<br>GAAGCCTGGGGCCTCAGTGAAGGTCTCCTGCAAGG<br>CTTCTGGATTTACCCTCACAAACTATGGAATGAAC<br>TGGGTGCGACAGGCCCCTGGACAAGGGCTTGAGTG<br>GATGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

| Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown. | | |
|---|---|---|
| | | GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum13-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 37 | DNA VL | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAA |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 39 | DNA LC | GACATCCAGATGACCCAGTCTCCATCCTCCCTGTC TGCATCTGTAGGAGACAGAGTCACCATCACTTGCA GTTCAAGTCAGGACATCAGCAATTATTTAAACTGG TATCAGCAGAAACCAGGGAAAGCTCCTAAGCTCCT GATCTATTACACATCAACCTTACACTTAGGGATCC CACCTCGATTCAGTGGCAGCGGGTATGGAACAGAT TTTACCCTCACAATTAATAACATAGAATCTGAGGA TGCTGCATATTACTTCTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-hum14-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 8 | VH | EVQLVQSGAEVKKPGATVKISCKVSGFTLTNYGMN<br>WIRQSPSRGLEWLGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 9 | DNA VH | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGATCAGGCAGTCCCCATCGAGAGGCCTTGAGTG<br>GCTGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCC |
| SEQ ID NO: 18 | HC | EVQLVQSGAEVKKPGATVKISCKVSGFTLTNYGMN<br>WIRQSPSRGLEWLGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLGK |
| SEQ ID NO: 19 | DNA HC | GAGGTCCAGCTGGTACAGTCTGGGGCTGAGGTGAA<br>GAAGCCTGGGGCTACAGTGAAAATCTCCTGCAAGG<br>TTTCTGGATTTACCCTCACAAACTATGGAATGAAC<br>TGGATCAGGCAGTCCCCATCGAGAGGCCTTGAGTG<br>GCTGGGTTGGATAAACACCGACACTGGAGAGCCAA<br>CATATGCTGATGACTTCAAGGGAAGATTTGTCTTC<br>TCCTTGGACACCTCTGTCAGCACGGCATATCTGCA<br>GATCAGCAGCCTAAAGGCTGAGGACACTGCCGTGT<br>ATTACTGTGCAAGAAACCCTCCCTATTACTACGGT<br>ACTAATAACGCGGAGGCTATGGACTACTGGGGCCA<br>GGGCACCACCGTGACCGTGTCCTCCGCTTCCACCA<br>AGGGCCCATCCGTCTTCCCCCTGGCGCCCTGCTCC<br>AGGAGCACCTCCGAGAGCACAGCCGCCCTGGGCTG<br>CCTGGTCAAGGACTACTTCCCCGAACCGGTGACGG<br>TGTCGTGGAACTCAGGCGCCCTGACCAGCGGCGTG<br>CACACCTTCCCGGCTGTCCTACAGTCCTCAGGACT<br>CTACTCCCTCAGCAGCGTGGTGACCGTGCCCTCCA<br>GCAGCTTGGGCACGAAGACCTACACCTGCAACGTA<br>GATCACAAGCCCAGCAACACCAAGGTGGACAAGAG<br>AGTTGAGTCCAAATATGGTCCCCCATGCCCACCGT<br>GCCCAGCACCTGAGTTCCTGGGGGGACCATCAGTC<br>TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum14-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 40 | VL | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IK |
| SEQ ID NO: 41 | DNA VL | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAA |
| SEQ ID NO: 42 | LC | EIVLTQSPATLPVTLGQPASISCSSSQDISNYLNW YQQKPGQAPRLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 43 | DNA LC | GAAATTGTGTTGACACAGTCTCCAGCCACCCTGCC CGTCACCCTTGGACAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CCTCGAGGTTCAGTGGCAGTGGATCTGGGACAGAT TTCACCTTTACCATCAGTAGCCTGGAAGCTGAAGA TGCTGCAACATATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA |

TABLE 1-continued

| Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown. | | |
|---|---|---|
| | | GAAACACAAAGTCTACGCCTGCGAAGTCACCCATC AGGGCCTGAGCTCGCCCGTCACAAAGAGCTTCAAC AGGGGAGAGTGT |
| BAP050-hum15-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 8 | VH | EVQLVQSGAEVKKPGATVKISCKVSGFTLTNYGMN WIRQSPSRGLEWLGWINTDTGEPTYADDFKGRFVF SLDTSVSTAYLQISSLKAEDTAVYYCARNPPYYYG TNNAEAMDYWGQGTTVTVSS |
| SEQ ID NO: 9 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 18 | HC | EVQLVQSGAEVKKPGATVKISCKVSGFTLTNYGMN WIRQSPSRGLEWLGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 19 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGATCAGGCAGTCCCCATCGAGAGGCCTTGAGTG GCTGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT GATCTCCCGGACCCCTGAGGTCACGTGCGTGGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum15-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 60 | VL | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 61 | DNA VL | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 62 | LC | EIVLTQSPDFQSVTPKEKVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 63 | DNA LC | GAAATTGTGCTGACTCAGTCTCCAGACTTTCAGTC TGTGACTCCAAAGGAGAAAGTCACCATCACCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC AGCAGCACCCTGACGCTGAGCAAAGCAGACTACGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GAAACACAAAGTCTACGCCTGCGAAGTCACCCATC AGGGCCTGAGCTCGCCCGTCACAAAGAGCTTCAAC AGGGGAGAGTGT |
| BAP050-hum18-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum18-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 88 | VL | AIQLTQSPSSLSASVGDRVTITCSSSQDISNYLNW YQQKPGQAPRLLIYYTSTLHLGVPSRFSGSGSGTD FTLTISSLQPEDFATYYCQQYYNLPWTFGQGTKVE IK |
| SEQ ID NO: 89 | DNA VL | GCCATCCAGTTGACCCAGTCTCCATCCTCCCTGTC TGCATCTGTAGGAGACAGAGTCACCATCACTTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAA |
| SEQ ID NO: 90 | LC | AIQLTQSPSSLSASVGDRVTITCSSSQDISNYLNW YQQKPGQAPRLLIYYTSTLHLGVPSRFSGSGSGTD FTLTISSLQPEDFATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 91 | DNA LC | GCCATCCAGTTGACCCAGTCTCCATCCTCCCTGTC TGCATCTGTAGGAGACAGAGTCACCATCACTTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGGTCC CATCAAGGTTCAGCGGCAGTGGATCTGGGACAGAT TTCACTCTCACCATCAGCAGCCTGCAGCCTGAAGA TTTTGCAACTTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum19-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 101 | DNA VH | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 102 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 103 | DNA HC | GAGGTCCAGCTGGTACAGTCTGGGGCTGAGGTGAA GAAGCCTGGGGCTACAGTGAAAATCTCCTGCAAGG TTTCTGGATTTACCCTCACAAACTATGGAATGAAC TGGGTGCGACAGGCCCCTGGACAAGGGCTTGAGTG GATGGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC TTCCTGTTCCCCCCAAAACCCAAGGACACTCTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCTCCCGGACCCCTGAGGTCACGTGCGTGGTGG<br>TGGACGTGAGCCAGGAAGACCCCGAGGTCCAGTTC<br>AACTGGTACGTGGATGGCGTGGAGGTGCATAATGC<br>CAAGACAAAGCCGCGGGAGGAGCAGTTCAACAGCA<br>CGTACCGTGTGGTCAGCGTCCTCACCGTCCTGCAC<br>CAGGACTGGCTGAACGGCAAGGAGTACAAGTGCAA<br>GGTGTCCAACAAAGGCCTCCCGTCCTCCATCGAGA<br>AAACCATCTCCAAAGCCAAAGGGCAGCCCCGAGAG<br>CCACAGGTGTACACCCTGCCCCCATCCCAGGAGGA<br>GATGACCAAGAACCAGGTCAGCCTGACCTGCCTGG<br>TCAAAGGCTTCTACCCCAGCGACATCGCCGTGGAG<br>TGGGAGAGCAATGGGCAGCCGGAGAACAACTACAA<br>GACCACGCCTCCCGTGCTGGACTCCGACGGCTCCT<br>TCTTCCTCTACAGCAGGCTAACCGTGGACAAGAGC<br>AGGTGGCAGGAGGGGAATGTCTTCTCATGCTCCGT<br>GATGCATGAGGCTCTGCACAACCACTACACACAGA<br>AGAGCCTCTCCCTGTCTCTGGGTAAA |
| BAP050-hum19-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 92 | VL | EIVLTQSPDFQSVTPKEKVTITCSSSQDISNYLNW<br>YQQKPGQAPRLLIYYTSTLHLGVPSRFSGSGSGTD<br>FTFTISSLEAEDAATYYCQQYYNLPWTFGQGTKVE<br>IK |
| SEQ ID NO: 93 | DNA VL | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAA |
| SEQ ID NO: 94 | LC | EIVLTQSPDFQSVTPKEKVTITCSSSQDISNYLNW<br>YQQKPGQAPRLLIYYTSTLHLGVPSRFSGSGSGTD<br>FTFTISSLEAEDAATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 95 | DNA LC | GAAATTGTGCTGACTCAGTCTCCAGACTTTCAGTC<br>TGTGACTCCAAAGGAGAAAGTCACCATCACCTGCA<br>GTTCAAGTCAGGACATCAGCAATTATTTAAACTGG<br>TACCAGCAGAAACCTGGCCAGGCTCCCAGGCTCCT<br>CATCTATTACACATCAACCTTACACTTAGGGGTCC<br>CCTCGAGGTTCAGTGGCAGTGGATCTGGGACAGAT<br>TTCACCTTTACCATCAGTAGCCTGGAAGCTGAAGA<br>TGCTGCAACATATTACTGTCAGCAGTATTATAACC<br>TTCCGTGGACGTTCGGCCAAGGGACCAAGGTGGAA<br>ATCAAACGTACGGTGGCTGCACCATCTGTCTTCAT<br>CTTCCCGCCATCTGATGAGCAGTTGAAATCTGGAA<br>CTGCCTCTGTTGTGTGCCTGCTGAATAACTTCTAT<br>CCCAGAGAGGCCAAAGTACAGTGGAAGGTGGATAA<br>CGCCCTCCAATCGGGTAACTCCCAGGAGAGTGTCA |

TABLE 1-continued

| Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown. | | |
|---|---|---|
| | | CAGAGCAGGACAGCAAGGACAGCACCTACAGCCTC AGCAGCACCCTGACGCTGAGCAAAGCAGACTACGA GAAACACAAAGTCTACGCCTGCGAAGTCACCCATC AGGGCCTGAGCTCGCCCGTCACAAAGAGCTTCAAC AGGGGAGAGTGT |
| BAP050-hum20-Ser HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 104 | VH | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSS |
| SEQ ID NO: 105 | DNA VH | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCC |
| SEQ ID NO: 106 | HC | QVQLVQSGAEVKKPGASVKVSCKASGFTLTNYGMN WVRQARGQRLEWIGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| SEQ ID NO: 107 | DNA HC | CAGGTTCAGCTGGTGCAGTCTGGAGCTGAGGTGAA GAAGCCTGGGGCCTCAGTGAAGGTCTCCTGCAAGG CTTCTGGATTTACCCTCACAAACTATGGAATGAAC TGGGTGCGACAGGCTCGTGGACAACGCCTTGAGTG GATAGGTTGGATAAACACCGACACTGGAGAGCCAA CATATGCTGATGACTTCAAGGGAAGATTTGTCTTC TCCTTGGACACCTCTGTCAGCACGGCATATCTGCA GATCAGCAGCCTAAAGGCTGAGGACACTGCCGTGT ATTACTGTGCAAGAAACCCTCCCTATTACTACGGT ACTAATAACGCGGAGGCTATGGACTACTGGGGCCA GGGCACCACCGTGACCGTGTCCTCCGCTTCCACCA AGGGCCCATCCGTCTTCCCCCTGGCGCCCTGCTCC AGGAGCACCTCCGAGAGCACAGCCGCCCTGGGCTG CCTGGTCAAGGACTACTTCCCCGAACCGGTGACGG TGTCGTGGAACTCAGGCGCCCTGACCAGCGGCGTG CACACCTTCCCGGCTGTCCTACAGTCCTCAGGACT CTACTCCCTCAGCAGCGTGGTGACCGTGCCCTCCA GCAGCTTGGGCACGAAGACCTACACCTGCAACGTA GATCACAAGCCCAGCAACACCAAGGTGGACAAGAG AGTTGAGTCCAAATATGGTCCCCCATGCCCACCGT GCCCAGCACCTGAGTTCCTGGGGGGACCATCAGTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCAAAACCCAAGGACACTCTCAT GATCTCCCGGACCCCTGAGGTCACGTGCGTGGTGG TGGACGTGAGCCAGGAAGACCCCGAGGTCCAGTTC AACTGGTACGTGGATGGCGTGGAGGTGCATAATGC CAAGACAAAGCCGCGGGAGGAGCAGTTCAACAGCA CGTACCGTGTGGTCAGCGTCCTCACCGTCCTGCAC CAGGACTGGCTGAACGGCAAGGAGTACAAGTGCAA GGTGTCCAACAAAGGCCTCCCGTCCTCCATCGAGA AAACCATCTCCAAAGCCAAAGGGCAGCCCCGAGAG CCACAGGTGTACACCCTGCCCCCATCCCAGGAGGA GATGACCAAGAACCAGGTCAGCCTGACCTGCCTGG TCAAAGGCTTCTACCCCAGCGACATCGCCGTGGAG TGGGAGAGCAATGGGCAGCCGGAGAACAACTACAA GACCACGCCTCCCGTGCTGGACTCCGACGGCTCCT TCTTCCTCTACAGCAGGCTAACCGTGGACAAGAGC AGGTGGCAGGAGGGGAATGTCTTCTCATGCTCCGT GATGCATGAGGCTCTGCACAACCACTACACACAGA AGAGCCTCTCCCTGTCTCTGGGTAAA |
| BAP050-hum20-Ser LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 96 | VL | DIVMTQTPLSLPVTPGEPASISCSSSQDISNYLNW YQQKPGQAPRLLIYYTSTLHLGIPDRFSGSGSGTD FTLTISRLEPEDFAVYYCQQYYNLPWTFGQGTKVE IK |
| SEQ ID NO: 97 | DNA VL | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAA |
| SEQ ID NO: 98 | LC | DIVMTQTPLSLPVTPGEPASISCSSSQDISNYLNW YQQKPGQAPRLLIYYTSTLHLGIPDRFSGSGSGTD FTLTISRLEPEDFAVYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 99 | DNA LC | GATATTGTGATGACCCAGACTCCACTCTCCCTGCC CGTCACCCCTGGAGAGCCGGCCTCCATCTCCTGCA GTTCAAGTCAGGACATCAGCAATTATTTAAACTGG TACCAGCAGAAACCTGGCCAGGCTCCCAGGCTCCT CATCTATTACACATCAACCTTACACTTAGGGATCC CAGACAGGTTCAGTGGCAGTGGGTCTGGGACAGAC TTCACTCTCACCATCAGCAGACTGGAGCCTGAAGA TTTTGCAGTGTATTACTGTCAGCAGTATTATAACC TTCCGTGGACGTTCGGCCAAGGGACCAAGGTGGAA ATCAAACGTACGGTGGCTGCACCATCTGTCTTCAT CTTCCCGCCATCTGATGAGCAGTTGAAATCTGGAA CTGCCTCTGTTGTGTGCCTGCTGAATAACTTCTAT CCCAGAGAGGCCAAAGTACAGTGGAAGGTGGATAA CGCCCTCCAATCGGGTAACTCCCAGGAGAGTGTCA CAGAGCAGGACAGCAAGGACAGCACCTACAGCCTC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACGCTGAGCAAAGCAGACTACGA<br>GAAACACAAAGTCTACGCCTGCGAAGTCACCCATC<br>AGGGCCTGAGCTCGCCCGTCACAAAGAGCTTCAAC<br>AGGGGAGAGTGT |
| BAP050-Clone-F HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 112 | DNA VH | GAAGTGCAGCTGGTGCAGTCTGGCGCCGAAGTGAA<br>GAAACCCGGCGCTACCGTGAAGATCTCCTGCAAGG<br>TGTCCGGCTTCACCCTGACCAACTACGGCATGAAC<br>TGGGTGCGACAGGCCCCTGGACAGGGCCTGGAATG<br>GATGGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCT |
| SEQ ID NO: 113 | HC | EVQLVQSGAEVKKPGATVKISCKVSGFTLTNYGMN<br>WVRQAPGQGLEWMGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLG |
| SEQ ID NO: 114 | DNA HC | GAAGTGCAGCTGGTGCAGTCTGGCGCCGAAGTGAA<br>GAAACCCGGCGCTACCGTGAAGATCTCCTGCAAGG<br>TGTCCGGCTTCACCCTGACCAACTACGGCATGAAC<br>TGGGTGCGACAGGCCCCTGGACAGGGCCTGGAATG<br>GATGGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCTGCTTCTACCA<br>AGGGGCCCAGCGTGTTCCCCCTGGCCCCCTGCTCC<br>AGAAGCACCAGCGAGAGCACAGCCGCCCTGGGCTG<br>CCTGGTGAAGGACTACTTCCCCGAGCCCGTGACCG<br>TGTCCTGGAACAGCGGAGCCCTGACCAGCGGCGTG<br>CACACCTTCCCCGCCGTGCTGCAGAGCAGCGGCCT<br>GTACAGCCTGAGCAGCGTGGTGACCGTGCCCAGCA<br>GCAGCCTGGGCACCAAGACCTACACCTGTAACGTG<br>GACCACAAGCCCAGCAACACCAAGGTGGACAAGAG<br>GGTGGAGAGCAAGTACGGCCCACCCTGCCCCCCCT<br>GCCCAGCCCCCGAGTTCCTGGGCGGACCCAGCGTG<br>TTCCTGTTCCCCCCCAAGCCCAAGGACACCCTGAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCAGCAGAACCCCCGAGGTGACCTGTGTGGTGG TGGACGTGTCCCAGGAGGACCCCGAGGTCCAGTTC AACTGGTACGTGGACGGCGTGGAGGTGCACAACGC CAAGACCAAGCCCAGAGAGGAGCAGTTTAACAGCA CCTACCGGGTGGTGTCCGTGCTGACCGTGCTGCAC CAGGACTGGCTGAACGGCAAAGAGTACAAGTGTAA GGTCTCCAACAAGGGCCTGCCAAGCAGCATCGAAA AGACCATCAGCAAGGCCAAGGGCCAGCCTAGAGAG CCCCAGGTCTACACCCTGCCACCCAGCCAAGAGGA GATGACCAAGAACCAGGTGTCCCTGACCTGTCTGG TGAAGGGCTTCTACCCAAGCGACATCGCCGTGGAG TGGGAGAGCAACGGCCAGCCCGAGAACAACTACAA GACCACCCCCCCAGTGCTGGACAGCGACGGCAGCT TCTTCCTGTACAGCAGGCTGACCGTGGACAAGTCC AGATGGCAGGAGGGCAACGTCTTTAGCTGCTCCGT GATGCACGAGGCCCTGCACAACCACTACACCCAGA AGAGCCTGAGCCTGTCCCTGGGC |
| BAP050-Clone-F LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 32 | VL | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IK |
| SEQ ID NO: 115 | DNA VL | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCGTGC CCTCCAGATTTTCCGGCTCTGGCTCTGGCACCGAC TTTACCTTCACCATCAGCTCCCTGGAAGCCGAGGA CGCCGCCACCTACTACTGCCAGCAGTACTACAACC TGCCCTGGACCTTCGGCCAGGGCACCAAGGTGGAA ATCAAG |
| SEQ ID NO: 34 | LC | DIQMTQSPSSLSASVGDRVTITCSSSQDISNYLNW YQQKPGKAPKLLIYYTSTLHLGVPSRFSGSGSGTD FTFTISSLEAEDAATYYCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 117 | DNA LC | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCGTGC CCTCCAGATTTTCCGGCTCTGGCTCTGGCACCGAC TTTACCTTCACCATCAGCTCCCTGGAAGCCGAGGA CGCCGCCACCTACTACTGCCAGCAGTACTACAACC TGCCCTGGACCTTCGGCCAGGGCACCAAGGTGGAA ATCAAGCGTACGGTGGCCGCTCCCAGCGTGTTCAT CTTCCCCCCCAAGCGACGAGCAGCTGAAGAGCGGCA CCGCCAGCGTGGTGTGTCTGCTGAACAACTTCTAC CCCAGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACCCTGAGCAAGGCCGACTACGA GAAGCACAAGGTGTACGCCTGTGAGGTGACCCACC AGGGCCTGTCCAGCCCCGTGACCAAGAGCTTCAAC AGGGGCGAGTGC |
| BAP050-Clone-G HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 100 | VH | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 112 | DNA VH | GAAGTGCAGCTGGTGCAGTCTGGCGCCGAAGTGAA GAAACCCGGCGCTACCGTGAAGATCTCCTGCAAGG TGTCCGGCTTCACCCTGACCAACTACGGCATGAAC TGGGTGCGACAGGCCCCTGGACAGGGCCTGGAATG GATGGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCT |
| SEQ ID NO: 113 | HC | EVQLVQSGAEVKKPGATVKISCKVSGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH QDWLNGKEYKCKVSNKGLPSSIEKTISKAKGQPRE PQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLG |
| SEQ ID NO: 114 | DNA HC | GAAGTGCAGCTGGTGCAGTCTGGCGCCGAAGTGAA GAAACCCGGCGCTACCGTGAAGATCTCCTGCAAGG TGTCCGGCTTCACCCTGACCAACTACGGCATGAAC TGGGTGCGACAGGCCCCTGGACAGGGCCTGGAATG GATGGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCTTACTACTACGGC ACCAACAACGCCGAGGCCATGGACTATTGGGGCCA GGGCACCACCGTGACCGTGTCCTCTGCTTCTACCA AGGGGCCCAGCGTGTTCCCCCTGGCCCCCTGCTCC AGAAGCACCAGCGAGAGCACAGCCGCCCTGGGCTG CCTGGTGAAGGACTACTTCCCCGAGCCCGTGACCG TGTCCTGGAACAGCGGAGCCCTGACCAGCGGCGTG CACACCTTCCCCGCCGTGCTGCAGAGCAGCGGCCT GTACAGCCTGAGCAGCGTGGTGACCGTGCCCAGCA GCAGCCTGGGCACCAAGACCTACACCTGTAACGTG GACCACAAGCCCAGCAACACCAAGGTGGACAAGAG GGTGGAGAGCAAGTACGGCCCACCCTGCCCCCCCT GCCCAGCCCCCGAGTTCCTGGGCGGACCCAGCGTG TTCCTGTTCCCCCCCAAGCCCAAGGACACCCTGAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GATCAGCAGAACCCCCGAGGTGACCTGTGTGGTGG<br>TGGACGTGTCCCAGGAGGACCCCGAGGTCCAGTTC<br>AACTGGTACGTGGACGGCGTGGAGGTGCACAACGC<br>CAAGACCAAGCCCAGAGAGGAGCAGTTTAACAGCA<br>CCTACCGGGTGGTGTCCGTGCTGACCGTGCTGCAC<br>CAGGACTGGCTGAACGGCAAAGAGTACAAGTGTAA<br>GGTCTCCAACAAGGGCCTGCCAAGCAGCATCGAAA<br>AGACCATCAGCAAGGCCAAGGGCCAGCCTAGAGAG<br>CCCCAGGTCTACACCCTGCCACCCAGCCAAGAGGA<br>GATGACCAAGAACCAGGTGTCCCTGACCTGTCTGG<br>TGAAGGGCTTCTACCCAAGCGACATCGCCGTGGAG<br>TGGGAGAGCAACGGCCAGCCCGAGAACAACTACAA<br>GACCACCCCCCCAGTGCTGGACAGCGACGGCAGCT<br>TCTTCCTGTACAGCAGGCTGACCGTGGACAAGTCC<br>AGATGGCAGGAGGGCAACGTCTTTAGCTGCTCCGT<br>GATGCACGAGGCCCTGCACAACCACTACACCCAGA<br>AGAGCCTGAGCCTGTCCCTGGGC |
| BAP050-Clone-G LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW<br>YQQKPGKAPKLLIYYTSTLHLGIPPRFSGSGYGTD<br>FTLTINNIESEDAAYYFCQQYYNLPWTFGQGTKVE<br>IK |
| SEQ ID NO: 118 | DNA VL | GACATCCAGATGACCCAGTCCCCCTCCAGCCTGTC<br>TGCTTCCGTGGGCGACAGAGTGACCATCACCTGTT<br>CCTCCAGCCAGGACATCTCCAACTACCTGAACTGG<br>TATCAGCAGAAGCCCGGCAAGGCCCCCAAGCTGCT<br>GATCTACTACACCTCCACCCTGCACCTGGGCATCC<br>CCCCTAGATTCTCCGGCTCTGGCTACGGCACCGAC<br>TTCACCCTGACCATCAACAACATCGAGTCCGAGGA<br>CGCCGCCTACTACTTCTGCCAGCAGTACTACAACC<br>TGCCCTGGACCTTCGGCCAGGGCACCAAGGTGGAA<br>ATCAAG |
| SEQ ID NO: 38 | LC | DIQMTQSPSSLSASVGDRVTITCSSSQDISNYLNW<br>YQQKPGKAPKLLIYYTSTLHLGIPPRFSGSGYGTD<br>FTLTINNIESEDAAYYFCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 120 | DNA LC | GACATCCAGATGACCCAGTCCCCCTCCAGCCTGTC<br>TGCTTCCGTGGGCGACAGAGTGACCATCACCTGTT<br>CCTCCAGCCAGGACATCTCCAACTACCTGAACTGG<br>TATCAGCAGAAGCCCGGCAAGGCCCCCAAGCTGCT<br>GATCTACTACACCTCCACCCTGCACCTGGGCATCC<br>CCCCTAGATTCTCCGGCTCTGGCTACGGCACCGAC<br>TTCACCCTGACCATCAACAACATCGAGTCCGAGGA<br>CGCCGCCTACTACTTCTGCCAGCAGTACTACAACC<br>TGCCCTGGACCTTCGGCCAGGGCACCAAGGTGGAA<br>ATCAAGCGTACGGTGGCCGCTCCCAGCGTGTTCAT<br>CTTCCCCCCCAAGCGACGAGCAGCTGAAGAGCGGCA<br>CCGCCAGCGTGGTGTGTCTGCTGAACAACTTCTAC<br>CCCAGGGAGGCCAAGGTGCAGTGGAAGGTGGACAA<br>CGCCCTGCAGAGCGGCAACAGCCAGGAGAGCGTCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CCGAGCAGGACAGCAAGGACTCCACCTACAGCCTG<br>AGCAGCACCCTGACCCTGAGCAAGGCCGACTACGA<br>GAAGCACAAGGTGTACGCCTGTGAGGTGACCCACC<br>AGGGCCTGTCCAGCCCCGTGACCAAGAGCTTCAAC<br>AGGGGCGAGTGCTGATGAATTC |
| BAP050-Clone-H HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 104 | VH | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 121 | DNA VH | CAGGTGCAGCTGGTGCAGTCTGGCGCCGAAGTGAA<br>GAAACCTGGCGCCTCCGTGAAGGTGTCCTGCAAGG<br>CCTCTGGCTTCACCCTGACCAACTACGGCATGAAC<br>TGGGTGCGACAGGCCAGGGGCCAGCGGCTGGAATG<br>GATCGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCT |
| SEQ ID NO: 122 | HC | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLG |
| SEQ ID NO: 123 | DNA HC | CAGGTGCAGCTGGTGCAGTCTGGCGCCGAAGTGAA<br>GAAACCTGGCGCCTCCGTGAAGGTGTCCTGCAAGG<br>CCTCTGGCTTCACCCTGACCAACTACGGCATGAAC<br>TGGGTGCGACAGGCCAGGGGCCAGCGGCTGGAATG<br>GATCGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCTGCTTCTACCA<br>AGGGGCCCAGCGTGTTCCCCCTGGCCCCCTGCTCC<br>AGAAGCACCAGCGAGAGCACAGCCGCCCTGGGCTG<br>CCTGGTGAAGGACTACTTCCCCGAGCCCGTGACCG<br>TGTCCTGGAACAGCGGAGCCCTGACCAGCGGCGTG<br>CACACCTTCCCCGCCGTGCTGCAGAGCAGCGGCCT<br>GTACAGCCTGAGCAGCGTGGTGACCGTGCCCAGCA<br>GCAGCCTGGGCACCAAGACCTACACCTGTAACGTG<br>GACCACAAGCCCAGCAACACCAAGGTGGACAAGAG<br>GGTGGAGAGCAAGTACGGCCCACCCTGCCCCCCCT<br>GCCCAGCCCCCGAGTTCCTGGGCGGACCCAGCGTG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | TTCCTGTTCCCCCCCAAGCCCAAGGACACCCTGAT<br>GATCAGCAGAACCCCCGAGGTGACCTGTGTGGTGG<br>TGGACGTGTCCCAGGAGGACCCCGAGGTCCAGTTC<br>AACTGGTACGTGGACGGCGTGGAGGTGCACAACGC<br>CAAGACCAAGCCCAGAGAGGAGCAGTTTAACAGCA<br>CCTACCGGGTGGTGTCCGTGCTGACCGTGCTGCAC<br>CAGGACTGGCTGAACGGCAAAGAGTACAAGTGTAA<br>GGTCTCCAACAAGGGCCTGCCAAGCAGCATCGAAA<br>AGACCATCAGCAAGGCCAAGGGCCAGCCTAGAGAG<br>CCCCAGGTCTACACCCTGCCACCCAGCCAAGAGGA<br>GATGACCAAGAACCAGGTGTCCCTGACCTGTCTGG<br>TGAAGGGCTTCTACCCAAGCGACATCGCCGTGGAG<br>TGGGAGAGCAACGGCCAGCCCGAGAACAACTACAA<br>GACCACCCCCCCAGTGCTGGACAGCGACGGCAGCT<br>TCTTCCTGTACAGCAGGCTGACCGTGGACAAGTCC<br>AGATGGCAGGAGGGCAACGTCTTTAGCTGCTCCGT<br>GATGCACGAGGCCCTGCACAACCACTACACCCAGA<br>AGAGCCTGAGCCTGTCCCTGGGC |
| BAP050-Clone-H LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW<br>YQQKPGKAPKLLIYYTSTLHLGIPPRFSGSGYGTD<br>FTLTINNIESEDAAYYFCQQYYNLPWTFGQGTKVE<br>IK |
| SEQ ID NO: 118 | DNA VL | GACATCCAGATGACCCAGTCCCCCTCCAGCCTGTC<br>TGCTTCCGTGGGCGACAGAGTGACCATCACCTGTT<br>CCTCCAGCCAGGACATCTCCAACTACCTGAACTGG<br>TATCAGCAGAAGCCCGGCAAGGCCCCCAAGCTGCT<br>GATCTACTACACCTCCACCCTGCACCTGGGCATCC<br>CCCCTAGATTCTCCGGCTCTGGCTACGGCACCGAC<br>TTCACCCTGACCATCAACAACATCGAGTCCGAGGA<br>CGCCGCCTACTACTTCTGCCAGCAGTACTACAACC<br>TGCCCTGGACCTTCGGCCAGGGCACCAAGGTGGAA<br>ATCAAG |
| SEQ ID NO: 38 | LC | DIQMTQSPSSLSASVGDRVTITCSSSQDISNYLNW<br>YQQKPGKAPKLLIYYTSTLHLGIPPRFSGSGYGTD<br>FTLTINNIESEDAAYYFCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| Nucleotides 1-642 of SEQ ID NO: 120 | DNA LC | GACATCCAGATGACCCAGTCCCCCTCCAGCCTGTC<br>TGCTTCCGTGGGCGACAGAGTGACCATCACCTGTT<br>CCTCCAGCCAGGACATCTCCAACTACCTGAACTGG<br>TATCAGCAGAAGCCCGGCAAGGCCCCCAAGCTGCT<br>GATCTACTACACCTCCACCCTGCACCTGGGCATCC<br>CCCCTAGATTCTCCGGCTCTGGCTACGGCACCGAC<br>TTCACCCTGACCATCAACAACATCGAGTCCGAGGA<br>CGCCGCCTACTACTTCTGCCAGCAGTACTACAACC<br>TGCCCTGGACCTTCGGCCAGGGCACCAAGGTGGAA<br>ATCAAGCGTACGGTGGCCGCTCCCAGCGTGTTCAT<br>CTTCCCCCCCAAGCGACGAGCAGCTGAAGAGCGGCA<br>CCGCCAGCGTGGTGTGTCTGCTGAACAACTTCTAC<br>CCCAGGGAGGCCAAGGTGCAGTGGAAGGTGGACAA<br>CGCCCTGCAGAGCGGCAACAGCCAGGAGAGCGTCA<br>CCGAGCAGGACAGCAAGGACTCCACCTACAGCCTG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | AGCAGCACCCTGACCCTGAGCAAGGCCGACTACGA<br>GAAGCACAAGGTGTACGCCTGTGAGGTGACCCACC<br>AGGGCCTGTCCAGCCCCGTGACCAAGAGCTTCAAC<br>AGGGGCGAGTGC |
| BAP050-Clone-I HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 104 | VH | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSS |
| SEQ ID NO: 124 | DNA VH | CAAGTGCAGCTGGTGCAGTCGGGAGCCGAAGTGAA<br>GAAGCCTGGAGCCTCGGTGAAGGTGTCGTGCAAGG<br>CATCCGGATTCACCCTCACCAATTACGGGATGAAC<br>TGGGTCAGACAGGCCCGGGGTCAACGGCTGGAGTG<br>GATCGGATGGATTAACACCGACACCGGGGAGCCTA<br>CCTACGCGGACGATTTCAAGGGACGGTTCGTGTTC<br>TCCCTCGACACCTCCGTGTCCACCGCCTACCTCCA<br>AATCTCCTCACTGAAAGCGGAGGACACCGCCGTGT<br>ACTATTGCGCGAGGAACCCGCCCTACTACTACGGA<br>ACCAACAACGCCGAAGCCATGGACTACTGGGGCCA<br>GGGCACCACTGTGACTGTGTCCAGC |
| SEQ ID NO: 125 | DNA VH | CAGGTGCAGCTGGTGCAGTCTGGCGCCGAAGTGAA<br>GAAACCTGGCGCCTCCGTGAAGGTGTCCTGCAAGG<br>CCTCTGGCTTCACCCTGACCAACTACGGCATGAAC<br>TGGGTGCGACAGGCCAGGGGCCAGCGGCTGGAATG<br>GATCGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCT |
| SEQ ID NO: 122 | HC | QVQLVQSGAEVKKPGASVKVSCKASGFTLTNYGMN<br>WVRQARGQRLEWIGWINTDTGEPTYADDFKGRFVF<br>SLDTSVSTAYLQISSLKAEDTAVYYCARNPPYYYG<br>TNNAEAMDYWGQGTTVTVSSASTKGPSVFPLAPCS<br>RSTSESTAALGCLVKDYFPEPVTVSWNSGALTSGV<br>HTFPAVLQSSGLYSLSSVVTVPSSSLGTKTYTCNV<br>DHKPSNTKVDKRVESKYGPPCPPCPAPEFLGGPSV<br>FLFPPKPKDTLMISRTPEVTCVVVDVSQEDPEVQF<br>NWYVDGVEVHNAKTKPREEQFNSTYRVVSVLTVLH<br>QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLG |
| SEQ ID NO: 126 | DNA HC | CAAGTGCAGCTGGTGCAGTCGGGAGCCGAAGTGAA<br>GAAGCCTGGAGCCTCGGTGAAGGTGTCGTGCAAGG<br>CATCCGGATTCACCCTCACCAATTACGGGATGAAC<br>TGGGTCAGACAGGCCCGGGGTCAACGGCTGGAGTG<br>GATCGGATGGATTAACACCGACACCGGGGAGCCTA<br>CCTACGCGGACGATTTCAAGGGACGGTTCGTGTTC<br>TCCCTCGACACCTCCGTGTCCACCGCCTACCTCCA<br>AATCTCCTCACTGAAAGCGGAGGACACCGCCGTGT<br>ACTATTGCGCGAGGAACCCGCCCTACTACTACGGA<br>ACCAACAACGCCGAAGCCATGGACTACTGGGGCCA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | GGGCACCACTGTGACTGTGTCCAGCGCGTCCACTA<br>AGGGCCCGTCCGTGTTCCCCCTGGCACCTTGTAGC<br>CGGAGCACTAGCGAATCCACCGCTGCCCTCGGCTG<br>CCTGGTCAAGGATTACTTCCCGGAGCCCGTGACCG<br>TGTCCTGGAACAGCGGAGCCCTGACCTCCGGAGTG<br>CACACCTTCCCCGCTGTGCTGCAGAGCTCCGGGCT<br>GTACTCGCTGTCGTCGGTGGTCACGGTGCCTTCAT<br>CTAGCCTGGGTACCAAGACCTACACTTGCAACGTG<br>GACCACAAGCCTTCCAACACTAAGGTGGACAAGCG<br>CGTCGAATCGAAGTACGGCCCACCGTGCCCGCCTT<br>GTCCCGCGCCGGAGTTCCTCGGCGGTCCCTCGGTC<br>TTTCTGTTCCCACCGAAGCCCAAGGACACTTTGAT<br>GATTTCCCGCACCCCTGAAGTGACATGCGTGGTCG<br>TGGACGTGTCACAGGAAGATCCGGAGGTGCAGTTC<br>AATTGGTACGTGGATGGCGTCGAGGTGCACAACGC<br>CAAAACCAAGCCGAGGGAGGAGCAGTTCAACTCCA<br>CTTACCGCGTCGTGTCCGTGCTGACGGTGCTGCAT<br>CAGGACTGGCTGAACGGGAAGGAGTACAAGTGCAA<br>AGTGTCCAACAAGGGACTTCCTAGCTCAATCGAAA<br>AGACCATCTCGAAAGCCAAGGGACAGCCCCGGGAA<br>CCCCAAGTGTATACCCTGCCACCGAGCCAGGAAGA<br>AATGACTAAGAACCAAGTCTCATTGACTTGCCTTG<br>TGAAGGGCTTCTACCCATCGGATATCGCCGTGGAA<br>TGGGAGTCCAACGGCCAGCCGGAAAACAACTACAA<br>GACCACCCCTCCGGTGCTGGACTCAGACGGATCCT<br>TCTTCCTCTACTCGCGGCTGACCGTGGATAAGAGC<br>AGATGGCAGGAGGGAAATGTGTTCAGCTGTTCTGT<br>GATGCATGAAGCCCTGCACAACCACTACACTCAGA<br>AGTCCCTGTCCCTCTCCCTGGGA |
| SEQ ID NO: 127 | DNA HC | CAGGTGCAGCTGGTGCAGTCTGGCGCCGAAGTGAA<br>GAAACCTGGCGCCTCCGTGAAGGTGTCCTGCAAGG<br>CCTCTGGCTTCACCCTGACCAACTACGGCATGAAC<br>TGGGTGCGACAGGCCAGGGGCCAGCGGCTGGAATG<br>GATCGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCTGCTTCTACCA<br>AGGGGCCCAGCGTGTTCCCCCTGGCCCCCTGCTCC<br>AGAAGCACCAGCGAGAGCACAGCCGCCCTGGGCTG<br>CCTGGTGAAGGACTACTTCCCCGAGCCCGTGACCG<br>TGTCCTGGAACAGCGGAGCCCTGACCAGCGGCGTG<br>CACACCTTCCCCGCCGTGCTGCAGAGCAGCGGCCT<br>GTACAGCCTGAGCAGCGTGGTGACCGTGCCCAGCA<br>GCAGCCTGGGCACCAAGACCTACACCTGTAACGTG<br>GACCACAAGCCCAGCAACACCAAGGTGGACAAGAG<br>GGTGGAGAGCAAGTACGGCCCACCCTGCCCCCCCT<br>GCCCAGCCCCCGAGTTCCTGGGCGGACCCAGCGTG<br>TTCCTGTTCCCCCCCAAGCCCAAGGACACCCTGAT<br>GATCAGCAGAACCCCCGAGGTGACCTGTGTGGTGG<br>TGGACGTGTCCCAGGAGGACCCCGAGGTCCAGTTC<br>AACTGGTACGTGGACGGCGTGGAGGTGCACAACGC<br>CAAGACCAAGCCCAGAGAGGAGCAGTTTAACAGCA<br>CCTACCGGGTGGTGTCCGTGCTGACCGTGCTGCAC<br>CAGGACTGGCTGAACGGCAAAGAGTACAAGTGTAA<br>GGTCTCCAACAAGGGCCTGCCAAGCAGCATCGAAA<br>AGACCATCAGCAAGGCCAAGGGCCAGCCTAGAGAG<br>CCCCAGGTCTACACCCTGCCACCCAGCCAAGAGGA<br>GATGACCAAGAACCAGGTGTCCCTGACCTGTCTGG<br>TGAAGGGCTTCTACCCAAGCGACATCGCCGTGGAG<br>TGGGAGAGCAACGGCCAGCCCGAGAACAACTACAA<br>GACCACCCCCCCAGTGCTGGACAGCGACGGCAGCT<br>TCTTCCTGTACAGCAGGCTGACCGTGGACAAGTCC<br>AGATGGCAGGAGGGCAACGTCTTTAGCTGCTCCGT<br>GATGCACGAGGCCCTGCACAACCACTACACCCAGA<br>AGAGCCTGAGCCTGTCCCTGGGC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

BAP050-Clone-I LC

| | | |
|---|---|---|
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 56 | VL | DIQMTQSPSSLSASVGDRVTITCSSSQDISNYLNW<br>YLQKPGQSPQLLIYYTSTLHLGVPSRFSGSGSGTE<br>FTLTISSLQPDDFATYYCQQYYNLPWTFGQGTKVE<br>IK |
| SEQ ID NO: 128 | DNA VL | GATATTCAGATGACTCAGTCACCTAGTAGCCTGAG<br>CGCTAGTGTGGGCGATAGAGTGACTATCACCTGTA<br>GCTCTAGTCAGGATATCTCTAACTACCTGAACTGG<br>TATCTGCAGAAGCCCGGTCAATCACCTCAGCTGCT<br>GATCTACTACACTAGCACCCTGCACCTGGGCGTGC<br>CCTCTAGGTTTAGCGGTAGCGGTAGTGGCACCGAG<br>TTCACCCTGACTATCTCTAGCCTGCAGCCCGACGA<br>CTTCGCTACCTACTACTGTCAGCAGTACTATAACC<br>TGCCCTGGACCTTCGGTCAAGGCACTAAGGTCGAG<br>ATTAAG |
| SEQ ID NO: 129 | DNA VL | GACATCCAGATGACCCAGTCCCCCTCCAGCCTGTC<br>TGCTTCCGTGGGCGACAGAGTGACCATCACCTGTT<br>CCTCCAGCCAGGACATCTCCAACTACCTGAACTGG<br>TATCTGCAGAAGCCCGGCCAGTCCCCTCAGCTGCT<br>GATCTACTACACCTCCACCCTGCACCTGGGCGTGC<br>CCTCCAGATTTTCCGGCTCTGGCTCTGGCACCGAG<br>TTTACCCTGACCATCAGCTCCCTGCAGCCCGACGA<br>CTTCGCCACCTACTACTGCCAGCAGTACTACAACC<br>TGCCCTGGACCTTCGGCCAGGGCACCAAGGTGGAA<br>ATCAAG |
| SEQ ID NO: 58 | LC | DIQMTQSPSSLSASVGDRVTITCSSSQDISNYLNW<br>YLQKPGQSPQLLIYYTSTLHLGVPSRFSGSGSGTE<br>FTLTISSLQPDDFATYYCQQYYNLPWTFGQGTKVE<br>IKRTVAAPSVFIFPPSDEQLKSGTASVVCLLNNFY<br>PREAKVQWKVDNALQSGNSQESVTEQDSKDSTYSL<br>SSTLTLSKADYEKHKVYACEVTHQGLSSPVTKSFN<br>RGEC |
| SEQ ID NO: 130 | DNA LC | GATATTCAGATGACTCAGTCACCTAGTAGCCTGAG<br>CGCTAGTGTGGGCGATAGAGTGACTATCACCTGTA<br>GCTCTAGTCAGGATATCTCTAACTACCTGAACTGG<br>TATCTGCAGAAGCCCGGTCAATCACCTCAGCTGCT<br>GATCTACTACACTAGCACCCTGCACCTGGGCGTGC<br>CCTCTAGGTTTAGCGGTAGCGGTAGTGGCACCGAG<br>TTCACCCTGACTATCTCTAGCCTGCAGCCCGACGA<br>CTTCGCTACCTACTACTGTCAGCAGTACTATAACC<br>TGCCCTGGACCTTCGGTCAAGGCACTAAGGTCGAG<br>ATTAAGCGTACGGTGGCCGCTCCCAGCGTGTTCAT<br>CTTCCCCCCCAGCGACGAGCAGCTGAAGAGCGGCA<br>CCGCCAGCGTGGTGTGCCTGCTGAACAACTTCTAC<br>CCCCGGGAGGCCAAGGTGCAGTGGAAGGTGGACAA<br>CGCCCTGCAGAGCGGCAACAGCCAGGAGAGCGTCA<br>CCGAGCAGGACAGCAAGGACTCCACCTACAGCCTG<br>AGCAGCACCCTGACCCTGAGCAAGGCCGACTACGA<br>GAAGCATAAGGTGTACGCCTGCGAGGTGACCCACC<br>AGGGCCTGTCCAGCCCCGTGACCAAGAGCTTCAAC<br>AGGGGCGAGTGC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 131 | DNA LC | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCTGCAGAAGCCCGGCCAGTCCCCTCAGCTGCT GATCTACTACACCTCCACCCTGCACCTGGGCGTGC CCTCCAGATTTTCCGGCTCTGGCTCTGGCACCGAG TTTACCCTGACCATCAGCTCCCTGCAGCCCGACGA CTTCGCCACCTACTACTGCCAGCAGTACTACAACC TGCCCTGGACCTTCGGCCAGGGCACCAAGGTGGAA ATCAAGCGTACGGTGGCCGCTCCCAGCGTGTTCAT CTTCCCCCCAAGCGACGAGCAGCTGAAGAGCGGCA CCGCCAGCGTGGTGTGTCTGCTGAACAACTTCTAC CCCAGGGAGGCCAAGGTGCAGTGGAAGGTGGACAA CGCCCTGCAGAGCGGCAACAGCCAGGAGAGCGTCA CCGAGCAGGACAGCAAGGACTCCACCTACAGCCTG AGCAGCACCCTGACCCTGAGCAAGGCCGACTACGA GAAGCACAAGGTGTACGCCTGTGAGGTGACCCACC AGGGCCTGTCCAGCCCCGTGACCAAGAGCTTCAAC AGGGGCGAGTGC |
| BAP050-Clone-J HC | | |
| SEQ ID NO: 1 (Kabat) | HCDR1 | NYGMN |
| SEQ ID NO: 2 (Kabat) | HCDR2 | WINTDTGEPTYADDFKG |
| SEQ ID NO: 3 (Kabat) | HCDR3 | NPPYYYGTNNAEAMDY |
| SEQ ID NO: 4 (Chothia) | HCDR1 | GFTLTNY |
| SEQ ID NO: 5 (Chothia) | HCDR2 | NTDTGE |
| SEQ ID NO: 3 (Chothia) | HCDR3 | NPPYYYGTNNAEAMDY |
| SEQ ID NO: 108 | VH | QVQLVQSGAEVKKPGASVKVSCKASGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSS |
| SEQ ID NO: 132 | DNA VH | CAGGTGCAGCTGGTGCAGTCAGGCGCCGAAGTGAA GAAACCCGGCGCTAGTGTGAAAGTCAGCTGTAAAG CTAGTGGCTTCACCCTGACTAACTACGGGATGAAC TGGGTCCGCCAGGCCCCAGGTCAAGGCCTCGAGTG GATGGGCTGGATTAACACCGACACCGGCGAGCCTA CCTACGCCGACGACTTTAAGGGCAGATTCGTGTTT AGCCTGGACACTAGTGTGTCTACCGCCTACCTGCA GATCTCTAGCCTGAAGGCCGAGGACACCGCCGTCT ACTACTGCGCTAGAAACCCCCCCTACTACTACGGC ACTAACAACGCCGAGGCTATGGACTACTGGGGTCA AGGCACTACCGTGACCGTGTCTAGC |
| SEQ ID NO: 133 | DNA VH | CAGGTGCAGCTGGTGCAGTCTGGCGCCGAAGTGAA GAAACCTGGCGCCTCCGTGAAGGTGTCCTGCAAGG CCTCTGGCTTCACCCTGACCAACTACGGCATGAAC TGGGTGCGACAGGCCCCTGGACAGGGCCTGGAATG GATGGGCTGGATCAACACCGACACCGGCGAGCCTA CCTACGCCGACGACTTCAAGGGCAGATTCGTGTTC TCCCTGGACACCTCCGTGTCCACCGCCTACCTGCA GATCTCCAGCCTGAAGGCCGAGGATACCGCCGTGT ACTACTGCGCCCGGAACCCCCCCTTACTACTACGGC ACCAACAACGCCGAGGCCATGGACTATTGGGGCCA GGGCACCACCGTGACCGTGTCCTCT |
| SEQ ID NO: 134 | HC | QVQLVQSGAEVKKPGASVKVSCKASGFTLTNYGMN WVRQAPGQGLEWMGWINTDTGEPTYADDFKGRFVF SLDTSVSTAYLQISSLKAEDTAVYYCARNPPYYYG TNNAEAMDYWGQGTTVTVSSASTKGPSVFPLAPCS RSTSESTAALGCLVKDYFPEPVTVSWNSGALTSGV HTFPAVLQSSGLYSLSSVVTVPSSSLGTKTYTCNV DHKPSNTKVDKRVESKYGPPCPPCPAPEFLGGPSV FLFPPKPKDTLMISRTPEVTCVVVDVSQEDPEVQF NWYVDGVEVHNAKTKPREEQFNSTYRVVSVLTVLH |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | QDWLNGKEYKCKVSNKGLPSSIEKTISKAKGQPRE<br>PQVYTLPPSQEEMTKNQVSLTCLVKGFYPSDIAVE<br>WESNGQPENNYKTTPPVLDSDGSFFLYSRLTVDKS<br>RWQEGNVFSCSVMHEALHNHYTQKSLSLSLG |
| SEQ ID NO: 135 | DNA HC | CAGGTGCAGCTGGTGCAGTCAGGCGCCGAAGTGAA<br>GAAACCCGGCGCTAGTGTGAAAGTCAGCTGTAAAG<br>CTAGTGGCTTCACCCTGACTAACTACGGGATGAAC<br>TGGGTCCGCCAGGCCCCAGGTCAAGGCCTCGAGTG<br>GATGGGCTGGATTAACACCGACACCGGCGAGCCTA<br>CCTACGCCGACGACTTTAAGGGCAGATTCGTGTTT<br>AGCCTGGACACTAGTGTGTCTACCGCCTACCTGCA<br>GATCTCTAGCCTGAAGGCCGAGGACACCGCCGTCT<br>ACTACTGCGCTAGAAACCCCCCCTACTACTACGGC<br>ACTAACAACGCCGAGGCTATGGACTACTGGGGTCA<br>AGGCACTACCGTGACCGTGTCTAGCGCTAGCACTA<br>AGGGCCCGTCCGTGTTCCCCCTGGCACCTTGTAGC<br>CGGAGCACTAGCGAATCCACCGCTGCCCTCGGCTG<br>CCTGGTCAAGGATTACTTCCCGGAGCCCGTGACCG<br>TGTCCTGGAACAGCGGAGCCCTGACCTCCGGAGTG<br>CACACCTTCCCCGCTGTGCTGCAGAGCTCCGGGCT<br>GTACTCGCTGTCGTCGGTGGTCACGGTGCCTTCAT<br>CTAGCCTGGGTACCAAGACCTACACTTGCAACGTG<br>GACCACAAGCCTTCCAACACTAAGGTGGACAAGCG<br>CGTCGAATCGAAGTACGGCCCACCGTGCCCGCCTT<br>GTCCCGCGCCGGAGTTCCTCGGCGGTCCCTCGGTC<br>TTTCTGTTCCCACCGAAGCCCAAGGACACTTTGAT<br>GATTTCCCGCACCCCTGAAGTGACATGCGTGGTCG<br>TGGACGTGTCACAGGAAGATCCGGAGGTGCAGTTC<br>AATTGGTACGTGGATGGCGTCGAGGTGCACAACGC<br>CAAAACCAAGCCGAGGGAGGAGCAGTTCAACTCCA<br>CTTACCGCGTCGTGTCCGTGCTGACGGTGCTGCAT<br>CAGGACTGGCTGAACGGGAAGGAGTACAAGTGCAA<br>AGTGTCCAACAAGGGACTTCCTAGCTCAATCGAAA<br>AGACCATCTCGAAAGCCAAGGGACAGCCCCGGGAA<br>CCCCAAGTGTATACCCTGCCACCGAGCCAGGAAGA<br>AATGACTAAGAACCAAGTCTCATTGACTTGCCTTG<br>TGAAGGGCTTCTACCCATCGGATATCGCCGTGGAA<br>TGGGAGTCCAACGGCCAGCCGGAAAACAACTACAA<br>GACCACCCCTCCGGTGCTGGACTCAGACGGATCCT<br>TCTTCCTCTACTCGCGGCTGACCGTGGATAAGAGC<br>AGATGGCAGGAGGGAAATGTGTTCAGCTGTTCTGT<br>GATGCATGAAGCCCTGCACAACCACTACACTCAGA<br>AGTCCCTGTCCCTCTCCCTGGGA |
| SEQ ID NO: 136 | DNA HC | CAGGTGCAGCTGGTGCAGTCTGGCGCCGAAGTGAA<br>GAAACCTGGCGCCTCCGTGAAGGTGTCCTGCAAGG<br>CCTCTGGCTTCACCCTGACCAACTACGGCATGAAC<br>TGGGTGCGACAGGCCCCTGGACAGGGCCTGGAATG<br>GATGGGCTGGATCAACACCGACACCGGCGAGCCTA<br>CCTACGCCGACGACTTCAAGGGCAGATTCGTGTTC<br>TCCCTGGACACCTCCGTGTCCACCGCCTACCTGCA<br>GATCTCCAGCCTGAAGGCCGAGGATACCGCCGTGT<br>ACTACTGCGCCCGGAACCCCCCTTACTACTACGGC<br>ACCAACAACGCCGAGGCCATGGACTATTGGGGCCA<br>GGGCACCACCGTGACCGTGTCCTCTGCTTCTACCA<br>AGGGGCCCAGCGTGTTCCCCCTGGCCCCCTGCTCC<br>AGAAGCACCAGCGAGAGCACAGCCGCCCTGGGCTG<br>CCTGGTGAAGGACTACTTCCCCGAGCCCGTGACCG<br>TGTCCTGGAACAGCGGAGCCCTGACCAGCGGCGTG<br>CACACCTTCCCCGCCGTGCTGCAGAGCAGCGGCCT<br>GTACAGCCTGAGCAGCGTGGTGACCGTGCCCAGCA<br>GCAGCCTGGGCACCAAGACCTACACCTGTAACGTG<br>GACCACAAGCCCAGCAACACCAAGGTGGACAAGAG<br>GGTGGAGAGCAAGTACGGCCCACCCTGCCCCCCCT<br>GCCCAGCCCCCGAGTTCCTGGGCGGACCCAGCGTG<br>TTCCTGTTCCCCCCCAAGCCCAAGGACACCCTGAT<br>GATCAGCAGAACCCCCGAGGTGACCTGTGTGGTGG<br>TGGACGTGTCCCAGGAGGACCCCGAGGTCCAGTTC<br>AACTGGTACGTGGACGGCGTGGAGGTGCACAACGC<br>CAAGACCAAGCCCAGAGAGGAGCAGTTTAACAGCA<br>CCTACCGGGTGGTGTCCGTGCTGACCGTGCTGCAC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CAGGACTGGCTGAACGGCAAAGAGTACAAGTGTAA GGTCTCCAACAAGGGCCTGCCAAGCAGCATCGAAA AGACCATCAGCAAGGCCAAGGGCCAGCCTAGAGAG CCCCAGGTCTACACCCTGCCACCCAGCCAAGAGGA GATGACCAAGAACCAGGTGTCCCTGACCTGTCTGG TGAAGGGCTTCTACCCAAGCGACATCGCCGTGGAG TGGGAGAGCAACGGCCAGCCCGAGAACAACTACAA GACCACCCCCCCAGTGCTGGACAGCGACGGCAGCT TCTTCCTGTACAGCAGGCTGACCGTGGACAAGTCC AGATGGCAGGAGGGCAACGTCTTTAGCTGCTCCGT GATGCACGAGGCCCTGCACAACCACTACACCCAGA AGAGCCTGAGCCTGTCCCTGGGC |
| BAP050-Clone-J LC | | |
| SEQ ID NO: 10 (Kabat) | LCDR1 | SSSQDISNYLN |
| SEQ ID NO: 11 (Kabat) | LCDR2 | YTSTLHL |
| SEQ ID NO: 12 (Kabat) | LCDR3 | QQYYNLPWT |
| SEQ ID NO: 13 (Chothia) | LCDR1 | SQDISNY |
| SEQ ID NO: 14 (Chothia) | LCDR2 | YTS |
| SEQ ID NO: 15 (Chothia) | LCDR3 | YYNLPW |
| SEQ ID NO: 36 | VL | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IK |
| SEQ ID NO: 137 | DNA VL | GATATTCAGATGACTCAGTCACCTAGTAGCCTGAG CGCTAGTGTGGGCGATAGAGTGACTATCACCTGTA GCTCTAGTCAGGATATCTCTAACTACCTGAACTGG TATCAGCAGAAGCCCGGTAAAGCCCCTAAGCTGCT GATCTACTACACTAGCACCCTGCACCTGGGAATCC CCCCTAGGTTTAGCGGTAGCGGCTACGGCACCGAC TTCACCCTGACTATTAACAATATCGAGTCAGAGGA CGCCGCCTACTACTTCTGTCAGCAGTACTATAACC TGCCCTGGACCTTCGGTCAAGGCACTAAGGTCGAG ATTAAG |
| SEQ ID NO: 118 | DNA VL | GACATCCAGATGACCCAGTCCCCCTCCAGCCTGTC TGCTTCCGTGGGCGACAGAGTGACCATCACCTGTT CCTCCAGCCAGGACATCTCCAACTACCTGAACTGG TATCAGCAGAAGCCCGGCAAGGCCCCCAAGCTGCT GATCTACTACACCTCCACCCTGCACCTGGGCATCC CCCCTAGATTCTCCGGCTCTGGCTACGGCACCGAC TTCACCCTGACCATCAACAACATCGAGTCCGAGGA CGCCGCCTACTACTTCTGCCAGCAGTACTACAACC TGCCCTGGACCTTCGGCCAGGGCACCAAGGTGGAA ATCAAG |
| SEQ ID NO: 38 | LC | DIQMTQSPSSLSASVGDRVTITCSSSQDISNYLNW YQQKPGKAPKLLIYYTSTLHLGIPPRFSGSGYGTD FTLTINNIESEDAAYYFCQQYYNLPWTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC |
| SEQ ID NO: 138 | DNA LC | GATATTCAGATGACTCAGTCACCTAGTAGCCTGAG CGCTAGTGTGGGCGATAGAGTGACTATCACCTGTA GCTCTAGTCAGGATATCTCTAACTACCTGAACTGG TATCAGCAGAAGCCCGGTAAAGCCCCTAAGCTGCT GATCTACTACACTAGCACCCTGCACCTGGGAATCC CCCCTAGGTTTAGCGGTAGCGGCTACGGCACCGAC TTCACCCTGACTATTAACAATATCGAGTCAGAGGA CGCCGCCTACTACTTCTGTCAGCAGTACTATAACC TGCCCTGGACCTTCGGTCAAGGCACTAAGGTCGAG ATTAAGCGTACGGTGGCCGCTCCCAGCGTGTTCAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| | | CTTCCCCCCCAGCGACGAGCAGCTGAAGAGCGGCA<br>CCGCCAGCGTGGTGTGCCTGCTGAACAACTTCTAC<br>CCCCGGGAGGCCAAGGTGCAGTGGAAGGTGGACAA<br>CGCCCTGCAGAGCGGCAACAGCCAGGAGAGCGTCA<br>CCGAGCAGGACAGCAAGGACTCCACCTACAGCCTG<br>AGCAGCACCCTGACCCTGAGCAAGGCCGACTACGA<br>GAAGCATAAGGTGTACGCCTGCGAGGTGACCCACC<br>AGGGCCTGTCCAGCCCCGTGACCAAGAGCTTCAAC<br>AGGGGCGAGTGC |
| SEQ ID NO: 139 | DNA LC | GACATCCAGATGACCCAGTCCCCCTCCAGCCTGTC<br>TGCTTCCGTGGGCGACAGAGTGACCATCACCTGTT<br>CCTCCAGCCAGGACATCTCCAACTACCTGAACTGG<br>TATCAGCAGAAGCCCGGCAAGGCCCCCAAGCTGCT<br>GATCTACTACACCTCCACCCTGCACCTGGGCATCC<br>CCCCTAGATTCTCCGGCTCTGGCTACGGCACCGAC<br>TTCACCCTGACCATCAACAACATCGAGTCCGAGGA<br>CGCCGCCTACTACTTCTGCCAGCAGTACTACAACC<br>TGCCCTGGACCTTCGGCCAGGGCACCAAGGTGGAA<br>ATCAAGCGTACGGTGGCCGCTCCCAGCGTGTTCAT<br>CTTCCCCCCAAGCGACGAGCAGCTGAAGAGCGGCA<br>CCGCCAGCGTGGTGTGTCTGCTGAACAACTTCTAC<br>CCCAGGGAGGCCAAGGTGCAGTGGAAGGTGGACAA<br>CGCCCTGCAGAGCGGCAACAGCCAGGAGAGCGTCA<br>CCGAGCAGGACAGCAAGGACTCCACCTACAGCCTG<br>AGCAGCACCCTGACCCTGAGCAAGGCCGACTACGA<br>GAAGCACAAGGTGTACGCCTGTGAGGTGACCCACC<br>AGGGCCTGTCCAGCCCCGTGACCAAGAGCTTCAAC<br>AGGGGCGAGTGC |
| BAP050 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC<br>TGATGACTTCAAGGGA |
| SEQ ID NO: 142 (Kabat) | HCDR3 | AACCCCCCTTATTACTACGGTACTAATAACGCGGA<br>GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 142 (Chothia) | HCDR3 | AACCCCCCTTATTACTACGGTACTAATAACGCGGA<br>GGCTATGGACTAC |
| BAP050 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-chi HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC<br>TGATGACTTCAAGGGA |
| SEQ ID NO: 142 (Kabat) | HCDR3 | AACCCCCCTTATTACTACGGTACTAATAACGCGGA<br>GGCTATGGACTAC |
| SEQ ID NO: 143 (Chothia) | HCDR1 | GGATTTACCCTCACAAACTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 144 (Chothia) | HCDR2 | AACACCGACACTGGAGAG |
| SEQ ID NO: 142 (Chothia) | HCDR3 | AACCCCCCTTATTACTACGGTACTAATAACGCGGA GGCTATGGACTAC |
| BAP050-chi LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum01 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum01 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum02 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050-hum02 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum03 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum03 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum04 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum04 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 149 (Chothia) | LCDR2 | TACACATCA |
| SEQ ID NO: 150 (Chothia) | LCDR3 | TATTATAACCTTCCGTGG |
| BAP050-hum05 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum05 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum06 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum06 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum07 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum07 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum08 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum08 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum09 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050-hum09 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum10 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum10 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum11 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum11 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 149 (Chothia) | LCDR2 | TACACATCA |
| SEQ ID NO: 150 (Chothia) | LCDR3 | TATTATAACCTTCCGTGG |
| BAP050-hum12 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum12 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum13 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum13 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050-hum14 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum14 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum15 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum15 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum16 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA |
| BAP050-hum16 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum17 HC | | |
| SEQ ID NO: 152 (Kabat) | HCDR1 | AACTATGGCATGAAT |
| SEQ ID NO: 153 (Kabat) | HCDR2 | TGGATCAACACCGACACTGGGGAGCCAACGTATGC CGATGACTTCAAGGGA |
| SEQ ID NO: 142 (Kabat) | HCDR3 | AACCCCCCTTATTACTACGGTACTAATAACGCGGA GGCTATGGACTAC |
| SEQ ID NO: 154 (Chothia) | HCDR1 | GGATTCACCCTGACTAACTAT |
| SEQ ID NO: 155 (Chothia) | HCDR2 | AACACCGACACTGGGGAG |
| SEQ ID NO: 142 (Chothia) | HCDR3 | AACCCCCCTTATTACTACGGTACTAATAACGCGGA GGCTATGGACTAC |
| BAP050-hum17 LC | | |
| SEQ ID NO: 156 (Kabat) | LCDR1 | TCCTCTAGTCAGGACATTAGCAACTATTTAAAT |
| SEQ ID NO: 157 (Kabat) | LCDR2 | TATACATCCACTTTGCACCTG |
| SEQ ID NO: 158 (Kabat) | LCDR3 | CAACAGTATTATAATCTCCCTTGGACG |
| SEQ ID NO: 159 (Chothia) | LCDR1 | AGTCAGGACATTAGCAACTAT |
| SEQ ID NO: 160 (Chothia) | LCDR2 | TATACATCC |
| SEQ ID NO: 161 (Chothia) | LCDR3 | TATTATAATCTCCCTTGG |
| BAP050-hum18 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050-hum18 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum19 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum19 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum20 HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum20 LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 149 (Chothia) | LCDR2 | TACACATCA |
| SEQ ID NO: 150 (Chothia) | LCDR3 | TATTATAACCTTCCGTGG |
| BAP050-hum01-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum01-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum02-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum02-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum03-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum03-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum04-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum04-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum05-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050-hum05-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum06-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum06-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum07-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum07-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 149 (Chothia) | LCDR2 | TACACATCA |
| SEQ ID NO: 150 (Chothia) | LCDR3 | TATTATAACCTTCCGTGG |
| BAP050-hum08-Ser HC | | |
| SEQ ID NO: 140 (Kabat) | HCDR1 | AACTATGGAATGAAC |
| SEQ ID NO: 141 (Kabat) | HCDR2 | TTGGATAAACACCGACACTGGAGAGCCAACATATGC GATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum08-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum09-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum09-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050-hum10-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum10-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum11-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum11-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum12-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum12-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum13-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum13-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum14-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050-hum14-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum15-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum15-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum18-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum18-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 149 (Chothia) | LCDR2 | TACACATCA |
| SEQ ID NO: 150 (Chothia) | LCDR3 | TATTATAACCTTCCGTGG |
| BAP050-hum19-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum19-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |
| BAP050-hum20-Ser HC | | |
| SEQ ID NO: 140 (Kabat) | HCDR1 | AACTATGGAATGAAC |
| SEQ ID NO: 141 (Kabat) | HCDR2 | TGGATAAACACCGACACTGGAGAGCCAACATATGC TGATGACTTCAAGGGA |
| SEQ ID NO: 151 (Kabat) | HCDR3 | AACCCTCCCTATTACTACGGTACTAATAACGCGGA GGCTATGGACTAC |
| SEQ ID NO: 143 (Chothia) | HCDR1 | GGATTTACCCTCACAAACTAT |
| SEQ ID NO: 144 (Chothia) | HCDR2 | AACACCGACACTGGAGAG |
| SEQ ID NO: 151 (Chothia) | HCDR3 | AACCCTCCCTATTACTACGGTACTAATAACGCGGA GGCTATGGACTAC |
| BAP050-hum20-Ser LC | | |
| SEQ ID NO: 145 (Kabat) | LCDR1 | AGTTCAAGTCAGGACATCAGCAATTATTTAAAC |
| SEQ ID NO: 146 (Kabat) | LCDR2 | TACACATCAACCTTACACTTA |
| SEQ ID NO: 147 (Kabat) | LCDR3 | CAGCAGTATTATAACCTTCCGTGGACG |
| SEQ ID NO: 148 (Chothia) | LCDR1 | AGTCAGGACATCAGCAATTAT |
| SEQ ID NO: 149 (Chothia) | LCDR2 | TACACATCA |
| SEQ ID NO: 150 (Chothia) | LCDR3 | TATTATAACCTTCCGTGG |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| BAP050-Clone-F HC | | |
| SEQ ID NO: 162 (Kabat) | HCDR1 | AACTACGGCATGAAC |
| SEQ ID NO: 163 (Kabat) | HCDR2 | TGGATCAACACCGACACCGGCGAGCCTACCTACGC CGACGACTTCAAGGGC |
| SEQ ID NO: 164 (Kabat) | HCDR3 | AACCCCCCTTACTACTACGGCACCAACAACGCCGA GGCCATGGACTAT |
| SEQ ID NO: 165 (Chothia) | HCDR1 | GGCTTCACCCTGACCAACTAC |
| SEQ ID NO: 166 (Chothia) | HCDR2 | AACACCGACACCGGCGAG |
| SEQ ID NO: 164 (Chothia) | HCDR3 | AACCCCCCTTACTACTACGGCACCAACAACGCCGA GGCCATGGACTAT |
| BAP050-Clone-F LC | | |
| SEQ ID NO: 167 (Kabat) | LCDR1 | TCCTCCAGCCAGGACATCTCCAACTACCTGAAC |
| SEQ ID NO: 168 (Kabat) | LCDR2 | TACACCTCCACCCTGCACCTG |
| SEQ ID NO: 169 (Kabat) | LCDR3 | CAGCAGTACTACAACCTGCCCTGGACC |
| SEQ ID NO: 170 (Chothia) | LCDR1 | AGCCAGGACATCTCCAACTAC |
| SEQ ID NO: 171 (Chothia) | LCDR2 | TACACCTCC |
| SEQ ID NO: 172 (Chothia) | LCDR3 | TACTACAACCTGCCCTGG |
| BAP050-Clone-G HC | | |
| SEQ ID NO: 162 (Kabat) | HCDR1 | AACTACGGCATGAAC |
| SEQ ID NO: 163 (Kabat) | HCDR2 | TGGATCAACACCGACACCGGCGAGCCTACCTACGC CGACGACTTCAAGGGC |
| SEQ ID NO: 164 (Kabat) | HCDR3 | AACCCCCCTTACTACTACGGCACCAACAACGCCGA GGCCATGGACTAT |
| SEQ ID NO: 165 (Chothia) | HCDR1 | GGCTTCACCCTGACCAACTAC |
| SEQ ID NO: 166 (Chothia) | HCDR2 | AACACCGACACCGGCGAG |
| SEQ ID NO: 164 (Chothia) | HCDR3 | AACCCCCCTTACTACTACGGCACCAACAACGCCGA GGCCATGGACTAT |
| BAP050-Clone-G LC | | |
| SEQ ID NO: 167 (Kabat) | LCDR1 | TCCTCCAGCCAGGACATCTCCAACTACCTGAAC |
| SEQ ID NO: 168 (Kabat) | LCDR2 | TACACCTCCACCCTGCACCTG |
| SEQ ID NO: 169 (Kabat) | LCDR3 | CAGCAGTACTACAACCTGCCCTGGACC |
| SEQ ID NO: 170 (Chothia) | LCDR1 | AGCCAGGACATCTCCAACTAC |
| SEQ ID NO: 171 (Chothia) | LCDR2 | TACACCTCC |
| SEQ ID NO: 172 (Chothia) | LCDR3 | TACTACAACCTGCCCTGG |
| BAP050-Clone-H HC | | |
| SEQ ID NO: 162 (Kabat) | HCDR1 | AACTACGGCATGAAC |
| SEQ ID NO: 163 (Kabat) | HCDR2 | TGGATCAACACCGACACCGGCGAGCCTACCTACGC CGACGACTTCAAGGGC |
| SEQ ID NO: 164 (Kabat) | HCDR3 | AACCCCCCTTACTACTACGGCACCAACAACGCCGA GGCCATGGACTAT |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 165 (Chothia) | HCDR1 | GGCTTCACCCTGACCAACTAC |
| SEQ ID NO: 166 (Chothia) | HCDR2 | AACACCGACACCGGCGAG |
| SEQ ID NO: 164 (Chothia) | HCDR3 | AACCCCCCTTACTACTACGGCACCAACAACGCCGA GGCCATGGACTAT |
| BAP050-Clone-H LC | | |
| SEQ ID NO: 167 (Kabat) | LCDR1 | TCCTCCAGCCAGGACATCTCCAACTACCTGAAC |
| SEQ ID NO: 168 (Kabat) | LCDR2 | TACACCTCCACCCTGCACCTG |
| SEQ ID NO: 169 (Kabat) | LCDR3 | CAGCAGTACTACAACCTGCCCTGGACC |
| SEQ ID NO: 170 (Chothia) | LCDR1 | AGCCAGGACATCTCCAACTAC |
| SEQ ID NO: 171 (Chothia) | LCDR2 | TACACCTCC |
| SEQ ID NO: 172 (Chothia) | LCDR3 | TACTACAACCTGCCCTGG |
| BAP050-Clone-I HC | | |
| SEQ ID NO: 173 (Kabat) | HCDR1 | AATTACGGGATGAAC |
| SEQ ID NO: 162 (Kabat) | HCDR1 | AACTACGGCATGAAC |
| SEQ ID NO: 174 (Kabat) | HCDR2 | TGGATTAACACCGACACCGGGGAGCCTACCTACGC GGACGATTTCAAGGGA |
| SEQ ID NO: 163 (Kabat) | HCDR2 | TGGATCAACACCGACACCGGCGAGCCTACCTACGC CGACGACTTCAAGGGC |
| SEQ ID NO: 175 (Kabat) | HCDR3 | AACCCGCCCTACTACTACGGAACCAACAACGCCGA AGCCATGGACTAC |
| SEQ ID NO: 164 (Kabat) | HCDR3 | AACCCCCCTTACTACTACGGCACCAACAACGCCGA GGCCATGGACTAT |
| SEQ ID NO: 176 (Chothia) | HCDR1 | GGATTCACCCTCACCAATTAC |
| SEQ ID NO: 165 (Chothia) | HCDR1 | GGCTTCACCCTGACCAACTAC |
| SEQ ID NO: 177 (Chothia) | HCDR2 | AACACCGACACCGGGGAG |
| SEQ ID NO: 166 (Chothia) | HCDR2 | AACACCGACACCGGCGAG |
| SEQ ID NO: 175 (Chothia) | HCDR3 | AACCCGCCCTACTACTACGGAACCAACAACGCCGA AGCCATGGACTAC |
| SEQ ID NO: 164 (Chothia) | HCDR3 | AACCCCCCTTACTACTACGGCACCAACAACGCCGA GGCCATGGACTAT |
| BAP050-Clone-I LC | | |
| SEQ ID NO: 178 (Kabat) | LCDR1 | AGCTCTAGTCAGGATATCTCTAACTACCTGAAC |
| SEQ ID NO: 167 (Kabat) | LCDR1 | TCCTCCAGCCAGGACATCTCCAACTACCTGAAC |
| SEQ ID NO: 179 (Kabat) | LCDR2 | TACACTAGCACCCTGCACCTG |
| SEQ ID NO: 168 (Kabat) | LCDR2 | TACACCTCCACCCTGCACCTG |
| SEQ ID NO: 180 (Kabat) | LCDR3 | CAGCAGTACTATAACCTGCCCTGGACC |
| SEQ ID NO: 169 (Kabat) | LCDR3 | CAGCAGTACTACAACCTGCCCTGGACC |
| SEQ ID NO: 181 (Chothia) | LCDR1 | AGTCAGGATATCTCTAACTAC |
| SEQ ID NO: 170 (Chothia) | LCDR1 | AGCCAGGACATCTCCAACTAC |
| SEQ ID NO: 182 (Chothia) | LCDR2 | TACACTAGC |

TABLE 1-continued

Amino acid and nucleotide sequences for murine, chimeric and humanized antibody molecules. The antibody molecules include murine mAb BAP050, chimeric mAbs BAP050-chi, humanized mAbs BAP050- hum01 to BAP050-hum20, humanized mAbs BAP050-hum01-Ser to BAP050-hum15-Ser. BAP050-hum18-Ser to BAP050-hum20-Ser. and humanized mAbs BAP050- Clone-F to BAP050-Clone-J. The amino acid and nucleotide sequences of the heavy and light chain CDRs, the heavy and light chain variable regions, and the heavy and light chains are shown.

| | | |
|---|---|---|
| SEQ ID NO: 171 (Chothia) | LCDR2 | TACACCTCC |
| SEQ ID NO: 183 (Chothia) | LCDR3 | TACTATAACCTGCCCTGG |
| SEQ ID NO: 172 (Chothia) | LCDR3 | TACTACAACCTGCCCTGG |
| BAP050-Clone-J HC | | |
| SEQ ID NO: 184 (Kabat) | HCDR1 | AACTACGGGATGAAC |
| SEQ ID NO: 162 (Kabat) | HCDR1 | AACTACGGCATGAAC |
| SEQ ID NO: 185 (Kabat) | HCDR2 | TGGATTAACACCGACACCGGCGAGCCTACCTACGC CGACGACTTTAAGGGC |
| SEQ ID NO: 163 (Kabat) | HCDR2 | TGGATCAACACCGACACCGGCGAGCCTACCTACGC CGACGACTTCAAGGGC |
| SEQ ID NO: 186 (Kabat) | HCDR3 | AACCCCCCCTACTACTACGGCACTAACAACGCCGA GGCTATGGACTAC |
| SEQ ID NO: 164 (Kabat) | HCDR3 | AACCCCCCTTACTACTACGGCACCAACAACGCCGA GGCCATGGACTAT |
| SEQ ID NO: 287 (Chothia) | HCDR1 | GGCTTCACCCTGACTAACTAC |
| SEQ ID NO: 165 (Chothia) | HCDR1 | GGCTTCACCCTGACCAACTAC |
| SEQ ID NO: 177 (Chothia) | HCDR2 | AACACCGACACCGGGGAG |
| SEQ ID NO: 166 (Chothia) | HCDR2 | AACACCGACACCGGCGAG |
| SEQ ID NO: 186 (Chothia) | HCDR3 | AACCCCCCCTACTACTACGGCACTAACAACGCCGA GGCTATGGACTAC |
| SEQ ID NO: 164 (Chothia) | HCDR3 | AACCCCCCTTACTACTACGGCACCAACAACGCCGA GGCCATGGACTAT |
| BAP050-Clone-J LC | | |
| SEQ ID NO: 178 (Kabat) | LCDR1 | AGCTCTAGTCAGGATATCTCTAACTACCTGAAC |
| SEQ ID NO: 167 (Kabat) | LCDR1 | TCCTCCAGCCAGGACATCTCCAACTACCTGAAC |
| SEQ ID NO: 179 (Kabat) | LCDR2 | TACACTAGCACCCTGCACCTG |
| SEQ ID NO: 168 (Kabat) | LCDR2 | TACACCTCCACCCTGCACCTG |
| SEQ ID NO: 180 (Kabat) | LCDR3 | CAGCAGTACTATAACCTGCCCTGGACC |
| SEQ ID NO: 169 (Kabat) | LCDR3 | CAGCAGTACTACAACCTGCCCTGGACC |
| SEQ ID NO: 181 (Chothia) | LCDR1 | AGTCAGGATATCTCTAACTAC |
| SEQ ID NO: 170 (Chothia) | LCDR1 | AGCCAGGACATCTCCAACTAC |
| SEQ ID NO: 182 (Chothia) | LCDR2 | TACACTAGC |
| SEQ ID NO: 171 (Chothia) | LCDR2 | TACACCTCC |
| SEQ ID NO: 183 (Chothia) | LCDR3 | TACTATAACCTGCCCTGG |
| SEQ ID NO: 172 (Chothia) | LCDR3 | TACTACAACCTGCCCTGG |

TABLE 2

Amino acid and nucleotide sequences of the heavy and light chain framework regions for humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J

| | Amino Acid Sequence | Nucleotide Sequence |
|---|---|---|
| VHFW1 (type a) | EVQLVQSGAEVKKPGATVKISCKVS (SEQ ID NO: 187) | GAAGTGCAGCTGGTGCAGTCTGGCGCCGAAGTGAAGAAACCCGGCGCTACCGTGAAGATCTCCTGCAAGGTGTCC (SEQ ID NO: 188)<br>GAGGTCCAGCTGGTACAGTCTGGGGCTGAGGTGAAGAAGCCTGGGGCTACAGTGAAAATCTCCTGCAAGGTTTCT (SEQ ID NO: 189) |
| VHFW1 (type b) | QVQLVQSGAEVKKPGASVKVSCKAS (SEQ ID NO: 190) | CAAGTGCAGCTGGTGCAGTCGGGAGCCGAAGTGAAGAAGCCTGGAGCCTCGGTGAAGGTGTCGTGCAAGGCATCC (SEQ ID NO: 191)<br>CAGGTGCAGCTGGTGCAGTCTGGCGCCGAAGTGAAGAAACCTGGCGCCTCCGTGAAGGTGTCCTGCAAGGCCTCT (SEQ ID NO: 192)<br>CAGGTTCAGCTGGTGCAGTCCGGAGCTGAGGTGAAGAAGCCTGGGGCCTCAGTGAAGGTCTCCTGCAAGGCTTCT (SEQ ID NO: 193) |
| VHFW1 (type c) | EVQLVQSGAEVKKPGESLRISCKGS (SEQ ID NO: 194) | GAAGTGCAGCTGGTGCAGTCTGGAGCAGAGGTGAAAAAGCCCGGGGAGTCTCTGAGGATCTCCTGTAAGGGTTCT (SEQ ID NO: 195) |
| VHFW1 (type d) | QVQLVQSGSELKKPGASVKVSCKAS (SEQ ID NO: 196) | CAGGTGCAGCTGGTGCAATCTGGGTCTGAGTTGAAGAAGCCTGGGGCCTCAGTGAAGGTTTCCTGCAAGGCTTCT (SEQ ID NO: 197) |
| VHFW2 (type a) | WVRQAPGQGLEWMG (SEQ ID NO: 198) | TGGGTCCGCCAGGCCCCAGGTCAAGGCCTCGAGTGGATGGGC (SEQ ID NO: 199)<br>TGGGTGCGACAGGCCCCTGGACAGGGCCTGGAATGGATGGGC (SEQ ID NO: 200)<br>TGGGTGCGACAGGCCCCTGGACAAGGGCTTGAGTGGATGGGT (SEQ ID NO: 201) |
| VHFW2 (type b) | WVRQARGQRLEWIG (SEQ ID NO: 202) | TGGGTCAGACAGGCCCGGGGTCAACGGCTGGAGTGGATCGGA (SEQ ID NO: 203)<br>TGGGTGCGACAGGCCAGGGGCCAGCGGCTGGAATGGATCGGC (SEQ ID NO: 204)<br>TGGGTGCGACAGGCTCGTGGACAACGCCTTGAGTGGATAGGT (SEQ ID NO: 205) |
| VHFW2 (type c) | WIRQSPSRGLEWLG (SEQ ID NO: 206) | TGGATCAGGCAGTCCCCATCGAGAGGCCTTGAGTGGCTGGGT (SEQ ID NO: 207) |
| VHFW2 (type d) | WVRQATGQGLEWMG (SEQ ID NO: 208) | TGGGTGCGACAGGCCACTGGACAAGGGCTTGAGTGGATGGGT (SEQ ID NO: 209) |
| VHFW3 (type a) | RFVFSLDTSVSTAYLQICSLKAEDTAVYYCAR (SEQ ID NO: 210) | AGATTTGTCTTCTCCTTGGACACCTCTGTCAGCACGGCATATCTGCAGATCTGCAGCCTAAAGGCTGAGGACACTGCCGTGTATTACTGTGCAAGA (SEQ ID NO: 211) |
| VHFW3 (type a-Ser) | RFVFSLDTSVSTAYLQISSLKAEDTAVYYCAR (SEQ ID NO: 212) | CGGTTCGTGTTCTCCCTCGACACCTCCGTGTCCACCGCCTACCTCCAAATCTCCTCACTGAAAGCGGAGGACACCGCCGTGTACTATTGCGCGAGG SEQ ID NO: 213)<br>AGATTCGTGTTTAGCCTGGACACTAGTGTGTCTACCGCCTACCTGCAGATCTCTAGCCTGAAGGCCGAGGACACCGCCGTCTACTACTGCGCTAGA SEQ ID NO: 214)<br>AGATTCGTGTTCTCCCTGGACACCTCCGTGTCCACCGCCTACCTGCAGATCTCCAGCCTGAAGGCCGAGGATACCGCCGTGTACTACTGCGCCCGG (SEQ ID NO: 215)<br>AGATTTGTCTTCTCCTTGGACACCTCTGTCAGCACGGCATATCTGCAGATCAGCAGCCTAAAGGCTGAGGACACTGCCGTGTATTACTGTGCAAGA (SEQ ID NO: 216) |
| VHFW3 (type b) | RVTISADKSISTAYLQWSSLKASDTAMYYCAR (SEQ ID NO: 217) | AGAGTCACCATCTCAGCCGACAAGTCCATCAGCACCGCCTACCTGCAGTGGAGCAGCCTGAAGGCCTCGGACACCGCCATGTATTACTGTGCAAGA (SEQ ID NO: 218) |

TABLE 2-continued

Amino acid and nucleotide sequences of the heavy and light chain framework regions for humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J

| | Amino Acid Sequence | Nucleotide Sequence |
|---|---|---|
| VHFW3 (type c) | RFVFSLDTSVSTAYLQISTLKAEDTATYFCAR (SEQ ID NO: 219) | CGGTTTGTCTTCTCCTTGGACACCTCTGTCAGCACGGCATATCTGCAGATCAGCACGCTAAAGGCTGAGGACACTGCTACATATTTCTGTGCAAGA (SEQ ID NO: 220) |
| VHFW4 | WGQGTTVTVSS (SEQ ID NO: 221) | TGGGGCCAGGGCACCACTGTGACTGTGTCCAGC (SEQ ID NO: 222)<br>TGGGGTCAAGGCACTACCGTGACCGTGTCTAGC (SEQ ID NO: 223)<br>TGGGGCCAGGGCACCACCGTGACCGTGTCCTCT (SEQ ID NO: 224)<br>TGGGGCCAGGGCACCACCGTGACCGTGTCCTCC (SEQ ID NO: 225) |
| VLFW1 (type a) | DIQMTQSPSSLSASVGDRVTITC (SEQ ID NO: 226) | GATATTCAGATGACTCAGTCACCTAGTAGCCTGAGCGCTAGTGTGGGCGATAGAGTGACTATCACCTGT (SEQ ID NO: 227)<br>GACATCCAGATGACCCAGTCCCCCTCCAGCCTGTCTGCTTCCGTGGGCGACAGAGTGACCATCACCTGT (SEQ ID NO: 228)<br>GACATCCAGATGACCCAGTCTCCATCCTCCCTGTCTGCATCTGTAGGAGACAGAGTCACCATCACTTGC (SEQ ID NO: 229) |
| VLFW1 (type b) | EIVLTQSPATLPVTLGQPASISC (SEQ ID NO: 230) | GAAATTGTGTTGACACAGTCTCCAGCCACCCTGCCCGTCACCCTTGGACAGCCGGCCTCCATCTCCTGC (SEQ ID NO: 231) |
| VLFW1 (type c) | EIVLTQSPATLSLSPGERATLSC (SEQ ID NO: 232) | GAAATTGTGTTGACACAGTCTCCAGCCACCCTGTCTTTGTCTCCAGGGGAAAGAGCCACCCTCTCCTGC (SEQ ID NO: 233) |
| VLFW1 (type d) | DIVMTQTPLSLPVTPGEPASISC (SEQ ID NO: 234) | GATATTGTGATGACCCAGACTCCACTCTCCCTGCCCGTCACCCCTGGAGAGCCGGCCTCCATCTCCTGC (SEQ ID NO: 235) |
| VLFW1 (type e) | EIVLTQSPDFQSVTPKEKVTITC (SEQ ID NO: 236) | GAAATTGTGCTGACTCAGTCTCCAGACTTTCAGTCTGTGACTCCAAAGGAGAAAGTCACCATCACCTGC (SEQ ID NO: 237) |
| VLFW1 (type f) | AIQLTQSPSSLSASVGDRVTITC (SEQ ID NO: 238) | GCCATCCAGTTGACCCAGTCTCCATCCTCCCTGTCTGCATCTGTAGGAGACAGAGTCACCATCACTTGC (SEQ ID NO: 239) |
| VLFW2 (type a) | WYQQKPGKAPKLLIY (SEQ ID NO: 240) | TGGTATCAGCAGAAGCCCGGTAAAGCCCCTAAGCTGCTGATCTAC (SEQ ID NO: 241)<br>TGGTATCAGCAGAAGCCCGGCAAGGCCCCCAAGCTGCTGATCTAC (SEQ ID NO: 242)<br>TGGTATCAGCAGAAACCAGGGAAAGCTCCTAAGCTCCTGATCTAT (SEQ ID NO: 243) |
| VLFW2 (type b) | WYQQKPGQAPRLLIY (SEQ ID NO: 244) | TGGTACCAGCAGAAACCTGGCCAGGCTCCCAGGCTCCTCATCTAT (SEQ ID NO: 245) |
| VLFW2 (type c) | WYLQKPGQSPQLLIY (SEQ ID NO: 246) | TGGTACCTGCAGAAGCCAGGGCAGTCTCCACAGCTCCTGATCTAT (SEQ ID NO: 247) |
| VLFW2 (type d) | WYLQKPGQSPQLLIY (SEQ ID NO: 248) | TGGTATCTGCAGAAGCCCGGTCAATCACCTCAGCTGCTGATCTAC (SEQ ID NO: 249)<br>TGGTATCTGCAGAAGCCCGGCCAGTCCCCTCAGCTGCTGATCTAC (SEQ ID NO: 250)<br>TGGTACCTGCAGAAGCCAGGGCAGTCTCCACAGCTCCTGATCTAT (SEQ ID NO: 251) |
| VLFW3 (type a) | GVPSRFSGSGSGTDFTFTISSLEAEDAATYYC (SEQ ID NO: 252) | GGCGTGCCCTCCAGATTTTCCGGCTCTGGCTCTGGCACCGACTTTACCTTCACCATCAGCTCCCTGGAAGCCGAGGACGCCGCCACCTACTACTGC (SEQ ID NO: 253)<br>GGGGTCCCCTCGAGGTTCAGTGGCAGTGGATCTGGGACAGATTTCACCTTTACCATCAGTAGCCTGGAAGCTGAAGATGCTGCAACATATTACTGT (SEQ ID NO: 254) |

TABLE 2-continued

Amino acid and nucleotide sequences of the heavy and light chain framework regions for humanized mAbs BAP050-hum01 to BAP050-hum20, BAP050-hum01-Ser to BAP050-hum15-Ser, BAP050-hum18-Ser to BAP050-hum20-Ser, and BAP050-Clone-F to BAP050-Clone-J

| | Amino Acid Sequence | Nucleotide Sequence |
|---|---|---|
| VLFW3 (type b) | GIPPRFSGSGYGTDFTLTINNIESE DAAYYFC (SEQ ID NO: 255) | GGAATCCCCCCTAGGTTTAGCGGTAGCGGCTACGG CACCGACTTCACCCTGACTATTAACAATATCGAGT CAGAGGACGCCGCCTACTACTTCTGT (SEQ ID NO: 256)<br>GGCATCCCCCCTAGATTCTCCGGCTCTGGCTACGG CACCGACTTCACCCTGACCATCAACAACATCGAGT CCGAGGACGCCGCCTACTACTTCTGC (SEQ ID NO: 257)<br>GGGATCCCACCTCGATTCAGTGGCAGCGGGTATGG AACAGATTTTACCCTCACAATTAATAACATAGAAT CTGAGGATGCTGCATATTACTTCTGT (SEQ ID NO: 258) |
| VLFW3 (type c) | GIPDRFSGSGSGTDFTLTISRLEPE DFAVYYC (SEQ ID NO: 259) | GGGATCCCAGACAGGTTCAGTGGCAGTGGGTCTGG GACAGACTTCACTCTCACCATCAGCAGACTGGAGC CTGAAGATTTTGCAGTGTATTACTGT (SEQ ID NO: 260) |
| VLFW3 (type d) | GVPSRFSGSGSGTEFTLTISSLQPD DFATYYC (SEQ ID NO: 261) | GGCGTGCCCTCTAGGTTTAGCGGTAGCGGTAGTGG CACCGAGTTCACCCTGACTATCTCTAGCCTGCAGC CCGACGACTTCGCTACCTACTACTGT (SEQ ID NO: 262)<br>GGCGTGCCCTCCAGATTTTCCGGCTCTGGCTCTGG CACCGAGTTTACCCTGACCATCAGCTCCCTGCAGC CCGACGACTTCGCCACCTACTACTGC (SEQ ID NO: 263)<br>GGGGTCCCATCAAGGTTCAGCGGCAGTGGATCTGG GACAGAATTCACTCTCACCATCAGCAGCCTGCAGC CTGATGATTTTGCAACTTATTACTGT (SEQ ID NO: 264) |
| VLFW3 (type e) | GVPSRFSGSGSGTDFTLTISSLQPE DFATYYC (SEQ ID NO: 265) | GGGGTCCCATCAAGGTTCAGCGGCAGTGGATCTGG GACAGATTTCACTCTCACCATCAGCAGCCTGCAGC CTGAAGATTTTGCAACTTATTACTGT (SEQ ID NO: 266) |
| VLFW3 (type f) | GVPSRFSGSGSGTDFTFTISSLQPE DIATYYC (SEQ ID NO: 267) | GGGGTCCCATCAAGGTTCAGTGGAAGTGGATCTGG GACAGATTTTACTTTCACCATCAGCAGCCTGCAGC CTGAAGATATTGCAACATATTACTGT (SEQ ID NO: 268) |
| VLFW3 (type g) | GIPDRFSGSGSGTDFTLISRLEPE DFAVYYC (SEQ ID NO: 269) | GGGATCCCAGACAGGTTCAGTGGCAGTGGGTCTGG GACAGACTTCACTCTCACCATCAGCAGACTGGAGC CTGAAGATTTTGCAGTGTATTACTGT (SEQ ID NO: 270) |
| VLFW4 | FGQGTKVEIK (SEQ ID NO: 271) | TTCGGTCAAGGCACTAAGGTCGAGATTAAG (SEQ ID NO: 272)<br>TTCGGCCAGGGCACCAAGGTGGAAATCAAG (SEQ ID NO: 273)<br>TTCGGCCAAGGGACCAAGGTGGAAATCAAA (SEQ ID NO: 274) |

TABLE 3

Constant region amino acid sequences of human IgG heavy chains and human kappa light chain HC IgG4 (S228P) mutant constant region amino acid sequence (EU Numbering)
ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGK (SEQ ID NO: 275)

TABLE 3-continued

| Constant region amino acid sequences of human IgG heavy chains and human kappa light chain |
|---|
| LC Human kappa constant region amino acid sequence<br>RTVAAPSVFI FPPSDEQLKS GTASVVCLLN NFYPREAKVQ WKVDNALQSG NSQESVTEQD<br>SKDSTYSLSS TLTLSKADYE KHKVYACEVT HQGLSSPVTK<br>SFNRGEC (SEQ ID NO: 276) |
| HC IgG4 (S228P) mutant constant region amino acid sequence lacking the C-terminal Lysine (K) (EU Numbering)<br>ASTKGPSVFP LAPCSRSTSE STAALGCLVK DYFPEPVTVS WNSGALTSGV HTFPAVLQSS<br>GLYSLSSVVT VPSSSLGTKT YTCNVDHKPS NTKVDKRVES KYGPPCPPCP APEFLGGPSV<br>FLFPPKPKDT LMISRTPEVT CVVVDVSQED PEVQFNWYVD GVEVHNAKTK PREEQFNSTY<br>RVVSVLTVLH QDWLNGKEYK CKVSNKGLPS SIEKTISKAK GQPREPQVYT LPPSQEEMTK<br>NQVSLTCLVK GFYPSDIAVE WESNGQPENN YKTTPPVLDS DGSFFLYSRL TVDKSRWQEG<br>NVFSCSVMHE ALHNHYTQKS LSLSLG (SEQ ID NO: 277) |
| HC IgG1 wild type<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKRVEP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSREE<br>MTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK (SEQ ID NO: 278) |
| HC IgG1 (N297A) mutant constant region amino acid sequence (EU Numbering)<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKRVEP KSCDKTHTCP PCPAPELLGG<br>PSVFLFPPKP KDTLMISRTP EVTCVVVDVS HEDPEVKFNW YVDGVEVHNA KTKPREEQYA<br>STYRVVSVLT VLHQDWLNGK EYKCKVSNKA LPAPIEKTIS KAKGQPREPQ VYTLPPSREE<br>MTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK (SEQ ID NO: 279) |
| HC IgG1 (D265A, P329A) mutant constant region amino acid sequence (EU Numbering)<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKRVEP KSCDKTHTCP PCPAPELLGG<br>PSVFLFPPKP KDTLMISRTP EVTCVVVAVS HEDPEVKFNW YVDGVEVHNA KTKPREEQYN<br>STYRVVSVLT VLHQDWLNGK EYKCKVSNKA LAAPIEKTIS KAKGQPREPQ VYTLPPSREE<br>MTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK (SEQ ID NO: 280) |
| HC IgG1 (L234A, L235A) mutant constant region amino acid sequence (EU Numbering)<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKRVEP KSCDKTHTCP PCPAPEAAGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSREE<br>MTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK (SEQ ID NO: 281) |

TABLE 4

| Amino acid sequences of the heavy and light chain leader sequences for humanized mAbs BAP050-Clone-F to BAP050-Clone-J | | |
|---|---|---|
| BAP050-Clone-F | HC | MEWSWVFLFFLSVTTGVHS (SEQ ID NO: 282) |
| BAP050-Clone-F | LC | MSVPTQVLGLLLLWLTDARC (SEQ ID NO: 283) |
| BAP050-Clone-G | HC | MEWSWVFLFFLSVTTGVHS (SEQ ID NO: 282) |
| BAP050-Clone-G | LC | MSVPTQVLGLLLLWLTDARC (SEQ ID NO: 283) |
| BAP050-Clone-H | HC | MEWSWVFLFFLSVTTGVHS (SEQ ID NO: 282) |
| BAP050-Clone-H | LC | MSVPTQVLGLLLLWLTDARC (SEQ ID NO: 283) |
| BAP050-Clone-I | HC | MAWVWTLPFLMAAAQSVQA (SEQ ID NO: 284)<br>MEWSWVFLFFLSVTTGVHS (SEQ ID NO: 282) |
| BAP050-Clone-I | LC | MSVLTQVLALLLLWLTGTRC (SEQ ID NO: 285)<br>MSVPTQVLGLLLLWLTDARC (SEQ ID NO: 283) |
| BAP050-Clone-J | HC | MAWVWTLPFLMAAAQSVQA (SEQ ID NO: 284)<br>MEWSWVFLFFLSVTTGVHS (SEQ ID NO: 282) |
| BAP050-Clone-J | LC | MSVLTQVLALLLLWLTGTRC (SEQ ID NO: 285)<br>MSVPTQVLGLLLLWLTDARC (SEQ ID NO: 283) |

Table 5. See Examples.
Table 6. See Examples.

TABLE 7

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A1 | Sotrastaurin | 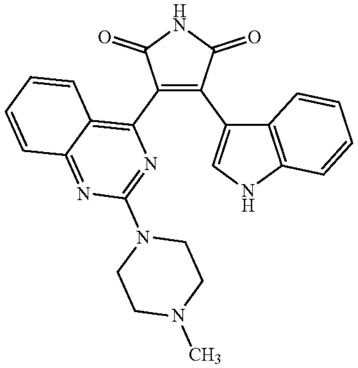 [SMILES: CN1CCN(c2nc(C3=C(c4c[nH]c5ccccc45)C(=O)NC3=O)c3ccccc3n2)CC1] | EP 1682103<br>US 2007/142401<br>WO 2005/039549 |
| A2 | Nilotinib HCl monohydrate TASIGNA ® | 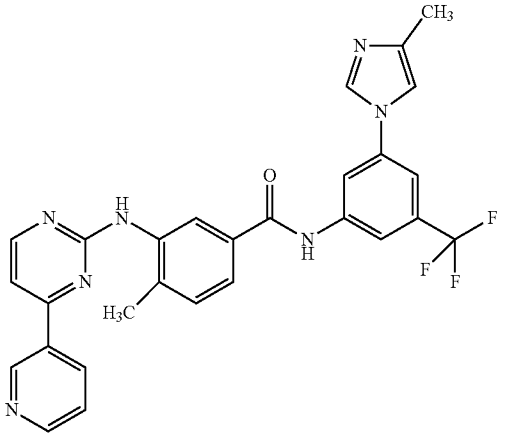<br>HCl • $H_2O$ | WO 2004/005281<br>US 7,169,791 |
| A3 | | 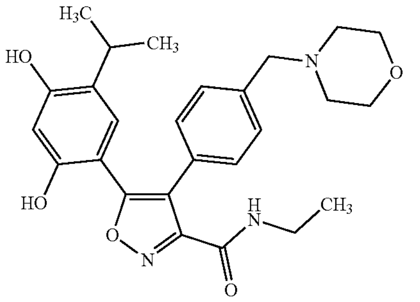 [SMILES: CCNC(=O)c1noc(-c2cc(C(C)C)c(O)cc2O)c1-c1ccc(CN2CCOCC2)cc1] | WO 2010/060937<br>WO 2004/072051<br>EP 1611112<br>US 8,450,310 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A4 | Dactolisib | 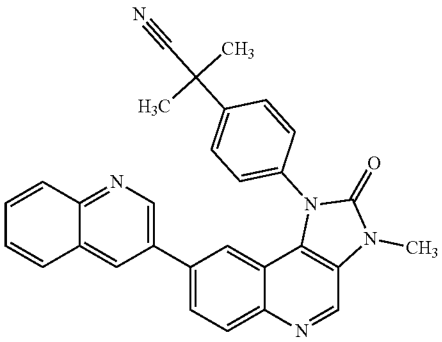 [SMILES: Cn1c(=O)n(-c2ccc(C(C)(C)C#N)cc2)c2c3cc(-c4cnc5ccccc5c4)ccc3ncc21] | WO 2006/122806 |
| A5 | | 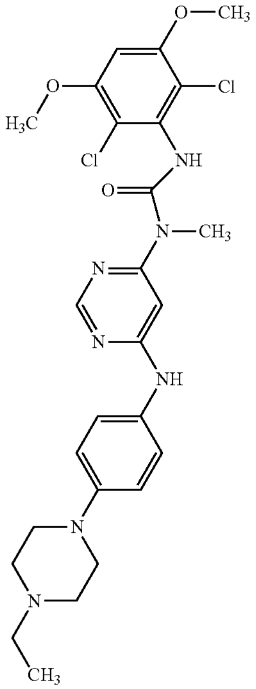 [SMILES: CCN1CCN(c2ccc(Nc3cc(N(C)C(=O)Nc4c(Cl)c(OC)cc(OC)c4Cl)ncn3)cc2)CC1] | US 8,552,002 |
| A6 | Buparlisib | 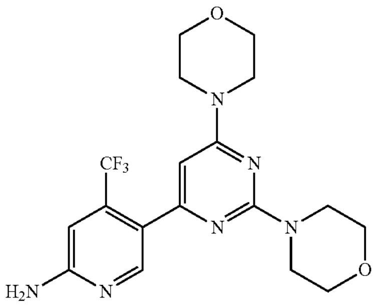 [SMILES: Nc1cc(C(F)(F)F)c(-c2cc(N3CCOCC3)nc(N3CCOCC3)n2)cn1] | WO 2007/084786 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A7 | | 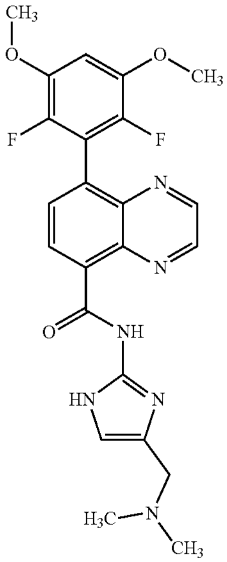 [SMILES: COc1cc(OC)c(F)c(-c2ccc(C(=O)Nc3nc(CN(C)C)c[nH]3)c3nccnc23)c1F] | WO 2009/141386<br>US 2010/0105667 |
| A8 | | 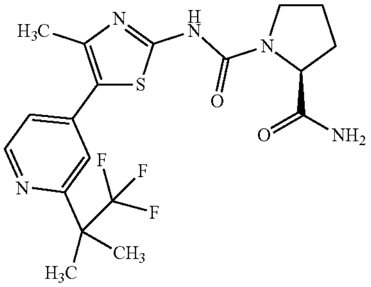 [SMILES: Cc1nc(NC(=O)N2CCC[C@H]2C(N)=O)sc1-c1ccnc(C(C)(C)C(F)(F)F)c1] | WO 2010/029082 |
| A9 | | CYP17 inhibitor | WO 2010/149755<br>US 8,263,635 B2 EP 2445903 B1 |
| A10 | | 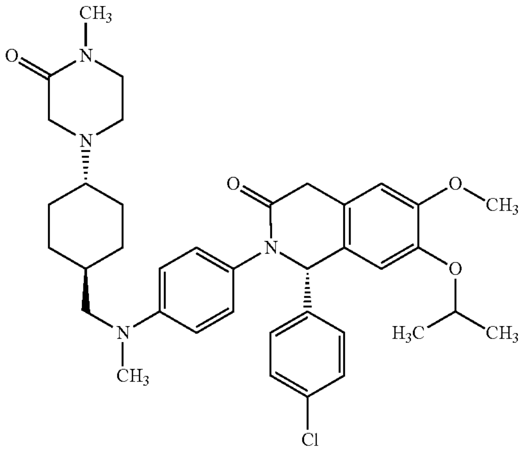 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] | WO 2011/076786 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A11 | Deferasirox EXJADE ® | 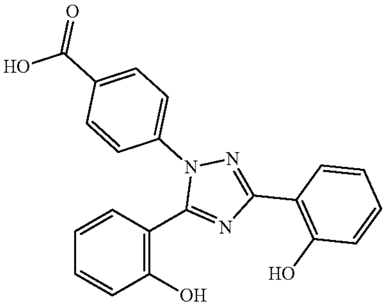 [SMILES: O=C(O)c1ccc(-n2nc(-c3ccccc3O)nc2-c2ccccc2O)cc1] | WO 1997/049395 |
| A12 | Letrozole FEMARA ® | 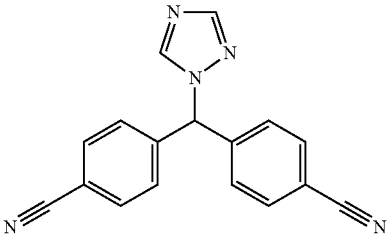 [SMILES: N#Cc1ccc(C(c2ccc(C#N)cc2)n2cncn2)cc1] | US 4,978,672 |
| A13 | | 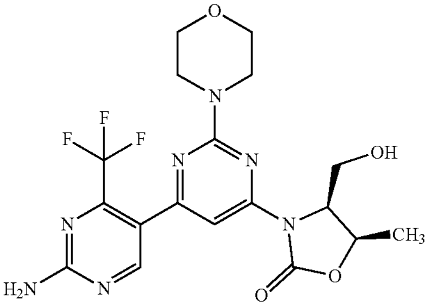 [SMILES: C[C@H]1OC(=O)N(c2cc(-c3cnc(N)nc3C(F)(F)F)nc(N3CCOCC3)n2)[C@H]1CO] | WO 2013/124826 US 2013/0225574 |
| A14 | | 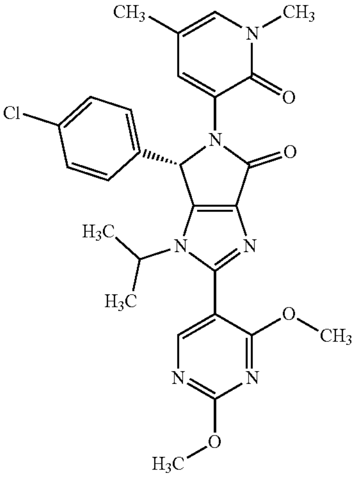 [SMILES: COc1ncc(-c2nc3c(n2C(C)C)[C@H](c2ccc(Cl)cc2)N(c2cc(C)cn(C)c2=O)C3=O)c(OC)n1] | WO 2013/111105 |

TABLE 7-continued

| Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein. | | | |
|---|---|---|---|
| Compound No. | Generic Name Tradename | Compound Structure | Patents/Patent Application Publications |
| A15 | | 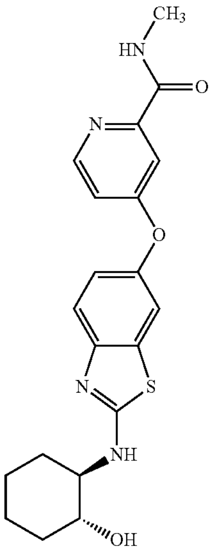 [SMILES: CNC(=O)c1cc(Oc2ccc3nc(N[C@@H]4CCCC[C@H]4O)sc3c2)ccn1] | WO 2005/073224 |
| A16 | Imatinib mesylate GLEEVEC ® | 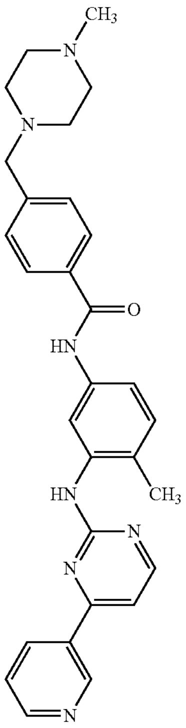 Mesylate | WO 1999/003854 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A17 | | 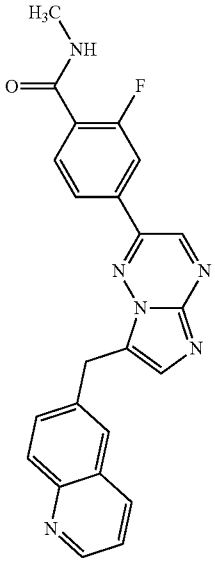 Dihydrochloric salt | EP 2099447<br>US 7,767,675<br>US 8,420,645 |
| A18 | Ruxolitinib Phosphate JAKAFI ® | 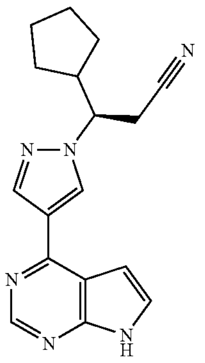 $H_3PO_4$ | WO 2007/070514<br>EP 2474545<br>US 7,598,257<br>WO 2014/018632 |
| A19 | Panobinostat | 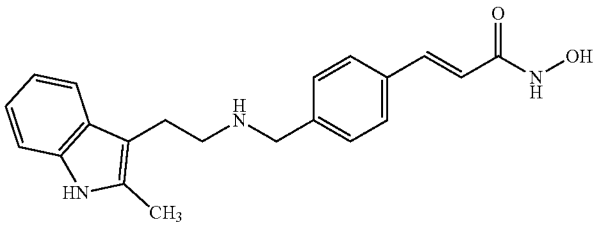 [SMILES: Cc1[nH]c2ccccc2c1CCNCc1ccc(/C=C/C(=O)NO)cc1] | WO 2014/072493<br>WO 2002/022577<br>EP 1870399 |
| A20 | Osilodrostat | 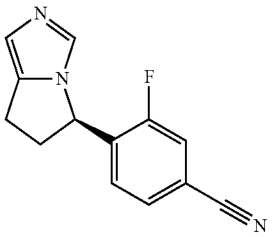 [SMILES: N#Cc1ccc([C@H]2CCc3cncn32)c(F)c1] | WO 2007/024945 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A21 | | 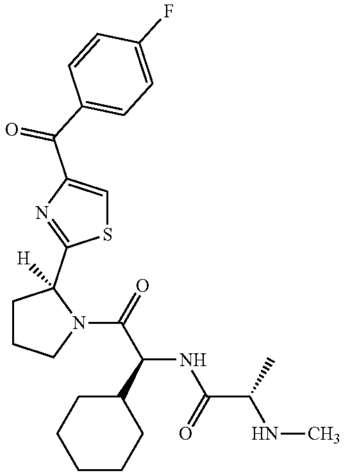 [SMILES: CN[C@@H](C)C(=O)N[C@H](C(=O)N1CCC[C@H]1c1nc(C(=O)c2ccc(F)cc2)cs1)C1CCCCC1] | WO 2008/016893<br>EP 2051990<br>US 8,546,336 |
| A22 | Sonidegib phosphate | 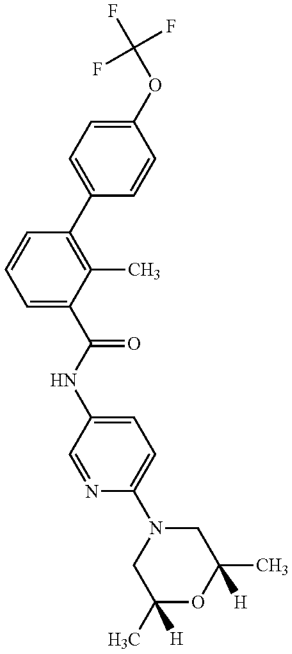 [SMILES: Cc1c(C(=O)Nc2ccc(N3C[C@@H](C)O[C@@H](C)C3)nc2)cccc1-c1ccc(OC(F)(F)F)cc1] | WO 2007/131201<br>EP 2021328<br>US 8,178,563 |
| A23 | ceritinib ZYKADIA ™ | 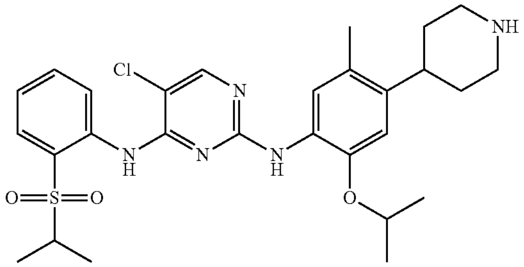 [SMILES: Cc1cc(Nc2ncc(Cl)c(Nc3ccccc3S(=O)(=O)C(C)C)n2)c(OC(C)C)cc1C1CCNCC1] | WO 2008/073687<br>US 8,039,479 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A24 | | 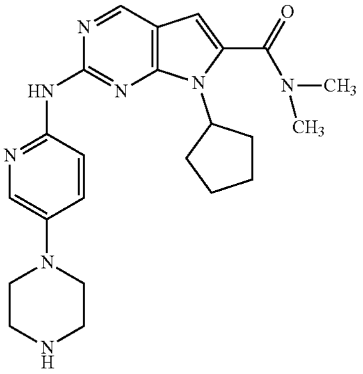 [SMILES: CN(C)C(=O)c1cc2cnc(Nc3ccc(N4CCNCC4)cn3)nc2n1C1CCCC1] | US 8,415,355<br>US 8,685,980 |
| A25 | | 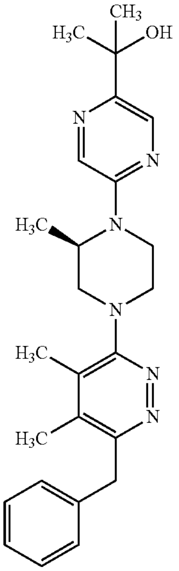 [SMILES: Cc1c(Cc2ccccc2)nnc(N2CCN(c3cnc(C(C)(C)O)cn3)[C@H](C)C2)c1C] | WO 2010/007120 |
| A26 | | Human monoclonal antibody to PRLR | US 7,867,493 |
| A27 | | 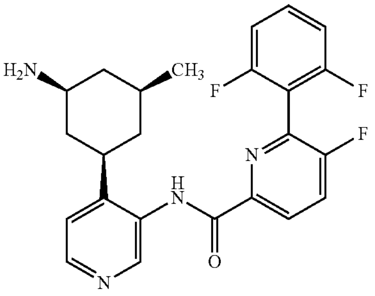 [SMILES: C[C@@H]1C[C@H](N)C[C@H](c2ccncc2NC(=O)c2ccc(F)c(-c3c(F)cccc3F)n2)C1] | WO 2010/026124<br>EP 2344474<br>US 2010/0056576<br>WO 2008/106692 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A28 | | 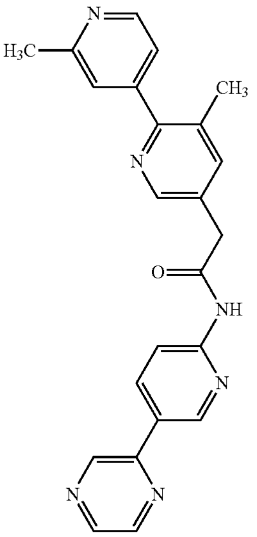 [SMILES: Cc1cc(-c2ncc(CC(=O)Nc3ccc(-c4cnccn4)cn3)cc2C)ccn1] | WO 2010/101849 |
| A29 | Encorafenib | 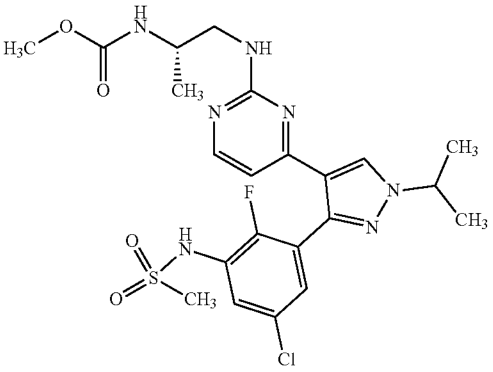 [SMILES: COC(=O)N[C@@H](C)CNc1nccc(-c2cn(C(C)C)nc2-c2cc(Cl)cc(NS(C)(=O)=O)c2F)n1] | WO 2011/025927 |
| A30 | | 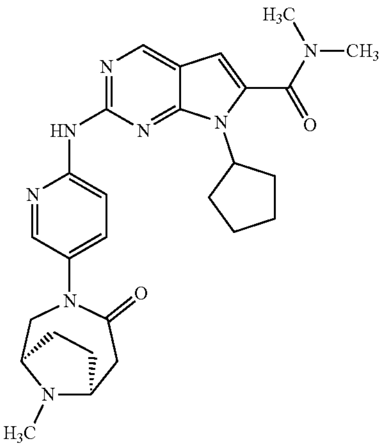 [SMILES: CN(C)C(=O)c1cc2cnc(Nc3ccc(N4C[C@H]5CC[C@@H](CC4=O)N5C)cn3)nc2n1C1CCCC1] | WO 2011/101409 |
| A31 | | Human monoclonal antibody to HER3 | WO 2012/022814<br>EP 2606070<br>US 8,735,551 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A32 | | Antibody Drug Conjugate (ADC) | WO 2014/160160 Ab: 12425 (see Table 1, paragraph [00191]) Linker: SMCC (see paragraph [00117] Payload: DM1 (see paragraph [00111] See also Claim 29 |
| A33 | | Monoclonal antibody or Fab to M-CSF | WO 2004/045532 |
| A34 | Binimetinib | 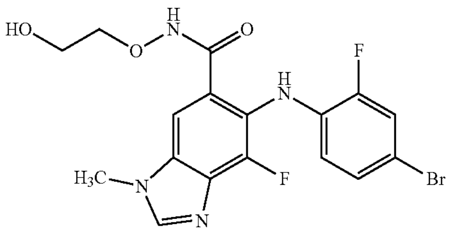 [SMILES: Cn1cnc2c(F)c(Nc3ccc(Br)cc3F)c(C(=O)NOCCO)cc21] | WO 2003/077914 |
| A35 | Midostaurin | 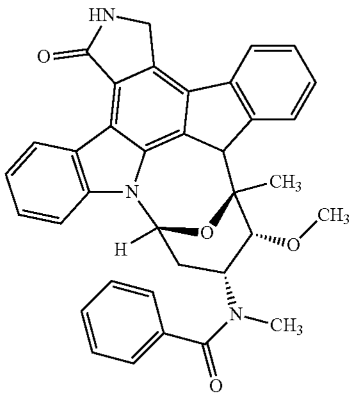 [SMILES: CO[C@@H]1[C@H](N(C)C(=O)c2ccccc2)C[C@H]2O[C@]1(C)C1c3ccccc3-c3c4c(c5c6ccccc6n2c5c31)C(=O)NC4] | WO 2003/037347 EP 1441737 US 2012/252785 |

TABLE 7-continued

| Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein. | | | |
|---|---|---|---|
| Compound No. | Generic Name Tradename | Compound Structure | Patents/Patent Application Publications |
| A36 | Everolimus AFINITOR ® | 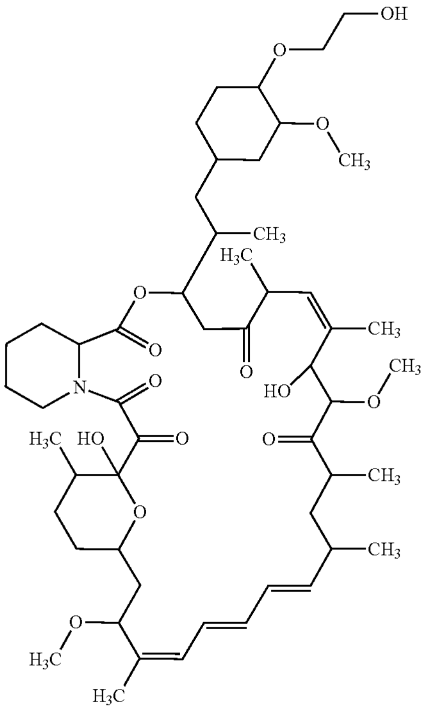 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] | WO 2014/085318 |
| A37 | | 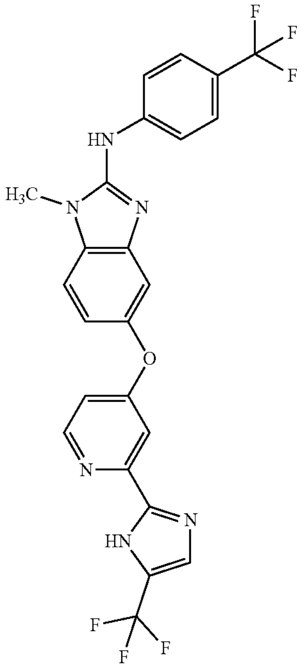 [SMILES: Cn1c(Nc2ccc(C(F)(F)F)cc2)nc2cc(Oc3ccnc(-c4ncc(C(F)(F)F)[nH]4)c3)ccc21] | WO 2007/030377 US 7,482,367 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
| --- | --- | --- | --- |
| A38 | Pasireotide diaspartate SIGNIFOR ® | 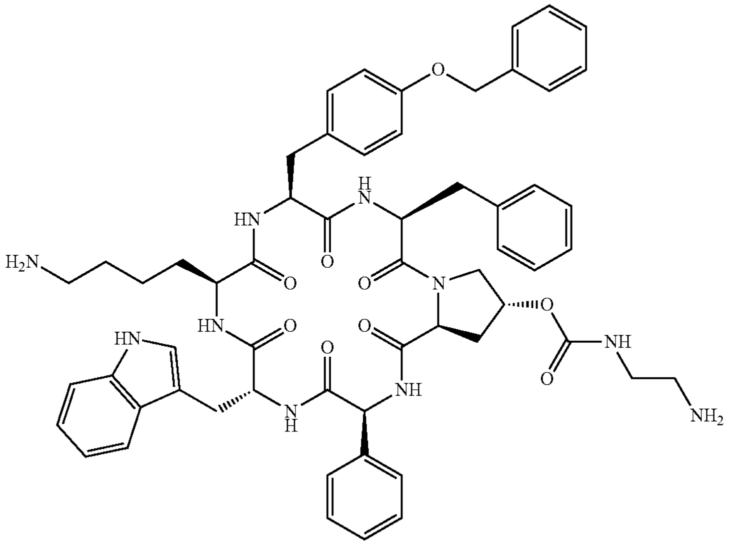 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O] | WO 2002/010192<br>US 7,473,761 |
| A39 | Dovitinib | 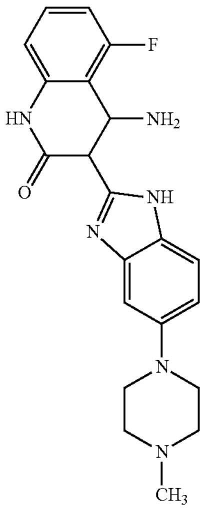 [SMILES: CN1CCN(c2ccc3[nH]c(C4C(=O)Nc5cccc(F)c5C4N)nc3c2)CC1] | WO 2009/115562<br>US 8,563,556 |
| A40 | | 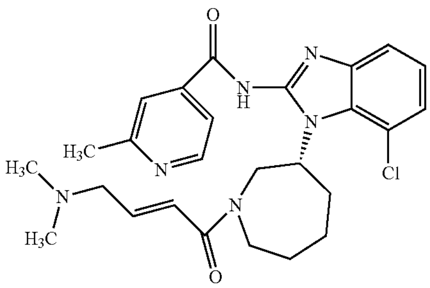 [SMILES: Cc1cc(C(=O)Nc2nc3cccc(Cl)c3n2[C@@H]2CCCCN(C(=O)/C=C/CN(C)C)C2)ccn1] | WO 2013/184757 |

TABLE 7-continued

| Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein. | | | |
|---|---|---|---|
| Compound No. | Generic Name Tradename | Compound Structure | Patents/Patent Application Publications |
| A41 | | 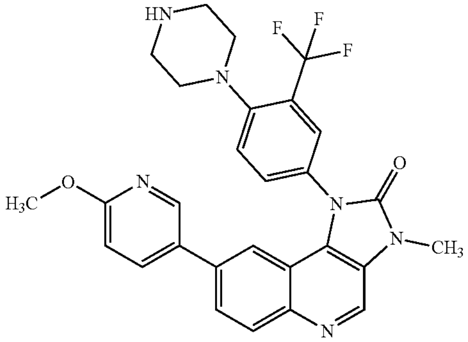 | WO 2006/122806 |
| A42 | | 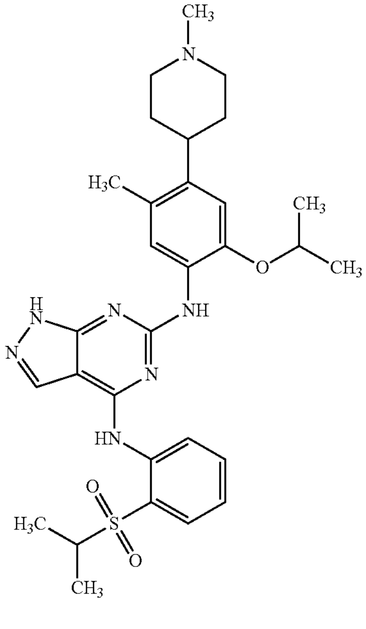 [SMILES: Cc1cc(Nc2nc(Nc3ccccc3S(=O)(=O)C(C)C)c3cn[nH]c3n2)c(OC(C)C)cc1C1CCN(C)CC1] | WO 2008/073687<br>US 8,372,858 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A43 | | 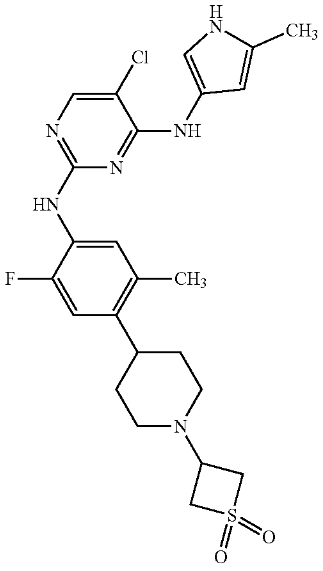 [SMILES: Cc1cc(Nc2nc(Nc3cc(C)c(C4CCN(C5CS(=O)(=O)C5)CC4)cc3F)ncc2Cl)c[nH]1] | WO 2010/002655 US 8,519,129 |
| A44 | | 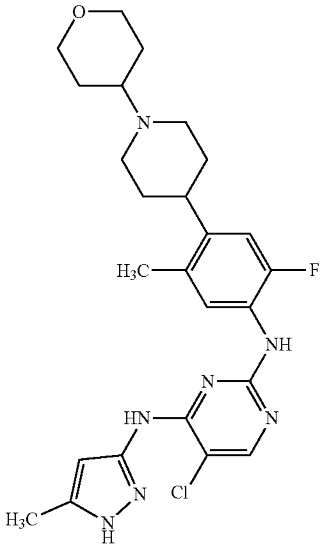 [SMILES: Cc1cc(Nc2nc(Nc3cc(C)c(C4CCN(C5CCOCC5)CC4)cc3F)ncc2Cl)n[nH]1] | WO 2010/002655 US 8,519,129 |

TABLE 7-continued

| Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein. | | | |
|---|---|---|---|
| Compound No. | Generic Name Tradename | Compound Structure | Patents/Patent Application Publications |
| A45 | | 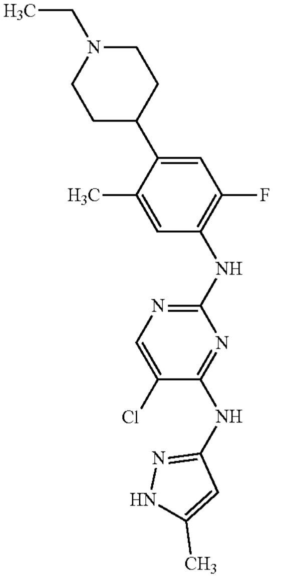 [SMILES: CCN1CCC(c2cc(F)c(Nc3ncc(Cl)c(Nc4cc(C)[nH]n4)n3)cc2C)CC1] | WO 2010/002655 |
| A46 | Valspodar AMDRAY ™ | 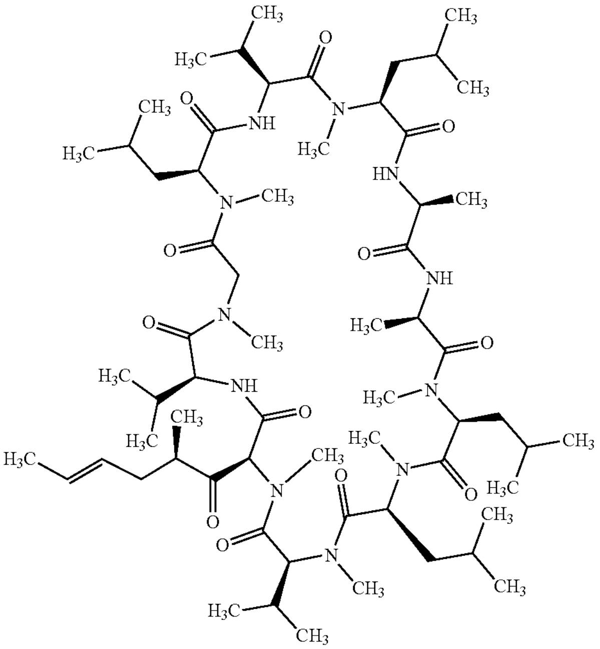 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | EP 296122 |

TABLE 7-continued

Selected therapeutic agents that can be administered in combination with the anti-LAG-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A47 | Vatalanib succinate | 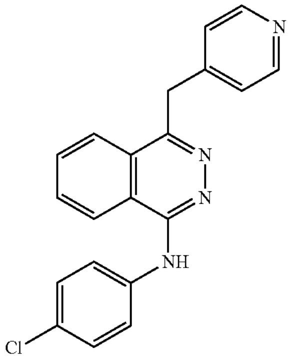 succinate | WO 98/35958 |
| A48 | | IDH inhibitor | WO 2014/141104 |
| A49 | | BCR-ABL inhibitor | WO 2013/171639<br>WO 2013/171640<br>WO 2013/171641<br>WO 2013/171642 |
| A50 | | cRAF inhibitor | WO 2014/151616 |
| A51 | | ERK1/2 ATP competitive inhibitor | WO 2015/066188 |

EXAMPLES

The Examples below are set forth to aid in the understanding of the inventions but are not intended to, and should not be construed to, limit its scope in any way.

Example 1: Humanization of Anti-LAG-3 Antibody, BAP050

A murine anti-LAG-3 monoclonal antibody, BAP050, was humanized. The sequences and test samples of twenty humanized BAP050 clones with unique variable region sequences were obtained. These clones were further analyzed for their biological functions (e.g., antigen binding and ligand blocking), structural features, and transient expression in CHO cells.

Example 1.1: Humanization Technology and Process

Humanization of BAP050 was performed using a combinatorial library of human germ line variable region frameworks (FWs). The technology entails transferring the murine CDRs in frame to a library of human variable regions (VRs) that had been constructed by randomly combining human germ line FW1, FW2 and FW3 sequences. Only one FW4 sequence is used, which is WGQGTTVTVSS (SEQ ID NO: 221) for the heavy chain (HC) (Kabat human HC subgroup I, No. 21) and FGQGTKVEIK (SEQ ID NO: 271) for the light chain (LC) (Kabat human κ subgroup I, No. 5). The library of VR sequences is fused to human constant region (CR) sequences, human IgG4(S228P) of HC and human κ CR of LC, and the resulting library of whole IgG is expressed in CHO cells for screening. Screening was performed with tissue culture supernatants measuring binding avidity on antigen-expressing cells in a whole cell ELISA format or on FACS.

The humanization process was performed in a stepwise manner starting with the construction and expression of the appropriate chimeric mAb (murine VR, IgG4(S228P), human x), which can serve as a comparator for the screening of the humanized clones. The constant region amino acid sequences for human IgG4(S228P) heavy chain and human kappa light chain are shown in Table 6.

Humanization of the VR of LC and HC were performed in two independent steps. The library of humanized LC (huLC) was paired with the chimeric HC (murine VR, IgG4(S228P)) and the resulting "half-humanized" mAbs were screened for binding activity by ELISA. The huLC of clones with adequate binding activity (≥binding of chimeric mAb) were selected. Analogously, the library of humanized HC (huHC) was paired with the chimeric LC (murine VR, human κ) and screened for binding activity by ELISA. The huHC of clones with appropriate binding activity (≥binding of chimeric mAb) were selected.

The variable regions of the selected huLC and huHC were then sequenced to identify the huLC and huHC with unique sequences (some clones from the initial selection process may share the same LC or HC). The unique huLC and huHC were then randomly combined to form a small library of humAbs, which was expressed in CHO cells and screened on antigen-expressing cells in an ELISA and FACS format. Clones with binding activities that were equal or better than the binding of the chimeric comparator mAb are the final product of the humanization process.

Example 1.2: Sequence of Murine mAb BAP050

The LC and HC variable region sequences of the murine anti-LAG-3 mAb were determined. The sequences obtained from two independent analyses were identical and are shown in FIG. 1.

Germline analysis was performed and part of the result is shown in FIG. 2 as an amino acid sequence alignment. For the light chain, the V-gene is 96.88% identical to mIGkV10-94*01F (279/288 nts) and the J-gene is 97.30% identical to mIGkJ1*01F (36/37 nts). For the heavy chain, the V-gene is 96.88% identical to mIGHV9-3-1*01F (279/288 nts), the J-gene is 86.79% identical to mIGHJ4*01F, and the D-gene is mIGHD1-1*01F.

Example 1.3: Humanized Antibody Clones

Figure 3:
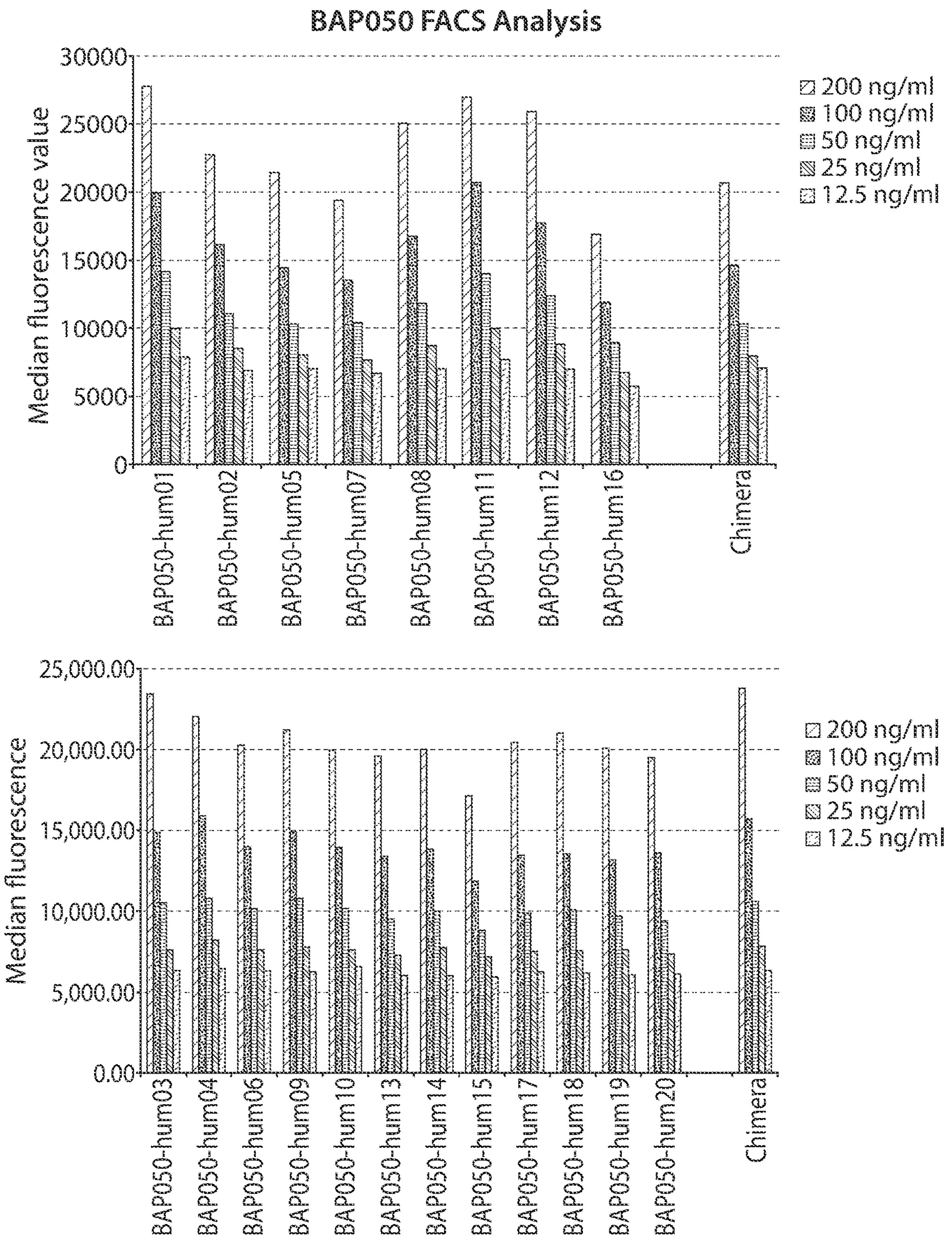
FIG. 3 depicts bar graphs showing the results of FACS binding analysis for the twenty humanized BAP050 clones (BAP050-hum01 to BAP050-hum20) and the chimeric mAb (BAP050-chi). The antibody concentrations are 200, 100, 50, 25 and 12.5 ng/ml from the leftmost bar to the rightmost bar for each tested mAb.

As shown in FIG. 3, the process of humanization yielded twenty humanized clones with binding affinities comparable to that of the chimeric antibody. In addition to binding data, for each clone, the VR sequences were provided along with a sample of the mAb. The samples had been prepared by transient transfections of CHO cells and were concentrated tissue culture supernatants. The mAb concentrations in the solutions had been determined by an IgG4-specific ELISA.

As shown in FIG. 4, the twenty unique clones are combinations of six unique HC and twelve unique LC. The amino acid and nucleotide sequences of the heavy and light chain variable domains for the humanized BAP050 clones are shown in Table 1. The amino acid and nucleotide sequences of the heavy and light chain CDRs of the humanized BAP050 clones are shown in Table 1.

Limited diversity was obtained for the HC FW3 region with eighteen clones having the same FWH3, which is from the human germ line IGHV7-4 and has an exposed Cys residue at position 84 of the humanized clones. Closely related VHFW3 sequences typically have a Ser or Ala residue in this position. Therefore, Cys84 was replaced by Ser in selected humanized clones.

FIG. 4 indicates that the samples varied in the concentration of the mAb, ranging from 3.2 μg/mL to 35.8 μg/mL. These numbers were representative of several transient expression experiments.

Example 1.4: Analysis of the Humanized Clones

Figure 5A:
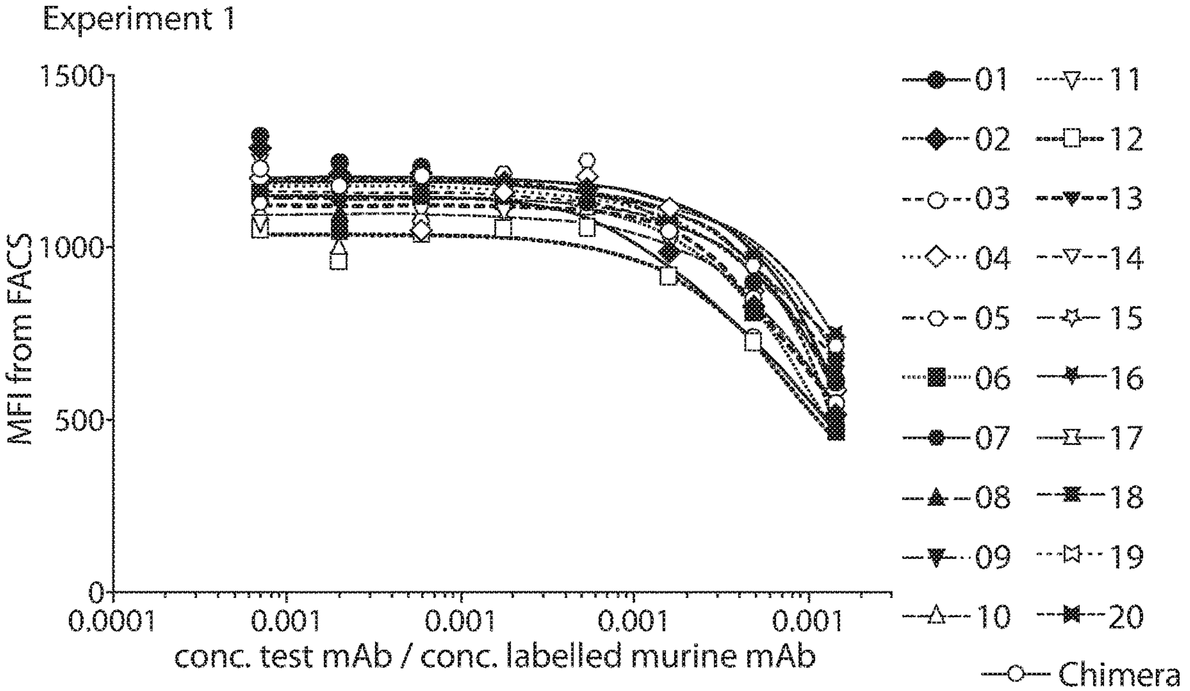
FIG. 5A-5B depicts the binding affinity and specificity of humanized mAbs measured in a competition binding assay using a constant concentration of FITC-labeled murine mAb, serial dilutions of the test antibodies, and LAG-3-expressing CHO cells. Experiment was performed twice, and the results are shown in FIGS. 5A and 5B, respectively.
Figure 5B:
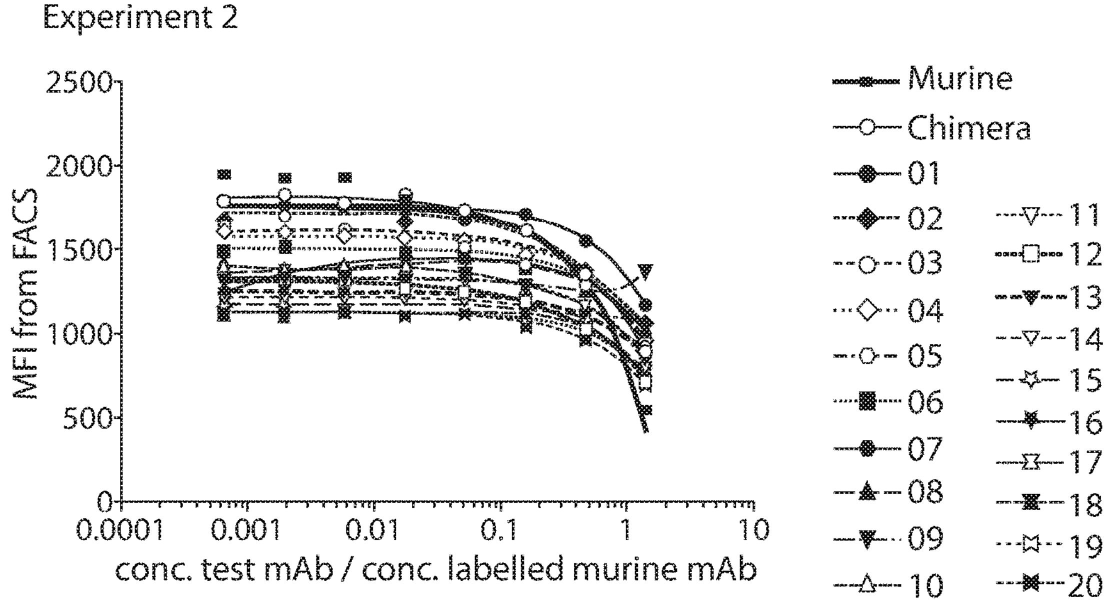

Example 1.4.1: Analysis of Binding Activity and Binding Specificity of Humanized Clones The binding activity and specificity was measured in a competition binding assay using a constant concentration of FITC-labeled murine mAb, serial dilutions of the test mAbs, and LAG-3-expressing CHO cells. Incubations with the mAb mixtures having different concentration ratios of test mAb to labeled mAb was at 4° C. for 30 min. Bound labeled murine mAb was then quantified using a FACS machine. The experiment was performed twice. The results are shown in FIGS. 5A-5B.

Within the accuracy of the experiment, all humanized clones show similar activity for competing with binding of labeled murine mAb. The activity is also comparable to the activity of the parent murine mAb and chimeric mAb. MAbs were ranked relative to each other. For example, it can be a weaker competitor if in both experiments the curve of a certain clone is to the right of the chimeric mAb curve or it can be a better competitor if the curve of a certain clone is to the left of the chimeric mAb curve. Such a ranking system was used in FIG. 6.

Example 1.4.2: Sequence Analysis of Humanized Clones

Based on structural features, the twenty humanized mAbs were divided into six groups and ranked them from A to F. The results are shown in FIG. 6.

Example 1.4.3: Selection of Humanized Clones and Generation of New Versions with the C84S Mutation FIG. 6 summarizes the data which was considered for the selection of humanized clones. Expression data ($2^{nd}$ column), the diversity in the composition of the variable regions ($3^{rd}$ column), relative rankings in binding studies ($4^{th}$ and $5^{th}$ columns), and structural analysis ($6^{th}$ column), were considered. Certain characteristics that lead to the selection of individual clones are marked with grey fields.

Certain clones were mutated at position 84 of VHFW3 from Cys to Ser (see Example 1.3 above). The new versions are called clones Nos. 1S, 2S, 5S, 9S, 11S, 12S, and 13S, and together huBAP050(Ser) clones.

Figure 7:
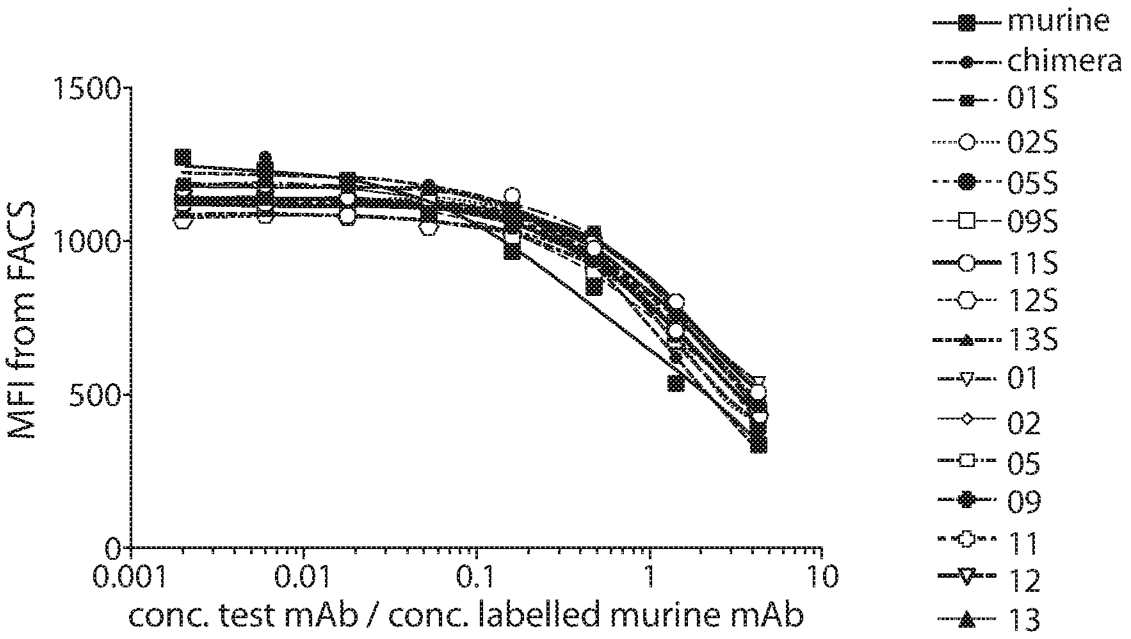
FIG. 7 depicts the binding affinity and specificity of huBAP050(Ser) clones measured in a competition binding assay using a constant concentration of FITC-labeled murine mAb, serial dilutions of the test antibodies, and LAG-3-expressing CHO cells. HuBAP050(Ser) clones, such as, BAP050-hum01-Ser, BAP050-hum02-Ser, BAP050-hum05-Ser, BAP050-hum09-Ser, BAP050-hum11-Ser, BAP050-hum12-Ser, and BAP050-hum13-Ser, were evaluated. Murine mAb BAP050, chimeric mAb BAP050-chi, and humanized BAP050-hum01, BAP050-hum02, BAP050-hum05, BAP050-hum09, BAP050-hum11, BAP050-hum12, and BAP050-hum13 were also included in the analyses.

Example 1.4.4: Analysis of Binding Activity and Binding Specificity of huBAP050(Ser) Clones The new versions of the selected clones with the C84S mutation in VHFW3 were subject to an analogous competition binding assay as described under Example 1.4.1. The experiment included the original humanized clones with the Cys84 residue, the new humanized clones with the Ser84 residue, chimeric mAb and the parent murine mAb. The results are shown in FIG. 7.

All tested variants were comparable to the murine parent mAb in blocking the binding of labeled murine mAb to LAG-3-expressing CHO cells. It follows that the behavior of the new humanized clones with the Ser84 residue was not different from the behavior of the original humanized clones with the Cys84 residue.

Example 1.4.5: Blocking of Binding of LAG-3-Ig to MHC Class II on Daudi Cells

Figure 8:
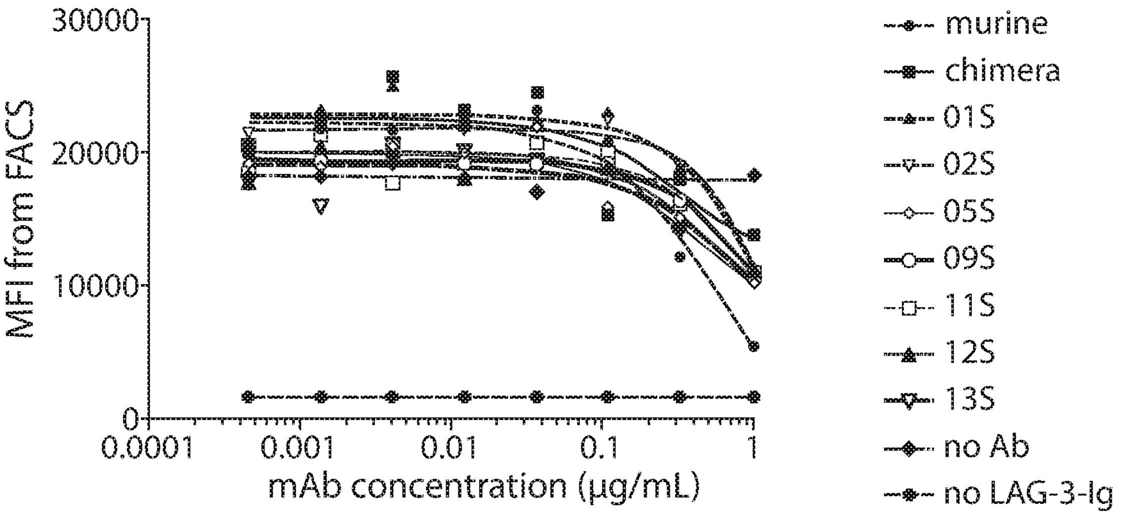
FIG. 8 depicts blocking of binding of LAG-3-Ig to Daudi cells by huBAP050(Ser) clones. HuBAP050(Ser) clones, such as, BAP050-hum01-Ser, BAP050-hum02-Ser, BAP050-hum05-Ser, BAP050-hum09-Ser, BAP050-hum11-Ser, BAP050-hum12-Ser, and BAP050-hum13-Ser, were evaluated. Murine mAb BAP050 and chimeric mAb BAP050-chi were also included in the analyses.

LAG-3 binds to MHC class II, therefore the selected huBAP050(Ser) clones were tested for their ability to block the binding of soluble LAG-3-Ig to Daudi cells (a Burkitt's lymphoma cell line) that express MHC class II. The blocking capacity of the mAbs was evaluated in a competition binding assay using a constant concentration of LAG-3-huIgG1 Fc fusion protein (2 μg/mL), serial dilutions of the mAbs to be tested, and Daudi cells. Incubation was at 4° C. for 30 min. Bound ligand fusion protein was detected with PE-conjugated F(ab')2 fragment of goat anti-human IgG which doesn't recognize IgG4 mAbs (Southern Biotech 2043-09), and flow cytometry. The results are shown in FIG. 8.

Within the accuracy of the experiments, the seven huBAP050(Ser) clones, chimeric mAb and murine parent mAb demonstrated comparable blocking activity for LAG-3-Ig.

Example 1.4.6: T Cell Epitope Analysis

Humanized mAbs were analyzed for T cell epitopes using Epibase™. The algorithm analyzes each possible peptide (each 10-mer along the protein advancing by one amino acid) for binding to HLA class II. It estimates free energy of binding ($\Delta G_{bind}$) for each peptide and calculates a putative $K_D$ ($\Delta G_{bind}$=RT $\ln K_D$). Then peptides are labeled S, M, or N for strong, medium, and non-binders. Threshold values used for this classification are different for each allotype.

The data was normalized to a risk score. The overall "risk score" is the sum of all potential epitopes to all tested alleles, weighted by the affinities of the respective peptides but leaving out all potential epitopes in germ line sequences (lower value therefor is "better") There are roughly three categories of mAbs, derived from a large set of mAbs of different composition as described below.

Risk score of around 500: fully human mAbs generated from humans, "humanized" mice, and phage libraries ("values below 500 are really good even for fully human antibodies"). Humanized mAbs specifically engineered (even the CDRs) to have a low score are typically in the 500-700 risk category.

Risk score around 900: typical CDR-grafted antibodies, which have fully murine CDRs with or without changes in the FW region ("Gary Queen technology"); approved CDR-grafted mAbs are basically all in this category.

Risk score around 1500: chimeric mAbs.

The results for selected humanized BAP050 mAbs are:

| Clone No. | Risk score |
|---|---|
| 01 | 999 |
| 02 | 1006 |
| 05 | 967 |
| 09 | 998 |
| 11 | 1042 |
| 12 | 1042 |
| 13 | 950 |

The risk scores of the seven selected humanized clones are in the typical CDR-grafted mAb category. For example, the human mAb, adalimumab (Humira®), has a score of 654, which is relatively high for human mAbs (at the upper end of the Gaussian curve) but low in comparison to a typical CDR-grafted mAb.

The scores come from the murine CDRs, specifically the Y residues. These are acceptable scores for antibodies for cancer treatment. Changing the score would mean engineering the murine CDRs, specifically removing Y residues.

Summary and Conclusions

Murine anti-LAG-3 monoclonal antibody, BAP050, was humanized. The technology entails the cloning of the murine CDRs in-frame into an ordered library of human germ line variable region frameworks, expressing the library of cloned variable regions as intact IgG4(S228P) humanized mAbs in CHO cells, and selecting clones that bind with comparable or higher affinity to the target as the parent mAb. Therefore, the murine CDRs were asked to select the best human germ line framework sequences that preserve their conformations and thus the binding affinity and specificity of the parent murine mAb. The sequences and test samples of twenty humanized versions with unique variable region sequences were obtained, which had also passed a binding test with LAG-3-transfected CHO cells. Eighteen clones contained the same HC FW3 germ line sequence, which has a rare Cys at position 84. In seven selected clones, Cys was replaced by Ser creating new mAbs labeled huBAP050(Ser) clones.

These clones were further analyzed for their biological functions (e.g., antigen binding and ligand blocking), structural features, and transcient expression in CHO cells.

Example 2: Expression of Humanized Anti-LAG-3 Antibody, BAP050

Five humanized clones described in Example 1 were selected for evaluation of expression in Chinese Hamster Ovary (CHO) cells.

Single gene vectors (SGVs) were constructed using Lonza's GS Xceed vectors (IgG4proΔk for heavy chain and Kappa for light chain). The SGVs were amplified and transiently co-transfected into CHOK1SV GS-KO cells for expression at a volume of 2.8 L.

Expression cultures were harvested Day 6 post-transfection and clarified by centrifugation and sterile filtration. The clarified cell culture supernatant was purified using one-step Protein A chromatography. Product quality analysis in the form of SE-HPLC, SDS-PAGE, IEF, and LAL was carried out using purified material at a concentration of 1 mg/ml including an antibody as a control sample.

Example 2.1: Vector Construction

The sequences of the light and heavy chain variable domain encoding regions were synthesised by GeneArt AG. Light chain variable domain encoding regions were sub-cloned into pXC-Kappa and heavy chain variable domain encoding regions into pXC-IgG4pro AK vectors respectively using the N-terminal restriction site Hind III and the C-terminal restriction sites BsiWI (light chain) and ApaI (heavy chain). Positive clones were screened by PCR amplification (primers 1053: GCTGACAGACTAACAGACTGTTCC (SEQ ID NO: 288) and 1072: CAAATGTGGTATGGCTGA (SEQ ID NO: 289)) and verified by restriction digest (using a double digest of EcoRI-HF and HindIII-HF) and nucleotide sequencing of the gene of interest.

Example 2.2: DNA Amplification

A single bacterial colony was picked into 15 ml Luria Bertani (LB) medium (LB Broth, Sigma-Aldrich, L7275) containing 50 μg/ml ampicillin and incubated at 37° C. overnight with shaking at 220 rpm. The resulting starter culture was used to inoculate 1 L Luria Bertani (LB) medium containing 50 μg/ml ampicillin and incubated at 37° C. overnight with shaking at 220 rpm. Vector DNA was isolated using the QIAGEN Plasmid Plus Gigaprep system (QIAGEN, 12991). In all instances, DNA concentration was measured using a Nanodrop 1000 spectrophotometer (Thermo-Scientific) and adjusted to 1 mg/ml with EB buffer (10 mM Tris-Cl, pH 8.5). DNA quality for the single gene vectors was assessed by measuring the absorbance ratio A260/A280. This was found to be between 1.88 and 1.90.

Example 2.3: Culture of CHOKISV GS-KO Cells

CHOK1SV GS-KO cells were cultured in CD-CHO media (Invitrogen, 10743-029) supplemented with 6 mM glutamine (Invitrogen, 25030-123). Cells were incubated in a shaking incubator at 36.5° C., 5% $CO_2$, 85% humidity, 140 rpm. Cells were routinely sub-cultured every 3-4 days, seeding at $2\times10^5$ cells/ml and were propagated in order to have sufficient cells available for transfection. Cells were discarded by passage 20.

Example 2.4: Transient Transfections of CHOKISV GS-KO Cells

Transient transfections were performed using CHOK1SV GS-KO cells which had been in culture a minimum two weeks. Cells were sub-cultured 24 h prior to transfection and cell viability was >99% at the time of transfection.

All transfections were carried out via electroporation using a Gene Pulse MXCell (Bio-Rad), a plate based system for electroporation. For each transfection, viable cells were resuspended in pre-warmed media to $2.86 \times 10^7$ cells/ml. 80 µg DNA (1:1 ratio of heavy and light chain SGVs) and 700 µl cell suspension were aliquotted into each cuvette/well. Cells were electroporated at 300 V, 1300 µF. Transfected cells were transferred to pre-warmed media in Erlenmeyer flasks and the cuvette/wells rinsed twice with pre-warmed media which was also transferred to the flasks. Transfected cell cultures were incubated in a shaking incubator at 36.5° C., 5% $CO_2$, 85% humidity, 140 rpm for 6 days. Cell viability and viable cell concentrations were measured at the time of harvest using a Cedex HiRes automated cell counter (Roche).

Example 2.5: Protein A Affinity Chromatography

Cell culture supernatant was harvested and clarified by centrifugation at 2000 rpm for 10 min, then filtered through a 0.22 µm PES membrane filter. Clarified supernatant was purified using a pre-packed 5 ml HiTrap MabSelect SuRE column (GE Healthcare, 11-0034-94) on an AKTA purifier (10 ml/min). The column was equilibrated with 50 mM sodium phosphate, 125 mM sodium chloride, pH 7.0 (equilibration buffer) for 5 column volumes (CVs). After sample loading, the column was washed with 2 CVs of equilibration buffer followed by 3 CVs of 50 mM sodium phosphate, 1 M sodium chloride pH 7.0 and a repeat wash of 2 CVs of equilibration buffer. The Product was then eluted with 10 mM sodium formate, pH 3.5 over 5 CVs. Protein containing, eluted fractions were immediately pH adjusted to pH 7.2 and filtered through a 0.2 µm filter.

A single protein-containing peak was observed during the elution phase. This peak was shown to contain the mAb, when analyzed by SE-HPLC and SDS-PAGE. Recovered protein yield is shown in Table 5. The clones expressed transiently in a range from 21.9 to 29.4 mg/L.

TABLE 5

Summary of yield, titre, monomer content and endotoxin levels

| Product | Yield* (mg) | Titre* (mg/L) | Monomer Content (%) | Endotoxin levels (EU/mg) |
|---|---|---|---|---|
| Clone F | 79.1 | 28.25 | 95.63 | 0.22 |
| Clone G | 61.3 | 21.88 | 95.31 | 0.15 |
| Clone H | 76.0 | 27.13 | 97.07 | 0.20 |
| Clone I | 82.3 | 29.38 | 97.82 | 0.05 |
| Clone J | 64.0 | 24.63‡ | 96.97 | 0.27 |

*Post Protein A purification;
‡from a 2.6 L expression culture

Example 2.6: SE-HPLC Analysis

Samples of Protein A purified antibodies were analyzed in duplicate by SE-HPLC on an Agilent 1200 series HPLC system, using a Zorbax GF-250 4 µm 9.4 mm ID×250 mm column (Agilent). Aliquots of sample at a concentration of 1 mg/ml were filtered through a 0.2 µm filter prior to injection. 80 µl aliquots were injected respectively and run at 1 ml/min for 15 minutes. Soluble aggregate levels were analysed using Chemstation (Agilent) software.

Chromatography profiles with retention time showing the percentage of the overall detected peak areas were obtained for the tested antibodies and a control IgG4 antibody. The products show a single protein peak at approximately 8.59 to 8.61 min comparable to the human IgG4 antibody control (about 8.64 min) and consistent with a monomeric antibody. Small amounts (up to about 3-4%) of higher molecular weight impurities, consistent with soluble aggregates, were detected at retention times around 7.90 min.

Example 2.7: SDS-PAGE Analysis

Reduced samples were prepared for analysis by mixing with NuPage 4× LDS sample buffer (Invitrogen, NP0007) and NuPage 10× sample reducing agent (Invitrogen, NP0009), and incubated at 70° C., 10 min. For non-reduced samples, the reducing agent and heat incubation were omitted. Samples were electrophoresed on 1.5 mm NuPage 4-12% Bis-Tris Novex pre-cast gels (Invitrogen, NP0335PK2) with NuPage MES SDS running buffer under denaturing conditions. 10 µl aliquots of SeeBlue Plus 2 pre-stained molecular weight standard (Invitrogen, LC5925) and a control IgG4 antibody at 1 mg/ml were included on the gel. 1 µl of each sample at 1 mg/ml were loaded onto the gel. Once electrophoresed, gels were stained with InstantBlue (TripleRed, ISBO1L) for 30 min at room temperature. Images of the stained gels were analysed on a BioSpectrum Imaging System (UVP).

The analysis confirmed the presence of the antibody products and good levels of purity. Under non-reducing conditions, a predominant protein band close to 98 kDa was observed comparable with the control IgG4 antibody. The control IgG4 antibody and one tested clone display an additional fainter band corresponding to a heavy plus light chain half-antibody at approximately 70 kDa under non-reducing conditions. This is expected for the control antibody. Two bands were observed under reducing conditions consistent with the size of heavy (close to the position of the 49 kDa marker) and light chains (close to the position of the 28 kDa marker) and comparable with the bands found for the control IgG4 antibody.

Example 2.8: Iso-electric Focussing (IEF) Analysis

Non-reduced samples of Protein A purified antibody were electrophoresed as described below.

5 µg of Protein A purified samples were electrophoresed on a 1.0 mm Novex pH 3-10 gradient gel (Invitrogen, EC66552BOX) using manufacturers recommended running conditions. A 10 µl aliquot of IEF pH 3-10 markers (Invitrogen, 39212-01) was included on the gel. Once electrophoresed, gels were fixed with 10% TCA solution for 30 min and then stained with InstantBlue (TripleRed, ISBO1L) over night at room temperature. Images of the stained gels were analysed on a BioSpectrum Imaging System (UVP).

As shown in Table 6, the tested clones display charge isoforms between pH 6.0 and 7.45. The detected charge isoforms are comparable to the theorectically calculated pIs for these antibodies which were predicted to be between 6.35 and 6.82. Clones F and G both have a predicted pI of 6.35 and show comparable charge isoforms, which is also consistent with the theorectically calculated pI being the same for both (6.35). The control IgG4 antibody behaved as expected.

TABLE 6

| Charge isoforms as detected by Novex IEF analysis | | | |
|---|---|---|---|
| Product | pI of predominant charge isoform* | Acidic charge isoforms* | Basic charge isoforms* |
| Clone F | 6.2 | 2x; 6.0 to 6.1 | 6.3 |
| Clone G | 6.2 | 2x; 6.0 to 6.1 | 6.3 |
| Clone H | 7.4 | 2x; 6.9 to 7.3 | 7.45 |
| Clone I | 7.0 | 2x; 6.7 to 6.9 | 7.3 |
| Clone J | 6.5 | 2x; 6.0 to 6.4 | 6.8 |

*pI readings are estimated from the staining positions correlated against the IEF 3-10 marker.

Example 2.9: Endotoxin Analysis

Endotoxin levels of purified proteins were measured at final concentrations (up to 3.44 mg/ml) using an Endosafe-PTS instrument, a cartridge based method based on the LAL assay (Charles River).

As shown in Table 8, the endotoxin content was found to range from 0.05 to 0.27 EU/mg.

Conclusion

GS single gene expression vectors for selected humanized anti-LAG-3 mAbs were constructed and used to transiently transfect CHOK1SV GS-KO cells. 2.6 to 2.8 litres of expression culture were incubated under standard conditions for 6 days and the resulting cell culture supernatant purified using Protein A chromatography. Post-purification titres are indicated in Table 8 and were found to be ranging from 21.88 to 29.38 mg/L. The recovered yields range from 61.3 to 82.3 mg.

SDS-PAGE and SE-HPLC analysis indicated the presence of a small amount (up to 4.69%) of soluble aggregates present in the products being predominantly consistent with dimeric antibody for the mAb. The mAbs also showed higher molecular weight impurities at retention times consistent with that of trimeric antibodies.

Iso-electric focusing detected a number of charge isoforms for all mAbs. The mAbs showed isoforms generally more basic when based on theoretically calculated pI for these molecules indicating some level of post translation modification. The mAbs were found to be comparable to their theoretically calculated pI values.

The endotoxin levels for all samples were measured prior to provision of samples and found to be below 0.63 EU/mg.

Example 3: Characterization of Murine and Humanized Anti-LAG-3 Antibodies

Example 3.1: Characterization of Murine Anti-LAG-3 Antibody

The binding affinity of murine anti-LAG-3 antibody BAP050 to LAG-3 was investigated. As shown by FACS analyses, the murine anti-LAG-3 antibody binds to human LAG-3 transfected CHO cells with a $K_D$ of 0.2 nM, to human T cells with a $K_D$ of 0.26 nM, and to human LAG-3 transfected 300.19 cells with a $K_D$ of 13.6 nM.

The blocking activity of murine anti-LAG-3 antibody BAP050 was examined by competition binding assays. The murine anti-LAG-3 antibody blocked LAG-3-Ig binding to MHC class II molecules on Raji cells with an IC50 of 2.3 nM.

The effect of murine anti-LAG-3 antibody BAP050 on interferon gamma (IFN-γ) expression was tested. The murine anti-LAG-3 antibody resulted in 3.0±2.1 fold increase in IFN-γ expression on cells stimulated with anti-CD3 (0.1 μg/mL), 1.6±0.4 fold increase on cells stimulated with Staphylococcal enterotoxin B (SEB) (3 μg/mL), and 1.4±0.3 fold increase on cells stimulated with CMV peptides.

The regions in LAG-3 that may bind murine anti-LAG-3 antibody BAP050 were examined. As shown by ELISA, the murine anti-LAG-3 antibody binds a LAG-3 Ig fusion protein (sLAG-3 D1-D4Ig) that contains all four extracellular Ig-like domains (D1-D4), as well as a LAG-3 Ig fusion protein (sLAG-3 D1-D2Ig) that only contains Domain 1 (D1) to Domain 2 (D2). Further analysis shows that the anti-LAG-3 antibody binds CHO cells that express full length LAG-3, LAG-3 with D2 deletion (CHO-LAG-3ΔD2), and LAG-3 with partial deletion of D1 extra loop (CHO-LAG-3AP48A60). Thus, the anti-LAG-3 antibody binds D1 of LAG-3.

The murine anti-LAG-3 antibody BAP050 was also found to increase IFN-γ secretion in CD3-stimulated PBMCs compared to mouse IgG1 control and no antibody control. The fold of increase ranges from 1.4 to 2.9-fold among four donors.

Example 3.2: Characterization of Humanized Anti-LAG-3 Antibody

Binding Affinity and Specificity

The binding of an exemplary humanized anti-LAG-3 antibody on human LAG-3 protein was measured using Biacore method. The results are: Ka=$6.41\times10^5$ $M^{-1}$ $s^{-1}$; Kd=$7.00\times10^{-5}$ $s^{-1}$; $K_D$=0.109±0.008 nM. The anti-LAG-3 antibody also binds cynomolgus LAG-3 as measured by Biacore method.

The binding of the same humanized anti-LAG-3 antibody on human LAG-3-expressing CHO cells and cynomologous monkey LAG-3 expressing HEK 209 cells. was measured using FACS analysis. The result shows that the anti-LAG-3 antibody (human IgG4) binds with high affinity to human LAG-3 compared to a human IgG4 isotype control. The anti-LAG-3 antibody binds human LAG-3-expressing cells with a $K_D$ of 1.92 nM and binds cynomologous monkey LAG-3-expressing cells with a $K_D$ of 2.3 nM.

The binding of the anti-LAG-3 antibody on rhesus LAG-3-expressing 300.19 cells was also measured. The results show that the anti-LAG-3 antibody binds rhesus LAG-3 with a $K_D$ of 8.03 nM.

Additional binding analyses show that the exemplary humanized anti-LAG-3 antibody is not cross-reactive with mouse LAG-3 or cross-reactive with parental cell line.

Blocking of Interactions Between LAG-3 and its Ligands

The ability of the exemplary humanized anti-LAG-3 antibody to block the interactions between LAG-3 and both of its known ligand, MHC class II molecules, was examined. The results show that the anti-LAG-3 antibody blocked the interaction between LAG-3 and MHC class II molecules on Daudi cells with an IC50 of 5.5 nM, compared to a human IgG4 isotype control.

LAG-3 Stimulation of Cytokine Release In Vitro in the Absence of T Cell Receptor Engagement Anti-LAG-3 antibody is not expected to stimulate detectable cytokine responses without specific stimulation by the T cell receptor. Anti-LAG-3 antibody was immobilized and highly crosslinked by air-drying on a tissue culture plate and tested for its ability to stimulate cytokine production using a method derived from Stebbings R., et al. (J Immunol. 2007 179(5):3325-3331). No IL-2 or IFN-γ production was induced by anti-LAG-3 antibody or control IgG in the absence of staphylococcal enterotoxin B (SEB) stimulation of whole blood.

Example 4: Patient Selection Based on PD-L1/CD8/IFN-γ Status

Figure 11:
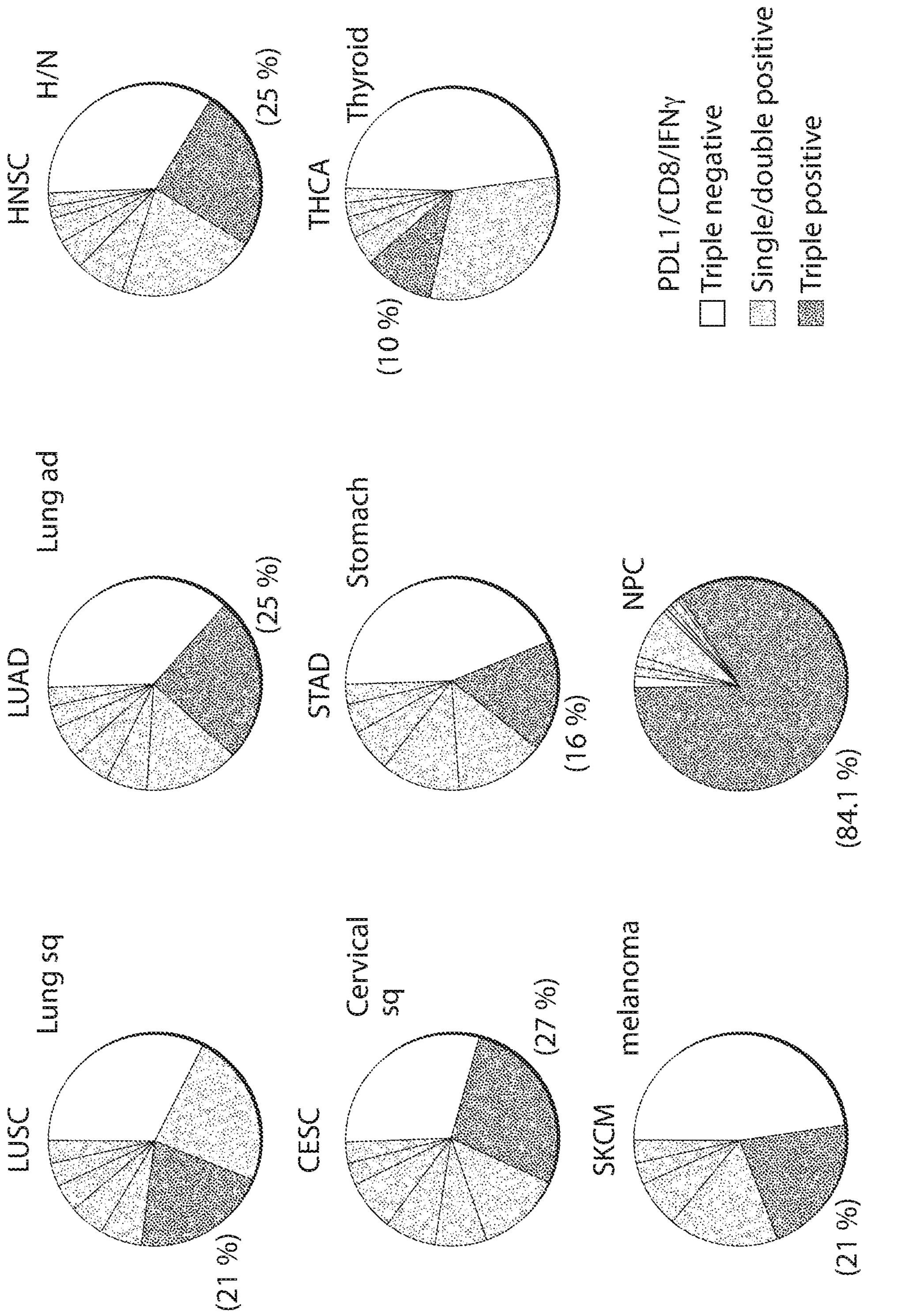
FIG. 11 shows exemplary cancers having relatively high proportions of patients that are triple-positive for PD-L1/CD8/IFN-γ.

For each of several types of cancer, samples from multiple patients were tested for PD-L1/CD8/IFN-γ status. Each sample was classified as: triple-negative for PD-L1/CD8/IFN-γ, single or double positive for these markers, or triple-positive for these markers. FIG. 11 shows that in this experiment, within a population of patients, the following types of cancer are frequently triple-positive for PD-L1/CD8/IFN-γ: Lung cancer (squamous), lung cancer (adenocarcinoma), head and neck cancer, cervical cancer (squamous), stomach cancer, thyroid cancer, melanoma, and nasopharyngeal cancer. Patients having these types of cancer are good candidates for therapy with anti PD-1 antibodies in combination therapies as described herein, e.g., anti-LAG-3 antibodies. The likelihood of successful treatment can be further boosted by determining which patients are triple-positive for PD-L1/CD8/IFN-γ, and treating the triple-positive patients with anti-PD-1 or anti-PD-L1 antibodies and combination therapies as described herein, e.g., anti-LAG-3 antibodies.

Figure 12:
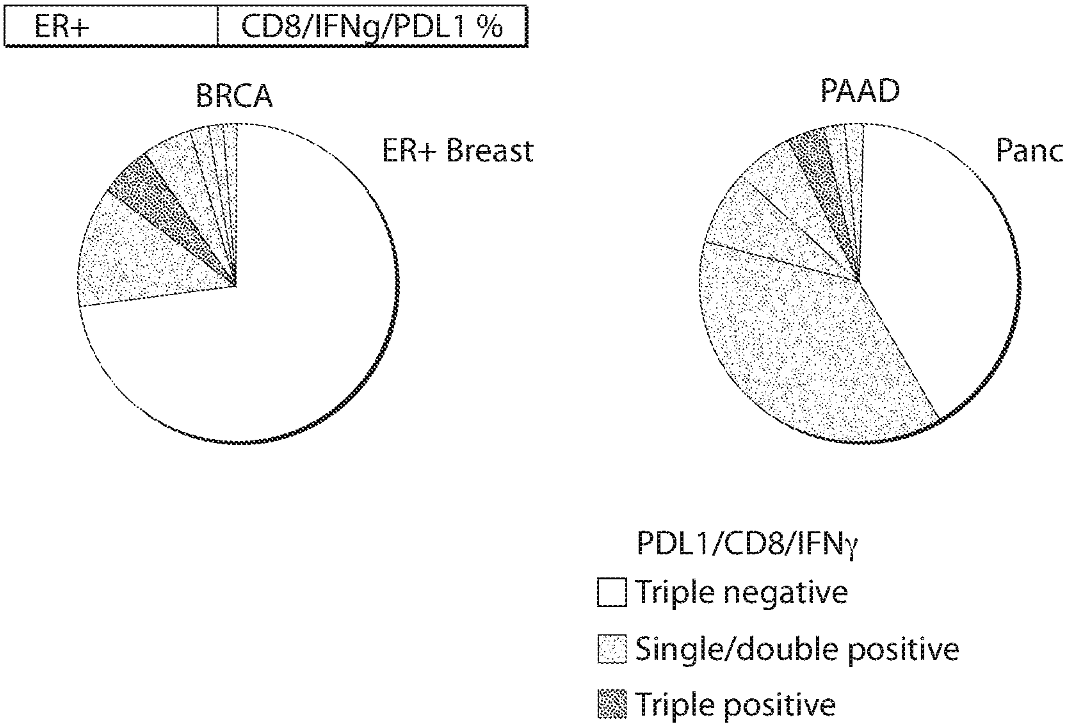
FIG. 12 shows exemplary ER+ breast cancer and pancreatic cancer having relatively low proportions for patients that are triple positive for PD-L1/CD8/IFN-γ.

FIG. 12 shows that within a population of patients, the following types of cancer are rarely triple positive for PD-L1/CD8/IFN-γ: ER+ breast cancer and pancreatic cancer. Notably, even in cancers that are generally not positive for for PD-L1/CD8/IFN-γ, one can increase the likelihood of successful treatment by determining which patients are triple-positive for PD-L1/CD8/IFN-γ, and treating the triple-positive patients with anti-PD-1 or anti-PD-L1 antibodies and combination therapies as described herein, e.g., anti-LAG-3 antibodies.

Figure 13:
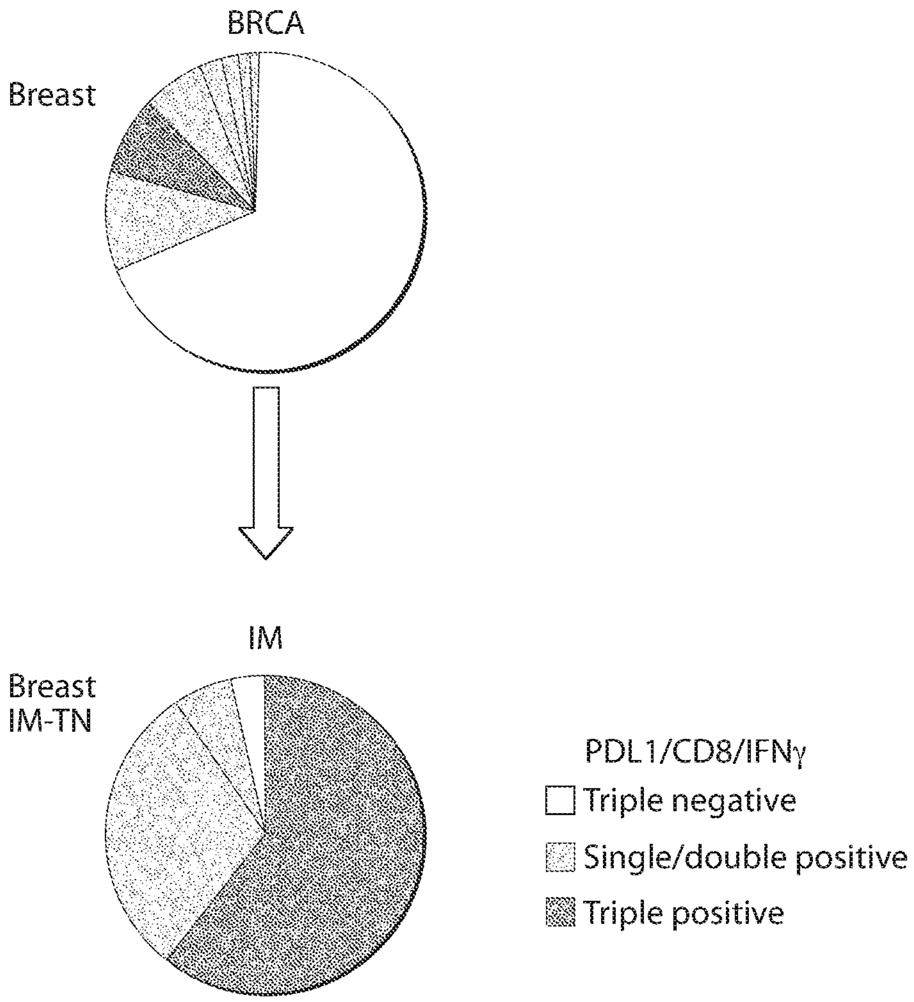
FIG. 13 shows the proportion of exemplary breast cancer patients that are triple positive for PD-L1/CD8/IFN-γ.

FIG. 13 shows the proportion of breast cancer patients that are triple positive for PDL1/CD8/IFN-7. Considering breast cancer in general, the proportion of triple-positives is somewhat low. However, when one focuses only on IM-TN breast cancer, it can be seen that a much larger percentage of patients is triple positive for PD-L1/CD8/IFN-γ. IM-TN breast cancer is particularly difficult to treat with conventional therapies. The discovery that IM-TN breast cancer is often triple-postive for PD-L1/CD8/IFN-γ opens up new avenues of therapy for this cancer with anti-PD-1 or anti-PD-L1 antibodies and combination therapies as described herein, e.g., anti-LAG-3 antibodies.

Figure 14:
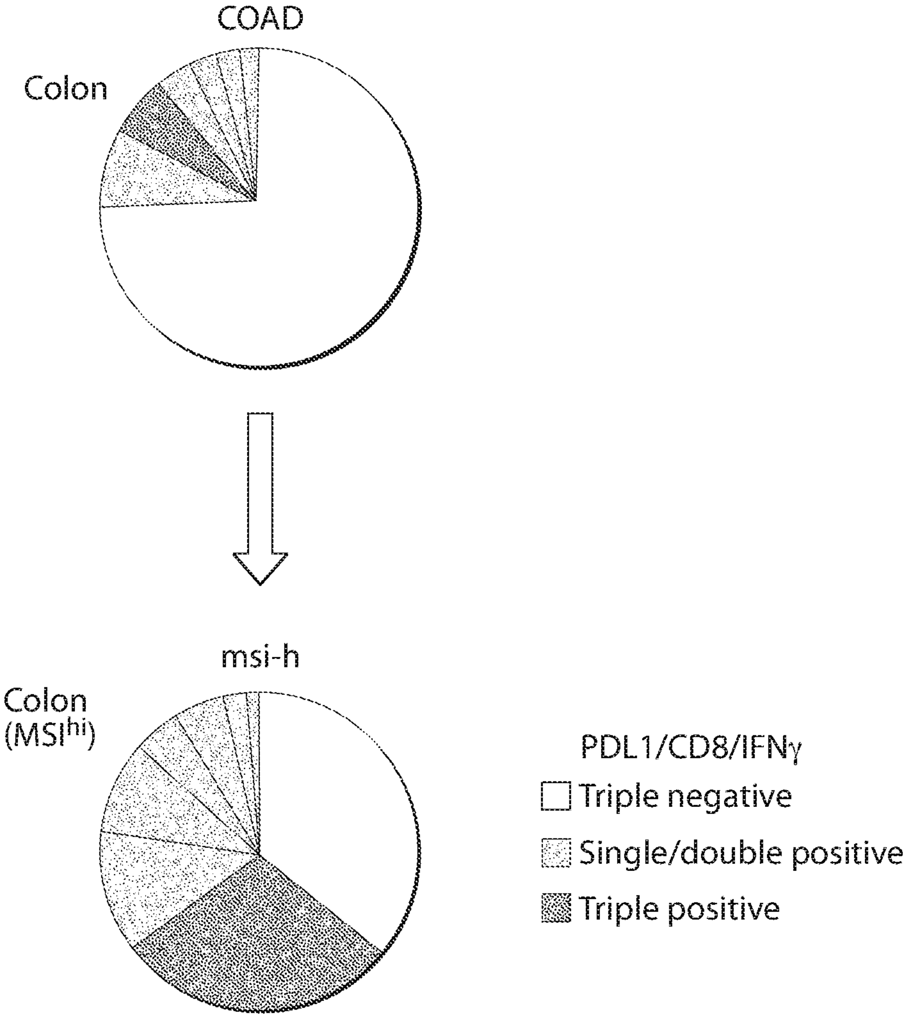
FIG. 14 shows the proportion of exemplary colon cancer patients that are triple positive for PD-L1/CD8/IFN-γ.

FIG. 14 shows the proportion of colon cancer patients that are triple positive for PD-L1/CD8/IFN-7. Considering colon cancer in general, the proportion of triple-positive is somewhat low. However, when one focuses only on MSI-high (high microsatellite instability) breast cancer, it can be seen that a much larger percentage of patients is triple positive for PD-L1/CD8/IFN-γ. MSI levels can be assayed using, e.g., commercially available PCR-based methods.

Gastric cancer samples were tested for levels of PD-L1/CD8/IFN-γ (data not shown). It was found that in MSI-high or EBV+ gastric cancers, about 49% were positive for PD-L1, and a high proportion of the PD-L1-positive cells were triple positive for PD-L1/CD8/IFN-γ. It was also found that a proportion of PD-L1-positive cells and PD-L1/CD8/IFN-γ positive cells were also positive for PIK3CA. This finding suggests that these cancers may be treated with a PD-1 or an anti-PD-L1 antibody, e.g., in combination with an anti-LAG-3 antibody, optionally in combination with a PIK3 therapeutic.

MSI-high CRC samples were tested for a combination of markers (data not shown). It was found that in MSI-high CRC samples, a high proportion of the PD-L1/CD8/IFN-γ samples are also positive for LAG-3, PD-1 (also called PDCD1), RNF43, and BRAF. This finding suggests that these cancers may be treated with a LAG-3 antibody, optionally in combination with a therapeutic that targets one or more of PD-1, PD-L1, PDCD1, RNF43, and BRAF.

Squamous cell lung cancers were tested for a combination of markers (data not shown). It was found that in squamous cell lung cancer samples, a high proportion of the PD-L1/CD8/IFN-γ samples are also positive for LAG-3. This finding suggests that these cancers may be treated with a LAG-3 antibody, optionally in combination with a therapeutic that targets PD-1 or PD-L1, e.g., an anti-PD-1 antibody or an anti-PD-L1 antibody.

Papillary thyroid cancers were tested for a combination of markers including the BRAF V600E mutation (data not shown). It was found that a high proportion of thyroid cancer samples that are positive for PD-L1 are also positive for BRAF V600E. This finding suggests that these cancers may be treated with an anti-PD-1 antibody or an anti-PD-L1 antibody, e.g., in combination with an anti-LAG-3 antibody, optionally in combination with a therapeutic that targets BRAF.

Example 5: Patient Selection Based on PD-L1 Status

To enable broad examination of cancer indications for immunomodulator (e.g., LAG-3 alone or in combination with PD1/PD-L1) based therapies, PD-L1 expression was evaluated at both the protein and mRNA levels in human cancers including both lung and hepatic tumors.

PD-L1 protein expression was evaluated in a set of formalin-fixed paraffin-embedded non-small cell lung (NSCLC) adenocarcinoma (ACA), NSCLC squamous cell carcinoma (SCC), and hepatocellular carcinoma (HCC) tumors by immunohistochemistry (IHC). PD-L1 expression was scored semi-quantitatively by a manual histo-score (H-score) methodology based on staining intensity and percentage of positive tumor cells. In our IHC analysis, PD-L1 positivity (PD-L1+) was defined as an H-score $\geqslant 20$. In parallel, PD-L1 mRNA expression data was examined from The Cancer Genome Atlas (TCGA) in these same indications (503 NSCLC ACA, 489 NSCLC SCC, and 191 HCC) and analyzed by comparing the expression in matched normal tissues from TCGA.

With RNAseq analysis, data was calculated as log 2 (RPKM+0.1) after RSEM normalization, utilizing OmicSoft RNASeq pipelines across TCGA tumor indications. The expression of PD-L1 is elevated in NSCLC ACA and SCC, relative to that in HCC. By overlaying the distributions and comparing the expression levels across all indications in TCGA, we ranked overexpression profiles for PD-L1 and found the TCGA HCC cohort to have much reduced PD-L1 mRNA levels, with a median level of -0.8 compared to 1.3 for ACA and 1.5 for SCC, which amounts to more than a 2-fold change of median level expression. With RNAseq, our analysis defines 50% of NSCLC adenocarcinoma, 54% of NSCLC squamous cell carcinoma, and 6% of HCC as high expressers for PD-L1.

Tumor cell PD-L1 protein expression was measured in 45 lung adenocarcinoma (ACA) samples, 47 lung squamous cell carcinoma (SCC) samples, and 36 hepatocellular carcinoma (HCC) samples. 16/45 (35.6%) lung ACA, 21/47

(44.7%) lung SCC were PD-L1 positive. In contrast, PD-L1 positivity was seen in only 2/36 (5.6%) HCC samples.

In summary, with IHC and RNAseq analysis in large and independent human NSCLC and HCC sample sets, PD-L1 expression was found to be more enriched in NSCLC than in HCC. Within NSCLC, there are comparable findings between adenocarcinoma and squamous cell carcinomas. Importantly, amongst the large number of samples (128 for IHC and 1183 for RNAseq) in the 3 indications, very good concordance is observed between protein- and mRNA-based analyses. This finding thus establishes the basis for large scale mRNA-based data mining in TCGA for indications and patient segments that may be enriched for responses to immunomodulator (e.g., PD-1/PD-L1, e.g., in combination with LAG-3) based immune therapies.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of treating a cancer in a subject, comprising administering to the subject an anti-LAG-3 antibody molecule and an agent that enhances tumor antigen presentation thereby treating the cancer, wherein the anti-LAG-3 antibody molecule, comprises:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;

(c) a VH comprising a VHCDR1 amino acid sequence of SEQ ID NO: 286, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or (d) a VH comprising a VHCDR1 amino acid sequence of SEQ ID NO: 286; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12, and wherein the agent that enhances tumor antigen presentation is a STING agonist, a TLR agonist, an A2AR antagonist, or an oncolytic virus, or a combination thereof.

2. The method of claim 1, wherein the anti-LAG-3 antibody molecule comprises:

(a) a VH comprising the amino acid sequence of SEQ ID NO: 28 or SEQ ID NO: 100; and a VL comprising the amino acid sequence of SEQ ID NO: 32;

(b) a VH comprising the amino acid sequence of SEQ ID NO: 28 or SEQ ID NO: 100; and a VL comprising the amino acid sequence of SEQ ID NO: 36;

(c) a VH comprising the amino acid sequence of SEQ ID NO: 28 or SEQ ID NO: 100; and a VL comprising the amino acid sequence of SEQ ID NO: 40;

(d) a VH comprising the amino acid sequence of SEQ ID NO: 28 or SEQ ID NO: 100; and a VL comprising the amino acid sequence of SEQ ID NO: 44;

(e) a VH comprising the amino acid sequence of SEQ ID NO: 28 or SEQ ID NO: 100; and a VL comprising the amino acid sequence of SEQ ID NO: 48;

(f) a VH comprising the amino acid sequence of SEQ ID NO: 28 or SEQ ID NO: 100; and a VL comprising the amino acid sequence of SEQ ID NO: 52;

(g) a VH comprising the amino acid sequence of SEQ ID NO: 28 or SEQ ID NO: 100; and a VL comprising the amino acid sequence of SEQ ID NO: 56;

(h) a VH comprising the amino acid sequence of SEQ ID NO: 28 or SEQ ID NO: 100; and a VL comprising the amino acid sequence of SEQ ID NO: 60;

(i) a VH comprising the amino acid sequence of SEQ ID NO: 64 or SEQ ID NO: 104; and a VL comprising the amino acid sequence of SEQ ID NO: 36;

(j) a VH comprising the amino acid sequence of SEQ ID NO: 64 or SEQ ID NO: 104; and a VL comprising the amino acid sequence of SEQ ID NO: 40;

(k) a VH comprising the amino acid sequence of SEQ ID NO: 64 or SEQ ID NO: 104; and a VL comprising the amino acid sequence of SEQ ID NO: 56;

(l) a VH comprising the amino acid sequence of SEQ ID NO: 64 or SEQ ID NO: 104; and a VL comprising the amino acid sequence of SEQ ID NO: 60;

(m) a VH comprising the amino acid sequence of SEQ ID NO: 68 or SEQ ID NO: 108; and a VL comprising the amino acid sequence of SEQ ID NO: 36;

(n) a VH comprising the amino acid sequence of SEQ ID NO: 72 or SEQ ID NO: 8; and a VL comprising the amino acid sequence of SEQ ID NO: 40;

(o) a VH comprising the amino acid sequence of SEQ ID NO: 72 or SEQ ID NO: 8; and a VL comprising the amino acid sequence of SEQ ID NO: 60;

(p) a VH comprising the amino acid sequence of SEQ ID NO: 76; and a VL comprising the amino acid sequence of SEQ ID NO: 60;

(q) a VH comprising the amino acid sequence of SEQ ID NO: 80; and a VL comprising the amino acid sequence of SEQ ID NO: 84;

(r) a VH comprising the amino acid sequence of SEQ ID NO: 28 or SEQ ID NO: 100; and a VL comprising the amino acid sequence of SEQ ID NO: 88;

(s) a VH comprising the amino acid sequence of SEQ ID NO: 28 or SEQ ID NO: 100; and a VL comprising the amino acid sequence of SEQ ID NO: 92; or (t) a VH comprising the amino acid sequence of SEQ ID NO: 64 or SEQ ID NO: 104; and a VL comprising the amino acid sequence of SEQ ID NO: 96.

3. The method of claim 1, wherein the cancer is a lung cancer, a melanoma, a renal cancer, a liver cancer, a prostate cancer, a breast cancer, a colorectal cancer, a gastric cancer, a pancreatic cancer, a thyroid cancer, a head and neck cancer, an endometrial cancer, a brain cancer, a nasopharyngeal cancer, a hematological cancer, or a metastatic lesion of the cancer.

4. The method of claim 3, wherein the melanoma is an advanced melanoma, an unresectable melanoma, a metastatic melanoma, a melanoma with a BRAF mutation, a melanoma with an NRAS mutation, a cutaneous melanoma, or an intraocular melanoma.

5. The method of claim 3, wherein the breast cancer is a triple negative breast cancer or an ER+ breast cancer.

6. The method of claim 1, wherein the method further comprises an agent that enhances tumor antigen presentation that is one or more of: a TIM-3 modulator, a vascular endothelial growth factor receptor (VEGFR) inhibitor, a c-Met inhibitor, a TGFb inhibitor, an IDO/TDO inhibitor, a vaccine, or a bi- or tri-specific cell engager.

7. The method of claim 1, wherein the combination further comprises an agent that decreases tumor immunosuppression that is one or more of: a GITR agonist, an inhibitor of an immune checkpoint molecule that is one or more of PD-1, PD-L1, LAG-3, TIM-3, or CTLA-4, a CSF-1/1R inhibitor, an IL-17 inhibitor, an IL-1β inhibitor, a CXCR2 inhibitor, an inhibitor of PI3Kγ or PI3Kδ, a BAFF-R inhibitor, a MALT-1/BTK inhibitor, a JAK inhibitor, a CRTH2 inhibitor, a VEGFR inhibitor, an IL-15 or a variant thereof, an IDO/TDO inhibitor, an A2aR antagonist, a TGFb inhibitor, or a PFKFB3 inhibitor.

* * * * *

```
                         SEQUENCE LISTING


<160> NUMBER OF SEQ ID NOS: 548

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Gly Met Asn
1               5


<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ile Asn Thr Asp Thr Gly Glu Pro Thr Tyr Ala Asp Asp Phe Lys
1               5                   10                  15

Gly


<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Pro Pro Tyr Tyr Tyr Gly Thr Asn Asn Ala Glu Ala Met Asp Tyr
1               5                   10                  15


<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 4

Gly Phe Thr Leu Thr Asn Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Thr Asp Thr Gly Glu
1               5

<210> SEQ ID NO 6
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Leu Thr Asn Tyr
            20                  25                  30

Gly Met Asn Trp Val Arg Gln Thr Pro Gly Lys Gly Leu Lys Trp Met
        35                  40                  45

Gly Trp Ile Asn Thr Asp Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Ala Asp Thr Ala Thr Tyr Phe Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Ala Val Thr Val Ser Ser
        115                 120                 125

<210> SEQ ID NO 7
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
cagatccagt tggtgcagtc tggacctgag ctgaagaagc ctggagagac agtcaagatc     60
tcctgcaagg cttctggatt taccctcaca aactatggaa tgaactgggt gaggcagact    120
ccaggaaagg gtttaaagtg gatgggctgg ataaacaccg acactggaga gccaacatat    180
gctgatgact tcaagggacg gtttgccttc tctttggaga cctctgccag cactgcctct    240
ttgcagatca acaacctcaa aaatgcggac acggctacat atttctgtgc aagaaacccc    300
ccttattact acggtactaa taacgcggag gctatggact actggggtca aggaaccgca    360
gtcaccgtct cctca                                                      375

<210> SEQ ID NO 8
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Ile Arg Gln Ser Pro Ser Arg Gly Leu Glu Trp Leu
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125
```

<210> SEQ ID NO 9
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gaggtccagc tggtacagtc tggggctgag gtgaagaagc ctggggctac agtgaaaatc     60

tcctgcaagg tttctggatt taccctcaca aactatggaa tgaactggat caggcagtcc    120

ccatcgagag gccttgagtg gctgggttgg ataaacaccg acactggaga gccaacatat    180

gctgatgact tcaagggaag atttgtcttc tccttggaca cctctgtcag cacggcatat    240

ctgcagatca gcagcctaaa ggctgaggac actgccgtgt attactgtgc aagaaaccct    300

ccctattact acggtactaa taacgcggag gctatggact actggggcca gggcaccacc    360

gtgaccgtgt cctcc                                                     375
```

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Ser Ser Ser Gln Asp Ile Ser Asn Tyr Leu Asn
1               5                   10
```

<210> SEQ ID NO 11
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 11

Tyr Thr Ser Thr Leu His Leu
1 5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gln Gln Tyr Tyr Asn Leu Pro Trp Thr
1 5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Ser Gln Asp Ile Ser Asn Tyr
1 5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Tyr Thr Ser
1

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Tyr Tyr Asn Leu Pro Trp
1 5

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

Asp Ile Gln Met Thr Gln Thr Thr Ser Ser Leu Ser Ala Ser Leu Gly
1 5 10 15

```
Asp Arg Val Thr Ile Ser Cys Ser Ser Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Tyr Ser Leu Thr Ile Ser Asn Leu Glu Leu
65                  70                  75                  80

Glu Asp Ile Ala Thr Tyr Tyr Cys Gln Gln Tyr Tyr Asn Leu Pro Trp
                85                  90                  95

Thr Phe Gly Gly Gly Thr Lys Leu Glu Ile Lys
            100                 105


<210> SEQ ID NO 17
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

gatatccaga tgacacagac tacatcctcc ctgtctgcct ctctgggaga cagagtcacc     60

atcagttgca gttcaagtca ggacatcagc aattatttaa actggtatca gcagaaacca    120

gatggaactg ttaaagtcct gatctattac acatcaacct tacacttagg agtcccatca    180

aggttcagtg gcagtgggtc tgggacagat tattctctca ccatcagcaa cctggaactc    240

gaagatattg ccacatacta ttgtcagcag tattataacc ttccgtggac gttcggtgga    300

ggcaccaagt tggaaatcaa a                                              321


<210> SEQ ID NO 18
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Ile Arg Gln Ser Pro Ser Arg Gly Leu Glu Trp Leu
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140
```

```
Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 19
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gaggtccagc tggtacagtc tggggctgag gtgaagaagc ctggggctac agtgaaaatc      60

tcctgcaagg tttctggatt taccctcaca aactatggaa tgaactggat caggcagtcc     120

ccatcgagag gccttgagtg gctgggttgg ataaacaccg acactggaga gccaacatat     180

gctgatgact tcaagggaag atttgtcttc tccttggaca cctctgtcag cacggcatat     240
```

ctgcagatca gcagcctaaa ggctgaggac actgccgtgt attactgtgc aagaaaccct 300
ccctattact acggtactaa taacgcggag gctatggact actggggcca gggcaccacc 360
gtgaccgtgt cctccgcttc caccaagggc ccatccgtct tcccccctggc gccctgctcc 420 aggagcacct ccgagagcac agccgccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcacga agacctacac ctgcaacgta gatcacaagc ccagcaacac caaggtggac 660
aagagagttg agtccaaata tggtccccca tgcccaccgt gcccagcacc tgagttcctg 720
gggggaccat cagtcttcct gttcccccca aaacccaagg acactctcat gatctcccgg 780
acccctgagg tcacgtgcgt ggtggtggac gtgagccagg aagaccccga ggtccagttc 840
aactggtacg tggatggcgt ggaggtgcat aatgccaaga caaagccgcg ggaggagcag 900
ttcaacagca cgtaccgtgt ggtcagcgtc ctcaccgtcc tgcaccagga ctggctgaac 960
ggcaaggagt acaagtgcaa ggtgtccaac aaaggcctcc cgtcctccat cgagaaaacc 1020
atctccaaag ccaaagggca gccccgagag ccacaggtgt acaccctgcc cccatcccag 1080
gaggagatga ccaagaacca ggtcagcctg acctgcctgg tcaaaggctt ctaccccagc 1140
gacatcgccg tggagtggga gagcaatggg cagccggaga acaactacaa gaccacgcct 1200
cccgtgctgg actccgacgg ctccttcttc ctctacagca ggctaaccgt ggacaagagc 1260
aggtggcagg aggggaatgt cttctcatgc tccgtgatgc atgaggctct gcacaaccac 1320
tacacacaga agagcctctc cctgtctctg ggtaaa 1356

<210> SEQ ID NO 20
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

Gln Ile Gln Leu Val Gln Ser Gly Pro Glu Leu Lys Lys Pro Gly Glu
1 5 10 15

Thr Val Lys Ile Ser Cys Lys Ala Ser Gly Phe Thr Leu Thr Asn Tyr
20 25 30

Gly Met Asn Trp Val Arg Gln Thr Pro Gly Lys Gly Leu Lys Trp Met
35 40 45

Gly Trp Ile Asn Thr Asp Thr Gly Glu Pro Thr Tyr Ala Asp Asp Phe
50 55 60

Lys Gly Arg Phe Ala Phe Ser Leu Glu Thr Ser Ala Ser Thr Ala Ser
65 70 75 80

Leu Gln Ile Asn Asn Leu Lys Asn Ala Asp Thr Ala Thr Tyr Phe Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser
115 120 125

<210> SEQ ID NO 21
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21
cagatccagt tggtgcagtc tggacctgag ctgaagaagc ctggagagac agtcaagatc 60
tcctgcaagg cttctggatt taccctcaca aactatggaa tgaactgggt gaggcagact 120
ccaggaaagg gtttaaagtg gatgggctgg ataaacaccg acactggaga gccaacatat 180
gctgatgact tcaagggacg gtttgccttc tctttggaga cctctgccag cactgcctct 240
ttgcagatca acaacctcaa aaatgcggac acggctacat atttctgtgc aagaaacccc 300
ccttattact acggtactaa taacgcggag gctatggact actggggcca gggcaccacc 360
gtgaccgtgt cctcc 375

<210> SEQ ID NO 22
<211> LENGTH: 452
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Gln Ile Gln Leu Val Gln Ser Gly Pro Glu Leu Lys Lys Pro Gly Glu
1 5 10 15

Thr Val Lys Ile Ser Cys Lys Ala Ser Gly Phe Thr Leu Thr Asn Tyr
20 25 30

Gly Met Asn Trp Val Arg Gln Thr Pro Gly Lys Gly Leu Lys Trp Met
35 40 45

Gly Trp Ile Asn Thr Asp Thr Gly Glu Pro Thr Tyr Ala Asp Asp Phe
50 55 60

Lys Gly Arg Phe Ala Phe Ser Leu Glu Thr Ser Ala Ser Thr Ala Ser
65 70 75 80

Leu Gln Ile Asn Asn Leu Lys Asn Ala Asp Thr Ala Thr Tyr Phe Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Lys Thr Tyr Thr Cys
195 200 205

Asn Val Asp His Lys Pro Ser Asn Thr Lys Val Asp Lys Arg Val Glu
210 215 220

Ser Lys Tyr Gly Pro Pro Cys Pro Pro Cys Pro Ala Pro Glu Phe Leu
225 230 235 240

Gly Gly Pro Ser Val Phe Leu Phe Pro Pro Lys Pro Lys Asp Thr Leu
245 250 255

-continued

```
Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450


<210> SEQ ID NO 23
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

cagatccagt tggtgcagtc tggacctgag ctgaagaagc ctggagagac agtcaagatc     60

tcctgcaagg cttctggatt taccctcaca aactatggaa tgaactgggt gaggcagact    120

ccaggaaagg gtttaaagtg gatgggctgg ataaacaccg acactggaga gccaacatat    180

gctgatgact tcaagggacg gtttgccttc tctttggaga cctctgccag cactgcctct    240

ttgcagatca acaacctcaa aaatgcggac acggctacat atttctgtgc aagaaacccc    300

ccttattact acggtactaa taacgcggag gctatggact actggggcca gggcaccacc    360

gtgaccgtgt cctccgcttc caccaagggc ccatccgtct tccccctggc gccctgctcc    420

aggagcacct ccgagagcac agccgccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcacga agacctacac ctgcaacgta gatcacaagc ccagcaacac caaggtggac    660

aagagagttg agtccaaata tggtccccca tgcccaccgt gcccagcacc tgagttcctg    720

gggggaccat cagtcttcct gttcccccca aaacccaagg acactctcat gatctcccgg    780

acccctgagg tcacgtgcgt ggtggtggac gtgagccagg aagaccccga ggtccagttc    840

aactggtacg tggatggcgt ggaggtgcat aatgccaaga caaagccgcg ggaggagcag    900
```

```
ttcaacagca cgtaccgtgt ggtcagcgtc ctcaccgtcc tgcaccagga ctggctgaac     960

ggcaaggagt acaagtgcaa ggtgtccaac aaaggcctcc cgtcctccat cgagaaaacc    1020

atctccaaag ccaaagggca gccccgagag ccacaggtgt acaccctgcc cccatcccag    1080

gaggagatga ccaagaacca ggtcagcctg acctgcctgg tcaaaggctt ctaccccagc    1140

gacatcgccg tggagtggga gagcaatggg cagccggaga acaactacaa gaccacgcct    1200

cccgtgctgg actccgacgg ctccttcttc ctctacagca ggctaaccgt ggacaagagc    1260

aggtggcagg aggggaatgt cttctcatgc tccgtgatgc atgaggctct gcacaaccac    1320

tacacacaga agagcctctc cctgtctctg ggtaaa                              1356
```

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Asp Ile Gln Met Thr Gln Thr Thr Ser Ser Leu Ser Ala Ser Leu Gly
1               5                   10                  15

Asp Arg Val Thr Ile Ser Cys Ser Ser Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Tyr Ser Leu Thr Ile Ser Asn Leu Glu Leu
65                  70                  75                  80

Glu Asp Ile Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
gatatccaga tgacacagac tacatcctcc ctgtctgcct ctctgggaga cagagtcacc      60

atcagttgca gttcaagtca ggacatcagc aattatttaa actggtatca gcagaaacca     120

gatggaactg ttaaagtcct gatctattac acatcaacct tacacttagg agtcccatca     180

aggttcagtg gcagtgggtc tgggacagat tattctctca ccatcagcaa cctggaactc     240

gaagatattg ccacatacta ttgtcagcag tattataacc ttccgtggac gttcggccaa     300

gggaccaagg tggaaatcaa a                                               321
```

<210> SEQ ID NO 26
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Asp Ile Gln Met Thr Gln Thr Thr Ser Ser Leu Ser Ala Ser Leu Gly
1 5 10 15

Asp Arg Val Thr Ile Ser Cys Ser Ser Ser Gln Asp Ile Ser Asn Tyr
20 25 30

Leu Asn Trp Tyr Gln Gln Lys Pro Asp Gly Thr Val Lys Val Leu Ile
35 40 45

Tyr Tyr Thr Ser Thr Leu His Leu Gly Val Pro Ser Arg Phe Ser Gly
50 55 60

Ser Gly Ser Gly Thr Asp Tyr Ser Leu Thr Ile Ser Asn Leu Glu Leu
65 70 75 80

Glu Asp Ile Ala Thr Tyr Tyr Cys Gln Gln Tyr Tyr Asn Leu Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 27
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27
gatatccaga tgacacagac tacatcctcc ctgtctgcct ctctgggaga cagagtcacc 60
atcagttgca gttcaagtca ggacatcagc aattatttaa actggtatca gcagaaacca 120
gatggaactg ttaaagtcct gatctattac acatcaacct tacacttagg agtcccatca 180
aggttcagtg gcagtgggtc tgggacagat tattctctca ccatcagcaa cctggaactc 240
gaagatattg ccacatacta ttgtcagcag tattataacc ttccgtggac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 28
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

Glu Val Gln Leu Val Gln Ser Gly Ala Glu Val Lys Lys Pro Gly Ala
1 5 10 15

Thr Val Lys Ile Ser Cys Lys Val Ser Gly Phe Thr Leu Thr Asn Tyr
20 25 30

Gly Met Asn Trp Val Arg Gln Ala Pro Gly Gln Gly Leu Glu Trp Met
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Cys Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser
115 120 125

<210> SEQ ID NO 29
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
gaggtccagc tggtacagtc tggggctgag gtgaagaagc ctggggctac agtgaaaatc 60
tcctgcaagg tttctggatt taccctcaca aactatggaa tgaactgggt gcgacaggcc 120
cctggacaag ggcttgagtg gatgggttgg ataaacaccg acactggaga gccaacatat 180
gctgatgact tcaagggaag atttgtcttc tccttggaca cctctgtcag cacggcatat 240
ctgcagatct gcagcctaaa ggctgaggac actgccgtgt attactgtgc aagaaaccct 300
ccctattact acggtactaa taacgcggag gctatggact actggggcca gggcaccacc 360
gtgaccgtgt cctcc 375

<210> SEQ ID NO 30
<211> LENGTH: 452
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

Glu Val Gln Leu Val Gln Ser Gly Ala Glu Val Lys Lys Pro Gly Ala
1 5 10 15

Thr Val Lys Ile Ser Cys Lys Val Ser Gly Phe Thr Leu Thr Asn Tyr
20 25 30

Gly Met Asn Trp Val Arg Gln Ala Pro Gly Gln Gly Leu Glu Trp Met
35 40 45

-continued

```
Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 31
<211> LENGTH: 1356
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 31
gaggtccagc tggtacagtc tggggctgag gtgaagaagc ctggggctac agtgaaaatc 60
tcctgcaagg tttctggatt taccctcaca aactatggaa tgaactgggt gcgacaggcc 120
cctggacaag ggcttgagtg gatgggttgg ataaacaccg acactggaga gccaacatat 180
gctgatgact tcaagggaag atttgtcttc tccttggaca cctctgtcag cacggcatat 240
ctgcagatct gcagcctaaa ggctgaggac actgccgtgt attactgtgc aagaaaccct 300
ccctattact acggtactaa taacgcggag gctatggact actggggcca gggcaccacc 360
gtgaccgtgt cctccgcttc caccaagggc ccatccgtct tccccctggc gccctgctcc 420
aggagcacct ccgagagcac agccgccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcacga agacctacac ctgcaacgta gatcacaagc ccagcaacac caaggtggac 660
aagagagttg agtccaaata tggtccccca tgcccaccgt gcccagcacc tgagttcctg 720
gggggaccat cagtcttcct gttcccccca aaacccaagg acactctcat gatctcccgg 780
acccctgagg tcacgtgcgt ggtggtggac gtgagccagg aagaccccga ggtccagttc 840
aactggtacg tggatggcgt ggaggtgcat aatgccaaga caaagccgcg ggaggagcag 900
ttcaacagca cgtaccgtgt ggtcagcgtc ctcaccgtcc tgcaccagga ctggctgaac 960
ggcaaggagt acaagtgcaa ggtgtccaac aaaggcctcc cgtcctccat cgagaaaacc 1020
atctccaaag ccaaagggca gccccgagag ccacaggtgt acaccctgcc cccatcccag 1080
gaggagatga ccaagaacca ggtcagcctg acctgcctgg tcaaaggctt ctaccccagc 1140
gacatcgccg tggagtggga gagcaatggg cagccggaga acaactacaa gaccacgcct 1200
cccgtgctgg actccgacgg ctccttcttc ctctacagca ggctaaccgt ggacaagagc 1260
aggtggcagg aggggaatgt cttctcatgc tccgtgatgc atgaggctct gcacaaccac 1320
tacacacaga agagcctctc cctgtctctg ggtaaa 1356

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 32

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Thr Leu His Leu Gly Val Pro Ser Arg Phe Ser Gly
50 55 60

```
Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105


<210> SEQ ID NO 33
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

gacatccaga tgacccagtc tccatcctcc ctgtctgcat ctgtaggaga cagagtcacc     60

atcacttgca gttcaagtca ggacatcagc aattatttaa actggtatca gcagaaacca    120

gggaaagctc ctaagctcct gatctattac acatcaacct tacacttagg ggtcccctcg    180

aggttcagtg gcagtggatc tgggacagat ttcaccttta ccatcagtag cctggaagct    240

gaagatgctg caacatatta ctgtcagcag tattataacc ttccgtggac gttcggccaa    300

gggaccaagg tggaaatcaa a                                              321


<210> SEQ ID NO 34
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
195 200 205

Phe Asn Arg Gly Glu Cys
210

<210> SEQ ID NO 35
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
gacatccaga tgacccagtc tccatcctcc ctgtctgcat ctgtaggaga cagagtcacc 60
atcacttgca gttcaagtca ggacatcagc aattatttaa actggtatca gcagaaacca 120
gggaaagctc ctaagctcct gatctattac acatcaacct tacacttagg ggtcccctcg 180
aggttcagtg gcagtggatc tgggacagat ttcaccttta ccatcagtag cctggaagct 240
gaagatgctg caacatatta ctgtcagcag tattataacc ttccgtggac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Thr Leu His Leu Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln Tyr Tyr Asn Leu Pro Trp
85 90 95

Thr Phe Gly Gln Gly Thr Lys Val Glu Ile Lys
100 105

<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
gacatccaga tgacccagtc tccatcctcc ctgtctgcat ctgtaggaga cagagtcacc 60
atcacttgca gttcaagtca ggacatcagc aattatttaa actggtatca gcagaaacca 120
gggaaagctc ctaagctcct gatctattac acatcaacct tacacttagg gatcccacct 180
cgattcagtg gcagcgggta tggaacagat tttaccctca caattaataa catagaatct 240
gaggatgctg catattactt ctgtcagcag tattataacc ttccgtggac gttcggccaa 300
gggaccaagg tggaaatcaa a 321

<210> SEQ ID NO 38
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Thr Leu His Leu Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln Tyr Tyr Asn Leu Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 39
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39

```
gacatccaga tgacccagtc tccatcctcc ctgtctgcat ctgtaggaga cagagtcacc     60

atcacttgca gttcaagtca ggacatcagc aattatttaa actggtatca gcagaaacca    120

gggaaagctc ctaagctcct gatctattac acatcaacct tacacttagg gatcccacct    180

cgattcagtg gcagcgggta tggaacagat tttaccctca caattaataa catagaatct    240

gaggatgctg catattactt ctgtcagcag tattataacc ttccgtggac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Glu Ile Val Leu Thr Gln Ser Pro Ala Thr Leu Pro Val Thr Leu Gly
1               5                   10                  15

Gln Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 41
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
gaaattgtgt tgacacagtc tccagccacc ctgcccgtca cccttggaca gccggcctcc     60

atctcctgca gttcaagtca ggacatcagc aattatttaa actggtacca gcagaaacct    120

ggccaggctc ccaggctcct catctattac acatcaacct tacacttagg ggtcccctcg    180

aggttcagtg gcagtggatc tgggacagat ttcaccttta ccatcagtag cctggaagct    240

gaagatgctg caacatatta ctgtcagcag tattataacc ttccgtggac gttcggccaa    300

gggaccaagg tggaaatcaa a                                              321
```

<210> SEQ ID NO 42
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Glu Ile Val Leu Thr Gln Ser Pro Ala Thr Leu Pro Val Thr Leu Gly
1               5                   10                  15

Gln Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 43
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
gaaattgtgt tgacacagtc tccagccacc ctgcccgtca cccttggaca gccggcctcc     60

atctcctgca gttcaagtca ggacatcagc aattatttaa actggtacca gcagaaacct    120

ggccaggctc ccaggctcct catctattac acatcaacct tacacttagg ggtcccctcg    180

aggttcagtg gcagtggatc tgggacagat ttcaccttta ccatcagtag cctggaagct    240

gaagatgctg caacatatta ctgtcagcag tattataacc ttccgtggac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480
```

```
gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Leu Gln Lys Pro Gly Gln Ser Pro Gln Leu Leu Ile
        35                  40                  45

Tyr Tyr Thr Ser Thr Leu His Leu Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Tyr Asn Leu Pro Trp
                85                  90                  95

Thr Phe Gly Gln Gly Thr Lys Val Glu Ile Lys
            100                 105


<210> SEQ ID NO 45
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

gacatccaga tgacccagtc tccatcctcc ctgtctgcat ctgtaggaga cagagtcacc     60

atcacttgca gttcaagtca ggacatcagc aattatttaa actggtacct gcagaagcca    120

gggcagtctc cacagctcct gatctattac acatcaacct tacacttagg gatcccagac    180

aggttcagtg gcagtgggtc tgggacagac ttcactctca ccatcagcag actggagcct    240

gaagattttg cagtgtatta ctgtcagcag tattataacc ttccgtggac gttcggccaa    300

gggaccaagg tggaaatcaa a                                              321


<210> SEQ ID NO 46
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Leu Gln Lys Pro Gly Gln Ser Pro Gln Leu Leu Ile
```

```
        35                  40                  45

Tyr Tyr Thr Ser Thr Leu His Leu Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 47
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
gacatccaga tgacccagtc tccatcctcc ctgtctgcat ctgtaggaga cagagtcacc     60

atcacttgca gttcaagtca ggacatcagc aattatttaa actggtacct gcagaagcca    120

gggcagtctc cacagctcct gatctattac acatcaacct tacacttagg gatcccagac    180

aggttcagtg gcagtgggtc tgggacagac ttcactctca ccatcagcag actggagcct    240

gaagattttg cagtgtatta ctgtcagcag tattataacc ttccgtggac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

-continued

```
Glu Ile Val Leu Thr Gln Ser Pro Ala Thr Leu Ser Leu Ser Pro Gly
1               5                   10                  15

Glu Arg Ala Thr Leu Ser Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105


<210> SEQ ID NO 49
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

gaaattgtgt tgacacagtc tccagccacc ctgtctttgt ctccagggga aagagccacc      60

ctctcctgca gttcaagtca ggacatcagc aattatttaa actggtatca gcagaaacca     120

gggaaagctc ctaagctcct gatctattac acatcaacct tacacttagg ggtcccctcg     180

aggttcagtg gcagtggatc tgggacagat ttcaccttta ccatcagtag cctggaagct     240

gaagatgctg caacatatta ctgtcagcag tattataacc ttccgtggac gttcggccaa     300

gggaccaagg tggaaatcaa a                                               321


<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 51
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

gaaattgtgt tgacacagtc tccagccacc ctgtctttgt ctccagggga aagagccacc      60

ctctcctgca gttcaagtca ggacatcagc aattatttaa actggtatca gcagaaacca     120

gggaaagctc ctaagctcct gatctattac acatcaacct tacacttagg ggtcccctcg     180

aggttcagtg gcagtggatc tgggacagat ttcaccttta ccatcagtag cctggaagct     240

gaagatgctg caacatatta ctgtcagcag tattataacc ttccgtggac gttcggccaa     300

gggaccaagg tggaaatcaa acgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Val Met Thr Gln Thr Pro Leu Ser Leu Pro Val Thr Pro Gly
1               5                   10                  15

Glu Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95
```

-continued

```
Thr Phe Gly Gln Gly Thr Lys Val Glu Ile Lys
            100                 105


<210> SEQ ID NO 53
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

gatattgtga tgacccagac tccactctcc ctgcccgtca cccctggaga gccggcctcc      60

atctcctgca gttcaagtca ggacatcagc aattatttaa actggtacca gcagaaacct     120

ggccaggctc ccaggctcct catctattac acatcaacct tacacttagg ggtcccatca     180

aggttcagcg gcagtggatc tgggacagaa ttcactctca ccatcagcag cctgcagcct     240

gatgattttg caacttatta ctgtcagcag tattataacc ttccgtggac gttcggccaa     300

gggaccaagg tggaaatcaa a                                               321


<210> SEQ ID NO 54
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Met Thr Gln Thr Pro Leu Ser Leu Pro Val Thr Pro Gly
1               5                   10                  15

Glu Pro Ala Ser Ile Ser Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 55
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55
gatattgtga tgacccagac tccactctcc ctgcccgtca cccctggaga gccggcctcc 60
atctcctgca gttcaagtca ggacatcagc aattatttaa actggtacca gcagaaacct 120
ggccaggctc ccaggctcct catctattac acatcaacct tacacttagg ggtcccatca 180
aggttcagcg gcagtggatc tgggacagaa ttcactctca ccatcagcag cctgcagcct 240
gatgattttg caacttatta ctgtcagcag tattataacc ttccgtggac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Leu Gln Lys Pro Gly Gln Ser Pro Gln Leu Leu Ile
35 40 45

Tyr Tyr Thr Ser Thr Leu His Leu Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Tyr Asn Leu Pro Trp
85 90 95

Thr Phe Gly Gln Gly Thr Lys Val Glu Ile Lys
100 105

<210> SEQ ID NO 57
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57
gacatccaga tgacccagtc tccatcctcc ctgtctgcat ctgtaggaga cagagtcact 60
atcacttgca gttcaagtca ggacatcagc aattatttaa actggtacct gcagaagcca 120
gggcagtctc cacagctcct gatctattac acatcaacct tacacttagg ggtcccatca 180
aggttcagcg gcagtggatc tgggacagaa ttcactctca ccatcagcag cctgcagcct 240
gatgattttg caacttatta ctgtcagcag tattataacc ttccgtggac gttcggccaa 300
gggaccaagg tggaaatcaa a 321

<210> SEQ ID NO 58
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Leu Gln Lys Pro Gly Gln Ser Pro Gln Leu Leu Ile
35 40 45

Tyr Tyr Thr Ser Thr Leu His Leu Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Tyr Asn Leu Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 59
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59
gacatccaga tgacccagtc tccatcctcc ctgtctgcat ctgtaggaga cagagtcact 60
atcacttgca gttcaagtca ggacatcagc aattatttaa actggtacct gcagaagcca 120
gggcagtctc cacagctcct gatctattac acatcaacct tacacttagg ggtcccatca 180
aggttcagcg gcagtggatc tgggacagaa ttcactctca ccatcagcag cctgcagcct 240
gatgattttg caacttatta ctgtcagcag tattataacc ttccgtggac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Glu Ile Val Leu Thr Gln Ser Pro Asp Phe Gln Ser Val Thr Pro Lys
1               5                   10                  15

Glu Lys Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 61
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61
gaaattgtgc tgactcagtc tccagacttt cagtctgtga ctccaaagga gaaagtcacc 60
atcacctgca gttcaagtca ggacatcagc aattatttaa actggtacca gcagaaacct 120
ggccaggctc ccaggctcct catctattac acatcaacct tacacttagg ggtcccatca 180
aggttcagcg gcagtggatc tgggacagat ttcactctca ccatcagcag cctgcagcct 240
gaagattttg caacttatta ctgtcagcag tattataacc ttccgtggac gttcggccaa 300
gggaccaagg tggaaatcaa a 321

<210> SEQ ID NO 62
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Glu Ile Val Leu Thr Gln Ser Pro Asp Phe Gln Ser Val Thr Pro Lys
1 5 10 15

Glu Lys Val Thr Ile Thr Cys Ser Ser Ser Gln Asp Ile Ser Asn Tyr
20 25 30

Leu Asn Trp Tyr Gln Gln Lys Pro Gly Gln Ala Pro Arg Leu Leu Ile
35 40 45

Tyr Tyr Thr Ser Thr Leu His Leu Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Asn Leu Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 63
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63
gaaattgtgc tgactcagtc tccagacttt cagtctgtga ctccaaagga gaaagtcacc 60
atcacctgca gttcaagtca ggacatcagc aattatttaa actggtacca gcagaaacct 120
ggccaggctc ccaggctcct catctattac acatcaacct tacacttagg ggtcccatca 180
aggttcagcg gcagtggatc tgggacagat ttcactctca ccatcagcag cctgcagcct 240
gaagattttg caacttatta ctgtcagcag tattataacc ttccgtggac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 64
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125
```

<210> SEQ ID NO 65
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
caggttcagc tggtgcagtc tggagctgag gtgaagaagc ctggggcctc agtgaaggtc      60

tcctgcaagg cttctggatt taccctcaca aactatggaa tgaactgggt gcgacaggct     120

cgtggacaac gccttgagtg gataggttgg ataaacaccg acactggaga gccaacatat     180

gctgatgact tcaagggaag atttgtcttc tccttggaca cctctgtcag cacggcatat     240

ctgcagatct gcagcctaaa ggctgaggac actgccgtgt attactgtgc aagaaaccct     300

ccctattact acggtactaa taacgcggag gctatggact actggggcca gggcaccacc     360

gtgaccgtgt cctcc                                                      375
```

<210> SEQ ID NO 66
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45
```

-continued

```
Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 67
<211> LENGTH: 1356
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67
caggttcagc tggtgcagtc tggagctgag gtgaagaagc ctggggcctc agtgaaggtc 60
tcctgcaagg cttctggatt taccctcaca aactatggaa tgaactgggt gcgacaggct 120
cgtggacaac gccttgagtg gataggttgg ataaacaccg acactggaga gccaacatat 180
gctgatgact tcaagggaag atttgtcttc tccttggaca cctctgtcag cacggcatat 240
ctgcagatct gcagcctaaa ggctgaggac actgccgtgt attactgtgc aagaaaccct 300
ccctattact acggtactaa taacgcggag gctatggact actggggcca gggcaccacc 360
gtgaccgtgt cctccgcttc caccaagggc ccatccgtct tccccctggc gccctgctcc 420
aggagcacct ccgagagcac agccgccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcacga agacctacac ctgcaacgta gatcacaagc ccagcaacac caaggtggac 660
aagagagttg agtccaaata tggtccccca tgcccaccgt gcccagcacc tgagttcctg 720
gggggaccat cagtcttcct gttcccccca aaacccaagg acactctcat gatctcccgg 780
acccctgagg tcacgtgcgt ggtggtggac gtgagccagg aagaccccga ggtccagttc 840
aactggtacg tggatggcgt ggaggtgcat aatgccaaga caaagccgcg ggaggagcag 900
ttcaacagca cgtaccgtgt ggtcagcgtc ctcaccgtcc tgcaccagga ctggctgaac 960
ggcaaggagt acaagtgcaa ggtgtccaac aaaggcctcc cgtcctccat cgagaaaacc 1020
atctccaaag ccaaagggca gccccgagag ccacaggtgt acaccctgcc cccatcccag 1080
gaggagatga ccaagaacca ggtcagcctg acctgcctgg tcaaaggctt ctaccccagc 1140
gacatcgccg tggagtggga gagcaatggg cagccggaga acaactacaa gaccacgcct 1200
cccgtgctgg actccgacgg ctccttcttc ctctacagca ggctaaccgt ggacaagagc 1260
aggtggcagg aggggaatgt cttctcatgc tccgtgatgc atgaggctct gcacaaccac 1320
tacacacaga agagcctctc cctgtctctg ggtaaa 1356

<210> SEQ ID NO 68
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 68

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Leu Thr Asn Tyr
20 25 30

Gly Met Asn Trp Val Arg Gln Ala Pro Gly Gln Gly Leu Glu Trp Met
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Cys Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser
115 120 125

<210> SEQ ID NO 69
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69
caggttcagc tggtgcagtc cggagctgag gtgaagaagc ctggggcctc agtgaaggtc 60
tcctgcaagg cttctggatt taccctcaca aactatggaa tgaactgggt gcgacaggcc 120
cctggacaag ggcttgagtg gatgggttgg ataaacaccg acactggaga gccaacatat 180
gctgatgact tcaagggaag atttgtcttc tccttggaca cctctgtcag cacggcatat 240
ctgcagatct gcagcctaaa ggctgaggac actgccgtgt attactgtgc aagaaaccct 300
ccctattact acggtactaa taacgcggag gctatggact actggggcca gggcaccacc 360
gtgaccgtgt cctcc 375

<210> SEQ ID NO 70
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Leu Thr Asn Tyr
20 25 30

Gly Met Asn Trp Val Arg Gln Ala Pro Gly Gln Gly Leu Glu Trp Met
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Cys Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

-continued

```
Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 71
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
caggttcagc tggtgcagtc cggagctgag gtgaagaagc ctggggcctc agtgaaggtc      60

tcctgcaagg cttctggatt taccctcaca aactatggaa tgaactgggt gcgacaggcc     120

cctggacaag ggcttgagtg gatgggttgg ataaacaccg acactggaga gccaacatat     180

gctgatgact tcaagggaag atttgtcttc tccttggaca cctctgtcag cacggcatat     240

ctgcagatct gcagcctaaa ggctgaggac actgccgtgt attactgtgc aagaaaccct     300

ccctattact acggtactaa taacgcggag gctatggact actggggcca gggcaccacc     360
```

```
gtgaccgtgt cctccgcttc caccaagggc ccatccgtct tcccccctggc gccctgctcc    420

aggagcacct ccgagagcac agccgccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcacga agacctacac ctgcaacgta gatcacaagc ccagcaacac caaggtggac    660

aagagagttg agtccaaata tggtccccca tgcccaccgt gcccagcacc tgagttcctg    720

gggggaccat cagtcttcct gttcccccca aaacccaagg acactctcat gatctcccgg    780

acccctgagg tcacgtgcgt ggtggtggac gtgagccagg aagaccccga ggtccagttc    840

aactggtacg tggatggcgt ggaggtgcat aatgccaaga caaagccgcg ggaggagcag    900

ttcaacagca cgtaccgtgt ggtcagcgtc ctcaccgtcc tgcaccagga ctggctgaac    960

ggcaaggagt acaagtgcaa ggtgtccaac aaaggcctcc cgtcctccat cgagaaaacc   1020

atctccaaag ccaaagggca gccccgagag ccacaggtgt acaccctgcc cccatcccag   1080

gaggagatga ccaagaacca ggtcagcctg acctgcctgg tcaaaggctt ctaccccagc   1140

gacatcgccg tggagtggga gagcaatggg cagccggaga acaactacaa gaccacgcct   1200

cccgtgctgg actccgacgg ctccttcttc ctctacagca ggctaaccgt ggacaagagc   1260

aggtggcagg aggggaatgt cttctcatgc tccgtgatgc atgaggctct gcacaaccac   1320

tacacacaga agagcctctc cctgtctctg ggtaaa                             1356
```

```
<210> SEQ ID NO 72
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Ile Arg Gln Ser Pro Ser Arg Gly Leu Glu Trp Leu
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125


<210> SEQ ID NO 73
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 73
gaggtccagc tggtacagtc tggggctgag gtgaagaagc ctggggctac agtgaaaatc 60
tcctgcaagg tttctggatt taccctcaca aactatggaa tgaactggat caggcagtcc 120
ccatcgagag gccttgagtg gctgggttgg ataaacaccg acactggaga gccaacatat 180
gctgatgact tcaagggaag atttgtcttc tccttggaca cctctgtcag cacggcatat 240
ctgcagatct gcagcctaaa ggctgaggac actgccgtgt attactgtgc aagaaaccct 300
ccctattact acggtactaa taacgcggag gctatggact actggggcca gggcaccacc 360
gtgaccgtgt cctcc 375

<210> SEQ ID NO 74
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Glu Val Gln Leu Val Gln Ser Gly Ala Glu Val Lys Lys Pro Gly Ala
1 5 10 15

Thr Val Lys Ile Ser Cys Lys Val Ser Gly Phe Thr Leu Thr Asn Tyr
20 25 30

Gly Met Asn Trp Ile Arg Gln Ser Pro Ser Arg Gly Leu Glu Trp Leu
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Cys Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Lys Thr Tyr Thr Cys
195 200 205

Asn Val Asp His Lys Pro Ser Asn Thr Lys Val Asp Lys Arg Val Glu
210 215 220

Ser Lys Tyr Gly Pro Pro Cys Pro Pro Cys Pro Ala Pro Glu Phe Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

Gln Glu Asp Pro Glu Val Gln Phe Asn Trp Tyr Val Asp Gly Val Glu

-continued

```
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450


<210> SEQ ID NO 75
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

gaggtccagc tggtacagtc tggggctgag gtgaagaagc ctggggctac agtgaaaatc      60

tcctgcaagg tttctggatt taccctcaca aactatggaa tgaactggat caggcagtcc     120

ccatcgagag gccttgagtg gctgggttgg ataaacaccg acactggaga gccaacatat     180

gctgatgact tcaagggaag atttgtcttc tccttggaca cctctgtcag cacggcatat     240

ctgcagatct gcagcctaaa ggctgaggac actgccgtgt attactgtgc aagaaaccct     300

ccctattact acggtactaa taacgcggag gctatggact actggggcca gggcaccacc     360

gtgaccgtgt cctccgcttc caccaagggc ccatccgtct tccccctggc gccctgctcc     420

aggagcacct ccgagagcac agccgccctg ggctgcctgg tcaaggacta cttccccgaa     480

ccggtgacgg tgtcgtggaa ctcaggcgcc ctgaccagcg gcgtgcacac cttcccggct     540

gtcctacagt cctcaggact ctactccctc agcagcgtgg tgaccgtgcc ctccagcagc     600

ttgggcacga agacctacac ctgcaacgta gatcacaagc ccagcaacac caaggtggac     660

aagagagttg agtccaaata tggtccccca tgcccaccgt gcccagcacc tgagttcctg     720

gggggaccat cagtcttcct gttcccccca aaacccaagg acactctcat gatctcccgg     780

acccctgagg tcacgtgcgt ggtggtggac gtgagccagg aagaccccga ggtccagttc     840

aactggtacg tggatggcgt ggaggtgcat aatgccaaga caaagccgcg ggaggagcag     900

ttcaacagca cgtaccgtgt ggtcagcgtc ctcaccgtcc tgcaccagga ctggctgaac     960

ggcaaggagt acaagtgcaa ggtgtccaac aaaggcctcc cgtcctccat cgagaaaacc    1020
```

atctccaaag ccaaagggca gccccgagag ccacaggtgt acaccctgcc cccatcccag 1080
gaggagatga ccaagaacca ggtcagcctg acctgcctgg tcaaaggctt ctaccccagc 1140
gacatcgccg tggagtggga gagcaatggg cagccggaga acaactacaa gaccacgcct 1200
cccgtgctgg actccgacgg ctccttcttc ctctacagca ggctaaccgt ggacaagagc 1260
aggtggcagg aggggaatgt cttctcatgc tccgtgatgc atgaggctct gcacaaccac 1320
tacacacaga agagcctctc cctgtctctg ggtaaa 1356

<210> SEQ ID NO 76
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

Glu Val Gln Leu Val Gln Ser Gly Ala Glu Val Lys Lys Pro Gly Glu
1 5 10 15

Ser Leu Arg Ile Ser Cys Lys Gly Ser Gly Phe Thr Leu Thr Asn Tyr
20 25 30

Gly Met Asn Trp Val Arg Gln Ala Thr Gly Gln Gly Leu Glu Trp Met
35 40 45

Gly Trp Ile Asn Thr Asp Thr Gly Glu Pro Thr Tyr Ala Asp Asp Phe
50 55 60

Lys Gly Arg Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser
115 120 125

<210> SEQ ID NO 77
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77
gaagtgcagc tggtgcagtc tggagcagag gtgaaaaagc ccggggagtc tctgaggatc 60
tcctgtaagg gttctggatt taccctcaca aactatggaa tgaactgggt gcgacaggcc 120
actggacaag ggcttgagtg gatgggttgg ataaacaccg acactggaga gccaacatat 180
gctgatgact tcaagggaag agtcaccatc tcagccgaca agtccatcag caccgcctac 240
ctgcagtgga gcagcctgaa ggcctcggac accgccatgt attactgtgc aagaaaccct 300
ccctattact acggtactaa taacgcggag gctatggact actggggcca gggcaccacc 360
gtgaccgtgt cctcc 375

<210> SEQ ID NO 78
<211> LENGTH: 452
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 78

Glu Val Gln Leu Val Gln Ser Gly Ala Glu Val Lys Lys Pro Gly Glu
1               5                   10                  15

Ser Leu Arg Ile Ser Cys Lys Gly Ser Gly Phe Thr Leu Thr Asn Tyr
            20                  25                  30

Gly Met Asn Trp Val Arg Gln Ala Thr Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
405 410 415

Val Asp Lys Ser Arg Trp Gln Glu Gly Asn Val Phe Ser Cys Ser Val
420 425 430

Met His Glu Ala Leu His Asn His Tyr Thr Gln Lys Ser Leu Ser Leu
435 440 445

Ser Leu Gly Lys
450

<210> SEQ ID NO 79
<211> LENGTH: 1356
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 79
gaagtgcagc tggtgcagtc tggagcagag gtgaaaaagc ccggggagtc tctgaggatc 60
tcctgtaagg gttctggatt taccctcaca aactatggaa tgaactgggt gcgacaggcc 120
actggacaag ggcttgagtg gatgggttgg ataaacaccg acactggaga gccaacatat 180
gctgatgact tcaagggaag agtcaccatc tcagccgaca agtccatcag caccgcctac 240
ctgcagtgga gcagcctgaa ggcctcggac accgccatgt attactgtgc aagaaaccct 300
ccctattact acggtactaa taacgcggag gctatggact actggggcca gggcaccacc 360
gtgaccgtgt cctccgcttc caccaagggc ccatccgtct tccccctggc gccctgctcc 420
aggagcacct ccgagagcac agccgccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcacga agacctacac ctgcaacgta gatcacaagc ccagcaacac caaggtggac 660
aagagagttg agtccaaata tggtccccca tgcccaccgt gcccagcacc tgagttcctg 720
gggggaccat cagtcttcct gttcccccca aaacccaagg acactctcat gatctcccgg 780
acccctgagg tcacgtgcgt ggtggtggac gtgagccagg aagaccccga ggtccagttc 840
aactggtacg tggatggcgt ggaggtgcat aatgccaaga caaagccgcg ggaggagcag 900
ttcaacagca cgtaccgtgt ggtcagcgtc ctcaccgtcc tgcaccagga ctggctgaac 960
ggcaaggagt acaagtgcaa ggtgtccaac aaaggcctcc cgtcctccat cgagaaaacc 1020
atctccaaag ccaaagggca gccccgagag ccacaggtgt acaccctgcc cccatcccag 1080
gaggagatga ccaagaacca ggtcagcctg acctgcctgg tcaaaggctt ctaccccagc 1140
gacatcgccg tggagtggga gagcaatggg cagccggaga acaactacaa gaccacgcct 1200
cccgtgctgg actccgacgg ctccttcttc ctctacagca ggctaaccgt ggacaagagc 1260
aggtggcagg aggggaatgt cttctcatgc tccgtgatgc atgaggctct gcacaaccac 1320
tacacacaga agagcctctc cctgtctctg ggtaaa 1356

<210> SEQ ID NO 80
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Thr Leu Lys Ala Glu Asp Thr Ala Thr Tyr Phe Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125

<210> SEQ ID NO 81
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81
caggtgcagc tggtgcaatc tgggtctgag ttgaagaagc ctggggcctc agtgaaggtt 60
tcctgcaagg cttctggatt caccctgact aactatggca tgaattgggt gcgacaggcc 120
cctggacaag ggcttgagtg gatgggatgg atcaacaccg acactgggga gccaacgtat 180
gccgatgact tcaagggacg gtttgtcttc tccttggaca cctctgtcag cacggcatat 240
ctgcagatca gcacgctaaa ggctgaggac actgctacat atttctgtgc aagaaacccc 300
ccttattact acggtactaa taacgcggag gctatggact actggggcca gggcaccacc 360
gtgaccgtgt cctcc 375

<210> SEQ ID NO 82
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Gln Val Gln Leu Val Gln Ser Gly Ser Glu Leu Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Thr Leu Lys Ala Glu Asp Thr Ala Thr Tyr Phe Cys
                85                  90                  95

-continued

```
Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 83
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caggtgcagc tggtgcaatc tgggtctgag ttgaagaagc ctggggcctc agtgaaggtt 60
tcctgcaagg cttctggatt caccctgact aactatggca tgaattgggt gcgacaggcc 120
cctggacaag ggcttgagtg gatgggatgg atcaacaccg acactgggga gccaacgtat 180
gccgatgact tcaagggacg gtttgtcttc tccttggaca cctctgtcag cacggcatat 240
ctgcagatca gcacgctaaa ggctgaggac actgctacat atttctgtgc aagaaacccc 300
ccttattact acggtactaa taacgcggag gctatggact actggggcca gggcaccacc 360
gtgaccgtgt cctccgcttc caccaagggc ccatccgtct tccccctggc gccctgctcc 420
aggagcacct ccgagagcac agccgccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcacga agacctacac ctgcaacgta gaccacaagc ccagcaacac caaggtggac 660
aagagagttg agtccaaata tggtccccca tgcccaccgt gcccagcacc tgagttcctg 720
gggggaccat cagtcttcct gttcccccca aaacccaagg acactctcat gatctcccgg 780
acccctgagg tcacgtgcgt ggtggtggac gtgagccagg aagaccccga ggtccagttc 840
aactggtacg tggatggcgt ggaggtgcat aatgccaaga caaagccgcg ggaggagcag 900
ttcaacagca cgtaccgtgt ggtcagcgtc ctcaccgtcc tgcaccagga ctggctgaac 960
ggcaaggagt acaagtgcaa ggtgtccaac aaaggcctcc cgtcctccat cgagaaaacc 1020
atctccaaag ccaaagggca gccccgagag ccacaggtgt acaccctgcc cccatcccag 1080
gaggagatga ccaagaacca ggtcagcctg acctgcctgg tcaaaggctt ctaccccagc 1140
gacatcgccg tggagtggga gagcaatggg cagccggaga acaactacaa gaccacgcct 1200
cccgtgctgg actccgacgg ctccttcttc ctctacagca ggctaaccgt ggacaagagc 1260
aggtggcagg aggggaatgt cttctcatgc tccgtgatgc atgaggctct gcacaaccac 1320
tacacacaga agagcctctc cctgtctctg ggtaaa 1356

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 84

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Thr Leu His Leu Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Tyr Asn Leu Pro Trp
85 90 95

Thr Phe Gly Gln Gly Thr Lys Val Glu Ile Lys
100 105

<210> SEQ ID NO 85
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 85
gacatccaga tgacccagtc tccatcctcc ctgtctgcat ctgtaggaga cagagtcacc 60
atcacttgct cctctagtca ggacattagc aactatttaa attggtatca gcagaaacca 120
gggaaagccc ctaagctcct gatctactat acatccactt tgcacctggg ggtcccatca 180
aggttcagtg gaagtggatc tgggacagat tttactttca ccatcagcag cctgcagcct 240
gaagatattg caacatatta ctgtcaacag tattataatc tcccttggac gttcggccaa 300
gggaccaagg tggaaatcaa a 321

<210> SEQ ID NO 86
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Thr Leu His Leu Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Tyr Asn Leu Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 87

<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
gacatccaga tgacccagtc tccatcctcc ctgtctgcat ctgtaggaga cagagtcacc     60

atcacttgct cctctagtca ggacattagc aactatttaa attggtatca gcagaaacca    120

gggaaagccc ctaagctcct gatctactat acatccactt tgcacctggg ggtcccatca    180

aggttcagtg gaagtggatc tgggacagat tttactttca ccatcagcag cctgcagcct    240

gaagatattg caacatatta ctgtcaacag tattataatc tcccttggac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Ala Ile Gln Leu Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 89
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
gccatccagt tgacccagtc tccatcctcc ctgtctgcat ctgtaggaga cagagtcacc     60

atcacttgca gttcaagtca ggacatcagc aattatttaa actggtacca gcagaaacct    120

ggccaggctc ccaggctcct catctattac acatcaacct tacacttagg ggtcccatca    180
```

aggttcagcg gcagtggatc tgggacagat ttcactctca ccatcagcag cctgcagcct 240
gaagattttg caacttatta ctgtcagcag tattataacc ttccgtggac gttcggccaa 300
gggaccaagg tggaaatcaa a 321

<210> SEQ ID NO 90
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Ala Ile Gln Leu Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Gln Gln Lys Pro Gly Gln Ala Pro Arg Leu Leu Ile
35 40 45

Tyr Tyr Thr Ser Thr Leu His Leu Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Asn Leu Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 91
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91
gccatccagt tgacccagtc tccatcctcc ctgtctgcat ctgtaggaga cagagtcacc 60
atcacttgca gttcaagtca ggacatcagc aattatttaa actggtacca gcagaaacct 120
ggccaggctc ccaggctcct catctattac acatcaacct tacacttagg ggtcccatca 180
aggttcagcg gcagtggatc tgggacagat ttcactctca ccatcagcag cctgcagcct 240

```
gaagattttg caacttatta ctgtcagcag tattataacc ttccgtggac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Glu Ile Val Leu Thr Gln Ser Pro Asp Phe Gln Ser Val Thr Pro Lys
1               5                   10                  15

Glu Lys Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 93
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
gaaattgtgc tgactcagtc tccagacttt cagtctgtga ctccaaagga gaaagtcacc     60

atcacctgca gttcaagtca ggacatcagc aattatttaa actggtacca gcagaaacct    120

ggccaggctc ccaggctcct catctattac acatcaacct tacacttagg ggtcccctcg    180

aggttcagtg gcagtggatc tgggacagat ttcaccttta ccatcagtag cctggaagct    240

gaagatgctg caacatatta ctgtcagcag tattataacc ttccgtggac gttcggccaa    300

gggaccaagg tggaaatcaa a                                              321
```

<210> SEQ ID NO 94
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Glu Ile Val Leu Thr Gln Ser Pro Asp Phe Gln Ser Val Thr Pro Lys
1               5                   10                  15

Glu Lys Val Thr Ile Thr Cys Ser Ser Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 95
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
gaaattgtgc tgactcagtc tccagacttt cagtctgtga ctccaaagga gaaagtcacc     60

atcacctgca gttcaagtca ggacatcagc aattatttaa actggtacca gcagaaacct    120

ggccaggctc ccaggctcct catctattac acatcaacct tacacttagg ggtcccctcg    180

aggttcagtg gcagtggatc tgggacagat ttcaccttta ccatcagtag cctggaagct    240

gaagatgctg caacatatta ctgtcagcag tattataacc ttccgtggac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 96
<211> LENGTH: 107

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 96

Asp Ile Val Met Thr Gln Thr Pro Leu Ser Leu Pro Val Thr Pro Gly
1 5 10 15

Glu Pro Ala Ser Ile Ser Cys Ser Ser Ser Gln Asp Ile Ser Asn Tyr
20 25 30

Leu Asn Trp Tyr Gln Gln Lys Pro Gly Gln Ala Pro Arg Leu Leu Ile
35 40 45

Tyr Tyr Thr Ser Thr Leu His Leu Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Tyr Asn Leu Pro Trp
85 90 95

Thr Phe Gly Gln Gly Thr Lys Val Glu Ile Lys
100 105

<210> SEQ ID NO 97
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 97
gatattgtga tgacccagac tccactctcc ctgcccgtca cccctggaga gccggcctcc 60
atctcctgca gttcaagtca ggacatcagc aattatttaa actggtacca gcagaaacct 120
ggccaggctc ccaggctcct catctattac acatcaacct tacacttagg gatcccagac 180
aggttcagtg gcagtgggtc tgggacagac ttcactctca ccatcagcag actggagcct 240
gaagattttg cagtgtatta ctgtcagcag tattataacc ttccgtggac gttcggccaa 300
gggaccaagg tggaaatcaa a 321

<210> SEQ ID NO 98
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 98

Asp Ile Val Met Thr Gln Thr Pro Leu Ser Leu Pro Val Thr Pro Gly
1 5 10 15

Glu Pro Ala Ser Ile Ser Cys Ser Ser Ser Gln Asp Ile Ser Asn Tyr
20 25 30

Leu Asn Trp Tyr Gln Gln Lys Pro Gly Gln Ala Pro Arg Leu Leu Ile
35 40 45

Tyr Tyr Thr Ser Thr Leu His Leu Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Tyr Asn Leu Pro Trp

```
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 99
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
gatattgtga tgacccagac tccactctcc ctgcccgtca cccctggaga gccggcctcc     60

atctcctgca gttcaagtca ggacatcagc aattatttaa actggtacca gcagaaacct    120

ggccaggctc ccaggctcct catctattac acatcaacct tacacttagg gatcccagac    180

aggttcagtg gcagtgggtc tgggacagac ttcactctca ccatcagcag actggagcct    240

gaagattttg cagtgtatta ctgtcagcag tattataacc ttccgtggac gttcggccaa    300

gggaccaagg tggaaatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 100
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Val Arg Gln Ala Pro Gly Gln Gly Leu Glu Trp Met
        35                  40                  45
```

-continued

```
Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125


<210> SEQ ID NO 101
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

gaggtccagc tggtacagtc tggggctgag gtgaagaagc ctggggctac agtgaaaatc     60

tcctgcaagg tttctggatt taccctcaca aactatggaa tgaactgggt gcgacaggcc    120

cctggacaag ggcttgagtg gatgggttgg ataaacaccg acactggaga gccaacatat    180

gctgatgact tcaagggaag atttgtcttc tccttggaca cctctgtcag cacggcatat    240

ctgcagatca gcagcctaaa ggctgaggac actgccgtgt attactgtgc aagaaaccct    300

ccctattact acggtactaa taacgcggag gctatggact actggggcca gggcaccacc    360

gtgaccgtgt cctcc                                                      375


<210> SEQ ID NO 102
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Gln Ser Gly Ala Glu Val Lys Lys Pro Gly Ala
1               5                   10                  15

Thr Val Lys Ile Ser Cys Lys Val Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
```

```
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 103
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
gaggtccagc tggtacagtc tggggctgag gtgaagaagc ctggggctac agtgaaaatc     60

tcctgcaagg tttctggatt taccctcaca aactatggaa tgaactgggt gcgacaggcc    120

cctggacaag ggcttgagtg gatgggttgg ataaacaccg acactggaga gccaacatat    180

gctgatgact tcaagggaag atttgtcttc tccttggaca cctctgtcag cacggcatat    240

ctgcagatca gcagcctaaa ggctgaggac actgccgtgt attactgtgc aagaaaccct    300
```

-continued

```
ccctattact acggtactaa taacgcggag gctatggact actggggcca gggcaccacc    360

gtgaccgtgt cctccgcttc caccaagggc ccatccgtct tccccctggc gccctgctcc    420

aggagcacct ccgagagcac agccgccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcacga agacctacac ctgcaacgta gatcacaagc ccagcaacac caaggtggac    660

aagagagttg agtccaaata tggtccccca tgcccaccgt gcccagcacc tgagttcctg    720

gggggaccat cagtcttcct gttcccccca aaacccaagg acactctcat gatctcccgg    780

acccctgagg tcacgtgcgt ggtggtggac gtgagccagg aagaccccga ggtccagttc    840

aactggtacg tggatggcgt ggaggtgcat aatgccaaga caaagccgcg ggaggagcag    900

ttcaacagca cgtaccgtgt ggtcagcgtc ctcaccgtcc tgcaccagga ctggctgaac    960

ggcaaggagt acaagtgcaa ggtgtccaac aaaggcctcc cgtcctccat cgagaaaacc   1020

atctccaaag ccaaagggca gccccgagag ccacaggtgt acaccctgcc cccatcccag   1080

gaggagatga ccaagaacca ggtcagcctg acctgcctgg tcaaaggctt ctaccccagc   1140

gacatcgccg tggagtggga gagcaatggg cagccggaga acaactacaa gaccacgcct   1200

cccgtgctgg actccgacgg ctccttcttc ctctacagca ggctaaccgt ggacaagagc   1260

aggtggcagg aggggaatgt cttctcatgc tccgtgatgc atgaggctct gcacaaccac   1320

tacacacaga agagcctctc cctgtctctg ggtaaa                              1356
```

<210> SEQ ID NO 104
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125
```

<210> SEQ ID NO 105
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
caggttcagc tggtgcagtc tggagctgag gtgaagaagc ctggggcctc agtgaaggtc     60
tcctgcaagg cttctggatt taccctcaca aactatggaa tgaactgggt gcgacaggct    120
cgtggacaac gccttgagtg gataggttgg ataaacaccg acactggaga gccaacatat    180
gctgatgact tcaagggaag atttgtcttc tccttggaca cctctgtcag cacggcatat    240
ctgcagatca gcagcctaaa ggctgaggac actgccgtgt attactgtgc aagaaaccct    300
ccctattact acggtactaa taacgcggag gctatggact actggggcca gggcaccacc    360
gtgaccgtgt cctcc                                                     375
```

<210> SEQ ID NO 106
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450
```

<210> SEQ ID NO 107
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
caggttcagc tggtgcagtc tggagctgag gtgaagaagc ctggggcctc agtgaaggtc     60

tcctgcaagg cttctggatt taccctcaca aactatggaa tgaactgggt gcgacaggct    120

cgtggacaac gccttgagtg gataggttgg ataaacaccg acactggaga gccaacatat    180

gctgatgact tcaagggaag atttgtcttc tccttggaca cctctgtcag cacggcatat    240

ctgcagatca gcagcctaaa ggctgaggac actgccgtgt attactgtgc aagaaaccct    300

ccctattact acggtactaa taacgcggag gctatggact actggggcca gggcaccacc    360

gtgaccgtgt cctccgcttc caccaagggc ccatccgtct tccccctggc gccctgctcc    420

aggagcacct ccgagagcac agccgccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcacga agacctacac ctgcaacgta gatcacaagc ccagcaacac caaggtggac    660

aagagagttg agtccaaata tggtccccca tgcccaccgt gcccagcacc tgagttcctg    720

gggggaccat cagtcttcct gttcccccca aaacccaagg acactctcat gatctcccgg    780

acccctgagg tcacgtgcgt ggtggtggac gtgagccagg aagaccccga ggtccagttc    840

aactggtacg tggatggcgt ggaggtgcat aatgccaaga caaagccgcg ggaggagcag    900

ttcaacagca cgtaccgtgt ggtcagcgtc ctcaccgtcc tgcaccagga ctggctgaac    960
```

```
ggcaaggagt acaagtgcaa ggtgtccaac aaaggcctcc cgtcctccat cgagaaaacc   1020

atctccaaag ccaaagggca gccccgagag ccacaggtgt acaccctgcc cccatcccag   1080

gaggagatga ccaagaacca ggtcagcctg acctgcctgg tcaaaggctt ctaccccagc   1140

gacatcgccg tggagtggga gagcaatggg cagccggaga acaactacaa gaccacgcct   1200

cccgtgctgg actccgacgg ctccttcttc ctctacagca ggctaaccgt ggacaagagc   1260

aggtggcagg aggggaatgt cttctcatgc tccgtgatgc atgaggctct gcacaaccac   1320

tacacacaga agagcctctc cctgtctctg ggtaaa                             1356
```

<210> SEQ ID NO 108
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125
```

<210> SEQ ID NO 109
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

```
caggttcagc tggtgcagtc cggagctgag gtgaagaagc ctggggcctc agtgaaggtc     60

tcctgcaagg cttctggatt taccctcaca aactatggaa tgaactgggt gcgacaggcc    120

cctggacaag ggcttgagtg gatgggttgg ataaacaccg acactggaga gccaacatat    180

gctgatgact tcaagggaag atttgtcttc tccttggaca cctctgtcag cacggcatat    240

ctgcagatca gcagcctaaa ggctgaggac actgccgtgt attactgtgc aagaaaccct    300

ccctattact acggtactaa taacgcggag gctatggact actggggcca gggcaccacc    360

gtgaccgtgt cctcc                                                     375
```

<210> SEQ ID NO 110
<211> LENGTH: 452
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 110

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Leu Thr Asn Tyr
20 25 30

Gly Met Asn Trp Val Arg Gln Ala Pro Gly Gln Gly Leu Glu Trp Met
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Lys Thr Tyr Thr Cys
195 200 205

Asn Val Asp His Lys Pro Ser Asn Thr Lys Val Asp Lys Arg Val Glu
210 215 220

Ser Lys Tyr Gly Pro Pro Cys Pro Pro Cys Pro Ala Pro Glu Phe Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

Gln Glu Asp Pro Glu Val Gln Phe Asn Trp Tyr Val Asp Gly Val Glu
275 280 285

Val His Asn Ala Lys Thr Lys Pro Arg Glu Glu Gln Phe Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Gly Leu Pro Ser Ser
325 330 335

Ile Glu Lys Thr Ile Ser Lys Ala Lys Gly Gln Pro Arg Glu Pro Gln
340 345 350

Val Tyr Thr Leu Pro Pro Ser Gln Glu Glu Met Thr Lys Asn Gln Val
355 360 365

Ser Leu Thr Cys Leu Val Lys Gly Phe Tyr Pro Ser Asp Ile Ala Val
370 375 380

-continued

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Arg Leu Thr
405 410 415

Val Asp Lys Ser Arg Trp Gln Glu Gly Asn Val Phe Ser Cys Ser Val
420 425 430

Met His Glu Ala Leu His Asn His Tyr Thr Gln Lys Ser Leu Ser Leu
435 440 445

Ser Leu Gly Lys
450

<210> SEQ ID NO 111
<211> LENGTH: 1356
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111
caggttcagc tggtgcagtc cggagctgag gtgaagaagc ctggggcctc agtgaaggtc 60
tcctgcaagg cttctggatt taccctcaca aactatggaa tgaactgggt gcgacaggcc 120
cctggacaag ggcttgagtg gatgggttgg ataaacaccg acactggaga gccaacatat 180
gctgatgact tcaagggaag atttgtcttc tccttggaca cctctgtcag cacggcatat 240
ctgcagatca gcagcctaaa ggctgaggac actgccgtgt attactgtgc aagaaaccct 300
ccctattact acggtactaa taacgcggag gctatggact actggggcca gggcaccacc 360
gtgaccgtgt cctccgcttc caccaagggc ccatccgtct tcccctggc gccctgctcc 420 aggagcacct ccgagagcac agccgccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcacga agacctacac ctgcaacgta gatcacaagc ccagcaacac caaggtggac 660
aagagagttg agtccaaata tggtccccca tgcccaccgt gcccagcacc tgagttcctg 720
gggggaccat cagtcttcct gttcccccca aaacccaagg acactctcat gatctcccgg 780
acccctgagg tcacgtgcgt ggtggtggac gtgagccagg aagaccccga ggtccagttc 840
aactggtacg tggatggcgt ggaggtgcat aatgccaaga caaagccgcg ggaggagcag 900
ttcaacagca cgtaccgtgt ggtcagcgtc ctcaccgtcc tgcaccagga ctggctgaac 960
ggcaaggagt acaagtgcaa ggtgtccaac aaaggcctcc cgtcctccat cgagaaaacc 1020
atctccaaag ccaaagggca gccccgagag ccacaggtgt acaccctgcc cccatcccag 1080
gaggagatga ccaagaacca ggtcagcctg acctgcctgg tcaaaggctt ctaccccagc 1140
gacatcgccg tggagtggga gagcaatggg cagccggaga acaactacaa gaccacgcct 1200
cccgtgctgg actccgacgg ctccttcttc ctctacagca ggctaaccgt ggacaagagc 1260
aggtggcagg aggggaatgt cttctcatgc tccgtgatgc atgaggctct gcacaaccac 1320
tacacacaga agagcctctc cctgtctctg ggtaaa 1356

<210> SEQ ID NO 112
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112
gaagtgcagc tggtgcagtc tggcgccgaa gtgaagaaac ccggcgctac cgtgaagatc 60
tcctgcaagg tgtccggctt caccctgacc aactacggca tgaactgggt gcgacaggcc 120
cctggacagg gcctggaatg gatgggctgg atcaacaccg acaccggcga gcctacctac 180
gccgacgact tcaagggcag attcgtgttc tccctggaca cctccgtgtc caccgcctac 240
ctgcagatct ccagcctgaa ggccgaggat accgccgtgt actactgcgc ccggaacccc 300
ccttactact acggcaccaa caacgccgag gccatggact attggggcca gggcaccacc 360
gtgaccgtgt cctct 375

<210> SEQ ID NO 113
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

Glu Val Gln Leu Val Gln Ser Gly Ala Glu Val Lys Lys Pro Gly Ala
1 5 10 15

Thr Val Lys Ile Ser Cys Lys Val Ser Gly Phe Thr Leu Thr Asn Tyr
20 25 30

Gly Met Asn Trp Val Arg Gln Ala Pro Gly Gln Gly Leu Glu Trp Met
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Lys Thr Tyr Thr Cys
195 200 205

Asn Val Asp His Lys Pro Ser Asn Thr Lys Val Asp Lys Arg Val Glu
210 215 220

Ser Lys Tyr Gly Pro Pro Cys Pro Pro Cys Pro Ala Pro Glu Phe Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

```
Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450


<210> SEQ ID NO 114
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

gaagtgcagc tggtgcagtc tggcgccgaa gtgaagaaac ccggcgctac cgtgaagatc      60

tcctgcaagg tgtccggctt caccctgacc aactacggca tgaactgggt gcgacaggcc     120

cctggacagg gcctggaatg gatgggctgg atcaacaccg acaccggcga gcctacctac     180

gccgacgact tcaagggcag attcgtgttc tccctggaca cctccgtgtc caccgcctac     240

ctgcagatct ccagcctgaa ggccgaggat accgccgtgt actactgcgc ccggaacccc     300

ccttactact acggcaccaa caacgccgag gccatggact attggggcca gggcaccacc     360

gtgaccgtgt cctctgcttc taccaagggg cccagcgtgt tcccccctggc cccctgctcc     420

agaagcacca gcgagagcac agccgccctg ggctgcctgg tgaaggacta cttccccgag     480

cccgtgaccg tgtcctggaa cagcggagcc ctgaccagcg gcgtgcacac cttccccgcc     540

gtgctgcaga gcagcggcct gtacagcctg agcagcgtgg tgaccgtgcc cagcagcagc     600

ctgggcacca agacctacac ctgtaacgtg gaccacaagc ccagcaacac caaggtggac     660

aagagggtgg agagcaagta cggcccaccc tgccccccct gcccagcccc cgagttcctg     720

ggcggaccca gcgtgttcct gttccccccc aagcccaagg acaccctgat gatcagcaga     780

acccccgagg tgacctgtgt ggtggtggac gtgtcccagg aggaccccga ggtccagttc     840

aactggtacg tggacggcgt ggaggtgcac aacgccaaga ccaagcccag agaggagcag     900

tttaacagca cctaccgggt ggtgtccgtg ctgaccgtgc tgcaccagga ctggctgaac     960
```

ggcaaagagt acaagtgtaa ggtctccaac aagggcctgc caagcagcat cgaaaagacc 1020
atcagcaagg ccaagggcca gcctagagag ccccaggtct acaccctgcc acccagccaa 1080
gaggagatga ccaagaacca ggtgtccctg acctgtctgg tgaagggctt ctacccaagc 1140
gacatcgccg tggagtggga gagcaacggc cagcccgaga acaactacaa gaccaccccc 1200
ccagtgctgg acagcgacgg cagcttcttc ctgtacagca ggctgaccgt ggacaagtcc 1260
agatggcagg agggcaacgt ctttagctgc tccgtgatgc acgaggccct gcacaaccac 1320
tacacccaga agagcctgag cctgtccctg ggc 1353

<210> SEQ ID NO 115
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 115
gacatccaga tgacccagtc cccctccagc ctgtctgctt ccgtgggcga cagagtgacc 60
atcacctgtt cctccagcca ggacatctcc aactacctga actggtatca gcagaagccc 120
ggcaaggccc ccaagctgct gatctactac acctccaccc tgcacctggg cgtgccctcc 180
agattttccg gctctggctc tggcaccgac tttaccttca ccatcagctc cctggaagcc 240
gaggacgccg ccacctacta ctgccagcag tactacaacc tgccctggac cttcggccag 300
ggcaccaagg tggaaatcaa g 321

<210> SEQ ID NO 116

<400> SEQUENCE: 116

000

<210> SEQ ID NO 117
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117
gacatccaga tgacccagtc cccctccagc ctgtctgctt ccgtgggcga cagagtgacc 60
atcacctgtt cctccagcca ggacatctcc aactacctga actggtatca gcagaagccc 120
ggcaaggccc ccaagctgct gatctactac acctccaccc tgcacctggg cgtgccctcc 180
agattttccg gctctggctc tggcaccgac tttaccttca ccatcagctc cctggaagcc 240
gaggacgccg ccacctacta ctgccagcag tactacaacc tgccctggac cttcggccag 300
ggcaccaagg tggaaatcaa gcgtacggtg gccgctccca gcgtgttcat cttccccccca 360 agcgacgagc agctgaagag cggcaccgcc agcgtggtgt gtctgctgaa caacttctac 420
cccagggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac aggggcgagt gc 642

<210> SEQ ID NO 118
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 118
gacatccaga tgacccagtc cccctccagc ctgtctgctt ccgtgggcga cagagtgacc 60
atcacctgtt cctccagcca ggacatctcc aactacctga actggtatca gcagaagccc 120
ggcaaggccc ccaagctgct gatctactac acctccaccc tgcacctggg catccccct 180 agattctccg gctctggcta cggcaccgac ttcaccctga ccatcaacaa catcgagtcc 240
gaggacgccg cctactactt ctgccagcag tactacaacc tgccctggac cttcggccag 300
ggcaccaagg tggaaatcaa g 321

<210> SEQ ID NO 119

<400> SEQUENCE: 119

000

<210> SEQ ID NO 120
<211> LENGTH: 652
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 120
gacatccaga tgacccagtc cccctccagc ctgtctgctt ccgtgggcga cagagtgacc 60
atcacctgtt cctccagcca ggacatctcc aactacctga actggtatca gcagaagccc 120
ggcaaggccc ccaagctgct gatctactac acctccaccc tgcacctggg catccccct 180 agattctccg gctctggcta cggcaccgac ttcaccctga ccatcaacaa catcgagtcc 240
gaggacgccg cctactactt ctgccagcag tactacaacc tgccctggac cttcggccag 300
ggcaccaagg tggaaatcaa gcgtacggtg gccgctccca gcgtgttcat cttcccccca 360
agcgacgagc agctgaagag cggcaccgcc agcgtggtgt gtctgctgaa caacttctac 420
cccagggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac aggggcgagt gctgatgaat tc 652

<210> SEQ ID NO 121
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 121
caggtgcagc tggtgcagtc tggcgccgaa gtgaagaaac ctggcgcctc cgtgaaggtg 60
tcctgcaagg cctctggctt caccctgacc aactacggca tgaactgggt gcgacaggcc 120
aggggccagc ggctggaatg gatcggctgg atcaacaccg acaccggcga gcctacctac 180

-continued

```
gccgacgact tcaagggcag attcgtgttc tccctggaca cctccgtgtc caccgcctac    240

ctgcagatct ccagcctgaa ggccgaggat accgccgtgt actactgcgc ccggaacccc    300

ccttactact acggcaccaa caacgccgag gccatggact attggggcca gggcaccacc    360

gtgaccgtgt cctct                                                     375


<210> SEQ ID NO 122
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30

Gly Met Asn Trp Val Arg Gln Ala Arg Gly Gln Arg Leu Glu Trp Ile
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320
```

-continued

```
Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450
```

<210> SEQ ID NO 123
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
caggtgcagc tggtgcagtc tggcgccgaa gtgaagaaac ctggcgcctc cgtgaaggtg     60

tcctgcaagg cctctggctt caccctgacc aactacggca tgaactgggt gcgacaggcc    120

aggggccagc ggctggaatg gatcggctgg atcaacaccg acaccggcga gcctacctac    180

gccgacgact tcaagggcag attcgtgttc tccctggaca cctccgtgtc caccgcctac    240

ctgcagatct ccagcctgaa ggccgaggat accgccgtgt actactgcgc ccggaacccc    300

ccttactact acggcaccaa caacgccgag gccatggact attggggcca gggcaccacc    360

gtgaccgtgt cctctgcttc taccaagggg cccagcgtgt tcccccctggc cccctgctcc    420

agaagcacca gcgagagcac agccgccctg ggctgcctgg tgaaggacta cttccccgag    480

cccgtgaccg tgtcctggaa cagcggagcc ctgaccagcg gcgtgcacac cttccccgcc    540

gtgctgcaga gcagcggcct gtacagcctg agcagcgtgg tgaccgtgcc cagcagcagc    600

ctgggcacca agacctacac ctgtaacgtg gaccacaagc ccagcaacac caaggtggac    660

aagagggtgg agagcaagta cggcccaccc tgccccccct gcccagcccc cgagttcctg    720

ggcggaccca gcgtgttcct gttccccccc aagcccaagg acaccctgat gatcagcaga    780

acccccgagg tgacctgtgt ggtggtggac gtgtcccagg aggaccccga ggtccagttc    840

aactggtacg tggacggcgt ggaggtgcac aacgccaaga ccaagcccag agaggagcag    900

tttaacagca cctaccgggt ggtgtccgtg ctgaccgtgc tgcaccagga ctggctgaac    960

ggcaaagagt acaagtgtaa ggtctccaac aagggcctgc caagcagcat cgaaaagacc   1020

atcagcaagg ccaagggcca gcctagagag ccccaggtct acaccctgcc acccagccaa   1080

gaggagatga ccaagaacca ggtgtccctg acctgtctgg tgaagggctt ctacccaagc   1140

gacatcgccg tggagtggga gagcaacggc cagcccgaga acaactacaa gaccaccccc   1200

ccagtgctgg acagcgacgg cagcttcttc ctgtacagca ggctgaccgt ggacaagtcc   1260
```

agatggcagg agggcaacgt ctttagctgc tccgtgatgc acgaggccct gcacaaccac 1320
tacacccaga agagcctgag cctgtccctg ggc 1353

<210> SEQ ID NO 124
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124
caagtgcagc tggtgcagtc gggagccgaa gtgaagaagc ctggagcctc ggtgaaggtg 60
tcgtgcaagg catccggatt caccctcacc aattacggga tgaactgggt cagacaggcc 120
cggggtcaac ggctggagtg gatcggatgg attaacaccg acaccgggga gcctacctac 180
gcggacgatt tcaagggacg gttcgtgttc tccctcgaca cctccgtgtc caccgcctac 240
ctccaaatct cctcactgaa agcggaggac accgccgtgt actattgcgc gaggaacccg 300
ccctactact acggaaccaa caacgccgaa gccatggact actggggcca gggcaccact 360
gtgactgtgt ccagc 375

<210> SEQ ID NO 125
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125
caggtgcagc tggtgcagtc tggcgccgaa gtgaagaaac ctggcgcctc cgtgaaggtg 60
tcctgcaagg cctctggctt caccctgacc aactacggca tgaactgggt gcgacaggcc 120
aggggccagc ggctggaatg gatcggctgg atcaacaccg acaccggcga gcctacctac 180
gccgacgact tcaagggcag attcgtgttc tccctggaca cctccgtgtc caccgcctac 240
ctgcagatct ccagcctgaa ggccgaggat accgccgtgt actactgcgc ccggaacccc 300
ccttactact acggcaccaa caacgccgag gccatggact attggggcca gggcaccacc 360
gtgaccgtgt cctct 375

<210> SEQ ID NO 126
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126
caagtgcagc tggtgcagtc gggagccgaa gtgaagaagc ctggagcctc ggtgaaggtg 60
tcgtgcaagg catccggatt caccctcacc aattacggga tgaactgggt cagacaggcc 120
cggggtcaac ggctggagtg gatcggatgg attaacaccg acaccgggga gcctacctac 180
gcggacgatt tcaagggacg gttcgtgttc tccctcgaca cctccgtgtc caccgcctac 240
ctccaaatct cctcactgaa agcggaggac accgccgtgt actattgcgc gaggaacccg 300
ccctactact acggaaccaa caacgccgaa gccatggact actggggcca gggcaccact 360
gtgactgtgt ccagcgcgtc cactaagggc ccgtccgtgt tccccctggc accttgtagc 420
cggagcacta gcgaatccac cgctgccctc ggctgcctgg tcaaggatta cttcccggag 480
cccgtgaccg tgtcctggaa cagcggagcc ctgacctccg gagtgcacac cttccccgct 540
gtgctgcaga gctccgggct gtactcgctg tcgtcggtgg tcacggtgcc ttcatctagc 600
ctgggtacca agacctacac ttgcaacgtg gaccacaagc cttccaacac taaggtggac 660
aagcgcgtcg aatcgaagta cggcccaccg tgcccgcctt gtcccgcgcc ggagttcctc 720
ggcggtccct cggtctttct gttcccaccg aagcccaagg acactttgat gatttcccgc 780
acccctgaag tgacatgcgt ggtcgtggac gtgtcacagg aagatccgga ggtgcagttc 840
aattggtacg tggatggcgt cgaggtgcac aacgccaaaa ccaagccgag ggaggagcag 900
ttcaactcca cttaccgcgt cgtgtccgtg ctgacggtgc tgcatcagga ctggctgaac 960
gggaaggagt acaagtgcaa agtgtccaac aagggacttc ctagctcaat cgaaaagacc 1020
atctcgaaag ccaagggaca gccccgggaa ccccaagtgt ataccctgcc accgagccag 1080
gaagaaatga ctaagaacca agtctcattg acttgccttg tgaagggctt ctacccatcg 1140
gatatcgccg tggaatggga gtccaacggc cagccggaaa acaactacaa gaccacccct 1200
ccggtgctgg actcagacgg atccttcttc ctctactcgc ggctgaccgt ggataagagc 1260
agatggcagg agggaaatgt gttcagctgt tctgtgatgc atgaagccct gcacaaccac 1320
tacactcaga agtccctgtc cctctccctg gga 1353

<210> SEQ ID NO 127
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
caggtgcagc tggtgcagtc tggcgccgaa gtgaagaaac ctggcgcctc cgtgaaggtg 60
tcctgcaagg cctctggctt caccctgacc aactacggca tgaactgggt gcgacaggcc 120
aggggccagc ggctggaatg gatcggctgg atcaacaccg acaccggcga gcctacctac 180
gccgacgact tcaagggcag attcgtgttc tccctggaca cctccgtgtc caccgcctac 240
ctgcagatct ccagcctgaa ggccgaggat accgccgtgt actactgcgc ccggaacccc 300
ccttactact acggcaccaa caacgccgag gccatggact attggggcca gggcaccacc 360
gtgaccgtgt cctctgcttc taccaagggg cccagcgtgt tcccccctggc cccctgctcc 420 agaagcacca gcgagagcac agccgccctg ggctgcctgg tgaaggacta cttccccgag 480
cccgtgaccg tgtcctggaa cagcggagcc ctgaccagcg gcgtgcacac cttccccgcc 540
gtgctgcaga gcagcggcct gtacagcctg agcagcgtgg tgaccgtgcc cagcagcagc 600
ctgggcacca agacctacac ctgtaacgtg gaccacaagc ccagcaacac caaggtggac 660
aagagggtgg agagcaagta cggcccaccc tgcccccct gcccagcccc cgagttcctg 720
ggcggaccca gcgtgttcct gttccccccc aagcccaagg acaccctgat gatcagcaga 780
acccccgagg tgacctgtgt ggtggtggac gtgtcccagg aggaccccga ggtccagttc 840
aactggtacg tggacggcgt ggaggtgcac aacgccaaga ccaagcccag agaggagcag 900
tttaacagca cctaccgggt ggtgtccgtg ctgaccgtgc tgcaccagga ctggctgaac 960
ggcaaagagt acaagtgtaa ggtctccaac aagggcctgc caagcagcat cgaaaagacc 1020
atcagcaagg ccaagggcca gcctagagag ccccaggtct acaccctgcc acccagccaa 1080
gaggagatga ccaagaacca ggtgtccctg acctgtctgg tgaagggctt ctacccaagc 1140
gacatcgccg tggagtggga gagcaacggc cagcccgaga acaactacaa gaccaccccc 1200
ccagtgctgg acagcgacgg cagcttcttc ctgtacagca ggctgaccgt ggacaagtcc 1260
agatggcagg agggcaacgt ctttagctgc tccgtgatgc acgaggccct gcacaaccac 1320
tacacccaga agagcctgag cctgtccctg ggc 1353

<210> SEQ ID NO 128
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128
gatattcaga tgactcagtc acctagtagc ctgagcgcta gtgtgggcga tagagtgact 60
atcacctgta gctctagtca ggatatctct aactacctga actggtatct gcagaagccc 120
ggtcaatcac ctcagctgct gatctactac actagcaccc tgcacctggg cgtgccctct 180
aggtttagcg gtagcggtag tggcaccgag ttcaccctga ctatctctag cctgcagccc 240
gacgacttcg ctacctacta ctgtcagcag tactataacc tgccctggac cttcggtcaa 300
ggcactaagg tcgagattaa g 321

<210> SEQ ID NO 129
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129
gacatccaga tgacccagtc cccctccagc ctgtctgctt ccgtgggcga cagagtgacc 60
atcacctgtt cctccagcca ggacatctcc aactacctga actggtatct gcagaagccc 120
ggccagtccc ctcagctgct gatctactac acctccaccc tgcacctggg cgtgccctcc 180
agattttccg gctctggctc tggcaccgag tttaccctga ccatcagctc cctgcagccc 240
gacgacttcg ccacctacta ctgccagcag tactacaacc tgccctggac cttcggccag 300
ggcaccaagg tggaaatcaa g 321

<210> SEQ ID NO 130
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130
gatattcaga tgactcagtc acctagtagc ctgagcgcta gtgtgggcga tagagtgact 60
atcacctgta gctctagtca ggatatctct aactacctga actggtatct gcagaagccc 120
ggtcaatcac ctcagctgct gatctactac actagcaccc tgcacctggg cgtgccctct 180
aggtttagcg gtagcggtag tggcaccgag ttcaccctga ctatctctag cctgcagccc 240
gacgacttcg ctacctacta ctgtcagcag tactataacc tgccctggac cttcggtcaa 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 131
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 131
gacatccaga tgacccagtc cccctccagc ctgtctgctt ccgtgggcga cagagtgacc 60
atcacctgtt cctccagcca ggacatctcc aactacctga actggtatct gcagaagccc 120
ggccagtccc ctcagctgct gatctactac acctccaccc tgcacctggg cgtgccctcc 180
agattttccg gctctggctc tggcaccgag tttaccctga ccatcagctc cctgcagccc 240
gacgacttcg ccacctacta ctgccagcag tactacaacc tgccctggac cttcggccag 300
ggcaccaagg tggaaatcaa gcgtacggtg gccgctccca gcgtgttcat cttccccccca 360 agcgacgagc agctgaagag cggcaccgcc agcgtggtgt gtctgctgaa caacttctac 420
cccagggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac aggggcgagt gc 642

<210> SEQ ID NO 132
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 132
caggtgcagc tggtgcagtc aggcgccgaa gtgaagaaac ccggcgctag tgtgaaagtc 60
agctgtaaag ctagtggctt caccctgact aactacggga tgaactgggt ccgccaggcc 120
ccaggtcaag gcctcgagtg gatgggctgg attaacaccg acaccggcga gcctacctac 180
gccgacgact ttaagggcag attcgtgttt agcctggaca ctagtgtgtc taccgcctac 240
ctgcagatct ctagcctgaa ggccgaggac accgccgtct actactgcgc tagaaacccc 300
ccctactact acggcactaa caacgccgag gctatggact actggggtca aggcactacc 360
gtgaccgtgt ctagc 375

<210> SEQ ID NO 133
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 133
caggtgcagc tggtgcagtc tggcgccgaa gtgaagaaac ctggcgcctc cgtgaaggtg 60
tcctgcaagg cctctggctt caccctgacc aactacggca tgaactgggt gcgacaggcc 120
cctggacagg gcctggaatg gatgggctgg atcaacaccg acaccggcga gcctacctac 180
gccgacgact tcaagggcag attcgtgttc tccctggaca cctccgtgtc caccgcctac 240
ctgcagatct ccagcctgaa ggccgaggat accgccgtgt actactgcgc ccggaacccc 300
ccttactact acggcaccaa caacgccgag gccatggact attggggcca gggcaccacc 360
gtgaccgtgt cctct 375

<210> SEQ ID NO 134
<211> LENGTH: 451
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 134

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Leu Thr Asn Tyr
20 25 30

Gly Met Asn Trp Val Arg Gln Ala Pro Gly Gln Gly Leu Glu Trp Met
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Lys Thr Tyr Thr Cys
195 200 205

Asn Val Asp His Lys Pro Ser Asn Thr Lys Val Asp Lys Arg Val Glu
210 215 220

Ser Lys Tyr Gly Pro Pro Cys Pro Pro Cys Pro Ala Pro Glu Phe Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

Gln Glu Asp Pro Glu Val Gln Phe Asn Trp Tyr Val Asp Gly Val Glu
275 280 285

```
Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450


<210> SEQ ID NO 135
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

caggtgcagc tggtgcagtc aggcgccgaa gtgaagaaac ccggcgctag tgtgaaagtc     60

agctgtaaag ctagtggctt caccctgact aactacggga tgaactgggt ccgccaggcc    120

ccaggtcaag gcctcgagtg gatgggctgg attaacaccg acaccggcga gcctacctac    180

gccgacgact ttaagggcag attcgtgttt agcctggaca ctagtgtgtc taccgcctac    240

ctgcagatct ctagcctgaa ggccgaggac accgccgtct actactgcgc tagaaacccc    300

ccctactact acggcactaa caacgccgag gctatggact actggggtca aggcactacc    360

gtgaccgtgt ctagcgctag cactaagggc ccgtccgtgt tccccctggc accttgtagc    420

cggagcacta gcgaatccac cgctgccctc ggctgcctgg tcaaggatta cttcccggag    480

cccgtgaccg tgtcctggaa cagcggagcc ctgacctccg gagtgcacac cttccccgct    540

gtgctgcaga gctccgggct gtactcgctg tcgtcggtgg tcacggtgcc ttcatctagc    600

ctgggtacca agacctacac ttgcaacgtg gaccacaagc cttccaacac taaggtggac    660

aagcgcgtcg aatcgaagta cggcccaccg tgcccgcctt gtcccgcgcc ggagttcctc    720

ggcggtccct cggtctttct gttcccaccg aagcccaagg acactttgat gatttcccgc    780

acccctgaag tgacatgcgt ggtcgtggac gtgtcacagg aagatccgga ggtgcagttc    840

aattggtacg tggatggcgt cgaggtgcac aacgccaaaa ccaagccgag ggaggagcag    900

ttcaactcca cttaccgcgt cgtgtccgtg ctgacggtgc tgcatcagga ctggctgaac    960

gggaaggagt acaagtgcaa agtgtccaac aagggacttc ctagctcaat cgaaaagacc   1020
```

-continued

```
atctcgaaag ccaagggaca gccccgggaa ccccaagtgt ataccctgcc accgagccag   1080

gaagaaatga ctaagaacca agtctcattg acttgccttg tgaagggctt ctacccatcg   1140

gatatcgccg tggaatggga gtccaacggc cagccggaaa acaactacaa gaccacccct   1200

ccggtgctgg actcagacgg atccttcttc ctctactcgc ggctgaccgt ggataagagc   1260

agatggcagg agggaaatgt gttcagctgt tctgtgatgc atgaagccct gcacaaccac   1320

tacactcaga agtccctgtc cctctccctg gga                                1353
```

<210> SEQ ID NO 136
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

```
caggtgcagc tggtgcagtc tggcgccgaa gtgaagaaac ctggcgcctc cgtgaaggtg     60

tcctgcaagg cctctggctt caccctgacc aactacggca tgaactgggt gcgacaggcc    120

cctggacagg gcctggaatg gatgggctgg atcaacaccg acaccggcga gcctacctac    180

gccgacgact tcaagggcag attcgtgttc tccctggaca cctccgtgtc caccgcctac    240

ctgcagatct ccagcctgaa ggccgaggat accgccgtgt actactgcgc ccggaacccc    300

ccttactact acggcaccaa caacgccgag gccatggact attggggcca gggcaccacc    360

gtgaccgtgt cctctgcttc taccaagggg cccagcgtgt tcccccctggc cccctgctcc    420

agaagcacca gcgagagcac agccgccctg ggctgcctgg tgaaggacta cttccccgag    480

cccgtgaccg tgtcctggaa cagcggagcc ctgaccagcg gcgtgcacac cttccccgcc    540

gtgctgcaga gcagcggcct gtacagcctg agcagcgtgg tgaccgtgcc cagcagcagc    600

ctgggcacca agacctacac ctgtaacgtg gaccacaagc ccagcaacac caaggtggac    660

aagagggtgg agagcaagta cggcccaccc tgcccccccct gcccagcccc cgagttcctg    720

ggcggaccca gcgtgttcct gttccccccc aagcccaagg acaccctgat gatcagcaga    780

acccccgagg tgacctgtgt ggtggtggac gtgtcccagg aggaccccga ggtccagttc    840

aactggtacg tggacggcgt ggaggtgcac aacgccaaga ccaagcccag agaggagcag    900

tttaacagca cctaccgggt ggtgtccgtg ctgaccgtgc tgcaccagga ctggctgaac    960

ggcaaagagt acaagtgtaa ggtctccaac aagggcctgc caagcagcat cgaaaagacc   1020

atcagcaagg ccaagggcca gcctagagag ccccaggtct acaccctgcc acccagccaa   1080

gaggagatga ccaagaacca ggtgtccctg acctgtctgg tgaagggctt ctacccaagc   1140

gacatcgccg tggagtggga gagcaacggc cagcccgaga acaactacaa gaccaccccc   1200

ccagtgctgg acagcgacgg cagcttcttc ctgtacagca ggctgaccgt ggacaagtcc   1260

agatggcagg agggcaacgt ctttagctgc tccgtgatgc acgaggccct gcacaaccac   1320

tacacccaga agagcctgag cctgtccctg ggc                                1353
```

<210> SEQ ID NO 137
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gatattcaga tgactcagtc acctagtagc ctgagcgcta gtgtgggcga tagagtgact 60
atcacctgta gctctagtca ggatatctct aactacctga actggtatca gcagaagccc 120
ggtaaagccc ctaagctgct gatctactac actagcaccc tgcacctggg aatccccccct 180 aggtttagcg gtagcggcta cggcaccgac ttcaccctga ctattaacaa tatcgagtca 240
gaggacgccg cctactactt ctgtcagcag tactataacc tgccctggac cttcggtcaa 300
ggcactaagg tcgagattaa g 321

<210> SEQ ID NO 138
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138
gatattcaga tgactcagtc acctagtagc ctgagcgcta gtgtgggcga tagagtgact 60
atcacctgta gctctagtca ggatatctct aactacctga actggtatca gcagaagccc 120
ggtaaagccc ctaagctgct gatctactac actagcaccc tgcacctggg aatccccccct 180 aggtttagcg gtagcggcta cggcaccgac ttcaccctga ctattaacaa tatcgagtca 240
gaggacgccg cctactactt ctgtcagcag tactataacc tgccctggac cttcggtcaa 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 139
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 139
gacatccaga tgacccagtc cccctccagc ctgtctgctt ccgtgggcga cagagtgacc 60
atcacctgtt cctccagcca ggacatctcc aactacctga actggtatca gcagaagccc 120
ggcaaggccc ccaagctgct gatctactac acctccaccc tgcacctggg catccccccct 180 agattctccg gctctggcta cggcaccgac ttcaccctga ccatcaacaa catcgagtcc 240
gaggacgccg cctactactt ctgccagcag tactacaacc tgccctggac cttcggccag 300
ggcaccaagg tggaaatcaa gcgtacggtg gccgctccca gcgtgttcat cttcccccca 360
agcgacgagc agctgaagag cggcaccgcc agcgtggtgt gtctgctgaa caacttctac 420
cccagggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac aggggcgagt gc 642

<210> SEQ ID NO 140
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 140
aactatggaa tgaac 15

<210> SEQ ID NO 141
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 141
tggataaaca ccgacactgg agagccaaca tatgctgatg acttcaaggg a 51

<210> SEQ ID NO 142
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142 aaccccctt attactacgg tactaataac gcggaggcta tggactac 48

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
ggatttaccc tcacaaacta t 21

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
aacaccgaca ctggagag 18

<210> SEQ ID NO 145
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
agttcaagtc aggacatcag caattattta aac 33

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146
tacacatcaa ccttacactt a 21

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
cagcagtatt ataaccttcc gtggacg 27

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148
agtcaggaca tcagcaatta t 21

<210> SEQ ID NO 149
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149 tacacatca 9

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
tattataacc ttccgtgg 18

<210> SEQ ID NO 151
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 151
aaccctccct attactacgg tactaataac gcggaggcta tggactac 48

<210> SEQ ID NO 152

<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 152
aactatggca tgaat 15

<210> SEQ ID NO 153
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 153
tggatcaaca ccgacactgg ggagccaacg tatgccgatg acttcaaggg a 51

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
ggattcaccc tgactaacta t 21

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 155
aacaccgaca ctggggag 18

<210> SEQ ID NO 156
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
tcctctagtc aggacattag caactattta aat 33

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
tatacatcca ctttgcacct g 21

<210> SEQ ID NO 158
<211> LENGTH: 27

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 158
caacagtatt ataatctccc ttggacg 27

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 159
agtcaggaca ttagcaacta t 21

<210> SEQ ID NO 160
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 160 tatacatcc 9

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 161
tattataatc tcccttgg 18

<210> SEQ ID NO 162
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 162
aactacggca tgaac 15

<210> SEQ ID NO 163
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 163
tggatcaaca ccgacaccgg cgagcctacc tacgccgacg acttcaaggg c 51

<210> SEQ ID NO 164
<211> LENGTH: 48
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 164
aacccccctt actactacgg caccaacaac gccgaggcca tggactat 48

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ggcttcaccc tgaccaacta c 21

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
aacaccgaca ccggcgag 18

<210> SEQ ID NO 167
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tcctccagcc aggacatctc caactacctg aac 33

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tacacctcca ccctgcacct g 21

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
cagcagtact acaacctgcc ctggacc 27

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
agccaggaca tctccaacta c 21

<210> SEQ ID NO 171
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171 tacacctcc 9

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tactacaacc tgccctgg 18

<210> SEQ ID NO 173
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
aattacggga tgaac 15

<210> SEQ ID NO 174
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tggattaaca ccgacaccgg ggagcctacc tacgcggacg atttcaaggg a 51

<210> SEQ ID NO 175
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aacccgccct actactacgg aaccaacaac gccgaagcca tggactac 48

<210> SEQ ID NO 176
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 176
ggattcaccc tcaccaatta c                                              21

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
aacaccgaca ccggggag                                                  18

<210> SEQ ID NO 178
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
agctctagtc aggatatctc taactacctg aac                                 33

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tacactagca ccctgcacct g                                              21

<210> SEQ ID NO 180
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cagcagtact ataacctgcc ctggacc                                        27

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
agtcaggata tctctaacta c                                              21

<210> SEQ ID NO 182
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 182 tacactagc 9

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
tactataacc tgccctgg 18

<210> SEQ ID NO 184
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
aactacggga tgaac 15

<210> SEQ ID NO 185
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
tggattaaca ccgacaccgg cgagcctacc tacgccgacg actttaaggg c 51

<210> SEQ ID NO 186
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186 aacccccct actactacgg cactaacaac gccgaggcta tggactac 48

<210> SEQ ID NO 187
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 187

Glu Val Gln Leu Val Gln Ser Gly Ala Glu Val Lys Lys Pro Gly Ala
1 5 10 15

Thr Val Lys Ile Ser Cys Lys Val Ser
20 25

<210> SEQ ID NO 188
<211> LENGTH: 75
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 188
gaagtgcagc tggtgcagtc tggcgccgaa gtgaagaaac ccggcgctac cgtgaagatc 60
tcctgcaagg tgtcc 75

<210> SEQ ID NO 189
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
gaggtccagc tggtacagtc tggggctgag gtgaagaagc ctggggctac agtgaaaatc 60
tcctgcaagg tttct 75

<210> SEQ ID NO 190
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Gln Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 191
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
caagtgcagc tggtgcagtc gggagccgaa gtgaagaagc ctggagcctc ggtgaaggtg 60
tcgtgcaagg catcc 75

<210> SEQ ID NO 192
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 192
caggtgcagc tggtgcagtc tggcgccgaa gtgaagaaac ctggcgcctc cgtgaaggtg 60
tcctgcaagg cctct 75

<210> SEQ ID NO 193
<211> LENGTH: 75
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 193
caggttcagc tggtgcagtc cggagctgag gtgaagaagc ctggggcctc agtgaaggtc     60
tcctgcaagg cttct                                                      75

<210> SEQ ID NO 194
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Val Gln Leu Val Gln Ser Gly Ala Glu Val Lys Lys Pro Gly Glu
1               5                   10                  15

Ser Leu Arg Ile Ser Cys Lys Gly Ser
            20                  25

<210> SEQ ID NO 195
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gaagtgcagc tggtgcagtc tggagcagag gtgaaaaagc ccggggagtc tctgaggatc     60
tcctgtaagg gttct                                                      75

<210> SEQ ID NO 196
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Val Gln Leu Val Gln Ser Gly Ser Glu Leu Lys Lys Pro Gly Ala
1               5                   10                  15

Ser Val Lys Val Ser Cys Lys Ala Ser
            20                  25

<210> SEQ ID NO 197
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
caggtgcagc tggtgcaatc tgggtctgag ttgaagaagc ctggggcctc agtgaaggtt     60
tcctgcaagg cttct                                                      75

<210> SEQ ID NO 198
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 198

Trp Val Arg Gln Ala Pro Gly Gln Gly Leu Glu Trp Met Gly
1               5                   10

<210> SEQ ID NO 199
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tgggtccgcc aggccccagg tcaaggcctc gagtggatgg gc                        42

<210> SEQ ID NO 200
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tgggtgcgac aggcccctgg acagggcctg gaatggatgg gc                        42

<210> SEQ ID NO 201
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tgggtgcgac aggcccctgg acaagggctt gagtggatgg gt                        42

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Trp Val Arg Gln Ala Arg Gly Gln Arg Leu Glu Trp Ile Gly
1               5                   10

<210> SEQ ID NO 203
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tgggtcagac aggcccgggg tcaacggctg gagtggatcg ga                        42

<210> SEQ ID NO 204
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
tgggtgcgac aggccagggg ccagcggctg gaatggatcg gc 42

<210> SEQ ID NO 205
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 205
tgggtgcgac aggctcgtgg acaacgcctt gagtggatag gt 42

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 206

Trp Ile Arg Gln Ser Pro Ser Arg Gly Leu Glu Trp Leu Gly
1 5 10

<210> SEQ ID NO 207
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 207
tggatcaggc agtccccatc gagaggcctt gagtggctgg gt 42

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 208

Trp Val Arg Gln Ala Thr Gly Gln Gly Leu Glu Trp Met Gly
1 5 10

<210> SEQ ID NO 209
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 209
tgggtgcgac aggccactgg acaagggctt gagtggatgg gt 42

<210> SEQ ID NO 210
<211> LENGTH: 32
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 210

Arg Phe Val Phe Ser Leu Asp Thr Ser Val Ser Thr Ala Tyr Leu Gln
1               5                   10                  15

Ile Cys Ser Leu Lys Ala Glu Asp Thr Ala Val Tyr Tyr Cys Ala Arg
            20                  25                  30

<210> SEQ ID NO 211
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
agatttgtct tctccttgga cacctctgtc agcacggcat atctgcagat ctgcagccta     60
aaggctgagg acactgccgt gtattactgt gcaaga                               96

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Arg Phe Val Phe Ser Leu Asp Thr Ser Val Ser Thr Ala Tyr Leu Gln
1               5                   10                  15

Ile Ser Ser Leu Lys Ala Glu Asp Thr Ala Val Tyr Tyr Cys Ala Arg
            20                  25                  30

<210> SEQ ID NO 213
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cggttcgtgt tctccctcga cacctccgtg tccaccgcct acctccaaat ctcctcactg     60
aaagcggagg acaccgccgt gtactattgc gcgagg                               96

<210> SEQ ID NO 214
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
agattcgtgt ttagcctgga cactagtgtg tctaccgcct acctgcagat ctctagcctg     60
aaggccgagg acaccgccgt ctactactgc gctaga                               96

<210> SEQ ID NO 215
<211> LENGTH: 96
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 215
agattcgtgt tctccctgga cacctccgtg tccaccgcct acctgcagat ctccagcctg 60
aaggccgagg ataccgccgt gtactactgc gcccgg 96

<210> SEQ ID NO 216
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
agatttgtct tctccttgga cacctctgtc agcacggcat atctgcagat cagcagccta 60
aaggctgagg acactgccgt gtattactgt gcaaga 96

<210> SEQ ID NO 217
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 217

Arg Val Thr Ile Ser Ala Asp Lys Ser Ile Ser Thr Ala Tyr Leu Gln
1 5 10 15

Trp Ser Ser Leu Lys Ala Ser Asp Thr Ala Met Tyr Tyr Cys Ala Arg
20 25 30

<210> SEQ ID NO 218
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 218
agagtcacca tctcagccga caagtccatc agcaccgcct acctgcagtg gagcagcctg 60
aaggcctcgg acaccgccat gtattactgt gcaaga 96

<210> SEQ ID NO 219
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 219

Arg Phe Val Phe Ser Leu Asp Thr Ser Val Ser Thr Ala Tyr Leu Gln
1 5 10 15

Ile Ser Thr Leu Lys Ala Glu Asp Thr Ala Thr Tyr Phe Cys Ala Arg
20 25 30

<210> SEQ ID NO 220
<211> LENGTH: 96
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 220
cggtttgtct tctccttgga cacctctgtc agcacggcat atctgcagat cagcacgcta 60
aaggctgagg acactgctac atatttctgt gcaaga 96

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Trp Gly Gln Gly Thr Thr Val Thr Val Ser Ser
1 5 10

<210> SEQ ID NO 222
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 222
tggggccagg gcaccactgt gactgtgtcc agc 33

<210> SEQ ID NO 223
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 223
tggggtcaag gcactaccgt gaccgtgtct agc 33

<210> SEQ ID NO 224
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 224
tggggccagg gcaccaccgt gaccgtgtcc tct 33

<210> SEQ ID NO 225
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 225
tggggccagg gcaccaccgt gaccgtgtcc tcc 33

<210> SEQ ID NO 226

<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 227
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 227
gatattcaga tgactcagtc acctagtagc ctgagcgcta gtgtgggcga tagagtgact 60
atcacctgt 69

<210> SEQ ID NO 228
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
gacatccaga tgacccagtc cccctccagc ctgtctgctt ccgtgggcga cagagtgacc 60
atcacctgt 69

<210> SEQ ID NO 229
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 229
gacatccaga tgacccagtc tccatcctcc ctgtctgcat ctgtaggaga cagagtcacc 60
atcacttgc 69

<210> SEQ ID NO 230
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Glu Ile Val Leu Thr Gln Ser Pro Ala Thr Leu Pro Val Thr Leu Gly
1 5 10 15

Gln Pro Ala Ser Ile Ser Cys
20

<210> SEQ ID NO 231

<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 231
gaaattgtgt tgacacagtc tccagccacc ctgcccgtca cccttggaca gccggcctcc 60
atctcctgc 69

<210> SEQ ID NO 232
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Glu Ile Val Leu Thr Gln Ser Pro Ala Thr Leu Ser Leu Ser Pro Gly
1 5 10 15

Glu Arg Ala Thr Leu Ser Cys
20

<210> SEQ ID NO 233
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 233
gaaattgtgt tgacacagtc tccagccacc ctgtctttgt ctccagggga aagagccacc 60
ctctcctgc 69

<210> SEQ ID NO 234
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Asp Ile Val Met Thr Gln Thr Pro Leu Ser Leu Pro Val Thr Pro Gly
1 5 10 15

Glu Pro Ala Ser Ile Ser Cys
20

<210> SEQ ID NO 235
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 235
gatattgtga tgacccagac tccactctcc ctgcccgtca cccctggaga gccggcctcc 60
atctcctgc 69

<210> SEQ ID NO 236

<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 236

Glu Ile Val Leu Thr Gln Ser Pro Asp Phe Gln Ser Val Thr Pro Lys
1 5 10 15

Glu Lys Val Thr Ile Thr Cys
20

<210> SEQ ID NO 237
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 237
gaaattgtgc tgactcagtc tccagacttt cagtctgtga ctccaaagga gaaagtcacc 60
atcacctgc 69

<210> SEQ ID NO 238
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

Ala Ile Gln Leu Thr Gln Ser Pro Ser Ser Leu Ser Ala Ser Val Gly
1 5 10 15

Asp Arg Val Thr Ile Thr Cys
20

<210> SEQ ID NO 239
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 239
gccatccagt tgacccagtc tccatcctcc ctgtctgcat ctgtaggaga cagagtcacc 60
atcacttgc 69

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Trp Tyr Gln Gln Lys Pro Gly Lys Ala Pro Lys Leu Leu Ile Tyr
1 5 10 15

<210> SEQ ID NO 241
<211> LENGTH: 45

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 241
tggtatcagc agaagcccgg taaagcccct aagctgctga tctac 45

<210> SEQ ID NO 242
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
tggtatcagc agaagcccgg caaggccccc aagctgctga tctac 45

<210> SEQ ID NO 243
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 243
tggtatcagc agaaaccagg gaaagctcct aagctcctga tctat 45

<210> SEQ ID NO 244
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Trp Tyr Gln Gln Lys Pro Gly Gln Ala Pro Arg Leu Leu Ile Tyr
1 5 10 15

<210> SEQ ID NO 245
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 245
tggtaccagc agaaacctgg ccaggctccc aggctcctca tctat 45

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Trp Tyr Leu Gln Lys Pro Gly Gln Ser Pro Gln Leu Leu Ile Tyr
1 5 10 15

<210> SEQ ID NO 247

<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tggtacctgc agaagccagg gcagtctcca cagctcctga tctat 45

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Trp Tyr Leu Gln Lys Pro Gly Gln Ser Pro Gln Leu Leu Ile Tyr
1               5                   10                  15

<210> SEQ ID NO 249
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tggtatctgc agaagcccgg tcaatcacct cagctgctga tctac 45

<210> SEQ ID NO 250
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tggtatctgc agaagcccgg ccagtcccct cagctgctga tctac 45

<210> SEQ ID NO 251
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tggtacctgc agaagccagg gcagtctcca cagctcctga tctat 45

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys 20 25 30

<210> SEQ ID NO 253
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 253
ggcgtgccct ccagattttc cggctctggc tctggcaccg actttacctt caccatcagc 60
tccctggaag ccgaggacgc cgccacctac tactgc 96

<210> SEQ ID NO 254
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 254
ggggtcccct cgaggttcag tggcagtgga tctgggacag atttcacctt taccatcagt 60
agcctggaag ctgaagatgc tgcaacatat tactgt 96

<210> SEQ ID NO 255
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 255

Gly Ile Pro Pro Arg Phe Ser Gly Ser Gly Tyr Gly Thr Asp Phe Thr
1 5 10 15

Leu Thr Ile Asn Asn Ile Glu Ser Glu Asp Ala Ala Tyr Tyr Phe Cys
20 25 30

<210> SEQ ID NO 256
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 256
ggaatccccc ctaggtttag cggtagcggc tacggcaccg acttcaccct gactattaac 60
aatatcgagt cagaggacgc cgcctactac ttctgt 96

<210> SEQ ID NO 257
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 257
ggcatccccc ctagattctc cggctctggc tacggcaccg acttcaccct gaccatcaac 60
aacatcgagt ccgaggacgc cgcctactac ttctgc 96

<210> SEQ ID NO 258
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 258
gggatcccac ctcgattcag tggcagcggg tatggaacag attttaccct cacaattaat 60
aacatagaat ctgaggatgc tgcatattac ttctgt 96

<210> SEQ ID NO 259
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 259

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 260
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 260
gggatcccag acaggttcag tggcagtggg tctgggacag acttcactct caccatcagc 60
agactggagc ctgaagattt tgcagtgtat tactgt 96

<210> SEQ ID NO 261
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 261

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 262
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 262
ggcgtgccct ctaggtttag cggtagcggt agtggcaccg agttcaccct gactatctct 60
agcctgcagc ccgacgactt cgctacctac tactgt 96

<210> SEQ ID NO 263
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 263
ggcgtgccct ccagattttc cggctctggc tctggcaccg agtttaccct gaccatcagc 60
tccctgcagc ccgacgactt cgccacctac tactgc 96

<210> SEQ ID NO 264
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 264
ggggtcccat caaggttcag cggcagtgga tctgggacag aattcactct caccatcagc 60
agcctgcagc ctgatgattt tgcaacttat tactgt 96

<210> SEQ ID NO 265
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 265

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 266
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 266
ggggtcccat caaggttcag cggcagtgga tctgggacag atttcactct caccatcagc 60
agcctgcagc ctgaagattt tgcaacttat tactgt 96

<210> SEQ ID NO 267
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 267

Gly Val Pro Ser Arg Phe Ser Gly Ser Gly Ser Gly Thr Asp Phe Thr
1 5 10 15

Phe Thr Ile Ser Ser Leu Gln Pro Glu Asp Ile Ala Thr Tyr Tyr Cys
20 25 30

<210> SEQ ID NO 268
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 268
ggggtcccat caaggttcag tggaagtgga tctgggacag attttacttt caccatcagc 60
agcctgcagc ctgaagatat tgcaacatat tactgt 96

<210> SEQ ID NO 269
<211> LENGTH: 32
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 269

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Tyr Tyr Cys
20 25 30

<210> SEQ ID NO 270
<211> LENGTH: 96
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 270
gggatcccag acaggttcag tggcagtggg tctgggacag acttcactct caccatcagc 60
agactggagc ctgaagattt tgcagtgtat tactgt 96

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 271

Phe Gly Gln Gly Thr Lys Val Glu Ile Lys
1 5 10

<210> SEQ ID NO 272
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 272
ttcggtcaag gcactaaggt cgagattaag 30

<210> SEQ ID NO 273
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ttcggccagg gcaccaaggt ggaaatcaag                                        30

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ttcggccaag ggaccaaggt ggaaatcaaa                                        30

<210> SEQ ID NO 275
<211> LENGTH: 327
<212> TYPE: PRT
<213> ORGANISM: Homo sapiens

<400> SEQUENCE: 275

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 276
<211> LENGTH: 107
<212> TYPE: PRT
<213> ORGANISM: Homo sapiens

<400> SEQUENCE: 276

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 277
<211> LENGTH: 326
<212> TYPE: PRT
<213> ORGANISM: Homo sapiens

<400> SEQUENCE: 277

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325


<210> SEQ ID NO 278
<211> LENGTH: 330
<212> TYPE: PRT
<213> ORGANISM: Homo sapiens

<400> SEQUENCE: 278

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 279
<211> LENGTH: 330
<212> TYPE: PRT
<213> ORGANISM: Homo sapiens

<400> SEQUENCE: 279

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 280
<211> LENGTH: 330
<212> TYPE: PRT
<213> ORGANISM: Homo sapiens

<400> SEQUENCE: 280

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 281
<211> LENGTH: 330
<212> TYPE: PRT
<213> ORGANISM: Homo sapiens

<400> SEQUENCE: 281

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

325 330

<210> SEQ ID NO 282
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 282

Met Glu Trp Ser Trp Val Phe Leu Phe Phe Leu Ser Val Thr Thr Gly
1 5 10 15

Val His Ser

<210> SEQ ID NO 283
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 283

Met Ser Val Pro Thr Gln Val Leu Gly Leu Leu Leu Leu Trp Leu Thr
1 5 10 15

Asp Ala Arg Cys
20

<210> SEQ ID NO 284
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 284

Met Ala Trp Val Trp Thr Leu Pro Phe Leu Met Ala Ala Ala Gln Ser
1 5 10 15

Val Gln Ala

<210> SEQ ID NO 285
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

Met Ser Val Leu Thr Gln Val Leu Ala Leu Leu Leu Leu Trp Leu Thr
1 5 10 15

Gly Thr Arg Cys
20

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

-continued

```
Gly Phe Thr Leu Thr Asn Tyr Gly Met Asn
1               5                   10


<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287

ggcttcaccc tgactaacta c                                              21


<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288

gctgacagac taacagactg ttcc                                           24


<210> SEQ ID NO 289
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289

caaatgtggt atggctga                                                  18


<210> SEQ ID NO 290
<211> LENGTH: 95
<212> TYPE: PRT
<213> ORGANISM: Mus musculus

<400> SEQUENCE: 290

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro
                85                  90                  95


<210> SEQ ID NO 291
<211> LENGTH: 98
<212> TYPE: PRT
<213> ORGANISM: Mus musculus

<400> SEQUENCE: 291

Gln Ile Gln Leu Val Gln Ser Gly Pro Glu Leu Lys Lys Pro Gly Glu
1               5                   10                  15
```

-continued

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

Gly Trp Ile Asn Thr Tyr Thr Gly Glu Pro Thr Tyr Ala Asp Asp Phe
50 55 60

Lys Gly Arg Phe Ala Phe Ser Leu Glu Thr Ser Ala Ser Thr Ala Tyr
65 70 75 80

Leu Gln Ile Asn Asn Leu Lys Asn Glu Asp Thr Ala Thr Tyr Phe Cys
85 90 95

Ala Arg

<210> SEQ ID NO 292
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 292

Glu Ile Val Leu Thr Gln Ser Pro Ala Thr Leu Pro Val Ser Leu Gly
1 5 10 15

Gln Thr Ala Ser Ile Ser Cys Ser Ser Ser Gln Asp Ile Ser Asn Tyr
20 25 30

Leu Asn Trp Tyr Gln Gln Lys Pro Gly Gln Ala Pro Arg Leu Leu Ile
35 40 45

Tyr Tyr Thr Ser Thr Leu His Leu Gly Val Pro Ser Arg Phe Ser Gly
50 55 60

Ser Gly Ser Gly Thr Asp Phe Thr Phe Thr Ile Ser Ser Leu Glu Ala
65 70 75 80

Glu Asp Ala Ala Thr Tyr Tyr Cys Gln Gln Tyr Tyr Asn Leu Pro Trp
85 90 95

Thr Phe Gly Gln Gly Thr Lys Val Glu Ile Lys
100 105

<210> SEQ ID NO 293
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 293

Cys Asn Gly Arg Cys
1 5

<210> SEQ ID NO 294
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 294

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Ser Ser Asn
20 25 30

-continued

```
Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 295
<211> LENGTH: 215
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 295

Glu Thr Val Leu Thr Gln Ser Pro Gly Thr Leu Ser Leu Ser Pro Gly
1 5 10 15

Glu Arg Ala Thr Leu Ser Cys Arg Ala Ser Gln Ser Leu Gly Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Pro Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Ala Asp Ser Pro
85 90 95

Ile Thr Phe Gly Gln Gly Thr Arg Leu Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 296
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 296

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

```
Met Glu Leu Ser Ser Leu Arg Ser Glu Asp Thr Ala Val Tyr Tyr Cys
                85                  90                  95

Ala Arg Gly Leu Trp Glu Val Arg Ala Leu Pro Ser Val Tyr Trp Gly
            100                 105                 110

Gln Gly Thr Leu Val Thr Val Ser Ser
        115                 120


<210> SEQ ID NO 297
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Ser Tyr Glu Leu Thr Gln Pro Pro Ser Val Ser Val Ala Pro Gly Gln
1               5                   10                  15

Thr Ala Arg Ile Thr Cys Gly Ala Asn Asp Ile Gly Ser Lys Ser Val
            20                  25                  30

His Trp Tyr Gln Gln Lys Ala Gly Gln Ala Pro Val Leu Val Val Ser
        35                  40                  45

Glu Asp Ile Ile Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Asp Ser Asp Gln
                85                  90                  95

Tyr Val Phe Gly Thr Gly Thr Lys Val Thr Val Leu Gly
            100                 105


<210> SEQ ID NO 298
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140
```

-continued

Tyr Phe Pro Glu Pro Val Thr Val Ser Trp Asn Ser Gly Ala Leu Thr
145 150 155 160

Ser Gly Val His Thr Phe Pro Ala Val Leu Gln Ser Ser Gly Leu Tyr
165 170 175

Ser Leu Ser Ser Val Val Thr Val Pro Ser Ser Ser Leu Gly Thr Lys
180 185 190

Thr Tyr Thr Cys Asn Val Asp His Lys Pro Ser Asn Thr Lys Val Asp
195 200 205

Lys Arg Val Glu Ser Lys Tyr Gly Pro Pro Cys Pro Pro Cys Pro Ala
210 215 220

Pro Glu Phe Leu Gly Gly Pro Ser Val Phe Leu Phe Pro Pro Lys Pro
225 230 235 240

Lys Asp Thr Leu Met Ile Ser Arg Thr Pro Glu Val Thr Cys Val Val
245 250 255

Val Asp Val Ser Gln Glu Asp Pro Glu Val Gln Phe Asn Trp Tyr Val
260 265 270

Asp Gly Val Glu Val His Asn Ala Lys Thr Lys Pro Arg Glu Glu Gln
275 280 285

Phe Asn Ser Thr Tyr Arg Val Val Ser Val Leu Thr Val Leu His Gln
290 295 300

Asp Trp Leu Asn Gly Lys Glu Tyr Lys Cys Lys Val Ser Asn Lys Gly
305 310 315 320

Leu Pro Ser Ser Ile Glu Lys Thr Ile Ser Lys Ala Lys Gly Gln Pro
325 330 335

Arg Glu Pro Gln Val Tyr Thr Leu Pro Pro Ser Gln Glu Glu Met Thr
340 345 350

Lys Asn Gln Val Ser Leu Thr Cys Leu Val Lys Gly Phe Tyr Pro Ser
355 360 365

Asp Ile Ala Val Glu Trp Glu Ser Asn Gly Gln Pro Glu Asn Asn Tyr
370 375 380

Lys Thr Thr Pro Pro Val Leu Asp Ser Asp Gly Ser Phe Phe Leu Tyr
385 390 395 400

Ser Arg Leu Thr Val Asp Lys Ser Arg Trp Gln Glu Gly Asn Val Phe
405 410 415

Ser Cys Ser Val Met His Glu Ala Leu His Asn His Tyr Thr Gln Lys
420 425 430

Ser Leu Ser Leu Ser Leu Gly Lys
435 440

<210> SEQ ID NO 299
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 299

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser Ser Asn Trp Pro Arg
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 300
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 300

Gln Val Gln Leu Val Gln Ser Gly Val Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met Tyr Trp Val Arg Gln Ala Pro Gly Gln Gly Leu Glu Trp Met
35 40 45

Gly Gly Ile Asn Pro Ser Asn Gly Gly Thr Asn Phe Asn Glu Lys Phe
50 55 60

Lys Asn Arg Val Thr Leu Thr Thr Asp Ser Ser Thr Thr Thr Ala Tyr
65 70 75 80

Met Glu Leu Lys Ser Leu Gln Phe Asp Asp Thr Ala Val Tyr Tyr Cys
85 90 95

Ala Arg Arg Asp Tyr Arg Phe Asp Met Gly Phe Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys

```
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 301
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110
```

-continued

```
Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 302
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Thr Val Asp Tyr Trp Gly Gln Gly Thr
            100                 105                 110

Leu Val Thr Val Ser Ser
        115


<210> SEQ ID NO 303
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60
```

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Arg Val Phe Gly Thr Gly Thr Lys Val Thr Val Leu
100 105 110

<210> SEQ ID NO 304
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Arg Gly Asp Ser
1

<210> SEQ ID NO 305
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 305

Met Ala Pro Arg Arg Ala Arg Gly Cys Arg Thr Leu Gly Leu Pro Ala
1 5 10 15

Leu Leu Leu Leu Leu Leu Leu Arg Pro Pro Ala Thr Arg Gly Asp Tyr
20 25 30

Lys Asp Asp Asp Asp Lys Ile Glu Gly Arg Ile Thr Cys Pro Pro Pro
35 40 45

Met Ser Val Glu His Ala Asp Ile Trp Val Lys Ser Tyr Ser Leu Tyr
50 55 60

Ser Arg Glu Arg Tyr Ile Cys Asn Ser Gly Phe Lys Arg Lys Ala Gly
65 70 75 80

Thr Ser Ser Leu Thr Glu Cys Val Leu Asn Lys Ala Thr Asn Val Ala
85 90 95

His Trp Thr Thr Pro Ser Leu Lys Cys Ile Arg Asp Pro Ala Leu Val
100 105 110

His Gln Arg Pro Ala Pro Pro Ser Gly Gly Ser Gly Gly Gly Gly Ser
115 120 125

Gly Gly Gly Ser Gly Gly Gly Gly Ser Leu Gln Asn Trp Val Asn Val
130 135 140

Ile Ser Asp Leu Lys Lys Ile Glu Asp Leu Ile Gln Ser Met His Ile
145 150 155 160

Asp Ala Thr Leu Tyr Thr Glu Ser Asp Val His Pro Ser Cys Lys Val
165 170 175

Thr Ala Met Lys Cys Phe Leu Leu Glu Leu Gln Val Ile Ser Leu Glu
180 185 190

Ser Gly Asp Ala Ser Ile His Asp Thr Val Glu Asn Leu Ile Ile Leu
195 200 205

Ala Asn Asn Ser Leu Ser Ser Asn Gly Asn Val Thr Glu Ser Gly Cys
210 215 220

Lys Glu Cys Glu Glu Leu Glu Glu Lys Asn Ile Lys Glu Phe Leu Gln
225 230 235 240

```
Ser Phe Val His Ile Val Gln Met Phe Ile Asn Thr Ser
                245                 250


<210> SEQ ID NO 306
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Met Asp Ser Lys Gly Ser Ser Gln Lys Ala Gly Ser Arg Leu Leu Leu
1               5                   10                  15

Leu Leu Val Val Ser Asn Leu Leu Leu Cys Gln Gly Val Val Ser Thr
            20                  25                  30

Thr Arg Asp Tyr Lys Asp Asp Asp Asp Lys Ile Glu Gly Arg Asn Trp
        35                  40                  45

Val Asn Val Ile Ser Asp Leu Lys Lys Ile Glu Asp Leu Ile Gln Ser
    50                  55                  60

Met His Ile Asp Ala Thr Leu Tyr Thr Glu Ser Asp Val His Pro Ser
65                  70                  75                  80

Cys Lys Val Thr Ala Met Lys Cys Phe Leu Leu Glu Leu Gln Val Ile
                85                  90                  95

Ser Leu Glu Ser Gly Asp Ala Ser Ile His Asp Thr Val Glu Asn Leu
            100                 105                 110

Ile Ile Leu Ala Asn Asn Ser Leu Ser Ser Asn Gly Asn Val Thr Glu
        115                 120                 125

Ser Gly Cys Lys Glu Cys Glu Glu Leu Glu Glu Lys Asn Ile Lys Glu
    130                 135                 140

Phe Leu Gln Ser Phe Val His Ile Val Gln Met Phe Ile Asn Thr Ser
145                 150                 155                 160

Ser Gly Gly Gly Ser Gly Gly Gly Gly Ser Gly Gly Gly Gly Ser Gly
                165                 170                 175

Gly Gly Gly Ser Gly Gly Gly Ser Leu Gln Ile Thr Cys Pro Pro Pro
            180                 185                 190

Met Ser Val Glu His Ala Asp Ile Trp Val Lys Ser Tyr Ser Leu Tyr
        195                 200                 205

Ser Arg Glu Arg Tyr Ile Cys Asn Ser Gly Phe Lys Arg Lys Ala Gly
    210                 215                 220

Thr Ser Ser Leu Thr Glu Cys Val Leu Asn Lys Ala Thr Asn Val Ala
225                 230                 235                 240

His Trp Thr Thr Pro Ser Leu Lys Cys Ile Arg Asp Pro Ala Leu Val
                245                 250                 255

His Gln Arg Pro Ala Pro Pro
            260


<210> SEQ ID NO 307
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Ser Tyr Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Asn Phe Gly Met Asp Tyr Trp Gly Gln Gly Thr Leu
            100                 105                 110

Val Thr Val Ser Ser
        115


<210> SEQ ID NO 308
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Arg Asn Pro Pro
                85                  90                  95

Thr Phe Gly Gln Gly Thr Lys Leu Glu Ile Lys
            100                 105


<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Phe Thr Phe Ser Ser Tyr Ala
1               5


<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ile Gly Ser Tyr Gly Gly Gly Thr
```

1 5

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

Ala Arg Tyr Val Asn Phe Gly Met Asp Tyr
1 5 10

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 312

Gln Ser Ile Ser Ser Tyr
1 5

<210> SEQ ID NO 313
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 313

Ala Ala Ser
1

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 314

Gln Gln Tyr Gly Arg Asn Pro Pro Thr
1 5

<210> SEQ ID NO 315
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 315

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Trp Gly Phe Asp Tyr Trp Gly Gln Gly Thr Leu Val
            100                 105                 110

Thr Val Ser Ser
        115


<210> SEQ ID NO 316
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Val Tyr Pro Phe
                85                  90                  95

Thr Phe Gly Gln Gly Thr Lys Leu Glu Ile Lys
            100                 105


<210> SEQ ID NO 317
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Ile Ser Gly Ser Gly Gly Ser Thr
1               5


<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ala Arg Arg Val Trp Gly Phe Asp Tyr
1               5


<210> SEQ ID NO 319
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 319

Gln Gln Tyr Gly Val Tyr Pro Phe Thr
1               5


<210> SEQ ID NO 320
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (120)..(120)
<223> OTHER INFORMATION: Any amino acid
<220> FEATURE:
<221> NAME/KEY: MOD_RES
<222> LOCATION: (124)..(125)
<223> OTHER INFORMATION: Any amino acid

<400> SEQUENCE: 320

Glu Val Arg Leu Gln Gln Ser Gly Ala Asp Leu Val Lys Pro Gly Ala
1               5                   10                  15

Ser Val Lys Leu Ser Cys Ala Ser Gly Phe Ile Ile Lys Ala Thr Tyr
            20                  25                  30

Met His Trp Val Arg Gln Arg Pro Glu Gln Gly Leu Glu Trp Ile Gly
        35                  40                  45

Arg Ile Asp Pro Ala Asn Gly Glu Lys Tyr Asp Pro Lys Phe Gln Val
    50                  55                  60

Lys Ala Ile Thr Ala Asp Thr Ser Ser Ser Thr Ala Tyr Leu Gln Leu
65                  70                  75                  80

Asn Ser Leu Thr Ser Asp Asp Thr Ala Val Tyr Tyr Cys Ala Arg Tyr
                85                  90                  95

Ala Trp Tyr Phe Asp Val Trp Gly Ala Gly Thr Thr Val Thr Val Ser
            100                 105                 110

Ser Ala Lys Thr Thr Pro Pro Xaa Val Tyr Pro Xaa Xaa Pro Gly Ser
        115                 120                 125


<210> SEQ ID NO 321
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Asp Ile Gln Met Thr Gln Ser Pro Ala Ser Leu Ser Ala Ser Val Gly
1               5                   10                  15

Asp Thr Val Thr Ile Thr Cys Arg Ala Ser Glu Asn Ile Tyr Ser Phe
            20                  25                  30

Leu Ala Trp Tyr His Gln Lys Gln Gly Arg Ser Pro Gln Leu Leu Val
        35                  40                  45

Tyr His Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Ala
65                  70                  75                  80

Glu Asp Phe Gly Ser Tyr Tyr Cys Gln His Tyr Tyr Gly Ser Pro Leu
```

-continued 85 90 95

Thr Phe Gly Ala Gly Thr Lys Leu Glu Val Lys Arg Ala Asp Ala Ala
100 105 110

Pro Thr Val Ser Ile Phe Pro Pro Ser Ser Glu Glu Leu Ser Leu
115 120 125

<210> SEQ ID NO 322
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Gly Phe Ile Ile Lys Ala Thr Tyr Met His
1 5 10

<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 323

Arg Ile Asp Pro Ala Asn Gly Glu Thr Lys Tyr Asp Pro Lys Phe Gln
1 5 10 15

Val

<210> SEQ ID NO 324
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Tyr Ala Trp Tyr Phe Asp Val
1 5

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Arg Ala Ser Glu Asn Ile Tyr Ser Phe Leu Ala
1 5 10

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 326

His Ala Lys Thr Leu Ala Glu
1 5

-continued

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 327

Gln His Tyr Tyr Gly Ser Pro Leu Thr
1 5

<210> SEQ ID NO 328
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 328

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Trp Met Asn Trp Val Arg Gln Ala Pro Gly Lys Gly Leu Glu Trp Val
35 40 45

Ala Ala Ile Asn Gln Asp Gly Ser Glu Lys Tyr Tyr Val Gly Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Val Glu Asp Thr Ala Val Tyr Tyr Cys
85 90 95

Val Arg Asp Tyr Tyr Asp Ile Leu Thr Asp Tyr Tyr Ile His Tyr Trp
100 105 110

Tyr Phe Asp Leu Trp Gly Arg Gly Thr Leu Val Thr Val Ser Ser
115 120 125

<210> SEQ ID NO 329
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 329

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Cys Thr Phe Gly Gln Gly Thr Arg Leu Glu Ile Lys Arg
100 105

<210> SEQ ID NO 330
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 330

Asn Tyr Trp Met Asn
1 5

<210> SEQ ID NO 331
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 331

Ala Ile Asn Gln Asp Gly Ser Glu Lys Tyr Tyr Val Gly Ser Val Lys
1 5 10 15

Gly

<210> SEQ ID NO 332
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 332

Asp Tyr Tyr Asp Ile Leu Thr Asp Tyr Tyr Ile His Tyr Trp Tyr Phe
1 5 10 15

Asp Leu

<210> SEQ ID NO 333
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 333

Arg Ala Ser Gln Ser Val Ser Ser Ser Tyr Leu Ala
1 5 10

<210> SEQ ID NO 334
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 334

Gly Ala Ser Ser Arg Ala Thr
1 5

<210> SEQ ID NO 335

<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 335

Gln Gln Tyr Gly Ser Ser Pro Cys Thr
1               5

<210> SEQ ID NO 336
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 336

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ser Leu Tyr Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 337
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 337

```
Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Asn Trp Glu
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

210

<210> SEQ ID NO 338
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 338

Gln Val Gln Leu Val Gln Ser Gly Ala Glu Val Lys Lys Pro Gly Ser
1 5 10 15

Ser Val Lys Val Ser Cys Lys Ala Ser Gly Tyr Ser Phe Thr Asp Tyr
20 25 30

His Ile His Trp Val Arg Gln Ala Pro Gly Gln Gly Leu Glu Trp Met
35 40 45

Gly Val Ile Asn Pro Met Tyr Gly Thr Thr Asp Tyr Asn Gln Arg Phe
50 55 60

Lys Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Tyr Asp Tyr Phe Thr Gly Thr Gly Val Tyr Trp Gly Gln Gly
100 105 110

Thr Leu Val Thr Val Ser Ser
115

<210> SEQ ID NO 339
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 339

Asp Ile Val Met Thr Gln Thr Pro Leu Ser Leu Ser Val Thr Pro Gly
1 5 10 15

Gln Pro Ala Ser Ile Ser Cys Arg Ser Ser Arg Ser Leu Val His Ser
20 25 30

Arg Gly Asn Thr Tyr Leu His Trp Tyr Leu Gln Lys Pro Gly Gln Ser
35 40 45

Pro Gln Leu Leu Ile Tyr Lys Val Ser Asn Arg Phe Ile Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Leu Pro Phe Thr Phe Gly Gln Gly Thr Lys Leu Glu Ile Lys
100 105 110

<210> SEQ ID NO 340
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 340

Arg Tyr Gly Ile Ser
1 5

<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Trp Ile Ser Thr Tyr Ser Gly Asn Thr Asn Tyr Ala Gln Lys Leu Gln
1 5 10 15

Gly

<210> SEQ ID NO 342
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Arg Gln Leu Tyr Phe Asp Tyr
1 5

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Arg Ala Ser Gln Ser Val Ser Ser Asn Leu Ala
1 5 10

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Asp Ala Ser Thr Arg Ala Thr
1 5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Gln Gln Tyr Asp Asn Trp Pro Leu Thr
1 5

<210> SEQ ID NO 346
<211> LENGTH: 137

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 346

Met Glu Phe Gly Leu Ser Trp Val Phe Leu Val Ala Leu Leu Arg Gly
1 5 10 15

Val Gln Cys Gln Val Gln Leu Val Glu Ser Gly Gly Gly Val Val Gln
20 25 30

Pro Gly Arg Ser Leu Arg Leu Ser Cys Ala Ala Ser Gly Phe Thr Phe
35 40 45

Ser Val Tyr Gly Met Asn Trp Val Arg Gln Ala Pro Gly Lys Gly Leu
50 55 60

Glu Trp Val Ala Ile Ile Trp Tyr Asp Gly Asp Asn Gln Tyr Tyr Ala
65 70 75 80

Asp Ser Val Lys Gly Arg Phe Thr Ile Ser Arg Asp Asn Ser Lys Asn
85 90 95

Thr Leu Tyr Leu Gln Met Asn Gly Leu Arg Ala Glu Asp Thr Ala Val
100 105 110

Tyr Tyr Cys Ala Arg Asp Leu Arg Thr Gly Pro Phe Asp Tyr Trp Gly
115 120 125

Gln Gly Thr Leu Val Thr Val Ser Ser
130 135

<210> SEQ ID NO 347
<211> LENGTH: 126
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 347

Met Leu Pro Ser Gln Leu Ile Gly Phe Leu Leu Leu Trp Val Pro Ala
1 5 10 15

Ser Arg Gly Glu Ile Val Leu Thr Gln Ser Pro Asp Phe Gln Ser Val
20 25 30

Thr Pro Lys Glu Lys Val Thr Ile Thr Cys Arg Ala Ser Gln Ser Ile
35 40 45

Gly Ser Ser Leu His Trp Tyr Gln Gln Lys Pro Asp Gln Ser Pro Lys
50 55 60

Leu Leu Ile Lys Tyr Ala Ser Gln Ser Phe Ser Gly Val Pro Ser Arg
65 70 75 80

Phe Ser Gly Ser Gly Ser Gly Thr Asp Phe Thr Leu Thr Ile Asn Ser
85 90 95

Leu Glu Ala Glu Asp Ala Ala Ala Tyr Tyr Cys His Gln Ser Ser Ser
100 105 110

Leu Pro Phe Thr Phe Gly Pro Gly Thr Lys Val Asp Ile Lys
115 120 125

<210> SEQ ID NO 348
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

Gly Asp Ser Val Ser Ser Asn Ser Ala Ala Trp Gly
1 5 10

<210> SEQ ID NO 349
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Arg Ile Tyr Tyr Arg Ser Lys Trp Tyr Asn Ser Tyr Ala Val Ser Val
1 5 10 15

Lys Ser

<210> SEQ ID NO 350
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Tyr Asp Trp Val Pro Lys Ile Gly Val Phe Asp Ser
1 5 10

<210> SEQ ID NO 351
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Arg Ala Ser Gln Phe Ile Ser Ser Ser Tyr Leu Ser
1 5 10

<210> SEQ ID NO 352
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Leu Leu Ile Tyr Gly Ser Ser Ser Arg Ala Thr
1 5 10

<210> SEQ ID NO 353
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Gln Gln Leu Tyr Ser Ser Pro Met
1 5

<210> SEQ ID NO 354

<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 354

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
        115                 120
```

<210> SEQ ID NO 355
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 355

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr
            100                 105                 110
```

<210> SEQ ID NO 356
<211> LENGTH: 454
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 356

```
Gln Val Gln Leu Gln Gln Ser Gly Pro Gly Leu Val Lys Pro Ser Gln
1               5                   10                  15
```

-continued

```
Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
```

```
        435                 440                 445

Ser Leu Ser Pro Gly Lys
    450


<210> SEQ ID NO 357
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 358
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Thr Tyr Trp Met His
1               5


<210> SEQ ID NO 359
<211> LENGTH: 17
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 359

Asn Ile Tyr Pro Gly Thr Gly Gly Ser Asn Phe Asp Glu Lys Phe Lys
1 5 10 15

Asn

<210> SEQ ID NO 360
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 360

Trp Thr Thr Gly Thr Gly Ala Tyr
1 5

<210> SEQ ID NO 361
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 361

Gly Tyr Thr Phe Thr Thr Tyr
1 5

<210> SEQ ID NO 362
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Tyr Pro Gly Thr Gly Gly
1 5

<210> SEQ ID NO 363
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 363

Gln Val Gln Leu Gln Gln Pro Gly Ser Glu Leu Val Arg Pro Gly Ala
1 5 10 15

Ser Val Lys Leu Ser Cys Lys Ala Ser Gly Tyr Thr Phe Thr Thr Tyr
20 25 30

Trp Met His Trp Val Arg Gln Arg Pro Gly Gln Gly Leu Glu Trp Ile
35 40 45

Gly Asn Ile Tyr Pro Gly Thr Gly Gly Ser Asn Phe Asp Glu Lys Phe
50 55 60

Lys Asn Arg Thr Ser Leu Thr Val Asp Thr Ser Ser Thr Thr Ala Tyr
65 70 75 80

Met His Leu Ala Ser Leu Thr Ser Glu Asp Ser Ala Val Tyr Tyr Cys
85 90 95

Thr Arg Trp Thr Thr Gly Thr Gly Ala Tyr Trp Gly Gln Gly Thr Leu
100 105 110

Val Thr Val Ser Ala
115

<210> SEQ ID NO 364
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 364
caggtccagc tgcagcaacc tgggtctgag ctggtgaggc ctggagcttc agtgaagctg 60
tcctgcaagg cgtctggcta cacattcacc acttactgga tgcactgggt gaggcagagg 120
cctggacaag gccttgagtg gattggaaat atttatcctg gtactggtgg ttctaacttc 180
gatgagaagt tcaaaaacag gacctcactg actgtagaca catcctccac cacagcctac 240
atgcacctcg ccagcctgac atctgaggac tctgcggtct attactgtac aagatggact 300
actgggacgg gagcttattg gggccaaggg actctggtca ctgtctctgc a 351

<210> SEQ ID NO 365
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 365

Gln Val Gln Leu Gln Gln Ser Gly Ser Glu Leu Val Arg Pro Gly Ala
1 5 10 15

Ser Val Lys Leu Ser Cys Lys Ala Ser Gly Tyr Thr Phe Thr Thr Tyr
20 25 30

Trp Met His Trp Val Arg Gln Arg Pro Gly Gln Gly Leu Glu Trp Ile
35 40 45

Gly Asn Ile Tyr Pro Gly Thr Gly Gly Ser Asn Phe Asp Glu Lys Phe
50 55 60

Lys Asn Arg Thr Ser Leu Thr Val Asp Thr Ser Ser Thr Thr Ala Tyr
65 70 75 80

Met His Leu Ala Ser Leu Thr Ser Glu Asp Ser Ala Val Tyr Tyr Cys
85 90 95

Thr Arg Trp Thr Thr Gly Thr Gly Ala Tyr Trp Gly Gln Gly Thr Leu
100 105 110

Val Thr Val Ser Ala
115

<210> SEQ ID NO 366
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 366
caggtccagc tgcagcagtc tgggtctgag ctggtgaggc ctggagcttc agtgaagctg 60
tcctgcaagg cgtctggcta cacattcacc acttactgga tgcactgggt gaggcagagg 120
cctggacaag gccttgagtg gattggaaat atttatcctg gtactggtgg ttctaacttc 180
gatgagaagt tcaaaaacag gacctcactg actgtagaca catcctccac cacagcctac 240
atgcacctcg ccagcctgac atctgaggac tctgcggtct attactgtac aagatggact 300
actgggacgg gagcttattg gggccaaggg actctggtca ctgtctctgc a 351

<210> SEQ ID NO 367
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 367

Lys Ser Ser Gln Ser Leu Leu Asp Ser Gly Asn Gln Lys Asn Phe Leu
1 5 10 15

Thr

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 368

Trp Ala Ser Thr Arg Glu Ser
1 5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 369

Gln Asn Asp Tyr Ser Tyr Pro Cys Thr
1 5

<210> SEQ ID NO 370
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 370

Ser Gln Ser Leu Leu Asp Ser Gly Asn Gln Lys Asn Phe
1 5 10

<210> SEQ ID NO 371
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 371

Trp Ala Ser

1

<210> SEQ ID NO 372
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 372

Asp Tyr Ser Tyr Pro Cys
1 5

<210> SEQ ID NO 373
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 373

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Pro Pro Lys Leu Leu Ile Phe Trp Ala Ser Thr Arg Glu Ser Gly Val
50 55 60

Pro Asp Arg Phe Thr Gly Ser Gly Ser Val Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Ser Tyr Pro Cys Thr Phe Gly Gly Gly Thr Lys Leu Glu Ile
100 105 110

Lys

<210> SEQ ID NO 374
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 374
gacattgtga tgacccagtc tccatcctcc ctgactgtga cagcaggaga gaaggtcact 60
atgagctgca agtccagtca gagtctgtta gacagtggaa atcaaaagaa cttcttgacc 120
tggtaccagc agaaaccagg gcagcctcct aaactgttga tcttctgggc atccactagg 180
gaatctgggg tccctgatcg cttcacaggc agtggatctg taacagattt cactctcacc 240
atcagcagtg tgcaggctga agacctggca gtttattact gtcagaatga ttatagttat 300
ccgtgcacgt tcggaggggg gaccaagctg gaaataaaa 339

<210> SEQ ID NO 375
<211> LENGTH: 117
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 375

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115

<210> SEQ ID NO 376
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376
caggtccagc tgcagcagcc tgggtctgag ctggtgaggc ctggagcttc agtgaagctg     60
tcctgcaagg cgtctggcta cacattcacc acttactgga tgcactgggt gaggcagagg    120
cctggacaag gccttgagtg gattggaaat atttatcctg gtactggtgg ttctaacttc    180
gatgagaagt tcaaaaacag gacctcactg actgtagaca catcctccac cacagcctac    240
atgcacctcg ccagcctgac atctgaggac tctgcggtct attactgtac aagatggact    300
actgggacgg gagcttattg gggccagggc accaccgtga ccgtgtcctc c             351

<210> SEQ ID NO 377
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys

```
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 378
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 378

-continued

```
caggtccagc tgcagcagcc tgggtctgag ctggtgaggc ctggagcttc agtgaagctg      60
tcctgcaagg cgtctggcta cacattcacc acttactgga tgcactgggt gaggcagagg     120
cctggacaag gccttgagtg gattggaaat atttatcctg gtactggtgg ttctaacttc     180
gatgagaagt tcaaaaacag gacctcactg actgtagaca catcctccac cacagcctac     240
atgcacctcg ccagcctgac atctgaggac tctgcggtct attactgtac aagatggact     300
actgggacgg gagcttattg gggccagggc accaccgtga ccgtgtcctc cgcttccacc     360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacgaagac ctacacctgc     600
aacgtagatc acaagcccag caacaccaag gtggacaaga gagttgagtc caaatatggt     660
cccccatgcc caccgtgccc agcacctgag ttcctggggg gaccatcagt cttcctgttc     720
cccccaaaac ccaaggacac tctcatgatc tcccggaccc ctgaggtcac gtgcgtggtg     780
gtggacgtga gccaggaaga ccccgaggtc cagttcaact ggtacgtgga tggcgtggag     840
gtgcataatg ccaagacaaa gccgcgggag gagcagttca acagcacgta ccgtgtggtc     900
agcgtcctca ccgtcctgca ccaggactgg ctgaacggca aggagtacaa gtgcaaggtg     960
tccaacaaag gcctcccgtc ctccatcgag aaaaccatct ccaaagccaa agggcagccc    1020
cgagagccac aggtgtacac cctgccccca tcccaggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acgcctcccg tgctggactc cgacggctcc    1200
ttcttcctct acagcaggct aaccgtggac aagagcaggt ggcaggaggg gaatgtcttc    1260
tcatgctccg tgatgcatga ggctctgcac aaccactaca cacagaagag cctctccctg    1320
tctctgggta aa                                                        1332
```

<210> SEQ ID NO 379
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 379

```
Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
```

115

<210> SEQ ID NO 380
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 380
caggtccagc tgcagcagtc tgggtctgag ctggtgaggc ctggagcttc agtgaagctg 60
tcctgcaagg cgtctggcta cacattcacc acttactgga tgcactgggt gaggcagagg 120
cctggacaag gccttgagtg gattggaaat atttatcctg gtactggtgg ttctaacttc 180
gatgagaagt tcaaaaacag gacctcactg actgtagaca catcctccac cacagcctac 240
atgcacctcg ccagcctgac atctgaggac tctgcggtct attactgtac aagatggact 300
actgggacgg gagcttattg gggccagggc accaccgtga ccgtgtcctc c 351

<210> SEQ ID NO 381
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 381

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Pro Pro Lys Leu Leu Ile Phe Trp Ala Ser Thr Arg Glu Ser Gly Val
50 55 60

Pro Asp Arg Phe Thr Gly Ser Gly Ser Val Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Ser Tyr Pro Cys Thr Phe Gly Gln Gly Thr Lys Val Glu Ile
100 105 110

Lys

<210> SEQ ID NO 382
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 382
gacattgtga tgacccagtc tccatcctcc ctgactgtga cagcaggaga gaaggtcact 60
atgagctgca agtccagtca gagtctgtta gacagtggaa atcaaaagaa cttcttgacc 120
tggtaccagc agaaaccagg gcagcctcct aaactgttga tcttctgggc atccactagg 180
gaatctgggg tccctgatcg cttcacaggc agtggatctg taacagattt cactctcacc 240
atcagcagtg tgcaggctga agacctggca gtttattact gtcagaatga ttatagttat 300
ccgtgcacgt tcggccaagg gaccaaggtg gaaatcaaa 339

<210> SEQ ID NO 383
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 383

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Pro Pro Lys Leu Leu Ile Phe Trp Ala Ser Thr Arg Glu Ser Gly Val
50 55 60

Pro Asp Arg Phe Thr Gly Ser Gly Ser Val Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Ser Tyr Pro Cys Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 384
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 384
gacattgtga tgacccagtc tccatcctcc ctgactgtga cagcaggaga gaaggtcact 60
atgagctgca agtccagtca gagtctgtta gacagtggaa atcaaaagaa cttcttgacc 120
tggtaccagc agaaaccagg gcagcctcct aaactgttga tcttctgggc atccactagg 180
gaatctgggg tccctgatcg cttcacaggc agtggatctg taacagattt cactctcacc 240
atcagcagtg tgcaggctga agacctggca gtttattact gtcagaatga ttatagttat 300
ccgtgcacgt tcggccaagg gaccaaggtg gaaatcaaac gtacggtggc tgcaccatct 360

-continued

```
gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660


<210> SEQ ID NO 385
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Gln Val Gln Leu Gln Gln Ser Gly Ser Glu Leu Val Arg Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Arg Gln Arg Pro Gly Gln Gly Leu Glu Trp Ile
        35                  40                  45

Gly Asn Ile Tyr Pro Gly Thr Gly Gly Ser Asn Phe Asp Glu Lys Phe
    50                  55                  60

Lys Asn Arg Thr Ser Leu Thr Val Asp Thr Ser Ser Thr Thr Ala Tyr
65                  70                  75                  80

Met His Leu Ala Ser Leu Thr Ser Glu Asp Ser Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
```

-continued

```
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 386
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 386

caggtccagc tgcagcagtc tgggtctgag ctggtgaggc ctggagcttc agtgaagctg      60

tcctgcaagg cgtctggcta cacattcacc acttactgga tgcactgggt gaggcagagg     120

cctggacaag gccttgagtg gattggaaat atttatcctg gtactggtgg ttctaacttc     180

gatgagaagt tcaaaaacag gacctcactg actgtagaca catcctccac cacagcctac     240

atgcacctcg ccagcctgac atctgaggac tctgcggtct attactgtac aagatggact     300

actgggacgg gagcttattg gggccagggc accaccgtga ccgtgtcctc cgcttccacc     360

aagggcccat ccgtcttccc cctggcgccc tgctccagga gcacctccga gagcacagcc     420

gccctgggct gcctggtcaa ggactacttc cccgaaccgg tgacggtgtc gtggaactca     480

ggcgccctga ccagcggcgt gcacaccttc ccggctgtcc tacagtcctc aggactctac     540

tccctcagca gcgtggtgac cgtgccctcc agcagcttgg gcacgaagac ctacacctgc     600

aacgtagatc acaagcccag caacaccaag gtggacaaga gagttgagtc caaatatggt     660

cccccatgcc caccgtgccc agcacctgag ttcctggggg gaccatcagt cttcctgttc     720

cccccaaaac ccaaggacac tctcatgatc tcccggaccc ctgaggtcac gtgcgtggtg     780

gtggacgtga gccaggaaga ccccgaggtc cagttcaact ggtacgtgga tggcgtggag     840

gtgcataatg ccaagacaaa gccgcgggag gagcagttca acagcacgta ccgtgtggtc     900

agcgtcctca ccgtcctgca ccaggactgg ctgaacggca aggagtacaa gtgcaaggtg     960

tccaacaaag gcctcccgtc ctccatcgag aaaaccatct ccaaagccaa agggcagccc    1020

cgagagccac aggtgtacac cctgccccca tcccaggagg agatgaccaa gaaccaggtc    1080

agcctgacct gcctggtcaa aggcttctac cccagcgaca tcgccgtgga gtgggagagc    1140

aatgggcagc cggagaacaa ctacaagacc acgcctcccg tgctggactc cgacggctcc    1200

ttcttcctct acagcaggct aaccgtggac aagagcaggt ggcaggaggg gaatgtcttc    1260
```

```
tcatgctccg tgatgcatga ggctctgcac aaccactaca cacagaagag cctctccctg   1320

tctctgggta aa                                                       1332


<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gln Asn Asp Tyr Ser Tyr Pro Tyr Thr
1               5


<210> SEQ ID NO 388
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Asp Tyr Ser Tyr Pro Tyr
1               5


<210> SEQ ID NO 389
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Val Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys


<210> SEQ ID NO 390
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 390

gacattgtga tgacccagtc tccatcctcc ctgactgtga cagcaggaga gaaggtcact     60
```

atgagctgca agtccagtca gagtctgtta gacagtggaa atcaaaagaa cttcttgacc 120
tggtaccagc agaaaccagg gcagcctcct aaactgttga tcttctgggc atccactagg 180
gaatctgggg tccctgatcg cttcacaggc agtggatctg taacagattt cactctcacc 240
atcagcagtg tgcaggctga agacctggca gtttattact gtcagaatga ttatagttat 300
ccgtacacgt tcggccaagg gaccaaggtg gaaatcaaa 339

<210> SEQ ID NO 391
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 391

Asp Ile Val Met Thr Gln Ser Pro Ser Ser Leu Thr Val Thr Ala Gly
1 5 10 15

Glu Lys Val Thr Met Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Pro Pro Lys Leu Leu Ile Phe Trp Ala Ser Thr Arg Glu Ser Gly Val
50 55 60

Pro Asp Arg Phe Thr Gly Ser Gly Ser Val Thr Asp Phe Thr Leu Thr
65 70 75 80

Ile Ser Ser Val Gln Ala Glu Asp Leu Ala Val Tyr Tyr Cys Gln Asn
85 90 95

Asp Tyr Ser Tyr Pro Tyr Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 392
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 392
gacattgtga tgacccagtc tccatcctcc ctgactgtga cagcaggaga gaaggtcact 60
atgagctgca agtccagtca gagtctgtta gacagtggaa atcaaaagaa cttcttgacc 120
tggtaccagc agaaaccagg gcagcctcct aaactgttga tcttctgggc atccactagg 180

-continued

```
gaatctgggg tccctgatcg cttcacaggc agtggatctg taacagattt cactctcacc    240

atcagcagtg tgcaggctga agacctggca gtttattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 393
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

<210> SEQ ID NO 394
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 394

```
gaagtgcagc tggtgcagtc tggagcagag gtgaaaaagc ccggggagtc tctgaggatc     60

tcctgtaagg gttctggcta cacattcacc acttactgga tgcactgggt gcgacaggcc    120

actggacaag ggcttgagtg gatgggtaat atttatcctg gtactggtgg ttctaacttc    180

gatgagaagt tcaagaacag agtcacgatt accgcggaca aatccacgag cacagcctac    240

atggagctga gcagcctgag atctgaggac acggccgtgt attactgtac aagatggact    300

actgggacgg gagcttattg gggccagggc accaccgtga ccgtgtcctc c             351
```

<210> SEQ ID NO 395
<211> LENGTH: 444
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 395

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380
```

-continued

```
Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 396
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 396

```
gaagtgcagc tggtgcagtc tggagcagag gtgaaaaagc ccggggagtc tctgaggatc     60

tcctgtaagg gttctggcta cacattcacc acttactgga tgcactgggt gcgacaggcc    120

actggacaag ggcttgagtg gatgggtaat atttatcctg gtactggtgg ttctaacttc    180

gatgagaagt tcaagaacag agtcacgatt accgcggaca aatccacgag cacagcctac    240

atggagctga gcagcctgag atctgaggac acggccgtgt attactgtac aagatggact    300

actgggacgg gagcttattg gggccagggc accaccgtga ccgtgtcctc cgcttccacc    360

aagggcccat ccgtcttccc cctggcgccc tgctccagga gcacctccga gagcacagcc    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacgaagac ctacacctgc    600

aacgtagatc acaagcccag caacaccaag gtggacaaga gagttgagtc caaatatggt    660

cccccatgcc caccgtgccc agcacctgag ttcctggggg gaccatcagt cttcctgttc    720

cccccaaaac ccaaggacac tctcatgatc tcccggaccc ctgaggtcac gtgcgtggtg    780

gtggacgtga gccaggaaga ccccgaggtc cagttcaact ggtacgtgga tggcgtggag    840

gtgcataatg ccaagacaaa gccgcgggag gagcagttca acagcacgta ccgtgtggtc    900

agcgtcctca ccgtcctgca ccaggactgg ctgaacggca aggagtacaa gtgcaaggtg    960

tccaacaaag gcctcccgtc ctccatcgag aaaaccatct ccaaagccaa agggcagccc   1020

cgagagccac aggtgtacac cctgccccca tcccaggagg agatgaccaa gaaccaggtc   1080

agcctgacct gcctggtcaa aggcttctac cccagcgaca tcgccgtgga gtgggagagc   1140

aatgggcagc cggagaacaa ctacaagacc acgcctcccg tgctggactc cgacggctcc   1200

ttcttcctct acagcaggct aaccgtggac aagagcaggt ggcaggaggg gaatgtcttc   1260

tcatgctccg tgatgcatga ggctctgcac aaccactaca cacagaagag cctctccctg   1320

tctctgggta aa                                                        1332
```

<210> SEQ ID NO 397
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 397

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Glu Phe Thr Leu Thr
65                  70                  75                  80

Ile Ser Ser Leu Gln Pro Asp Asp Phe Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys


<210> SEQ ID NO 398
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 398

gaaattgtgt tgacacagtc tccagccacc ctgtctttgt ctccagggga aagagccacc     60

ctctcctgca agtccagtca gagtctgtta gacagtggaa atcaaaagaa cttcttgacc    120

tggtaccagc agaaacctgg ccaggctccc aggctcctca tctattgggc atccactagg    180

gaatctgggg tcccatcaag gttcagcggc agtggatctg ggacagaatt cactctcacc    240

atcagcagcc tgcagcctga tgattttgca acttattact gtcagaatga ttatagttat    300

ccgtacacgt tcggccaagg gaccaaggtg gaaatcaaa                           339


<210> SEQ ID NO 399
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Glu Phe Thr Leu Thr
65                  70                  75                  80

Ile Ser Ser Leu Gln Pro Asp Asp Phe Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110
```

```
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 400
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 400

```
gaaattgtgt tgacacagtc tccagccacc ctgtctttgt ctccagggga aagagccacc     60

ctctcctgca agtccagtca gagtctgtta gacagtggaa atcaaaagaa cttcttgacc    120

tggtaccagc agaaacctgg ccaggctccc aggctcctca tctattgggc atccactagg    180

gaatctgggg tcccatcaag gttcagcggc agtggatctg ggacagaatt cactctcacc    240

atcagcagcc tgcagcctga tgattttgca acttattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 401
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 401

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Pro Arg Phe Ser Gly Ser Gly Tyr Gly Thr Asp Phe Thr Leu Thr
65                  70                  75                  80
```

Ile Asn Asn Ile Glu Ser Glu Asp Ala Ala Tyr Tyr Phe Cys Gln Asn
85 90 95

Asp Tyr Ser Tyr Pro Tyr Thr Phe Gly Gln Gly Thr Lys Val Glu Ile
100 105 110

Lys

<210> SEQ ID NO 402
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 402
gacatccaga tgacccagtc tccatcctcc ctgtctgcat ctgtaggaga cagagtcacc 60
atcacttgca agtccagtca gagtctgtta gacagtggaa atcaaaagaa cttcttgacc 120
tggtaccagc agaaacctgg ccaggctccc aggctcctca tctattgggc atccactagg 180
gaatctggga tcccacctcg attcagtggc agcgggtatg gaacagattt taccctcaca 240
attaataaca tagaatctga ggatgctgca tattacttct gtcagaatga ttatagttat 300
ccgtacacgt tcggccaagg gaccaaggtg gaaatcaaa 339

<210> SEQ ID NO 403
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 403

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Ile
50 55 60

Pro Pro Arg Phe Ser Gly Ser Gly Tyr Gly Thr Asp Phe Thr Leu Thr
65 70 75 80

Ile Asn Asn Ile Glu Ser Glu Asp Ala Ala Tyr Tyr Phe Cys Gln Asn
85 90 95

Asp Tyr Ser Tyr Pro Tyr Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

```
Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 404
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404

gacatccaga tgacccagtc tccatcctcc ctgtctgcat ctgtaggaga cagagtcacc     60

atcacttgca agtccagtca gagtctgtta gacagtggaa atcaaaagaa cttcttgacc    120

tggtaccagc agaaacctgg ccaggctccc aggctcctca tctattgggc atccactagg    180

gaatctggga tcccacctcg attcagtggc agcgggtatg gaacagattt taccctcaca    240

attaataaca tagaatctga ggatgctgca tattacttct gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660


<210> SEQ ID NO 405
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115


<210> SEQ ID NO 406
<211> LENGTH: 351
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 406
gaagtgcagc tggtgcagtc tggagcagag gtgaaaaagc ccggggagtc tctgaggatc 60
tcctgtaagg gttctggcta cacattcacc acttactgga tgcactggat caggcagtcc 120
ccatcgagag gccttgagtg gctgggtaat atttatcctg gtactggtgg ttctaacttc 180
gatgagaagt tcaagaacag attcaccatc tccagagaca attccaagaa cacgctgtat 240
cttcaaatga acagcctgag agccgaggac acggccgtgt attactgtac aagatggact 300
actgggacgg gagcttattg gggccagggc accaccgtga ccgtgtcctc c 351

<210> SEQ ID NO 407
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 407

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

```
Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 408
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 408

```
gaagtgcagc tggtgcagtc tggagcagag gtgaaaaagc ccggggagtc tctgaggatc     60

tcctgtaagg gttctggcta cacattcacc acttactgga tgcactggat caggcagtcc    120

ccatcgagag gccttgagtg gctgggtaat atttatcctg gtactggtgg ttctaacttc    180

gatgagaagt tcaagaacag attcaccatc tccagagaca attccaagaa cacgctgtat    240

cttcaaatga acagcctgag agccgaggac acggccgtgt attactgtac aagatggact    300

actgggacgg gagcttattg gggccagggc accaccgtga ccgtgtcctc cgcttccacc    360

aagggcccat ccgtcttccc cctggcgccc tgctccagga gcacctccga gagcacagcc    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacgaagac ctacacctgc    600

aacgtagatc acaagcccag caacaccaag gtggacaaga gagttgagtc caaatatggt    660

cccccatgcc caccgtgccc agcacctgag ttcctggggg gaccatcagt cttcctgttc    720

cccccaaaac ccaaggacac tctcatgatc tcccggaccc ctgaggtcac gtgcgtggtg    780

gtggacgtga gccaggaaga ccccgaggtc cagttcaact ggtacgtgga tggcgtggag    840

gtgcataatg ccaagacaaa gccgcgggag gagcagttca acagcacgta ccgtgtggtc    900

agcgtcctca ccgtcctgca ccaggactgg ctgaacggca aggagtacaa gtgcaaggtg    960

tccaacaaag gcctcccgtc ctccatcgag aaaaccatct ccaaagccaa agggcagccc   1020
```

```
cgagagccac aggtgtacac cctgccccca tcccaggagg agatgaccaa gaaccaggtc   1080

agcctgacct gcctggtcaa aggcttctac cccagcgaca tcgccgtgga gtgggagagc   1140

aatgggcagc cggagaacaa ctacaagacc acgcctcccg tgctggactc cgacggctcc   1200

ttcttcctct acagcaggct aaccgtggac aagagcaggt ggcaggaggg gaatgtcttc   1260

tcatgctccg tgatgcatga ggctctgcac aaccactaca cacagaagag cctctccctg   1320

tctctgggta aa                                                       1332
```

<210> SEQ ID NO 409
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 409

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 410
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 410

```
gaaattgtgt tgacacagtc tccagccacc ctgtctttgt ctccagggga aagagccacc     60

ctctcctgca agtccagtca gagtctgtta gacagtggaa atcaaaagaa cttcttgacc    120

tggtatcagc agaaaccagg gaaagctcct aagctcctga tctattgggc atccactagg    180

gaatctgggg tcccatcaag gttcagtgga agtggatctg ggacagattt tactttcacc    240

atcagcagcc tgcagcctga agatattgca acatattact gtcagaatga ttatagttat    300

ccgtacacgt tcggccaagg gaccaaggtg gaaatcaaa                           339
```

<210> SEQ ID NO 411
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 411

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 412
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 412

```
gaaattgtgt tgacacagtc tccagccacc ctgtctttgt ctccagggga aagagccacc     60

ctctcctgca agtccagtca gagtctgtta gacagtggaa atcaaaagaa cttcttgacc    120

tggtatcagc agaaaccagg gaaagctcct aagctcctga tctattgggc atccactagg    180

gaatctgggg tcccatcaag gttcagtgga agtggatctg ggacagattt tactttcacc    240

atcagcagcc tgcagcctga agatattgca acatattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 413
<211> LENGTH: 113

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 413

Asp Ile Val Met Thr Gln Thr Pro Leu Ser Leu Pro Val Thr Pro Gly
1 5 10 15

Glu Pro Ala Ser Ile Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys

<210> SEQ ID NO 414
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 414
gatattgtga tgacccagac tccactctcc ctgcccgtca cccctggaga gccggcctcc 60
atctcctgca agtccagtca gagtctgtta gacagtggaa atcaaaagaa cttcttgacc 120
tggtaccagc agaaacctgg ccaggctccc aggctcctca tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaa 339

<210> SEQ ID NO 415
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 415

Asp Ile Val Met Thr Gln Thr Pro Leu Ser Leu Pro Val Thr Pro Gly
1 5 10 15

Glu Pro Ala Ser Ile Ser Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

```
Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 416
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 416

```
gatattgtga tgacccagac tccactctcc ctgcccgtca cccctggaga gccggcctcc     60

atctcctgca agtccagtca gagtctgtta gacagtggaa atcaaaagaa cttcttgacc    120

tggtaccagc agaaacctgg ccaggctccc aggctcctca tctattgggc atccactagg    180

gaatctgggg tcccctcgag gttcagtggc agtggatctg ggacagattt cacctttacc    240

atcagtagcc tggaagctga agatgctgca acatattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 417
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 417

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
```

```
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys


<210> SEQ ID NO 418
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 418

gaaattgtgt tgacacagtc tccagccacc ctgtctttgt ctccagggga aagagccacc      60

ctctcctgca agtccagtca gagtctgtta gacagtggaa atcaaaagaa cttcttgacc     120

tggtatcagc agaaaccagg gaaagctcct aagctcctga tctattgggc atccactagg     180

gaatctgggg tcccctcgag gttcagtggc agtggatctg ggacagattt cacctttacc     240

atcagtagcc tggaagctga agatgctgca acatattact gtcagaatga ttatagttat     300

ccgtacacgt tcggccaagg gaccaaggtg gaaatcaaa                            339


<210> SEQ ID NO 419
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 420
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 420

gaaattgtgt tgacacagtc tccagccacc ctgtctttgt ctccagggga aagagccacc     60

ctctcctgca agtccagtca gagtctgtta gacagtggaa atcaaaagaa cttcttgacc    120

tggtatcagc agaaaccagg gaaagctcct aagctcctga tctattgggc atccactagg    180

gaatctgggg tcccctcgag gttcagtggc agtggatctg ggacagattt cacctttacc    240

atcagtagcc tggaagctga agatgctgca acatattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660


<210> SEQ ID NO 421
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Glu Ile Val Leu Thr Gln Ser Pro Asp Phe Gln Ser Val Thr Pro Lys
1               5                   10                  15

Glu Lys Val Thr Ile Thr Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 422
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 422
gaaattgtgc tgactcagtc tccagacttt cagtctgtga ctccaaagga gaaagtcacc 60
atcacctgca agtccagtca gagtctgtta gacagtggaa atcaaaagaa cttcttgacc 120
tggtaccagc agaaacctgg ccaggctccc aggctcctca tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaa 339

<210> SEQ ID NO 423
<211> LENGTH: 220
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 423

Glu Ile Val Leu Thr Gln Ser Pro Asp Phe Gln Ser Val Thr Pro Lys
1 5 10 15

Glu Lys Val Thr Ile Thr Cys Lys Ser Ser Gln Ser Leu Leu Asp Ser
20 25 30

Gly Asn Gln Lys Asn Phe Leu Thr Trp Tyr Gln Gln Lys Pro Gly Gln
35 40 45

Ala Pro Arg Leu Leu Ile Tyr Trp Ala Ser Thr Arg Glu Ser Gly Val
50 55 60

Pro Ser Arg Phe Ser Gly Ser Gly Ser Gly Thr Asp Phe Thr Phe Thr
65 70 75 80

Ile Ser Ser Leu Glu Ala Glu Asp Ala Ala Thr Tyr Tyr Cys Gln Asn
85 90 95

Asp Tyr Ser Tyr Pro Tyr Thr Phe Gly Gln Gly Thr Lys Val Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

Ser Thr Tyr Ser Leu Ser Ser Thr Leu Thr Leu Ser Lys Ala Asp Tyr
180 185 190

Glu Lys His Lys Val Tyr Ala Cys Glu Val Thr His Gln Gly Leu Ser
195 200 205

Ser Pro Val Thr Lys Ser Phe Asn Arg Gly Glu Cys
210 215 220

<210> SEQ ID NO 424

<211> LENGTH: 660
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 424
gaaattgtgc tgactcagtc tccagacttt cagtctgtga ctccaaagga gaaagtcacc 60
atcacctgca agtccagtca gagtctgtta gacagtggaa atcaaaagaa cttcttgacc 120
tggtaccagc agaaacctgg ccaggctccc aggctcctca tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 425
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 425

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 426
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 426
gaaattgtgt tgacacagtc tccagccacc ctgtctttgt ctccagggga aagagccacc 60
ctctcctgca agtccagtca gagtctgtta gacagtggaa atcaaaagaa cttcttgacc 120

```
tggtaccagc agaaacctgg ccaggctccc aggctcctca tctattgggc atccactagg    180

gaatctgggg tcccctcgag gttcagtggc agtggatctg ggacagattt cacctttacc    240

atcagtagcc tggaagctga agatgctgca acatattact gtcagaatga ttatagttat    300

ccgtacacgt tcggccaagg gaccaaggtg gaaatcaaa                            339


<210> SEQ ID NO 427
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 428
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 428

gaaattgtgt tgacacagtc tccagccacc ctgtctttgt ctccagggga aagagccacc     60

ctctcctgca agtccagtca gagtctgtta gacagtggaa atcaaaagaa cttcttgacc    120

tggtaccagc agaaacctgg ccaggctccc aggctcctca tctattgggc atccactagg    180
```

gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 429
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 429

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys

<210> SEQ ID NO 430
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 430
gacatccaga tgacccagtc tccatcctcc ctgtctgcat ctgtaggaga cagagtcacc 60
atcacttgca agtccagtca gagtctgtta gacagtggaa atcaaaagaa cttcttgacc 120
tggtacctgc agaagccagg gcagtctcca cagctcctga tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaa 339

<210> SEQ ID NO 431
<211> LENGTH: 220
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 431

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asp Ser
            20                  25                  30

Gly Asn Gln Lys Asn Phe Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 432
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 432
gacatccaga tgacccagtc tccatcctcc ctgtctgcat ctgtaggaga cagagtcacc 60
atcacttgca agtccagtca gagtctgtta gacagtggaa atcaaaagaa cttcttgacc 120
tggtacctgc agaagccagg gcagtctcca cagctcctga tctattgggc atccactagg 180
gaatctgggg tcccctcgag gttcagtggc agtggatctg ggacagattt cacctttacc 240
atcagtagcc tggaagctga agatgctgca acatattact gtcagaatga ttatagttat 300
ccgtacacgt tcggccaagg gaccaaggtg gaaatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 433
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 434
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 434

```
gatgttgtga tgactcagtc tccactctcc ctgcccgtca cccttggaca gccggcctcc      60

atctcctgca agtccagtca gagtctgtta gacagtggaa atcaaaagaa cttcttaacc     120

tggtatcagc agaaaccagg gaaagctcct aagctcctga tctattgggc atccactagg     180

gaatctgggg tcccctcgag gttcagtggc agtggatctg ggacagattt cacctttacc     240

atcagtagcc tggaagctga agatgctgca acatattact gtcagaatga ttatagttat     300

ccgtacacgt tcggccaagg gaccaaggtg gaaatcaaa                             339
```

<210> SEQ ID NO 435
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
```

```
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 436
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 436

```
gatgttgtga tgactcagtc tccactctcc ctgcccgtca cccttggaca gccggcctcc     60

atctcctgca agtccagtca gagtctgtta gacagtggaa atcaaaagaa cttcttaacc    120

tggtatcagc agaaaccagg gaaagctcct aagctcctga tctattgggc atccactagg    180

gaatctgggg tcccctcgag gttcagtggc agtggatctg ggacagattt cacctttacc    240

atcagtagcc tggaagctga agatgctgca acatattact gtcagaatga ttatagttat    300

ccgtacacgt tcggccaagg gaccaaggtg gaaatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660
```

<210> SEQ ID NO 437
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 437

```
Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Thr Tyr
20 25 30

Trp Met His Trp Ile Arg Gln Ser Pro Ser Arg Gly Leu Glu Trp Leu
35 40 45

Gly Asn Ile Tyr Pro Gly Thr Gly Gly Ser Asn Phe Asp Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Thr Arg Trp Thr Thr Gly Thr Gly Ala Tyr Trp Gly Gln Gly Thr Thr
100 105 110

Val Thr Val Ser Ser
115

<210> SEQ ID NO 438
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 438
caggttcagc tggtgcagtc tggagctgag gtgaagaagc ctggggcctc agtgaaggtc 60
tcctgcaagg cttctggcta cacattcacc acttactgga tgcactggat caggcagtcc 120
ccatcgagag gccttgagtg gctgggtaat atttatcctg gtactggtgg ttctaacttc 180
gatgagaagt tcaagaacag attcaccatc tccagagaca attccaagaa cacgctgtat 240
cttcaaatga acagcctgag agccgaggac acggccgtgt attactgtac aagatggact 300
actgggacgg gagcttactg gggccagggc accaccgtga ccgtgtcctc c 351

<210> SEQ ID NO 439
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 439

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Thr Tyr
20 25 30

Trp Met His Trp Ile Arg Gln Ser Pro Ser Arg Gly Leu Glu Trp Leu
35 40 45

Gly Asn Ile Tyr Pro Gly Thr Gly Gly Ser Asn Phe Asp Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Thr Arg Trp Thr Thr Gly Thr Gly Ala Tyr Trp Gly Gln Gly Thr Thr
100 105 110

Val Thr Val Ser Ser Ala Ser Thr Lys Gly Pro Ser Val Phe Pro Leu
115 120 125

-continued

```
Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 440
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 440

```
caggttcagc tggtgcagtc tggagctgag gtgaagaagc ctggggcctc agtgaaggtc      60

tcctgcaagg cttctggcta cacattcacc acttactgga tgcactggat caggcagtcc     120

ccatcgagag gccttgagtg gctgggtaat atttatcctg gtactggtgg ttctaacttc     180

gatgagaagt tcaagaacag attcaccatc tccagagaca attccaagaa cacgctgtat     240
```

```
cttcaaatga acagcctgag agccgaggac acggccgtgt attactgtac aagatggact    300

actgggacgg gagcttactg gggccagggc accaccgtga ccgtgtcctc cgcttccacc    360

aagggcccat ccgtcttccc cctggcgccc tgctccagga gcacctccga gagcacagcc    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacgaagac ctacacctgc    600

aacgtagatc acaagcccag caacaccaag gtggacaaga gagttgagtc caaatatggt    660

cccccatgcc caccgtgccc agcacctgag ttcctggggg gaccatcagt cttcctgttc    720

cccccaaaac ccaaggacac tctcatgatc tcccggaccc ctgaggtcac gtgcgtggtg    780

gtggacgtga gccaggaaga ccccgaggtc cagttcaact ggtacgtgga tggcgtggag    840

gtgcataatg ccaagacaaa gccgcgggag gagcagttca acagcacgta ccgtgtggtc    900

agcgtcctca ccgtcctgca ccaggactgg ctgaacggca aggagtacaa gtgcaaggtg    960

tccaacaaag gcctcccgtc ctccatcgag aaaaccatct ccaaagccaa agggcagccc   1020

cgagagccac aggtgtacac cctgccccca tcccaggagg agatgaccaa gaaccaggtc   1080

agcctgacct gcctggtcaa aggcttctac cccagcgaca tcgccgtgga gtgggagagc   1140

aatgggcagc cggagaacaa ctacaagacc acgcctcccg tgctggactc cgacggctcc   1200

ttcttcctct acagcaggct aaccgtggac aagagcaggt ggcaggaggg gaatgtcttc   1260

tcatgctccg tgatgcatga ggctctgcac aaccactaca cacagaagag cctctccctg   1320

tctctgggta aa                                                       1332
```

<210> SEQ ID NO 441
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 441

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
        115
```

<210> SEQ ID NO 442
<211> LENGTH: 351
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 442
gaagtgcagc tggtgcagtc tggagcagag gtgaaaaagc ccggggagtc tctgaggatc 60
tcctgtaagg gttctggcta cacattcacc acttactgga tgcactgggt gcgacaggcc 120
cctggacaag ggcttgagtg gatgggtaat atttatcctg gtactggtgg ttctaacttc 180
gatgagaagt tcaagaacag attcaccatc tccagagaca attccaagaa cacgctgtat 240
cttcaaatga acagcctgag agccgaggac acggccgtgt attactgtac aagatggact 300
actgggacgg gagcttattg gggccagggc accaccgtga ccgtgtcctc c 351

<210> SEQ ID NO 443
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 443

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Thr Tyr
20 25 30

Trp Met His Trp Val Arg Gln Ala Pro Gly Gln Gly Leu Glu Trp Met
35 40 45

Gly Asn Ile Tyr Pro Gly Thr Gly Gly Ser Asn Phe Asp Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Thr Arg Trp Thr Thr Gly Thr Gly Ala Tyr Trp Gly Gln Gly Thr Thr
100 105 110

Val Thr Val Ser Ser Ala Ser Thr Lys Gly Pro Ser Val Phe Pro Leu
115 120 125

Ala Pro Cys Ser Arg Ser Thr Ser Glu Ser Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Lys Thr Tyr Thr Cys Asn Val Asp His Lys Pro Ser Asn
195 200 205

Thr Lys Val Asp Lys Arg Val Glu Ser Lys Tyr Gly Pro Pro Cys Pro
210 215 220

Pro Cys Pro Ala Pro Glu Phe Leu Gly Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser Gln Glu Asp Pro Glu Val Gln Phe
260 265 270

-continued

```
Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 444
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 444

gaagtgcagc tggtgcagtc tggagcagag gtgaaaaagc ccggggagtc tctgaggatc     60

tcctgtaagg gttctggcta cacattcacc acttactgga tgcactgggt gcgacaggcc    120

cctggacaag ggcttgagtg gatgggtaat atttatcctg gtactggtgg ttctaacttc    180

gatgagaagt tcaagaacag attcaccatc tccagagaca attccaagaa cacgctgtat    240

cttcaaatga acagcctgag agccgaggac acggccgtgt attactgtac aagatggact    300

actgggacgg gagcttattg gggccagggc accaccgtga ccgtgtcctc cgcttccacc    360

aagggcccat ccgtcttccc cctggcgccc tgctccagga gcacctccga gagcacagcc    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacgaagac ctacacctgc    600

aacgtagatc acaagcccag caacaccaag gtggacaaga gagttgagtc caaatatggt    660

cccccatgcc caccgtgccc agcacctgag ttcctggggg gaccatcagt cttcctgttc    720

cccccaaaac ccaaggacac tctcatgatc tcccggaccc ctgaggtcac gtgcgtggtg    780

gtggacgtga gccaggaaga ccccgaggtc cagttcaact ggtacgtgga tggcgtggag    840

gtgcataatg ccaagacaaa gccgcgggag gagcagttca acagcacgta ccgtgtggtc    900

agcgtcctca ccgtcctgca ccaggactgg ctgaacggca aggagtacaa gtgcaaggtg    960

tccaacaaag gcctcccgtc ctccatcgag aaaaccatct ccaaagccaa agggcagccc   1020

cgagagccac aggtgtacac cctgccccca tcccaggagg agatgaccaa gaaccaggtc   1080
```

```
agcctgacct gcctggtcaa aggcttctac cccagcgaca tcgccgtgga gtgggagagc   1140

aatgggcagc cggagaacaa ctacaagacc acgcctcccg tgctggactc cgacggctcc   1200

ttcttcctct acagcaggct aaccgtggac aagagcaggt ggcaggaggg gaatgtcttc   1260

tcatgctccg tgatgcatga ggctctgcac aaccactaca cacagaagag cctctccctg   1320

tctctgggta aa                                                       1332


<210> SEQ ID NO 445
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 445

gaagtgcagc tggtgcagtc tggcgccgaa gtgaagaagc ctggcgagtc cctgcggatc     60

tcctgcaagg gctctggcta caccttcacc acctactgga tgcactgggt gcgacaggct    120

accggccagg gcctggaatg gatgggcaac atctatcctg gcaccggcgg ctccaacttc    180

gacgagaagt tcaagaacag agtgaccatc accgccgaca agtccacctc caccgcctac    240

atggaactgt cctccctgag atccgaggac accgccgtgt actactgcac ccggtggaca    300

accggcacag gcgcttattg gggccagggc accacagtga ccgtgtcctc t             351


<210> SEQ ID NO 446
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

```
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 447
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 447

```
gaagtgcagc tggtgcagtc tggcgccgaa gtgaagaagc ctggcgagtc cctgcggatc      60

tcctgcaagg gctctggcta caccttcacc acctactgga tgcactgggt gcgacaggct     120

accggccagg gcctggaatg gatgggcaac atctatcctg gcaccggcgg ctccaacttc     180

gacgagaagt tcaagaacag agtgaccatc accgccgaca agtccacctc caccgcctac     240

atggaactgt cctccctgag atccgaggac accgccgtgt actactgcac ccggtggaca     300

accggcacag gcgcttattg gggccagggc accacagtga ccgtgtcctc tgcttctacc     360

aaggggccca gcgtgttccc cctggccccc tgctccagaa gcaccagcga gagcacagcc     420

gccctgggct gcctggtgaa ggactacttc cccgagcccg tgaccgtgtc ctggaacagc     480

ggagccctga ccagcggcgt gcacaccttc cccgccgtgc tgcagagcag cggcctgtac     540
```

```
agcctgagca gcgtggtgac cgtgcccagc agcagcctgg gcaccaagac ctacacctgt    600

aacgtggacc acaagcccag caacaccaag gtggacaaga gggtggagag caagtacggc    660

ccaccctgcc ccccctgccc agcccccgag ttcctgggcg gacccagcgt gttcctgttc    720

ccccccaagc ccaaggacac cctgatgatc agcagaaccc ccgaggtgac ctgtgtggtg    780

gtggacgtgt cccaggagga ccccgaggtc cagttcaact ggtacgtgga cggcgtggag    840

gtgcacaacg ccaagaccaa gcccagagag gagcagttta acagcaccta ccgggtggtg    900

tccgtgctga ccgtgctgca ccaggactgg ctgaacggca aagagtacaa gtgtaaggtc    960

tccaacaagg gcctgccaag cagcatcgaa aagaccatca gcaaggccaa gggccagcct   1020

agagagcccc aggtctacac cctgccaccc agccaagagg agatgaccaa gaaccaggtg   1080

tccctgacct gtctggtgaa gggcttctac ccaagcgaca tcgccgtgga gtgggagagc   1140

aacggccagc ccgagaacaa ctacaagacc acccccccag tgctggacag cgacggcagc   1200

ttcttcctgt acagcaggct gaccgtggac aagtccagat ggcaggaggg caacgtcttt   1260

agctgctccg tgatgcacga ggccctgcac aaccactaca cccagaagag cctgagcctg   1320

tccctgggc                                                           1329
```

```
<210> SEQ ID NO 448
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 448

gagatcgtgc tgacccagtc ccctgccacc ctgtcactgt ctccaggcga gagagctacc     60

ctgtcctgca agtcctccca gtccctgctg gactccggca accagaagaa cttcctgacc    120

tggtatcagc agaagcccgg ccaggccccc agactgctga tctactgggc ctccacccgg    180

gaatctggcg tgccctctag attctccggc tccggctctg gcaccgagtt taccctgacc    240

atctccagcc tgcagcccga cgacttcgcc acctactact gccagaacga ctactcctac    300

ccctacacct tcggccaggg caccaaggtg gaaatcaag                           339
```

```
<210> SEQ ID NO 449
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 449

gagatcgtgc tgacccagtc ccctgccacc ctgtcactgt ctccaggcga gagagctacc     60

ctgtcctgca agtcctccca gtccctgctg gactccggca accagaagaa cttcctgacc    120

tggtatcagc agaagcccgg ccaggccccc agactgctga tctactgggc ctccacccgg    180

gaatctggcg tgccctctag attctccggc tccggctctg gcaccgagtt taccctgacc    240

atctccagcc tgcagcccga cgacttcgcc acctactact gccagaacga ctactcctac    300

ccctacacct tcggccaggg caccaaggtg gaaatcaagc gtacggtggc cgctcccagc    360

gtgttcatct tcccccccaag cgacgagcag ctgaagagcg gcaccgccag cgtggtgtgt    420

ctgctgaaca acttctaccc cagggaggcc aaggtgcagt ggaaggtgga caacgccctg    480

cagagcggca acagccagga gagcgtcacc gagcaggaca gcaaggactc cacctacagc    540
```

ctgagcagca ccctgaccct gagcaaggcc gactacgaga agcacaaggt gtacgcctgt 600
gaggtgaccc accagggcct gtccagcccc gtgaccaaga gcttcaacag gggcgagtgc 660

<210> SEQ ID NO 450
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 450
gaggtgcagc tggtgcagtc aggcgccgaa gtgaagaagc ccggcgagtc actgagaatt 60
agctgtaaag gttcaggcta caccttcact acctactgga tgcactgggt ccgccaggct 120
accggtcaag gcctcgagtg gatgggtaat atctaccccg gcaccggcgg ctctaacttc 180
gacgagaagt ttaagaatag agtgactatc accgccgata agtctactag caccgcctat 240
atggaactgt ctagcctgag atcagaggac accgccgtct actactgcac taggtggact 300
accggcacag gcgcctactg gggtcaaggc actaccgtga ccgtgtctag c 351

<210> SEQ ID NO 451
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 451
gaggtgcagc tggtgcagtc aggcgccgaa gtgaagaagc ccggcgagtc actgagaatt 60
agctgtaaag gttcaggcta caccttcact acctactgga tgcactgggt ccgccaggct 120
accggtcaag gcctcgagtg gatgggtaat atctaccccg gcaccggcgg ctctaacttc 180
gacgagaagt ttaagaatag agtgactatc accgccgata agtctactag caccgcctat 240
atggaactgt ctagcctgag atcagaggac accgccgtct actactgcac taggtggact 300
accggcacag gcgcctactg gggtcaaggc actaccgtga ccgtgtctag cgctagcact 360
aagggcccgt ccgtgttccc cctggcacct tgtagccgga gcactagcga atccaccgct 420
gccctcggct gcctggtcaa ggattacttc ccggagcccg tgaccgtgtc ctggaacagc 480
ggagccctga cctccggagt gcacaccttc cccgctgtgc tgcagagctc cgggctgtac 540
tcgctgtcgt cggtggtcac ggtgccttca tctagcctgg gtaccaagac ctacacttgc 600
aacgtggacc acaagccttc caacactaag gtggacaagc gcgtcgaatc gaagtacggc 660
ccaccgtgcc cgccttgtcc cgcgccggag ttcctcggcg gtccctcggt ctttctgttc 720
ccaccgaagc ccaaggacac tttgatgatt tcccgcaccc ctgaagtgac atgcgtggtc 780
gtggacgtgt cacaggaaga tccggaggtg cagttcaatt ggtacgtgga tggcgtcgag 840
gtgcacaacg ccaaaaccaa gccgagggag gagcagttca actccactta ccgcgtcgtg 900
tccgtgctga cggtgctgca tcaggactgg ctgaacggga aggagtacaa gtgcaaagtg 960
tccaacaagg gacttcctag ctcaatcgaa aagaccatct cgaaagccaa gggacagccc 1020
cgggaacccc aagtgtatac cctgccaccg agccaggaag aaatgactaa gaaccaagtc 1080
tcattgactt gccttgtgaa gggcttctac ccatcggata tcgccgtgga atgggagtcc 1140
aacggccagc cggaaaacaa ctacaagacc acccctccgg tgctggactc agacggatcc 1200
ttcttcctct actcgcggct gaccgtggat aagagcagat ggcaggaggg aaatgtgttc 1260
agctgttctg tgatgcatga agccctgcac aaccactaca ctcagaagtc cctgtccctc 1320
tccctggga 1329

<210> SEQ ID NO 452
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 452
gagatcgtcc tgactcagtc acccgctacc ctgagcctga gccctggcga gcgggctaca 60
ctgagctgta aatctagtca gtcactgctg gatagcggta atcagaagaa cttcctgacc 120
tggtatcagc agaagcccgg taaagcccct aagctgctga tctactgggc ctctactaga 180
gaatcaggcg tgccctctag gtttagcggt agcggtagtg gcaccgactt caccttcact 240
atctctagcc tgcagcccga ggatatcgct acctactact gtcagaacga ctatagctac 300
ccctacacct tcggtcaagg cactaaggtc gagattaag 339

<210> SEQ ID NO 453
<211> LENGTH: 660
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 453
gagatcgtcc tgactcagtc acccgctacc ctgagcctga gccctggcga gcgggctaca 60
ctgagctgta aatctagtca gtcactgctg gatagcggta atcagaagaa cttcctgacc 120
tggtatcagc agaagcccgg taaagcccct aagctgctga tctactgggc ctctactaga 180
gaatcaggcg tgccctctag gtttagcggt agcggtagtg gcaccgactt caccttcact 240
atctctagcc tgcagcccga ggatatcgct acctactact gtcagaacga ctatagctac 300
ccctacacct tcggtcaagg cactaaggtc gagattaagc gtacggtggc cgctcccagc 360
gtgttcatct tcccccccag cgacgagcag ctgaagagcg gcaccgccag cgtggtgtgc 420
ctgctgaaca acttctaccc ccgggaggcc aaggtgcagt ggaaggtgga caacgccctg 480
cagagcggca acagccagga gagcgtcacc gagcaggaca gcaaggactc cacctacagc 540
ctgagcagca ccctgaccct gagcaaggcc gactacgaga agcataaggt gtacgcctgc 600
gaggtgaccc accagggcct gtccagcccc gtgaccaaga gcttcaacag gggcgagtgc 660

<210> SEQ ID NO 454
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 454
gagatcgtgc tgacccagtc ccccgacttc cagtccgtga cccccaaaga aaaagtgacc 60
atcacatgca agtcctccca gtccctgctg gactccggca accagaagaa cttcctgacc 120
tggtatcagc agaagcccgg ccaggccccc agactgctga tctactgggc ctccacccgg 180

```
gaatctggcg tgccctctag attctccggc tccggctctg gcaccgactt taccttcacc    240

atctccagcc tggaagccga ggacgccgcc acctactact gccagaacga ctactcctac    300

ccctacacct tcggccaggg caccaaggtg gaaatcaag                           339


<210> SEQ ID NO 455
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 455

gagatcgtgc tgacccagtc cccgacttc cagtccgtga cccccaaaga aaaagtgacc      60

atcacatgca agtcctccca gtccctgctg gactccggca accagaagaa cttcctgacc    120

tggtatcagc agaagcccgg ccaggccccc agactgctga tctactgggc ctccacccgg    180

gaatctggcg tgccctctag attctccggc tccggctctg gcaccgactt taccttcacc    240

atctccagcc tggaagccga ggacgccgcc acctactact gccagaacga ctactcctac    300

ccctacacct tcggccaggg caccaaggtg gaaatcaagc gtacggtggc cgctcccagc    360

gtgttcatct tcccccccaag cgacgagcag ctgaagagcg gcaccgccag cgtggtgtgt    420

ctgctgaaca acttctaccc cagggaggcc aaggtgcagt ggaaggtgga caacgccctg    480

cagagcggca acagccagga gagcgtcacc gagcaggaca gcaaggactc cacctacagc    540

ctgagcagca ccctgaccct gagcaaggcc gactacgaga agcacaaggt gtacgcctgt    600

gaggtgaccc accagggcct gtccagcccc gtgaccaaga gcttcaacag gggcgagtgc    660


<210> SEQ ID NO 456
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456

gaagtgcagc tggtgcagtc tggcgccgaa gtgaagaagc ctggcgagtc cctgcggatc     60

tcctgcaagg gctctggcta caccttcacc acctactgga tgcactggat ccggcagtcc    120

ccctctaggg gcctggaatg gctgggcaac atctaccctg gcaccggcgg ctccaacttc    180

gacgagaagt tcaagaacag gttcaccatc tcccgggaca actccaagaa caccctgtac    240

ctgcagatga actccctgcg ggccgaggac accgccgtgt actactgtac cagatggacc    300

accggaaccg gcgcctattg gggccagggc acaacagtga ccgtgtcctc c             351


<210> SEQ ID NO 457
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30
```

-continued

```
Trp Met His Trp Ile Arg Gln Ser Pro Ser Arg Gly Leu Glu Trp Leu
        35                  40                  45

Gly Asn Ile Tyr Pro Gly Thr Gly Gly Ser Asn Phe Asp Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 458
<211> LENGTH: 1329
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 458
gaagtgcagc tggtgcagtc tggcgccgaa gtgaagaagc ctggcgagtc cctgcggatc 60
tcctgcaagg gctctggcta caccttcacc acctactgga tgcactggat ccggcagtcc 120
ccctctaggg gcctggaatg gctgggcaac atctaccctg gcaccggcgg ctccaacttc 180
gacgagaagt tcaagaacag gttcaccatc tcccgggaca actccaagaa caccctgtac 240
ctgcagatga actccctgcg ggccgaggac accgccgtgt actactgtac cagatggacc 300
accggaaccg gcgcctattg ggccagggc acaacagtga ccgtgtcctc cgcttctacc 360
aaggggccca gcgtgttccc cctggccccc tgctccagaa gcaccagcga gagcacagcc 420
gccctgggct gcctggtgaa ggactacttc cccgagcccg tgaccgtgtc ctggaacagc 480
ggagccctga ccagcggcgt gcacaccttc cccgccgtgc tgcagagcag cggcctgtac 540
agcctgagca gcgtggtgac cgtgcccagc agcagcctgg gcaccaagac ctacacctgt 600
aacgtggacc acaagcccag caacaccaag gtggacaaga gggtggagag caagtacggc 660
ccaccctgcc ccccctgccc agcccccgag ttcctgggcg gacccagcgt gttcctgttc 720
ccccccaagc ccaaggacac cctgatgatc agcagaaccc ccgaggtgac ctgtgtggtg 780
gtggacgtgt cccaggagga ccccgaggtc cagttcaact ggtacgtgga cggcgtggag 840
gtgcacaacg ccaagaccaa gcccagagag gagcagttta acagcaccta ccgggtggtg 900
tccgtgctga ccgtgctgca ccaggactgg ctgaacggca aagagtacaa gtgtaaggtc 960
tccaacaagg gcctgccaag cagcatcgaa aagaccatca gcaaggccaa gggccagcct 1020
agagagcccc aggtctacac cctgccaccc agccaagagg agatgaccaa gaaccaggtg 1080
tccctgacct gtctggtgaa gggcttctac ccaagcgaca tcgccgtgga gtgggagagc 1140
aacggccagc ccgagaacaa ctacaagacc acccccccag tgctggacag cgacggcagc 1200
ttcttcctgt acagcaggct gaccgtggac aagtccagat ggcaggaggg caacgtcttt 1260
agctgctccg tgatgcacga ggccctgcac aaccactaca cccagaagag cctgagcctg 1320
tccctgggc 1329

<210> SEQ ID NO 459
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 459
gagatcgtgc tgacccagtc ccctgccacc ctgtcactgt ctccaggcga gagagctacc 60
ctgtcctgca agtcctccca gtccctgctg gactccggca accagaagaa cttcctgacc 120
tggtatcagc agaagcccgg ccaggccccc agactgctga tctactgggc ctccacccgg 180
gaatctggcg tgccctctag attctccggc tccggctctg gcaccgactt taccttcacc 240
atctccagcc tggaagccga ggacgccgcc acctactact gccagaacga ctactcctac 300
ccctacacct tcggccaggg caccaaggtg gaaatcaag 339

<210> SEQ ID NO 460
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 460
gagatcgtgc tgacccagtc ccctgccacc ctgtcactgt ctccaggcga gagagctacc 60
ctgtcctgca agtcctccca gtccctgctg gactccggca accagaagaa cttcctgacc 120
tggtatcagc agaagcccgg ccaggccccc agactgctga tctactgggc ctccacccgg 180
gaatctggcg tgccctctag attctccggc tccggctctg gcaccgactt taccttcacc 240
atctccagcc tggaagccga ggacgccgcc acctactact gccagaacga ctactcctac 300
ccctacacct tcggccaggg caccaaggtg gaaatcaagc gtacggtggc cgctcccagc 360
gtgttcatct tcccccccaag cgacgagcag ctgaagagcg gcaccgccag cgtggtgtgt 420
ctgctgaaca acttctaccc cagggaggcc aaggtgcagt ggaaggtgga caacgccctg 480
cagagcggca acagccagga gagcgtcacc gagcaggaca gcaaggactc cacctacagc 540
ctgagcagca ccctgaccct gagcaaggcc gactacgaga agcacaaggt gtacgcctgt 600
gaggtgaccc accagggcct gtccagcccc gtgaccaaga gcttcaacag gggcgagtgc 660

<210> SEQ ID NO 461
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 461
gagatcgtcc tgactcagtc acccgctacc ctgagcctga gccctggcga gcgggctaca 60
ctgagctgta aatctagtca gtcactgctg gatagcggta atcagaagaa cttcctgacc 120
tggtatcagc agaagcccgg tcaagcccct agactgctga tctactgggc ctctactaga 180
gaatcaggcg tgccctctag gtttagcggt agcggtagtg gcaccgactt caccttcact 240
atctctagcc tggaagccga ggacgccgct acctactact gtcagaacga ctatagctac 300
ccctacacct tcggtcaagg cactaaggtc gagattaag 339

<210> SEQ ID NO 462
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 462
gagatcgtcc tgactcagtc acccgctacc ctgagcctga gccctggcga gcgggctaca 60
ctgagctgta aatctagtca gtcactgctg gatagcggta atcagaagaa cttcctgacc 120
tggtatcagc agaagcccgg tcaagcccct agactgctga tctactgggc ctctactaga 180
gaatcaggcg tgccctctag gtttagcggt agcggtagtg gcaccgactt caccttcact 240
atctctagcc tggaagccga ggacgccgct acctactact gtcagaacga ctatagctac 300
ccctacacct tcggtcaagg cactaaggtc gagattaagc gtacggtggc cgctcccagc 360

-continued gtgttcatct tcccccccag cgacgagcag ctgaagagcg gcaccgccag cgtggtgtgc 420
ctgctgaaca acttctaccc ccgggaggcc aaggtgcagt ggaaggtgga caacgccctg 480
cagagcggca acagccagga gagcgtcacc gagcaggaca gcaaggactc cacctacagc 540
ctgagcagca ccctgaccct gagcaaggcc gactacgaga agcataaggt gtacgcctgc 600
gaggtgaccc accagggcct gtccagcccc gtgaccaaga gcttcaacag gggcgagtgc 660

<210> SEQ ID NO 463
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 463
acttactgga tgcac 15

<210> SEQ ID NO 464
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 464
aatatttatc ctggtactgg tggttctaac ttcgatgaga agttcaagaa c 51

<210> SEQ ID NO 465
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 465
tggactactg ggacgggagc ttat 24

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 466
ggctacacat tcaccactta c 21

<210> SEQ ID NO 467
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 467
tatcctggta ctggtggt 18

<210> SEQ ID NO 468
<211> LENGTH: 51
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 468
aagtccagtc agagtctgtt agacagtgga aatcaaaaga acttcttgac c 51

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
tgggcatcca ctagggaatc t 21

<210> SEQ ID NO 470
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
cagaatgatt atagttatcc gtgcacg 27

<210> SEQ ID NO 471
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
agtcagagtc tgttagacag tggaaatcaa aagaacttc 39

<210> SEQ ID NO 472
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472 tgggcatcc 9

<210> SEQ ID NO 473
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
gattatagtt atccgtgc 18

<210> SEQ ID NO 474
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 474
cagaatgatt atagttatcc gtacacg 27

<210> SEQ ID NO 475
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 475
gattatagtt atccgtac 18

<210> SEQ ID NO 476
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 476
aagtccagtc agagtctgtt agacagtgga aatcaaaaga acttcttaac c 51

<210> SEQ ID NO 477
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 477
acctactgga tgcac 15

<210> SEQ ID NO 478
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 478
aacatctatc ctggcaccgg cggctccaac ttcgacgaga agttcaagaa c 51

<210> SEQ ID NO 479
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 479
tggacaaccg gcacaggcgc ttat 24

<210> SEQ ID NO 480
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 480
ggctacacct tcaccaccta c 21

<210> SEQ ID NO 481
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 481
tatcctggca ccggcggc 18

<210> SEQ ID NO 482
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 482
aagtcctccc agtccctgct ggactccggc aaccagaaga acttcctgac c 51

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 483
tgggcctcca cccgggaatc t 21

<210> SEQ ID NO 484
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 484
cagaacgact actcctaccc ctacacc 27

<210> SEQ ID NO 485
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 485
tcccagtccc tgctggactc cggcaaccag aagaacttc 39

<210> SEQ ID NO 486
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 486 tggggcctcc 9

<210> SEQ ID NO 487
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 487
gactactcct acccctac 18

<210> SEQ ID NO 488
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 488
acctactgga tgcac 15

<210> SEQ ID NO 489
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 489
aatatctacc ccggcaccgg cggctctaac ttcgacgaga agtttaagaa t 51

<210> SEQ ID NO 490
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 490
tggactaccg gcacaggcgc ctac 24

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 491
ggctacacct tcactaccta c 21

<210> SEQ ID NO 492
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 492
taccccggca ccggcggc 18

<210> SEQ ID NO 493
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 493
aaatctagtc agtcactgct ggatagcggt aatcagaaga acttcctgac c 51

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 494
tgggcctcta ctagagaatc a 21

<210> SEQ ID NO 495
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 495
cagaacgact atagctaccc ctacacc 27

<210> SEQ ID NO 496
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 496
agtcagtcac tgctggatag cggtaatcag aagaacttc 39

<210> SEQ ID NO 497
<211> LENGTH: 9
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 497 tgggcctct 9

<210> SEQ ID NO 498
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 498
gactatagct acccctac 18

<210> SEQ ID NO 499
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 499
aacatctacc ctggcaccgg cggctccaac ttcgacgaga agttcaagaa c 51

<210> SEQ ID NO 500
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 500
tggaccaccg gaaccggcgc ctat 24

<210> SEQ ID NO 501
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 501
taccctggca ccggcggc 18

<210> SEQ ID NO 502
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 502

Met Glu Trp Ser Trp Val Phe Leu Phe Phe Leu Ser Val Thr Thr Gly
1 5 10 15

Val His Ser

<210> SEQ ID NO 503
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 503

Met Ser Val Pro Thr Gln Val Leu Gly Leu Leu Leu Leu Trp Leu Thr
1 5 10 15

Asp Ala Arg Cys
20

<210> SEQ ID NO 504
<211> LENGTH: 19

<212> TYPE: PRT
<213> ORGANISM: Artificial Sequence
<220> FEATURE:
<223> OTHER INFORMATION: Description of Artificial Sequence: Synthetic peptide

<400> SEQUENCE: 504

Met Ala Trp Val Trp Thr Leu Pro Phe Leu Met Ala Ala Ala Gln Ser
1 5 10 15

Val Gln Ala

<210> SEQ ID NO 505
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 505

Met Ser Val Leu Thr Gln Val Leu Ala Leu Leu Leu Leu Trp Leu Thr
1 5 10 15

Gly Thr Arg Cys
20

<210> SEQ ID NO 506
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 506
tggactactg ggacgggagc ttac 24

<210> SEQ ID NO 507
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 507

Ser Tyr Trp Met Tyr
1 5

<210> SEQ ID NO 508
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 508

Arg Ile Asp Pro Asn Ser Gly Ser Thr Lys Tyr Asn Glu Lys Phe Lys
1 5 10 15

Asn

<210> SEQ ID NO 509
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 509

Asp Tyr Arg Lys Gly Leu Tyr Ala Met Asp Tyr
1               5                   10

<210> SEQ ID NO 510
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Gly Tyr Thr Phe Thr Ser Tyr
1               5

<210> SEQ ID NO 511
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Asp Pro Asn Ser Gly Ser
1               5

<210> SEQ ID NO 512
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Lys Ala Ser Gln Asp Val Gly Thr Ala Val Ala
1               5                   10

<210> SEQ ID NO 513
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Trp Ala Ser Thr Arg His Thr
1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Gln Gln Tyr Asn Ser Tyr Pro Leu Thr
1               5

<210> SEQ ID NO 515
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 515

Ser Gln Asp Val Gly Thr Ala
1 5

<210> SEQ ID NO 516
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 516

Trp Ala Ser
1

<210> SEQ ID NO 517
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 517

Tyr Asn Ser Tyr Pro Leu
1 5

<210> SEQ ID NO 518
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 518

Gly Tyr Thr Phe Thr Ser Tyr Trp Met Tyr
1 5 10

<210> SEQ ID NO 519
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 519

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr 65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr
100 105 110

Leu Val Thr Val Ser Ala
115

<210> SEQ ID NO 520
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 520

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Leu Tyr His Pro Ala
85 90 95

Thr Phe Gly Gln Gly Thr Lys Val Glu Ile Lys Arg
100 105

<210> SEQ ID NO 521
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 521

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Leu Tyr His Pro Ala
85 90 95

Thr Phe Gly Gln Gly Thr Lys Val Glu Ile Lys Arg
100 105

<210> SEQ ID NO 522
<211> LENGTH: 118
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 522

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr
100 105 110

Leu Val Thr Val Ser Ser
115

<210> SEQ ID NO 523
<211> LENGTH: 108
<212> TYPE: PRT
<213> ORGANISM: Homo sapiens

<400> SEQUENCE: 523

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Arg Val Ser Ser Ser
20 25 30

Tyr Leu Ala Trp Tyr Gln Gln Lys Pro Gly Gln Ala Pro Arg Leu Leu
35 40 45

Ile Tyr Asp Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Leu Pro
85 90 95

Trp Thr Phe Gly Gln Gly Thr Lys Val Glu Ile Lys
100 105

<210> SEQ ID NO 524
<211> LENGTH: 121
<212> TYPE: PRT
<213> ORGANISM: Homo sapiens

<400> SEQUENCE: 524

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Gly Gly Trp Phe Gly Glu Leu Ala Phe Asp Tyr Trp Gly
100 105 110

Gln Gly Thr Leu Val Thr Val Ser Ser
115 120

<210> SEQ ID NO 525
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 525

Ser Tyr Asn Met His
1 5

<210> SEQ ID NO 526
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 526

Asp Ile Tyr Pro Gly Asn Gly Asp Thr Ser Tyr Asn Gln Lys Phe Lys
1 5 10 15

Gly

<210> SEQ ID NO 527
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 527

Val Gly Gly Ala Phe Pro Met Asp Tyr
1 5

<210> SEQ ID NO 528
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 528

Arg Ala Ser Glu Ser Val Glu Tyr Tyr Gly Thr Ser Leu Met Gln
1 5 10 15

<210> SEQ ID NO 529
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 529

Ala Ala Ser Asn Val Glu Ser
1               5

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Gln Gln Ser Arg Lys Asp Pro Ser Thr
1               5

<210> SEQ ID NO 531
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Gly Tyr Thr Phe Thr Ser Tyr
1               5

<210> SEQ ID NO 532
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Tyr Pro Gly Asn Gly Asp
1               5

<210> SEQ ID NO 533
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Ser Glu Ser Val Glu Tyr Tyr Gly Thr Ser Leu
1               5                   10

<210> SEQ ID NO 534
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Ala Ala Ser
1

<210> SEQ ID NO 535
<211> LENGTH: 6

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 535

Ser Arg Lys Asp Pro Ser
1 5

<210> SEQ ID NO 536
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 536

Asp Ile Tyr Pro Gly Ser Gly Asp Thr Ser Tyr Asn Gln Lys Phe Lys
1 5 10 15

Gly

<210> SEQ ID NO 537
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 537

Tyr Pro Gly Ser Gly Asp
1 5

<210> SEQ ID NO 538
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 538

Asp Ile Tyr Pro Gly Gln Gly Asp Thr Ser Tyr Asn Gln Lys Phe Lys
1 5 10 15

Gly

<210> SEQ ID NO 539
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 539

Tyr Pro Gly Gln Gly Asp
1 5

<210> SEQ ID NO 540
<211> LENGTH: 122
<212> TYPE: PRT
<213> ORGANISM: Mus sp.

<400> SEQUENCE: 540

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Asn Pro Tyr Tyr Asp Tyr Val Ser Tyr Tyr Ala Met Asp Tyr Trp
            100                 105                 110

Gly His Gly Thr Ser Val Thr Val Ser Ser
        115                 120


<210> SEQ ID NO 541
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 541

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120


<210> SEQ ID NO 542
<211> LENGTH: 107
<212> TYPE: PRT
<213> ORGANISM: Mus sp.

<400> SEQUENCE: 542

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Leu Tyr Thr Gly Val Pro Asp Arg Phe Thr Gly
    50                  55                  60
```

Ser Gly Ser Gly Thr Asp Phe Thr Phe Thr Ile Ser Ser Val Gln Ala
65 70 75 80

Glu Asp Leu Ala Val Tyr Tyr Cys Gln Gln His Tyr Ser Thr Pro Arg
85 90 95

Thr Phe Gly Gly Gly Thr Lys Leu Glu Ile Lys
100 105

<210> SEQ ID NO 543
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 543

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Tyr Leu Tyr Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln His Tyr Ser Thr Pro Arg
85 90 95

Thr Phe Gly Gln Gly Thr Lys Leu Glu Ile Lys
100 105

<210> SEQ ID NO 544
<211> LENGTH: 120
<212> TYPE: PRT
<213> ORGANISM: Mus sp.

<400> SEQUENCE: 544

Glu Val Gln Leu Val Glu Ser Gly Gly Gly Leu Val Gln Pro Gly Glu
1 5 10 15

Ser Leu Lys Leu Ser Cys Glu Ser Asn Glu Tyr Glu Phe Pro Ser His
20 25 30

Asp Met Ser Trp Val Arg Lys Thr Pro Glu Lys Arg Leu Glu Leu Val
35 40 45

Ala Ala Ile Asn Ser Asp Gly Gly Ser Thr Tyr Tyr Pro Asp Thr Met
50 55 60

Glu Arg Arg Phe Ile Ile Ser Arg Asp Asn Thr Lys Lys Thr Leu Tyr
65 70 75 80

Leu Gln Met Ser Ser Leu Arg Ser Glu Asp Thr Ala Leu Tyr Tyr Cys
85 90 95

Ala Arg His Tyr Asp Asp Tyr Tyr Ala Trp Phe Ala Tyr Trp Gly Gln
100 105 110

Gly Thr Leu Val Thr Val Ser Ala
115 120

<210> SEQ ID NO 545
<211> LENGTH: 120
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 545

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
        115                 120

<210> SEQ ID NO 546
<211> LENGTH: 111
<212> TYPE: PRT
<213> ORGANISM: Mus sp.

<400> SEQUENCE: 546

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 547
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala

-continued

```
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110


<210> SEQ ID NO 548
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Gly Tyr Thr Phe Thr Thr Tyr Trp Met His
1               5                   10
```